US012630633B2

(12) United States Patent     (10) Patent No.:    US 12,630,633 B2

Bilic et al.     (45) Date of Patent:    *May 19, 2026

(54) ANTIBODY MOLECULES TO PD-1 AND USES THEREOF

(71) Applicant: Novartis AG, Basel (CH)

(72) Inventors: Sanela Bilic, Urbandale, IA (US); Danny Roland Howard, Jr., Washington, NJ (US); John Scott Cameron, Belmont, MA (US); Glenn Dranoff, Sudbury, MA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/062,427

(22) PCT Filed: Dec. 16, 2016

(86) PCT No.: PCT/US2016/067200

§ 371 (c)(1),
(2) Date: Jun. 14, 2018

(87) PCT Pub. No.: WO2017/106656

PCT Pub. Date: Jun. 22, 2017

(65) Prior Publication Data

US 2018/0371093 A1     Dec. 27, 2018

Related U.S. Application Data

(60) Provisional application No. 62/431,846, filed on Dec. 9, 2016, provisional application No. 62/414,128, filed on Oct. 28, 2016, provisional application No. 62/400,787, filed on Sep. 28, 2016, provisional application No. 62/381,384, filed on Aug. 30, 2016, provisional application No. 62/359,781, filed on Jul. 8, 2016, provisional application No. 62/347,331, filed on Jun. 8, 2016, provisional application No. 62/344,784, filed on Jun. 2, 2016, provisional application No. 62/331,371, filed on May 3, 2016, provisional application No. 62/269,044, filed on Dec. 17, 2015.

(51) Int. Cl.

| | |
|---|---|
| *C07K 16/28* | (2006.01) |
| *A61K 31/337* | (2006.01) |
| *A61K 39/00* | (2006.01) |
| *A61K 39/395* | (2006.01) |
| *A61K 45/06* | (2006.01) |
| *A61P 35/00* | (2006.01) |

(52) U.S. Cl.
CPC ........ *C07K 16/2818* (2013.01); *A61K 31/337* (2013.01); *A61K 39/39558* (2013.01); *A61K 45/06* (2013.01); *A61P 35/00* (2018.01); *A61K 2039/545* (2013.01); *A61K 2300/00* (2013.01)

(58) Field of Classification Search
CPC .......... C07K 16/00–468; A61K 39/395; A61K 39/3955; A61K 39/39558
See application file for complete search history.

(56) References Cited

U.S. PATENT DOCUMENTS

| | | | |
|---|---|---|---|
| 5,324,514 | A | 6/1994 | Sipos |
| 5,434,131 | A | 7/1995 | Linsley et al. |
| 5,629,204 | A | 5/1997 | Honjo et al. |
| 5,698,520 | A | 12/1997 | Honjo et al. |
| 5,773,578 | A | 6/1998 | Hercend et al. |
| 5,811,097 | A | 9/1998 | Allison et al. |
| 5,874,250 | A | 2/1999 | Hercend et al. |
| 5,897,862 | A | 4/1999 | Hardy et al. |
| 5,968,511 | A | 10/1999 | Akita et al. |
| 5,976,877 | A | 11/1999 | Hercend et al. |
| 6,051,227 | A | 4/2000 | Allison et al. |
| 6,084,083 | A | 7/2000 | Levinson |
| 6,143,273 | A | 11/2000 | Faure et al. |
| 6,197,524 | B1 | 3/2001 | Romagnani |
| 6,204,371 | B1 | 3/2001 | Levinson |
| 6,288,218 | B1 | 9/2001 | Levinson |
| 6,414,117 | B1 | 7/2002 | Levinson |
| 6,482,925 | B1 | 11/2002 | El Tayar et al. |
| 6,562,343 | B1 | 5/2003 | Levinson |
| 6,596,536 | B1 | 7/2003 | Hercend et al. |
| 6,632,927 | B2 | 10/2003 | Adair et al. |
| 6,632,976 | B1 | 10/2003 | Tomizuka et al. |
| RE38,313 | E | 11/2003 | Faure et al. |
| 6,803,192 | B1 | 10/2004 | Chen |
| 6,808,710 | B1 | 10/2004 | Wood et al. |
| 6,936,704 | B1 | 8/2005 | Freeman et al. |
| 7,029,674 | B2 | 4/2006 | Carreno et al. |
| 7,038,013 | B2 | 5/2006 | Freeman et al. |

(Continued)

FOREIGN PATENT DOCUMENTS

| | | |
|---|---|---|
| AU | 774391 B2 | 6/2004 |
| CN | 102492038 A | 6/2012 |

(Continued)

OTHER PUBLICATIONS

Wang et al., J Clin Pharmacol 49:1012-24 (Year: 2009).*

(Continued)

*Primary Examiner* — Julie Wu
*Assistant Examiner* — Francesca Edgingtongiordano
(74) *Attorney, Agent, or Firm* — K&L Gates LLP

(57) ABSTRACT

Antibody molecules that specifically bind to PD-1 are disclosed. The antibody molecules can be used to treat or prevent cancerous or infectious conditions and disorders.

43 Claims, 28 Drawing Sheets

Specification includes a Sequence Listing.

(56) References Cited

U.S. PATENT DOCUMENTS

| | | | |
|---|---|---|---|
| 7,041,474 B2 | 5/2006 | Kingsbury | |
| 7,101,550 B2 | 9/2006 | Wood et al. | |
| 7,105,328 B2 | 9/2006 | Wood et al. | |
| 7,122,372 B2 | 10/2006 | Hardy et al. | |
| 7,138,501 B2 | 11/2006 | Ruben et al. | |
| 7,169,791 B2 | 1/2007 | Breitenstein et al. | |
| 7,172,750 B2 | 2/2007 | Levinson | |
| 7,306,906 B2 | 12/2007 | Maruyama et al. | |
| 7,329,639 B2 | 2/2008 | Hardy et al. | |
| 7,329,737 B2 | 2/2008 | Sexton et al. | |
| 7,332,582 B2 | 2/2008 | Hardy et al. | |
| 7,414,171 B2 | 8/2008 | Honjo et al. | |
| 7,423,128 B2 | 9/2008 | Gazit-Bornstein et al. | |
| 7,449,300 B2 | 11/2008 | Chen et al. | |
| 7,470,428 B2 | 12/2008 | Kuchroo et al. | |
| 7,488,802 B2 | 2/2009 | Collins et al. | |
| 7,521,051 B2 | 4/2009 | Collins et al. | |
| 7,524,498 B2 | 4/2009 | Hardy et al. | |
| 7,553,939 B2 | 6/2009 | McIntire et al. | |
| 7,563,441 B2 | 7/2009 | Graus et al. | |
| 7,563,869 B2 | 7/2009 | Honjo et al. | |
| 7,595,048 B2 | 9/2009 | Honjo et al. | |
| 7,598,257 B2 | 10/2009 | Rodgers et al. | |
| 7,605,238 B2 | 10/2009 | Korman et al. | |
| 7,635,757 B2 | 12/2009 | Freeman et al. | |
| 7,695,715 B2 | 4/2010 | Hardy et al. | |
| 7,722,868 B2 | 5/2010 | Freeman et al. | |
| 7,767,675 B2 | 8/2010 | Zhuo et al. | |
| 7,790,160 B2 | 9/2010 | Von Strandmann et al. | |
| 7,794,710 B2 | 9/2010 | Chen et al. | |
| 7,838,220 B2 | 11/2010 | McIntire et al. | |
| 7,850,965 B2 | 12/2010 | Jensen et al. | |
| 7,858,746 B2 | 12/2010 | Honjo et al. | |
| 7,943,743 B2 | 5/2011 | Korman et al. | |
| 8,008,449 B2 | 8/2011 | Korman et al. | |
| 8,039,273 B2 | 10/2011 | Jeffrey | |
| 8,039,479 B2 | 10/2011 | Michellys et al. | |
| 8,088,905 B2 | 1/2012 | Collins et al. | |
| 8,101,176 B2 | 1/2012 | Kuchroo et al. | |
| 8,168,179 B2 | 5/2012 | Honjo et al. | |
| 8,168,757 B2 | 5/2012 | Finnefrock et al. | |
| 8,217,149 B2 | 7/2012 | Irving et al. | |
| 8,287,856 B2 | 10/2012 | Li et al. | |
| 8,329,660 B2 | 12/2012 | Kuchroo et al. | |
| 8,354,509 B2 | 1/2013 | Carven et al. | |
| 8,361,736 B2 | 1/2013 | Majeti et al. | |
| 8,415,355 B2 | 4/2013 | Brain et al. | |
| 8,460,886 B2 | 6/2013 | Shibayama et al. | |
| 8,460,927 B2 | 6/2013 | Chen | |
| 8,461,330 B2 | 6/2013 | Zhuo et al. | |
| 8,501,758 B2 | 8/2013 | Huang et al. | |
| 8,546,336 B2 | 10/2013 | Chen et al. | |
| 8,551,481 B2 | 10/2013 | Pardoll et al. | |
| 8,552,002 B2 | 10/2013 | Ding et al. | |
| 8,552,154 B2 | 10/2013 | Freeman et al. | |
| 8,552,156 B2 | 10/2013 | Takayanagi et al. | |
| 8,568,728 B2 | 10/2013 | Jeffrey | |
| 8,580,247 B2 | 11/2013 | Li et al. | |
| 8,609,089 B2 | 12/2013 | Langermann et al. | |
| 8,617,546 B2 | 12/2013 | Kang et al. | |
| 8,647,623 B2 | 2/2014 | Takayanagi et al. | |
| 8,685,980 B2 | 4/2014 | Besong et al. | |
| 8,697,069 B2 | 4/2014 | Kuchroo et al. | |
| 8,709,412 B2 | 4/2014 | Jones et al. | |
| 8,709,416 B2 | 4/2014 | Langermann et al. | |
| 8,709,429 B2 | 4/2014 | Majeti et al. | |
| 8,715,619 B2 | 5/2014 | Karsunky | |
| 8,728,474 B2 | 5/2014 | Honjo et al. | |
| 8,735,551 B2 | 5/2014 | Garner et al. | |
| 8,735,553 B1 | 5/2014 | Li et al. | |
| 8,779,105 B2 | 7/2014 | Korman et al. | |
| 8,779,108 B2 | 7/2014 | Queva et al. | |
| 8,841,418 B2 | 9/2014 | Karsunky et al. | |
| 8,900,587 B2 | 12/2014 | Carven et al. | |
| 8,927,697 B2 | 1/2015 | Davis et al. | |
| 8,952,136 B2 | 2/2015 | Carven et al. | |
| 9,005,629 B2 | 4/2015 | Pardoll et al. | |
| 9,045,545 B1 | 6/2015 | Clube | |
| 9,067,999 B1 | 6/2015 | Honjo et al. | |
| 9,073,994 B2 | 7/2015 | Honjo et al. | |
| 9,084,776 B2 | 7/2015 | Korman et al. | |
| 9,102,727 B2 | 8/2015 | Freeman et al. | |
| 9,103,832 B2 | 8/2015 | Takayanagi et al. | |
| 9,109,034 B1 | 8/2015 | Clube | |
| 9,132,281 B2 | 9/2015 | Zeng et al. | |
| 9,175,082 B2 | 11/2015 | Zhou et al. | |
| 9,333,256 B2 | 5/2016 | Kuchroo et al. | |
| 9,358,289 B2 | 6/2016 | Korman et al. | |
| 9,387,247 B2 | 7/2016 | Korman et al. | |
| 9,409,970 B2 | 8/2016 | Mikesell et al. | |
| 9,457,080 B2 | 10/2016 | Freeman et al. | |
| 9,492,539 B2 | 11/2016 | Korman et al. | |
| 9,492,540 B2 | 11/2016 | Korman et al. | |
| 9,505,839 B2 | 11/2016 | Lonberg et al. | |
| 9,605,070 B2 | 3/2017 | Sabatos-Peyton et al. | |
| 9,683,048 B2 * | 6/2017 | Freeman | A61P 43/00 |
| 9,815,898 B2 * | 11/2017 | Freeman | A61P 37/02 |
| 9,815,901 B2 | 11/2017 | Brogdon et al. | |
| 9,834,605 B2 | 12/2017 | Carven et al. | |
| 9,884,913 B2 | 2/2018 | Sabatos-Peyton et al. | |
| 9,908,936 B2 | 3/2018 | Triebel et al. | |
| 9,944,645 B2 | 4/2018 | Zhuo et al. | |
| 9,988,452 B2 | 6/2018 | Freeman et al. | |
| 10,005,832 B2 | 6/2018 | Yoshida et al. | |
| 10,253,086 B2 | 4/2019 | Bitter et al. | |
| 10,472,419 B2 | 11/2019 | Sabatos-Peyton et al. | |
| 10,513,558 B2 | 12/2019 | Tipton et al. | |
| 10,561,653 B2 | 2/2020 | Bilic et al. | |
| 10,570,204 B2 | 2/2020 | Johnson et al. | |
| 10,711,060 B2 | 7/2020 | Triebel et al. | |
| 10,752,687 B2 * | 8/2020 | Freeman | A61P 17/00 |
| 10,851,165 B2 | 12/2020 | Freeman et al. | |
| 10,933,064 B2 * | 3/2021 | Cui | A61K 31/506 |
| 10,981,990 B2 | 4/2021 | Sabatos-Peyton et al. | |
| 11,078,191 B2 * | 8/2021 | Bilic | C07D 403/14 |
| 11,155,620 B2 | 10/2021 | Sabatos-Peyton et al. | |
| 11,344,620 B2 | 5/2022 | Lebwohl et al. | |
| 11,406,633 B2 * | 8/2022 | Dobson | A61K 45/06 |
| 11,654,144 B2 * | 5/2023 | Cui | A61K 31/506 |
| | | | 424/133.1 |
| 11,708,412 B2 | 7/2023 | Johnson et al. | |
| 11,827,704 B2 | 11/2023 | Freeman et al. | |
| 2002/0086014 A1 | 7/2002 | Korman et al. | |
| 2002/0146753 A1 | 10/2002 | Ditzel et al. | |
| 2002/0164660 A1 | 11/2002 | Spaulding et al. | |
| 2003/0039653 A1 | 2/2003 | Chen et al. | |
| 2003/0059937 A1 | 3/2003 | Ruben et al. | |
| 2003/0129601 A1 | 7/2003 | Cole | |
| 2003/0232323 A1 | 12/2003 | Freeman et al. | |
| 2004/0072164 A1 | 4/2004 | Maruyama et al. | |
| 2004/0073957 A1 | 4/2004 | Tomizuka et al. | |
| 2004/0171551 A1 | 9/2004 | Triebel | |
| 2004/0241745 A1 | 12/2004 | Honjo et al. | |
| 2005/0009136 A1 | 1/2005 | Nixon et al. | |
| 2005/0191721 A1 | 9/2005 | Kuchroo et al. | |
| 2005/0226876 A1 | 10/2005 | Graus et al. | |
| 2005/0276756 A1 | 12/2005 | Hoo et al. | |
| 2006/0110383 A1 | 5/2006 | Honjo et al. | |
| 2006/0177442 A1 | 8/2006 | Von Strandmann et al. | |
| 2006/0210567 A1 | 9/2006 | Collins et al. | |
| 2006/0240024 A1 | 10/2006 | Pardoll et al. | |
| 2007/0004910 A1 | 1/2007 | Sexton et al. | |
| 2007/0041982 A1 | 2/2007 | Ponath et al. | |
| 2007/0065427 A1 | 3/2007 | Freeman et al. | |
| 2007/0071675 A1 | 3/2007 | Wu et al. | |
| 2007/0122378 A1 | 5/2007 | Freeman et al. | |
| 2007/0160598 A1 | 7/2007 | Dennis et al. | |
| 2007/0202100 A1 | 8/2007 | Wood et al. | |
| 2008/0025979 A1 | 1/2008 | Honjo et al. | |
| 2008/0038264 A1 | 2/2008 | Bodary et al. | |
| 2008/0069822 A1 | 3/2008 | Jensen et al. | |
| 2008/0167287 A1 | 7/2008 | Zhuo et al. | |
| 2008/0311117 A1 | 12/2008 | Collins et al. | |
| 2009/0055944 A1 | 2/2009 | Korman et al. | |

(56) References Cited

U.S. PATENT DOCUMENTS

| | | |
|---|---|---|
| 2009/0076250 A1 | 3/2009 | Honjo et al. |
| 2009/0155275 A1 | 6/2009 | Wu et al. |
| 2009/0304693 A1 | 12/2009 | Ghayur et al. |
| 2009/0311253 A1 | 12/2009 | Ghayur et al. |
| 2010/0028330 A1 | 2/2010 | Collins et al. |
| 2010/0056576 A1 | 3/2010 | Burger et al. |
| 2010/0061992 A1 | 3/2010 | Anderson et al. |
| 2010/0074900 A1 | 3/2010 | Ghayur et al. |
| 2010/0076178 A1 | 3/2010 | Ghayur et al. |
| 2010/0105667 A1 | 4/2010 | Furet et al. |
| 2010/0136009 A1 | 6/2010 | Papkoff et al. |
| 2010/0203056 A1 | 8/2010 | Irving et al. |
| 2010/0233079 A1 | 9/2010 | Jakob et al. |
| 2010/0233183 A1 | 9/2010 | Triebel et al. |
| 2010/0260668 A1 | 10/2010 | Ghayur et al. |
| 2010/0266531 A1 | 10/2010 | Hsieh et al. |
| 2010/0266617 A1 | 10/2010 | Carven et al. |
| 2011/0008766 A1 | 1/2011 | Ghayur et al. |
| 2011/0044894 A1 | 2/2011 | Karsunky |
| 2011/0044980 A1 | 2/2011 | Ghayur et al. |
| 2011/0054151 A1 | 3/2011 | Lazar et al. |
| 2011/0059106 A1 | 3/2011 | Kuchroo et al. |
| 2011/0070238 A1 | 3/2011 | Triebel et al. |
| 2011/0081341 A1 | 4/2011 | Honjo et al. |
| 2011/0091372 A1 | 4/2011 | Ghayur et al. |
| 2011/0091463 A1 | 4/2011 | Ghayur et al. |
| 2011/0110852 A1 | 5/2011 | Miller et al. |
| 2011/0123550 A1 | 5/2011 | Shibayama et al. |
| 2011/0136781 A1 | 6/2011 | Zhuo et al. |
| 2011/0150892 A1 | 6/2011 | Thudium et al. |
| 2011/0171220 A1 | 7/2011 | Davis |
| 2011/0177088 A1 | 7/2011 | Olive et al. |
| 2011/0195068 A1 | 8/2011 | Langermann et al. |
| 2011/0209230 A1 | 8/2011 | Korman et al. |
| 2011/0212094 A1 | 9/2011 | Ghayur et al. |
| 2011/0229461 A1 | 9/2011 | Tyson |
| 2011/0236375 A1 | 9/2011 | Lazar et al. |
| 2011/0263827 A1 | 10/2011 | Ghayur et al. |
| 2011/0271358 A1 | 11/2011 | Freeman et al. |
| 2011/0280800 A1 | 11/2011 | Wu et al. |
| 2011/0280877 A1 | 11/2011 | Tamada |
| 2011/0287009 A1 | 11/2011 | Scheer et al. |
| 2012/0014957 A1 | 1/2012 | Ghayur et al. |
| 2012/0034160 A1 | 2/2012 | Ghayur et al. |
| 2012/0039870 A9 | 2/2012 | Dolk et al. |
| 2012/0039906 A1 | 2/2012 | Olive |
| 2012/0070450 A1 | 3/2012 | Ishikawa et al. |
| 2012/0076805 A1 | 3/2012 | Sharpe et al. |
| 2012/0087858 A1 | 4/2012 | Ghayur et al. |
| 2012/0100131 A1 | 4/2012 | Takayanagi et al. |
| 2012/0107234 A1 | 5/2012 | Pedersen et al. |
| 2012/0114649 A1 | 5/2012 | Langermann et al. |
| 2012/0141501 A1 | 6/2012 | Yoshida et al. |
| 2012/0195900 A1 | 8/2012 | Ghayur et al. |
| 2012/0201746 A1 | 8/2012 | Liu et al. |
| 2012/0201824 A1 | 8/2012 | Wasik |
| 2012/0258108 A1 | 10/2012 | Ghayur et al. |
| 2012/0263722 A1 | 10/2012 | Ghayur et al. |
| 2013/0005216 A1 | 1/2013 | Rittberger |
| 2013/0017199 A1 | 1/2013 | Langermann |
| 2013/0022623 A1 | 1/2013 | Karsunky et al. |
| 2013/0039911 A1 | 2/2013 | Bedi et al. |
| 2013/0058947 A1 | 3/2013 | Stull et al. |
| 2013/0095098 A1 | 4/2013 | Tyson |
| 2013/0109843 A1 | 5/2013 | Carven et al. |
| 2013/0133091 A1 | 5/2013 | Korman et al. |
| 2013/0156774 A1 | 6/2013 | Kuchroo et al. |
| 2013/0183688 A1 | 7/2013 | Kuchroo et al. |
| 2013/0202623 A1 | 8/2013 | Chomont et al. |
| 2013/0230514 A1 | 9/2013 | Langermann et al. |
| 2013/0324515 A1 | 12/2013 | Zhuo et al. |
| 2014/0044728 A1 | 2/2014 | Takayanagi et al. |
| 2014/0044738 A1 | 2/2014 | Langermann et al. |
| 2014/0065142 A1 | 3/2014 | Roschke et al. |
| 2014/0093511 A1 | 4/2014 | Lonberg et al. |

| | | | |
|---|---|---|---|
| 2014/0127226 A1 | 5/2014 | Pardoll et al. | |
| 2014/0155678 A1 | 6/2014 | Zeng et al. | |
| 2014/0178370 A1 | 6/2014 | Freeman et al. | |
| 2014/0212422 A1 | 7/2014 | Korman et al. | |
| 2014/0234320 A1 | 8/2014 | Croft et al. | |
| 2014/0242094 A1 | 8/2014 | Kuchroo et al. | |
| 2014/0274788 A1 | 9/2014 | Ishikawa et al. | |
| 2014/0294852 A1 | 10/2014 | Korman et al. | |
| 2014/0314714 A1 | 10/2014 | Honjo et al. | |
| 2014/0328833 A1 | 11/2014 | Korman et al. | |
| 2014/0341902 A1 | 11/2014 | Maecker et al. | |
| 2014/0348743 A1 | 11/2014 | Korman et al. | |
| 2015/0017185 A1 | 1/2015 | Akbar et al. | |
| 2015/0023986 A1 | 1/2015 | Jones et al. | |
| 2015/0079109 A1 | 3/2015 | Li et al. | |
| 2015/0086574 A1 | 3/2015 | Karsunky et al. | |
| 2015/0093380 A1 | 4/2015 | Honjo et al. | |
| 2015/0210769 A1* | 7/2015 | Freeman | G01N 33/566 |
| | | | 424/136.1 |
| 2015/0218274 A1 | 8/2015 | Sabatos-Peyton et al. | |
| 2015/0232555 A1 | 8/2015 | Carven et al. | |
| 2015/0259420 A1 | 9/2015 | Triebel et al. | |
| 2015/0290316 A1 | 10/2015 | Graziano et al. | |
| 2015/0307609 A1 | 10/2015 | Lonberg et al. | |
| 2016/0002334 A1 | 1/2016 | Kuchroo et al. | |
| 2016/0016979 A1 | 1/2016 | Anklekar et al. | |
| 2016/0068601 A1 | 3/2016 | Brogdon et al. | |
| 2016/0108123 A1 | 4/2016 | Freeman et al. | |
| 2016/0159905 A1 | 6/2016 | Abdiche et al. | |
| 2016/0222121 A1 | 8/2016 | Johnson et al. | |
| 2016/0326178 A1 | 11/2016 | Zhuo et al. | |
| 2016/0362472 A1 | 12/2016 | Bitter et al. | |
| 2017/0044259 A1 | 2/2017 | Tipton et al. | |
| 2017/0088615 A1 | 3/2017 | Korman et al. | |
| 2017/0137514 A1 | 5/2017 | Lonberg et al. | |
| 2017/0190777 A1 | 7/2017 | Sabatos-Peyton et al. | |
| 2017/0198041 A1 | 7/2017 | Sabatos-Peyton et al. | |
| 2017/0209574 A1 | 7/2017 | Cao et al. | |
| 2017/0210804 A1 | 7/2017 | Triebel et al. | |
| 2017/0247456 A1 | 8/2017 | Freeman et al. | |
| 2017/0281624 A1 | 10/2017 | Peters et al. | |
| 2017/0296659 A1 | 10/2017 | Lebwohl et al. | |
| 2017/0304443 A1 | 10/2017 | Lebwohl et al. | |
| 2017/0340733 A1 | 11/2017 | Cao | |
| 2018/0066054 A1 | 3/2018 | Thudium et al. | |
| 2018/0086830 A1 | 3/2018 | Triebel et al. | |
| 2018/0155427 A1 | 6/2018 | Freeman et al. | |
| 2018/0186882 A1 | 7/2018 | Freeman et al. | |
| 2018/0207273 A1 | 7/2018 | Dranoff et al. | |
| 2018/0222982 A1 | 8/2018 | Dranoff et al. | |
| 2018/0282340 A1 | 10/2018 | Zhuo et al. | |
| 2018/0340025 A1 | 11/2018 | Dranoff et al. | |
| 2018/0371093 A1 | 12/2018 | Bilic et al. | |
| 2019/0000944 A1 | 1/2019 | Brogdon et al. | |
| 2019/0016797 A1 | 1/2019 | Arenas-Ramirez et al. | |
| 2019/0031766 A1 | 1/2019 | Prinz et al. | |
| 2019/0062365 A1 | 2/2019 | Katibah et al. | |
| 2019/0113513 A1 | 4/2019 | Shaked | |
| 2019/0151365 A1 | 5/2019 | Anak et al. | |
| 2019/0185511 A1 | 6/2019 | Kanne et al. | |
| 2019/0202917 A1 | 7/2019 | Campbell et al. | |
| 2020/0030442 A1 | 1/2020 | Cao | |
| 2020/0037760 A1 | 2/2020 | Han | |
| 2020/0172617 A1 | 6/2020 | Stein et al. | |
| 2020/0223917 A1 | 7/2020 | Sabatos-Peyton et al. | |
| 2020/0223924 A1 | 7/2020 | Stein et al. | |
| 2020/0277378 A1 | 9/2020 | Sabatos-Peyton et al. | |
| 2020/0308277 A1 | 10/2020 | Sabatos-Peyton et al. | |
| 2020/0339689 A1 | 10/2020 | Freeman et al. | |
| 2020/0369762 A1 | 11/2020 | Bruederle et al. | |
| 2020/0377600 A1 | 12/2020 | Johnson et al. | |
| 2021/0000951 A1 | 1/2021 | Cao et al. | |
| 2021/0009687 A1 | 1/2021 | Triebel et al. | |
| 2021/0284737 A1 | 9/2021 | Freeman et al. | |
| 2022/0133889 A1 | 5/2022 | Dranoff et al. | |
| 2022/0153835 A1 | 5/2022 | Dranoff et al. | |
| 2022/0185883 A1 | 6/2022 | Sabatos-Peyton et al. | |
| 2022/0306737 A1 | 9/2022 | Eliasson et al. | |
| 2023/0013364 A1 | 1/2023 | Dranoff et al. | |

(56) References Cited

U.S. PATENT DOCUMENTS

| | | |
|---|---|---|
| 2023/0057071 A1 | 2/2023 | Vanasse et al. |
| 2023/0058489 A1 | 2/2023 | Menssen et al. |
| 2023/0088070 A1 | 3/2023 | Bruederle et al. |
| 2024/0043541 A1 | 2/2024 | Johnson et al. |
| 2024/0075136 A1 | 3/2024 | Lebwohl et al. |
| 2024/0301053 A1 | 9/2024 | Menssen et al. |
| 2024/0301054 A1 | 9/2024 | Vanasse et al. |
| 2024/0310266 A1 | 9/2024 | Brase et al. |
| 2024/0343808 A1 | 10/2024 | Freeman et al. |
| 2025/0213684 A1 | 7/2025 | Dranoff et al. |
| 2025/0382365 A1 | 12/2025 | Triebel et al. |

FOREIGN PATENT DOCUMENTS

| | | |
|---|---|---|
| CN | 103079644 A | 5/2013 |
| CN | 103242448 A | 8/2013 |
| EP | 0670369 A2 | 9/1995 |
| EP | 0742795 A1 | 11/1996 |
| EP | 0510079 B1 | 5/1999 |
| EP | 1165616 A1 | 1/2002 |
| EP | 1210424 A1 | 6/2002 |
| EP | 1334659 A1 | 8/2003 |
| EP | 1385533 A1 | 2/2004 |
| EP | 1445264 A1 | 8/2004 |
| EP | 1537878 A1 | 6/2005 |
| EP | 1576014 A1 | 9/2005 |
| EP | 1591527 A1 | 11/2005 |
| EP | 0758383 B1 | 1/2007 |
| EP | 1870399 A1 | 12/2007 |
| EP | 1896582 A1 | 3/2008 |
| EP | 2161336 A1 | 3/2010 |
| EP | 2195347 A1 | 6/2010 |
| EP | 2206517 A1 | 7/2010 |
| EP | 2243493 A1 | 10/2010 |
| EP | 2270051 A2 | 1/2011 |
| EP | 2307050 A1 | 4/2011 |
| EP | 2328920 A2 | 6/2011 |
| EP | 2342228 A1 | 7/2011 |
| EP | 2342229 A1 | 7/2011 |
| EP | 2360254 A1 | 8/2011 |
| EP | 2370593 A2 | 10/2011 |
| EP | 2397155 A1 | 12/2011 |
| EP | 2397156 A1 | 12/2011 |
| EP | 2412825 A1 | 2/2012 |
| EP | 2417984 A1 | 2/2012 |
| EP | 2418278 A2 | 2/2012 |
| EP | 2439272 A2 | 4/2012 |
| EP | 2439273 A2 | 4/2012 |
| EP | 2482849 A2 | 8/2012 |
| EP | 2482849 B1 | 8/2012 |
| EP | 2504364 A1 | 10/2012 |
| EP | 2504364 B1 | 10/2012 |
| EP | 2099447 B1 | 11/2012 |
| EP | 2535354 A1 | 12/2012 |
| EP | 2545076 A1 | 1/2013 |
| EP | 2545078 A1 | 1/2013 |
| EP | 2051990 B1 | 2/2013 |
| EP | 2581113 A1 | 4/2013 |
| EP | 1897548 B1 | 8/2013 |
| EP | 2170959 B1 | 10/2013 |
| EP | 2691112 A1 | 2/2014 |
| EP | 2691112 B1 | 2/2014 |
| EP | 2699264 A1 | 2/2014 |
| EP | 2699264 B1 | 2/2014 |
| EP | 2723381 A2 | 4/2014 |
| EP | 2320940 B1 | 3/2015 |
| EP | 2905030 A1 | 8/2015 |
| EP | 2344474 B1 | 9/2015 |
| EP | 2927240 A1 | 10/2015 |
| EP | 2142210 B1 | 8/2016 |
| EP | 2474545 B1 | 11/2016 |
| EP | 2867258 B1 | 6/2017 |
| EP | 3222634 A1 | 9/2017 |
| JP | H07291996 A | 11/1995 |
| JP | 2002194491 A | 7/2002 |
| JP | 2003029846 A | 1/2003 |
| JP | 2004512005 A | 4/2004 |
| JP | 2006521783 A | 9/2006 |
| JP | 2006340714 A | 12/2006 |
| JP | 2010514791 A | 5/2010 |
| JP | 2012503984 A | 2/2012 |
| RU | 2494107 C2 | 9/2013 |
| WO | 8808135 A1 | 10/1988 |
| WO | 1990003394 A2 | 4/1990 |
| WO | 9110682 A1 | 7/1991 |
| WO | 1992013949 A1 | 8/1992 |
| WO | 1992013950 A2 | 8/1992 |
| WO | 9520605 A1 | 8/1995 |
| WO | 9530750 A2 | 11/1995 |
| WO | 1996027603 A1 | 9/1996 |
| WO | 9703695 A1 | 2/1997 |
| WO | 9707671 A1 | 3/1997 |
| WO | 9713852 A1 | 4/1997 |
| WO | 1998023741 A1 | 6/1998 |
| WO | 9858059 A1 | 12/1998 |
| WO | 1999004810 A2 | 2/1999 |
| WO | 0032231 A1 | 6/2000 |
| WO | 0058363 A1 | 10/2000 |
| WO | 0069914 A2 | 11/2000 |
| WO | 0071078 A2 | 11/2000 |
| WO | 0073498 A1 | 12/2000 |
| WO | 0114424 A2 | 3/2001 |
| WO | 0114556 A1 | 3/2001 |
| WO | 0114557 A1 | 3/2001 |
| WO | 0139722 A2 | 6/2001 |
| WO | 01077342 A1 | 10/2001 |
| WO | 01083750 A2 | 11/2001 |
| WO | 200194413 A2 | 12/2001 |
| WO | 0200692 A2 | 1/2002 |
| WO | 0200730 A2 | 1/2002 |
| WO | 2002/22577 A2 | 3/2002 |
| WO | 0224891 A2 | 3/2002 |
| WO | 0232378 A2 | 4/2002 |
| WO | 0234205 A2 | 5/2002 |
| WO | 0239813 A1 | 5/2002 |
| WO | 02078731 A1 | 10/2002 |
| WO | 02079499 A1 | 10/2002 |
| WO | 02086083 A2 | 10/2002 |
| WO | 03000066 A1 | 1/2003 |
| WO | 03002722 A2 | 1/2003 |
| WO | 03011911 A1 | 2/2003 |
| WO | 03033644 A2 | 4/2003 |
| WO | 03042402 A2 | 5/2003 |
| WO | 03063792 A2 | 8/2003 |
| WO | 03077914 A1 | 9/2003 |
| WO | 03088808 A2 | 10/2003 |
| WO | 03099196 A2 | 12/2003 |
| WO | 2004004771 A1 | 1/2004 |
| WO | 2004005281 A1 | 1/2004 |
| WO | 2004007679 A2 | 1/2004 |
| WO | 2004039956 A2 | 5/2004 |
| WO | 2004056875 A1 | 7/2004 |
| WO | 2004072286 A1 | 8/2004 |
| RU | 2004078928 A2 | 9/2004 |
| WO | 2005027854 A2 | 3/2005 |
| WO | 2005033144 A2 | 4/2005 |
| WO | 2005034733 A2 | 4/2005 |
| WO | 2005097211 A2 | 10/2005 |
| WO | 2006004988 A2 | 1/2006 |
| WO | 2006007850 A1 | 1/2006 |
| WO | 2006021955 A2 | 3/2006 |
| WO | 2006042237 A2 | 4/2006 |
| WO | 2006121168 A1 | 11/2006 |
| WO | 2006124269 A2 | 11/2006 |
| WO | 2006133396 A2 | 12/2006 |
| WO | 2007005874 A2 | 1/2007 |
| WO | 2007011968 A2 | 1/2007 |
| WO | 2007024705 A2 | 3/2007 |
| WO | 2007024715 A2 | 3/2007 |
| WO | 2007070514 A1 | 6/2007 |
| WO | 2007082154 A2 | 7/2007 |
| WO | 2007084786 A1 | 7/2007 |
| WO | 2007113648 A2 | 10/2007 |
| WO | 2007146968 A2 | 12/2007 |

(56) References Cited

FOREIGN PATENT DOCUMENTS

| | | | |
|---|---|---|---|
| WO | 2008007648 A1 | 1/2008 |
| WO | 2008016893 A1 | 2/2008 |
| WO | 2008060617 A2 | 5/2008 |
| WO | 2008064157 A1 | 5/2008 |
| WO | 2008071447 A2 | 6/2008 |
| WO | 2008073160 A2 | 6/2008 |
| WO | 2008073687 A2 | 6/2008 |
| WO | 2008083174 A2 | 7/2008 |
| WO | 2008085562 A2 | 7/2008 |
| WO | 2008132601 A1 | 11/2008 |
| WO | 2008156712 A1 | 12/2008 |
| WO | 2009014708 A2 | 1/2009 |
| WO | 2009024531 A1 | 2/2009 |
| WO | 2009029342 A2 | 3/2009 |
| WO | 2009032256 A2 | 3/2009 |
| WO | 2009044273 A2 | 4/2009 |
| WO | 2009091547 A1 | 7/2009 |
| WO | 2009097394 A2 | 8/2009 |
| WO | 2009101611 A1 | 8/2009 |
| WO | 2009114335 A2 | 9/2009 |
| WO | 2009120905 A2 | 10/2009 |
| WO | 2009141386 A1 | 11/2009 |
| WO | 2010001617 A1 | 1/2010 |
| WO | 2010019570 A2 | 2/2010 |
| WO | 2010019571 A2 | 2/2010 |
| WO | 2010026124 A1 | 3/2010 |
| WO | 2010027423 A2 | 3/2010 |
| WO | 2010027827 A2 | 3/2010 |
| WO | 2010027828 A2 | 3/2010 |
| WO | 2010029082 A1 | 3/2010 |
| WO | 2010029434 A1 | 3/2010 |
| WO | 2010029435 A1 | 3/2010 |
| WO | 2010036959 A2 | 4/2010 |
| WO | 2010051502 A2 | 5/2010 |
| WO | 2010063011 A2 | 6/2010 |
| WO | 2010077634 A1 | 7/2010 |
| WO | 2010084999 A1 | 7/2010 |
| WO | 2010089411 A2 | 8/2010 |
| WO | 2010098788 A2 | 9/2010 |
| WO | 2010102278 A1 | 9/2010 |
| WO | 2010110346 A1 | 9/2010 |
| WO | 2010117057 A1 | 10/2010 |
| WO | 2011005481 A1 | 1/2011 |
| WO | 2011011027 A1 | 1/2011 |
| WO | 2011025927 A1 | 3/2011 |
| WO | 2011034605 A2 | 3/2011 |
| WO | 2011041613 A2 | 4/2011 |
| WO | 2011066342 A2 | 6/2011 |
| WO | 2011066389 A1 | 6/2011 |
| WO | 2011069104 A2 | 6/2011 |
| WO | 2011076786 A1 | 6/2011 |
| WO | 2011100841 A1 | 8/2011 |
| WO | 2011110604 A1 | 9/2011 |
| WO | 2011110621 A1 | 9/2011 |
| WO | 2011131472 A1 | 10/2011 |
| WO | 2011155607 A1 | 12/2011 |
| WO | 2011159877 A2 | 12/2011 |
| WO | 2012018538 A2 | 2/2012 |
| WO | 2012022814 A1 | 2/2012 |
| WO | 2012054438 A1 | 4/2012 |
| WO | 2012064733 A2 | 5/2012 |
| WO | 2012079000 A1 | 6/2012 |
| WO | 2012106587 A1 | 8/2012 |
| WO | 2012135408 A1 | 10/2012 |
| WO | 2012145493 A1 | 10/2012 |
| WO | 2012177624 A2 | 12/2012 |
| WO | 2012177788 A1 | 12/2012 |
| WO | 2013006490 A2 | 1/2013 |
| WO | 2013006727 A1 | 1/2013 |
| WO | 2013019906 A1 | 2/2013 |
| WO | 2013043647 A1 | 3/2013 |
| WO | 2013066761 A1 | 5/2013 |
| WO | 2013079174 A1 | 6/2013 |
| WO | 2013079945 A1 | 6/2013 |
| WO | 2013169693 A1 | 11/2013 |
| WO | 2013173223 A1 | 11/2013 |
| WO | 2013181452 A1 | 12/2013 |
| WO | 2013181634 A2 | 12/2013 |
| WO | 2013184757 A1 | 12/2013 |
| WO | 2014008218 A1 | 1/2014 |
| WO | 2014018632 A1 | 1/2014 |
| WO | 2014022138 A2 | 2/2014 |
| WO | 2014022332 A1 | 2/2014 |
| WO | 2014022758 A1 | 2/2014 |
| WO | 2014047350 A1 | 3/2014 |
| WO | 2014055648 A1 | 4/2014 |
| WO | 2014055897 A2 | 4/2014 |
| WO | 2014072493 A1 | 5/2014 |
| WO | 2014085318 A1 | 6/2014 |
| WO | 2014100079 A1 | 6/2014 |
| WO | 2014140180 A1 | 9/2014 |
| WO | 2014165082 A2 | 10/2014 |
| WO | 2014165422 A1 | 10/2014 |
| WO | 2014179664 A2 | 11/2014 |
| WO | 2014189805 A1 | 11/2014 |
| WO | 2014195852 A1 | 12/2014 |
| WO | 2015009856 A2 | 1/2015 |
| WO | 2015026634 A1 | 2/2015 |
| WO | 2015026684 A1 | 2/2015 |
| WO | 2015035606 A1 | 3/2015 |
| WO | 2015036394 A1 | 3/2015 |
| WO | 2015036499 A1 | 3/2015 |
| WO | 2015036511 A1 | 3/2015 |
| WO | 2015042246 A1 | 3/2015 |
| WO | 2015048312 A1 | 4/2015 |
| WO | 2015048520 A1 | 4/2015 |
| WO | 2015061668 A1 | 4/2015 |
| WO | 2015070060 A1 | 5/2015 |
| WO | 2015081158 A1 | 6/2015 |
| WO | 2015085847 A1 | 6/2015 |
| WO | 2015088847 A1 | 6/2015 |
| WO | 2015095423 A2 | 6/2015 |
| WO | 2015095811 A2 | 6/2015 |
| WO | 2015103602 A1 | 7/2015 |
| WO | 2015109124 A2 | 7/2015 |
| WO | 2015109391 A1 | 7/2015 |
| WO | 2015112800 A1 | 7/2015 |
| WO | 2015112805 A1 | 7/2015 |
| WO | 2015112900 A1 | 7/2015 |
| WO | 2015116539 A1 | 8/2015 |
| WO | 2015117002 A1 | 8/2015 |
| WO | 2015118175 A2 | 8/2015 |
| WO | 2015119944 A1 | 8/2015 |
| WO | 2015120198 A1 | 8/2015 |
| WO | 2015134605 A1 | 9/2015 |
| WO | 2015138920 A1 | 9/2015 |
| WO | WO-2015176033 A1 * | 11/2015 | ............ C07K 16/22 |
| WO | 2015181342 A1 | 12/2015 |
| WO | 2015195163 A1 | 12/2015 |
| WO | 2016000619 A1 | 1/2016 |
| WO | 2016028672 A1 | 2/2016 |
| WO | 2016040880 A1 | 3/2016 |
| WO | 2016040882 A1 | 3/2016 |
| WO | 2016040892 A1 | 3/2016 |
| WO | 2016054555 A2 | 4/2016 |
| WO | 2016061142 A1 | 4/2016 |
| WO | 2016069727 A1 | 5/2016 |
| WO | 2016079049 A1 | 5/2016 |
| WO | 2016100882 A1 | 6/2016 |
| WO | 2016161239 A1 | 10/2016 |
| WO | 2016161270 A1 | 10/2016 |
| WO | 2016168716 A1 | 10/2016 |
| WO | 2017017623 A1 | 2/2017 |
| WO | 2017017624 A1 | 2/2017 |
| WO | 2017019894 A1 | 2/2017 |
| WO | 2017019896 A1 | 2/2017 |
| WO | 2017019897 A1 | 2/2017 |
| WO | 2017034916 A1 | 3/2017 |
| WO | 2017097407 A1 | 6/2017 |
| WO | 2017106656 A1 | 6/2017 |
| WO | 2017189433 A1 | 11/2017 |
| WO | 2018222718 A1 | 12/2018 |
| WO | 2019006007 A1 | 1/2019 |
| WO | 2019018640 A1 | 1/2019 |

(56)                References Cited

FOREIGN PATENT DOCUMENTS

| WO | 2019018730 A1 | 1/2019 |
| WO | 2019099838 A1 | 5/2019 |
| WO | 2019200229 A1 | 10/2019 |
| WO | 2020128636 A1 | 6/2020 |
| WO | 2021053490 A1 | 3/2021 |
| WO | 2021079188 A1 | 4/2021 |
| WO | 2021079195 A1 | 4/2021 |
| WO | 2021123902 A1 | 6/2021 |
| WO | 2021144657 A1 | 7/2021 |
| WO | 2022195551 A1 | 9/2022 |

OTHER PUBLICATIONS

Larkin et al. JAMA Oncology. 1(4):433-440 (2015) (Year: 2015).*

Wang et al., "The Mdm2 inhibitor, NVP-CGM097, in combination with the BRAF inhibitor NVP-LGX818 elicits synergistic antitumor effects in melanoma" Cancer Research (2014) , Abstract 5466, Retrieved from the Internet: URL: http://cancerres.aacrjournals.orgjcontent/74/19 Supplement/5466 [retrieved on Apr. 14, 2016].

Wang et al., "VISTA, a novel mouse Ig superfamily ligand that negatively regulates T cell responses" The Journal of Experimental Medicine (2011) vol. 208 No 3 pp. 577-592.

Wang et al: "Abstract 2929: The Mdm2 inhibitor NVP-CGM097 enhances the anti-tumor activityof NVP-LDK378 in ALK mutant neuroblastomamodels", Cancer Research (2014) Retrieved from the Internet: URL:http:jjcancerres.aacrjournals.orgjcontent/74/19 Supplement/2929 [retrieved on Apr. 14, 2016].

Weber, J.S., et al., "Safety, Efficacy, and Biomarkers of Nivolumab with Vaccine in Ipilimumab-Refractory or -Naive Melanoma," Journal of Clinical Oncology 31 (34):4311-4318, American Society of Clinical Oncology, United States (2013).

Wilson, I.A. and Stanfield, R.L., "Antibody-antigen interactions," Current Opinion in Sturctural Biology 3:113-118, Current Biology, United States (1993).

Winslow, R., "New Cancer Drugs Harness Power of Immune System", The Wall Street Journal, May 15, 2013, accessed at http://www.wsj.com/articles/ SB10001424127887323398204578485401089823868, accessed on Jun. 1, 2016, 4 pages.

Wolchok, J.D., et al., "Nivolumab plus Ipilimumab in Advanced Melanoma," The New England Journal of Medicine 369 (2):122-133, Massachusetts Medical Society, United States (2013).

Wong, R.M., et al., "Programmed death-1 blockade enhances expansion and functional capacity of human melanoma antigen-specific CTLs," International Immunology 19(10):1223-1234, Oxford University Press, England (2007).

Woods David M et al: "HDAC Inhibition Upregulates PD-1 Ligands in Melanoma and Augments Immunotherapy with PD-1 Blockade," Cancer Immunology Research, vol. 3, No. 12, Dec. 2015 (Dec. 2015), pp. 1375-1385.

Woods David M et al: "The antimelanoma activity of the histone deacetylase inhibitor panobinostat (LBH589) is mediated by direct tumor cytotoxicity and increased tumor immunogenicity.", Melanoma Research, vol. 23, No. 5, Oct. 2013 (Oct. 2013), pp. 341-348.

Woods et al: "Abstract 4090: Inhibition of class I histone deacetylases promotes robust and durable enhancement of PDL 1 expression in melanoma: Rationale for combination therapy", Cancer Research (2014) Retrieved from the Internet: URL:http://cancerres.aacrjournals.orgjcontent/74/19Supplement/4090.short [retrieved on Apr. 14, 2016].

Wu, K-P., et al., "Structural Basis of a Flavivirus Recognized by Its Neutralizing Antibody: Solution Structure of the Domain III of the Japanese Encephalitis Virus Envelope Protein," The Journal of Biological Chemistry 278 (46):46007-46013, AmericanSociety for Biochemistry and Molecular Biology, Inc., United States (Nov. 2003).

Yamazaki, T., et al., "Expression of programmed death 1 ligands by murine T cells and APC," The Journal of Immunology 169(10):5538-5545, The American Association of Immunologists, United States (2002).

Yang et al., "Lack of TIM-3 Immunoregulation in Multiple Sclerosis" The Journal of Immunology (2008) vol. 180 No. 7 pp. 4409-14.

Yi, J., et al., "Mapping the Epitope of an Inhibitory Monoclonal Antibody to the C-terminal DNA-binding Domain of HIV-1 Integrase," The Journal of Biological Chemistry 277(14):12164-12174, American Society for Biochemistry and Molecular Biology, Inc., United States (2002).

Youngnak, Pornpan, et al.; "Differential binding properties of B7-H1 and B7-DC to programmed death-1"; Biochem. Biophys. Res. Commun.; 307:672-677 (2003).

Yuan Z. et al., "Blockade of inhibitors of apoptosis (IAPs) in combination with tumor-targeted delivery of tumor necrosis factor-[alpha] leads to synergistic antitumor activity" Cancer Gene Therapy (2013) vol. 20 No. 1 pp. 46-56.

Zehavi-Willner, Tova, et al.; "The mitogenic activity of staphylococcal enterotoxin B (Seb): a monovalent T cell mitogen that stimulates cytolytic T lymphocytes but cannot mediate their lytic interaction"; J. Immunol.; 137(8):2682-2687 (1986).

Zhang, "Oral 31—PD1 Axis Inhibition," Abstract from Poster Presentation from International Association for the Study of Lung Cancer, Aug. 9, 2015, retrieved from library.iaslc.org/search-speaker?search_speaker=30076.

Zhang, Xuewu, et al.; "Structural and Functional Ana ysis of the Costimulatory Receptor Programmed Death-1"; Immunity; 20:337-347 (2004).

Zhou et al., "Coexpression of Tim-3 and PD-1 identifies a CD8+ T-cell exhaustion phenotype in mice with disseminated acute myelogenous leukemia" Blood (2011) vol. 117 No. 17 pp. 4501-4510.

Zhuang J et al: "Selective IAP inhibition results in sensitization of unstimulated but not CD40-stimulated chronic lymphocytic leukaemia cells to TRAIL-induced apoptosis" Pharmacology Research & Perspectives (2014) vol. 2 Issue 6, Article E00081, 14 pages.

Zou, W. and Chen, L., "Inhibitory B7-family Molecules in the Tumour Microenvironment," Nature Reviews Immunology 8(6):467-477, Nature Publishing Group, England (2008).

Zuberek, K., "The role of in vivo PD-1/PD-L1 interactions in syngeneic and allogeneic antitumor responses in murine tumor models," Blood 98(11):42B (2001).

Zuberek, Krystyna, et al.; "In vitro and in vivo expression regulation of PD-1 and PD-L1 in murine tumor models"; Blood; 98(11 Part 1):25a (2001).

[No Author Listed] "Crean un ADN sintético capaz de evolucionar," retrieved from www.nationalgeographic.es/ciencia/crean-un-adn-sintetico-capaz-de-evolucionar, Apr. 25, 2012, last accessed Oct. 18, 2019.

[No Author Listed] Press Release: "Bristol-Myers Squibb Announces Collaboration to Evaludate Opdivo (nivolumab) in Combination with Targeted Therapies from Novartis to Treat Non-Small Cell Lung Cancer (NSCLC)," dated Oct. 6, 2014.

Abbas et al. "Functional diversity of helper T lymphocytes" Nature (1996) vol. 383, pp. 787-793.

Anderson "TIM-3 as a therapeutic target in human inflammatory diseases" Expert Opinion on Therapeutic Targets (2007) vol. 11, issue 8, pp. 1005-1009.

Anderson et al. "Lag-3, Tim-3, and TIGIT: Co-inhibitory Receptors with Specialized Functions in Immune Regulation" Immunity (2016) vol. 44, pp. 989-1004.

Anderson et al. "Promotion of Tissue Inflammation by the Immune Receptor Tim-3 Expressed on Innate Immune Cells" Science (2007) vol. 318, pp. 1141-1143.

Anderson, "Tim-3: An Emerging Target in the Cancer Immunotherapy Landscape" Cancer Immunology Research (2014) vol. 2 No. 5 pp. 393-398.

Ascierto et al. "Future perspectives in melanoma research" meeting report from the "Melanoma Bridge", Napoli, Dec. 5-8, 2013 Journal of Translational Medicine (2014) vol. 12, No. 277, pp. 1-29.

Baixeras et al., "Characterization of the Lymphocyte Activation Gene 3-Encoded Protein. A New Ligand for Human Leukocyte Antigen Class II Antgens," J Exp Med (1992) vol. 176, pp. 327-337.

Beckman et al. "Antibody Constructs in Cancer Therapy" Cancer (2007) vol. 109, No. 2, pp. 170-179.

(56) References Cited

OTHER PUBLICATIONS

Berrien-Elliott et al., "Durable Adoptive Immunotherapy for Leukemia Produced by Manipulation of Multiple Regulatory Pathways of CD8+ T-Cell Tolerance," Cancer Research (2012) vol. 73, pp. 605-616.

Bigras, et al. "Spatial distribution of DNA ploidy in colorectal carcinoma" Analytic Cellular Pathology (1994) vol. 7, pp. 289-300.

Borate et al., "Phase Ib Study of the Anti-TIM-3 Antibody MBG453 in Combination with Decitabine in Patients with High-Risk Myelodysplastic Syndrome (MDS) and Acute Myeloid Leukemia (AML)," Blood (2019) vol. 134, Supp. 1, Abstract 637, 5 pages.

Brahmer et al., "Safety and Activity of Anti-PD-L1 Antibody in Patients with Advanced Cancer," N Engl J Med (2012) vol. 366, pp. 2455-2465.

Brand et al., "Prospect for Anti-HER2 Receptor Therapy in Breast Cancer," Anticancer Research (2006) vol. 26, pp. 463-470.

Brunet et al., "A new member of the immunoglobin superfamily CTLA-4," Nature (1987) vol. 328, pp. 267-270.

Butte et al., "Interaction of human PD-L1 and B7-1", Mol Immunol (2008) vol. 45, pp. 3567-3572.

Butte et al., "Programmed Death-1 Ligand 1 Interacts Specifically with the B7-1 Costimulatory Molecule to Inhibit T Cell Responses," Immunity (2007) vol. 27, pp. 111-122.

Cao et al. "Genetic variations and haplotypes in TIM-3 gene and the risk pf gastric cancer" Cancer Immunol Immunother (2010) vol. 59 pp. 1851-1857.

Carvalho et al., "Doxorubicin: the good, the bad and the ugly effect," Current Medicinal Chemistry (2009) vol. 16, No. 25, pp. 3267-3285.

Casati et al., "Soluble Human LAG-3 Molecule Amplifies the In vitro Generation of Type 1 Tumor-Specific Immunity," Cancer Res (2006) vol. 66, No. 8, pp. 4450-4460.

Catherine Sabatos-Peyton, MBG453: A high affinity, ligand-blocking anti-TIM-3 monoclonal Ab. American Association for Cancer Research (AACR) Annual Meeting, Apr. 17, 2016, New Orleans, Louisiana.

Ceeraz et al., "B7 family checkpoint regulators in immune regulation and disease," Trends Immunol (2013) vol. 34, No. 11, pp. 556-563.

Cespedes "Mouse models in ocogenesis and cancer therapy" Clin. Tranl. Oncol. (2006) vol. 8, No. 5, pp. 318-329.

Chesi et al., "IAP antagonists induce anti-tumor immunity in multiple myeloma," Nat Med (2016) vol. 22, No. 12, pp. 1411-1420.

Christensen et al., "c-Met as a target for human cancer and characterization of inhibitors for therapeutic intervention," Cancer Letters (2005) vol. 225, pp. 1-26.

ClincalTrials.gov Identifier: NCT02323126 "Study of Efficacy and Safety of Nivolumab in Combination With EGF816 and of Nivolumab in Combination With INC280 in Patients With Previously Treated Non-small Cell Lung Cancer (EGF816)," Clinicaltrials.gov, last updated Jun. 6, 2018.

ClinicalTrials.gov "History of Changes for Study NCT01454102," ClinicalTrials.Gov, latest version submitted on Nov. 3, 2017.

ClinicalTrials.gov Identifier: NCT02608268, Safety and Efficacy of MBG453 as Single Agent and in Combination With PDR001 in Patients With Advanced Malignancies, Information provided by Novartis (Novartis Pharmaceuticals), last updated Oct. 13, 2016.

ClinicalTrials.gov Identifier: NCT02817633, A Phase 1 Study of TSR-022, an Anti-TIM-3 Monoclonal Antibody, in Patients With Advanced Solid Tumors, Information provided by Tesaro, Inc., last updated Aug. 26, 2016.

Cohen et al., "Image Cytometry of Estrogen Receptors in Breaast Carcinomas" Cytometry (1988) vol. 9 pp. 579-587.

Curigliano et al., "Abstract CT183: Phase (Ph) I/II study of MBG453 +/− spartalizumab (PDR001) in patients (pts) ith advanced malignancies," AACR Annual Meeting 2019, Cancer Research, vol. 79, Issue 13, Supplement, 2 pages.

Dekruyff et al., "T Cell/Transmembrane, Ig, and Mucin-3 Allelic Variants Differentially Recognize Phosphatidylserine and MEdiate Phagocytosis of Apoptotic Cells" The Journal of Immunology (2010) vol. 184 pp. 1918-1930.

Demaria et al., "Immune-mediated inhibition of Metastases after Treatment with Local Radiation and CTLA-4 Bloackade in a Mouse Model of Breast Cancer," Clinical Cancer Research (2005) vol. 11, pp. 728-734.

Dennis "Off by a whisker" Nature (2006) vol. 442, pp. 739-741.

Dong et al., "Tumor-associated B7-H1 promotes T-cell apoptosis: A potential mechanism of immune evasion", Nat Med (2002) vol. 8 pp. 793-800.

Dorfman et al., "The phosphatidylserine receptors, T cell immunoglobulin mucin proteins 3 and 4, are markers of histiocytic sarcoma and other histiocytic and decdritic cell neoplasms" Hum Pathol (2010) vol. 41 No. 10 pp. 1486-1494.

Dougan et al., "Regulation of innate and adaptive antitumor immunity by IAP antagonists," Immunotherapy (2018) vol. 10, No. 9, pp. 787-796.

Drake et al., "Blocking the regulatory T cell molecule LAG-3 augments in vivo anti-tumor immunity in an autochthonous model of prostate cancer," J Clin Oncol (2006) vol. 24, No. 18S, Abstract 2573.

Du Manoir et al., "Ki-67 Labeling in Postmitotic Cells Defines Different Ki-67 Pathways Within the 2c Compartment" Cytometry (1991) vol. 12 pp. 455-463.

El Mir et al., "A Soluble Lymphocyte Activation Gene-3 Molecule Used as a Vaccine Adjuvant Elicits Greater Humoral and Cellular Immune Responses to Both Particulate and Soluble Antigens," J Immunol (2000) vol. 164, pp. 5583-5589.

Entzminger et al., "De novo design of antibody complementarity determining regions binding a FLAG tetrapeptide," Sci Rep (2017), retrived from www.nature.com/ articles/s41598-017-10737-9.pdf?origin=ppub, last accessed Jan. 12, 2018.

Extended European Search Report for European Application No. EP 1484888, mailed May 31, 2017.

Extended European Search Report issued in European Application No. 19199437.5, mailed Mar. 12, 2020, 8 pages.

Extended European Search Report issued in European Patent Application No. 18211373.8, mailed Jun. 25, 2019.

Fessas et al., "A molecular and preclinical comparison of the PD-1-targeted T-cell checkpoint inhibitors nivolumab and pembrolizumab," Seminars in Oncology (2017) vol. 44, pp. 136-140.

Fourcade et al., "Upregulation of Tim-3 and PD-1 expression is associated with tumor antigen-specific CD8+ T cell dysfunction in melanoma patients" The Journal of Experimental Medicine (2010) vol. 207 No. 10 pp. 2175-2186.

Freeman et al., "Cloning of B7-2: a CTLA-4 counter-receptor that costimulates human T cell proliferation," Science (1999) vol. 262, pp. 909-911.

Freeman et al., "TIM genes: a family of cell surface phosphatidylserine receptors that regulate innate and adaptive immunity" Immunol Rev (2010) vol. 235 No. 1 pp. 172-189.

Fujimori et al. "A Modeling Analysis of Monoclonal Antibody Percolation Through Tumors: A Binding-Site Barrier" J Mucl Med (1990) vol. 31, pp. 1191-1198.

Search Report and Written Opinion issued in Singapore Application No. 11201605627T dated Aug. 15, 2017.

Search Report and Written Opinion issued in Singapore Application No. 11201702401R, completed Mar. 29, 2018.

Shakhov et al., "Smuckler/TIM4 is a distinct member of TIM family expressed by stromal cells of secondary lymphoid tissues and associated with lymphotoxin signaling" Eur. J. Immunol (2004) vol. 34 pp. 494-503.

Sher et al. "Regulation of Immunity to Parasited by T cells and T Cell-derived Cytokines" Annual Review Immunol (1992) vol. 10, pp. 385-409.

Simeone et al., "Immunomodulating antibodies in the treatment of metastatic melanoma: The experience with anti-CTLA-4, anti-CD137, and anti-PD1," Journal of Immunotoxicology (2012) vol. 9, No. 3, pp. 241-247.

(56)            References Cited

OTHER PUBLICATIONS

Simmons et al., "Tim-3+ T-bet+ Tumor-Specific Th1 Cells Colocalize with and Inhibit Development and Growth of Murine Neoplasms" The Journal of Immunology (2005) vol. 174 pp. 1405-1415.
Soares et al. "Recombinant Himan Tumor Antigen MUC1 Expressed in Insect Cells: Structure and Immunogenicity" Protein Expression and Purification (2001) vol. 22, pp. 92-100.
Steele et al., "CXCR2 Inhibition Profoundly Suppresses Metastases and Augments Immunotherapy in Pancreatic Ductal Adenocarcinoma," Cancel Cell (2016) vol. 29, pp. 832-845.
Stewart et al., "MEDI4736: Delivering effective blockade of immunosuppression to enhance tumour rejection: Monoclonal antibody discovery and practical development," Cancer Res (2011) vol. 71, No. 8 (Supp), Abstract LB-158.
Strome et al., "A Mechanistic Perspective of Monoclonal Antibodies in Cancer Therapy Beyond Target-Related Effects," The Oncologist (2007) vol. 12, pp. 1084-1095.
Stromnes et al., "Pancreatic Cancer: Planning Ahead for Metastatic Spread," Cancel Cell (2016) vol. 29, No. 6, pp. 774-776.
Swallow et al., "B7h, a Novel Costimulatory Homolog of B7.1 and B7.2, Is Induced by TNFa," Immunity (1999) vol. 11, pp. 423-432.
Sánchez-Fueyo et al., "Tim-3 inhibits T helper type 1-mediated auto- and alloimmune responses and promotes immunological tolerance," Nat Immunol (2003) vol. 4, No. 11, pp. 1093-1101.
Takamura et al., "Premature Terminal Exhaustion of Friend Virus-Specific Effector CD8+ T Cells by Rapid Induction of Multiple Inhibitory Receptors" J Immunol (2010) vol. 184 pp. 4696-4707.
Talmadge et al. "Murine Models to Evaluate Novel and Conventional Therapeutic Strategies for Cancer" The American Journal of Pathology (2007) vol. 170, No. 3, pp. 793-804.
Thangamathesvaran et al., "Immune checkpoint inhibitors and radiotherapy—concept and review of current literature," Ann Transl Med (2018) vol. 6, No. 8, Article 155, 11 pages.
Thomas et al "Combined Effects of RU486 and Tamoxifen on the Growth and Cell Cycle Phases of the MCF-7 Cell Line" Journal of Clinical Endocrinology and Metabolism (1992) vol. 75, Issue 3, pp. 865-870.
Thomas et al. "Effects of Gossypol on the Cell Cycle Phases in T-47D Human Breast Cancer Cells" Anticancer Research (1991) vol. 11, No. 4, pp. 1469-1476.
Thompson et al, "Tumor B7-H1 Is Associated with Poor Prognosis in Renal Cell Carcinoma Patients with Long-term Follow-up" Cancer Res. (2006) vol. 66, pp. 3381-3385.
Thurber et al. "Antibody tumor penetration: Transport opposed by systemic and antigen-mediated clearance" Advanced Drug Delivery Reviews (2008) vol. 60, pp. 1421-1434.
Topalian et al., "Safety, Activity, and Immune Correlates of Anti-PD-1 Antibody in Cancer," N Engl J Med (2012) vol. 366, No. 26, pp. 2443-2454.
Triebel et al., "LAG-3, A Novel Lymphocyte Activation Gene Closely Related to CD4," J Exp Med (1990) vol. 171, pp. 1393-1405.
Triebel, "LAG-3: a regulator of T-cell and DC responses and its use in therapeutc vaccination," Trends Immunol (2003) vol. 24, No. 12, pp. 619-622.
Tuskan et al., "Real-time PCR analysis of candidate imprinted genes on mouse chromosome 11 shows balanced expression from the maternal and paternal chromosomes and strain-specific variation in expression levels" Epigenetics (2008) vol. 3 No. 1 pp. 43-50.
U.S. Appl. No. 15/536,718, filed Jun. 16, 2017.
Van De Weyer et al. "A highly conserved tyosine of Tim-3 is phosphorylated upon stimulation by its ligand galectin-9" Biochemical and Biophysical Research Communications (2006) vol. 351, pp. 571-576.
Villalobos, "Primer organismo con ADN artificial logra reproducirse," retrieved from www.fayerwayer.com/2014/05/primer-organismo-con-adn-artificial-logra-reproducirse (2014) last accessed Oct. 18, 2019.

Vivier et al., "Immunoreceptor tyrosine-based inhibition motifs," Immunol Today (1997) vol. 18, No. 6, pp. 286-291.
Voskoglou-Nomikos et al. "Clinical Predictive Value of the in Vitro Cell Line, Human Xenograft, and Mouse Allograft Preclinical Cancer Models" Clinical Cancer Research (2003) vol. 9, pp. 4227-4239.
Walunas et al., "CTLA-4 can function as a negative regulator of T cell activation," Immunity (1994) vol. 1, No. 5, pp. 405-413.
Wang, "Interaction of TIM4-TIM1 Modulates the Function of CD4+CD25+Treg in Food Allergic Mice," Master's Thesis submitted at Zhengzhou University (2010) 65 pages, Chinese with English Abstract.
Watanabe et al., "Current approaches for the treatment of multiple myeloma," Int J Hematol (2013) vol. 97, pp. 333-344.
Weisberg et al., "Smac mimetics: implications for enhancement of targeted therapies in leukemia: Treating leukemia with Smac mimetics," Leukemia (2010) vol. 24, No. 12, pp. 2100-2109.
Wiener et al., "TIM-3 Is Expressed in Melanoma Cells and Is Upregulated in TGF-Beta Stimulated Mast Cells" Journal of Investigative Dermatology (2007) vol. 127 pp. 906-914.
Wolchok et al., "Nivolumab plus Ipilimumab in Advanced Melanoma," N Engl J Med (2013) vol. 369, pp. 122-133.
Woo et al. "Immune Inhibitory Molecules LAG-3 and PD-1 Synergistically Regulate T-cell Function to Promote Tumoral Immune Escape" Cancer Research (2011) vol. 72, No. 4, pp. 917-927.
Workman et al., "Negative Regulation of T Cell Homeostasis by Lymphocyte Activation Gene-3 (CD223)," J Immunol (2005) vol. 174, pp. 688-695.
Wu et al., "Endothelial cell-expressed Tim-3 facilitates metastasis of melanoma cells by activating the NF-kB pathway" Oncology Reports (2010) vol. 24 pp. 693-699.
Wu et al., "Immunotherapies: The Blockade of Inhibitory Signals," Int J Biol Sci (2012) vol. 8, No. 10, pp. 1420-1430.
Yan et al., "Tim-3 Expression Defines Regulatory T Cells in Human Tumors" PLoS ONE (2013) vol. 8 No. 3 e58006.
Yervoy (ipilimumab) Drug Label, Initial U.S. Approval: 2011, Revised Oct. 2015.
Zamarin et al. "Immune checkpoint modulation: Rational design of combindation strategies" Pharmacology & Therapeutics (2015) vol. 150, pp. 23-32.
Zhang et al., "Tim-3 regulates pro-and anti-inflammatory cytokine expression in human CD14+ monocytes" Journal of Leucyte Biology (2012) vol. 91 pp. 189-196.
Zhu et al., "CSF1/CSF1R Blockade Reprograms Tumor-Infiltrating Macrophages and Improves Response to T-cell Checkpoint Immunotherapy in Pancreatic Cancer Models," Cancer Research (2014) vol. 74, No. 18, pp. 5057-5069.
Hendrikx et al., "Fixed Dosing of Monoclonal Antibodies in Oncology," The Oncologist (2017) vol. 22, pp. 1212-1221.
Johne, B., "Protocol: Epitope Mapping by Surface Plasmon Resonance in the BIAcore," Molecular Biotechnology 9(1):65-71, Humana Press, United States (1998).
Ju et al., "T cell immunoglobulin-and mucin-domain-containing molecule-3 (Tim-3) mediates natural killer cell suppression in chronic hepatitis B" Journal of Hepatology (2010) vol. 52 No. 3 pp. 322-329.
Kanai, T., et al., "Blockade of B7-H1 Suppresses the Development of Chronic Intestinal Inflammation," The Journal of Immunology 171(8):4156-4163, American Association of Immunologists, Inc., United States (2003).
Karu et al., "Recombinant Antibody Technology," ILAR Journal, vol. 37, No. 3, pp. 132-141 (1995).
Kasagi, S., et al., "Anti-programmed cell death 1 antibody reduces CD4+PD-1+ T cells and relieves the lupus-like nephritis of NZB/W FI mice," The Journal Immunology 184(5):2337-2347, The American Association of Immunologists, United States (2010).
Kaveri, S., "Epitope and idiotope mapping using monoclonal antibodies," Medthods in Molecular Biology 51:171-181, Humana Press, United States (1995).
Kearley et al., "Th-2 driven, allergen-induced airway inflammation is reduced after treatment with anti-Tim-3 antibody in vivo" The Journal of Experimental Medicine (2007) vol. 204 No. 6 pp. 1289-1294.

(56) References Cited

OTHER PUBLICATIONS

Keytruda (pembrolizumab) Drug Label, Initial U.S. Approval: 2014, Revised Oct. 2016.

Kier et al., "PD-1 and its ligands in tolerance and immunity" Annu. Rev. Immunol. (2008) vol. 26 pp. 677-704.

Kikushige et al., "TIM-3 Is a Promising Target to Selectively Kill Acute Myeloid Leukemia Stem Cells" Cell Stem Cell (2010) vol. 7 pp. 708-717.

Kim et al: "Eradication of metastatic mouse cancers resistant to inmune checkpoint blockade by suppression of myeloid-derived cells. (Includes Supporting Information)", Proceedings of the National Academy of Sciences of the United States of America, vol. 111, No. 32, Aug. 12, 2014 (Aug. 12, 2014), pp. 11774-11777.

Kirkwood et al., "Immunotherapy of cancer in 2012" CA: A Cancer Journal for Clinicians (2012) vol. 62 No. 5 pp. 309-335.

Klein Jan M et al: "The histone deacetylase inhibitor LBH589 (panobinostat) modulates the crosstalk of lymphocytes with Hodgkin lymphoma cell lines.", PLOS ONE (2013) vol. 8, No. 11, E79582, 2813, pp. 1-6.

Knight et al. "Host immunity contributes to the antimelanoma activity of BRAE inhibitors" The Journal of Clinical Investigation (2013) vol. 123, No. 3, pp. 1371-1381.

Knights et al., "Inhibitor of apoptosis protein (IAP) antagonists demonstrate divergent immunomodulatory properties in human immune subsets with implications for combination therapy" Cancer Immunology and Immunotherapy (2013) vol. 62 No. 2 pp. 321-335.

Koga, N., et al., "Blockade of the interaction between PD-1 and PD-L1 accelerates graft arterial disease in cardiac allografts," Arteriosclerosis, Thrombosis, and Vascular Biology 24(11):2057-2062, American Heart Association, Inc., United States(2004).

Konishi, J., et al., "B7-H1 expression on non-small cell lung cancer cells and its relationship with tumor-infiltrating lymphocytes and their PD-1 expression," Clinical Cancer Research 10(15):5094-5100, American Association for Cancer Research, United States (2004).

Korman et al, "Checkpoint Blockade in Cancer Immunotherapy" Adv Immunol (2006) vol. 90 pp. 297-339.

Ladner, R.C., "Mapping the epitopes of Antibodies," Biotechnology and Genetic Engineering Reviews 24(1):1-30, Taylor & Francis, England (2007).

Laricchia,Robbio, L., et al., "Mapping of Monoclonal Antibody-and Receptor-Binding Domains on Human Granulocyte-Macrophage Colony-Stimulation Factor (rhGM-CSF) Using a Surface Plasmon Resonance-Based Biosensor," Hybridoma 15(5):343-350, Mary AnnLiebert, Inc. United States (1996).

Latchman, Y., et al., "PD-L2 is a second ligand for PD-1 and inhibits T cell activation," Nature Immunology 2 (3):261-268, Nature Publishing Group, United States (2001).

Leach, D.R., et al., "Enhancement of antitumor immunity by CTLA-4 blockade," Science 271(5256):1734-1736, American Association for the Advancement of Science, United States (1996).

Lesokhin, A.M., et al., "291 Preliminary Results of a Phase I Study of Nivolumab (BMS-936558) in Patients with Relapsed of Refractory Lymphoid Malignancies," 56th ASH Annual Meeting and Exposition, Abstracts & Program, San Francisco, CA, UnitedStates, Dec. 6-9, 2014.

Lewis, D.E., et al., "Tumor Necrosis Factor-.alpha. and CD80 Modulate CD28 Expression through a Similar Mechanism of T-cell Receptor-Independent of Transcription," The Journal of Biological Chemistry 279(28):29130-29138, The American Society forBiochemistry and Molecular Biology, Inc., United States (2004).

Li et al., "Contribution of PD-L1 to oncogenesis of lymphoma and its RNAi-based targeting therapy" Leukemia & Lymphoma (2012) vol. 53, No. 10, pp. 2015-2023.

Li, L., et al., "A pathway regulated by cell cycle inhibitor p27Kip1 and checkpoint inhibitor Smad3 is involved in the induction of T cell tolerance," Nature Immunology 7(11):1157-1165, Nature Publishing, United States (2006).

Li, L., et al., "CD4+CD25+ regulatory T-cell lines from human cord blood have functional and molecular properties and T-cell anergy," Blood 106(9):3068-3073, American Society of Hematology, United States (Nov. 2005).

Li, L., et al., "IL-1beta-Mediated Signals Preferentially Drive Conversion of Regulatory T Cells but Not Coventional T Cells into IL-17-Producing Cells," The Journal of Immunology 185(7):4148-4153, American Association of Immunologists, Inc., UnitedStates (2010).

Li, L., et al., "Rap1-GTP is a Negative Regulator of Th Cell Function and Promotes the Generation of CD4+CD103+ Regulatory T Cells In Vivo," The Journal of Immunology 175(5):3133-3139, American Association of Immunologists, Inc., United States (Sep. 2005).

Li, L., et al., "The cyclin dependent kinase inhibitor (R)-roscovitine prevents alloreactive T cell clonal expansion and protects against acute GvHD," Cell Cycle 8(11):1794-1802, Landes Bioscience, United States (2009).

Lin, David Yin-Wei, et al.; "The PD-1/PD-L1 complex resembles the antigen-binding Fv domains of antibodies and T cell receptors"; Proc. Natl. Acad. Sci. USA 105(8):3011-3016 (2008).

Linsley et al., "Intracellular Trafficking of CTLA-4 and Focal Localization Towards Sites of TCR Engagement" Immunity (1996) vol. 4 pp. 535-543.

List of clinical trials identified in ClinicalTrials.gov relating to PDR001 as of Dec. 22, 2016.

Lonberg, N., et al., "Antigen-specific human antibodies from mice comprising four distinct genetic modifications," Nature 368(6474):856-859, Nature Publishing Group, United States (1994).

Lute, K.D., et al., "Human CTLA4 knock-in mice unravel the quantitative link between tumor immunity and autoimmunity induced by anti-CTLA-4 antibodies," Blood 106(9):3127-3133, American Society of Hematology, United States (2005).

Mahoney et al. "The Next Immune-Checkpoint Inhibitors: PD-1/PDD-L1 Blockade in Melanoma" Clinical Therapeutics (2015) vol. 37, No. 4, pp. 764-782.

Marri et al., "Human Biochemistry" Mir Publishing, Moscow (1993) vol. 1, p. 34. Russian.

Masters et al., "Abstract 5016: Antitumor activity of anti-PD-1 in combination with tyrosine kinase inhibitors in a preclinical renal cell carcinoma model" AACR Annual Meeting (2014) vol. 74, No. 5016.

May, K.F., Jr., et al., "Anti-human CTLA-4 monoclonal antibody promotes T-cell expansion and immunity it a hu-PBL-SCID model: a new method for preclinical screening of costimulatory monoclonal antibodies," Blood 105(3):1114-1120, American Society ofHematology, United States (2005).

Menzies et al. "Systemic treatment for BRAF-mutant melanoma: where do we go next?" Lancet Oncology (2014) vol. 15, pp. e371-e381.

Menzies et al., "Recent advances in melanoma systemic therapy. BRAF inhibitors, CTLA antibodies and beyond" European Journal of Cancer (2013) vol. 49 No. 15 pp. 3229-3241.

Mittendorf Elizabeth A et al: "PD-L1 expression in triple-negative breast cancer." Cancer Immunology Research. vol. 2. No. 4. Apr. 2014 (Apr. 2014). pp. 361-370.

Moreira Da Silva, "Nivolumab Anti-PD-1 monoclonal antibody cancer immunotherapy" Drugs of the Future (2014) vol. 39 No. 1 pp. 15-24.

Naing et al. "A first-in-human phase I study of the anti-PD-1 antibody PDR001 in patients with advanced solid tumors" 2016 ASCO Annual Meeting, J Clin Oncol 34, 2016 (suppl; abstr 3060).

Nakae et al., "Mast cells enhance T cell activation: importance of mast cell costimulatory molecules and secreted TNF" The Journal of Immunology (2006) vol. 176 No. 4 pp. 2238-2248.

Nellore, A., et al., "The cyclin dependent kinase inhibitor (R)-roscovitine mediates selective suppression of alloreactive human T cells but preserves pathogen-specific and leukemia-specific effectors," Clinical Immunology 152(1-2):48-57 (May-Jun. 2014; Epub Mar. 12, 2014).

(56)　　　　References Cited

OTHER PUBLICATIONS

Nielsen, C., et al., "A putative regulatory polymorphism in PD-1 is associated with nephropathy in a population-based cohort of systemic lupus erythematosus patients," Lupus 13(7):510-516, SAGE, England (2004).

Nishimura, H., et al., "Autoimmune dilated cardiomyopathy Science in PD-1 receptor-deficient mice," Science 291(5502):319-322, American Association for the Advancement of Science, United States (2001).

Nishimura, H., et al., "Development of lupus-like autoimmune diseases by disruption of the PD-1gene encoding an TIM motif-carrying immunoreceptor," Immunity 11(2):141-151, Cell Press, United States (1999).

Nishimura, H., et al., "Immunological studies on PD-1 deficient mice: implication of PD-1 as a negative regulator for B cell responses," International Immunology 10(10):1563-1572, Oxford University Press, England (1998).

[No Author Listed] Incyte, "Press Release—Incyte Reports 2014 Fourth Quarter and Year End Financial Results; Provides 2015 Financial Guidance; Updates Shareholders on Key Clinical Programs", Feb. 12, 2015, retrieved from businesswire.com/news/home/20150212005176/en/Incyte-Reports-2014-Fourth-Quarter-Year-End-Financial-Results, 6 pages.

Plieth et al., "PD-1 / PD-L1 Combination Therapies" retrieved from info.evaluategroup.com/rs/607-YGS-364/images/epv-pdct15.pdf, Evaluate Ltd. (2015), 17 pages.

Elassaiss-Schaap et al., "Using Model-Based "Learn and Confirm" to Reveal the Pharmacokinetics—Pharmacodynamics Relationship of Pembrolizumab in the KEYNOTE-001 Trial," CPT Pharmacometrics Syst Pharmacol (2017) vol. 6, pp. 21-28.

Agarwal et al., "Nivolumab dose selection: challenges, opportunities, and lessons learned for cancer immunotherapy," Journal for Immunotherapy of Cancer (2016) vol. 4, Article 72, 11 pages.

Zhao et al., "Assessment of nivolumab benefit-risk profile of a 240-mg flat does relative to a 3-mg/kg dosing regimen in patients with advanced tumors," Annals of Oncology (2017) vol. 28, pp. 2002-2008.

[No Author Listed] Rituxan (rituximab) FDA Product Label and Dosing Information, Aug. 12, 2014, 44 pages.

[No Author Listed] Arzerra (ofatumumab) FDA Product Label and Dosing Information, Apr. 14, 2014, 20 pages.

[No Author Listed] Humira (adalimumab) FDA Product Label and Dosing Information, Nov. 23, 2015, 90 pages.

[No Author Listed] Remicade (infleximab) FDA Product Label and Dosing Information, Oct. 2, 2015, 57 pages.

[No Author Listed] Keytruda (pembrolizumab) FDA Product Label and Dosing Information, Oct. 2, 2015, 20 pages.

[No Author Listed] Opdivo (nivolumab) FDA Product Label and Dosing Information, Mar. 4, 2015, 27 pages.

Fulda, "Molecular Pathways: Targeting Inhibitor of Apoptosis Proteins in Cancer—From Molecular Mechanism to Therapeutic Application," Clin Cancer Res (2013) vol. 20, No. 2, pp. 289-295.

Gao et al., "TIM-3 Expression Characterizes Regulatory T Cells in Tumor Tissues and Is Associated with Lung Cancer Progression" PLoS ONE (2012) vol. 7 No. 2 e30676.

Geng et al., "Soluble Form of T Cell Ig Mucin 3 Is an Inhibitory Molecule in T Cell-Mediated Immune Response" The Journal of Immunology (2006) vol. 176 pp. 1411-1420.

Ghebeh et al., "Doxorubicin downregulates cell surface B7-H1 expression and upregulates its nuclear expression in breast cancer cells: role of B7-H1 as an anti-apoptotic molecule," Breast Cancer Research (2010) vol. 12, No. 4, Article R48, 12 pages.

Golden-Mason et al., "Negative Immune Regulator Tim-3 Is Overexpressed on T Cells in Hepatitis C Virus Infection and Its Blockade Rescues Dysfunctional CD4+ and CD8+ T Cells," J Virol (2009) vol. 83, No. 18, pp. 9122-9130.

Henry et al., "Structure and evolution of the extended B7 family," Immunol Today (1999) vol. 20, No. 6, pp. 285-288.

Herbst et al., "A study of MPDL3280A, an engineered PD-L1 antibody in patients with locally advanced or metastatic tumors," J Clin Oncol (2013) vol. 31, No. 15 (Supp), Abstract 3000.

Highfill et al., "Disruption of CXCR2-Mediated MDSC Tumor Trafficking Enhances Anti-PD1 Efficacy," Science Translational Medicine (2014) vol. 6, Issue 237, Article 237ra67, 15 pages.

Hofstra et al., "Prevention of Th2-like cell responses by coadministration of IL-12 and IL-18 is associated with Inhibition of antigen-induced airway hyperresponsiveness, eosinophilia, and serum IgE levels." Journal of Immunology (1998) vol. 161 No. 9 pp. 5054-5060.

Huang et al., "Lymphoma endothelium preferentially expresses Tim-3 and facilitates the progression of lymphoma by mediating immune evasion" The Journal of Experimental Medicine (2010) vol. 207 No. 3 pp. 505-520.

Huang et al., "Role of LAG-3 in Regulatory T Cells, " Immunity (2004) vol. 21, pp. 503-513.

Huard et al., "Lymphocyte-activation gene 3/major histocompatibility complex class II interaction modulates the antigenic response of CD4+ T lymphocytes," Eur J Immunol (1994) vol. 24, pp. 3216-3221.

Huard et al., "T cell major histocompatibilty complex class II molecules down-regulate CD4+ T cell clone responses following LAG-3 binding," Eur J Immunol (1996) vol. 26, pp. 1180-1186.

International Search Report and Written Opinion for International Application No. PCT/US2015/049826 dated Dec. 16, 2015.

International Search Report and Written Opinion for International Application No. PCT/US2015/055390, dated Dec. 17, 2015.

International Search Report and Written Opinion for International Application No. PCT/US2016/044545 dated Oct. 28, 2016.

International Search Report and Written Opinion for International Application No. PCT/US2016/044549 dated Oct. 14, 2016.

International Search Report and Written Opinion issued in International Application No. PCT/US2018/039825, mailed Oct. 4, 2018.

International Search Report and Written Opinion issued in PCT/US2007/085100, mailed Apr. 28, 2008, 11 pages.

International Search Report and Written Opinion issued in PCT/US2018/061534, mailed Apr. 1, 2019, 9 pages.

Iouzalen et al., "LAP, a lymphocyte activation gene-3 (LAG-3)-associated protein that binds to a repeated EP motif In the intracellular region of LAG-3, may participate in the down-regulation of the CD3/TCR activation pathway," Eur J Immunol (2001) vol. 31, pp. 2885-2891.

Jan et al., "Prospective separation of normal and leukemic stem cells based on differential expression of TIM3, a human acute myeloid leukemia stem cell marker" PNAS (2011) vol. 108 No. 12 pp. 5009-5014.

Jin et al. "Cooperation of Tim-3 and PD-1 in CD8 T-cell exhaustion during chronic viral infection" PNAS (2010) vol. 107, Issue 33, pp. 14733-14738.

Jing et al., "Combined immune checkpoint protein blockade and low dose whole body irradiation as immunotherapy for melanoma," Journal for ImmunoTherapy of Cancer (2015) vol. 3, No. 2, 15 pages.

Jones et al., "Tim-3 expression defines a novel population of dysfunctional T cells with highly elevated frequencies in progressive HIV-1 infection," J Exp Med (2008) vol. 205, No. 12, pp. 2763-2779.

Kearl et al., "PD-1/PD-L1 Blockade after Transient Lymphodepletion to Treat Myeloma," Presentation from Society for Immunotherapy of Cancer Conference, Oct. 27, 2012, North Bethesda, Maryland, 19 pages.

Kearl et al., "Programmed Death Receptor-1/Programmed Death Receptor Ligand-1 Blockage after transient Lymphodepletion To Treat Myeloma," J Immunol (2013) vol. 190, pp. 5620-5628.

Keytruda (pembrolizumab) Drug Label, Initial U.S. Approval: 2014, Revised Aug. 2016.

Khaitov, Immunologia, Moscow, (2011) "GEOTAR-Media", p. 103.

Khalil et al. "The New Era of Cancer Immunotherapy: Manipulating T-Cell Activity to Overcome Malignancy" Immunotherapy of Cancer In: Advances in Cancer Research (2015) vol. 128, pp. 1-68.

(56)                References Cited

OTHER PUBLICATIONS

Kikushige et al. "TIM-3 as a therapeutic target for malignant stem cells in acute myelogenous leukemia" New York Academy of Sciences (2012) vol. 1266, pp. 118-123.

Klibi et al. "Blood diffusion and Th1-suppressive effects of galectin-9-containing exosomes released by Epstein-Barr virus-infected nasopharyngeal carcinoma cells" Blood (2009) vol. 113 No. 9 pp. 1957-1966.

Koya et al., "BRAF Inhibitor Vemurafenib Improves the Antitumor Activity of Adoptive Cell Immunotherapy," Cancer Res (2012) vol. 72, No. 16, pp. 3928-3937.

Kuchroo et al. "The TIM Gene Family: Emerging Roles in Immunity and Disease" Nature Reviews Immunology (2003) vol. 3, pp. 454-462.

Kuchroo et al., "B7-1 and B7-2 Costimulatory Molecules Activate Differentially the Th1/Th2 Developmental Pathways: Application to Autoimmune Disease Therapy" Cell (1995) vol. 80 No. 707-18.

Kwong et al., "Molecular Analysis of Tumor-Promoting CD8+ Cells in Two-Stage Cutaneous Chemical Carcinogenesis" J Invest Dermatol (2010) vol. 130 No. 6 pp. 1726-1736.

Lack et al. "Nebulized but not parenteral IFN-gamma decreases IgE production and normalizes airways function in a murine model of allergen sensitization" Journal of Immunology (1994) vol. 152, pp. 2546-2554.

Lee et al. "The inhibition of the T-cell immunoglobulin and mucin domain 3 (Tim3) pathway enhances the efficacy of tumor vaccine" Biochemical and Biophysical Reseach Communications (2010) vol. 402, pp. 88-93.

Lehmann et al., "Identification of human triple-negative breast cancer subtypes and preclinical models for selection of targeted therapies", J Clin Invest., 121(7): 2750-2767.

Lenschow et al., "Expression and functional significance of an additional ligand for CTLA-2," PNAS (1993) vol. 90, pp. 11054-11058.

Lenschow et al., "Long-term survival of xenogeneic pancreatic islet grafts induced by CTLA4Ig," Science (1992) vol. 257, Issue 5071, pp. 789-792.

Liblau et al. "Th1 and Th2 CD4+ T cells in the pathogenesis of organ-specific autoimune diseases" Immunology Today (1995) vol. 16, Issue 1, pp. 34-38.

Linsley et al., "CTLA-4 Is a Second Receptor for the B Cell Activation Antigen B7," J Exp Med (1991) vol. 174, pp. 561-569.

Linsley et al., "Immunosuppression in Vivo by a Soluble Form of the CTLA-4 T Cell Activation Molecule," Science (1992) vol. 257, pp. 792-795.

Liu et al., "A Novel Kinase Inhibitor, INC28060, Blocks c-MET-Dependent Signaling, Neoplastic Activities, and Cross-Talk with EGFR and HER-3," Clin Cancer Res (2011) vol. 17, No. 22, pp. 7127-7138.

Liu et al., "The BRAF and MEK Inhibitors Dabrafenib and Trametinib: Effects on Immune Function and in Combination with Immunomodulatory Antibodies Targeting PD-1, PD-L1, and CTLA-4," Clin Cancer Res (2015) vol. 21, No. 7, pp. 1639-1651.

Loser et al., "IL-10 Controls Ultraviolet-Induced Carcinogenesis in Mice" The Journal of Immunology (2007) vol. 179 pp. 365-371.

Lu et al., "Everolimus enhances the cytotoxicity of bendamustine in multiple myeloma cells through a network of pro-apoptotic and cell-cycle-progression regulatory proteins," Acta Biochim Biophys Sin (2013) vol. 45, pp. 683-691.

Mach et al., "Phase (PH) II Study of MBG453 + Spartalizumab in Patients (PTS) with Non-Small Cell Lung Cancer (NSCLC) and Melanoma Pretreated with Anti-PD-1/L1 Therapy," Poster Display Session 3 from ESMO Congress, Sep. 30, 2019, 3 pages.

Maier et al., "PD-1: PD-L1 Interactions Contribute to the Functional Suppression of Virus-Specific CD8+ T Lymphocytes in the Liver," J Immunol (2007) vol. 178, pp. 2714-2720.

Creelan, B.C., "Update on Immune Checkpoint Inhibitors in Lung Cancer," Journal of the Moffitt Cancer Center 21(1):80-89, H. Lee Moffitt Cancer Center and Research Institute, United States (2014).

Cruse, J.M. and Lewis, R.E., "Antigens and Immunogens," in Atlas of Immunology, 2nd ed., pp. 105-126, CRC Press, United States (Dec. 29, 2003).

Davies, D.R. and Cohen, G.H., "Interactions of protein antigens with antibodies," Proceedings of the National Academy of Sciences USA 93(1):7-12, National Academy of Sciences, United States (1996).

Davies, Julian, et al.; "Affinity improvement of single antibody VH domains: residues in all three hypervariable regions affect antigen binding"; ; 2:169-179 (1996).

Del-Rio, Maria-Luisa, et al.; "Antibody-mediated signaling through PD-1 costimulates T cells and enhances CD28-dependent proliferation"; Eur. J. Immunol.; 35(12):3545-3560 (2005).

Dey et al: "Nutl in-3 inhibits the NF[kappa]B Pathway in a p53 Dependent Manner: Implications in Lung Cancer Therapy". Cell Cycle, vol. 6, No. 17, Sep. 1, 2007 (Sep. 1, 2007), pp. 2178-2185.

Dong, H. and Chen, L., "B7-H1 pathway and its role in the evasion of tumor immunity," Journal of Molecular Medicine 81(5):281-287, Springer, Germany (2003).

Dong, H., et al., "Tumor-associated B7-H1 promotes T-cell apoptosis: a potential mechanism of immune evasion," Nature Medicine 8(8):793-800, Nature Publishing Company, United States (2002).

Dougan, D.A., et al., "Effects of subsitutions in the binding surface of an antibody on antigen affinity," Protein Engineering 11(1):65-74, Oxford University Press, England (1998).

Finger, L.R., et al., "The human PD-1 gene: complete cDNA, genomic organization, and developmentally regulated expression in B cell progenitors," Gene 197(1-2):177-187, Elsevier, United States (1997).

Fivash, M., et al., "BIAcore for macromolecular interaction," Current Opinion in Biotechnology 9(1):97-101, Current Biology, England (1998).

Fleischer, Bernhard, et al.; "T cell stimulation by staphylococcal enterotoxins"; J. Exp. Medicine; 167(5):1697-1707 (1988).

Franklin, M.C., et al., "Insights into ErbB signaling from the structure of the ErbB2-pertuzumab complex," Cancer Cell 5(4):317-328, Cell Press, United States (Apr. 2004).

Freeman, G.J., et al., "Engagement of PD-1 immunoinhibitory receptor by a novel B7 family member leads to negative regulation of lymphocyte activation," The Journal of Experimental Medicine 192(7):1027-1034, The Rockefeller University Press, UnitedStates (2000).

Fukushima et al., "Antibodies to T-cell Ig and mucin domain-containing proteins (Tim)-1 and -3 suppress the induction and progression of murine allergic conjunctivitis" Biochemical and Biophysical Research Communications (2006) vol. 353 No. 1 p. 211-16.

Garcia et al: "The Pan-PIM Kinase Inhibitor LGH447 Shows Activity In PIM2-Dependent Multiple Myeloma and In AML Models", Blood (2013) Retrieved from the Internet: URL:http://www.bloodjournal.orgjcontent/12 2/21/1666 [retrieved on Apr. 14, 2016].

Garrison K et al: "The small molecule TGF-[beta] signaling inhibitor SM16 synergizes with agonistic OX40 antibody to suppress established mammary tumors and reduce spontaneous metastasis" Cancer Immunology, Immunotherapy (2012) vol. 61 No. 4 pp. 511-521.

Ge, X., et al., "CD134—Allodepletion Allows Selective Elimination of Alloreactive Human T Cells without Loss of Virus-Specific and Leukemia-Specific Effectors," Biology of Blood and Marrow Transplantation 14(5):518-530, American Society for Bloodand Marrow Transplantation, United States (2008).

Gettinger et al. "Safety and Response 1-98 With Nivolumab (Anti-PD-1; BMS-936558, ONO-4538) Plus Erlotinib in Patients (Pts) With Epidermal Growth Factor Receptor Mutant (EGFR MT) Advanced Non-Small Cell Lung Cancer (NSCLC} Metastatic Non-Small Cell Lung Cancer" International Journal of Radiation: Oncology Biology Physics (2014) vol. 90, No. 5, pp. S34-S35.

Greenspan, N.S., "Epitopes, paratopes and other topes: do immunologists know what they are talking about?" Bulletin de l'Institut Pasteur 90(4):267-279, Elsevier, France (1992).

Grygielewicz Paulina et al: "Epithelial-mesenchymal transition confers resistance to selective FGFR inhibitors in SNU-16 gastric

(56)            References Cited

OTHER PUBLICATIONS cancer cells". Gastric Cancer. Springer Japan. Tokyo. vol . 19. No. 1., Nov. 19, 2014 (Nov. 19, 2014). pp. 53-62.

Haitov, "Immunology: Structure and Functions of the Immune System," Geotar-Media Publishing Group, Moscow (2013) p. 110. Russian.

Hallett et al., "Immunosuppressive Effects of Multiple Myeloma Are Oversome by PD-L1 Blockade" Biol Blood Marrow Transplant (2011) vol. 17, No. 8, pp. 1133-1145.

Hamid et al., "Safety and Tumor Responses with Lambrolizumab (Anti-PD-1) in Melanoma" New England Journal of Medicine (2013) vol. 369 No. 2 pp. 134-144.

Hansen, J.A., et al., "Monoclonal Antibodies Identifying a Novel T-Cell Antigen and la Antigens of Human Lymphocytes," Immunogenetics 10:247-260, Springer-Verlag (1980).

Harlow, E. and Lane, D., "Using Antibodies: A Laboratory Manual," Cold Spring Harbor Laboratory Press, Cold Spring Harbor, United States various pages (1999).

Hastings et al., "TIM-3 is Expressed on Activated Human CD4+ T Cells and Regulates Th1 and Th17 Cytokines" Eur J Immunol (2009) vol. 39 No. 9 pp. 2492-2501.

He, Y-F., et al., "Blocking programmed death-1 ligand-PD-1 interactions by local gene therapy results in enhancement of antitumor effect of secondary lymphoid tissue chemokine," The Journal of Immunology 173(8):4919-4928, The American Association ofImmunologists, United States (2004).

Hirano, F., et al., "Blockade of B7-H1 and PD-1 by monoclonal antibodies potentiates cancer therapeutic immunity," Cancer Research 65(3):1089-1096, American Association for Cancer Research, United States (2005).

Hogenesch et al. "Challenges in pre-clinical testing of anti-cancer drugs in cell culture and in animal models" Journal of Controlled Release (2012) vol. 164, No. 2, pp. 183-186.

Hu Yi et al: "Essential role of AKT in tumor cells addicted to FGFR.", Anti-Cancer Drugs, vol. 25, No. 2, Feb. 2014 (Feb. 2014), pp. 183-188.

Huang, Z., "Structural chemistry and therapeutic intervention of protein-protein interactions in immune response, human immunodeficiency virus entry, and apoptosis," Pharmacology & Therapeutics 86(3):201-215, Pergamon Press, England (2000).

Hutloff, A., et al., "ICOS is an inducible T-cell co-stimulator structurally and functionally related to CD28," Nature 397(6716):263-266, Nature Publishing Group, England (1999).

International Search Report and Written Opinion for International Application No. PCT/US2016/044547 dated Oct. 18, 2016.

International Search Report and Written Opinion for PCT/US2014/057491 dated Jan. 7, 2015.

International Search Report and Written Opinion for PCT/US2015/012754 dated May 20, 2015.

International Search Report and Written Opinion for PCT/US2015/013913 mailed May 4, 2015.

International Search Report and Written Opinion for PCT/US2015/049826 dated Dec. 16, 2015.

International Search Report and Written Opinion for PCT/US2015/053799 dated May 17, 2016.

International Search Report and Written Opinion issued in International Application No. PCT/US2016/067200, mailed Apr. 10, 2017.

Ishida et al., "Induced expression of PD-1, a novel member of the immunoglobulin gene superfamily, upon programmed cell death," The EMBO Journal (1992) vol. 11, No. 11, pp. 3887-3895.

Ishima, R. and Torchia, D.A., "Protein Dynamics from NMR," Nature Structural Biology 7(9):740-743, Nature Publishing Company, United States (2000).

Iwai et al, "Involvement of PD-L1 on tumor cells in the escape from host immune system and tumor immunotherapy by PD-L1 blockade" PNAS (2002) vol. 99, pp. 12293-12297.

Iwai et al, "PD-1 blockade inhibits hematogenous spread of poorly immunogenic tumor cells by enhanced recruitment of effector T cells", International Immunology (2005) vol. 17, No. 2, pp. 133-144.

Iwai, Y, et al., "Microanatomical localization of PD-1 in human tonsils," Immunology Letters 83(3):215-220, Elsevier, Netherlands (2002).

Iwai, Y., et al., "PD-1 inhibits antiviral immunity at the effector phase in the liver," The Journal of Experimental Medicine 198(1):39-50, The Rockefeller University Press, United States (2003).

Jason-Moller, L., et al., "Overview of Biacore Systems and Their Applications," Current Protocols in Protein Science S45:19.13.1-19.13.14, John Wiley & Sons, Inc., United States (2006).

Jiang et al, "mTOR Kinase Inhibitor AZD8855 Enhances the Inmunotherapeutic Activity of an Agonist CD40 Antibody in Cancer Treatment" Cancer Research (2011) vol. 71 No. 12, pp. 4074-4084.

Jiang X et al: "The activation of MAPK in melanoma cells resistant to BRAF inhibition promotes PD-L1 expression that is reversible by MEK and PI3K inhibition", Clinical Cancer Research, the American Association for Cancer Research, US, vol. 19, No. 3, Feb. 1, 2013 (Feb. 1, 2013). pp. 598-609.

Avice et al., "Lymphocyte Activation Gene-3, a MHC Class II Ligand Expressed on Activated T Cells, Stimulates TNF-a and IL-12 Production by Monocytes and Dendritic Cells" The Journal of Immunology (1999) vol. 162 pp. 2748-2753.

Chelius, Dirk et al., "Identification and Characterization of Deamidation Sites in the Conserved Regions of Human Immunoglobulin Gamma Antibiodies," Anal. Chemn., American Chemical Society, vol. 77(18): 6004-6011 (2005).

Daugherty et al., "Formulation and delivery issues for monoclonal antibody therapeutics," Advanced Drug Delivery Reviews (2006) vol. 58, pp. 686-706.

Fishwild, D.M. et al., "High-avidity human IgG kappa monoclonal antibodies from a novel strain of minilocus transgenic mice.," Nature Biotechnol., vol. 14, pp. 845-851 (1996).

Gagliani et al., "Coexpression of CD49b and LAG-3 identifies human and mouse T regulatory type 1 cells" Nature Medicine (2013) vol. 19 No. 6 pp. 739-746.

Goding S., et al., "Combination of adoptive cell transfer, anti-PD-L 1 and anti-LAG-3 antibodies for the treatment of recurrent tumors Better with More," Oncolmmunology, vol. 2 (8), 4 pages (2013).

Kroon D. et al., "Identification of Sites of Degradation in a Therapeutic Monoclonal Antibody by Peptide Mapping," Pharmaceutical Research, vol. 9(11 ): 1386-1393 (1992).

Lipson et al. "Initial Experience Administering BMS-986016, a Monoclonal Antibody That Targets Lymphocyte Activation Gene (LAG)-3, Alone and in Combination With Nivolumab to Patients With Hematologic and Solid Malignancies" Presented at the Society for Immunotherapy of Cancer Annual Meeting; Nov. 9-13, 2016, National Harbor, MD.

Tsai P.K. et al., "Origin of the Isoelectric Heterogeneity of Monoclonal Immunoglobulin h1B4," Pharmaceutical Research, vol. 10(11): 1580-1586 (1993).

Uchiyama, "Liquid formulation for antibody drugs," Biochimica et Biophysica Acta (2014) vol. 1844, pp. 2041-2052.

Abbas, A.K., et al., Cellular and Molecular Immunobiology, 2nd ed., pp. 8, 47-50, W.B. Saunders Company, United States (1991).

Acquaviva et al: "FGFR3 Translocations in Bladder Cancer: Differential Sensitivity to HSP90 Inhibition Based on Drug Metabolism". Molecular Cancer Research. vol. 12. No. 7. Jul. 1, 2014 (Jul. 1, 2014). pp. 1042-1054.

Adams, G.P. and Weiner, L.M., "Monoclonal antibody therapy of cancer," Nature Biotechnology 23(9):1147-1157, Nature Publishing Group, United States (2005).

Agata, Y., et al., "Expression of the PD-1 antigen on the surface of stimulated mouse T and B lymphocytes," International Immunology 8(5):765-772, Oxford University Press, England (1996).

Allard et al. "Targeting CD73 Enhances the Antitumor Activity of Anti-FD-1 and Anti-CTLA-4 mAbs" Clinical Cancer Research (2013) vol. 19, No. 20, pp. 5626-5635.

Allison, J.P. and Krummel, M.F., "The Yin and Yang of T Cell Costimulation," Science 270(5238):932-933, American Association for the Advancement of Science, United States (1995).

Almagro et al. "Humanization of Antibodies" Frontiers in Bioscience (2008) vol. 13, pp. 1619-1633.

Amin et al: "Nivolumab (anti-PD-1; BMS-936558, ONO-4538) in combination with sunitinib or pazopanib in patients (pts) with

(56)        References Cited

OTHER PUBLICATIONS metastatic renal cell carcinoma (mRCC)" Journal of Clinical Oncology (2014) vol. 32, No. 15 suppl, Abstract 5010.

Anderson et al. "Tim-3, a negative regulator of anti-tumor immunity" Current Opinion in Immunology (2012) vol. 24, No. 2, pp. 213-216.

Andre, E., et al., "Precise Characterization of the Epitope Recognized by a Monoclonal Antibody Against *Escherichia coli* RNA Polymerase," Hybridoma 24(1):1-5, Mary Ann Liebert, Inc., United States (Feb. 2005).

Ansari, M.J., et al., "The programmed death-1 (PD-1) pathway regulates autoimmune diabetes in nonobese diabetic (NOD) mice," The Journal of Experimental Medicine 198(1):63-69, The Rockefeller University Press, United States (2003).

Ansell, S.M., et al., "PD-1 Blockade with Nivolumab in Relapsed or Refractory Hodgkin's Lymphoma," The New England Journal of Medicine 372(4):311-319, Massachusetts Medical Society, United States (Jan. 22, 2015).

Armand, P., et al., "289 Nivolumab in Patients with relapsed or Refractory Hodgkin Lymphoma—Preliminary Safety, Efficacy and Biomarker Results of a Phase I Study," 56th ASH Annual Meeting and Exposition, Abstracts & Program, San Francisco, CA, Dec. 6-9, 2014.

Ashworth et al. "Management of a Patient With Advanced BRAF-Mutant Melanoma" Journal of the National Comprehensive Cancer Network (2014) vol. 12, No. 3, pp. 315-319.

Aspeslagh et al. "Rationale for anti-OX40 cancer immunotherapy" European Journal of Cancer (2016) vol. 52, pp. 50-66.

Barber, Daniel L., et al.; "Restoring function in exhausted CD8 T cells during chronic viral infection"; Nature 139:682-687 (2006).

Batus et al. "Optimal Management of Metastatic Melanoma: Current Strategies and Future Directions" Am. J. Clin. Dermatol. (2013) vol. 14, No. 3, pp. 179-194.

Bellucci et al: "JAK1 and JAK2 Modulate Tumor Cell Susceptibility To Natural Killer (NK) Cells Through Regulation Of PDLI Expression", Blood (Nov. 15, 2013), Retrieved from the Internet: URL:http://www.bloodjournal.orgjcontent/122/21/3472.full.pdf [retrieved on Apr. 14, 2016].

Bennett, F., et al., "Program death-1 engagement upon TCR activation has distinct effects on costimulation and cytokine-driven proliferation: attenuation of ICOS, IL-4, and IL-21, but not CD28, IL-7, and IL-15 responses," The Journal of Immunology 170(2):711-718, The American Association of Immunologists, United States (2003).

Benson et al. "The PD-1/PD-L1 axis modulates the natural killer cell versus multiple myeloma effect: a therapeutic target for CT-011, a novel monoclonal anti-PD-1 antibody" Blood (2010) vol. 116, No. 13, pp. 2286-2294.

Berg, J.M., et al., "The Immune System," in Biochemistry 5th ed., pp. 921-950, W.H. Freeman and Company, United States (2002).

Berger, R., et al., "Phase I safety and pharmacokinetic study of CT-011, a humanized antibody interacting with PD-1, In patients with advanced hematologic malignancies," Clinical Cancer Research 14(10):3044-3051, American Association for CancerResearch, United States (2008).

Blank et al "Combination of targeted therapy and immunotherapy in melanoma" Cancer Immunol Immunother (2011) vol. 60, pp. 1359-1371.

Blank, C., et al., "Interaction of PD-L1 on tumor cells with PD-1 on tumor-specific T cells as a mechanism of immune evasion: implications for tumor immunotherapy," Cancer Immunology Immunotherapy 54(4):307-314, Springer-Verlag, Germany (2005).

Blank, C., et al., "PD-L1/B7H-1 inhibits the effector phase of tumor rejection by T cell receptor (TCR) transgenic CD8+ T cells," Cancer Research 64(3):1140-1145, American Association for Cancer Research, United States (2004).

Blank, Christian, et al.; "Contribution of the PD-L1/PD-1 pathway to T-cell exhaustion: an update on implications for chronic infections and tumor evasion"; Cancer Immunol. Immunotherapy; 56(5):739-745 (2007).

Blazar, B.R., et al., "Infusion of anti-B7.1 (CD80) and anti-B7.2 (CD86) monoclenal antibodies inhibits murine graft- versus-host disease lethality in part via direct effects on CD4+ and CD8+ T cells," The Journal of Immunology 157(8):3250-3259, TheAmerican Association of Immunologists, United States (1996).

Brahmer, J.R., et al., "Safety and activity of MDX-1106 (ONO-4538) anti-PD-1 monoclonal antibody in patients with selected refractory or relapsed malignancies," Journal of Clinical Oncology 26:Abstract No. 3006, American Society of ClinicalOncology, United States (2008).

Brahmer., J.R., et al., "Phase I study of single-agent anti-programmed death-1 (MDX-1106) in refractory solid tumors: Safety, clinical activity, pharmacodynamics, and immunologic correlates," Journal of Clinical Oncology 28 (19):3167-3175, AmericanSociety of Clinical Oncology, United States (2005).

Brown et al, "Blockade of Programmed Death-1 Ligands on Dendritic Cells Enhances T Cell Activation and Cytokine Production", J. Immunol. (2003) vol. 170, pp. 1257-1266.

Brown et al., "Tolerance to Single, but Not Multiple, Amino Acid Replacements in Antibody VH CDR2: A Means of Minimizing B Cell Wastage from Somatic Hypermutation?" J Immunol (1996) vol. 156, pp. 3285-3291.

Brown, J.A., et al., "Expression and functional consequences PD-1 ligands on natural APCS and tumors," The FASEB Journal 15(4):A345 (abstract No. 275.23), Federation of American Societies for Experimental Biology, United States (2001).

Campbell, A.M., "Characterisation of monoclonal antibodies," in Laboratory Techniques in Biochemistry and Molecular Biology, Monoclonal Antibody Technology: The Production and Characterization of Rodent and Human Hybridomas, vol. 13, pp. 186-215, Elsevier, the Netherlands (1984).

Carreno, B,M, and Collins, M., "The B7 family of ligands and its receptors: new pathways for costimulation and inhibition of immune responses," Annual Review of Immunology 20:29-53, Annual Reviews, United States (2002).

Carreno, B.M., "BTLA: a new inhibitory receptor with a B7-like ligand," Trends in Immunology 24(10):524-527, Elsevier, England (2003).

Carter, L.L. and Carreno, B.M., et al., "Cytotoxic T-lymphocyte antigen-4 and programmed death-1 function as negative regulators of lymphocyte activation," Immunologic Research 28(1):49-59, Humana Press, United States (2003).

Carter, L.L., et al., "PD-1:PD-L inhibitory pathway affects both CD4(+) and CD8(+) T cells and is overcome by IL-2," European Journal of Immunology 32(3):634-643, Wiley-VCH Verlag GmbH, Germany (2002).

Chan et al. "Therapeutic antibodies for autoimmunity and inflammation" Nature Reviews Immunology (2010) vol. 10, pp. 301-316.

Chen, L., "Co-inhibitory molecules of the B7-CD28 family in the control of T-cell immunity," Nature Reviews Immunology 4(5):336-347, Nature Publishing Group, England (2004).

Chen, Y., et al., "Selection and Analysis of an Optimized Anti-VEGF Antibody: Crystal Structure of an Affinity-matured Fab in Complex with Antigen," Journal of Molecular Biology 293(4):865-881, Academic Press, England (1999).

Chervontseva A M et al: "Effect of cytarabine on expression of cell adhesion molecules and on endothelium-leukocyte interaction in vitro.", Terapeuticheskii Arkhiv 2006, vol. 78, No. 7, 2006, pp. 67-72.

Christiansen et al: "Eradication of solid tumors using histone deacetylase inhibitors combined with irrmune-stimulating antibodies", Proceedings of the National Academy of Sciences, vol. 108 No. 10, Feb. 22, 2011 (Feb. 22, 2011), pp. 4141-4146.

Christiansson Lisa et al: "The tyrosine kinase inhibitors imatinib and dasatinib reduce myeloid suppressor cells and release effector lymphocyte responses.", Molecular Cancer Therapeutics, vol. 14, No. 5, May 2015 (May 2015), pp. 1181-1191.

ClincalTrials.gov Identifier: NCT01988896 "A Phase 1 b Study of MPDL3280A (an Engineered Anti-PDL1 Antibody) in Combination With Cobimetinib in Patients With Locally Advanced or Metastatic Solid Tumors" Clinicaltrials.gov, last updated Dec. 1, 2014.

(56) References Cited

OTHER PUBLICATIONS

ClinicalTrials.gov Identifier: NCT02040064 "Tolerability and Efficacy of Tremelimumab in Combination With Gefitinib in NSCLC Patients", ClinicalTrials.gov; last updated Jan. 17, 2014.

ClinicalTrials.gov Identifier: NCT02263508 "A Phase 1 b/3, Multicenter, Open-label Trial of Tafimogene Laherparepvec in Combination With Pembrolizumab (MK-3475) for Treatment of Unresected, Stage IIIB to IVM1c Melanoma (MASTERKEY-265)", ClinicalTrials.gov; last updated Jun. 22, 2015.

ClinicalTrials.gov Identifier: NCT02339571 "Randomized Phase II/III Study of Nivolumab Plus Ipilimumab Plus Sargramostim Versus Nivolumab Plus Ipilimumab in Patients With Unresectable Stage III or Stage IV Melanoma", ClinicalTrials.gov; last updated Apr. 9, 2015.

Cloeckaert, A., et al., "O-Polysaccharide epitopic heterogeneity at the surface of Brucella spp.studied by enzyme-linked immunosorbent assay and flow cytometry," Clinical and Diagnostic Laboratory Immunology 5(6):862-870, American Society for Microbiology, United States (1998).

Collins et al., "The B7 family of immune-regulatory ligands" Genome Biology (2005) vol. 6 No. 223.

Cragg, M.S. et al., "Complement-mediated lysis by anti-CD20 mAb correlated with segregation into lipid rafts," Blood 101(3):1045-1052, American Society of Hematology, United States (2003).

Makishi et al. "Retracted: A modified version of galectin-9 induces cell cycle arrest and apoptosis of Burkitt and Hodgkin lymphoma cells" British Journal of Hematology (2008) vol. 142 pp. 583-594.

Manning et al, "A model of multiple myeloma: culture of 5T33 murine myeloma cells and evaluation of tumorigenicity in the C57BL/KaLwRij mouse.", Br J Cancer., 66(6): 1088-1093 (1992).

Maçon-Lemaître et al., "The negative regulatory function of the lymphocyte-activation gene-3 co-receptor (CD223) on human T cells," Immunology (2005) vol. 115, pp. 170-178.

Miko et al., "Involvement of Galectin-9/TIM-3 Pathway in the Systemic Inflammatory Response in Early-Onset Preeclampsia," PLOS One (2013) vol. 8, No. 8, Article e71811, 9 pages.

Miska et al., "Autoimmunity-mediated antitumor immunity: Tumor as an immunoprivileged self," Eur J Immunol (2012) vol. 42, pp. 2584-2596.

Mocellin et al., "CTLA-4 blockade and the renaissance of cancer immunotherapy," Biochim Biophys Acta (2013) vol. 1836, pp. 187-196.

Mokyr et al., "Realization of the Therapeutic Potential of CTLA-4 Blockade in Low-Dose Chemotherapy-treated Tumor-bearing Mice", Cancer Research, 58:5301-5304 (1998).

Monney et al. "Th1-specific cell surface protein Tim-3 regulates macrophage activation and severity of an autoimmune disease" Nature (2002) vol. 415, pp. 536-541.

Mosmann et al. "The expanding universe of T-cell subsets: Th1, Th2 and more" Immunology Today (1996) vol. 17, Issue 3, pp. 138-146.

Mossman et al. "Two Types of Murine Helper T Cell Clone" Journal of Immunology (1986) vol. 136, Issue 7, pp. 2348-2357).

Mou et al., "Association Between TIM-1 Gene Polymorphisms and Allergic Rhinitis in a Han Chinese Population" J Investig Allergol Clin Immunol (2010) vol. 20 No. 1 pp. 3-8.

Murrey et al., Biokhimiya cheloveka, Mir (1993) vol. 1, p. 34.

Nagahara et al., "Galectin-9 Increases Tim-3+ Dendritic Cells and Cd+ T Cells and Enhances Antitumor Immunity via Galectin-9-Tim-3 Interactions" The Journal of Immunology (2008) vol. 181 pp. 7660-7669.

Najjar et al., "Myeloid-Derived Suppressor Cell Subset Accumulation in Renal Cell Carcinoma Parenchyma Is Associated with Intratumoral Expression of IL1beta, IL8, CXCL5, and Mip-1alpha," Clinical Cancer Research (2016) vol. 23, No. 9, pp. 2346-2355.

Neubert et al., "T cell-induced CSF1 promotes melanoma resistance to PD1 blockade," Science Translational Medicine (2018) vol. 10, No. 436, Article eaan3311, 14 pages.

Ngiow et al. "Prospects for TIM3-Targeted Antitumor Immunotherapy" Cancer Research (2011) vol. 71, Issue 21, pp. 6567-6571.

Ngiow et al., "Anti-TIM3 Antibody Promotes T Cell IFN-γ-Mediated Antitumor Immunity and Suppresses Established Tumors" Cancer Research (2011) vol. 71 No. 10 pp. 3540-3551.

Nicholson et al., "An Altered Peptide Ligand Mediates Immune Deviation and Prevents Autoimmune Encephalomyelitis" Immunity (1995) vol. 3 pp. 397-405.

Nirschl et al., "Molecular Pathways: Coexpression of Immune Checkpoint Molecules: Signaling Pathways and Implications for Cancer Immunotherapy," Cancer Res (2013) vol. 19, No. 18, pp. 4917-4924.

Nishimura et al., "Developmentally regulated expression of the PD-1 protein on the surface of double-negative (CD4-CD8-) thymocytes," Int Immunol (1996) vol. 8, No. 5, pp. 773-780.

Ohigashi et al., "Clinical Significance of Programmed Death-1 Ligand-1 and Programmed Death-1 Ligand-2 Expression in Human Esophageal Cancer" Clin Cancer Research (2005) vol. 11, pp. 2947-2953.

Ohno et al., "Antigen-binding specificities of antibodies are primarily determined by seven residues of VH," PNAS (1985) vol. 82, pp. 2945-2949.

Okamoto et al., "T-Helper Type 1/T-Helper Type 2 Balance in Malignant Pleural Effusions Compared to Tuberculous Pleural Effusions" Chest (2005) vol. 128 pp. 4030-4035.

Okazaki et al, "PD-1 and PD-1 ligands: from discovery to clinical application" Intern. Immun. (2007) vol. 19, pp. 813-824.

Okudaira et al., "A modified version of galectin-9 suppresses cell growth and induces apoptosis of human T-cell leukemia virus type 1-infected T-cell lines" Int. J. Cancer (2007) vol. 120 pp. 2251-2261.

Opdivo (nivolumab) Drug Label, Initial U.S. Approval: 2014, Revised May 2016.

Opdivo (nivolumab) Drug Label, Initial U.S. Approval: 2014, Revised Nov. 2016, 58 pages.

Opposition filed by Asilfa AG in corresponding Chilean Application No. 2017-00888 on Oct. 24, 2017, assigned litigation file number by the National Institute of Industrial Property of Chile (INAPI) on Feb. 27, 2018, notified by NAPI to agent on Mar. 2, 2018.

Opposition filed by Laboratorios Legrand S.A. in corresponding Colombian Application No. NC2017/0003490 on Dec. 7, 2017, admitted Dec. 19, 2017, published Dec. 20, 2017.

Opposition filed in Colombian Application No. NC2016/0001001, filed Feb. 15, 2017.

Pal et al., "Programmed Death-1 Inhibition in Renal Cell Carcinoma: Clinical Insights and Future Directions," Clinical Adv Hem Onc (2014) vol. 12, Issue 2, pp. 90-99.

Partial European Search Report issued in European Patent Application No. 19206634.8, mailed Apr. 30, 2020.

Paterson et al., "The Programmed Death-1 Ligand 1:B7-1 Pathway Restrains Diabetogenic Effector T Cells In Vivo," J Immunol (2011) vol. 187, pp. 1097-1105.

Phong et al., "Tim-3 enhances Fc[epsilon]RI-proximal signaling to modulate mast cell activation," J Experimental Medicine (2015) vol. 212, No. 13, pp. 2289-2304.

Post Grant Opposition filed in Colombian Patent Application No. NC2016/0001001, dated Jul. 31, 2018.

Powles et al., "MPDL3280A (anti-PD-L1) treatment leads to clinical activity in metastatic bladder cancer," Nature (2014) vol. 515, pp. 558-562.

Prigent et al., "Lymphocyte activation gene-3 induces tumor regression and antitumor immune responses," Eur J Immunol (1999) vol. 29, pp. 3867-3876.

Raziorrouh et al. "The Immunoregulatory Role of CD244 in Chronic Hepatitis B Infection and its Inhibitory Potential on Virus-Specific CD8+ T-cell Function" Hepatology (2010) vol. 52 pp. 1934-1947.

Richter et al., "On the role of the inhibitory receptor LAG-3 in acute and chronic LCMV infection," Int Immunol (2009) vol. 22, No. 1, pp. 13-23.

Rothe et al. "Enhancing dendritic cell-induced T-cell responses by immunomodulating molecules" 13th CIMT Annual Meeting (2015) p. 74.

Rowe et al., "Innate IFN-gamma is essential for programmed death ligand-1-mediated T cell stimulation following Listeria monocytogenes infection," J Immunol (2012) vol. 189, No. 2, pp. 876-884.

(56) References Cited

OTHER PUBLICATIONS

Rudnick et al. "Affinity and Avidity in Antibody-Based Tumor Targeting" Cancer Biotherapy and Radiopharmaceuticals (2009) vol. 24, No. 2, pp. 155-160.

Sabatos et al. "Interaction of Tim-3 and Tim-3 ligand regulates T helper type 1 responses and induction of peripheral tolerance" Nature Immunology (2003) vol. 4, pp. 1102-1110.

Sabatos-Peyton et al., "Blockade of Tim-3 binding to phosphatidylserine and CEACAM1 is a shared feature of anti-Tim-3 antibodies that have functional efficacy," Oncoimmunology (2018) vol. 7, No. 2, Article e1385690, 9 pages.

Sachdev et al., "Phase 1/2a study of double immune suppression blockade by combining a CSF1R inhibitor (pexidartinib/PLX3397) with an anti-PD-1 antibody (pembrolizumab) to treat advanced melanoma and other solid tumors," Gynecologic Oncology (2016) vol. 141, pp. 147-148.

Sakuishi et al., "Emerging Tim-3 functions in anti-microbial and tumor immunity" Trends Immunol (2011) vol. 32 No. 8 pp. 345-349.

Sakuishi et al., "Targeting Tim-3 and PD-1 pathways to reverse T cell exhaustion and restore anti-tumor immunity," J Experimental Medicine (2010) vol. 207, No. 10, pp. 2187-2194.

Sakuishi et al., "TIM3+FOXP3+ regulatory T cells are tissue-specific promoters of T-cell dysfunction in cancer" OncoImmunology (2013) vol. 2 No. 4 pp. e23849-1-e23849-9.

Santiago et al., "Structures of T Cell Immunoglobulin Mucin Receptors 1 and 2 Reveal Mechanisms for Regulation of Immune Responses by the TIM Receptor Family" Immunity (2007) vol. 26 pp. 299-310.

Schroll, A. et al., "Tim3 Is Upregulated and Protective in Nephrotoxic Serum Nephritis", The American Journal of Pathology, vol. 176, No. 4, pp. 1716-1742, Apr. 2010.

Agoram, "Use of pharmacokinetic/pharmacodynamic modelling for starting dose selection in first-in-human trials of high-risk biologics," Br. J. Clin. Pharm., 67(2):153-160 (2009).

Agrawal, S., et al., "Clinical pharmacokinetics (PK) of BMS-936558, a fully human anti-PD-1 monoclonal antibody," 012 ASCO Annual Meeting, Website, 1 page (2012).

Andrews et al., "LAG3 (CD223) as a Cancer Immunotherapy Target," Immunol Rev. Mar. 2017 ; 276(1): 80-96.

Angevin et al., Analysis of T-Cell Imune Response in Renal Cell Carcinoma: Polarization to Type 1-Like Differentiation Pattern, Clonal T-Cell Expansion and Tumor-Specific Cytotoxicity Int. J. Cancer (1997) vol. 72 pp. 431-440.

Blackburn, Shawn D. et al., "Coregulation of CD8+ T cell exhaustion by multiple inhibitory receptors during chronic viral Infection," Nature Immunology, vol. 10(1):29-37 (2009).

Brignone et al., "First-line chemoimmunotherapy in metastatic breast carcinoma: combination of paclitaxel and IMP321 (LAG-3Ig) enhances immune responses and antitumor activity" Journal of Translational Medicine (2010) vol. 8 No. 71 pp. 1-11.

Camisaschi et al., "Alternative Activation of Human Plasmacytoid DCs In Vitro and in Melanoma Lesions: Involvement of LAG-3" Journal of Investigative Dermatology (2014) vol. 134 pp. 1893-1902.

Camisaschi et al., "LAG-3 Expression Defines a Subset of CD4+CD25highFoxp3+ Regulatory T Cells That Are Expanded at Tumor Sites" The Journal of Immunology (2010) vol. 184 pp. 6546-6551.

Castelli et al., "Lymphocyte activation gene-3 (LAG-3, CD223) in plasmacytoid dendritic cells (pDCs): a colecular target for the restoration of active antitumor immunity" OncoImmunology (2014) vol. 3 No. 11.

Chen & Flies, "Molecular mechanisms of T cell co-stimulation and co-inhibition" Nat Rev Immunol (2013) vol. 13 No. 4 pp. 227-242.

Clinicaltrials.gov (search terms "Novartis" and "LAG3", p. 1: Mar. 30, 2017).

Clinicaltrials.gov Identifier NCT01968109: A Phase 1 Dose Escalation and Cohort Expansion Study of the Safety, Tolerability, and Efficacy of Anti-LAG-3 Monoclonal Antibody (BMS-986016) Administered Alone and in Combination With Anti-PD-1 Monoclonal Antibody (Nivolumab, BMS-936558) in Advanced Solid Tumors. 2013.

Clinicaltrials.gov Identifier NCT02061761: A Phase 1 Dose Escalation and Cohort Expansion Study of the Safety, Tolerability, and Efficacy of Anti-LAG-3 (BMS-986016) in Relapsed or Refractory Chronic Lymphocytic Leukemia and Lymphomas. 2014.

Giraldo et al., "Orchestration and Prognostic Significance of Immune Checkpoints in the Microenvironment of Primary Metastatic Renal Cell Cancer" Clinical Cancer Research (2015) vol. 21 No. 13 pp. 3031-3040.

Goding et al. "Restoring immune function of tumor-specific CD4+ T cells during recurrence of melanoma" J. Immunol. (2013) vol. 190, No. 9, pp. 4899-4909.

Grimwood, Pharm. Therapeutics, 122(3):281-301 (2009).

Grosso et al "LAG-3 regulates CD8+ T cell accumulation and effector function in murine selfand tumor-tolerance systems" The Journal of Clinical Investigation (2007) vol. 117, No. 11, pp. 3383-3392.

Hemon et al,. "MHC Class II Engagement by Its Ligand LAG-3 (CD223) Contributes to Melanoma Resistance to Apoptosis" J Immunol (2011) vol. 186 pp. 5173-5183.

Hong et al., "Phase I/II study of LAG525 +/– spartalizumab (PDR001) in patients (pts) with advanced malignancies," J Clin Oncol (2018) vol. 36, No. 15, Supplement 1, Abstract Only.

Huard, B. et al., "Cellular expression and tissue distribution of the human LAG-3-encoded protein, an MHC class II ligand," Immunogenetics, vol. 39(3), pp. 213-217 (1994).

Huard, Bertrand et al., "Characterization of the major histocompatibility complex class II binding site on LAG-3 protein," Proc. Natl. Acad. Sci. USA, vol. 94:5744-5749 (1997).

International Search Report and Written Opinion for PCT/US2015/020474 dated Jun. 15, 2015.

Ji et al., "Challenges and Opportunities in Dose Finding in Oncology and Immuno-oncology," Clin Transl Sci (2018) vol. 11, pp. 345-351.

Kocak, Ergun et al., "Combination Therapy with Anti-CTL Antigen-4 and Anti-4-1 BB Antibodies Enhances Cancer Immunity and Reduces Autoimmunity," Cancer Res., vol. 66(14):7276-7284 (2006).

Koga et al., "Blockade of the Interaction Between PD-1 and PD-L1 Accelerates Graft Arterial Disease in Cardiac Allografts," Arterioscler Thromb Vasc Biol (2004) vol. 24, pp. 2057-2062.

List of anti-LAG-3 clinical trials identified in ClinicalTrials.gov as of Jan. 20, 2017.

Schöffski et al., "Phase I/II study of the LAG-3 inhibitor ieramilimab (LAG525) ± anti-PD-1 spartalizumab (PDR001) in patients with advanced malignancies," Journal for Immuno Therapy of Cancer (2022) vol. 10, Article e003776, 13 pages.

Scurr et al. "Highly prevalent colorectal cancer-infiltrating LAP+ Foxp3-T cells exhibit more potent immunosuppressive activity than Foxp3+ regulatory T cells" Mucosal Immunology (2013) doi:10.1038/mi.2013.62, pp. 1-12.

Search Report and Written Opinion issued in Singapore Application No. 11201605951Y, dated Oct. 16, 2017.

Subramanyam, Meena et al., "Soluble human lymphocyte activation gene-3 modulates allospecific T cell responses," International Immunology, vol. 10(4):679-689 (1998).

Supplementary European Search Report for European Application No. EP 14848888.5, dated May 31, 2017.

Tiwari, J. AAPS, 19(2):510-519 (2017).

Turnis M. et al., "Combinatorial immunotherapy: PD-1 may not be LAG-ing behind any more," OncoImmunolgy, vol. (7), pp. 1172-1174 (2012).

Workman et al., "LAG-3 Regulates Plasmacytoid Dendritic Cell Homeostatis" The Journal of Immunology (2009) vol. 182 pp. 1885-1891.

Workman, C.J. et al., "Phenotypic analysis of the murine CD4-related glycoprotein, CD223 (LAG-3).," Eur. J. Immunol., vol. 32(8): 2255-2263 (2002).

Xu et al., "LSECtin Expressed on Melanoma Cells Promotoes Tumor Progression by Inhibiting Antitumor T-cell Responses" Cancer Research (2014) vol. 74 No. 14 pp. 3418-3428.

(56) References Cited

OTHER PUBLICATIONS

Nomi, T., et al., "Clinical significance and therapeutic potential of the programmed death-1 ligand/programmed death-1 pathway in human pancreatic cancer," Clinical Cancer Research 13(7):2151-2157, The Association, United States (2007).

Okazaki, T., et al., "New regulatory co-receptors: inducible co-stimulator and PD-1," Current Opinion in Immunology 14(6):779-782, Elsevier, England (2002).

Okazaki, T., et al., "PD-1 immunoreceptor inhibits B cell receptor-mediated signaling by recruiting src homology 2-domain-containing tyrosine phosphatase 2 to phophotyrosine," Proceeding of the National Academy of Sciences 98(24):13866-13871, National Academy of Sciences, United States (2001).

Oki Y et al: "Immune regulatory effects of panobinostat in patients with Hodgkin lymphoma through modulation of serum cytokine levels and T-cell PD1 expression," Blood Cancer Journal, vol. 4, E236, 2014, pp. 1-4.

Opdivo (nivolumab) Drug Label, Initial U.S. Approval: 2014, Revised Nov. 2016.

Ozaki, S., et al., "Immunotherapy of Multiple Myeloma with a Monoclonal Antibody Directed Against a Plasma Cell-specific Antigen, HM1.24," Blood 90(8):3179-3186, American Society of Hematology, United States (1997).

Ozkaynak, E., et al., "Programmed death-1 targeting can promote allograft survival," The Journal of Immunology 169(11):6546-6553, The American Association of Immunologists, United States (2002).

Panka, et al.; "Variable region framework differences result in decreased or increased affinity of variant anti-digoxin antibodies"; Proc. Natl. Acad. Sci. USA; 85:3080-3084 (1988).

Pardoll, D.M., "The blockade of immune checkpoints in cancer immunotherapy," Nature Reviews Cancer 12(4):252-264, Nature Publishing Group, England (2012).

Park, J.W. and Smolen, J., "Monoclonal antibody therapy," Advances in Protein Chemistry 56:369-421, Academic Press, United States (2001).

Parry, Richard V., et al.; "CTLA-4 and PD-1 Receptors Inhibit T-Cell Activation by Distinct Mechanisms"; Molecular and Cellular Biology; 25(21):9543-9553 (2005).

Patel et al., "Taming dendritic cells with TIM-3: another immuno-suppressive strategy used by tumors" Immunotherapy (2012) vol. 4 No. 12 pp. 1795-1798.

Patsoukis, N., et al., "PD-1 Increases PTEN Phosphatase Activity While Decreasing PTEN Protein Stability by Inhibiting Casein Kinase 2," Molecular and Cellular Biology 33(16):3091-3098, American Society for Microbiology, United States (Aug. 2013).

Patsoukis, N., et al., "PD-1 inhibits T cell proliferation by upregulating p. 27 and p. 15 and suppressing Cdc25A," Cell Cycle 11(23):1-5, Landes Bioscience, United States (Dec. 2012).

Patsoukis, N., et al., "Selective Effects of PD-1 on Akt and Ras Pathways Regulate Molecular Components of the Cell Cycle and Inhibit T Cell Proliferation," Science Signaling 5(230): ra46, pp. 1-14, American Association for the Advancement ofScience, United States (Jun. 2012).

Perez-Gracia et al, "Orchestrating immune check-point blockade for cancer inmunotherapy in combinations", Current Opinion in Immunology (2014) vol. 27 pp. 89-97.

Pinzon-Ortiz et al: "S710: The combination of JAK inhibitor, ruxolitinib, pan-PIM inhibitor, LGH447, and CDK4/6 inhibitor, LEE011, in a preclinical mouse model of myeloproliferative neoplasia", Haematologica, The Hematology Journal: Official Organ of the European Hematology Association, vol. 99. No. Supp 1 (2014) p. 252.

Polyak, M.J. and Deans, J.P., "Alanine-170 and proline-172 are critical determinants for extracellular CD20 epitopes; heterogeneity in the fine specificity of CD20 monoclonal antibodies is defined by additional requirements imposed by both aminoacid sequence and quaternary structure," Blood 99(9):3256-3262, American Society of Hematology, United States (2002).

Postel-Vinay et al. "Challenges of phase 1 clinical trials evaluating immune checkpoint-targeted antibodies" Annals of Oncology (2016) vol. 27, pp. 214-224.

Prokunina, L. and Alarcon-Riquelme, M., "The genetic basis of systemic lupus erythematosus-knowledge of today and thoughts for tomorrow," Human Molecular Genetics 13(1):R143-R148, Oxford University Press, England (2004).

Quintarelli et al: "Selective strong synergism of Ruxolitinib and second generation tyrosine kinase inhibitors to overcome bone marrow stroma related drug resistance in chronic myelogenous leukemia", Leukemia Research, New York, Ny, US, vol. 38, No. 2, Nov. 15, 2013 (Nov. 15, 2013), pp. 236-242.

Riley, J.L. and June, C.H., "The CD28 family: a T-cell rheostat for therapeutic control of T-cell activation," Blood 105(1):13-21, American Society of Hematology, United States (Jan. 2005).

Rudikoff, et al.; "Single Amino Acid Substitution Altering Antigen-binding Specificity"; Proc. Natl. Acad. Sci. USA; 79:1979-1983 (1982).

Salama, A.D., et al., "Critical role of the programmed death-I (PD-1) pathway in regulation of experimental autoimmune encepha-lomyelitis," The Journal of Experimental Medicine 198(1):71-78, The Rockefeller University Press, United States (2003).

Sanmamed et al. "Agonists of Co-stimulation in Cancer Immunotherapy Directed Against CD137, OX40, GITR, CD27, CD28, and ICOS" Seminars in Oncology (2015) vol. 42, No. 4, pp. 640-655.

Shinohara, T., et al., "Structure and chromosomal localization of the human PD-1 gene (PDCD1)," Genomics 23(3):704-706, Academic Press, United States (1994).

Sho, M., et al., "Possibility of Clinical Applications for Novel Cancer Immunotherapy via Inhibition of T-cell Negative Pathway," Magazine of the Japan Society of Clinical Oncology 40(2):590 (PS22-5) (2005).

Soh, E.Y., et al., "Neutralizing vascular endothelial growth factor activity inhibits thyroid cancer growth in vivo," Surgery 128(6):1059-1066, Mosby, United States (2000).

Song et al: "3681 Phenotypic and Functional Effects of Novel HDAC Inhibitor LBH589 On Human Lymphocyte Populations", 51st ASH Annual Meeting and Exposition (2009) Retrieved from the Internet: URL:https:jjash.confex.comjash/2889/webpro gramjPaper22684.html [retrieved on Apr. 14, 2016].

Song W et al: "HDAC inhibition by LBH589 affects the phenotype and function of human myeloid dendritic cells.", Leukemia Jan 2811, vol. 25, No. 1, Jan. 2011 (Jan. 2011), pp. 161-168.

Supplementary Partial European Search Report for European Application No. EP 1484888, dated Mar. 1, 2017. 10 pages.

Tamura, H., et al., "B7-H1 costimulation preferentially enhances CD28-independent T-helper cell function," Blood 97(6):1809-1816, The American Society of Hematology, United States (2001).

Tang et al. "Immunotherapy and tumor microenvironment" Cancer Letters (2016) vol. 370, pp. 85-90.

Teeling, J.L., et al., "Characterization of new human CD20 mono-clonal antibodies with potent cytolytic activity against non-Hodgkin Lymphomas," Blood 104(6):1793-1800, American Society of Hema-tology, United States (2004).

Thomas, M.L., "Of ITAMs and ITIMs: turning on and off the B cell antigen receptor," The Journal of Experimental Medicine 181(6):1953-1956, The Rockefeller University Press, United States (1995).

Thompson, R. Houston, et al.; "PD-1 is expressed by tumor-infiltrating immune cells and is associated with poor outcome for patients with renal cell carcinoma"; Clin. Cancer Res. 13(6):1757-1761 (2007).

Tomlinson, I.M., et al., "The repertoire of human germline VH sequences reveals about fifty groups of VH segments with different hypervariable loops," Journal of Molecular Biology 227(3):776-798, Elsevier, Netherlands (1992).

Topalian, S., "Q&A: Suzanne Topalian on Immune Therapies", Cancer Discovery 3(7):712, American Association for Cancer Research, United States, published online Jun. 27, 2013.

Topalian, S., et al., "Nivolumab (anti-PD-1; BMS-936558; ONO-4538) in patients with advanced solid tumors: Survival and long-term safety in a phase I trial," accessed at http://meetinglibrary. asco.org/content/113543-132, accessed on Jun. 1, 2016, 2pages.

(56) References Cited

OTHER PUBLICATIONS

Topalian, S.L., et al., "Safety, Activity, and Immune Correlates of Anti-PD-1 Antibody in Cancer," The New England Journal of Medicine 366(26):2443-2454, Massachusetts Medical Society, United States (2012).

Trautmann, Lydie, et al.; "Upregulation of PD-1 expression on HIV-specific CD8+ T cells leads to reversible immune dysfunction"; Nat. Med.; 12(10):1198-1202 (2006).

Tsai, C-J., et al., "Protein Allostery, signal transmission and dynamics: a classification scheme of allosteric mechanisms," Molecular BioSystems 5(3):207-216, Royal Society of Chemistry, England (2009).

Tsushima, Fumihiko, et al.; "Predominant expression of B7-H1 and its immunoregulatory roles in oral squamous cell carcinoma"; Oral Oncology; 42:268-274 (2006).

UniProtKB/Swiss-Prot Database entry, PDCD1.sub.--HUMAN, accessed at http://www.uniprot.org/uniprot/Q15116.txt, accessed on Jun. 1, 2016, 5 pages.

Van Regenmortel, M.H.V., "The recognition of Proteins and Peptides by Antibodies," Journal of Immunoassay 21(2-3):85-108, Taylor & Francis, England (2000).

Vanneman et al: "Combining immunotherapy and targeted therapies in cancer treatment" Nature Reviews Cancer (2012) vol. 12 No. 4 pp. 237-251.

Verbrugge et al: "The curative outcome of radioinmunotherapy in a mouse breast cancer model relies on mTOR signaling", Radiation Research. Radiation Research Society, GB, (2014) vol. 182 No. 2 pp. 219-229.

Vietta et al. "Considering Therapeutic Antibodies" Science (2006) vol. 313, pp. 308-309.

Waldmann, Thomas A.; "Effective cancer therapy through immunomodulation"; Annual Rev.; 57(1):65-81 (2006).

Wang et al. "In Vitro Characterization of the Anti-PD-1 Antibody Nivolumab, BMS-936558, and In Vivo Toxicology in Non-Human Primates" Cancer Immunology Research (2014) vol. 2, No. 9, pp. 846-856.

Freeman et al., "Engagement of the PD-1 immunoinhibitory receptor by a novel B7 family member leads to negative regulation of lymphocyte activation", J Exp Med. (2000) vol. 192, No. 7, pp. 1027-1034.

Gatalica et al., "Programmed death 1 (PD-1) lymphocytes and ligand (PD-L1) in colorectal cancer and their relationship to microsatellite instability status", J Clin Oncol (2014) vol. 32, No. 15 Supp, Abstract 3625.

International Search Report and Written Opinion for International Application No. PCT/US2015/053799 dated May 17, 2016.

International Search Report and Written Opinion for International Application No. PCT/US2015/066812 dated Mar. 23, 2016.

Latchman et al., "PD-L2 is a second ligand for PD-1 and inhibits T cell activation," Nature Immunol (2001) vol. 2, No. 3, pp. 261-268.

Opdivo (nivolumab) Drug Label, Initial U.S. Approval: 2014, Revised Oct. 2016.

Pardoll et al. "The blockade of immune checkpoints in cancer immunotherapy" Nature Reviews Cancer (2012) vol. 12, pp. 252-264.

Triebel, Frederic et al., "LAG-3: a regulator T-cell and DC responses and its use in therapeutic vaccination," Trends in Immunology, vol. 24(12):619-622 (2003).

Workman, Creg J. et al., "Negative Regulation of T Cell Homeostasis by Lymphocyte Activation Gene-3 (CD223)," The Journal of Immunology, vol. 174:688-695 (2005).

Zhang, "P2.01—Poster Session/Treatment of Advanced Diseases—NSCLC (ID207) A Phase 3 Study of Pembrolizumab vs Platinum-Based Chemotherapy for PD-L1 ," (NSCLC ID 2182) Abstract from Poster Presentation from International Association for the Study of Lung Cancer, Aug. 9, 2015, retrieved from library.iaslc.org/search-speaker?search_speaker=30076.

* cited by examiner

Heavy Chain (murine IgG1)

```
                                         CDRH1          FWH2
        FWH1
QVQLQQSGSE LVRPGASVKL SCKAS GYTFT  TYWMHWVRQR PGQGLEWIGN I YPGTGGSNF DEKFKNRTSL
QVQLQQPGSE LVRPGASVKL SCKAS GYTFT  TYWMHWVRQR PGQGLEWIGN I YPGTGGSNF DEKFKNRTSL
                                                        CDRH2

CDRH3              FWH4
        FWH3
TVDTSSTTAY MHLASLTSED SAVYYCTR WT TGTGAY WGQG TLVTVSA
TVDTSSTTAY MHLASLTSED SAVYYCTR WT TGTGAY WGQG TLVTVSAAKT TPPSVPLAP GSAA
```

Light Chain (murine κ)

```
                                          CDRL1                      FWL2          CDRL2
        FWL1
DIVMTQSPSS LTVTAGEKVT MSCKS SQSLL DSGNQKNFLT WYQQKPGQPP KLLIF WASTR ESGVPDRFTG
DIVMTQSPSS LTVTAGEKVT MSCKS SQSLL DSGNQKNFLT WYQQKPGQPP KLLIF WASTR ESGVPDRFTG

CDRL3       FWL4
        FWL3
SGSVTDFTLT ISSVQAEDLA VYYCQN DYSY PC TFGGGTKL EIK
SGSVTDFTLT ISSVQAEDLA VYYCQN DYSY PC TFGGGTKL EIKRAD
```

FIGURE 1

Heavy Chain

```
GL      QVQLQQPGSE LVRPGASVKL SCKAS GYTFT SYWMHWVKQR HGQGLEWIGN I YPGSGSTNY
Mu mAb  ----S---              T------R-- P---       ---T-GS-F

GL      DEKFKSKGTL TVDTSSSTAY MHLSSLTSED SAVYYCTR
Mu mAb  ----NRTS-  ----T---   --A------            WT TGTGAYWGQG TLVTVSA
```

Light Chain

```
GL      DIVMTQSPSS LTVTAGEKVT MSCKS SQSLL NSGNQKNYLT WYQQKPGQPP KLLIY WASTR
Mu mAb                        D----F                                   --F

GL      ESGVPDRFTG SGSGTDFTLT ISSVQAEDLA VYYCQN DYSY P
Mu mAb             --V---                       -CTFGGGTKL EIK
```

FIGURE 2A

```
mAb        C       T   F   G   G   G   T   K   L   E   I   K
mAb     g tgc acg ttc gga ggg ggg acc aag ctg gaa ata aaa
J2      - --a- ---  --- --- --- --- --- --- --- --- ---c
J2        Y
```

FIGURE 2B

| Clone No. | Concentration μg/mL | Sequence | | | | | |
|---|---|---|---|---|---|---|---|
| | | HC | | | LC | | |
| | | FW1 | FW2 | FW3 | FW1 | FW2 | FW3 |
| | | 4 unique HC | | | 9 unique LC | | |
| 1 | 23.3 | a | a | a | b | a | c |
| 2 | 45.5 | a | a | a | e | a | b |
| 3 | 58.4 | a | b | b | e | a | b |
| 4 | 52.9 | a | b | b | b | b | d |
| 5 | 30 | a | a | a | b | b | d |
| 6 | 7.9 | a | a | a | c | a | a |
| 7 | 24.9 | a | a | a | b | b | a |
| 8 | 32.8 | a | b | b | a | a | a |
| 9 | 16.3 | a | a | a | a | a | a |
| 10 | 61.5 | a | b | b | b | a | a |
| 11 | 31.4 | a | a | a | b | a | a |
| 12 | 34.8 | a | a | a | e | c | a |
| 13 | 8.6 | a | a | a | d | b | a |
| 14 | 48.4 | b | b | b | b | a | a |
| 15 | 20.7 | b | b | b | a | a | a |
| 16 | 32.8 | a | c | b | a | a | a |

FIGURE 5

| Clone No. | Conc. μg/mL | Sequence | | | | | | Ranking | Competition Binding | | Ranking |
|---|---|---|---|---|---|---|---|---|---|---|---|
| | | HC | | | LC | | | FACS data | 1st exp. | 2nd exp.* | |
| | | FW1 | FW2 | FW3 | FW1 | FW2 | FW3 | | | | |
| Chimeric | 20.6 | 4 unique HC | | | 9 unique LC | | | | | | |
| 1 | 23.3 | a | a | a | b | a | c | 2 | 7 | 2 | A |
| 2 | 45.5 | a | a | a | e | a | b | 6 | 3 | 2 | D |
| 3 | 58.4 | a | b | b | e | a | b | 7 | 8 | 14 | E |
| 4 | 52.9 | a | b | b | b | b | d | 14 | 15 | 15 | B |
| 5 | 30 | a | a | a | b | b | d | 5 | 5 | | A |
| 6 | 7.9 | a | a | a | c | a | a | 1 | 7 | 3 | D |
| 7 | 24.9 | a | a | a | b | b | a | 4 | 7 | | D |
| 8 | 32.8 | a | b | b | a | a | a | 7 | 7 | 4 | C |
| 9 | 16.3 | a | a | a | a | a | a | 7 | 2 | 4 | B |
| 10 | 61.5 | a | b | b | b | a | a | 7 | 6 | | C |
| 11 | 31.4 | a | a | a | b | a | a | 6 | 4 | | B |
| 12 | 34.8 | a | a | a | e | c | a | 3 | 8 | 16 | D |
| 13 | 8.6 | a | a | a | d | b | a | 6 | 1 | 1 | D |
| 14 | 48.4 | b | b | b | b | a | a | 16 | 7 | 15 | C |
| 15 | 20.7 | b | b | b | a | a | a | 6 | 7 | 15 | C |
| 16 | 32.8 | a | c | b | a | a | a | 15 | 16 | 15 | C |

*empty boxes means worse than 4

FIGURE 7

```
                            10        20        30        40        50        60
                     ....|....|....|....|....|....|....|....|....|....|....|....|
BAP049-chi-HC        QVQLQQSGSELVRPGASVKLSCKASGYTFTTYWMHWVRQRPGQGLEWIGNIYPGTGGSNF
BAP049-hum01-HC      EVQLVQSGAEVKKPGESLRISCKGSGYTFTTYWMHWVRQATGQGLEWMGNIYPGTGGSNF
BAP049-hum02-HC      EVQLVQSGAEVKKPGESLRISCKGSGYTFTTYWMHWVRQATGQGLEWMGNIYPGTGGSNF
BAP049-hum05-HC      EVQLVQSGAEVKKPGESLRISCKGSGYTFTTYWMHWVRQATGQGLEWMGNIYPGTGGSNF
BAP049-hum06-HC      EVQLVQSGAEVKKPGESLRISCKGSGYTFTTYWMHWVRQATGQGLEWMGNIYPGTGGSNF
BAP049-hum07-HC      EVQLVQSGAEVKKPGESLRISCKGSGYTFTTYWMHWVRQATGQGLEWMGNIYPGTGGSNF
BAP049-hum09-HC      EVQLVQSGAEVKKPGESLRISCKGSGYTFTTYWMHWVRQATGQGLEWMGNIYPGTGGSNF
BAP049-hum11-HC      EVQLVQSGAEVKKPGESLRISCKGSGYTFTTYWMHWVRQATGQGLEWMGNIYPGTGGSNF
BAP049-hum12-HC      EVQLVQSGAEVKKPGESLRISCKGSGYTFTTYWMHWVRQATGQGLEWMGNIYPGTGGSNF
BAP049-hum13-HC      EVQLVQSGAEVKKPGESLRISCKGSGYTFTTYWMHWVRQATGQGLEWMGNIYPGTGGSNF
BAP049-hum03-HC      EVQLVQSGAEVKKPGESLRISCKGSGYTFTTYWMHWIRQSPSRGLEWLGNIYPGTGGSNF
BAP049-hum04-HC      EVQLVQSGAEVKKPGESLRISCKGSGYTFTTYWMHWIRQSPSRGLEWLGNIYPGTGGSNF
BAP049-hum08-HC      EVQLVQSGAEVKKPGESLRISCKGSGYTFTTYWMHWIRQSPSRGLEWLGNIYPGTGGSNF
BAP049-hum10-HC      EVQLVQSGAEVKKPGESLRISCKGSGYTFTTYWMHWIRQSPSRGLEWLGNIYPGTGGSNF
BAP049-hum14-HC      QVQLVQSGAEVKKPGASVKVSCKASGYTFTTYWMHWIRQSPSRGLEWLGNIYPGTGGSNF
BAP049-hum15-HC      QVQLVQSGAEVKKPGASVKVSCKASGYTFTTYWMHWIRQSPSRGLEWLGNIYPGTGGSNF
BAP049-hum16-HC      EVQLVQSGAEVKKPGESLRISCKGSGYTFTTYWMHWVRQAPGQGLEWMGNIYPGTGGSNF 70        80        90        100       110
                     ....|....|....|....|....|....|....|....|....|....|....|..
BAP049-chi-HC        DEKFKNRTSLTVDTSSTTAYMHLASLTSEDSAVYYCTRWTTGTGAYWGQGTTVTVSS
BAP049-hum01-HC      DEKFKNRVTITADKSTSTAYMELSSLRSEDTAVYYCTRWTTGTGAYWGQGTTVTVSS
BAP049-hum02-HC      DEKFKNRVTITADKSTSTAYMELSSLRSEDTAVYYCTRWTTGTGAYWGQGTTVTVSS
BAP049-hum05-HC      DEKFKNRVTITADKSTSTAYMELSSLRSEDTAVYYCTRWTTGTGAYWGQGTTVTVSS
BAP049-hum06-HC      DEKFKNRVTITADKSTSTAYMELSSLRSEDTAVYYCTRWTTGTGAYWGQGTTVTVSS
BAP049-hum07-HC      DEKFKNRVTITADKSTSTAYMELSSLRSEDTAVYYCTRWTTGTGAYWGQGTTVTVSS
BAP049-hum09-HC      DEKFKNRVTITADKSTSTAYMELSSLRSEDTAVYYCTRWTTGTGAYWGQGTTVTVSS
BAP049-hum11-HC      DEKFKNRVTITADKSTSTAYMELSSLRSEDTAVYYCTRWTTGTGAYWGQGTTVTVSS
BAP049-hum12-HC      DEKFKNRVTITADKSTSTAYMELSSLRSEDTAVYYCTRWTTGTGAYWGQGTTVTVSS
BAP049-hum13-HC      DEKFKNRVTITADKSTSTAYMELSSLRSEDTAVYYCTRWTTGTGAYWGQGTTVTVSS
BAP049-hum03-HC      DEKFKNRFTISRDNSKNTLYLQMNSLRAEDTAVYYCTRWTTGTGAYWGQGTTVTVSS
BAP049-hum04-HC      DEKFKNRFTISRDNSKNTLYLQMNSLRAEDTAVYYCTRWTTGTGAYWGQGTTVTVSS
BAP049-hum08-HC      DEKFKNRFTISRDNSKNTLYLQMNSLRAEDTAVYYCTRWTTGTGAYWGQGTTVTVSS
BAP049-hum10-HC      DEKFKNRFTISRDNSKNTLYLQMNSLRAEDTAVYYCTRWTTGTGAYWGQGTTVTVSS
BAP049-hum14-HC      DEKFKNRFTISRDNSKNTLYLQMNSLRAEDTAVYYCTRWTTGTGAYWGQGTTVTVSS
BAP049-hum15-HC      DEKFKNRFTISRDNSKNTLYLQMNSLRAEDTAVYYCTRWTTGTGAYWGQGTTVTVSS
BAP049-hum16-HC      DEKFKNRFTISRDNSKNTLYLQMNSLRAEDTAVYYCTRWTTGTGAYWGQGTTVTVSS
```

FIGURE 9A

```
                          10        20        30        40        50        60
                   ....|....|....|....|....|....|....|....|....|....|....|....|
BAP049-chi-HC      QVQLQQSGSELVRPGASVKLSCKASGYTFTTYWMHWVRQRPGQGLEWIGNIYPGTGGSNF
BAP049-hum01-HC    E...V...A.VKK..E.LRI...G.................AT......M...........
BAP049-hum02-HC    E...V...A.VKK..E.LRI...G.................AT......M...........
BAP049-hum05-HC    E...V...A.VKK..E.LRI...G.................AT......M...........
BAP049-hum06-HC    E...V...A.VKK..E.LRI...G.................AT......M...........
BAP049-hum07-HC    E...V...A.VKK..E.LRI...G.................AT......M...........
BAP049-hum09-HC    E...V...A.VKK..E.LRI...G.................AT......M...........
BAP049-hum11-HC    E...V...A.VKK..E.LRI...G.................AT......M...........
BAP049-hum12-HC    E...V...A.VKK..E.LRI...G.................AT......M...........
BAP049-hum13-HC    E...V...A.VKK..E.LRI...G.................AT......M...........
BAP049-hum03-HC    E...V...A.VKK..E.LRI...G............I..S.SR....L...........
BAP049-hum04-HC    E...V...A.VKK..E.LRI...G............I..S.SR....L...........
BAP049-hum08-HC    E...V...A.VKK..E.LRI...G............I..S.SR....L...........
BAP049-hum10-HC    E...V...A.VKK..E.LRI...G............I..S.SR....L...........
BAP049-hum14-HC    ....V...A.VKK.....V................I..S.SR....L...........
BAP049-hum15-HC    ....V...A.VKK.....V................I..S.SR....L...........
BAP049-hum16-HC    E...V...A.VKK..E.LRI...G.................A.......M...........

70        80        90        100       110
                   ....|....|....|....|....|....|....|....|....|....|....|..
BAP049-chi-HC      DEKFKNRTSLTVDTSSTTAYMHLASLTSEDSAVYYCTRWTTGTGAYWGQGTTVTVSS
BAP049-hum01-HC    .......VTI.A.K.TS....E.S..R...T..........................
BAP049-hum02-HC    .......VTI.A.K.TS....E.S..R...T..........................
BAP049-hum05-HC    .......VTI.A.K.TS....E.S..R...T..........................
BAP049-hum06-HC    .......VTI.A.K.TS....E.S..R...T..........................
BAP049-hum07-HC    .......VTI.A.K.TS....E.S..R...T..........................
BAP049-hum09-HC    .......VTI.A.K.TS....E.S..R...T..........................
BAP049-hum11-HC    .......VTI.A.K.TS....E.S..R...T..........................
BAP049-hum12-HC    .......VTI.A.K.TS....E.S..R...T..........................
BAP049-hum13-HC    .......VTI.A.K.TS....E.S..R...T..........................
BAP049-hum03-HC    .......FTISR.N.KN.L.LQMN..RA..T..........................
BAP049-hum04-HC    .......FTISR.N.KN.L.LQMN..RA..T..........................
BAP049-hum08-HC    .......FTISR.N.KN.L.LQMN..RA..T..........................
BAP049-hum10-HC    .......FTISR.N.KN.L.LQMN..RA..T..........................
BAP049-hum14-HC    .......FTISR.N.KN.L.LQMN..RA..T..........................
BAP049-hum15-HC    .......FTISR.N.KN.L.LQMN..RA..T..........................
BAP049-hum16-HC    .......FTISR.N.KN.L.LQMN..RA..T..........................
```

FIGURE 9B

```
                       10        20        30        40        50        60
                 ....|....|....|....|....|....|....|....|....|....|....|....|
BAP049-chi-LC    DIVMTQSPSSLTVTAGEKVTMSCKSSQSLLDSGNQKNFLTWYQQKPGQPPKLLIFWASTR
BAP049-hum08-LC  EIVLTQSPDFQSVTPKEKVTITCKSSQSLLDSGNQKNFLTWYQQKPGQAPRLLIYWASTR
BAP049-hum09-LC  EIVLTQSPDFQSVTPKEKVTITCKSSQSLLDSGNQKNFLTWYQQKPGQAPRLLIYWASTR
BAP049-hum15-LC  EIVLTQSPDFQSVTPKEKVTITCKSSQSLLDSGNQKNFLTWYQQKPGQAPRLLIYWASTR
BAP049-hum16-LC  EIVLTQSPDFQSVTPKEKVTITCKSSQSLLDSGNQKNFLTWYQQKPGQAPRLLIYWASTR
BAP049-hum10-LC  EIVLTQSPATLSLSPGERATLSCKSSQSLLDSGNQKNFLTWYQQKPGQAPRLLIYWASTR
BAP049-hum11-LC  EIVLTQSPATLSLSPGERATLSCKSSQSLLDSGNQKNFLTWYQQKPGQAPRLLIYWASTR
BAP049-hum14-LC  EIVLTQSPATLSLSPGERATLSCKSSQSLLDSGNQKNFLTWYQQKPGQAPRLLIYWASTR
BAP049-hum06-LC  DIVMTQTPLSLPVTPGEPASISCKSSQSLLDSGNQKNFLTWYQQKPGQAPRLLIYWASTR
BAP049-hum07-LC  EIVLTQSPATLSLSPGERATLSCKSSQSLLDSGNQKNFLTWYQQKPGKAPKLLIYWASTR
BAP049-hum13-LC  DVVMTQSPLSLPVTLGQPASISCKSSQSLLDSGNQKNFLTWYQQKPGKAPKLLIYWASTR
BAP049-hum12-LC  DIQMTQSPSSLSASVGDRVTITCKSSQSLLDSGNQKNFLTWYLQKPGQSPQLLIYWASTR
BAP049-hum02-LC  DIQMTQSPSSLSASVGDRVTITCKSSQSLLDSGNQKNFLTWYQQKPGQAPRLLIYWASTR
BAP049-hum03-LC  DIQMTQSPSSLSASVGDRVTITCKSSQSLLDSGNQKNFLTWYQQKPGQAPRLLIYWASTR
BAP049-hum01-LC  EIVLTQSPATLSLSPGERATLSCKSSQSLLDSGNQKNFLTWYQQKPGQAPRLLIYWASTR
BAP049-hum04-LC  EIVLTQSPATLSLSPGERATLSCKSSQSLLDSGNQKNFLTWYQQKPGKAPKLLIYWASTR
BAP049-hum05-LC  EIVLTQSPATLSLSPGERATLSCKSSQSLLDSGNQKNFLTWYQQKPGKAPKLLIYWASTR 70        80        90        100       110
                 ....|....|....|....|....|....|....|....|....|....|....|...
BAP049-chi-LC    ESGVPDRFTGSGSVTDFTLTISSVQAEDLAVYYCQNDYSYPCTFGQGTKVEIK
BAP049-hum08-LC  ESGVPSRFSGSGSGTDFTFTISSLEAEDAATYYCQNDYSYPYTFGQGTKVEIK
BAP049-hum09-LC  ESGVPSRFSGSGSGTDFTFTISSLEAEDAATYYCQNDYSYPYTFGQGTKVEIK
BAP049-hum15-LC  ESGVPSRFSGSGSGTDFTFTISSLEAEDAATYYCQNDYSYPYTFGQGTKVEIK
BAP049-hum16-LC  ESGVPSRFSGSGSGTDFTFTISSLEAEDAATYYCQNDYSYPYTFGQGTKVEIK
BAP049-hum10-LC  ESGVPSRFSGSGSGTDFTFTISSLEAEDAATYYCQNDYSYPYTFGQGTKVEIK
BAP049-hum11-LC  ESGVPSRFSGSGSGTDFTFTISSLEAEDAATYYCQNDYSYPYTFGQGTKVEIK
BAP049-hum14-LC  ESGVPSRFSGSGSGTDFTFTISSLEAEDAATYYCQNDYSYPYTFGQGTKVEIK
BAP049-hum06-LC  ESGVPSRFSGSGSGTDFTFTISSLEAEDAATYYCQNDYSYPYTFGQGTKVEIK
BAP049-hum07-LC  ESGVPSRFSGSGSGTDFTFTISSLEAEDAATYYCQNDYSYPYTFGQGTKVEIK
BAP049-hum13-LC  ESGVPSRFSGSGSGTDFTFTISSLEAEDAATYYCQNDYSYPYTFGQGTKVEIK
BAP049-hum12-LC  ESGVPSRFSGSGSGTDFTFTISSLEAEDAATYYCQNDYSYPYTFGQGTKVEIK
BAP049-hum02-LC  ESGIPPRFSGSGYGTDFTLTINNIESEDAAYYFCQNDYSYPYTFGQGTKVEIK
BAP049-hum03-LC  ESGIPPRFSGSGYGTDFTLTINNIESEDAAYYFCQNDYSYPYTFGQGTKVEIK
BAP049-hum01-LC  ESGVPSRFSGSGSGTEFTLTISSLQPDDFATYYCQNDYSYPYTFGQGTKVEIK
BAP049-hum04-LC  ESGVPSRFSGSGSGTDFTFTISSLQPEDIATYYCQNDYSYPYTFGQGTKVEIK
BAP049-hum05-LC  ESGVPSRFSGSGSGTDFTFTISSLQPEDIATYYCQNDYSYPYTFGQGTKVEIK
```

FIGURE 10A

```
                              10        20        30        40        50        60
                         ....|....|....|....|....|....|....|....|....|....|....|....|
BAP049-chi-LC    DIVMTQSPSSLTVTAGEKVTMSCKSSQSLLDSGNQKNFLTWYQQKPGQPPKLLIFWASTR
BAP049-hum08-LC  E..L....DFQS..PK....IT..........................A.R...Y.....
BAP049-hum09-LC  E..L....DFQS..PK....IT..........................A.R...Y.....
BAP049-hum15-LC  E..L....DFQS..PK....IT..........................A.R...Y.....
BAP049-hum16-LC  E..L....DFQS..PK....IT..........................A.R...Y.....
BAP049-hum10-LC  E..L....AT.SLSP..RA.L...........................A.R...Y.....
BAP049-hum11-LC  E..L....AT.SLSP..RA.L...........................A.R...Y.....
BAP049-hum14-LC  E..L....AT.SLSP..RA.L...........................A.R...Y.....
BAP049-hum06-LC  ......T.L..P..P..PASI...........................A.R...Y.....
BAP049-hum07-LC  E..L....AT.SLSP..RA.L...........................KA.....Y.....
BAP049-hum13-LC  .V......L..P..L.QPASI...........................KA.....Y.....
BAP049-hum12-LC  ..Q........SASV.DR..IT....................L.....S.Q...Y.....
BAP049-hum02-LC  ..Q........SASV.DR..IT..........................A.R...Y.....
BAP049-hum03-LC  ..Q........SASV.DR..IT..........................A.R...Y.....
BAP049-hum01-LC  E..L....AT.SLSP..RA.L...........................A.R...Y.....
BAP049-hum04-LC  E..L....AT.SLSP..RA.L...........................KA.....Y.....
BAP049-hum05-LC  E..L....AT.SLSP..RA.L...........................KA.....Y.....

70        80        90        100       110
                         ....|....|....|....|....|....|....|....|....|....|....|...
BAP049-chi-LC    ESGVPDRFTGSGSVTDFTLTISSVQAEDLAVYYCQNDYSYPCTFGQGTKVEIK
BAP049-hum08-LC  .....S..S....G....F....LE...A.T..........Y...........
BAP049-hum09-LC  .....S..S....G....F....LE...A.T..........Y...........
BAP049-hum15-LC  .....S..S....G....F....LE...A.T..........Y...........
BAP049-hum16-LC  .....S..S....G....F....LE...A.T..........Y...........
BAP049-hum10-LC  .....S..S....G....F....LE...A.T..........Y...........
BAP049-hum11-LC  .....S..S....G....F....LE...A.T..........Y...........
BAP049-hum14-LC  .....S..S....G....F....LE...A.T..........Y...........
BAP049-hum06-LC  .....S..S....G....F....LE...A.T..........Y...........
BAP049-hum07-LC  .....S..S....G....F....LE...A.T..........Y...........
BAP049-hum13-LC  .....S..S....G....F....LE...A.T..........Y...........
BAP049-hum12-LC  .....S..S....G....F....LE...A.T..........Y...........
BAP049-hum02-LC  ...I.P..S...YG.......NNIES..A.Y.F........Y...........
BAP049-hum03-LC  ...I.P..S...YG.......NNIES..A.Y.F........Y...........
BAP049-hum01-LC  .....S..S....G.E.......L.PD.F.T..........Y...........
BAP049-hum04-LC  .....S..S....G....F....L.P..I.T..........Y...........
BAP049-hum05-LC  .....S..S....G....F....L.P..I.T..........Y...........
```

FIGURE 10B

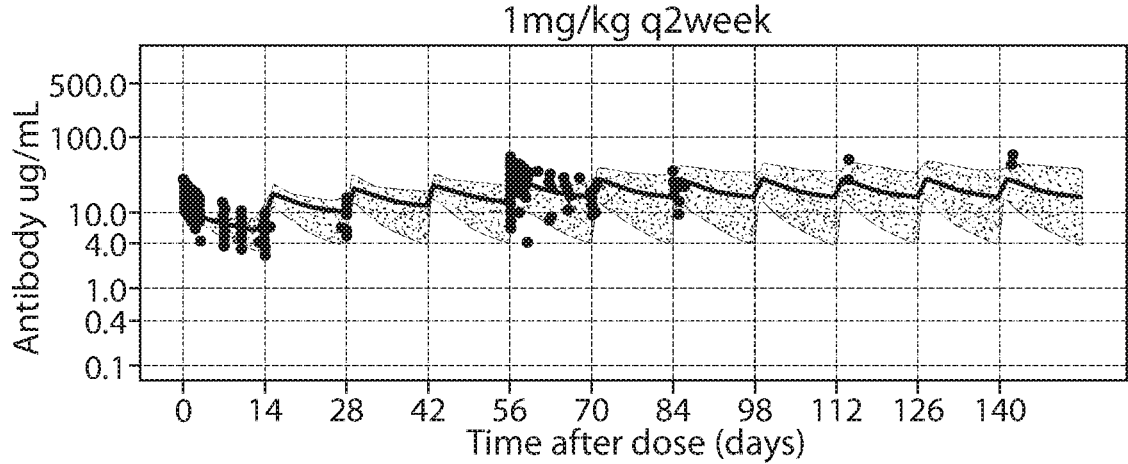
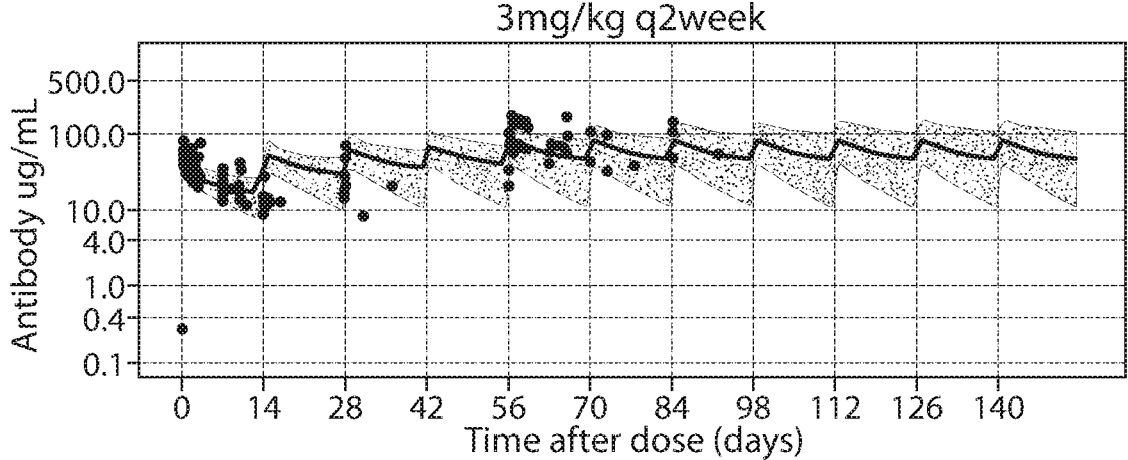
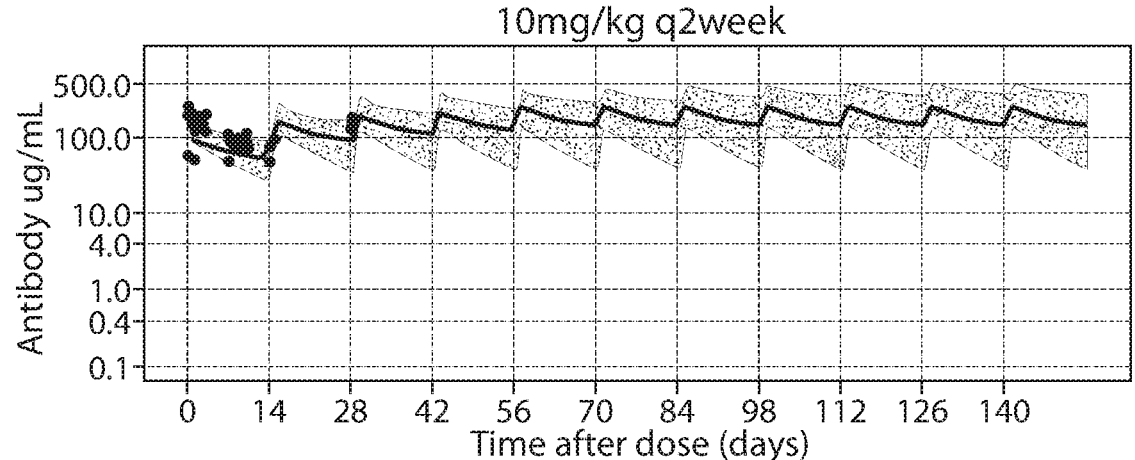
FIGURE 14A

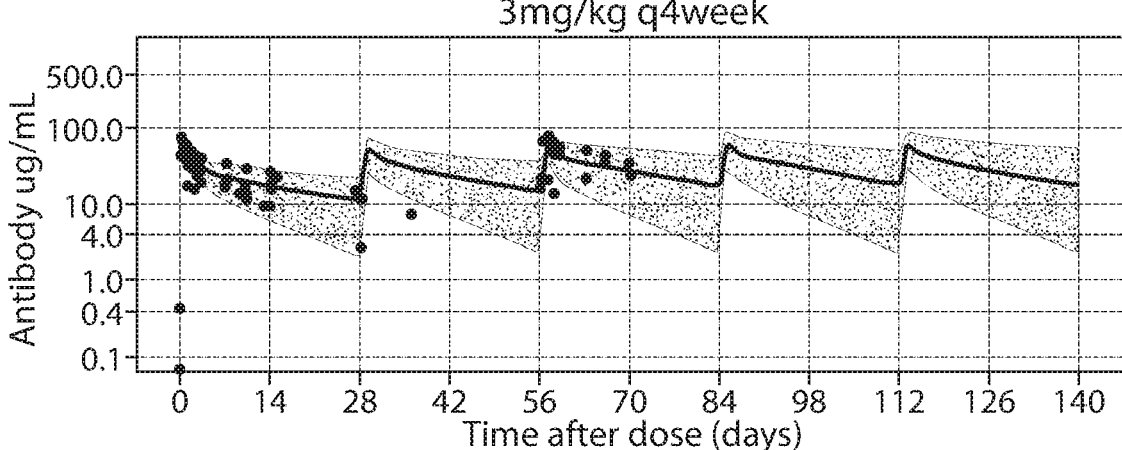
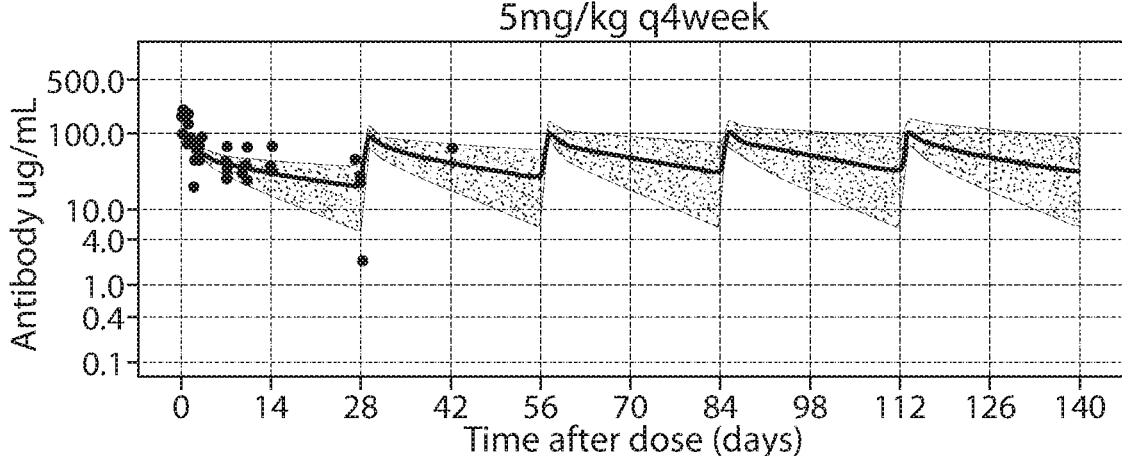
FIGURE 14B

Prior to Treatment          1st Restaging          2nd Restaging

Months

| BL archival-CD8 %<br>marker area: 3.49 | BL fresh-CD8 %<br>marker area: 5.61 | C2D1-CD8 %<br>marker area: 37.55 |

ANTIBODY MOLECULES TO PD-1 AND USES THEREOF

CROSS REFERENCE TO RELATED APPLICATIONS

This application is a U.S. National Phase Application under 35 U.S.C. § 371 of International Application No. PCT/US2016/067200, filed Dec. 16, 2016, which claims the benefit of U.S. Provisional Application No. 62/269,044, filed Dec. 17, 2015, U.S. Provisional Application No. 62/331, 371, filed May 3, 2016, U.S. Provisional Application No. 62/344,784, filed Jun. 2, 2016, U.S. Provisional Application No. 62/347,331, filed Jun. 8, 2016, U.S. Provisional Application No. 62/359,781, filed Jul. 8, 2016, U.S. Provisional Application No. 62/381,384, filed Aug. 30, 2016, U.S. Provisional Application No. 62/400,787, filed Sep. 28, 2016, U.S. Provisional Application No. 62/414,128, filed Oct. 28, 2016, and U.S. Provisional Application No. 62/431,846, filed Dec. 9, 2016. The contents of the aforementioned applications are hereby incorporated by reference in their entirety.

SEQUENCE LISTING

The instant application contains a Sequence Listing which has been submitted electronically in ASCII format and is hereby incorporated by reference in its entirety. Said ASCII copy, created on, Dec. 14, 2016, is named C2160-7015WO-_SL.txt and is 280,741 bytes in size.

BACKGROUND

The ability of T cells to mediate an immune response against an antigen requires two distinct signaling interactions (Viglietta, V. et al. (2007) *Neurotherapeutics* 4:666-675; Korman, A. J. et al. (2007) *Adv. Immunol.* 90:297-339). First, an antigen that has been arrayed on the surface of antigen-presenting cells (APC) is presented to an antigen-specific naive CD4$^+$ T cell. Such presentation delivers a signal via the T cell receptor (TCR) that directs the T cell to initiate an immune response specific to the presented antigen. Second, various co-stimulatory and inhibitory signals mediated through interactions between the APC and distinct T cell surface molecules trigger the activation and proliferation of the T cells and ultimately their inhibition.

The immune system is tightly controlled by a network of costimulatory and co-inhibitory ligands and receptors. These molecules provide the second signal for T cell activation and provide a balanced network of positive and negative signals to maximize immune responses against infection, while limiting immunity to self (Wang, L. et al. (Epub Mar. 7, 2011) *J. Exp. Med.* 208(3):577-92; Lepenies, B. et al. (2008) *Endocrine, Metabolic & Immune Disorders—Drug Targets* 8:279-288). Examples of costimulatory signals include the binding between the B7.1 (CD80) and B7.2 (CD86) ligands of the APC and the CD28 and CTLA-4 receptors of the CD4$^+$ T-lymphocyte (Sharpe, A. H. et al. (2002) *Nature Rev. Immunol.* 2:116-126; Lindley, P. S. et al. (2009) *Immunol. Rev.* 229:307-321). Binding of B7.1 or B7.2 to CD28 stimulates T cell activation, whereas binding of B7.1 or B7.2 to CTLA-4 inhibits such activation (Dong, C. et al. (2003) *Immunolog. Res.* 28(1):39-48; Greenwald, R. J. et al. (2005) *Ann. Rev. Immunol.* 23:515-548). CD28 is constitutively expressed on the surface of T cells (Gross, J., et al. (1992) *J. Immunol.* 149:380-388), whereas CTLA-4 expression is rapidly up-regulated following T-cell activation (Linsley, P. et al. (1996) *Immunity* 4:535-543).

Other ligands of the CD28 receptor include a group of related B7 molecules, also known as the "B7 Superfamily" (Coyle, A. J. et al. (2001) *Nature Immunol.* 2(3):203-209; Sharpe, A. H. et al. (2002) *Nature Rev. Immunol.* 2:116-126; Collins, M. et al. (2005) *Genome Biol.* 6:223.1-223.7; Korman, A. J. et al. (2007) *Adv. Immunol.* 90:297-339). Several members of the B7 Superfamily are known, including B7.1 (CD80), B7.2 (CD86), the inducible co-stimulator ligand (ICOS-L), the programmed death-1 ligand (PD-L1; B7-H1), the programmed death-2 ligand (PD-L2; B7-DC), B7-H3, B7-H4 and B7-H6 (Collins, M. et al. (2005) *Genome Biol.* 6:223.1-223.7).

The Programmed Death 1 (PD-1) protein is an inhibitory member of the extended CD28/CTLA-4 family of T cell regulators (Okazaki et al. (2002) *Curr Opin Immunol* 14:391779-82; Bennett et al. (2003) *J. Immunol.* 170:711-8). Other members of the CD28 family include CD28, CTLA-4, ICOS and BTLA. PD-1 is suggested to exist as a monomer, lacking the unpaired cysteine residue characteristic of other CD28 family members. PD-1 is expressed on activated B cells, T cells, and monocytes.

The PD-1 gene encodes a 55 kDa type I transmembrane protein (Agata et al. (1996) *Int Immunol.* 8:765-72). Although structurally similar to CTLA-4, PD-1 lacks the MYPPY motif (SEQ ID NO: 236) that is important for B7-1 and B7-2 binding. Two ligands for PD-1 have been identified, PD-L1 (B7-H1) and PD-L2 (B7-DC), that have been shown to downregulate T cell activation upon binding to PD-1 (Freeman et al. (2000) *J. Exp. Med.* 192:1027-34; Carter et al. (2002) *Eur. J. Immunol.* 32:634-43). Both PD-L1 and PD-L2 are B7 homologs that bind to PD-1, but do not bind to other CD28 family members. PD-L1 is abundant in a variety of human cancers (Dong et al. (2002) *Nat. Med.* 8:787-9).

PD-1 is known as an immunoinhibitory protein that negatively regulates TCR signals (Ishida, Y. et al. (1992) *EMBO J.* 11:3887-3895; Blank, C. et al. (Epub 2006 Dec. 29) *Immunol. Immunother.* 56(5):739-745). The interaction between PD-1 and PD-L1 can act as an immune checkpoint, which can lead to, e.g., a decrease in tumor infiltrating lymphocytes, a decrease in T-cell receptor mediated proliferation, and/or immune evasion by cancerous cells (Dong et al. (2003) *J. Mol. Med.* 81:281-7; Blank et al. (2005) *Cancer Immunol. Immunother.* 54:307-314; Konishi et al. (2004) *Clin. Cancer Res.* 10:5094-100). Immune suppression can be reversed by inhibiting the local interaction of PD-1 with PD-L1 or PD-L2; the effect is additive when the interaction of PD-1 with PD-L2 is blocked as well (Iwai et al. (2002) *Proc. Nat'l. Acad. Sci. USA* 99:12293-7; Brown et al. (2003) *J. Immunol.* 170:1257-66).

Given the importance of immune checkpoint pathways in regulating an immune response, the need exists for developing novel combination therapies that modulate the activity of immunoinhibitory proteins, such as PD-1, thus leading to activation of the immune system. Such agents can be used, e.g., for cancer immunotherapy and treatment of other conditions, such as chronic infection.

SUMMARY

Disclosed herein, at least in part, are antibody molecules (e.g., humanized antibody molecules) that bind to Programmed Death 1 (PD-1) with high affinity and specificity. Nucleic acid molecules encoding the antibody molecules, expression vectors, host cells and methods for making the antibody molecules are also provided. Pharmaceutical compositions and dose formulations comprising the antibody molecules are also provided. The anti-PD-1 antibody molecules disclosed herein can be used (alone or in combination with other agents or therapeutic modalities) to treat, prevent and/or diagnose disorders, such as cancerous disorders (e.g., solid and soft-tissue tumors), as well as infectious diseases (e.g., chronic infectious disorders or sepsis). Thus, compositions and methods for detecting PD-1, as well as methods for treating various disorders including cancer and/or infectious diseases, using the anti-PD-1 antibody molecules are disclosed herein. In certain embodiments, the anti-PD-1 antibody molecule is administered or used at a flat or fixed dose.

Accordingly, in one aspect, the invention features a method of treating (e.g., inhibiting, reducing, ameliorating, or preventing) a disorder, e.g., a hyperproliferative condition or disorder (e.g., a cancer) in a subject. The method includes administering to the subject an anti-PD-1 antibody molecule, e.g., an anti-PD-1 antibody molecule described herein, at a dose of about 300 mg to 400 mg once every three weeks or once every four weeks. In certain embodiments, the anti-PD-1 antibody molecule is administered at a dose of about 300 mg once every three weeks. In other embodiments, the anti-PD-1 antibody molecule is administered at a dose of about 400 mg once every four weeks. In some embodiments, the disorder is a cancer, e.g., a cancer described herein. In certain embodiments, the cancer is a skin cancer, e.g., a Merkel cell carcinoma or a melanoma. In one embodiment, the cancer is a Merkel cell carcinoma. In other embodiments, the cancer is a melanoma. In other embodiments, the cancer is a breast cancer, e.g., a triple negative breast cancer (TNBC) or a HER2-negative breast cancer. In other embodiments, the cancer is kidney cancer, e.g., a renal cell carcinoma (e.g., a clear cell renal cell carcinoma (CCRCC) or a non-clear cell renal cell carcinoma (nccRCC)). In other embodiments, the cancer is a thyroid cancer, e.g., an anaplastic thyroid carcinoma (ATC). In other embodiments, the cancer is a neuroendocrine tumor (NET), e.g., an atypical pulmonary carcinoid tumor or an NET in pancreas, gastrointestinal (GI) tract, or lung. In certain embodiments, the cancer is a lung cancer, e.g., a non-small cell lung cancer (NSCLC) (e.g., a squamous NSCLC or a non-squamous NSCLC). In certain embodiments, the cancer is an ovarian cancer. In certain embodiments, the cancer is a fallopian tube cancer. In certain embodiments, the cancer is a colorectal cancer (CRC) (e.g., a microsatellite instability-high colorectal cancer (MSI-high CRC) or a microsatellite stable colorectal cancer (MSS CRC)). In certain embodiments, the cancer is a leukemia (e.g., an acute myeloid leukemia (AML), e.g., a relapsed or refractory AML or a de novo AML). In certain embodiments, the cancer is a myelodysplastic syndrome (MDS) (e.g., a high risk MDS).

In some embodiments, the anti-PD-1 antibody molecule is administered at a dose of about 400 mg once every four weeks or about 300 mg once every three weeks to treat a lung cancer, e.g., a non-small cell lung cancer (NSCLC) (e.g., a squamous NSCLC or a non-squamous NSCLC). In some embodiments, the anti-PD-1 antibody molecule is administered at a dose of about 300 mg once every three weeks to treat a lung cancer, e.g., a non-small cell lung cancer (NSCLC) (e.g., a squamous NSCLC or a non-squamous NSCLC). In some embodiments, the anti-PD-1 antibody molecule is administered at a dose of about 400 mg once every four weeks to treat a skin cancer, e.g., a Merkel cell carcinoma or a melanoma. In certain embodiments, the anti-PD-1 antibody molecule is administered at a dose of about 400 mg once every four weeks to treat a Merkel cell carcinoma. In other embodiments, the anti-PD-1 antibody molecule is administered at a dose of about 400 mg once every four weeks to treat a melanoma. In some embodiments, the anti-PD-1 antibody molecule is administered at a dose of about 400 mg once every four weeks to treat a breast cancer, e.g., a triple negative breast cancer (TNBC) or a HER2-negative breast cancer. In some embodiments, the anti-PD-1 antibody molecule is administered at a dose of about 400 mg once every four weeks to treat a thyroid cancer, e.g., an anaplastic thyroid carcinoma (ATC). In some embodiments, the anti-PD-1 antibody molecule is administered at a dose of about 400 mg once every four weeks to treat a neuroendocrine tumor (NET), e.g., an atypical pulmonary carcinoid tumor or an NET in pancreas, gastrointestinal (GI) tract, or lung. In some embodiments, the anti-PD-1 antibody molecule is administered at a dose of about 400 mg once every four weeks to treat a kidney cancer, e.g., a renal cell carcinoma (e.g., a clear cell renal cell carcinoma (CCRCC) or a non-clear cell renal cell carcinoma (nccRCC)). In some embodiments, the anti-PD-1 antibody molecule is administered at a dose of about 400 mg once every four weeks to treat an ovarian cancer. In some embodiments, the anti-PD-1 antibody molecule is administered at a dose of about 400 mg once every four weeks to treat a fallopian tube cancer. In some embodiments, the anti-PD-1 antibody molecule is administered at a dose of about 400 mg once every four weeks to treat a colorectal cancer (e.g., a microsatellite instability-high colorectal cancer (MSI-high CRC) or a microsatellite stable colorectal cancer (MSS CRC)). In some embodiments, the anti-PD-1 antibody molecule is administered at a dose of about 400 mg once every four weeks to treat a leukemia (e.g., an AML, e.g., a relapsed or refractory AML or a de novo AML). In some embodiments, the anti-PD-1 antibody molecule is administered at a dose of about 400 mg once every four weeks to treat a myelodysplastic syndrome (MDS) (e.g., a high risk MDS).

In some embodiments, the anti-PD-1 antibody molecule is administered by injection (e.g., subcutaneously or intravenously) at a dose (e.g., a flat dose) of about 100 mg to 600 mg, e.g., about 200 mg to 500 mg, e.g., about 100 mg to 300 mg, about 250 mg to 450 mg, about 300 mg to 400 mg, about 250 mg to 350 mg, about 350 mg to 450 mg, or about 100 mg, about 200 mg, about 300 mg, or about 400 mg. The dosing schedule (e.g., flat dosing schedule) can vary from e.g., once a week to once every 2, 3, 4, 5, or 6 weeks. In one embodiment, the anti-PD-1 antibody molecule is administered at a dose from about 300 mg to 400 mg once every three weeks or once every four weeks. In one embodiment, the anti-PD-1 antibody molecule is administered at a dose from about 300 mg once every three weeks. In one embodiment, the anti-PD-1 antibody molecule is administered at a dose from about 400 mg once every four weeks. In one embodiment, the anti-PD-1 antibody molecule is administered at a dose from about 300 mg once every four weeks. In one embodiment, the anti-PD-1 antibody molecule is administered at a dose from about 400 mg once every three weeks.

In another aspect, the invention features a method of reducing an activity (e.g., growth, survival, or viability, or all), of a hyperproliferative (e.g., a cancer) cell. The method includes contacting the cell with an anti-PD-1 antibody molecule, e.g., an anti-PD-1 antibody molecule described herein. The method can be performed in a subject, e.g., as part of a therapeutic protocol, e.g., at a dose of about 300 mg to 400 mg of an anti-PD-1 antibody molecule once every three weeks or once every four weeks, In certain embodiments, the dose is about 300 mg of an anti-PD-1 antibody molecule once every three weeks. In other embodiments, the dose is about 400 mg of an anti-PD-1 antibody molecule once every four weeks. The cancer cell can be, e.g., a cell from a cancer described herein, such as lung cancer (squamous), lung cancer (adenocarcinoma), head and neck cancer, cervical cancer (squamous), stomach cancer, thyroid cancer, skin cancer, melanoma, nasopharyngeal cancer (e.g., differentiated or undifferentiated metastatic or locally recurrent nasopharyngeal carcinoma), kidney cancer, neuroendocrine tumor (NET), ovarian cancer, fallopian tube cancer, colorectal cancer, or breast cancer. In certain embodiments, the cancer is a skin cancer, e.g., a Merkel cell carcinoma or a melanoma. In one embodiment, the cancer is a Merkel cell carcinoma. In other embodiments, the cancer is a melanoma. In other embodiments, the cancer is a breast cancer, e.g., a triple negative breast cancer (TNBC) or a HER2-negative breast cancer. In other embodiments, the cancer is a kidney cancer, e.g., a renal cell carcinoma (e.g., clear cell renal cell carcinoma (CCRCC) or a non-clear cell renal cell carcinoma (nccRCC)). In other embodiments, the cancer is a thyroid cancer, e.g., an anaplastic thyroid carcinoma (ATC). In other embodiments, the cancer is a neuroendocrine tumor (NET), e.g., an atypical pulmonary carcinoid tumor or an NET in pancreas, gastrointestinal (GI) tract, or lung. In certain embodiments, the cancer is a lung cancer, e.g., a non-small cell lung cancer (NSCLC) (e.g., a squamous NSCLC or a non-squamous NSCLC). In certain embodiments, the cancer is an ovarian cancer. In certain embodiments, the cancer is a fallopian tube cancer. In certain embodiments, the cancer is a colorectal cancer (CRC) (e.g., a microsatellite instability-high colorectal cancer (MSI-high CRC) or a microsatellite stable colorectal cancer (MSS CRC)). In certain embodiments, the cancer is a leukemia (e.g., an acute myeloid leukemia (AML), e.g., a relapsed or refractory AML or a de novo AML). In certain embodiments, the cancer is a myelodysplastic syndrome (MDS) (e.g., a high risk MDS).

In another aspect, the invention features a composition (e.g., one or more compositions or dosage forms), that includes an anti-PD-1 antibody molecule (e.g., an anti-PD-1 antibody molecule as described herein). Formulations, e.g., dosage formulations, and kits, e.g., therapeutic kits, that include an anti-PD-1 antibody molecule (e.g., an anti-PD-1 antibody molecule as described herein), are also described herein. In certain embodiments, the composition or formulation comprises 300 mg or 400 mg of an anti-PD-1 antibody molecule (e.g., an anti-PD-1 antibody molecule as described herein). In some embodiments, the composition of formulation is administered or used once every three weeks or once every four weeks.

Also disclosed herein are methods and compositions comprising a combination of two, three or more therapeutic agents chosen from one, two, or all of the following categories (i)-(iii): (i) an agent that enhances antigen presentation (e.g., tumor antigen presentation); (ii) an agent that enhances an effector cell response (e.g., B cell and/or T cell activation and/or mobilization); or (iii) an agent that decreases tumor immunosuppression. In some embodiments, the combination includes an inhibitor of PD-1 (e.g., an anti-PD-1 antibody molecule as described herein). In certain embodiments, the anti-PD-1 antibody molecule is administered or used at a flat or fixed dose.

Without wishing to be bound by theory, it is believed that therapeutic approaches that enhance anti-tumor immunity work more effectively when the immune response is optimized by targeting multiple components at one or more stages of an immune response, e.g., an anti-tumor immune response. For example, approaches that enhance antigen presentation, e.g., by activation and/or maturation of dendritic cells, combined with approaches that enhance cellular and humoral immune responses (e.g., by stimulating, e.g., disinhibiting, phagocytes and/or tumor infiltrating lymphocytes (e.g., NK cells and T cells)), while blocking tumor immunosuppressive signaling (e.g., by increasing macrophage polarization, increasing $T_{reg}$ depletion and/or decreasing myeloid-derived suppressive cells (MDSCs)) can result in a more effective and/or prolonged therapeutic response. Accordingly, disclosed herein are combination therapies that optimize one, two, or all of: (i) antigen presentation, e.g., increasing antigen presentation (e.g., by enhancing one or more of dendritic cell activity or maturation, antigen uptake, or antigen processing); (ii) effector cell response, e.g., increasing effector cell response (e.g., enhancing B cell and/or T cell activation and/or mobilization, e.g., in the lymph node); or (iii) tumor immunosuppression, e.g., decreasing tumor immunosuppression (e.g., increasing T cell infiltration and tumor cell killing). The combinations described herein can provide a superior beneficial effect, e.g., in the treatment of a disorder, such as an enhanced anti-cancer effect, reduced toxicity and/or reduced side effects, compared to monotherapy administration of the therapeutic agents in the combination. For example, one or more of the therapeutic agents in the combination can be administered at a lower dosage, or for a shorter period of administration, than would be required to achieve the same therapeutic effect compared to the monotherapy administration. Thus, compositions and methods for treating cancer and other immune disorders using the aforesaid combination therapies are disclosed.

Accordingly, in one aspect, the invention features a method of treating (e.g., inhibiting, reducing, ameliorating, or preventing) a disorder, e.g., a hyperproliferative condition or disorder (e.g., a cancer) in a subject. The method includes administering to the subject a combination of two, three or more therapeutic agents chosen from one, two or all of the following categories (i)-(iii): (i) an agent that enhances antigen (e.g., tumor antigen) presentation; (ii) an agent that enhances an effector cell response (e.g., B cell and/or T cell activation and/or mobilization); or (iii) an agent that decreases tumor immunosuppression, thereby treating the disorder, e.g., the hyperproliferative condition or disorder (e.g., the cancer). In some embodiments, the combination includes a PD-1 inhibitor (e.g., an anti-PD-1 antibody molecule as described herein). The cancer treated can be, e.g., a cancer described herein, such as lung cancer (squamous), lung cancer (adenocarcinoma), head and neck cancer, cervical cancer (squamous), stomach cancer, thyroid cancer, skin cancer, melanoma, nasopharyngeal cancer (e.g., differentiated or undifferentiated metastatic or locally recurrent nasopharyngeal carcinoma), kidney cancer, neuroendocrine tumor (NET), or breast cancer. In certain embodiments, the cancer is a skin cancer, e.g., a Merkel cell carcinoma or a melanoma. In one embodiment, the cancer is a Merkel cell carcinoma. In other embodiments, the cancer is a melanoma. In other embodiments, the cancer is a breast cancer, e.g., a triple negative breast cancer (TNBC) or a HER2-negative breast cancer. In other embodiments, the cancer is kidney cancer, e.g., a renal cell carcinoma (e.g., clear cell renal cell carcinoma (CCRCC) or a non-clear cell renal cell carcinoma (nccRCC)). In other embodiments, the cancer is a thyroid cancer, e.g., an anaplastic thyroid carcinoma (ATC). In other embodiments, the cancer is a neuroendocrine tumor (NET), e.g., an atypical pulmonary carcinoid tumor or an NET in pancreas, gastrointestinal (GI) tract, or lung. In certain embodiments, the cancer is a lung cancer, e.g., a non-small cell lung cancer (NSCLC) (e.g., a squamous NSCLC or a non-squamous NSCLC). In certain embodiments, the cancer is an ovarian cancer. In certain embodiments, the cancer is a fallopian tube cancer. In certain embodiments, the cancer is a colorectal cancer (CRC) (e.g., a microsatellite instability-high colorectal cancer (MSI-high CRC) or a microsatellite stable colorectal cancer (MSS CRC)). In certain embodiments, the cancer is a leukemia (e.g., an acute myeloid leukemia (AML), e.g., a relapsed or refractory AML or a de novo AML). In certain embodiments, the cancer is a myelodysplastic syndrome (MDS) (e.g., a high risk MDS).

In another aspect, the invention features a method of reducing an activity (e.g., growth, survival, or viability, or all), of a hyperproliferative (e.g., a cancer) cell. The method includes contacting the cell with a combination of two, three or more therapeutic agents chosen from one, two or all of the following categories (i)-(iii): (i) an agent that enhances antigen (e.g., tumor antigen) presentation; (ii) an agent that enhances an effector cell response (e.g., B cell and/or T cell activation and/or mobilization); or (iii) an agent that decreases tumor immunosuppression, thereby reducing an activity in the hyperproliferative cell. In some embodiments, the combination includes a PD-1 inhibitor (e.g., an anti-PD-1 antibody molecule as described herein). The method can be performed in a subject, e.g., as part of a therapeutic protocol. The cancer cell can be, e.g., a cell from a cancer described herein, such as lung cancer (squamous), lung cancer (adenocarcinoma), head and neck cancer, cervical cancer (squamous), stomach cancer, thyroid cancer, skin cancer, melanoma, nasopharyngeal cancer (e.g., differentiated or undifferentiated metastatic or locally recurrent nasopharyngeal carcinoma), kidney cancer, neuroendocrine tumor (NET), ovarian cancer, fallopian tube cancer, colorectal cancer, or breast cancer. In certain embodiments, the cancer is a skin cancer, e.g., a Merkel cell carcinoma or a melanoma. In one embodiment, the cancer is a Merkel cell carcinoma. In other embodiments, the cancer is a melanoma. In other embodiments, the cancer is a breast cancer, e.g., a triple negative breast cancer (TNBC) or a HER2-negative breast cancer. In other embodiments, the cancer is kidney cancer, e.g., a renal cell carcinoma (e.g., clear cell renal cell carcinoma (CCRCC) or a non-clear cell renal cell carcinoma (nccRCC)). In other embodiments, the cancer is a thyroid cancer, e.g., an anaplastic thyroid carcinoma (ATC). In other embodiments, the cancer is a neuroendocrine tumor (NET), e.g., an atypical pulmonary carcinoid tumor, or an NET in pancreas, gastrointestinal (GI) tract, or lung. In certain embodiments, the cancer is a lung cancer, e.g., a non-small cell lung cancer (NSCLC) (e.g., a squamous NSCLC or a non-squamous NSCLC). In certain embodiments, the cancer is an ovarian cancer. In certain embodiments, the cancer is a fallopian tube cancer. In certain embodiments, the cancer is a colorectal cancer (CRC) (e.g., a microsatellite instability-high colorectal cancer (MSI-high CRC) or a microsatellite stable colorectal cancer (MSS CRC)). In certain embodiments, the cancer is a leukemia (e.g., an acute myeloid leukemia (AML), e.g., a relapsed or refractory AML or a de novo AML). In certain embodiments, the cancer is a myelodysplastic syndrome (MDS) (e.g., a high risk MDS).

In certain embodiments of the methods disclosed herein, the method further includes determining the level of an immune cell (e.g., a T cell) infiltrate (e.g., the level of tumor infiltrating lymphocytes (TIL)) in the subject. In one embodiment, the level of the immune cell infiltrate is determined in vivo, e.g., non-invasively (e.g., by detecting an antibody to a T cell marker detectably labeled using a suitable imaging technique, e.g., positron emission tomography (PET) scan). In other embodiments, the level of the immune cell infiltrate is determined in a sample (e.g., a tumor biopsy) acquired from the subject (e.g., using immunohistochemical techniques). In embodiments, responsive to a low level of, or no detectable, tumor infiltrate in the subject, one or more agents of categories (i) or (ii), or both (i) and (ii), is/are administered. In other embodiments, responsive to a detectable level, or an elevated level, of tumor infiltrate in the subject, one or more agents of category (iii) is/are administered. The detection steps can also be used, e.g., to monitor the effectiveness of a therapeutic agent described herein. For example, the detection step can be used to monitor the effectiveness of therapeutic agents of categories (i), (ii) and/or (iii).

In another aspect, the invention features a composition (e.g., one or more compositions or dosage forms), that includes a combination of two, three or more therapeutic agents chosen from one, two or all of the following categories (i)-(iii): (i) an agent that enhances antigen (e.g., tumor antigen) presentation; (ii) an agent that enhances an effector cell response (e.g., activation and/or mobilization of B cell and/or T cell); or (iii) an agent that decreases tumor immunosuppression. In some embodiments, the combination includes a PD-1 inhibitor (e.g., an anti-PD-1 antibody molecule as described herein).

In yet another aspect, the invention features a composition (e.g., one or more compositions or dosage forms as described herein), for use in treating a disorder, e.g., a cancer. In embodiments, the composition for use includes a combination of two, three or more therapeutic agents chosen from one, two or all of the following categories (i)-(iii): (i) an agent that enhances antigen (e.g., tumor antigen) presentation; (ii) an agent that enhances an effector cell response (e.g., activation and/or mobilization of B cell and/or T cell); or (iii) an agent that decreases tumor immunosuppression. In some embodiments, the combination used includes a PD-1 inhibitor (e.g., an anti-PD-1 antibody molecule as described herein). The cancer can be, e.g., a cancer described herein, such as lung cancer (squamous), lung cancer (adenocarcinoma), head and neck cancer, cervical cancer (squamous), stomach cancer, thyroid cancer, skin cancer, melanoma, nasopharyngeal cancer (e.g., differentiated or undifferentiated metastatic or locally recurrent nasopharyngeal carcinoma), kidney cancer, neuroendocrine tumor (NET), ovarian cancer, fallopian tube cancer, colorectal cancer, or breast cancer. In certain embodiments, the cancer is a skin cancer, e.g., a Merkel cell carcinoma or a melanoma. In one embodiment, the cancer is a Merkel cell carcinoma. In other embodiments, the cancer is a melanoma. In other embodiments, the cancer is a breast cancer, e.g., a triple negative breast cancer (TNBC) or a HER2-negative breast cancer. In other embodiments, the cancer is kidney cancer, e.g., a renal cell carcinoma (e.g., clear cell renal cell carcinoma (CCRCC) or a non-clear cell renal cell carcinoma (nccRCC)). In other embodiments, the cancer is a thyroid cancer, e.g., an anaplastic thyroid carcinoma (ATC). In other embodiments, the cancer is a neuroendocrine tumor (NET), e.g., an atypical pulmonary carcinoid tumor, or an NET in pancreas, gastrointestinal (GI) tract, or lung. In certain embodiments, the cancer is a lung cancer, e.g., a non-small cell lung cancer (NSCLC) (e.g., a squamous NSCLC or a non-squamous NSCLC). In certain embodiments, the cancer is an ovarian cancer. In certain embodiments, the cancer is a fallopian tube cancer. In certain embodiments, the cancer is a colorectal cancer (CRC) (e.g., a microsatellite instability-high colorectal cancer (MSI-high CRC) or a microsatellite stable colorectal cancer (MSS CRC)). In certain embodiments, the cancer is a leukemia (e.g., an acute myeloid leukemia (AML), e.g., a relapsed or refractory AML or a de novo AML). In certain embodiments, the cancer is a myelodysplastic syndrome (MDS) (e.g., a high risk MDS).

Formulations, e.g., dosage formulations, and kits, e.g., therapeutic kits, that include a combination of two, three or more therapeutic agents chosen from one, two or all of the following categories (i)-(iii): (i) an agent that enhances antigen (e.g., tumor antigen) presentation; (ii) an agent that enhances an effector cell response (e.g., activation and/or mobilization of B cell and/or T cell); or (iii) an agent that decreases tumor immunosuppression, thereby reducing an activity in the cell, and (optionally) instructions for use, are also disclosed. In some embodiments, the combination includes a PD-1 inhibitor (e.g., an anti-PD-1 antibody molecule as described herein).

The combinations of therapeutic agents disclosed herein include two or more therapeutic agents described herein. The therapeutic agents in the combination can belong to the same category, e.g., two or more therapeutic agents of category (i), or can include at least one agent of two or more categories (e.g., a therapeutic agent of category (i) combined with a therapeutic agent of category (ii)), as described below. Certain therapeutic agents can belong to two or more categories of categories (i)-(iii). For example, a therapeutic agent (e.g., a GITR agonist, an IDO antagonist, a TGF-b inhibitor, among others) can act as a therapeutic agent in multiple categories.

Additional features or embodiments of the methods, compositions, dosage formulations, and kits described herein include one or more of the following:

Combinations

In certain embodiments, the combination includes one, two, three, four or more therapeutic agents that enhance antigen (e.g., tumor antigen) presentation (referred to herein as an "antigen-presentation combination"). In certain embodiments, the antigen presentation combination includes one or more of: an agent that enhances antigen presentation (e.g., a vaccine, e.g., a cell- or antigen-based vaccine); an agent that enhances lysis of tumor cells (e.g., an oncolytic virus); an agent that stimulates (e.g., disinhibits) a phagocyte, e.g., a Type I interferon (IFN) activator (e.g., a TLR agonist, a RIG-I-like receptor agonist (RLRs)), and/or an agent that activates and/or recruits a dendritic cell or a macrophage (e.g., a macrophage I), e.g., a bi- or tri-specific cell engager.

In some embodiments, the antigen-presentation combination includes one, two, three, four, five or more therapeutic agents chosen from: (i) an agonist of Stimulator of Interferon Genes (a STING agonist), (ii) an agonist of a Toll-like receptor (TLR) (e.g., an agonist of TLR-3, -4, -5, -7, -8, or -9), (iii) a TIM-3 modulator (e.g., an anti-TIM-3 antibody molecule), (iv) a vascular endothelial growth factor receptor (VEGFR) inhibitor, (v) a c-Met inhibitor, (vi) a TGFb inhibitor (e.g., an anti-TGFb antibody), (vii) an IDO/TDO inhibitor, (viii) an A2AR antagonist, (ix) an oncolytic virus, (x) a vaccine (e.g., a scaffold vaccine), or (xi) a bi- or tri-specific cell engager. Any combination of the aforesaid agents (i)-(xi) can be used in the antigen-presentation combination. In one exemplary embodiment, the antigen-presentation combination includes a STING agonist. In another exemplary embodiment, the antigen-presentation combination includes a TLR agonist (e.g., a TLR7 agonist). In another exemplary embodiment, the antigen-presentation combination includes a STING agonist and a TLR agonist (e.g., a TLR7 agonist). In some embodiments, the antigen presentation combination is chosen from a STING agonist, a TLR agonist, an A2AR antagonist, or an oncolytic virus or a combination thereof, and optionally, one or more of (iii)-(vii) or (x)-(xi). In some embodiments, the antigen presentation combination is chosen from a STING agonist or a TLR agonist, or a combination of both, and optionally, one or more of (iii)-(xi). In another embodiment, the antigen-presentation combination includes a STING agonist, a TLR agonist (e.g., a TLR7 agonist) and a TIM-3 modulator (e.g., an anti-TIM-3 inhibitor). In another embodiment, the antigen-presentation combination includes a STING agonist, a TLR agonist (e.g., a TLR7 agonist) and a VEGFR inhibitor. In another embodiment, the antigen-presentation combination includes a STING agonist, a TLR agonist (e.g., a TLR7 agonist) and a c-MET inhibitor. In yet other embodiments, the antigen-presenting combination includes an oncolytic virus. In other embodiments, the antigen-presenting combination includes an oncolytic virus and a cytokine, e.g., an oncolytic virus expressing one or more of GM-CSF, or a CSF (e.g., CSF1, or CSF2). In some embodiments, the antigen-presenting combination includes a bi- or tri-specific cell engager, e.g., a bi- or tri-specific antibody molecule to CD47 and CD19, with or without an Fc domain. In some embodiments, the antigen-presenting combination includes a TGFb inhibitor (e.g., an anti-TGFb antibody). In other embodiments, the antigen-presenting combination includes an IDO/TDO inhibitor. In yet other embodiments, the antigen-presenting combination includes an A2AR antagonist. In yet other embodiments, the antigen-presenting combination includes a vaccine (e.g., IL-2 in combination with MUC1, or a dendritic cell based vaccine (e.g., Provenge®)). In yet other embodiments, the antigen-presenting combination includes a vaccine and a TLR agonist (e.g., a TLR agonist as described herein). In certain embodiment, the antigen-presentation combination includes a vaccine and a STING agonist. In certain embodiment, the antigen-presentation combination includes a vaccine, a STING agonist and a TLR agonist.

In certain embodiments, the combination includes one, two, three, four, five or more therapeutic agents that enhance an effector cell response (referred to herein as an "effector cell combination"). In some embodiments, the effector cell combination includes a lymphocyte activator, e.g., an NK cell activator and/or a T cell activator. In some embodiments, the effector cell combination activates (e.g., disinhibits) a tumor infiltrating lymphocyte (TIL), e.g., an NK cell or a T cell. In some embodiments, the effector cell combination includes an NK cell modulator chosen from a modulator (e.g., an antibody molecule) of an NK receptor (e.g., a modulator of one or more of NKG2A, KIR3DL, NKp46, MICA or CEACAM1); an interleukin or an interleukin variant (e.g., IL-2, IL-15, IL-21, IL-13R or IL-12 cytokine or variant thereof, or a combination thereof); a bi- or tri-specific cell engager (e.g., a bispecific antibody molecule of NKG2A and CD138, or a bispecific antibody molecule of CD3 and TCR); an NK cell therapy; or a vaccine that includes NK cells and an antigen/immune stimulant. In some embodiments, the effector cell combination includes an immunomodulator (e.g., one or more of: an activator of a costimulatory molecule or an inhibitor of an immune checkpoint molecule as described herein). In some embodiments, the effector cell combination includes a T cell modulator chosen from an inhibitor of a checkpoint inhibitor (e.g., an inhibitor of one or more of: PD-1, PD-L1, TIM-3, LAG-3, VISTA, DKG-α, B7-H3, B7-H4, TIGIT, CTLA-4, BTLA, CD160, TIM1, IDO, LAIR1, IL-12, or a combination thereof, e.g., an inhibitor of PD-1 and TIM-3, or an inhibitor of PD-1 and LAG-3). In one embodiment, the inhibitor of the checkpoint inhibitor is an antibody molecule (e.g., a mono- or bispecific antibody or fragment thereof as described herein). For example, the inhibitor of the checkpoint inhibitor is an antibody molecule against PD-1, PD-L1, TIM-3, LAG-3, VISTA, B7-H4, CTLA-4 or TIGIT, or any combination thereof (e.g. a combination as described herein). In some embodiments, the effector cell combination includes a T cell modulator chosen from an agonist or an activator of a costimulatory molecule. In one embodiment, the agonist of the costimulatory molecule is chosen from an agonist (e.g., an agonistic antibody or antigen-binding fragment thereof, or a soluble fusion) of GITR, OX40, ICOS, SLAM (e.g., SLAMF7), HVEM, LIGHT, CD2, CD27, CD28, CDS, ICAM-1, LFA-1 (CD11a/CD18), ICOS (CD278), 4-1BB (CD137), CD30, CD40, BAFFR, CD7, NKG2C, NKp80, CD160, B7-H3, or CD83 ligand. In other embodiments, the effector cell combination includes a bispecific T cell engager (e.g., a bispecific antibody molecule that binds to CD3 and a tumor antigen (e.g., EGFR, PSCA, PSMA, EpCAM, HER2 among others)).

In some embodiments, the effector cell combination includes one, two, three, four, five or more therapeutic agents chosen from: (i) a GITR modulator (e.g., a GITR agonist), (ii) a PD-1 inhibitor (e.g., an anti-PD-1 antibody molecule as described herein), (iii) a PD-L1 inhibitor, (iv) an inhibitor of IAP (Inhibitor of Apoptosis Protein), (v) an inhibitor of EGFR (Epidermal Growth Factor Receptor), (vi) an inhibitor of target of rapamycin (mTOR), (vii) IL-15 or a variant thereof, (viii) a CTLA-4 inhibitor, (ix) a bispecific T cell engager (e.g., a bispecific antibody molecule that binds to CD3 and a tumor antigen (e.g., EGFR, PSCA, PSMA, EpCAM, HER2 among others), (x) a CD40 agonist (e.g., an anti-CD40 antibody molecule), (xi) an OX40 agonist (e.g., an anti-OX40 antibody molecule), or (xii) a CD27 agonist (e.g., an anti-CD27 antibody molecule). Any combination of the aforesaid agents can be used in the effector cell combination. In one exemplary embodiment, the effector cell combination includes a GITR agonist. In another embodiment, the effector cell combination includes a PD-1 inhibitor (e.g., an anti-PD-1 antibody molecule as described herein). In another embodiment, the effector cell combination includes a PD-L1 inhibitor. In other embodiments, the effector cell combination includes a GITR agonist and a PD-1 inhibitor (e.g., an anti-PD-1 antibody molecule as described herein). In other embodiments, the effector cell combination includes a GITR agonist and a PD-L1 inhibitor. In other embodiments, the effector cell combination includes a GITR agonist, a PD-1 inhibitor (e.g., an anti-PD-1 antibody molecule as described herein), and a PD-L1 inhibitor. In other embodiments, the effector cell combination includes a PD-1 inhibitor (e.g., an anti-PD-1 antibody molecule as described herein), and a PD-L1 inhibitor. In one embodiment, the effector cell combination includes a GITR agonist and an inhibitor of IAP. In another embodiment, the effector cell combination includes a GITR agonist and an inhibitor of an EGFR inhibitor. In yet another embodiment, the effector cell combination includes a GITR agonist and an inhibitor of an mTOR inhibitor. In one embodiment, the effector cell combination includes IL-15 or a variant thereof. In one embodiment, the effector cell combination includes a CTLA-4 inhibitor. In one embodiment, the effector cell combination includes a bispecific T cell engager (e.g., a bispecific antibody molecule that binds to CD3 and a tumor antigen (e.g., EGFR, PSCA, PSMA, EpCAM, HER2 among others). In one embodiment, the effector cell combination includes a CD40 agonist (e.g., an anti-CD40 antibody molecule). In one embodiment, the effector cell combination includes an OX40 agonist (e.g., an anti-OX40 antibody molecule). In one embodiment, the effector cell combination includes a CD27 agonist (e.g., an anti-CD27 antibody molecule).

In certain embodiments, the combination includes one, two, three, four, five or more therapeutic agents that decrease tumor immunosuppression (referred to herein as an "anti-tumor immunosuppression combination"). In some embodiments, the combination modulates the activity or level of one or more of $T_{reg}$, macrophage 2 or MDSCs. In some embodiments, the combination increases one or more of M2 polarization, $T_{reg}$ depletion, or T cell recruitment. In some embodiments, the anti-tumor immunosuppression combination includes one, two, three, four, five or more therapeutic agents chosen from: (i) an immunomodulator (e.g., one or more of: an activator of a costimulatory molecule (e.g., a GITR agonist), or an inhibitor of an immune checkpoint molecule (e.g., one or more of PD-1, PD-L1, LAG-3, TIM-3 or CTLA-4), as described herein), (ii) a CSF-1/1R inhibitor (e.g., an inhibitor of macrophage colony-stimulating factor (M-CSF)), (iii) an IL-17 inhibitor, (iv) an IL-1β inhibitor, (v) a CXCR2 inhibitor, (vi) an inhibitor of a phosphoinositide 3-kinase (PI3K, e.g., PI3Kγ or PI3Kδ), (vii) a BAFF-R inhibitor, (viii) a MALT-1/BTK inhibitor, (ix) a JAK inhibitor, (x) a CRTH2 inhibitor, (xi) a VEGFR inhibitor, (xiii) an IL-15 or a variant thereof, (xiv) a CTLA-4 inhibitor, (xv) an IDO/TDO inhibitor, (xvi) an A2AR antagonist, (xvii) a TGFb inhibitor, or (xviii) a PFKFB3 inhibitor. In certain embodiments, the immunomodulator is an inhibitor of an immune checkpoint molecule (e.g., an inhibitor of PD-1, PD-L1, LAG-3, TIM-3, CEACAM (e.g., CEACAM-1, -3 and/or -5), or CTLA-4, or any combination thereof). Any combination of the aforesaid agents can be used in the tumor immunosuppression combination. In one exemplary embodiment, the anti-tumor immunosuppression combination includes one, two, three, four, five or more therapeutic agents chosen from a PD-1 inhibitor (e.g., an anti-PD-1 antibody molecule as described herein), a PD-L1 inhibitor, a LAG-3 inhibitor, a TIM-3 modulator (e.g., an anti-TIM-3 inhibitor), a GITR agonist, a CSF-1/1R inhibitor (e.g., an M-CSF inhibitor), an IL-17 inhibitor, an IL-1β inhibitor, or a CXCR2 inhibitor. In one embodiment, the anti-tumor immunosuppression combination includes one, two, or all of a CSF-1/1R inhibitor (e.g., an M-CSF inhibitor), an IL-17 inhibitor, an IL-1β inhibitor. In one embodiment, the anti-tumor immunosuppression combination includes an IL-17 inhibitor, a CXCR2 inhibitor, a CRTH2 inhibitor, an A2AR antagonist, or a PFKFB3 inhibitor, or a combination thereof.

In some embodiments, the combination includes one or more therapeutic agents of the antigen-presentation combination. In other embodiments, the combination includes one or more therapeutic agents of the effector cell combination. In yet other embodiments, the combination includes one or more therapeutic agents of the anti-tumor immunosuppression combination. In other embodiments, the combination includes one or more therapeutic agents of the antigen-presentation combination and one or more therapeutic agents of the effector cell combination. In other embodiments, the combination includes one or more therapeutic agents of the antigen-presentation combination and one or more therapeutic agents of the anti-tumor immunosuppression combination. In other embodiments, the combination includes one or more therapeutic agents of the antigen-presentation combination, one or more therapeutic agents of the effector cell combination and one or more therapeutic agents of the anti-tumor immunosuppression combination. In other embodiments, the combination includes one or more therapeutic agents of the antigen-presentation combination, one or more therapeutic agents of the effector cell combination and one or more therapeutic agents of the anti-tumor immunosuppression combination.

In certain embodiments, the combination includes:

(i) one or more therapeutic agents of the antigen-presentation combination chosen from one, two or all of a STING agonist, a TLR agonist (e.g., a TLR7 agonist), or a TIM-3 modulator (e.g., a TIM-3 inhibitor);

(ii) one or more therapeutic agents of the effector cell combination chosen from one, two or all of a GITR modulator (e.g., a GITR agonist), a PD-1 inhibitor (e.g., an anti-PD-1 antibody molecule as described herein), or a PD-L1 inhibitor;

(iii) one or more therapeutic agents of the anti-tumor immunosuppression combination chosen from one, two or all of a CSF-1/1R inhibitor (e.g., an M-CSF inhibitor), an IL-17 inhibitor, or an IL-1β inhibitor:

(iv) a combination of (i) and (ii);

(v) a combination of (i) and (iii);

(vi) a combination of (ii) and (iii); or (vii) a combination of (i), (ii) and (iii).

The combination can be used to treat a cancer as described herein, such as lung cancer (squamous), lung cancer (adenocarcinoma), head and neck cancer, cervical cancer (squamous), stomach cancer, thyroid cancer, skin cancer, melanoma (e.g., advanced melanoma), nasopharyngeal cancer, kidney cancer, neuroendocrine tumor (NET), ovarian cancer, fallopian tube cancer, colorectal cancer, or breast cancer. In certain embodiments, the cancer is a skin cancer, e.g., a Merkel cell carcinoma or a melanoma. In one embodiment, the cancer is a Merkel cell carcinoma. In other embodiments, the cancer is a melanoma. In other embodiments, the cancer is a breast cancer, e.g., a triple negative breast cancer (TNBC) or a HER2-negative breast cancer. In other embodiments, the cancer is kidney cancer, e.g., a renal cell carcinoma (e.g., clear cell renal cell carcinoma (CCRCC) or a non-clear cell renal cell carcinoma (nccRCC)). In other embodiments, the cancer is a thyroid cancer, e.g., an anaplastic thyroid carcinoma (ATC). In other embodiments, the cancer is a neuroendocrine tumor (NET), e.g., an atypical pulmonary carcinoid tumor or an NET in pancreas, gastrointestinal (GI) tract, or lung. In certain embodiments, the cancer is a lung cancer, e.g., a non-small cell lung cancer (NSCLC) (e.g., a squamous NSCLC or a non-squamous NSCLC). In certain embodiments, the cancer is an ovarian cancer. In certain embodiments, the cancer is a fallopian tube cancer. In certain embodiments, the cancer is a colorectal cancer (CRC) (e.g., a microsatellite instability-high colorectal cancer (MSI-high CRC) or a microsatellite stable colorectal cancer (MSS CRC)). In certain embodiments, the cancer is a leukemia (e.g., an acute myeloid leukemia (AML), e.g., a relapsed or refractory AML or a de novo AML). In certain embodiments, the cancer is a myelodysplastic syndrome (MDS) (e.g., a high risk MDS).

In other embodiments, the combination includes a therapeutic agent from the antigen-presentation combination (e.g., one or more of a STING agonist, a TLR agonist, a vaccine or an oncolytic virus) in combination with a therapeutic agent from the effector cell and/or anti-tumor immunosuppression combination (e.g., an inhibitor of a checkpoint inhibitor, e.g., an inhibitor of PD-1, PD-L1, LAG-3, TIM-3, CEACAM (e.g., CEACAM-1, -3 and/or -5), or CTLA-4, or any combination thereof. In one embodiment, one or more of a STING agonist, a TLR agonist, a vaccine or an oncolytic virus is administered in combination with an anti-PD-1 antibody molecule as described herein. In one embodiment, a STING agonist and/or a vaccine is administered in combination with an anti-PD-1 antibody molecule as described herein. In one embodiment, an oncolytic virus is administered in combination with an anti-PD-1 antibody molecule as described herein. The combination can be used to treat a cancer as described herein, such as lung cancer (squamous), lung cancer (adenocarcinoma), head and neck cancer, cervical cancer (squamous), stomach cancer, thyroid cancer, skin cancer, melanoma (e.g., advanced melanoma), nasopharyngeal cancer, kidney cancer, neuroendocrine tumor (NET), ovarian cancer, fallopian tube cancer, colorectal cancer, or breast cancer. In certain embodiments, the cancer is a skin cancer, e.g., a Merkel cell carcinoma or a melanoma. In one embodiment, the cancer is a Merkel cell carcinoma. In other embodiments, the cancer is a melanoma. In other embodiments, the cancer is a breast cancer, e.g., a triple negative breast cancer (TNBC) or a HER2-negative breast cancer. In other embodiments, the cancer is kidney cancer, e.g., a renal cell carcinoma (e.g., clear cell renal cell carcinoma (CCRCC) or a non-clear cell renal cell carcinoma (nccRCC)). In other embodiments, the cancer is a thyroid cancer, e.g., an anaplastic thyroid carcinoma (ATC). In other embodiments, the cancer is a neuroendocrine tumor (NET), e.g., an atypical pulmonary carcinoid tumor or an NET in pancreas, gastrointestinal (GI) tract, or lung. In certain embodiments, the cancer is a lung cancer, e.g., a non-small cell lung cancer (NSCLC) (e.g., a squamous NSCLC or a non-squamous NSCLC). In certain embodiments, the cancer is an ovarian cancer. In certain embodiments, the cancer is a fallopian tube cancer. In certain embodiments, the cancer is a colorectal cancer (CRC) (e.g., a microsatellite instability-high colorectal cancer (MSI-high CRC) or a microsatellite stable colorectal cancer (MSS CRC)). In certain embodiments, the cancer is a leukemia (e.g., an acute myeloid leukemia (AML), e.g., a relapsed or refractory AML or a de novo AML). In certain embodiments, the cancer is a myelodysplastic syndrome (MDS) (e.g., a high risk MDS).

In certain embodiments, the combination includes a combination of therapeutic agents as provided in the section entitled "Exemplary Combinations of Antigen-Presentation Combinations, Effector Cell Combinations and Anti-tumor Immunosuppression Combinations" provided in the Detailed Description.

In certain embodiments, the combination includes an inhibitor of an immune checkpoint molecule, e.g., an inhibitor of PD-1 (e.g., an anti-PD-1 antibody molecule described herein), and an IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003. In some embodiments, the inhibitor of an immune checkpoint molecule, e.g., the inhibitor of PD-1 (e.g., the anti-PD-1 antibody molecule), is administered at a dose between 200 mg and 600 mg (e.g., at a dose of 400 mg), e.g., once every 4 weeks, e.g., intravenously. In some embodiments, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, is administered at a dose between 200 mg and 400 mg (e.g., at a dose of 300 mg), e.g., once every week, e.g., orally. In certain embodiments, the combination is used to treat a cancer described herein, e.g., a colorectal cancer, a lung cancer (e.g., a non-small cell lung cancer (NSCLC)), or a breast cancer (e.g., a triple-negative breast cancer (e.g., NTBC)).

In other embodiments, the combination includes an inhibitor of an immune checkpoint molecule, e.g., an inhibitor of PD-1 (e.g., an anti-PD-1 antibody molecule described herein), and an mTOR inhibitor, Everolimus (Compound A36), or a compound disclosed in PCT Publication No. WO 2014/085318. In some embodiments, the inhibitor of an immune checkpoint molecule, e.g., the inhibitor of PD-1 (e.g., the anti-PD-1 antibody molecule), is administered at a dose between 200 mg and 600 mg (e.g., at a dose of 400 mg), e.g., once every 4 weeks, e.g., intravenously. In some embodiments, the mTOR inhibitor, Everolimus (Compound A36), or a compound disclosed in PCT Publication No. WO 2014/085318, is administered at a dose between 2 mg and 8 mg (e.g., at a dose of 5 mg), e.g., once every week, e.g., orally. In certain embodiments, the combination is used to treat a cancer described herein, e.g., a colorectal cancer, a lung cancer (e.g., a non-small cell lung cancer (NSCLC)), or a breast cancer (e.g., a triple-negative breast cancer (e.g., NTBC)).

In other embodiments, the combination includes an inhibitor of an immune checkpoint molecule, e.g., an inhibitor of PD-1 (e.g., an anti-PD-1 antibody molecule described herein), and a DAC inhibitor, Panobinostat (Compound A19), or a compound disclosed in PCT Publication No. WO 2014/072493. In some embodiments, the inhibitor of an immune checkpoint molecule, e.g., the inhibitor of PD-1 (e.g., the anti-PD-1 antibody molecule), is administered at a dose between 200 mg and 600 mg (e.g., at a dose of 400 mg), e.g., once every 4 weeks, e.g., intravenously. In some embodiments, the DAC inhibitor, Panobinostat (Compound A19), or a compound disclosed in PCT Publication No. WO 2014/072493, is administered at a dose between 5 mg and 15 mg (e.g., at a dose of 10 mg), e.g., three times in a week (e.g., on the schedule of one week on/one week off), e.g., orally. In certain embodiments, the combination is used to treat a cancer described herein, e.g., a colorectal cancer, a lung cancer (e.g., a non-small cell lung cancer (NSCLC)), or a breast cancer (e.g., a triple-negative breast cancer (e.g., NTBC)).

In other embodiments, the combination includes an inhibitor of an immune checkpoint molecule, e.g., an inhibitor of PD-1 (e.g., an anti-PD-1 antibody molecule described herein), and an IL-1β inhibitor, canakinumab, or a compound disclosed in PCT Publication No. WO 2002/16436. In some embodiments, the inhibitor of an immune checkpoint molecule, e.g., the inhibitor of PD-1 (e.g., the anti-PD-1 antibody molecule), is administered at a dose between 200 mg and 600 mg (e.g., at a dose of 400 mg), e.g., once every 4 weeks, e.g., intravenously. In some embodiments, the IL-1β inhibitor, canakinumab, or a compound disclosed in PCT Publication No. WO 2002/16436, is administered at a dose between 50 mg and 150 mg (e.g., at a dose of 100 mg), e.g., once every eight weeks, e.g., subcutaneously. In certain embodiments, the combination is used to treat a cancer described herein, e.g., a colorectal cancer (e.g., a microsatellite stable colorectal cancer (MSS CRC)), a lung cancer (e.g., a non-small cell lung cancer (NSCLC)), or a breast cancer (e.g., a triple-negative breast cancer (e.g., NTBC)).

In other embodiments, the combination includes an inhibitor of an immune checkpoint molecule, e.g., an inhibitor of PD-1 (e.g., an anti-PD-1 antibody molecule described herein), and an IL-17 inhibitor, CJM112, or a compound disclosed in PCT Publication No. WO 2014/122613. In some embodiments, the inhibitor of an immune checkpoint molecule, e.g., the inhibitor of PD-1 (e.g., the anti-PD-1 antibody molecule), is administered at a dose between 200 mg and 600 mg (e.g., at a dose of 400 mg), e.g., once every 4 weeks, e.g., intravenously. In some embodiments, the IL-17 inhibitor, CJM112, or a compound disclosed in PCT Publication No. WO 2014/122613, is administered at a dose between 10 mg and 50 mg (e.g., at a dose of 25 mg), e.g., once every four weeks, e.g., intravenously. In certain embodiments, the combination is used to treat a cancer described herein, e.g., a colorectal cancer (e.g., an MSS CRC), a lung cancer (e.g., a non-small cell lung cancer (NSCLC)), or a breast cancer (e.g., a triple-negative breast cancer (e.g., NTBC)).

In other embodiments, the combination includes an inhibitor of an immune checkpoint molecule, e.g., an inhibitor of PD-1 (e.g., an anti-PD-1 antibody molecule described herein), and a MEK inhibitor or trametinib. In some embodiments, the inhibitor of an immune checkpoint molecule, e.g., the inhibitor of PD-1 (e.g., the anti-PD-1 antibody molecule), is administered at a dose between 200 mg and 600 mg (e.g., at a dose of 400 mg), e.g., once every 4 weeks, e.g., intravenously. In some embodiments, the MEK inhibitor or trametinib, is administered at a dose between 0.2 mg and 1 mg (e.g., at a dose of 0.5 mg), e.g., once a day, e.g., orally. In certain embodiments, the combination is used to treat a cancer described herein, e.g., a colorectal cancer, a lung cancer (e.g., a non-small cell lung cancer (NSCLC)), or a breast cancer (e.g., a triple-negative breast cancer (e.g., NTBC)).

In certain embodiments, the combination includes an inhibitor of an immune checkpoint molecule, e.g., an inhibitor of PD-1 (e.g., an anti-PD-1 antibody molecule described herein), a BRAF inhibitor or dabrafenib, and a MEK inhibitor or trametinib. In some embodiments, the inhibitor of an immune checkpoint molecule, e.g., the inhibitor of PD-1 (e.g., the anti-PD-1 antibody molecule), is administered at a dose between 200 mg and 600 mg (e.g., at a dose of 400 mg), e.g., once every 4 weeks, e.g., intravenously. In some embodiments, the inhibitor of an immune checkpoint molecule, e.g., the inhibitor of PD-1 (e.g., the anti-PD-1 antibody molecule), is administered at a dose between 200 mg and 600 mg (e.g., at a dose of 400 mg), e.g., once every 8 weeks, e.g., intravenously. In some embodiments, the BRAF inhibitor or dabrafenib, is administered at a dose between 50 mg and 250 mg (e.g., at a dose of 150 mg) twice a day, e.g., orally. In some embodiments, the MEK inhibitor or trametinib, is administered at a dose between 1 mg and 3 mg (e.g., at a dose of 2 mg), e.g., once a day, e.g., orally. In certain embodiments, the inhibitor of an immune checkpoint molecule, e.g., the inhibitor of PD-1 (e.g., the anti-PD-1 antibody molecule), is administered, e.g., at a dose between 200 mg and 600 mg (e.g., at a dose of 400 mg), e.g., once every 4 weeks, after the BRAF inhibitor or dabrafenib, the MEK inhibitor or trametinib, or both, is administered, e.g., for a period of 2 to 8 weeks, e.g., 4 weeks. In certain embodiments, the combination is used to treat a cancer described herein, e.g., a skin cancer (e.g., a melanoma, e.g., an unresectable or metastatic melanoma). In some embodiments, the combination is used to treat a cancer that has a BRAF mutation, e.g., a BRAF V600 mutation. In other embodiments, the combination is used to treat a cancer in a subject having an elevated level of serum lactate dehydrogenase (LDH), compared to a reference LDH level. In certain embodiments, the combination is used to treat a subject who has an unresectable or metastatic melanoma having a BRAF mutation (e.g., a BRAF V600 mutation) and has an elevated level of LDH in serum, compared to a reference serum LDH level.

In other embodiments, the combination includes an inhibitor of an immune checkpoint molecule, e.g., an inhibitor of PD-1 (e.g., an anti-PD-1 antibody molecule described herein), and an EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757. In some embodiments, the inhibitor of an immune checkpoint molecule, e.g., the inhibitor of PD-1 (e.g., the anti-PD-1 antibody molecule), is administered at a dose between 200 mg and 600 mg (e.g., at a dose of 400 mg), e.g., once every 4 weeks, e.g., intravenously. In some embodiments, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, is administered at a dose between 10 mg and 50 mg (e.g., at a dose of 25 mg), e.g., once a day (e.g., on day 1 to day 10 of a first dosing cycle), e.g., orally. In certain embodiments, the combination is used to treat a cancer described herein, e.g., a colorectal cancer, a lung cancer (e.g., a non-small cell lung cancer (NSCLC)), or a breast cancer (e.g., a triple-negative breast cancer (e.g., NTBC)).

In other embodiments, the combination includes an inhibitor of an immune checkpoint molecule, e.g., an inhibitor of PD-1 (e.g., an anti-PD-1 antibody molecule described herein), and a CSF-1/1R binding agent (e.g., a CSF-1R tyrosine kinase inhibitor), 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224. In some embodiments, the inhibitor of an immune checkpoint molecule, e.g., the inhibitor of PD-1 (e.g., the anti-PD-1 antibody molecule), is administered at a dose between 200 mg and 600 mg (e.g., at a dose of 400 mg), e.g., once every 4 weeks, e.g., intravenously. In some embodiments, the CSF-1/1R binding agent (e.g., a CSF-1R tyrosine kinase inhibitor), 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered at a dose between 50 mg and 1000 mg (e.g., at a dose of 100 mg, 150 mg, 300 mg, 600 mg, 900 mg), e.g., daily according to a 7 days on/7 days off schedule or once a week, e.g., orally. In certain embodiments, the combination is used to treat a cancer described herein, e.g., a brain cancer (e.g., a glioblastoma multiforme (GBM)), a breast cancer (e.g., a triple-negative breast cancer (e.g., NTBC)), or a pancreatic cancer.

In other embodiments, the combination includes an inhibitor of an immune checkpoint molecule, e.g., an inhibitor of PD-1 (e.g., an anti-PD-1 antibody molecule described herein), and an inhibitor of 6-phosphofructo-2-kinase/fructose-2,6-biphosphatase 3 (PFKFB3), PFK-158, or a compound disclosed in PCT Publication No. WO 2013/148228. In some embodiments, the inhibitor of an immune checkpoint molecule, e.g., the inhibitor of PD-1 (e.g., the anti-PD-1 antibody molecule), is administered at a dose between 200 mg and 600 mg (e.g., at a dose of 400 mg), e.g., once every 4 weeks, e.g., intravenously. In certain embodiments, the combination is used to treat a cancer described herein, e.g., an ovarian cancer, a fallopian tube cancer, or a colorectal cancer (CRC).

In one embodiment, a combination includes an inhibitor of an immune checkpoint molecule, e.g., an inhibitor of PD-1 (e.g., an anti-PD-1 antibody molecule described herein), and a chemotherapeutic agent, e.g., a paclitaxel (e.g., a nab-paclitaxel). In some embodiments, the inhibitor of an immune checkpoint molecule, e.g., the inhibitor of PD-1 (e.g., the anti-PD-1 antibody molecule), is administered at a dose between 200 mg and 600 mg (e.g., at a dose of 400 mg), e.g., once every 4 weeks, e.g., intravenously. In some embodiment, the chemotherapeutic agent, e.g., a paclitaxel (e.g., a nab-paclitaxel), is administered at a dose between 50 mg/m$^2$ and 200 mg/m$^2$ (e.g., at a dose of 100 mg/m$^2$), e.g., weekly at Day 1, Day 8, and Day 15 every four weeks (qw3/4), e.g., intravenously. In certain embodiments, the combination is used to treat a cancer described herein, e.g., a breast cancer (e.g., a HER2-negative breast cancer).

In other embodiments, the combination includes an inhibitor of an immune checkpoint molecule, e.g., an inhibitor of PD-1 (e.g., an anti-PD-1 antibody molecule described herein), and a TGF-β inhibitor, XOMA 089, or a compound disclosed in PCT Publication No. WO 2012/167143. In some embodiments, the inhibitor of an immune checkpoint molecule, e.g., the inhibitor of PD-1 (e.g., the anti-PD-1 antibody molecule), is administered at a dose between 100 mg and 600 mg (e.g., at a dose of 100 mg or 300 mg), e.g., once every 3 weeks, e.g., intravenously. In some embodiments, the TGF-β inhibitor, XOMA 089, or a compound disclosed in PCT Publication No. WO 2012/167143 is administered at a dose between 0.1 mg/kg and 15 mg/kg, e.g., between 0.1 mg/kg and 6 mg/kg or between 0.3 mg/kg and 3 mg/kg (e.g., at a dose of 0.1 mg/kg, 0.3 mg/kg, 1 mg/kg, 3 mg/kg, 6 mg/kg, 10 mg/kg, or 15 mg/kg), e.g., once every three weeks, e.g., intravenously. In some embodiments, the combination is used to treat a cancer described herein, e.g., a pancreatic cancer, a colorectal cancer (e.g., a microsatellite stable colorectal cancer (MSS-CRC)), a lung cancer (e.g., a non-small cell lung cancer), a breast cancer (e.g., a triple negative breast cancer), a liver cancer (e.g., a hepatocellular carcinoma), a prostate cancer, or a renal cancer (e.g., a clear cell renal cell carcinoma).

In other embodiments, the combination includes an inhibitor of an immune checkpoint molecule, e.g., an inhibitor of PD-1 (e.g., an anti-PD-1 antibody molecule described herein), and an inhibitor of PD-L1 or an anti-PD-L1 antibody molecule disclosed in U.S. Patent Application Publication No. 2016/0108123. In some embodiments, the inhibitor of an immune checkpoint molecule, e.g., the inhibitor of PD-1 (e.g., the anti-PD-1 antibody molecule), is administered at a dose between 100 mg and 600 mg (e.g., at a dose of 100 mg or 300 mg), e.g., once every 3 weeks, e.g., intravenously. In some embodiments, the inhibitor of PD-L1 or an anti-PD-L1 antibody molecule disclosed in U.S. Patent Application Publication No. 2016/0108123 is administered at a dose between 10 mg and 2000 mg (e.g., between 20 mg and 1600 mg or between 80 mg and 1200 mg (e.g., at a dose of 20 mg, 80 mg, 240 mg, 800 mg, or 1200 mg), e.g., once every three weeks or once every six weeks, e.g., intravenously. In some embodiments, the combination is used to treat a cancer described herein, e.g., a solid tumor, e.g., a lung cancer (e.g., a non-small cell lung cancer), a breast cancer (e.g., a triple negative breast cancer), a uterine cancer (e.g., an endometrial carcinoma), or a thyroid cancer (e.g., an anaplastic thyroid carcinoma).

In other embodiments, the combination includes an inhibitor of an immune checkpoint molecule, e.g., an inhibitor of PD-1 (e.g., an anti-PD-1 antibody molecule described herein), and a chemotherapeutic agent (e.g., a hypomethylating agent, e.g., decitabine). In some embodiments, the inhibitor of an immune checkpoint molecule, e.g., the inhibitor of PD-1 (e.g., the anti-PD-1 antibody molecule), is administered at a dose between 200 mg and 600 mg (e.g., between 300 mg and 500 mg, e.g., at a dose of 400 mg), e.g., once every 4 weeks, e.g., intravenously. In some embodiments, the chemotherapeutic agent (e.g., a hypomethylating agent, e.g., decitabine) is administered at a dose between 5 $mg/m^2$ and 50 $mg/m^2$ (e.g., between 10 $mg/m^2$ and 30 $mg/m^2$, e.g., at a dose of 20 $mg/m^2$), e.g., daily, e.g., for 1, 2, 3, 4, 5, 6, 7, 8, or more days, e.g., intravenously. In certain embodiments, the inhibitor of an immune checkpoint molecule, e.g., the inhibitor of PD-1 (e.g., the anti-PD-1 antibody molecule), is administered on day 8 of a 28-day cycle, and the chemotherapeutic agent (e.g., a hypomethylating agent, e.g., decitabine) is administered on days 1, 2, 3, 4, and 5 of the 28-day cycle. In some embodiments, the combination is used to treat a cancer described herein, e.g., a hematological cancer, e.g., a leukemia (e.g., an acute myeloid leukemia (AML), e.g., a relapsed or refractory AML or a de novo AML), or a myelodysplastic syndrome (MDS) (e.g., a high risk MDS).

In other embodiments, the combination includes an inhibitor of an immune checkpoint molecule, e.g., an inhibitor of TIM-3 or an anti-TIM-3 antibody molecule disclosed in U.S. Patent Application Publication No. 2015/0218274, and a chemotherapeutic agent (e.g., a hypomethylating agent, e.g., decitabine). In some embodiments, the inhibitor of an immune checkpoint molecule, e.g., the inhibitor of TIM-3 or an anti-TIM-3 antibody molecule disclosed in U.S. Patent Application Publication No. 2015/0218274, is administered at a dose between 50 mg and 500 mg (e.g., between 100 mg and 400 mg, e.g., at a dose of 240 mg), e.g., once every 2 weeks, e.g., intravenously. In some embodiments, the chemotherapeutic agent (e.g., a hypomethylating agent, e.g., decitabine) is administered at a dose between 5 $mg/m^2$ and 50 $mg/m^2$ (e.g., between 10 $mg/m^2$ and 30 $mg/m^2$, e.g., at a dose of 20 $mg/m^2$), e.g., daily, e.g., for 1, 2, 3, 4, 5, 6, 7, 8, or more days, e.g., intravenously. In certain embodiments, the inhibitor of an immune checkpoint molecule, e.g., the inhibitor of TIM-3 or an anti-TIM-3 antibody molecule disclosed in U.S. Patent Application Publication No. 2015/0218274, is administered on days 8 and 22 of a 28-day cycle, and the chemotherapeutic agent (e.g., a hypomethylating agent, e.g., decitabine) is administered on days 1, 2, 3, 4, and 5 of the 28-day cycle. In some embodiments, the combination is used to treat a cancer described herein, e.g., a hematological cancer, e.g., a leukemia (e.g., an acute myeloid leukemia (AML), e.g., a relapsed or refractory AML or a de novo AML), or a myelodysplastic syndrome (MDS) (e.g., a high risk MDS).

In other embodiments, the combination includes an inhibitor of PD-1 (e.g., an anti-PD-1 antibody molecule described herein), an inhibitor of TIM-3 (e.g., an anti-TIM-3 antibody molecule disclosed in U.S. Patent Application Publication No. 2015/0218274), and a chemotherapeutic agent (e.g., a hypomethylating agent, e.g., decitabine). In some embodiments, the inhibitor of PD-1 (e.g., the anti-PD-1 antibody molecule), is administered at a dose between 200 mg and 600 mg (e.g., between 300 mg and 500 mg, e.g., at a dose of 400 mg), e.g., once every 4 weeks, e.g., intravenously. In some embodiments, the inhibitor of TIM-3 (e.g., an anti-TIM-3 antibody molecule disclosed in U.S. Patent Application Publication No. 2015/0218274) is administered at a dose between 20 mg and 400 mg (e.g., between 40 mg and 200 mg or between 50 mg and 100 mg, e.g., at a dose of 80 mg), e.g., once every 2 weeks, e.g., intravenously. In some embodiments, the chemotherapeutic agent (e.g., a hypomethylating agent, e.g., decitabine) is administered at a dose between 5 $mg/m^2$ and 50 $mg/m^2$ (e.g., between 10 $mg/m^2$ and 30 $mg/m^2$, e.g., at a dose of 20 $mg/m^2$), e.g., daily, e.g., for 1, 2, 3, 4, 5, 6, 7, 8, or more days, e.g., intravenously. In certain embodiments, the inhibitor of PD-1 (e.g., the anti-PD-1 antibody molecule) is administered on day 8 of a 28-day cycle, the inhibitor of TIM-3 (e.g., an anti-TIM-3 antibody molecule disclosed in U.S. Patent Application Publication No. 2015/0218274) is administered on days 8 and 22 of a 28-day cycle, and the chemotherapeutic agent (e.g., decitabine) is administered on days 1, 2, 3, 4, and 5 of the 28-day cycle. In some embodiments, the combination is used to treat a cancer described herein, e.g., a hematological cancer, e.g., a leukemia (e.g., an acute myeloid leukemia (AML), e.g., a relapsed or refractory AML or a de novo AML), or a myelodysplastic syndrome (MDS) (e.g., a high risk MDS).

The combinations disclosed herein can be administered together in a single composition or administered separately in two or more different compositions, e.g., compositions or dosage forms as described herein. The administration of the therapeutic agents can be in any order. The first agent and the additional agents (e.g., second, third agents) can be administered via the same administration route or via different administration routes. For example, a first therapeutic agent can be administered concurrently with, prior to, or subsequent to, the additional agent. In certain embodiments, a first agent is administered locally, e.g., a therapeutic agent of any of categories (i)-(iii) can be coupled to a tumor targeting agent, e.g., a tumor-targeting antibody (e.g., to form an antibody-drug conjugate), or any other delivery agent (e.g., a formulation such as a targeted formulation) such that administration of the first agent is localized to a desired site, e.g., a tumor site (e.g., a dendritic cell-enriched site). In one embodiment, the therapeutic agent is an antigen (e.g., a vaccine, e.g., an in situ cancer vaccine), which is targeted to the tumor environment, thus resulting in activation of dendritic cells. The therapeutic agent also can be locally administered, e.g., injected, at a tumor site (e.g., intratumoral or peritumoral administration). Localized delivery or administration of the therapeutic agent can reduce one or more side effects or toxicities that would otherwise be associated with systemic administration of the therapeutic agent. In one exemplary embodiment, a therapeutic agent (e.g., STING or a TLR) can be conjugated to a tumor-binding antibody (e.g., an antibody that binds to HER2), thereby delivering the therapeutic agent to a HER-2-expressing cell.

When administered in combination, the first agent, the additional agent (e.g., second or third agent), or all, can be administered in an amount or dose that is higher, lower or the same than the amount or dosage of each agent used individually, e.g., as a monotherapy. In certain embodiments, the administered amount or dosage of the first agent, the additional agent (e.g., second or third agent), or all, is lower (e.g., at least 20%, at least 30%, at least 40%, or at least 50%) than the amount or dosage of each agent used individually, e.g., as a monotherapy. In other embodiments, the amount or dosage of the first agent, the additional agent (e.g., second or third agent), or all, that results in a desired effect (e.g., treatment of cancer) is lower (e.g., at least 20%, at least 30%, at least 40%, or at least 50% lower).

In certain embodiments, the combinations can be in the form of an antibody molecule, e.g., a bi- or tri-specific molecule, against one or more therapeutic agents chosen from the antigen-presentation combination, the effector cell combination, or the anti-tumor immunosuppression combination, or any combination thereof. For example, a bispe-
cific molecule against two or more checkpoint inhibitors
(e.g., an anti-PD-1 and an anti-LAG-3 antibody molecule).
In other embodiments, the combinations can be in the form
of an antibody molecule, e.g., a bi- or tri-specific molecule,
against one or more therapeutic agents chosen from two or
all of the antigen-presentation combination, the effector cell
combination, and/or the anti-tumor immunosuppression
combination. In one embodiment, the antibody molecule is
a full antibody or fragment thereof (e.g., a Fab, F(ab')$_2$, Fv,
or a single chain Fv fragment (scFv)). In yet other embodi-
ments, the antibody molecule has a heavy chain constant
region (Fc) chosen from, e.g., the heavy chain constant
regions of IgG1, IgG2, IgG3, IgG4, IgM, IgA1, IgA2, IgD,
and IgE; particularly, chosen from, e.g., the heavy chain
constant regions of IgG1, IgG2, IgG3, and IgG4, more
particularly, the heavy chain constant region of IgG1 or
IgG4 (e.g., human IgG1 or IgG4). In one embodiment, the
heavy chain constant region is human IgG1 or human IgG4.
In one embodiment, the constant region is altered, e.g.,
mutated, to modify the properties of the antibody molecule
(e.g., to increase or decrease one or more of: Fc receptor
binding, antibody glycosylation, the number of cysteine
residues, effector cell function, or complement function). In
certain embodiments, the antibody molecule is in the form
of a bispecific or multispecific antibody molecule, e.g., a
bispecific, trispecific antibody molecule as described herein.

Certain exemplary therapeutic agents and combinations
thereof are provided herein below. A more detailed descrip-
tion of the therapeutic agents used in the combinations is
provided in the detailed description.

Immunomodulators

In certain embodiments, the immunomodulator used in
the combinations disclosed herein (e.g., in combination with
a therapeutic agent chosen from an antigen-presentation
combination) is an inhibitor of an immune checkpoint
molecule. In one embodiment, the immunomodulator is an
inhibitor of PD-1, PD-L1, PD-L2, CTLA-4, TIM-3, LAG-3,
CEACAM (e.g., CEACAM-1, -3 and/or -5), VISTA, BTLA,
TIGIT, LAIR1, CD160, 2B4 and/or TGF beta. In one
embodiment, the inhibitor of an immune checkpoint mol-
ecule inhibits PD-1, PD-L1, LAG-3, TIM-3, CEACAM
(e.g., CEACAM-1, -3 and/or -5), CTLA-4, or any combi-
nation thereof.

Inhibition of an inhibitory molecule can be performed at
the DNA, RNA or protein level. In embodiments, an inhibi-
tory nucleic acid (e.g., a dsRNA, siRNA or shRNA), can be
used to inhibit expression of an inhibitory molecule. In other
embodiments, the inhibitor of an inhibitory signal is, a
polypeptide e.g., a soluble ligand (e.g., PD-1-Ig or CTLA-4
Ig), or an antibody or antigen-binding fragment thereof, that
binds to the inhibitory molecule; e.g., an antibody or frag-
ment thereof (also referred to herein as "an antibody mol-
ecule") that binds to PD-1, PD-L1, PD-L2, CEACAM (e.g.,
CEACAM-1, -3 and/or -5), CTLA-4, TIM-3, LAG-3,
VISTA, BTLA, TIGIT, LAIR1, CD160, 2B4 and/or TGF
beta, or a combination thereof.

In certain embodiments, the antibody molecule is in the
form of a bispecific or multispecific antibody molecule. In
one embodiment, the bispecific antibody molecule has a first
binding specificity to PD-1 or PD-L1 and a second binding
specificity, e.g., a second binding specificity to TIM-3,
CEACAM (e.g., CEACAM-1, -3 and/or -5), LAG-3, or
PD-L2. In one embodiment, the bispecific antibody mol-
ecule binds to PD-1 or PD-L1 and TIM-3. In another
embodiment, the bispecific antibody molecule binds to PD-1
or PD-L1 and LAG-3. In another embodiment, the bispecific antibody molecule binds to PD-1 or PD-L1 and CEACAM
(e.g., CEACAM-1, -3 and/or -5). In another embodiment,
the bispecific antibody molecule binds to PD-1 or PD-L1
and CEACAM-1. In still another embodiment, the bispecific
antibody molecule binds to PD-1 or PD-L1 and CEACAM-
3. In yet another embodiment, the bispecific antibody mol-
ecule binds to PD-1 or PD-L1 and CEACAM-5. In another
embodiment, the bispecific antibody molecule binds to PD-1
or PD-L1. In yet another embodiment, the bispecific anti-
body molecule binds to PD-1 and PD-L2. In another
embodiment, the bispecific antibody molecule binds to
TIM-3 and LAG-3. In another embodiment, the bispecific
antibody molecule binds to CEACAM (e.g., CEACAM-1,
-3 and/or -5) and LAG-3. In another embodiment, the
bispecific antibody molecule binds to CEACAM (e.g.,
CEACAM-1, -3 and/or -5) and TIM-3. Any combination of
the aforesaid molecules can be made in a multispecific
antibody molecule, e.g., a trispecific antibody that includes
a first binding specificity to PD-1 or PD-1, and a second and
third binding specificities to two or more of: TIM-3,
CEACAM (e.g., CEACAM-1, -3 and/or -5), LAG-3, or
PD-L2.

In certain embodiments, the immunomodulator is an
inhibitor of PD-1, e.g., human PD-1 (e.g., an antibody
molecule as described herein). In another embodiment, the
immunomodulator is an inhibitor of PD-L1, e.g., human
PD-L1. In one embodiment, the inhibitor of PD-1 or PD-L1
is an antibody molecule to PD-1 or PD-L1. The PD-1 or
PD-L1 inhibitor can be administered alone, or in combina-
tion with other immunomodulators, e.g., in combination
with an inhibitor of LAG-3, TIM-3, CEACAM (e.g.,
CEACAM-1, -3 and/or -5) or CTLA-4. In an exemplary
embodiment, the inhibitor of PD-1 or PD-L1, e.g., the
anti-PD-1 or PD-L1 antibody molecule, is administered in
combination with a LAG-3 inhibitor, e.g., an anti-LAG-3
antibody molecule. In another embodiment, the inhibitor of
PD-1 or PD-L1, e.g., the anti-PD-1 or PD-L1 antibody
molecule, is administered in combination with a TIM-3
inhibitor, e.g., an anti-TIM-3 antibody molecule. In another
embodiment, the inhibitor of PD-1 or PD-L1, e.g., the
anti-PD-1 or PD-L1 antibody molecule, is administered in
combination with a CEACAM inhibitor (e.g., CEACAM-1,
-3 and/or -5 inhibitor), e.g., an anti-CEACAM antibody
molecule. In another embodiment, the inhibitor of PD-1 or
PD-L1, e.g., the anti-PD-1 or PD-L1 antibody molecule, is
administered in combination with a CEACAM-1 inhibitor,
e.g., an anti-CEACAM-1 antibody molecule. In another
embodiment, the inhibitor of PD-1 or PD-L1, e.g., the
anti-PD-1 or PD-L1 antibody molecule, is administered in
combination with a CEACAM-5 inhibitor, e.g., an anti-
CEACAM-5 antibody molecule. In yet other embodiments,
the inhibitor of PD-1 or PD-L1, e.g., the anti-PD-1 antibody
molecule, is administered in combination with a LAG-3
inhibitor, e.g., an anti-LAG-3 antibody molecule, and a
TIM-3 inhibitor, e.g., an anti-TIM-3 antibody molecule.
Other combinations of immunomodulators with a PD-1
inhibitor (e.g., one or more of PD-L2, CTLA-4, TIM-3,
LAG-3, CEACAM (e.g., CEACAM-1, -3 and/or -5),
VISTA, BTLA, TIGIT, LAIR1, CD160, 2B4 and/or TGF
beta) are also within the present invention. Any of the
antibody molecules known in the art or disclosed herein can
be used in the aforesaid combinations of inhibitors of
checkpoint molecule.

In other embodiments, the immunomodulator is an inhibi-
tor of CEACAM (e.g., CEACAM-1, -3 and/or -5), e.g.,
human CEACAM (e.g., CEACAM-1, -3 and/or -5). In one
embodiment, the immunomodulator is an inhibitor of CEACAM-1, e.g., human CEACAM-1. In another embodiment, the immunomodulator is an inhibitor of CEACAM-3, e.g., human CEACAM-3. In another embodiment, the immunomodulator is an inhibitor of CEACAM-5, e.g., human CEACAM-5. In one embodiment, the inhibitor of CEACAM (e.g., CEACAM-1, -3 and/or -5) is an antibody molecule to CEACAM (e.g., CEACAM-1, -3 and/or -5). The CEACAM (e.g., CEACAM-1, -3 and/or -5) inhibitor can be administered alone, or in combination with other immunomodulators, e.g., in combination with an inhibitor of LAG-3, TIM-3, PD-1, PD-L1 or CTLA-4.

In other embodiments, the immunomodulator is an inhibitor of LAG-3, e.g., human LAG-3. In one embodiment, the inhibitor of LAG-3 is an antibody molecule to LAG-3. The LAG-3 inhibitor can be administered alone, or in combination with other immunomodulators, e.g., in combination with an inhibitor of CEACAM (e.g., CEACAM-1, -3 and/or -5), TIM-3, PD-1, PD-L1 or CTLA-4.

In other embodiments, the immunomodulator is an inhibitor of TIM-3, e.g., human TIM-3. In one embodiment, the inhibitor of TIM-3 is an antibody molecule to TIM-3. The TIM-3 inhibitor can be administered alone, or in combination with other immunomodulators, e.g., in combination with an inhibitor of CEACAM (e.g., CEACAM-1, -3 and/or -5), LAG-3, PD-1, PD-L1 or CTLA-4.

In certain embodiments, the immunomodulator used in the combinations disclosed herein (e.g., in combination with a therapeutic agent chosen from an antigen-presentation combination) is an activator or agonist of a costimulatory molecule. In one embodiment, the agonist of the costimulatory molecule is chosen from an agonist (e.g., an agonistic antibody or antigen-binding fragment thereof, or a soluble fusion) of OX40, CD2, CD27, CD28, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3, or CD83 ligand.

In other embodiments, the immunomodulator is a GITR agonist. In one embodiment, the GITR agonist is an antibody molecule to GITR. The GITR agonist can be administered alone, or in combination with other immunomodulators, e.g., in combination with an inhibitor of PD-1, PD-L1, CTLA-4, CEACAM (e.g., CEACAM-1, -3 and/or -5), TIM-3 or LAG-3. In some embodiments, the anti-GITR antibody molecule is a bispecific antibody that binds to GITR and PD-1, PD-L1, CTLA-4, CEACAM (e.g., CEACAM-1, -3 and/or -5), TIM-3 or LAG-3. In one exemplary embodiment, the anti-GITR antibody molecule is administered in combination with an anti-PD-1 antibody molecule (e.g., an anti-PD-1 molecule as described herein). The GITR antibody molecule and the anti-PD-1 antibody molecule may be in the form of separate antibody composition, or as a bispecific antibody molecule. In other embodiments, a GITR agonist can be administered in combination with other costimulatory molecule, e.g., an agonist of OX40, CD2, CD27, CD28, CDS, ICAM-1, LFA-1 (CD11a/CD18), ICOS (CD278), 4-1BB (CD137), CD30, CD40, BAFFR, HVEM, CD7, LIGHT, NKG2C, SLAMF7, NKp80, CD160, B7-H3, or CD83 ligand.

In other embodiments, the immunomodulator is an activator of a costimulatory molecule (e.g., an OX40 agonist). In one embodiment, the OX40 agonist is an antibody molecule to OX40. The OX40 agonist can be administered alone, or in combination with other immunomodulators, e.g., in combination with an inhibitor of PD-1, PD-L1, CTLA-4, CEACAM (e.g., CEACAM-1, -3 and/or -5), TIM-3 or LAG-3. In some embodiments, the anti-OX40 antibody molecule is a bispecific antibody that binds to GITR and PD-1, PD-L1, CTLA-4, CEACAM (e.g., CEACAM-1, -3 and/or -5), TIM-3 or LAG-3. In one exemplary embodiment, an OX40 antibody molecule is administered in combination with an anti-PD-1 antibody molecule (e.g., an anti-PD-1 molecule as described herein). The OX40 antibody molecule and the anti-PD-1 antibody molecule may be in the form of separate antibody composition, or as a bispecific antibody molecule. In other embodiments, the OX40 agonist can be administered in combination with other costimulatory molecule, e.g., an agonist of GITR, CD2, CD27, CD28, CDS, ICAM-1, LFA-1 (CD11a/CD18), ICOS (CD278), 4-1BB (CD137), CD30, CD40, BAFFR, HVEM, CD7, LIGHT, NKG2C, SLAMF7, NKp80, CD160, B7-H3, or CD83 ligand.

It is noted that only exemplary combinations of inhibitors of checkpoint inhibitors or agonists of costimulatory molecules are provided herein. Additional combinations of these agents are within the scope of the present invention.

Antibody Molecules to PD-1

In one embodiment, the PD-1 inhibitor is an anti-PD-1 antibody molecule as described in U.S. Patent Application Publication No. 2015/0210769 (U.S. Ser. No. 14/604,415), entitled "Antibody Molecules to PD-1 and Uses Thereof," incorporated by reference in its entirety. In one embodiment, the anti-PD-1 antibody molecule comprises at least one antigen-binding region, e.g., a variable region or an antigen-binding fragment thereof, from an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-1 antibody molecule comprises at least one, two, three or four variable regions from an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-1 antibody molecule comprises at least one or two heavy chain variable regions from an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-1 antibody molecule comprises at least one or two light chain variable regions from an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-1 antibody molecule includes a heavy chain constant region for an IgG4, e.g., a human IgG4. In one embodiment, the human IgG4 includes a substitution at position 228 according to EU numbering (e.g., a Ser to Pro substitution). In still another embodiment, the anti-PD-1 antibody molecule includes a heavy chain constant region for an IgG1, e.g., a human IgG1. In one embodiment, the human IgG1 includes a substitution at position 297 according to EU numbering (e.g., an Asn to Ala substitution). In one embodiment, the human IgG1 includes a substitution at position 265 according to EU numbering, a substitution at position 329 according to EU numbering, or both (e.g., an Asp to Ala substitution at position 265 and/or a Pro to Ala substitution at position 329). In one embodiment, the human IgG1 includes a substitution at position 234 according to EU numbering, a substitution at position 235 according to EU numbering, or both (e.g., a Leu to Ala substitution at position 234 and/or a Leu to Ala substitution at position 235). In one embodiment, the heavy chain constant region comprises an amino sequence set forth in Table 3, or a sequence substantially identical (e.g., at least 80%, 85%, 90%, 92%, 95%, 97%, 98%, 99% or higher identical) thereto.

In yet another embodiment, the anti-PD-1 antibody molecule includes a kappa light chain constant region, e.g., a human kappa light chain constant region. In one embodiment, the light chain constant region comprises an amino sequence set forth in Table 3, or a sequence substantially identical (e.g., at least 80%, 85%, 90%, 92%, 95%, 97%, 98%, 99% or higher identical) thereto.

In another embodiment, the anti-PD-1 antibody molecule includes a heavy chain constant region for an IgG4, e.g., a human IgG4, and a kappa light chain constant region, e.g., a human kappa light chain constant region, e.g., a heavy and light chain constant region comprising an amino sequence set forth in Table 3, or a sequence substantially identical (e.g., at least 80%, 85%, 90%, 92%, 95%, 97%, 98%, 99% or higher identical) thereto. In one embodiment, the human IgG4 includes a substitution at position 228 according to EU numbering (e.g., a Ser to Pro substitution). In yet another embodiment, the anti-PD-1 antibody molecule includes a heavy chain constant region for an IgG1, e.g., a human IgG1, and a kappa light chain constant region, e.g., a human kappa light chain constant region, e.g., a heavy and light chain constant region comprising an amino sequence set forth in Table 3, or a sequence substantially identical (e.g., at least 80%, 85%, 90%, 92%, 95%, 97%, 98%, 99% or higher identical) thereto. In one embodiment, the human IgG1 includes a substitution at position 297 according to EU numbering (e.g., an Asn to Ala substitution). In one embodiment, the human IgG1 includes a substitution at position 265 according to EU numbering, a substitution at position 329 according to EU numbering, or both (e.g., an Asp to Ala substitution at position 265 and/or a Pro to Ala substitution at position 329). In one embodiment, the human IgG1 includes a substitution at position 234 according to EU numbering, a substitution at position 235 according to EU numbering, or both (e.g., a Leu to Ala substitution at position 234 and/or a Leu to Ala substitution at position 235).

In another embodiment, the anti-PD-1 antibody molecule includes a heavy chain variable domain and a constant region, a light chain variable domain and a constant region, or both, comprising the amino acid sequence of BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences. The anti-PD-1 antibody molecule, optionally, comprises a leader sequence from a heavy chain, a light chain, or both, as shown in Table 4; or a sequence substantially identical thereto.

In yet another embodiment, the anti-PD-1 antibody molecule includes at least one, two, or three complementarity determining regions (CDRs) from a heavy chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-1 antibody molecule includes at least one, two, or three CDRs (or collectively all of the CDRs) from a heavy chain variable region comprising an amino acid sequence shown in Table 1, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In yet another embodiment, the anti-PD-1 antibody molecule includes at least one, two, or three CDRs from a light chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequence.

In yet another embodiment, the anti-PD-1 antibody molecule includes at least one, two, or three CDRs (or collectively all of the CDRs) from a light chain variable region comprising an amino acid sequence shown in Table 1, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1. In certain embodiments, the anti-PD-1 antibody molecule includes a substitution in a light chain CDR, e.g., one or more substitutions in a CDR1, CDR2 and/or CDR3 of the light chain. In one embodiment, the anti-PD-1 antibody molecule includes a substitution in the light chain CDR3 at position 102 of the light variable region, e.g., a substitution of a cysteine to tyrosine, or a cysteine to serine residue, at position 102 of the light variable region according to Table 1 (e.g., SEQ ID NO: 16 or 24 for murine or chimeric, unmodified; or any of SEQ ID NOs: 34, 42, 46, 54, 58, 62, 66, 70, 74, or 78 for a modified sequence).

In another embodiment, the anti-PD-1 antibody molecule includes at least one, two, three, four, five or six CDRs (or collectively all of the CDRs) from a heavy and light chain variable region comprising an amino acid sequence shown in Table 1, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In one embodiment, the anti-PD-1 antibody molecule includes all six CDRs from an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1, or closely related CDRs, e.g., CDRs which are identical or which have at least one amino acid alteration, but not more than two, three or four alterations (e.g., substitutions, deletions, or insertions, e.g., conservative substitutions). In one embodiment, the anti-PD-1 antibody molecule may include any CDR described herein. In certain embodiments, the anti-PD-1 antibody molecule includes a substitution in a light chain CDR, e.g., one or more substitutions in a CDR1, CDR2 and/or CDR3 of the light chain. In one embodiment, the anti-PD-1 antibody molecule includes a substitution in the light chain CDR3 at position 102 of the light variable region, e.g., a substitution of a cysteine to tyrosine, or a cysteine to serine residue, at position 102 of the light variable region according to Table 1 (e.g., SEQ ID NO: 16 or 24 for murine or chimeric, unmodified; or any of SEQ ID NOs: 34, 42, 46, 54, 58, 62, 66, 70, 74, or 78 for a modified sequence).

In another embodiment, the anti-PD-1 antibody molecule includes at least one, two, or three CDRs according to Kabat et al. (e.g., at least one, two, or three CDRs according to the Kabat definition as set out in Table 1) from a heavy chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049- hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat et al. shown in Table 1.

In another embodiment, the anti-PD-1 antibody molecule includes at least one, two, or three CDRs according to Kabat et al. (e.g., at least one, two, or three CDRs according to the Kabat definition as set out in Table 1) from a light chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat et al. shown in Table 1.

In yet another embodiment, the anti-PD-1 antibody molecule includes at least one, two, three, four, five, or six CDRs according to Kabat et al. (e.g., at least one, two, three, four, five, or six CDRs according to the Kabat definition as set out in Table 1) from the heavy and light chain variable regions of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, three, four, five, or six CDRs according to Kabat et al. shown in Table 1.

In yet another embodiment, the anti-PD-1 antibody molecule includes all six CDRs according to Kabat et al. (e.g., all six CDRs according to the Kabat definition as set out in Table 1) from the heavy and light chain variable regions of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to all six CDRs according to Kabat et al. shown in Table 1. In one embodiment, the anti-PD-1 antibody molecule may include any CDR described herein.

In another embodiment, the anti-PD-1 antibody molecule includes at least one, two, or three Chothia hypervariable loops (e.g., at least one, two, or three hypervariable loops according to the Chothia definition as set out in Table 1) from a heavy chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or at least the amino acids from those hypervariable loops that contact PD-1; or which have at least one amino acid alteration, but not more than two, three or four alterations (e.g., substitutions, deletions, or insertions, e.g., conservative substitutions) relative to one, two, or three hypervariable loops according to Chothia et al. shown in Table 1.

In another embodiment, the anti-PD-1 antibody molecule includes at least one, two, or three Chothia hypervariable loops (e.g., at least one, two, or three hypervariable loops according to the Chothia definition as set out in Table 1) of a light chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or at least the amino acids from those hypervariable loops that contact PD-1; or which have at least one amino acid alteration, but not more than two, three or four alterations (e.g., substitutions, deletions, or insertions, e.g., conservative substitutions) relative to one, two, or three hypervariable loops according to Chothia et al. shown in Table 1.

In yet another embodiment, the anti-PD-1 antibody molecule includes at least one, two, three, four, five, or six hypervariable loops (e.g., at least one, two, three, four, five, or six hypervariable loops according to the Chothia definition as set out in Table 1) from the heavy and light chain variable regions of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or at least the amino acids from those hypervariable loops that contact PD-1; or which have at least one amino acid alteration, but not more than two, three or four alterations (e.g., substitutions, deletions, or insertions, e.g., conservative substitutions) relative to one, two, three, four, five or six hypervariable loops according to Chothia et al. shown in Table 1.

In one embodiment, the anti-PD-1 antibody molecule includes all six hypervariable loops (e.g., all six hypervariable loops according to the Chothia definition as set out in Table 1) of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E, or closely related hypervariable loops, e.g., hypervariable loops which are identical or which have at least one amino acid alteration, but not more than two, three or four alterations (e.g., substitutions, deletions, or insertions, e.g., conservative substitutions); or which have at least one amino acid alteration, but not more than two, three or four alterations (e.g., substitutions, deletions, or insertions, e.g., conservative substitutions) relative to all six hypervariable loops according to Chothia et al. shown in Table 1. In one embodiment, the anti-PD-1 antibody molecule may include any hypervariable loop described herein.

In still another embodiment, the anti-PD-1 antibody molecule includes at least one, two, or three hypervariable loops that have the same canonical structures as the corresponding hypervariable loop of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E, e.g., the same canonical structures as at least loop 1 and/or loop 2 of the heavy and/or light chain variable domains of an antibody described herein. See, e.g., Chothia et al., (1992) *J. Mol. Biol.* 227:799-817; Tomlinson et al., (1992) *J. Mol. Biol.* 227:776-798 for descriptions of hypervariable loop canonical structures. These structures can be determined by inspection of the tables described in these references.

In certain embodiments, the anti-PD-1 antibody molecule includes a combination of CDRs or hypervariable loops defined according to the Kabat et al. and Chothia et al.

In one embodiment, the anti-PD-1 antibody molecule includes at least one, two or three CDRs or hypervariable loops from a heavy chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E, according to the Kabat and Chothia definition (e.g., at least one, two, or three CDRs or hypervariable loops according to the Kabat and Chothia definition as set out in Table 1); or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs or hypervariable loops according to Kabat and/or Chothia shown in Table 1.

For example, the anti-PD-1 antibody molecule can include VH CDR1 according to Kabat et al. or VH hypervariable loop 1 according to Chothia et al., or a combination thereof, e.g., as shown in Table 1. In one embodiment, the combination of Kabat and Chothia CDR of VH CDR1 comprises the amino acid sequence GYTFTTYWMH (SEQ ID NO: 224), or an amino acid sequence substantially identical thereto (e.g., having at least one amino acid alteration, but not more than two, three or four alterations (e.g., substitutions, deletions, or insertions, e.g., conservative substitutions)). The anti-PD-1 antibody molecule can further include, e.g., VH CDRs 2-3 according to Kabat et al. and VL CDRs 1-3 according to Kabat et al., e.g., as shown in Table 1. Accordingly, in some embodiments, framework regions are defined based on a combination of CDRs defined according to Kabat et al. and hypervariable loops defined according to Chothia et al. For example, the anti-PD-1 antibody molecule can include VH FR1 defined based on VH hypervariable loop 1 according to Chothia et al. and VH FR2 defined based on VH CDRs 1-2 according to Kabat et al., e.g., as shown in Table 1. The anti-PD-1 antibody molecule can further include, e.g., VH FRs 3-4 defined based on VH CDRs 2-3 according to Kabat et al. and VL FRs 1-4 defined based on VL CDRs 1-3 according to Kabat et al.

The anti-PD-1 antibody molecule can contain any combination of CDRs or hypervariable loops according to the Kabat and Chothia definitions. In one embodiment, the anti-PD-1 antibody molecule includes at least one, two or three CDRs from a light chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E, according to the Kabat and Chothia definition (e.g., at least one, two, or three CDRs according to the Kabat and Chothia definition as set out in Table 1).

In one embodiment, the anti-PD-1 antibody molecule includes:

(a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 33;

(b) a VH comprising a VHCDR1 amino acid sequence chosen from SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32;

(c) a VH comprising a VHCDR1 amino acid sequence of SEQ ID NO: 224, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33; or (d) a VH comprising a VHCDR1 amino acid sequence of SEQ ID NO: 224; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32.

In the combinations herein, in another embodiment, the anti-PD-1 antibody molecule comprises (i) a heavy chain variable region (VH) comprising a VHCDR1 amino acid sequence chosen from SEQ ID NO: 1, SEQ ID NO: 4, or SEQ ID NO: 224; a VHCDR2 amino acid sequence of SEQ ID NO: 2 or SEQ ID NO: 5; and a VHCDR3 amino acid sequence of SEQ ID NO: 3; and (ii) a light chain variable region (VL) comprising a VLCDR1 amino acid sequence of SEQ ID NO: 10 or SEQ ID NO: 13, a VLCDR2 amino acid sequence of SEQ ID NO: 11 or SEQ ID NO: 14, and a VLCDR3 amino acid sequence of SEQ ID NO: 32 or SEQ ID NO: 33.

In an embodiment, e.g., an embodiment comprising a variable region, a CDR (e.g., Chothia CDR or Kabat CDR), or other sequence referred to herein, e.g., in Table 1, the antibody molecule is a monospecific antibody molecule, a bispecific antibody molecule, or is an antibody molecule that comprises an antigen binding fragment of an antibody, e.g., a half antibody or antigen binding fragment of a half antibody. In certain embodiments the antibody molecule is a bispecific antibody molecule having a first binding specificity for PD-1 and a second binding specificity for TIM-3, LAG-3, CEACAM (e.g., CEACAM-1, CEACAM-3, and/or CEACAM-5), PD-L1 or PD-L2. In one embodiment, the bispecific antibody molecule binds to PD-1 and TIM-3. In another embodiment, the bispecific antibody molecule binds to PD-1 and LAG-3. In another embodiment, the bispecific antibody molecule binds to PD-1 and CEACAM (e.g., CEACAM-1, CEACAM-3, and/or CEACAM-5). In another embodiment, the bispecific antibody molecule binds to PD-1 and CEACAM-1. In yet another embodiment, the bispecific antibody molecule binds to PD-1 and CEACAM-5. In another embodiment, the bispecific antibody molecule binds to PD-1 and PD-L1. In yet another embodiment, the bispecific antibody molecule binds to PD-1 and PD-L2. Any combination of the aforesaid molecules can be made in a multispecific antibody molecule, e.g., a trispecific antibody that includes a first binding specificity to PD-1, and a second and third binding specificity to one or more of: TIM-3, LAG-3, CEACAM (e.g., CEACAM-1, CEACAM-3, or CEACAM-5), PD-L1 or PD-L2.

In other embodiments, the anti-PD-1 antibody molecule is used in combination with a bispecific molecule comprising one or more of: TIM-3, LAG-3, CEACAM (e.g., CEACAM-1, CEACAM-3, or CEACAM-5), PD-L1 or PD-L2. In one embodiment, the bispecific antibody molecule used in combination binds to CEACAM (e.g., CEACAM-1, CEACAM-3, and/or CEACAM-5) and LAG-3. In another embodiment, the bispecific antibody molecule used in combination binds to CEACAM (e.g., CEACAM-1, CEACAM-3, and/or CEACAM-5) and TIM-3. In another embodiment, the bispecific antibody molecule used in combination binds to LAG-3 and TIM-3.

Uses of the Combination Therapies

The combinations disclosed herein can result in one or more of: an increase in antigen presentation, an increase in effector cell function (e.g., one or more of T cell proliferation, IFN-γ secretion or cytolytic function), inhibition of regulatory T cell function, an effect on the activity of multiple cell types, such as regulatory T cell, effector T cells and NK cells), an increase in tumor infiltrating lymphocytes, an increase in T-cell receptor mediated proliferation, and a decrease in immune evasion by cancerous cells. In one embodiment, the use of a PD-1 inhibitor in the combinations inhibits, reduces or neutralizes one or more activities of PD-1, resulting in blockade or reduction of an immune checkpoint. Thus, such combinations can be used to treat or prevent disorders where enhancing an immune response in a subject is desired.

Accordingly, in another aspect, a method of modulating an immune response in a subject is provided. The method comprises administering to the subject a combination disclosed herein (e.g., a combination comprising a therapeutically effective amount of an anti-PD-1 antibody molecule), alone or in combination with one or more agents or procedures, such that the immune response in the subject is modulated. In one embodiment, the antibody molecule enhances, stimulates or increases the immune response in the subject. The subject can be a mammal, e.g., a primate, preferably a higher primate, e.g., a human (e.g., a patient having, or at risk of having, a disorder described herein). In one embodiment, the subject is in need of enhancing an immune response. In one embodiment, the subject has, or is at risk of, having a disorder described herein, e.g., a cancer or an infectious disorder as described herein. In certain embodiments, the subject is, or is at risk of being, immunocompromised. For example, the subject is undergoing or has undergone a chemotherapeutic treatment and/or radiation therapy. Alternatively, or in combination, the subject is, or is at risk of being, immunocompromised as a result of an infection.

In one aspect, a method of treating (e.g., one or more of reducing, inhibiting, or delaying progression) a cancer or a tumor in a subject is provided. The method comprises administering to the subject a combination disclosed herein (e.g., a combination comprising a therapeutically effective amount of an anti-PD-1 antibody molecule).

In certain embodiments, the cancer treated with the combination, includes but is not limited to, a solid tumor, a hematological cancer (e.g., leukemia, lymphoma, myeloma, e.g., multiple myeloma), and a metastatic lesion. In one embodiment, the cancer is a solid tumor. Examples of solid tumors include malignancies, e.g., sarcomas and carcinomas, e.g., adenocarcinomas of the various organ systems, such as those affecting the lung, breast, ovarian, lymphoid, gastrointestinal (e.g., colon), anal, genitals and genitourinary tract (e.g., renal, urothelial, bladder cells, prostate), pharynx, CNS (e.g., brain, neural or glial cells), head and neck, skin (e.g., melanoma), and pancreas, as well as adenocarcinomas which include malignancies such as colon cancers, rectal cancer, renal cancer (e.g., renal-cell carcinoma (clear cell or non-clear cell renal cell carcinoma), liver cancer, lung cancer (e.g., non-small cell lung cancer (squamous or non-squamous non-small cell lung cancer)), cancer of the small intestine and cancer of the esophagus. The cancer may be at an early, intermediate, late stage or metastatic cancer.

In one embodiment, the cancer is chosen from a lung cancer (e.g., a non-small cell lung cancer (NSCLC) (e.g., a NSCLC with squamous and/or non-squamous histology, or a NSCLC adenocarcinoma)), a skin cancer (e.g., a Merkel cell carcinoma or a melanoma (e.g., an advanced melanoma)), a kidney cancer (e.g., a renal cancer (e.g., a renal cell carcinoma)), a liver cancer, a myeloma (e.g., a multiple myeloma), a prostate cancer, a breast cancer (e.g., a breast cancer that does not express one, two or all of estrogen receptor, progesterone receptor, or Her2/neu, e.g., a triple negative breast cancer), a colorectal cancer, a pancreatic cancer, a head and neck cancer (e.g., head and neck squamous cell carcinoma (HNSCC), anal cancer, gastro-esophageal cancer, thyroid cancer (e.g., anaplastic thyroid carcinoma), cervical cancer, a neuroendocrine tumor (NET) (e.g., an atypical pulmonary carcinoid tumor), a lymphoproliferative disease (e.g., a post-transplant lymphoproliferative disease) or a hematological cancer, T-cell lymphoma, B-cell lymphoma, a non-Hodgkin lymphoma, or a leukemia (e.g., a myeloid leukemia or a lymphoid leukemia).

In another embodiment, the cancer is chosen form a carcinoma (e.g., advanced or metastatic carcinoma), melanoma or a lung carcinoma, e.g., a non-small cell lung carcinoma.

In one embodiment, the cancer is a lung cancer, e.g., a non-small cell lung cancer or small cell lung cancer. In some embodiments, the non-small cell lung cancer is a stage I (e.g., stage Ia or Ib), stage II (e.g., stage Ha or IIb), stage III (e.g., stage IIIc or IIIb), or stage IV, non-small cell lung cancer.

In one embodiment, the cancer is a melanoma, e.g., an advanced melanoma. In one embodiment, the cancer is an advanced or unresectable melanoma that does not respond to other therapies. In other embodiments, the cancer is a melanoma with a BRAF mutation (e.g., a BRAF V600 mutation). In yet other embodiments, the combination disclosed herein (e.g., the combination comprising the anti-PD-1 antibody molecule) is administered after treatment with an anti-CTLA-4 antibody (e.g., ipilimumab) with or without a BRAF inhibitor (e.g., vemurafenib or dabrafenib).

In another embodiment, the cancer is a hepatocarcinoma, e.g., an advanced hepatocarcinoma, with or without a viral infection, e.g., a chronic viral hepatitis.

In another embodiment, the cancer is a prostate cancer, e.g., an advanced prostate cancer.

In yet another embodiment, the cancer is a myeloma, e.g., multiple myeloma.

In yet another embodiment, the cancer is a renal cancer, e.g., a renal cell carcinoma (RCC) (e.g., a metastatic RCC, a non-clear cell renal cell carcinoma (nccRCC), or clear cell renal cell carcinoma (CCRCC)).

In one embodiment, the cancer microenvironment has an elevated level of PD-L1 expression. Alternatively, or in combination, the cancer microenvironment can have increased IFNγ and/or CD8 expression.

In some embodiments, the subject has, or is identified as having, a tumor that has one or more of high PD-L1 level or expression, or as being Tumor Infiltrating Lymphocyte (TIL)+ (e.g., as having an increased number of TILs), or both. In certain embodiments, the subject has, or is identified as having, a tumor that has high PD-L1 level or expression and that is TIL+. In some embodiments, the methods described herein further include identifying a subject based on having a tumor that has one or more of high PD-L1 level or expression, or as being TIL+, or both. In certain embodiments, the methods described herein further include identifying a subject based on having a tumor that has high PD-L1 level or expression and as being TIL+. In some embodiments, tumors that are TIL+ are positive for CD8 and IFNγ. In some embodiments, the subject has, or is identified as having, a high percentage of cells that are positive for one, two or more of PD-L1, CD8, and/or IFNγ. In certain embodiments, the subject has or is identified as having a high percentage of cells that are positive for all of PD-L1, CD8, and IFNγ.

In some embodiments, the methods described herein further include identifying a subject based on having a high percentage of cells that are positive for one, two or more of PD-L1, CD8, and/or IFNγ. In certain embodiments, the methods described herein further include identifying a subject based on having a high percentage of cells that are positive for all of PD-L1, CD8, and IFNγ. In some embodiments, the subject has, or is identified as having, one, two or more of PD-L1, CD8, and/or IFNγ, and one or more of a lung cancer, e.g., squamous cell lung cancer or lung adenocarcinoma (e.g., an NSCLC); a head and neck cancer; a squamous cell cervical cancer; a stomach cancer; an esophageal cancer; a thyroid cancer (e.g., anaplastic thyroid carcinoma); a skin cancer (e.g., a Merkel cell carcinoma or a melanoma), a breast cancer (e.g., an NTBC), and/or a nasopharyngeal cancer (NPC). In certain embodiments, the methods described herein further describe identifying a subject based on having one, two or more of PD-L1, CD8, and/or IFNγ, and one or more of a lung cancer, e.g., squamous cell lung cancer or lung adenocarcinoma (e.g., an NSCLC); a head and neck cancer; a squamous cell cervical cancer; a stomach cancer; a thyroid cancer (e.g., anaplastic thyroid carcinoma); a skin cancer (e.g., a Merkel cell carcinoma or a melanoma), an neuroendocrine tumor, a breast cancer (e.g., an NTBC), and/or a nasopharyngeal cancer.

Methods and compositions disclosed herein are useful for treating metastatic lesions associated with the aforementioned cancers.

In a further aspect, the invention provides a method of treating an infectious disease in a subject, comprising administering to a subject a combination as described herein, e.g., a combination comprising a therapeutically effective amount of an anti-PD-1 antibody molecule described herein. In one embodiment, the infection disease is chosen from hepatitis (e.g., hepatis C infection), or sepsis.

Still further, the invention provides a method of enhancing an immune response to an antigen in a subject, comprising administering to the subject: (i) the antigen; and (ii) a combination as described herein, e.g., a combination comprising a therapeutically effective amount of an anti-PD-1 antibody molecule described herein, such that an immune response to the antigen in the subject is enhanced. The antigen can be, for example, a tumor antigen, a viral antigen, a bacterial antigen or an antigen from a pathogen.

The combinations as described herein can be administered to the subject systemically (e.g., orally, parenterally, subcutaneously, intravenously, rectally, intramuscularly, intraperitoneally, intranasally, transdermally, or by inhalation or intracavitary installation), topically, or by application to mucous membranes, such as the nose, throat and bronchial tubes.

Dosages and therapeutic regimens of the therapeutic agents disclosed herein can be determined by a skilled artisan. In certain embodiments, the anti-PD-1 antibody molecule is administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg. The dosing schedule can vary from e.g., once a week to once every 2, 3, or 4 weeks. In one embodiment, the anti-PD-1 antibody molecule is administered at a dose from about 10 to 20 mg/kg every other week.

In some embodiments, the anti-PD-1 antibody molecule is administered by injection (e.g., subcutaneously or intravenously) at a dose (e.g., a flat dose) of about 100 mg to 600 mg, e.g., about 200 mg to 500 mg, e.g., about 250 mg to 450 mg, about 300 mg to 400 mg, about 250 mg to 350 mg, about 350 mg to 450 mg, or about 100 mg, about 200 mg, about 300 mg, or about 400 mg. The dosing schedule (e.g., flat dosing schedule) can vary from e.g., once a week to once every 2, 3, 4, 5, or 6 weeks. In one embodiment, the anti-PD-1 antibody molecule is administered at a dose from about 300 mg to 400 mg once every three weeks or once every four weeks. In one embodiment, the anti-PD-1 antibody molecule is administered at a dose from about 300 mg once every three weeks. In one embodiment, the anti-PD-1 antibody molecule is administered at a dose from about 400 mg once every four weeks. In one embodiment, the anti-PD-1 antibody molecule is administered at a dose from about 300 mg once every four weeks. In one embodiment, the anti-PD-1 antibody molecule is administered at a dose from about 400 mg once every three weeks.

In one embodiment, the anti-PD-1 antibody molecule is administered, alone or in combination (e.g., in combination with an anti-LAG-3 antibody molecule), at a dose of less than, or about, 5 mg/kg; less than, or about, 4 mg/kg; less than, or about, 3 mg/kg; less than, or about, 2 mg/kg; less than, or about, 1 mg/kg, every other week. In one embodiment, the anti-PD-1 antibody molecule is administered at a dose of 1 to 5 mg/kg every other week; 1 to 4 mg/kg every other week, 1 to 3 mg/kg every other week, or 1 to 2 mg/kg every other week. In one embodiment, the anti-LAG-3 antibody molecule is administered, alone or in combination (e.g., in combination with an anti-PD-1 antibody molecule) at a dose of 1 to 5 mg/kg every other week; 1 to 4 mg/kg every other week, 1 to 3 mg/kg every other week, or 1 to 2 mg/kg every other week.

The antibody molecules described herein are preferred for use in the methods described herein, although other anti-PD-1 antibodies can be used instead, or in combination with an anti-PD-1 antibody molecule of the invention.

Further Combination Therapies

The methods and combinations described herein can include, or be used in combination with, other agents or therapeutic modalities. In one embodiment, the methods described herein include administering to the subject a combination comprising an anti-PD-1 antibody molecule as described herein, in combination with an agent or therapeutic procedure or modality, in an amount effective to treat or prevent a disorder. The anti-PD-1 antibody molecule and the agent or therapeutic procedure or modality can be administered simultaneously or sequentially in any order. Any combination and sequence of the anti-PD-1 antibody molecules and other therapeutic agents, procedures or modalities (e.g., as described herein) can be used. The antibody molecule and/or other therapeutic agents, procedures or modalities can be administered during periods of active disorder, or during a period of remission or less active disease. The antibody molecule can be administered before the other treatment, concurrently with the treatment, post-treatment, or during remission of the disorder.

In certain embodiments, the methods and compositions described herein are administered in combination with one or more of other antibody molecules, chemotherapy, other anti-cancer therapy (e.g., targeted anti-cancer therapies, gene therapy, viral therapy, RNA therapy bone marrow transplantation, nanotherapy, or oncolytic drugs), cytotoxic agents, immune-based therapies (e.g., cytokines or cell-based immune therapies), surgical procedures (e.g., lumpectomy or mastectomy) or radiation procedures, or a combination of any of the foregoing. The additional therapy may be in the form of adjuvant or neoadjuvant therapy. In some embodiments, the additional therapy is an enzymatic inhibitor (e.g., a small molecule enzymatic inhibitor) or a metastatic inhibitor. Exemplary cytotoxic agents that can be administered in combination with include antimicrotubule agents, topoisomerase inhibitors, anti-metabolites, mitotic inhibitors, alkylating agents, anthracyclines, vinca alkaloids, intercalating agents, agents capable of interfering with a signal transduction pathway, agents that promote apoptosis, proteosome inhibitors, and radiation (e.g., local or whole body irradiation (e.g., gamma irradiation). In other embodiments, the additional therapy is surgery or radiation, or a combination thereof. In other embodiments, the additional therapy is a therapy targeting one or more of PI3K/AKT/mTOR pathway, an HSP90 inhibitor, or a tubulin inhibitor.

Alternatively, or in combination with the aforesaid combinations, the methods and compositions described herein can include, be administered in combination with, one or more of: an immunomodulator (e.g., an activator of a costimulatory molecule or an inhibitor of an inhibitory molecule, e.g., an immune checkpoint molecule); a vaccine, e.g., a therapeutic cancer vaccine; or other forms of cellular immunotherapy.

Exemplary non-limiting combinations and uses of the combinations disclosed herein, e.g., a combination comprising an anti-PD-1 antibody molecule, include the following.

In certain embodiments, the combination disclosed herein, e.g., a combination comprising an anti-PD-1 antibody molecule, includes or is administered in combination with a modulator of a costimulatory molecule or an inhibitory molecule, e.g., a co-inhibitory ligand or receptor.

In one embodiment, the combination disclosed herein, e.g., a combination comprising an anti-PD-1 antibody molecule, includes or is administered in combination with a modulator, e.g., agonist, of a costimulatory molecule. In one embodiment, the agonist of the costimulatory molecule is chosen from an agonist (e.g., an agonistic antibody or antigen-binding fragment thereof, or a soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In one embodiment, the combination disclosed herein, e.g., a combination comprising an anti-PD-1 antibody molecule, includes or is administered in combination with an inhibitor of an inhibitory (or immune checkpoint) molecule chosen from PD-L1, PD-L2, CTLA-4, TIM-3, LAG-3, CEACAM (e.g., CEACAM-1, CEACAM-3, and/or CEACAM-5), VISTA, BTLA, TIGIT, LAIR1, CD160, 2B4 and/or TGF beta. In one embodiment, the inhibitor is a soluble ligand (e.g., a CTLA-4-Ig), or an antibody or antibody fragment that binds to PD-L1, PD-L2 or CTLA-4. For example, the anti-PD-1 antibody molecule can be administered in combination with an anti-CTLA-4 antibody, e.g., ipilimumab, for example, to treat a cancer (e.g., a cancer chosen from: a melanoma, e.g., a metastatic melanoma; a lung cancer, e.g., a non-small cell lung carcinoma; or a prostate cancer). In one embodiment, the anti-PD-1 antibody molecule is administered after treatment with an anti-CTLA-4 antibody (e.g., ipilimumab) with or without a BRAF inhibitor (e.g., vemurafenib or dabrafenib).

In another embodiment, the combination disclosed herein, e.g., a combination comprising an anti-PD-1 antibody molecule, includes or is administered in combination with an anti-LAG-3 antibody or antigen-binding fragment thereof.

In another embodiment, the combination disclosed herein, e.g., a combination comprising an anti-PD-1 antibody molecule, includes or is administered in combination with an anti-TIM-3 antibody or antigen-binding fragment thereof.

In yet other embodiments, the combination disclosed herein, e.g., a combination comprising an anti-PD-1 antibody molecule, includes or is administered in combination with an anti-LAG-3 antibody and an anti-TIM-3 antibody (or antigen-binding fragments thereof).

In another embodiment, the combination disclosed herein, e.g., a combination comprising an anti-PD-1 antibody molecule, includes or is administered in combination with a CEACAM inhibitor (e.g., CEACAM-1 and/or CEACAM-5 inhibitor), e.g., an anti-CEACAM antibody molecule. In another embodiment, the anti-PD-1 antibody molecule is administered in combination with a CEACAM-1 inhibitor, e.g., an anti-CEACAM-1 antibody molecule. In another embodiment, the anti-PD-1 antibody molecule is administered in combination with a CEACAM-5 inhibitor, e.g., an anti-CEACAM-5 antibody molecule.

The combination of antibodies recited herein can be administered separately, e.g., as separate antibodies or antigen-binding fragments thereof, or linked, e.g., as a bispecific or trispecific antibody molecule. In one embodiment, a bispecific antibody that includes an anti-PD-1 antibody molecule and an anti-TIM-3, anti-CEACAM (e.g., anti-CEACAM-1, CEACAM-3, and/or anti-CEACAM-5), or anti-LAG-3 antibody, or an antigen-binding fragment thereof, is administered. In certain embodiments, the combination of antibodies recited herein is used to treat a cancer, e.g., a cancer as described herein (e.g., a solid tumor or a hematologic malignancy).

In other embodiments, the combination disclosed herein, e.g., a combination comprising an anti-PD-1 antibody molecule, includes or is administered in combination with a cytokine. The cytokine can be administered as a fusion molecule to the anti-PD-1 antibody molecule, or as separate compositions. In one embodiment, the anti-PD-1 antibody is administered in combination with one, two, three or more cytokines, e.g., as a fusion molecule or as separate compositions. In one embodiment, the cytokine is an interleukin (IL) chosen from one, two, three or more of IL-1, IL-2, IL-12, IL-15 or IL-21. In one embodiment, a bispecific antibody molecule has a first binding specificity to a first target (e.g., to PD-1), a second binding specificity to a second target (e.g., LAG-3 or TIM-3), and is optionally linked to an interleukin (e.g., IL-12) domain e.g., full length IL-12 or a portion thereof. In certain embodiments, the combination of anti-PD-1 antibody molecule and the cytokine described herein is used to treat a cancer, e.g., a cancer as described herein (e.g., a solid tumor).

In certain embodiments, the combination disclosed herein, e.g., a combination comprising an anti-PD-1 antibody molecule, includes or is administered in combination with an antibody specific against an HLA C, e.g., an antibody specific to Killer-cell Immunoglobulin-like Receptors (also referred to herein as an "anti-KIR antibody"). In certain embodiments, the combination of anti-PD-1 antibody molecule and anti-KIR antibody is used to treat a cancer, e.g., a cancer as described herein (e.g., a solid tumor, e.g., an advanced solid tumor).

In one embodiment, the combination disclosed herein, e.g., a combination comprising an anti-PD-1 antibody molecule, includes or is administered in combination with a cellular immunotherapy (e.g., Provenge® (e.g., Sipuleucel-T)), and optionally in combination with cyclophosphamide. In certain embodiments, the combination of anti-PD-1 antibody molecule, Provenge® and/or cyclophosphamide is used to treat a cancer, e.g., a cancer as described herein (e.g., a prostate cancer, e.g., an advanced prostate cancer).

In another embodiment, the combination disclosed herein, e.g., a combination comprising an anti-PD-1 antibody molecule, includes or is administered in combination with a vaccine, e.g., a cancer vaccine, (e.g., a dendritic cell renal carcinoma (DC-RCC) vaccine). In one embodiment, the vaccine is peptide-based, DNA-based, RNA-based, or antigen-based, or a combination thereof. In embodiments, the vaccine comprises one or more peptides, nucleic acids (e.g., DNA or RNA), antigens, or a combination thereof. In certain embodiments, the combination of anti-PD-1 antibody molecule and the DC-RCC vaccine is used to treat a cancer, e.g., a cancer as described herein (e.g., a renal carcinoma, e.g., metastatic renal cell carcinoma (RCC) or clear cell renal cell carcinoma (CCRCC)).

In another embodiment, the combination disclosed herein, e.g., a combination comprising an anti-PD-1 antibody molecule, includes or is administered in combination with an adjuvant.

In yet another embodiment, the combination disclosed herein, e.g., a combination comprising an anti-PD-1 antibody molecule, includes or is administered in combination with chemotherapy, and/or immunotherapy. For example, the anti-PD-1 antibody molecule can be used to treat a myeloma, alone or in combination with one or more of: chemotherapy or other anti-cancer agents (e.g., thalidomide analogs, e.g., lenalidomide), an anti-TIM-3 antibody, tumor antigen-pulsed dendritic cells, fusions (e.g., electrofusions) of tumor cells and dendritic cells, or vaccination with immunoglobulin idiotype produced by malignant plasma cells. In one embodiment, the anti-PD-1 antibody molecule is used in combination with an anti-TIM-3 antibody to treat a myeloma, e.g., a multiple myeloma.

In one embodiment, the combination disclosed herein, e.g., a combination comprising an anti-PD-1 antibody molecule, includes or is used in combination with chemotherapy to treat a lung cancer, e.g., non-small cell lung cancer. In one embodiment, the anti-PD-1 antibody molecule is used with standard lung, e.g., NSCLC, chemotherapy, e.g., platinum doublet therapy, to treat lung cancer. In yet other embodiments, the anti-PD-1 antibody molecule is used in combination with an indoleamine-pyrrole 2,3-dioxygenase (IDO) inhibitor (e.g., (4E)-4-[(3-chloro-4-fluoroanilino)-nitrosomethylidene]-1,2,5-oxadiazol-3-amine (also known as INCB24360), indoximod (1-methyl -D-tryptophan), α-cyclohexyl-5H-Imidazo[5,1-a]isoindole-5-ethanol (also known as NLG919), etc.) in a subject with advanced or metastatic cancer (e.g., a patient with metastic and recurrent NSCL cancer).

In yet other embodiments, the combination disclosed herein, e.g., a combination comprising an anti-PD-1 antibody molecule, includes or is used in combination with one or more of: an immune-based strategy (e.g., interleukin-2 or interferon-α), a targeting agent (e.g., a VEGF inhibitor such as a monoclonal antibody to VEGF); a VEGF tyrosine kinase inhibitor such as sunitinib, sorafenib, axitinib and pazopanib; an RNAi inhibitor; or an inhibitor of a downstream mediator of VEGF signaling, e.g., an inhibitor of the mammalian target of rapamycin (mTOR), e.g., everolimus and temsirolimus. Any of such combinations can be used to treat a renal cancer, e.g., renal cell carcinoma (RCC) (e.g., clear cell renal cell carcinoma (CCRCC) or a non-clear cell renal cell carcinoma (nccRCC) or metastatic RCC, or a liver cancer (e.g., a hepatocellular carcinoma).

In some embodiments, the combination disclosed herein, e.g., a combination comprising an anti-PD-1 antibody molecule, includes or is used in combination with a MEK inhibitor (e.g., a MEK inhibitor as described herein). In some embodiments, the combination of the anti-PD-1 antibody and the MEK inhibitor is used to treat a cancer (e.g., a cancer described herein). In some embodiments, the cancer treated with the combination is chosen from a melanoma, a colorectal cancer, a non-small cell lung cancer, an ovarian cancer, a breast cancer, a prostate cancer, a pancreatic cancer, a hematological malignancy or a renal cell carcinoma. In certain embodiments, the cancer includes a BRAF mutation (e.g., a BRAF V600E mutation), a BRAF wildtype, a KRAS wildtype or an activating KRAS mutation. The cancer may be at an early, intermediate or late stage.

In another embodiment, the combination disclosed herein, e.g., a combination comprising an anti-PD-1 antibody molecule, includes or is used in combination with one, two or all of oxaliplatin, leucovorin or 5-FU (e.g., a FOLFOX co-treatment). Alternatively or in combination, combination further includes a VEGF inhibitor (e.g., a VEGF inhibitor as disclosed herein). In some embodiments, the combination of the anti-PD-1 antibody, the FOLFOX co-treatment, and the VEGF inhibitor is used to treat a cancer (e.g., a cancer described herein). In some embodiments, the cancer treated with the combination is chosen from a melanoma, a colorectal cancer, a non-small cell lung cancer, an ovarian cancer, a breast cancer, a prostate cancer, a pancreatic cancer, a hematological malignancy or a renal cell carcinoma. The cancer may be at an early, intermediate or late stage.

In other embodiments, the combination disclosed herein, e.g., a combination comprising an anti-PD-1 antibody molecule, includes or is administered with a tyrosine kinase inhibitor (e.g., axitinib) to treat renal cell carcinoma and other solid tumors.

In other embodiments, the combination disclosed herein, e.g., a combination comprising an anti-PD-1 antibody molecule, includes or is administered with a 4-1BB receptor targeting agent (e.g., an antibody that stimulates signaling through 4-1BB (CD-137), e.g., PF-2566). In one embodiment, the anti-PD-1 antibody molecule is administered in combination with a tyrosine kinase inhibitor (e.g., axitinib) and a 4-1BB receptor targeting agent.

The anti-PD-1 antibody molecule can be bound to a substance, e.g., a cytotoxic agent or moiety (e.g., a therapeutic drug; a compound emitting radiation; molecules of plant, fungal, or bacterial origin; or a biological protein (e.g., a protein toxin) or particle (e.g., a recombinant viral particle, e.g., via a viral coat protein). For example, the antibody can be coupled to a radioactive isotope such as an α-, β-, or γ-emitter, or a β- and γ-emitter.

Any combination and sequence of the anti-PD-1 antibody molecules and other therapeutic agents, procedures or modalities (e.g., as described herein) can be used. The antibody molecule and/or other therapeutic agents, procedures or modalities can be administered during periods of active disorder, or during a period of remission or less active disease. The antibody molecule can be administered before the other treatment, concurrently with the treatment, post-treatment, or during remission of the disorder.

Additional Combination Therapies

In certain embodiments, any of the combinations disclosed herein, alternatively or in combination, further includes one or more of the agents described in Table 7.

In some embodiments, the additional therapeutic agent is chosen from one or more of: 1) a protein kinase C (PKC) inhibitor; 2) a heat shock protein 90 (HSP90) inhibitor; 3) an inhibitor of a phosphoinositide 3-kinase (PI3K) and/or target of rapamycin (mTOR); 4) an inhibitor of cytochrome P450 (e.g., a CYP17 inhibitor or a 17alpha-Hydroxylase/C17-20 Lyase inhibitor); 5) an iron chelating agent; 6) an aromatase inhibitor; 7) an inhibitor of p53, e.g., an inhibitor of a p53/Mdm2 interaction; 8) an apoptosis inducer; 9) an angiogenesis inhibitor; 10) an aldosterone synthase inhibitor; 11) a smoothened (SMO) receptor inhibitor; 12) a prolactin receptor (PRLR) inhibitor; 13) a Wnt signaling inhibitor; 14) a CDK4/6 inhibitor; 15) a fibroblast growth factor receptor 2 (FGFR2)/fibroblast growth factor receptor 4 (FGFR4) inhibitor; 16) an inhibitor of macrophage colony-stimulating factor (M-CSF); 17) an inhibitor of one or more of c-KIT, histamine release, Flt3 (e.g., FLK2/STK1) or PKC; 18) an inhibitor of one or more of VEGFR-2 (e.g., FLK-1/KDR), PDGFRbeta, c-KIT or Raf kinase C; 19) a somatostatin agonist and/or a growth hormone release inhibitor; 20) an anaplastic lymphoma kinase (ALK) inhibitor; 21) an insulin-like growth factor 1 receptor (IGF-1R) inhibitor; 22) a P-Glycoprotein 1 inhibitor; 23) a vascular endothelial growth factor receptor (VEGFR) inhibitor; 24) a BCR-ABL kinase inhibitor; 25) an FGFR inhibitor; 26) an inhibitor of CYP11B2; 27) a HDM2 inhibitor, e.g., an inhibitor of the HDM2-p53 interaction; 28) an inhibitor of a tyrosine kinase; 29) an inhibitor of c-MET; 30) an inhibitor of JAK; 31) an inhibitor of DAC; 32) an inhibitor of 11β-hydroxylase; 33) an inhibitor of IAP; 34) an inhibitor of PIM kinase; 35) an inhibitor of Porcupine; 36) an inhibitor of BRAF, e.g., BRAF V600E or wild-type BRAF; 37) an inhibitor of HER3; 38) an inhibitor of MEK; or 39) an inhibitor of a lipid kinase, e.g., as described herein and in Table 7.

In one embodiment, the additional therapeutic agent is chosen from one or more of: Compound A8, Compound A17, Compound A23, Compound A24, Compound A27, Compound A29, Compound A33, and Compound A13.

In other embodiments, the additional therapeutic agent is chosen from one or more of: Compound A5, Compound A8, Compound A17, Compound A23, Compound A24, Compound A29, and Compound A40.

In other embodiments, the additional therapeutic agent is chosen from one or more of: Compound A9, Compound A16, Compound A17, Compound A21, Compound A22, Compound A25, Compound A28, Compound A48, and Compound 49.

In one embodiment, the cancer is chosen from a lung cancer (e.g., a non-small cell lung cancer (NSCLC) (e.g., a NSCLC with squamous and/or non-squamous histology, or a NSCLC adenocarcinoma), or disclosed in a publication listed in Table 7.

Biomarkers

In another aspect, provided herein is a method of evaluating or monitoring the effectiveness of a therapy (e.g., a combination therapy) described herein, in a subject (e.g., a subject having a cancer, e.g., a cancer described herein). The method includes acquiring a value of effectiveness to the therapy, wherein said value is indicative of the effectiveness of the therapy.

In embodiments, the value of effectiveness to the therapy comprises a measure of one, two, three, four, five, six, seven, eight, nine or more (e.g., all) of the following:

(i) a parameter of a tumor infiltrating lymphocyte (TIL) phenotype;

(ii) a parameter of a myeloid cell population;

(iii) a parameter of a surface expression marker;

(iv) a parameter of a biomarker of an immunologic response;

(v) a parameter of a systemic cytokine modulation;

(vi) a parameter of circulating free DNA (cfDNA);

(vii) a parameter of systemic immune-modulation;

(viii) a parameter of microbiome;

(ix) a parameter of a marker of activation in a circulating immune cell; or (x) a parameter of a circulating cytokine.

In some embodiments, the parameter of a TIL phenotype comprises the level or activity of one, two, three, four or more (e.g., all) of Hematoxylin and eosin (H&E) staining for TIL counts, CD8, FOXP3, CD4, or CD3, in the subject, e.g., in a sample from the subject (e.g., a tumor sample).

In some embodiments, the parameter of a myeloid cell population comprises the level or activity of one or both of CD68 or CD163, in the subject, e.g., in a sample from the subject (e.g., a tumor sample).

In some embodiments, the parameter of a surface expression marker comprises the level or activity of one, two or more (e.g., all) of PD-L1, LAG-3, or TIM-3, in the subject, e.g., in a sample from the subject (e.g., a tumor sample).

In some embodiments, the parameter of a biomarker of an immunologic response comprises the level or sequence of one or more nucleic acid-based markers, in the subject, e.g., in a sample from the subject (e.g., a tumor sample).

In some embodiments, the parameter of systemic cytokine modulation comprises the level or activity of one, two, three, four, five, six, seven, eight, or more (e.g., all) of IL-18, IFN-γ, ITAC (CXCL11), IL-6, IL-10, IL-4, IL-17, IL-15, or TGF-beta, in the subject, e.g., in a sample from the subject (e.g., a blood sample, e.g., a plasma sample).

In some embodiments, the parameter of cfDNA comprises the sequence or level of one or more circulating tumor DNA (cfDNA) molecules, in the subject, e.g., in a sample from the subject (e.g., a blood sample, e.g., a plasma sample).

In some embodiments, the parameter of systemic immune-modulation comprises phenotypic characterization of an activated immune cell, e.g., a CD3-expressing cell, a CD8-expressing cell, or both, in the subject, e.g., in a sample from the subject (e.g., a blood sample, e.g., a PBMC sample). In some embodiments, the parameter of microbiome comprises the sequence or expression level of one or more genes in the microbiome, in the subject, e.g., in a sample from the subject (e.g., a stool sample).

In some embodiments, the parameter of a marker of activation in a circulating immune cell comprises the level or activity of one, two, three, four, five or more (e.g., all) of circulating CD8+, HLA-DR+Ki67+, T cells, IFN-γ, IL-18, or CXCL11 (IFN-γ induced CCK) expressing cells, in a sample (e.g., a blood sample, e.g., a plasma sample).

In some embodiments, the parameter of a circulating cytokine comprises the level or activity of IL-6, in the subject, e.g., in a sample from the subject (e.g., a blood sample, e.g., a plasma sample).

In some embodiments of any of the methods disclosed herein, the therapy comprises a combination of (a) an inhibitor of a immune checkpoint molecule, e.g., an inhibitor of PD-1 (e.g., an anti-PD-1 antibody molecule); and (b) one or more (e.g., two, three, four or more) of:

(i) an IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003;

(ii) an mTOR inhibitor, Everolimus (Compound A36), or a compound disclosed in PCT Publication No. WO 2014/085318;

(iii) a DAC inhibitor, Panobinostat (Compound A19), or a compound disclosed in PCT Publication No. WO 2014/072493;

(iv) an IL-1β inhibitor, canakinumab, or a compound disclosed in PCT Publication No. WO 2002/16436;

(v) an IL-17 inhibitor, CJM112, or a compound disclosed in PCT Publication No. WO 2014/122613;

(vi) a MEK inhibitor or trametinib; or (vii) an EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757.

In some embodiments of any of the methods disclosed herein, the measure of one or more of (i)-(x) is obtained from a sample acquired from the subject. In some embodiments, the sample is chosen from a tumor sample, a blood sample (e.g., a plasma sample or a PBMC sample), or a stool sample.

In some embodiments of any of the methods disclosed herein, the subject is evaluated prior to receiving, during, or after receiving, the therapy, e.g., the combination therapy.

In some embodiments of any of the methods disclosed herein, the measure of one or more of (i)-(x) evaluates a profile for one or more of gene expression, flow cytometry or protein expression.

In some embodiments of any of the methods disclosed herein, the presence of an increased level or activity of one, two, three, four, five, or more (e.g., all) of circulating CD8+, HLA-DR+Ki67+, T cells, IFN-γ, IL-18, or CXCL11 (IFN-γ induced CCK) expressing cells, and/or the presence of an decreased level or activity of IL-6, in the subject or sample, is a positive predictor of the effectiveness of the therapy.

Alternatively, or in combination with the methods disclosed herein, responsive to said value, performing one, two, three, four or more (e.g., all) of:

(i) administering to the subject the therapy (e.g., combination therapy);

(ii) administered an altered dosing of the therapy (e.g., a combination therapy);

(iii) altering the schedule or time course of the therapy (e.g., a combination therapy);

(iv) administering to the subject an additional agent (e.g., a therapeutic agent described herein) in combination with the therapy (e.g., a combination therapy); or (v) administering to the subject an alternative therapy (e.g., a therapy described herein).

ADDITIONAL EMBODIMENTS

Additional embodiments provide a method of treating a cancer, comprising: identifying in a subject or a sample (e.g., a subject's sample comprising cancer cells and optionally immune cells such as TILs) the presence of one, two or all of PD-L1, CD8, or IFN-γ, thereby providing a value for one, two or all of PD-L1, CD8, and IFN-γ. The method can further include comparing the PD-L1, CD8, and/or IFN-γ values to a reference value, e.g., a control value. If the PD-L1, CD8, and/or IFN-γ values are greater than the reference value, e.g., the control values, administering a therapeutically effective amount of a combination as described herein (e.g., a combination that includes an anti-PD-1 antibody described herein) to the subject, optionally in combination with one or more other agents, thereby treating the cancer. The cancer may be, e.g., a cancer described herein, such as lung cancer (squamous), lung cancer (adenocarcinoma), head and neck cancer, cervical cancer (squamous), stomach cancer, thyroid cancer (e.g., anaplastic thyroid carcinoma), skin cancer (e.g., Merkel cell carcinoma or melanoma), nasopharyngeal cancer, neuroendocrine tumor (e.g., an atypical pulmonary carcinoid tumor), or breast cancer, e.g., TN breast cancer, e.g., IM-TN breast cancer. In some embodiments, the cancer is ER+ breast cancer or pancreatic cancer.

Also provided is a method of treating a cancer, comprising: testing a subject or a sample (e.g., a subject's sample comprising cancer cells) for the presence of PD-L1, thereby identifying a PD-L1 value, comparing the PD-L1 value to a control value, and if the PD-L1 value is greater than the control value, administering a therapeutically effective amount of a combination as described herein (e.g., a combination that includes an anti-PD-1 antibody described herein) to the subject, optionally in combination with one or more other agents, thereby treating the cancer. The cancer may be, e.g., a cancer as described herein, such as cancer is non-small cell lung (NSCLC) adenocarcinoma (ACA), NSCLC squamous cell carcinoma (SCC), or hepatocellular carcinoma (HCC).

In another aspect, the invention features diagnostic or therapeutic kits that include the antibody molecules described herein and instructions for use.

All publications, patent applications, patents, and other references mentioned herein are incorporated by reference in their entirety.

Other features, objects, and advantages of the invention will be apparent from the description and drawings, and from the claims.

BRIEF DESCRIPTION OF THE DRAWINGS

FIG. 1 depicts the amino acid sequences of the light and heavy chain variable regions of murine anti-PD-1 mAb BAP049. The upper and lower sequences were from two independent analyses. The light and heavy chain CDR sequences based on Kabat numbering are underlined. The light heavy chain CDR sequences based on Chothia numbering are shown in bold italics. The unpaired Cys residue at position 102 of the light chain sequence is boxed. Sequences are disclosed as SEQ ID NOs: 8, 228, 16 and 229, respectively, in order of appearance.

FIG. 2A depicts the amino acid sequences of the light and heavy chain variable regions of murine anti-PD-1 mAb BAP049 aligned with the germline sequences. The upper and lower sequences are the germline (GL) and BAP049 (Mu mAb) sequences, respectively. The light and heavy chain CDR sequences based on Kabat numbering are underlined. The light heavy chain CDR sequences based on Chothia numbering are shown in bold italics. "-" means identical amino acid residue. Sequences disclosed as SEQ ID NOs: 230, 8, 231 and 16, respectively, in order of appearance.

FIG. 2B depicts the sequence of murine κJ2 gene and the corresponding mutation in murine anti-PD-1 mAb BAP049. "-" means identical nucleotide residue. Sequences disclosed as SEQ ID NOs: 233, 232, 234 and 235, respectively, in order of appearance.

FIG. 5 depicts the structural analysis of the humanized BAP049 clones (a, b, c, d and e represent various types of framework region sequences). The concentrations of the mAbs in the samples are also shown.

FIG. 7 depicts the ranking of humanized BAP049 clones based on FACS data, competition binding and structural analysis. The concentrations of the mAbs in the samples are also shown.

FIGS. 9A-9B depict the alignment of heavy chain variable domain sequences for the sixteen humanized BAP049 clones and BAP049 chimera (BAP049-chi). In FIG. 9A, all of the sequences are shown (SEQ ID NOs: 22, 38, 38, 38, 38, 38, 38, 38, 38, 38, 50, 50, 50, 50, 82, 82 and 86, respectively, in order of appearance). In FIG. 9B, only amino acid sequences that are different from mouse sequence are shown (SEQ ID NOs: 22, 38, 38, 38, 38, 38, 38, 38, 38, 38, 50, 50, 50, 50, 82, 82 and 86, respectively, in order of appearance).

FIGS. 10A-10B depict the alignment of light chain variable domain sequences for the sixteen humanized BAP049 clones and BAP049 chimera (BAP049-chi). In FIG. 10A, all of the sequences are shown (SEQ ID NOs: 24, 66, 66, 66, 66, 70, 70, 70, 58, 62, 78, 74, 46, 46, 42, 54 and 54, respectively, in order of appearance). In FIG. 10B, only amino acid sequences that are different from mouse sequence are shown (SEQ ID NOs: 24, 66, 66, 66, 66, 70, 70, 70, 58, 62, 78, 74, 46, 46, 42, 54 and 54, respectively, in order of appearance).

FIGS. 14A-14B depict the accumulation, time course and within subject variability of the model used to analyze pharmacokinetics. The shaded areas represent 90% prediction interval; solid lines are the median of prediction at each time point; black dots represent observed pharmacokinetic data.

FIG. 21A depicts CT scan images showing response in the patient. The left panel shows liver metastasis prior to antibody treatment. The middle panel shows pseudo-progression in the liver (accompanied by significant shrinkage of lung lesions not shown) in the first restaging. The right panel shows response in all lesions in the second restaging.

FIG. 21B depicts the reduction in metastatic atypical pulmonary carcinoid tumor burden (% change from baseline) and individual lesions (lesion size (nm)) in the patient.

FIG. 21C depicts the images of immunohistochemistry staining showing high levels of CD8+ T lymphocytes in a tumor sample obtained from the patient during Cycle 2, Day 1. BL, baseline; C2D1, Cycle 2, Day 1.

BRIEF DESCRIPTION OF THE TABLES

Figure 3A:
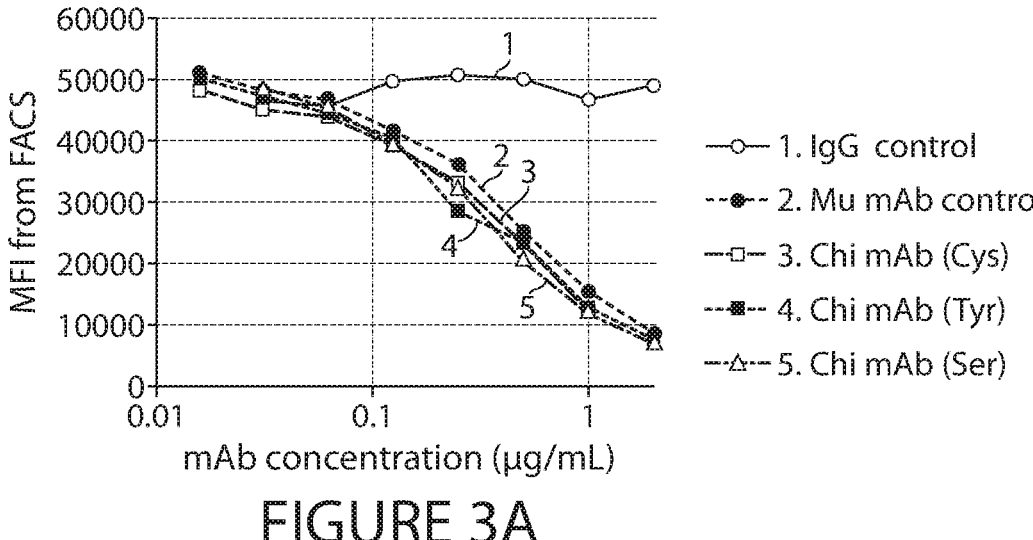
FIGS. 3A-3B depict the competition binding between fluorescently labeled murine anti-PD-1 mAb BAP049 (Mu mAb) and three chimeric versions of BAP049 (Chi mAb). Experiment was performed twice, and the results are shown in FIGS. 3A and 3B, respectively. The three chimeric BAP049 antibodies (Chi mAb (Cys), Chi mAb (Tyr) and Chi mAb (Ser)) have Cys, Tyr and Ser residue at position 102 of the light chain variable region, respectively. Chi mAb (Cys), Chi mAb (Tyr) and Chi mAb (Ser) are also known as BAP049-chi, BAP049-chi-Y, and BAP049-chi-S, respectively.
Figure 3B:
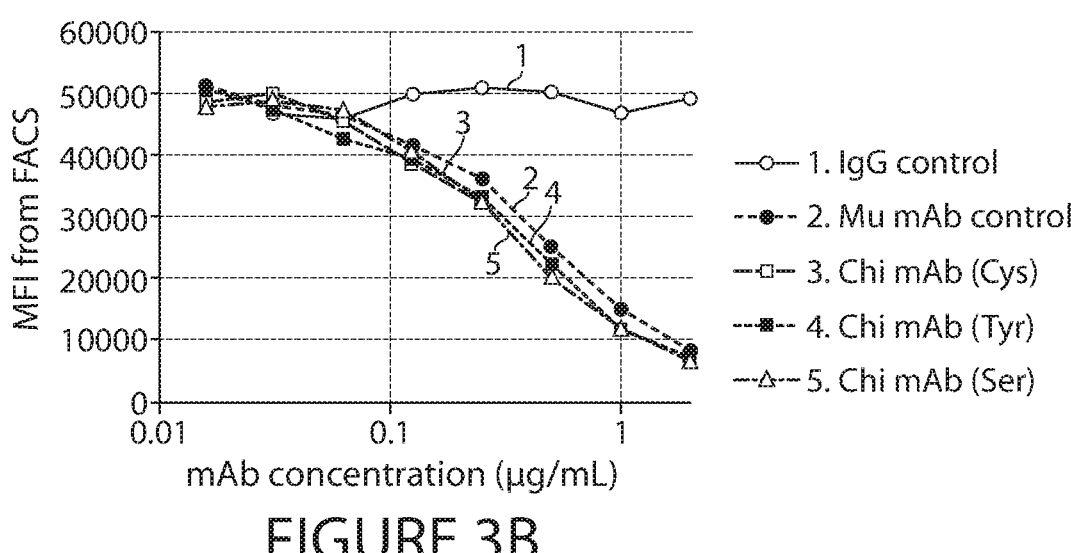

Table 1 is a summary of the amino acid and nucleotide sequences for the murine, chimeric and humanized anti-PD-1 antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the amino acid and nucleotide sequences of the heavy and light chain variable regions, and the amino acid and nucleotide sequences of the heavy and light chains are shown in this Table.

Table 2 depicts the amino acid and nucleotide sequences of the heavy and light chain framework regions for humanized mAbs BAP049-hum01 to BAP049-hum16 and BAP049-Clone-A to BAP049-Clone-E.

Table 3 depicts the constant region amino acid sequences of human IgG heavy chains and human kappa light chain.

Table 4 shows the amino acid sequences of the heavy and light chain leader sequences for humanized mAbs BAP049-Clone-A to BAP049-Clone-E.

Table 5 depicts exemplary PK parameters based on flat dosing schedules.

Table 6 provides an exemplary listing of the therapeutic agents from Antigen-Presentation Combinations (Category A), Effector Cell Combinations (Category B) and Anti-tumor Immunosuppression Combinations (Category C).

Table 7 is a summary of selected therapeutic agents that can be administered in combination with the anti-PD-1 antibody molecules and other immunomodulators (e.g., one or more of: an activator of a costimulatory molecule and/or an inhibitor of an immune checkpoint molecule) described herein. Table 7 provides from left to right the following: the Compound Designation of the second therapeutic agent, the Compound structure, and Patent publication(s) disclosing the Compound.

Table 8 is a summary of exemplary biomarkers and sample collection, e.g., for evaluation of the effectiveness of the therapies (e.g., combination therapies) described herein.

Table 9 is a summary of the objectives and endpoints in the phase I/II study.

Table 10 is a summary of the patient demographics and characteristics in the phase I/II study.

Table 11 shows the patient disposition in the phase I/II study.

Table 12 shows the adverse events regardless of study drug relationship in the phase I/II study (any grad occurring in ≥20% of patients—safety set).

Table 13 shows the best overall response (based on investigator's assessment of disease status using RECIST v1.1 criteria).

DETAILED DESCRIPTION

Disclosed herein, at least in part, are antibody molecules (e.g., humanized antibody molecules) that bind to Programmed Death 1 (PD-1) with high affinity and specificity. Nucleic acid molecules encoding the antibody molecules, expression vectors, host cells and methods for making the antibody molecules are also provided. Pharmaceutical compositions and dose formulations comprising the antibody molecules are also provided. The anti-PD-1 antibody molecules disclosed herein can be used (alone or in combination with other agents or therapeutic modalities) to treat, prevent and/or diagnose disorders, such as cancerous disorders (e.g., solid and soft-tissue tumors), as well as infectious diseases (e.g., chronic infectious disorders or sepsis). Thus, compositions and methods for detecting PD-1, as well as methods for treating various disorders including cancer and/or infectious diseases, using the anti-PD-1 antibody molecules are disclosed herein. In certain embodiments, the anti-PD-1 antibody molecule is administered or used at a flat or fixed dose.

Also disclosed herein are methods and compositions comprising a combination of two, three or more therapeutic agents chosen from one, two, or all of the following categories (i)-(iii): (i) an agent that enhances antigen presentation (e.g., tumor antigen presentation) (e.g., by enhancing one or more of dendritic cell activity or maturation, antigen uptake, or antigen processing); (ii) an agent that enhances an effector cell response (e.g., an immune effector cell response, e.g., B cell and/or T cell activation and/or mobilization, e.g., in the lymph node); or (iii) an agent that decreases tumor immunosuppression (e.g., increasing T cell infiltration and tumor cell killing). In some embodiments, the combination includes a PD-1 inhibitor (e.g., an anti-PD-1 antibody molecule as described herein). Without wishing to be bound by theory, it is believed that therapeutic approaches that enhance anti-tumor immunity work more effectively when the immune response is optimized via multiple targets at different stages of the immune response. Each of these stages in depicted in schematic form in FIG. 21. For example, approaches that result in activation of dendritic cells combined with approaches that enhance cellular and humoral immune can result in a more effective and/or prolonged therapeutic response.

Additional terms are defined below and throughout the application.

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

By "a combination" or "in combination with," it is not intended to imply that the therapy or the therapeutic agents must be administered at the same time and/or formulated for delivery together, although these methods of delivery are within the scope described herein. The therapeutic agents in the combination can be administered concurrently with, prior to, or subsequent to, one or more other additional therapies or therapeutic agents. The therapeutic agents or therapeutic protocol can be administered in any order. In general, each agent will be administered at a dose and/or on a time schedule determined for that agent. In will further be appreciated that the additional therapeutic agent utilized in this combination may be administered together in a single composition or administered separately in different compositions. In general, it is expected that additional therapeutic agents utilized in combination be utilized at levels that do not exceed the levels at which they are utilized individually. In some embodiments, the levels utilized in combination will be lower than those utilized individually.

In embodiments, the additional therapeutic agent is administered at a therapeutic or lower-than therapeutic dose. In certain embodiments, the concentration of the second therapeutic agent that is required to achieve inhibition, e.g., growth inhibition, is lower when the second therapeutic agent is administered in combination with the first therapeutic agent, e.g., the anti-PD-1 antibody molecule, than when the second therapeutic agent is administered individually. In certain embodiments, the concentration of the first therapeutic agent that is required to achieve inhibition, e.g., growth inhibition, is lower when the first therapeutic agent is administered in combination with the second therapeutic agent than when the first therapeutic agent is administered individually. In certain embodiments, in a combination therapy, the concentration of the second therapeutic agent that is required to achieve inhibition, e.g., growth inhibition, is lower than the therapeutic dose of the second therapeutic agent as a monotherapy, e.g., 10-20%, 20-30%, 30-40%, 40-50%, 50-60%, 60-70%, 70-80%, or 80-90% lower. In certain embodiments, in a combination therapy, the concentration of the first therapeutic agent that is required to achieve inhibition, e.g., growth inhibition, is lower than the therapeutic dose of the first therapeutic agent as a monotherapy, e.g., 10-20%, 20-30%, 30-40%, 40-50%, 50-60%, 60-70%, 70-80%, or 80-90% lower.

The term "inhibition," "inhibitor," or "antagonist" includes a reduction in a certain parameter, e.g., an activity, of a given molecule, e.g., an immune checkpoint inhibitor. For example, inhibition of an activity, e.g., a PD-1 or PD-L1 activity, of at least 5%, 10%, 20%, 30%, 40% or more is included by this term. Thus, inhibition need not be 100%.

The term "activation," "activator," or "agonist" includes an increase in a certain parameter, e.g., an activity, of a given molecule, e.g., a costimulatory molecule. For example, increase of an activity, e.g., a costimulatory activity, of at least 5%, 10%, 25%, 50%, 75% or more is included by this term.

The term "anti-cancer effect" refers to a biological effect which can be manifested by various means, including but not limited to, e.g., a decrease in tumor volume, a decrease in the number of cancer cells, a decrease in the number of metastases, an increase in life expectancy, decrease in cancer cell proliferation, decrease in cancer cell survival, or amelioration of various physiological symptoms associated with the cancerous condition. An "anti-cancer effect" can also be manifested by the ability of the peptides, polynucleotides, cells and antibodies in prevention of the occurrence of cancer in the first place.

The term "anti-tumor effect" refers to a biological effect which can be manifested by various means, including but not limited to, e.g., a decrease in tumor volume, a decrease in the number of tumor cells, a decrease in tumor cell proliferation, or a decrease in tumor cell survival.

The term "cancer" refers to a disease characterized by the rapid and uncontrolled growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. The terms "tumor" and "cancer" are used interchangeably herein, e.g., both terms encompass solid and liquid, e.g., diffuse or circulating, tumors. As used herein, the term "cancer" or "tumor" includes premalignant, as well as malignant cancers and tumors.

The term "antigen presenting cell" or "APC" refers to an immune system cell such as an accessory cell (e.g., a B-cell, a dendritic cell, and the like) that displays a foreign antigen complexed with major histocompatibility complexes (MHC's) on its surface. T-cells may recognize these complexes using their T-cell receptors (TCRs). APCs process antigens and present them to T-cells.

The term "costimulatory molecule" refers to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are required for an efficient immune response. Costimulatory molecules include, but are not limited to, an MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

"Immune effector cell," or "effector cell" as that term is used herein, refers to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NKT) cells, mast cells, and myeloid-derived phagocytes.

"Immune effector" or "effector" "function" or "response," as that term is used herein, refers to function or response, e.g., of an immune effector cell, that enhances or promotes an immune attack of a target cell. E.g., an immune effector function or response refers a property of a T or NK cell that promotes killing or the inhibition of growth or proliferation, of a target cell. In the case of a T cell, primary stimulation and co-stimulation are examples of immune effector function or response.

The term "effector function" refers to a specialized function of a cell. Effector function of a T cell, for example, may be cytolytic activity or helper activity including the secretion of cytokines.

As used herein, the terms "treat," "treatment" and "treating" refer to the reduction or amelioration of the progression, severity and/or duration of a disorder, e.g., a proliferative disorder, or the amelioration of one or more symptoms (preferably, one or more discernible symptoms) of the disorder resulting from the administration of one or more therapies. In specific embodiments, the terms "treat,"

"treatment" and "treating" refer to the amelioration of at least one measurable physical parameter of a proliferative disorder, such as growth of a tumor, not necessarily discernible by the patient. In other embodiments the terms "treat", "treatment" and "treating"-refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

The compositions and methods of the present invention encompass polypeptides and nucleic acids having the sequences specified, or sequences substantially identical or similar thereto, e.g., sequences at least 85%, 90%, 95% identical or higher to the sequence specified. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%. 91%, 92%, 93%, 94%, 95%, 96%, 97%, 98% or 99% identity to a reference sequence, e.g., a sequence provided herein.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence, e.g., a sequence provided herein.

The term "functional variant" refers to polypeptides that have a substantially identical amino acid sequence to the naturally-occurring sequence, or are encoded by a substantially identical nucleotide sequence, and are capable of having one or more activities of the naturally-occurring sequence.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) *CABIOS,* 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to a nucleic acid (SEQ ID NO: 1) molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used. See www.ncbi.nlm.nih.gov.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

It is understood that the molecules of the present invention may have additional conservative or non-essential amino acid substitutions, which do not have a substantial effect on their functions.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. As used herein the term "amino acid" includes both the D- or L-optical isomers and peptidomimetics.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The terms "polypeptide", "peptide" and "protein" (if single chain) are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The terms "nucleic acid," "nucleic acid sequence," "nucleotide sequence," or "polynucleotide sequence," and "polynucleotide" are used interchangeably. They refer to a polymeric form of nucleotides of any length, either deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a nonnatural arrangement.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

Various aspects of the invention are described in further detail below. Additional definitions are set out throughout the specification.

Exemplary Combinations of Antigen-Presentation Combinations, Effector Cell Combinations and Anti-Tumor Immunosuppression Combinations Exemplary combinations of therapeutic agents from two or more of the antigen-presentation category (A), effector cell category (B), and anti-tumor immunosuppression category (C) are provided herein.

TABLE 6

| Listing of Therapeutic Agents in Categories (A)-(C) | | |
|---|---|---|
| A = Antigen-Presentation | B = Effector Cell | C = Anti-tumor Immunosuppression |
| 1 STING agonist | GITR agonist | PD-1 inhibitor |
| 2 TLR agonist | PD-1 inhibitor | PD-L1 inhibitor |
| 3 TIM-3 modulator | PD-L1 inhibitor | LAG-3 inhibitor |
| 4 VEGFR inhibitor | IAP inhibitor | TIM-3 inhibitor |
| 5 c-MET inhibitor | EGFR inhibitor | GITR inhibitor |
| 6 TGFb inhibitor | mTOR inhibitor | CSF-1/1R inhibitor |
| 7 IDO/TDO inhibitor | IL-15 agonist | IL-17 inhibitor |
| 8 A2AR antagonist | CTLA-4 inhibitor | IL-1β inhibitor |
| 9 Oncolytic viruses | Bispecific T-cell engagers | CXCR2 inhibitor |
| 10 Scaffold vaccines | CD40 agonist | PI3K-γ, -δ inhibitor |
| 11 Bispecific T-cell engagers | OX40 agonist | BAFF-R inhibitor |
| 12 | CD27 agonist | MALT-1/BTK inhibitor |
| 13 | | JAK inhibitor |
| 14 | | CRTH2 inhibitor |
| 15 | | VEGFR inhibitor |
| 16 | | IL-15 agonist |
| 17 | | Anti-TGFb inhibitor |
| 18 | | IDO/TDO inhibitor |
| 19 | | A2AR antagonist |
| 20 | | CTLA-4 inhibitor |
| 21 | | PFKFB3 inhibitor |

In some embodiments, the combinations of the present invention include one or more of the following:

A1B1, A1B2, A1B3, A1B4, A1B5, A1B6, A1B7, A1B8, A1B9, A1B10, A1B11, A1B12, A2B1, A2B2, A2B3, A2B4, A2B5, A2B6, A2B7, A2B8, A2B9, A2B10, A2B11, A2B12, A3B1, A3B2, A3B3, A3B4, A3B5, A3B6, A3B7, A3B8, A3B9, A3B10, A3B11, A3B12, A4B1, A4B2, A4B3, A4B4, A4B5, A4B6, A4B7, A4B8, A4B9, A4B10, A4B11, A4B12, A5B1, A5B2, A5B3, A5B4, A5B5, A5B6, A5B7, A5B8, A5B9, A5B10, A5B11, A5B12, A6B1, A6B2, A6B3, A6B4, A6B5, A6B6, A6B7, A6B8, A6B9, A6B10, A6B11, A6B12, A7B1, A7B2, A7B3, A7B4, A7B5, A7B6, A7B7, A7B8, A7B9, A7B10, A7B11, A7B12, A8B1, A8B2, A8B3, A8B4, A8B5, A8B6, A8B7, A8B8, A8B9, A8B10, A8B11, A8B12, A9B1, A9B2, A9B3, A9B4, A9B5, A9B6, A9B7, A9B8, A9B9, A9B10, A9B11, A9B12, A10B1, A10B2, A10B3,

A10B4, A10B5, A10B6, A10B7, A10B8, A10B9, A10B10, A10B11, A10B12, A11B1, A11B2, A11B3, A11B4, A11B5, A11B6, A11B7, A11B8, A11B9, A11B10, A11B11, A11B12, A1C1, A1C2, A1C3, A1C4, A1C5, A1C6, A1C7, A1C8, A1C9, A1C10, A1C11, A1C12, A1C13, A1C14, A1C15, A1C16, A1C17, A1C18, A1C19, A1C20, A1C21, A2C1, A2C2, A2C3, A2C4, A2C5, A2C6, A2C7, A2C8, A2C9, A2C10, A2C11, A2C12, A2C13, A2C14, A2C15, A2C16, A2C17, A2C18, A2C19, A2C20, A2C21, A3C1, A3C2, A3C3, A3C4, A3C5, A3C6, A3C7, A3C8, A3C9, A3C10, A3C11, A3C12, A3C13, A3C14, A3C15, A3C16, A3C17, A3C18, A3C19, A3C20, A3C21, A4C1, A4C2, A4C3, A4C4, A4C5, A4C6, A4C7, A4C8, A4C9, A4C10, A4C11, A4C12, A4C13, A4C14, A4C15, A4C16, A4C17, A4C18, A4C19, A4C20, A4C21, A5C1, A5C2, A5C3, A5C4, A5C5, A5C6, A5C7, A5C8, A5C9, A5C10, A5C11, A5C12, A5C13, A5C14, A5C15, A5C16, A5C17, A5C18, A5C19, A5C20, A5C21, A6C1, A6C2, A6C3, A6C4, A6C5, A6C6, A6C7, A6C8, A6C9, A6C10, A6C11, A6C12, A6C13, A6C14, A6C15, A6C16, A6C17, A6C18, A6C19, A6C20, A6C21, A7C1, A7C2, A7C3, A7C4, A7C5, A7C6, A7C7, A7C8, A7C9, A7C10, A7C11, A7C12, A7C13, A7C14, A7C15, A7C16, A7C17, A7C18, A7C19, A7C20, A7C21, A8C1, A8C2, A8C3, A8C4, A8C5, A8C6, A8C7, A8C8, A8C9, A8C10, A8C11, A8C12, A8C13, A8C14, A8C15, A8C16, A8C17, A8C18, A8C19, A8C20, A8C21, A9C1, A9C2, A9C3, A9C4, A9C5, A9C6, A9C7, A9C8, A9C9, A9C10, A9C11, A9C12, A9C13, A9C14, A9C15, A9C16, A9C17, A9C18, A9C19, A9C20, A9C21, A10C1, A10C2, A10C3, A10C4, A1005, A1006, A1007, A1008, A10C9, A10C10, A10C11, A10C12, A10C13, A10C14, A10C15, A10C16, A10C17, A10C18, A10C19, A10C20, A10C21, A11C1, A11C2, A11C3, A11C4, A1105, A1106, A11C7, A11C8, A11C9, A11C10, A11C11, A11C12, A11C13, A11C14, A11C15, A11C16, A11C17, A11C18, A11C19, A11C20, A11C21, B1C1, B1C2, B1C3, B1C4, B1C5, B1C6, B1C7, B1C8, B1C9, B1C10, B1C11, B1C12, B1C13, B1C14, B1C15, B1C16, B1C17, B1C18, B1C19, B1C20, B1C21, B2C1, B2C2, B2C3, B2C4, B2C5, B2C6, B2C7, B2C8, B2C9, B2C10, B2C11, B2C12, B2C13, B2C14, B2C15, B2C16, B2C17, B2C18, B2C19, B2C20, B2C21, B3C1, B3C2, B3C3, B3C4, B3C5, B3C6, B3C7, B3C8, B3C9, B3C10, B3C11, B3C12, B3C13, B3C14, B3C15, B3C16, B3C17, B3C18, B3C19, B3C20, B3C21, B4C1, B4C2, B4C3, B4C4, B4C5, B4C6, B4C7, B4C8, B4C9, B4C10, B4C11, B4C12, B4C13, B4C14, B4C15, B4C16, B4C17, B4C18, B4C19, B4C20, B4C21, B5C1, B5C2, B5C3, B5C4, B5C5, B5C6, B5C7, B5C8, B5C9, B5C10, B5C11, B5C12, B5C13, B5C14, B5C15, B5C16, B5C17, B5C18, B5C19, B5C20, B5C21, B6C1, B6C2, B6C3, B6C4, B6C5, B6C6, B6C7, B6C8, B6C9, B6C10, B6C11, B6C12, B6C13, B6C14, B6C15, B6C16, B6C17, B6C18, B6C19, B6C20, B6C21, B7C1, B7C2, B7C3, B7C4, B7C5, B7C6, B7C7, B7C8, B7C9, B7C10, B7C11, B7C12, B7C13, B7C14, B7C15, B7C16, B7C17, B7C18, B7C19, B7C20, B7C21, B8C1, B8C2, B8C3, B8C4, B8C5, B8C6, B8C7, B8C8, B8C9, B8C10, B8C11, B8C12, B8C13, B8C14, B8C15, B8C16, B8C17, B8C18, B8C19, B8C20, B8C21, B9C1, B9C2, B9C3, B9C4, B9C5, B9C6, B9C7, B9C8, B9C9, B9C10, B9C11, B9C12, B9C13, B9C14, B9C15, B9C16, B9C17, B9C18, B9C19, B9C20, B9C21, B10C1, B10C2, B10C3, B10C4, B10C5, B10C6, B10C7, B10C8, B10C9, B10C10, B10C11, B10C12, B10C13, B10C14, B10C15, B10C16, B10C17, B10C18, B10C19, B10C20, B10C21, B11C1, B11C2, B11C3, B11C4, B11C5, B11C6, B11C7, B11C8, B11C9, B11C10, B11C11, B11C12, B11C13, B11C14, B11C15, B11C16,

B11C17, B11C18, B11C19, B11C20, B11C21, B12C1, B12C2, B12C3, B12C4, B12C5, B12C6, B12C7, B12C8, B12C9, B12C10, B12C11, B12C12, B12C13, B12C14, B12C15, B12C16, B12C17, B12C18, B12C19, B12C20, B12C21, A1B1C1, A1B1C2, A1B1C3, A1B1C4, A1B1C5, A1B1C6, A1B1C7, A1B1C8, A1B1C9, A1B1C10, A1B1C11, A1B1C12, A1B1C13, A1B1C14, A1B1C15, A1B1C16, A1B1C17, A1B1C18, A1B1C19, A1B1C20, A1B1C21, A1B2C1, A1B2C2, A1B2C3, A1B2C4, A1B2C5, A1B2C6, A1B2C7, A1B2C8, A1B2C9, A1B2C10, A1B2C11, A1B2C12, A1B2C13, A1B2C14, A1B2C15, A1B2C16, A1B2C17, A1B2C18, A1B2C19, A1B2C20, A1B2C21, A1B3C1, A1B3C2, A1B3C3, A1B3C4, A1B3C5, A1B3C6, A1B3C7, A1B3C8, A1B3C9, A1B3C10, A1B3C11, A1B3C12, A1B3C13, A1B3C14, A1B3C15, A1B3C16, A1B3C17, A1B3C18, A1B3C19, A1B3C20, A1B3C21, A1B4C1, A1B4C2, A1B4C3, A1B4C4, A1B4C5, A1B4C6, A1B4C7, A1B4C8, A1B4C9, A1B4C10, A1B4C11, A1B4C12, A1B4C13, A1B4C14, A1B4C15, A1B4C16, A1B4C17, A1B4C18, A1B4C19, A1B4C20, A1B4C21, A1B5C1, A1B5C2, A1B5C3, A1B5C4, A1B5C5, A1B5C6, A1B5C7, A1B5C8, A1B5C9, A1B5C10, A1B5C11, A1B5C12, A1B5C13, A1B5C14, A1B5C15, A1B5C16, A1B5C17, A1B5C18, A1B5C19, A1B5C20, A1B5C21, A1B6C1, A1B6C2, A1B6C3, A1B6C4, A1B6C5, A1B6C6, A1B6C7, A1B6C8, A1B6C9, A1B6C10, A1B6C11, A1B6C12, A1B6C13, A1B6C14, A1B6C15, A1B6C16, A1B6C17, A1B6C18, A1B6C19, A1B6C20, A1B6C21, A1B7C1, A1B7C2, A1B7C3, A1B7C4, A1B7C5, A1B7C6, A1B7C7, A1B7C8, A1B7C9, A1B7C10, A1B7C11, A1B7C12, A1B7C13, A1B7C14, A1B7C15, A1B7C16, A1B7C17, A1B7C18, A1B7C19, A1B7C20, A1B7C21, A1B8C1, A1B8C2, A1B8C3, A1B8C4, A1B8C5, A1B8C6, A1B8C7, A1B8C8, A1B8C9, A1B8C10, A1B8C11, A1B8C12, A1B8C13, A1B8C14, A1B8C15, A1B8C16, A1B8C17, A1B8C18, A1B8C19, A1B8C20, A1B8C21, A1B9C1, A1B9C2, A1B9C3, A1B9C4, A1B9C5, A1B9C6, A1B9C7, A1B9C8, A1B9C9, A1B9C10, A1B9C11, A1B9C12, A1B9C13, A1B9C14, A1B9C15, A1B9C16, A1B9C17, A1B9C18, A1B9C19, A1B9C20, A1B9C21, A1B10C1, A1B10C2, A1B10C3, A1B10C4, A1B10C5, A1B10C6, A1B10C7, A1B10C8, A1B10C9, A1B10C10, A1B10C11, A1B10C12, A1B10C13, A1B10C14, A1B10C15, A1B10C16, A1B10C17, A1B10C18, A1B10C19, A1B10C20, A1B10C21, A1B11C1, A1B11C2, A1B11C3, A1B11C4, A1B11C5, A1B11C6, A1B11C7, A1B11C8, A1B11C9, A1B11C10, A1B11C11, A1B11C12, A1B11C13, A1B11C14, A1B11C15, A1B11C16, A1B11C17, A1B11C18, A1B11C19, A1B11C20, A1B11C21, A1B12C1, A1B12C2, A1B12C3, A1B12C4, A1B12C5, A1B12C6, A1B12C7, A1B12C8, A1B12C9, A1B12C10, A1B12C11, A1B12C12, A1B12C13, A1B12C14, A1B12C15, A1B12C16, A1B12C17, A1B12C18, A1B12C19, A1B12C20, A1B12C21, A2B1C1, A2B1C2, A2B1C3, A2B1C4, A2B1C5, A2B1C6, A2B1C7, A2B1C8, A2B1C9, A2B1C10, A2B1C11, A2B1C12, A2B1C13, A2B1C14, A2B1C15, A2B1C16, A2B1C17, A2B1C18, A2B1C19, A2B1C20, A2B1C21, A2B2C1, A2B2C2, A2B2C3, A2B2C4, A2B2C5, A2B2C6, A2B2C7, A2B2C8, A2B2C9, A2B2C10, A2B2C11, A2B2C12, A2B2C13, A2B2C14, A2B2C15, A2B2C16, A2B2C17, A2B2C18, A2B2C19, A2B2C20, A2B2C21, A2B3C1, A2B3C2, A2B3C3, A2B3C4, A2B3C5, A2B3C6, A2B3C7, A2B3C8, A2B3C9, A2B3C10, A2B3C11, A2B3C12, A2B3C13, A2B3C14, A2B3C15, A2B3C16, A2B3C17, A2B3C18, A2B3C19, A2B3C20, A2B3C21, A2B4C1, A2B4C2, A2B4C3,

A2B4C4, A2B4C5, A2B4C6, A2B4C7, A2B4C8, A2B4C9, A2B4C10, A2B4C11, A2B4C12, A2B4C13, A2B4C14, A2B4C15, A2B4C16, A2B4C17, A2B4C18, A2B4C19, A2B4C20, A2B4C21, A2B5C1, A2B5C2, A2B5C3, A2B5C4, A2B5C5, A2B5C6, A2B5C7, A2B5C8, A2B5C9, A2B5C10, A2B5C11, A2B5C12, A2B5C13, A2B5C14, A2B5C15, A2B5C16, A2B5C17, A2B5C18, A2B5C19, A2B5C20, A2B5C21, A2B6C1, A2B6C2, A2B6C3, A2B6C4, A2B6C5, A2B6C6, A2B6C7, A2B6C8, A2B6C9, A2B6C10, A2B6C11, A2B6C12, A2B6C13, A2B6C14, A2B6C15, A2B6C16, A2B6C17, A2B6C18, A2B6C19, A2B6C20, A2B6C21, A2B7C1, A2B7C2, A2B7C3, A2B7C4, A2B7C5, A2B7C6, A2B7C7, A2B7C8, A2B7C9, A2B7C10, A2B7C11, A2B7C12, A2B7C13, A2B7C14, A2B7C15, A2B7C16, A2B7C17, A2B7C18, A2B7C19, A2B7C20, A2B7C21, A2B8C1, A2B8C2, A2B8C3, A2B8C4, A2B8C5, A2B8C6, A2B8C7, A2B8C8, A2B8C9, A2B8C10, A2B8C11, A2B8C12, A2B8C13, A2B8C14, A2B8C15, A2B8C16, A2B8C17, A2B8C18, A2B8C19, A2B8C20, A2B8C21, A2B9C1, A2B9C2, A2B9C3, A2B9C4, A2B9C5, A2B9C6, A2B9C7, A2B9C8, A2B9C9, A2B9C10, A2B9C11, A2B9C12, A2B9C13, A2B9C14, A2B9C15, A2B9C16, A2B9C17, A2B9C18, A2B9C19, A2B9C20, A2B9C21, A2B10C1, A2B10C2, A2B10C3, A2B10C4, A2B10C5, A2B10C6, A2B10C7, A2B10C8, A2B10C9, A2B10C10, A2B10C11, A2B10C12, A2B10C13, A2B10C14, A2B10C15, A2B10C16, A2B10C17, A2B10C18, A2B10C19, A2B10C20, A2B10C21, A2B11C1, A2B11C2, A2B11C3, A2B11C4, A2B11C5, A2B11C6, A2B11C7, A2B11C8, A2B11C9, A2B11C10, A2B11C11, A2B11C12, A2B11C13, A2B11C14, A2B11C15, A2B11C16, A2B11C17, A2B11C18, A2B11C19, A2B11C20, A2B11C21, A2B12C1, A2B12C2, A2B12C3, A2B12C4, A2B12C5, A2B12C6, A2B12C7, A2B12C8, A2B12C9, A2B12C10, A2B12C11, A2B12C12, A2B12C13, A2B12C14, A2B12C15, A2B12C16, A2B12C17, A2B12C18, A2B12C19, A2B12C20, A2B12C21, A3B1C1, A3B1C2, A3B1C3, A3B1C4, A3B1C5, A3B1C6, A3B1C7, A3B1C8, A3B1C9, A3B1C10, A3B1C11, A3B1C12, A3B1C13, A3B1C14, A3B1C15, A3B1C16, A3B1C17, A3B1C18, A3B1C19, A3B1C20, A3B1C21, A3B2C1, A3B2C2, A3B2C3, A3B2C4, A3B2C5, A3B2C6, A3B2C7, A3B2C8, A3B2C9, A3B2C10, A3B2C11, A3B2C12, A3B2C13, A3B2C14, A3B2C15, A3B2C16, A3B2C17, A3B2C18, A3B2C19, A3B2C20, A3B2C21, A3B3C1, A3B3C2, A3B3C3, A3B3C4, A3B3C5, A3B3C6, A3B3C7, A3B3C8, A3B3C9, A3B3C10, A3B3C11, A3B3C12, A3B3C13, A3B3C14, A3B3C15, A3B3C16, A3B3C17, A3B3C18, A3B3C19, A3B3C20, A3B3C21, A3B4C1, A3B4C2, A3B4C3, A3B4C4, A3B4C5, A3B4C6, A3B4C7, A3B4C8, A3B4C9, A3B4C10, A3B4C11, A3B4C12, A3B4C13, A3B4C14, A3B4C15, A3B4C16, A3B4C17, A3B4C18, A3B4C19, A3B4C20, A3B4C21, A3B5C1, A3B5C2, A3B5C3, A3B5C4, A3B5C5, A3B5C6, A3B5C7, A3B5C8, A3B5C9, A3B5C10, A3B5C11, A3B5C12, A3B5C13, A3B5C14, A3B5C15, A3B5C16, A3B5C17, A3B5C18, A3B5C19, A3B5C20, A3B5C21, A3B6C1, A3B6C2, A3B6C3, A3B6C4, A3B6C5, A3B6C6, A3B6C7, A3B6C8, A3B6C9, A3B6C10, A3B6C11, A3B6C12, A3B6C13, A3B6C14, A3B6C15, A3B6C16, A3B6C17, A3B6C18, A3B6C19, A3B6C20, A3B6C21, A3B7C1, A3B7C2, A3B7C3, A3B7C4, A3B7C5, A3B7C6, A3B7C7, A3B7C8, A3B7C9, A3B7C10, A3B7C11, A3B7C12, A3B7C13, A3B7C14, A3B7C15, A3B7C16, A3B7C17, A3B7C18, A3B7C19, A3B7C20, A3B7C21, A3B8C1, A3B8C2, A3B8C3, A3B8C4, A3B8C5, A3B8C6, A3B8C7, A3B8C8, A3B8C9,

A3B8C10, A3B8C11, A3B8C12, A3B8C13, A3B8C14, A3B8C15, A3B8C16, A3B8C17, A3B8C18, A3B8C19, A3B8C20, A3B8C21, A3B9C1, A3B9C2, A3B9C3, A3B9C4, A3B9C5, A3B9C6, A3B9C7, A3B9C8, A3B9C9, A3B9C10, A3B9C11, A3B9C12, A3B9C13, A3B9C14, A3B9C15, A3B9C16, A3B9C17, A3B9C18, A3B9C19, A3B9C20, A3B9C21, A3B10C1, A3B10C2, A3B10C3, A3B10C4, A3B10C5, A3B10C6, A3B10C7, A3B10C8, A3B10C9, A3B10C10, A3B10C11, A3B10C12, A3B10C13, A3B10C14, A3B10C15, A3B10C16, A3B10C17, A3B10C18, A3B10C19, A3B10C20, A3B10C21, A3B11C1, A3B11C2, A3B11C3, A3B11C4, A3B11C5, A3B11C6, A3B11C7, A3B11C8, A3B11C9, A3B11C10, A3B11C11, A3B11C12, A3B11C13, A3B11C14, A3B11C15, A3B11C16, A3B11C17, A3B11C18, A3B11C19, A3B11C20, A3B11C21, A3B12C1, A3B12C2, A3B12C3, A3B12C4, A3B12C5, A3B12C6, A3B12C7, A3B12C8, A3B12C9, A3B12C10, A3B12C11, A3B12C12, A3B12C13, A3B12C14, A3B12C15, A3B12C16, A3B12C17, A3B12C18, A3B12C19, A3B12C20, A3B12C21, A4B1C1, A4B1C2, A4B1C3, A4B1C4, A4B1C5, A4B1C6, A4B1C7, A4B1C8, A4B1C9, A4B1C10, A4B1C11, A4B1C12, A4B1C13, A4B1C14, A4B1C15, A4B1C16, A4B1C17, A4B1C18, A4B1C19, A4B1C20, A4B1C21, A4B2C1, A4B2C2, A4B2C3, A4B2C4, A4B2C5, A4B2C6, A4B2C7, A4B2C8, A4B2C9, A4B2C10, A4B2C11, A4B2C12, A4B2C13, A4B2C14, A4B2C15, A4B2C16, A4B2C17, A4B2C18, A4B2C19, A4B2C20, A4B2C21, A4B3C1, A4B3C2, A4B3C3, A4B3C4, A4B3C5, A4B3C6, A4B3C7, A4B3C8, A4B3C9, A4B3C10, A4B3C11, A4B3C12, A4B3C13, A4B3C14, A4B3C15, A4B3C16, A4B3C17, A4B3C18, A4B3C19, A4B3C20, A4B3C21, A4B4C1, A4B4C2, A4B4C3, A4B4C4, A4B4C5, A4B4C6, A4B4C7, A4B4C8, A4B4C9, A4B4C10, A4B4C11, A4B4C12, A4B4C13, A4B4C14, A4B4C15, A4B4C16, A4B4C17, A4B4C18, A4B4C19, A4B4C20, A4B4C21, A4B5C1, A4B5C2, A4B5C3, A4B5C4, A4B5C5, A4B5C6, A4B5C7, A4B5C8, A4B5C9, A4B5C10, A4B5C11, A4B5C12, A4B5C13, A4B5C14, A4B5C15, A4B5C16, A4B5C17, A4B5C18, A4B5C19, A4B5C20, A4B5C21, A4B6C1, A4B6C2, A4B6C3, A4B6C4, A4B6C5, A4B6C6, A4B6C7, A4B6C8, A4B6C9, A4B6C10, A4B6C11, A4B6C12, A4B6C13, A4B6C14, A4B6C15, A4B6C16, A4B6C17, A4B6C18, A4B6C19, A4B6C20, A4B6C21, A4B7C1, A4B7C2, A4B7C3, A4B7C4, A4B7C5, A4B7C6, A4B7C7, A4B7C8, A4B7C9, A4B7C10, A4B7C11, A4B7C12, A4B7C13, A4B7C14, A4B7C15, A4B7C16, A4B7C17, A4B7C18, A4B7C19, A4B7C20, A4B7C21, A4B8C1, A4B8C2, A4B8C3, A4B8C4, A4B8C5, A4B8C6, A4B8C7, A4B8C8, A4B8C9, A4B8C10, A4B8C11, A4B8C12, A4B8C13, A4B8C14, A4B8C15, A4B8C16, A4B8C17, A4B8C18, A4B8C19, A4B8C20, A4B8C21, A4B9C1, A4B9C2, A4B9C3, A4B9C4, A4B9C5, A4B9C6, A4B9C7, A4B9C8, A4B9C9, A4B9C10, A4B9C11, A4B9C12, A4B9C13, A4B9C14, A4B9C15, A4B9C16, A4B9C17, A4B9C18, A4B9C19, A4B9C20, A4B9C21, A4B10C1, A4B10C2, A4B10C3, A4B10C4, A4B10C5, A4B10C6, A4B10C7, A4B10C8, A4B10C9, A4B10C10, A4B10C11, A4B10C12, A4B10C13, A4B10C14, A4B10C15, A4B10C16, A4B10C17, A4B10C18, A4B10C19, A4B10C20, A4B10C21, A4B11C1, A4B11C2, A4B11C3, A4B11C4, A4B11C5, A4B11C6, A4B11C7, A4B11C8, A4B11C9, A4B11C10, A4B11C11, A4B11C12, A4B11C13, A4B11C14, A4B11C15, A4B11C16, A4B11C17, A4B11C18, A4B11C19, A4B11C20, A4B11C21, A4B12C1, A4B12C2, A4B12C3, A4B12C4, A4B12C5, A4B12C6,

A4B12C7, A4B12C8, A4B12C9, A4B12C10, A4B12C11, A4B12C12, A4B12C13, A4B12C14, A4B12C15, A4B12C16, A4B12C17, A4B12C18, A4B12C19, A4B12C20, A4B12C21, A5B1C1, A5B1C2, A5B1C3, A5B1C4, A5B1C5, A5B1C6, A5B1C7, A5B1C8, A5B1C9, A5B1C10, A5B1C11, A5B1C12, A5B1C13, A5B1C14, A5B1C15, A5B1C16, A5B1C17, A5B1C18, A5B1C19, A5B1C20, A5B1C21, A5B2C1, A5B2C2, A5B2C3, A5B2C4, A5B2C5, A5B2C6, A5B2C7, A5B2C8, A5B2C9, A5B2C10, A5B2C11, A5B2C12, A5B2C13, A5B2C14, A5B2C15, A5B2C16, A5B2C17, A5B2C18, A5B2C19, A5B2C20, A5B2C21, A5B3C1, A5B3C2, A5B3C3, A5B3C4, A5B3C5, A5B3C6, A5B3C7, A5B3C8, A5B3C9, A5B3C10, A5B3C11, A5B3C12, A5B3C13, A5B3C14, A5B3C15, A5B3C16, A5B3C17, A5B3C18, A5B3C19, A5B3C20, A5B3C21, A5B4C1, A5B4C2, A5B4C3, A5B4C4, A5B4C5, A5B4C6, A5B4C7, A5B4C8, A5B4C9, A5B4C10, A5B4C11, A5B4C12, A5B4C13, A5B4C14, A5B4C15, A5B4C16, A5B4C17, A5B4C18, A5B4C19, A5B4C20, A5B4C21, A5B5C1, A5B5C2, A5B5C3, A5B5C4, A5B5C5, A5B5C6, A5B5C7, A5B5C8, A5B5C9, A5B5C10, A5B5C11, A5B5C12, A5B5C13, A5B5C14, A5B5C15, A5B5C16, A5B5C17, A5B5C18, A5B5C19, A5B5C20, A5B5C21, A5B6C1, A5B6C2, A5B6C3, A5B6C4, A5B6C5, A5B6C6, A5B6C7, A5B6C8, A5B6C9, A5B6C10, A5B6C11, A5B6C12, A5B6C13, A5B6C14, A5B6C15, A5B6C16, A5B6C17, A5B6C18, A5B6C19, A5B6C20, A5B6C21, A5B7C1, A5B7C2, A5B7C3, A5B7C4, A5B7C5, A5B7C6, A5B7C7, A5B7C8, A5B7C9, A5B7C10, A5B7C11, A5B7C12, A5B7C13, A5B7C14, A5B7C15, A5B7C16, A5B7C17, A5B7C18, A5B7C19, A5B7C20, A5B7C21, A5B8C1, A5B8C2, A5B8C3, A5B8C4, A5B8C5, A5B8C6, A5B8C7, A5B8C8, A5B8C9, A5B8C10, A5B8C11, A5B8C12, A5B8C13, A5B8C14, A5B8C15, A5B8C16, A5B8C17, A5B8C18, A5B8C19, A5B8C20, A5B8C21, A5B9C1, A5B9C2, A5B9C3, A5B9C4, A5B9C5, A5B9C6, A5B9C7, A5B9C8, A5B9C9, A5B9C10, A5B9C11, A5B9C12, A5B9C13, A5B9C14, A5B9C15, A5B9C16, A5B9C17, A5B9C18, A5B9C19, A5B9C20, A5B9C21, A5B10C1, A5B10C2, A5B10C3, A5B10C4, A5B10C5, A5B10C6, A5B10C7, A5B10C8, A5B10C9, A5B10C10, A5B10C11, A5B10C12, A5B10C13, A5B10C14, A5B10C15, A5B10C16, A5B10C17, A5B10C18, A5B10C19, A5B10C20, A5B10C21, A5B11C1, A5B11C2, A5B11C3, A5B11C4, A5B11C5, A5B11C6, A5B11C7, A5B11C8, A5B11C9, A5B11C10, A5B11C11, A5B11C12, A5B11C13, A5B11C14, A5B11C15, A5B11C16, A5B11C17, A5B11C18, A5B11C19, A5B11C20, A5B11C21, A5B12C1, A5B12C2, A5B12C3, A5B12C4, A5B12C5, A5B12C6, A5B12C7, A5B12C8, A5B12C9, A5B12C10, A5B12C11, A5B12C12, A5B12C13, A5B12C14, A5B12C15, A5B12C16, A5B12C17, A5B12C18, A5B12C19, A5B12C20, A5B12C21, A6B1C1, A6B1C2, A6B1C3, A6B1C4, A6B1C5, A6B1C6, A6B1C7, A6B1C8, A6B1C9, A6B1C10, A6B1C11, A6B1C12, A6B1C13, A6B1C14, A6B1C15, A6B1C16, A6B1C17, A6B1C18, A6B1C19, A6B1C20, A6B1C21, A6B2C1, A6B2C2, A6B2C3, A6B2C4, A6B2C5, A6B2C6, A6B2C7, A6B2C8, A6B2C9, A6B2C10, A6B2C11, A6B2C12, A6B2C13, A6B2C14, A6B2C15, A6B2C16, A6B2C17, A6B2C18, A6B2C19, A6B2C20, A6B2C21, A6B3C1, A6B3C2, A6B3C3, A6B3C4, A6B3C5, A6B3C6, A6B3C7, A6B3C8, A6B3C9, A6B3C10, A6B3C11, A6B3C12, A6B3C13, A6B3C14, A6B3C15, A6B3C16, A6B3C17, A6B3C18, A6B3C19, A6B3C20, A6B3C21, A6B4C1, A6B4C2, A6B4C3, A6B4C4, A6B4C5, A6B4C6, A6B4C7, A6B4C8, A6B4C9,

A6B4C10, A6B4C11, A6B4C12, A6B4C13, A6B4C14, A6B4C15, A6B4C16, A6B4C17, A6B4C18, A6B4C19, A6B4C20, A6B4C21, A6B5C1, A6B5C2, A6B5C3, A6B5C4, A6B5C5, A6B5C6, A6B5C7, A6B5C8, A6B5C9, A6B5C10, A6B5C11, A6B5C12, A6B5C13, A6B5C14, A6B5C15, A6B5C16, A6B5C17, A6B5C18, A6B5C19, A6B5C20, A6B5C21, A6B6C1, A6B6C2, A6B6C3, A6B6C4, A6B6C5, A6B6C6, A6B6C7, A6B6C8, A6B6C9, A6B6C10, A6B6C11, A6B6C12, A6B6C13, A6B6C14, A6B6C15, A6B6C16, A6B6C17, A6B6C18, A6B6C19, A6B6C20, A6B6C21, A6B7C1, A6B7C2, A6B7C3, A6B7C4, A6B7C5, A6B7C6, A6B7C7, A6B7C8, A6B7C9, A6B7C10, A6B7C11, A6B7C12, A6B7C13, A6B7C14, A6B7C15, A6B7C16, A6B7C17, A6B7C18, A6B7C19, A6B7C20, A6B7C21, A6B8C1, A6B8C2, A6B8C3, A6B8C4, A6B8C5, A6B8C6, A6B8C7, A6B8C8, A6B8C9, A6B8C10, A6B8C11, A6B8C12, A6B8C13, A6B8C14, A6B8C15, A6B8C16, A6B8C17, A6B8C18, A6B8C19, A6B8C20, A6B8C21, A6B9C1, A6B9C2, A6B9C3, A6B9C4, A6B9C5, A6B9C6, A6B9C7, A6B9C8, A6B9C9, A6B9C10, A6B9C11, A6B9C12, A6B9C13, A6B9C14, A6B9C15, A6B9C16, A6B9C17, A6B9C18, A6B9C19, A6B9C20, A6B9C21, A6B10C1, A6B10C2, A6B10C3, A6B10C4, A6B10C5, A6B10C6, A6B10C7, A6B10C8, A6B10C9, A6B10C10, A6B10C11, A6B10C12, A6B10C13, A6B10C14, A6B10C15, A6B10C16, A6B10C17, A6B10C18, A6B10C19, A6B10C20, A6B10C21, A6B11C1, A6B11C2, A6B11C3, A6B11C4, A6B11C5, A6B11C6, A6B11C7, A6B11C8, A6B11C9, A6B11C10, A6B11C11, A6B11C12, A6B11C13, A6B11C14, A6B11C15, A6B11C16, A6B11C17, A6B11C18, A6B11C19, A6B11C20, A6B11C21, A6B12C1, A6B12C2, A6B12C3, A6B12C4, A6B12C5, A6B12C6, A6B12C7, A6B12C8, A6B12C9, A6B12C10, A6B12C11, A6B12C12, A6B12C13, A6B12C14, A6B12C15, A6B12C16, A6B12C17, A6B12C18, A6B12C19, A6B12C20, A6B12C21, A7B1C1, A7B1C2, A7B1C3, A7B1C4, A7B1C5, A7B1C6, A7B1C7, A7B1C8, A7B1C9, A7B1C10, A7B1C11, A7B1C12, A7B1C13, A7B1C14, A7B1C15, A7B1C16, A7B1C17, A7B1C18, A7B1C19, A7B1C20, A7B1C21, A7B2C1, A7B2C2, A7B2C3, A7B2C4, A7B2C5, A7B2C6, A7B2C7, A7B2C8, A7B2C9, A7B2C10, A7B2C11, A7B2C12, A7B2C13, A7B2C14, A7B2C15, A7B2C16, A7B2C17, A7B2C18, A7B2C19, A7B2C20, A7B2C21, A7B3C1, A7B3C2, A7B3C3, A7B3C4, A7B3C5, A7B3C6, A7B3C7, A7B3C8, A7B3C9, A7B3C10, A7B3C11, A7B3C12, A7B3C13, A7B3C14, A7B3C15, A7B3C16, A7B3C17, A7B3C18, A7B3C19, A7B3C20, A7B3C21, A7B4C1, A7B4C2, A7B4C3, A7B4C4, A7B4C5, A7B4C6, A7B4C7, A7B4C8, A7B4C9, A7B4C10, A7B4C11, A7B4C12, A7B4C13, A7B4C14, A7B4C15, A7B4C16, A7B4C17, A7B4C18, A7B4C19, A7B4C20, A7B4C21, A7B5C1, A7B5C2, A7B5C3, A7B5C4, A7B5C5, A7B5C6, A7B5C7, A7B5C8, A7B5C9, A7B5C10, A7B5C11, A7B5C12, A7B5C13, A7B5C14, A7B5C15, A7B5C16, A7B5C17, A7B5C18, A7B5C19, A7B5C20, A7B5C21, A7B6C1, A7B6C2, A7B6C3, A7B6C4, A7B6C5, A7B6C6, A7B6C7, A7B6C8, A7B6C9, A7B6C10, A7B6C11, A7B6C12, A7B6C13, A7B6C14, A7B6C15, A7B6C16, A7B6C17, A7B6C18, A7B6C19, A7B6C20, A7B6C21, A7B7C1, A7B7C2, A7B7C3, A7B7C4, A7B7C5, A7B7C6, A7B7C7, A7B7C8, A7B7C9, A7B7C10, A7B7C11, A7B7C12, A7B7C13, A7B7C14, A7B7C15, A7B7C16, A7B7C17, A7B7C18, A7B7C19, A7B7C20, A7B7C21, A7B8C1, A7B8C2, A7B8C3, A7B8C4, A7B8C5, A7B8C6, A7B8C7, A7B8C8, A7B8C9, A7B8C10, A7B8C11, A7B8C12, A7B8C13, A7B8C14,

A7B8C15, A7B8C16, A7B8C17, A7B8C18, A7B8C19, A7B8C20, A7B8C21, A7B9C1, A7B9C2, A7B9C3, A7B9C4, A7B9C5, A7B9C6, A7B9C7, A7B9C8, A7B9C9, A7B9C10, A7B9C11, A7B9C12, A7B9C13, A7B9C14, A7B9C15, A7B9C16, A7B9C17, A7B9C18, A7B9C19, A7B9C20, A7B9C21, A7B10C1, A7B10C2, A7B10C3, A7B10C4, A7B10C5, A7B10C6, A7B10C7, A7B10C8, A7B10C9, A7B10C10, A7B10C11, A7B10C12, A7B10C13, A7B10C14, A7B10C15, A7B10C16, A7B10C17, A7B10C18, A7B10C19, A7B10C20, A7B10C21, A7B11C1, A7B11C2, A7B11C3, A7B11C4, A7B11C5, A7B11C6, A7B11C7, A7B11C8, A7B11C9, A7B11C10, A7B11C11, A7B11C12, A7B11C13, A7B11C14, A7B11C15, A7B11C16, A7B11C17, A7B11C18, A7B11C19, A7B11C20, A7B11C21, A7B12C1, A7B12C2, A7B12C3, A7B12C4, A7B12C5, A7B12C6, A7B12C7, A7B12C8, A7B12C9, A7B12C10, A7B12C11, A7B12C12, A7B12C13, A7B12C14, A7B12C15, A7B12C16, A7B12C17, A7B12C18, A7B12C19, A7B12C20, A7B12C21, A8B1C1, A8B1C2, A8B1C3, A8B1C4, A8B1C5, A8B1C6, A8B1C7, A8B1C8, A8B1C9, A8B1C10, A8B1C11, A8B1C12, A8B1C13, A8B1C14, A8B1C15, A8B1C16, A8B1C17, A8B1C18, A8B1C19, A8B1C20, A8B1C21, A8B2C1, A8B2C2, A8B2C3, A8B2C4, A8B2C5, A8B2C6, A8B2C7, A8B2C8, A8B2C9, A8B2C10, A8B2C11, A8B2C12, A8B2C13, A8B2C14, A8B2C15, A8B2C16, A8B2C17, A8B2C18, A8B2C19, A8B2C20, A8B2C21, A8B3C1, A8B3C2, A8B3C3, A8B3C4, A8B3C5, A8B3C6, A8B3C7, A8B3C8, A8B3C9, A8B3C10, A8B3C11, A8B3C12, A8B3C13, A8B3C14, A8B3C15, A8B3C16, A8B3C17, A8B3C18, A8B3C19, A8B3C20, A8B3C21, A8B4C1, A8B4C2, A8B4C3, A8B4C4, A8B4C5, A8B4C6, A8B4C7, A8B4C8, A8B4C9, A8B4C10, A8B4C11, A8B4C12, A8B4C13, A8B4C14, A8B4C15, A8B4C16, A8B4C17, A8B4C18, A8B4C19, A8B4C20, A8B4C21, A8B5C1, A8B5C2, A8B5C3, A8B5C4, A8B5C5, A8B5C6, A8B5C7, A8B5C8, A8B5C9, A8B5C10, A8B5C11, A8B5C12, A8B5C13, A8B5C14, A8B5C15, A8B5C16, A8B5C17, A8B5C18, A8B5C19, A8B5C20, A8B5C21, A8B6C1, A8B6C2, A8B6C3, A8B6C4, A8B6C5, A8B6C6, A8B6C7, A8B6C8, A8B6C9, A8B6C10, A8B6C11, A8B6C12, A8B6C13, A8B6C14, A8B6C15, A8B6C16, A8B6C17, A8B6C18, A8B6C19, A8B6C20, A8B6C21, A8B7C1, A8B7C2, A8B7C3, A8B7C4, A8B7C5, A8B7C6, A8B7C7, A8B7C8, A8B7C9, A8B7C10, A8B7C11, A8B7C12, A8B7C13, A8B7C14, A8B7C15, A8B7C16, A8B7C17, A8B7C18, A8B7C19, A8B7C20, A8B7C21, A8B8C1, A8B8C2, A8B8C3, A8B8C4, A8B8C5, A8B8C6, A8B8C7, A8B8C8, A8B8C9, A8B8C10, A8B8C11, A8B8C12, A8B8C13, A8B8C14, A8B8C15, A8B8C16, A8B8C17, A8B8C18, A8B8C19, A8B8C20, A8B8C21, A8B9C1, A8B9C2, A8B9C3, A8B9C4, A8B9C5, A8B9C6, A8B9C7, A8B9C8, A8B9C9, A8B9C10, A8B9C11, A8B9C12, A8B9C13, A8B9C14, A8B9C15, A8B9C16, A8B9C17, A8B9C18, A8B9C19, A8B9C20, A8B9C21, A8B10C1, A8B10C2, A8B10C3, A8B10C4, A8B10C5, A8B10C6, A8B10C7, A8B10C8, A8B10C9, A8B10C10, A8B10C11, A8B10C12, A8B10C13, A8B10C14, A8B10C15, A8B10C16, A8B10C17, A8B10C18, A8B10C19, A8B10C20, A8B10C21, A8B11C1, A8B11C2, A8B11C3, A8B11C4, A8B11C5, A8B11C6, A8B11C7, A8B11C8, A8B11C9, A8B11C10, A8B11C11, A8B11C12, A8B11C13, A8B11C14, A8B11C15, A8B11C16, A8B11C17, A8B11C18, A8B11C19, A8B11C20, A8B11C21, A8B12C1, A8B12C2, A8B12C3, A8B12C4, A8B12C5, A8B12C6, A8B12C7, A8B12C8, A8B12C9, A8B12C10, A8B12C11,

A8B12C12, A8B12C13, A8B12C14, A8B12C15, A8B12C16, A8B12C17, A8B12C18, A8B12C19, A8B12C20, A8B12C21, A9B1C1, A9B1C2, A9B1C3, A9B1C4, A9B1C5, A9B1C6, A9B1C7, A9B1C8, A9B1C9, A9B1C10, A9B1C11, A9B1C12, A9B1C13, A9B1C14, A9B1C15, A9B1C16, A9B1C17, A9B1C18, A9B1C19, A9B1C20, A9B1C21, A9B2C1, A9B2C2, A9B2C3, A9B2C4, A9B2C5, A9B2C6, A9B2C7, A9B2C8, A9B2C9, A9B2C10, A9B2C11, A9B2C12, A9B2C13, A9B2C14, A9B2C15, A9B2C16, A9B2C17, A9B2C18, A9B2C19, A9B2C20, A9B2C21, A9B3C1, A9B3C2, A9B3C3, A9B3C4, A9B3C5, A9B3C6, A9B3C7, A9B3C8, A9B3C9, A9B3C10, A9B3C11, A9B3C12, A9B3C13, A9B3C14, A9B3C15, A9B3C16, A9B3C17, A9B3C18, A9B3C19, A9B3C20, A9B3C21, A9B4C1, A9B4C2, A9B4C3, A9B4C4, A9B4C5, A9B4C6, A9B4C7, A9B4C8, A9B4C9, A9B4C10, A9B4C11, A9B4C12, A9B4C13, A9B4C14, A9B4C15, A9B4C16, A9B4C17, A9B4C18, A9B4C19, A9B4C20, A9B4C21, A9B5C1, A9B5C2, A9B5C3, A9B5C4, A9B5C5, A9B5C6, A9B5C7, A9B5C8, A9B5C9, A9B5C10, A9B5C11, A9B5C12, A9B5C13, A9B5C14, A9B5C15, A9B5C16, A9B5C17, A9B5C18, A9B5C19, A9B5C20, A9B5C21, A9B6C1, A9B6C2, A9B6C3, A9B6C4, A9B6C5, A9B6C6, A9B6C7, A9B6C8, A9B6C9, A9B6C10, A9B6C11, A9B6C12, A9B6C13, A9B6C14, A9B6C15, A9B6C16, A9B6C17, A9B6C18, A9B6C19, A9B6C20, A9B6C21, A9B7C1, A9B7C2, A9B7C3, A9B7C4, A9B7C5, A9B7C6, A9B7C7, A9B7C8, A9B7C9, A9B7C10, A9B7C11, A9B7C12, A9B7C13, A9B7C14, A9B7C15, A9B7C16, A9B7C17, A9B7C18, A9B7C19, A9B7C20, A9B7C21, A9B8C1, A9B8C2, A9B8C3, A9B8C4, A9B8C5, A9B8C6, A9B8C7, A9B8C8, A9B8C9, A9B8C10, A9B8C11, A9B8C12, A9B8C13, A9B8C14, A9B8C15, A9B8C16, A9B8C17, A9B8C18, A9B8C19, A9B8C20, A9B8C21, A9B9C1, A9B9C2, A9B9C3, A9B9C4, A9B9C5, A9B9C6, A9B9C7, A9B9C8, A9B9C9, A9B9C10, A9B9C11, A9B9C12, A9B9C13, A9B9C14, A9B9C15, A9B9C16, A9B9C17, A9B9C18, A9B9C19, A9B9C20, A9B9C21, A9B10C1, A9B10C2, A9B10C3, A9B10C4, A9B10C5, A9B10C6, A9B10C7, A9B10C8, A9B10C9, A9B10C10, A9B10C11, A9B10C12, A9B10C13, A9B10C14, A9B10C15, A9B10C16, A9B10C17, A9B10C18, A9B10C19, A9B10C20, A9B10C21, A9B11C1, A9B11C2, A9B11C3, A9B11C4, A9B11C5, A9B11C6, A9B11C7, A9B11C8, A9B11C9, A9B11C10, A9B11C11, A9B11C12, A9B11C13, A9B11C14, A9B11C15, A9B11C16, A9B11C17, A9B11C18, A9B11C19, A9B11C20, A9B11C21, A9B12C1, A9B12C2, A9B12C3, A9B12C4, A9B12C5, A9B12C6, A9B12C7, A9B12C8, A9B12C9, A9B12C10, A9B12C11, A9B12C12, A9B12C13, A9B12C14, A9B12C15, A9B12C16, A9B12C17, A9B12C18, A9B12C19, A9B12C20, A9B12C21, A10B1C1, A10B1C2, A10B1C3, A10B1C4, A10B1C5, A10B1C6, A10B1C7, A10B1C8, A10B1C9, A10B1C10, A10B1C11, A10B1C12, A10B1C13, A10B1C14, A10B1C15, A10B1C16, A10B1C17, A10B1C18, A10B1C19, A10B1C20, A10B1C21, A10B2C1, A10B2C2, A10B2C3, A10B2C4, A10B2C5, A10B2C6, A10B2C7, A10B2C8, A10B2C9, A10B2C10, A10B2C11, A10B2C12, A10B2C13, A10B2C14, A10B2C15, A10B2C16, A10B2C17, A10B2C18, A10B2C19, A10B2C20, A10B2C21, A10B3C1, A10B3C2, A10B3C3, A10B3C4, A10B3C5, A10B3C6, A10B3C7, A10B3C8, A10B3C9, A10B3C10, A10B3C11, A10B3C12, A10B3C13, A10B3C14, A10B3C15, A10B3C16, A10B3C17, A10B3C18, A10B3C19, A10B3C20, A10B3C21, A10B4C1, A10B4C2,

A10B4C3, A10B4C4, A10B4C5, A10B4C6, A10B4C7, A10B4C8, A10B4C9, A10B4C10, A10B4C11, A10B4C12, A10B4C13, A10B4C14, A10B4C15, A10B4C16, A10B4C17, A10B4C18, A10B4C19, A10B4C20, A10B4C21, A10B5C1, A10B5C2, A10B5C3, A10B5C4, A10B5C5, A10B5C6, A10B5C7, A10B5C8, A10B5C9, A10B5C10, A10B5C11, A10B5C12, A10B5C13, A10B5C14, A10B5C15, A10B5C16, A10B5C17, A10B5C18, A10B5C19, A10B5C20, A10B5C21, A10B6C1, A10B6C2, A10B6C3, A10B6C4, A10B6C5, A10B6C6, A10B6C7, A10B6C8, A10B6C9, A10B6C10, A10B6C11, A10B6C12, A10B6C13, A10B6C14, A10B6C15, A10B6C16, A10B6C17, A10B6C18, A10B6C19, A10B6C20, A10B6C21, A10B7C1, A10B7C2, A10B7C3, A10B7C4, A10B7C5, A10B7C6, A10B7C7, A10B7C8, A10B7C9, A10B7C10, A10B7C11, A10B7C12, A10B7C13, A10B7C14, A10B7C15, A10B7C16, A10B7C17, A10B7C18, A10B7C19, A10B7C20, A10B7C21, A10B8C1, A10B8C2, A10B8C3, A10B8C4, A10B8C5, A10B8C6, A10B8C7, A10B8C8, A10B8C9, A10B8C10, A10B8C11, A10B8C12, A10B8C13, A10B8C14, A10B8C15, A10B8C16, A10B8C17, A10B8C18, A10B8C19, A10B8C20, A10B8C21, A10B9C1, A10B9C2, A10B9C3, A10B9C4, A10B9C5, A10B9C6, A10B9C7, A10B9C8, A10B9C9, A10B9C10, A10B9C11, A10B9C12, A10B9C13, A10B9C14, A10B9C15, A10B9C16, A10B9C17, A10B9C18, A10B9C19, A10B9C20, A10B9C21, A10B10C1, A10B10C2, A10B10C3, A10B10C4, A10B10C5, A10B10C6, A10B10C7, A10B10C8, A10B10C9, A10B10C10, A10B10C11, A10B10C12, A10B10C13, A10B10C14, A10B10C15, A10B10C16, A10B10C17, A10B10C18, A10B10C19, A10B10C20, A10B10C21, A10B11C1, A10B11C2, A10B11C3, A10B11C4, A10B11C5, A10B11C6, A10B11C7, A10B11C8, A10B11C9, A10B11C10, A10B11C11, A10B11C12, A10B11C13, A10B11C14, A10B11C15, A10B11C16, A10B11C17, A10B11C18, A10B11C19, A10B11C20, A10B11C21, A10B12C1, A10B12C2, A10B12C3, A10B12C4, A10B12C5, A10B12C6, A10B12C7, A10B12C8, A10B12C9, A10B12C10, A10B12C11, A10B12C12, A10B12C13, A10B12C14, A10B12C15, A10B12C16, A10B12C17, A10B12C18, A10B12C19, A10B12C20, A10B12C21, A11B1C1, A11B1C2, A11B1C3, A11B1C4, A11B1C5, A11B1C6, A11B1C7, A11B1C8, A11B1C9, A11B1C10, A11B1C11, A11B1C12, A11B1C13, A11B1C14, A11B1C15, A11B1C16, A11B1C17, A11B1C18, A11B1C19, A11B1C20, A11B1C21, A11B2C1, A11B2C2, A11B2C3, A11B2C4, A11B2C5, A11B2C6, A11B2C7, A11B2C8, A11B2C9, A11B2C10, A11B2C11, A11B2C12, A11B2C13, A11B2C14, A11B2C15, A11B2C16, A11B2C17, A11B2C18, A11B2C19, A11B2C20, A11B2C21, A11B3C1, A11B3C2, A11B3C3, A11B3C4, A11B3C5, A11B3C6, A11B3C7, A11B3C8, A11B3C9, A11B3C10, A11B3C11, A11B3C12, A11B3C13, A11B3C14, A11B3C15, A11B3C16, A11B3C17, A11B3C18, A11B3C19, A11B3C20, A11B3C21, A11B4C1, A11B4C2, A11B4C3, A11B4C4, A11B4C5, A11B4C6, A11B4C7, A11B4C8, A11B4C9, A11B4C10, A11B4C11, A11B4C12, A11B4C13, A11B4C14, A11B4C15, A11B4C16, A11B4C17, A11B4C18, A11B4C19, A11B4C20, A11B4C21, A11B5C1, A11B5C2, A11B5C3, A11B5C4, A11B5C5, A11B5C6, A11B5C7, A11B5C8, A11B5C9, A11B5C10, A11B5C11, A11B5C12, A11B5C13, A11B5C14, A11B5C15, A11B5C16, A11B5C17, A11B5C18, A11B5C19, A11B5C20, A11B5C21, A11B6C1, A11B6C2, A11B6C3, A11B6C4, A11B6C5, A11B6C6,

A11B6C7, A11B6C8, A11B6C9, A11B6C10, A11B6C11, A11B6C12, A11B6C13, A11B6C14, A11B6C15, A11B6C16, A11B6C17, A11B6C18, A11B6C19, A11B6C20, A11B6C21, A11B7C1, A11B7C2, A11B7C3, A11B7C4, A11B7C5, A11B7C6, A11B7C7, A11B7C8, A11B7C9, A11B7C10, A11B7C11, A11B7C12, A11B7C13, A11B7C14, A11B7C15, A11B7C16, A11B7C17, A11B7C18, A11B7C19, A11B7C20, A11B7C21, A11B8C1, A11B8C2, A11B8C3, A11B8C4, A11B8C5, A11B8C6, A11B8C7, A11B8C8, A11B8C9, A11B8C10, A11B8C11, A11B8C12, A11B8C13, A11B8C14, A11B8C15, A11B8C16, A11B8C17, A11B8C18, A11B8C19, A11B8C20, A11B8C21, A11B9C1, A11B9C2, A11B9C3, A11B9C4, A11B9C5, A11B9C6, A11B9C7, A11B9C8, A11B9C9, A11B9C10, A11B9C11, A11B9C12, A11B9C13, A11B9C14, A11B9C15, A11B9C16, A11B9C17, A11B9C18, A11B9C19, A11B9C20, A11B9C21, A11B10C1, A11B10C2, A11B10C3, A11B10C4, A11B10C5, A11B10C6, A11B10C7, A11B10C8, A11B10C9, A11B10C10, A11B10C11, A11B10C12, A11B10C13, A11B10C14, A11B10C15, A11B10C16, A11B10C17, A11B10C18, A11B10C19, A11B10C20, A11B10C21, A11B11C1, A11B11C2, A11B11C3, A11B11C4, A11B11C5, A11B11C6, A11B11C7, A11B11C8, A11B11C9, A11B11C10, A11B11C11, A11B11C12, A11B11C13, A11B11C14, A11B11C15, A11B11C16, A11B11C17, A11B11C18, A11B11C19, A11B11C20, A11B11C21, A11B12C1, A11B12C2, A11B12C3, A11B12C4, A11B12C5, A11B12C6, A11B12C7, A11B12C8, A11B12C9, A11B12C10, A11B12C11, A11B12C12, A11B12C13, A11B12C14, A11B12C15, A11B12C16, A11B12C17, A11B12C18, A11B12C19, A11B12C20, or A11B12C21.

Antibody Molecules

In one embodiment, the antibody molecule binds to a mammalian, e.g., human, PD-1. For example, the antibody molecule binds specifically to an epitope, e.g., linear or conformational epitope, (e.g., an epitope as described herein) on PD-1.

As used herein, the term "antibody molecule" refers to a protein, e.g., an immunoglobulin chain or fragment thereof, comprising at least one immunoglobulin variable domain sequence. The term "antibody molecule" includes, for example, a monoclonal antibody (including a full length antibody which has an immunoglobulin Fc region). In an embodiment, an antibody molecule comprises a full length antibody, or a full length immunoglobulin chain. In an embodiment, an antibody molecule comprises an antigen binding or functional fragment of a full length antibody, or a full length immunoglobulin chain. In an embodiment, an antibody molecule is a multispecific antibody molecule, e.g., it comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope.

In an embodiment, an antibody molecule is a monospecific antibody molecule and binds a single epitope. E.g., a monospecific antibody molecule having a plurality of immunoglobulin variable domain sequences, each of which binds the same epitope.

In an embodiment an antibody molecule is a multispecific antibody molecule, e.g., it comprises a plurality of immunoglobulin variable domains sequences, wherein a first immunoglobulin variable domain sequence of the plurality has binding specificity for a first epitope and a second immunoglobulin variable domain sequence of the plurality has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a multispecific antibody molecule comprises a third, fourth or fifth immunoglobulin variable domain. In an embodiment, a multispecific antibody molecule is a bispecific antibody molecule, a trispecific antibody molecule, or tetraspecific antibody molecule, In an embodiment a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv, or fragment thereof, have binding specificity for a first epitope and a scFv, or fragment thereof, have binding specificity for a second epitope. In an embodiment the first epitope is located on PD-1 and the second epitope is located on a TIM-3, LAG-3, CEACAM (e.g., CEACAM-1 and/or CEACAM-5), PD-L1, or PD-L2.

In an embodiment, an antibody molecule comprises a diabody, and a single-chain molecule, as well as an antigen-binding fragment of an antibody (e.g., Fab, F(ab')$_2$, and Fv). For example, an antibody molecule can include a heavy (H) chain variable domain sequence (abbreviated herein as VH), and a light (L) chain variable domain sequence (abbreviated herein as VL). In an embodiment an antibody molecule comprises or consists of a heavy chain and a light chain (referred to herein as a half antibody). In another example, an antibody molecule includes two heavy (H) chain variable domain sequences and two light (L) chain variable domain sequence, thereby forming two antigen binding sites, such as Fab, Fab', F(ab')$_2$, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The preparation of antibody molecules can be monoclonal or polyclonal. An antibody molecule can also be a human, humanized, CDR-grafted, or in vitro generated antibody. The antibody can have a heavy chain constant region chosen from, e.g., IgG1, IgG2, IgG3, or IgG4. The antibody can also have a light chain chosen from, e.g., kappa or lambda. The term "immunoglobulin" (Ig) is used interchangeably with the term "antibody" herein.

Examples of antigen-binding fragments of an antibody molecule include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) *Science* 242:423-426; and Huston et al. (1988) *Proc. Natl. Acad. Sci. USA* 85:5879-5883); (viii) a single domain antibody. These antibody fragments are obtained using conventional techniques known to those with skill in the art, and the fragments are screened for utility in the same manner as are intact antibodies.

The term "antibody" includes intact molecules as well as functional fragments thereof. Constant regions of the antibodies can be altered, e.g., mutated, to modify the properties of the antibody (e.g., to increase or decrease one or more of: Fc receptor binding, antibody glycosylation, the number of cysteine residues, effector cell function, or complement function).

Antibody molecules can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to another aspect of the invention, a single domain antibody is a naturally occurring single domain antibody known as heavy chain antibody devoid of light chains. Such single domain antibodies are disclosed in WO 9404678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are within the scope of the invention.

The VH and VL regions can be subdivided into regions of hypervariability, termed "complementarity determining regions" (CDR), interspersed with regions that are more conserved, termed "framework regions" (FR or FW).

The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) J. Mol. Biol. 196:901-917; and the AbM definition used by Oxford Molecular's AbM antibody modeling software. See, generally, e.g., Protein Sequence and Structure Analysis of Antibody Variable Domains. In: Antibody Engineering Lab Manual (Ed.: Duebel, S. and Kontermann, R., Springer-Verlag, Heidelberg).

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273,927-948 ("Chothia" numbering scheme). As used herein, the CDRs defined according the "Chothia" number scheme are also sometimes referred to as "hypervariable loops."

For example, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL.

Generally, unless specifically indicated, the anti-PD-1 antibody molecules can include any combination of one or more Kabat CDRs and/or Chothia hypervariable loops, e.g., described in Table 1. In one embodiment, the following definitions are used for the anti-PD-1 antibody molecules described in Table 1: HCDR1 according to the combined CDR definitions of both Kabat and Chothia, and HCCDRs 2-3 and LCCDRs 1-3 according the CDR definition of Kabat. Under all definitions, each VH and VL typically includes three CDRs and four FRs, arranged from amino-terminus to carboxy-terminus in the following order: FR1, CDR1, FR2, CDR2, FR3, CDR3, FR4.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may or may not include one, two, or more N- or C-terminal amino acids, or may include other alterations that are compatible with formation of the protein structure.

The term "antigen-binding site" refers to the part of an antibody molecule that comprises determinants that form an interface that binds to the PD-1 polypeptide, or an epitope thereof. With respect to proteins (or protein mimetics), the antigen-binding site typically includes one or more loops (of at least four amino acids or amino acid mimics) that form an interface that binds to the PD-1 polypeptide. Typically, the antigen-binding site of an antibody molecule includes at least one or two CDRs and/or hypervariable loops, or more typically at least three, four, five or six CDRs and/or hypervariable loops.

The terms "compete" or "cross-compete" are used interchangeably herein to refer to the ability of an antibody molecule to interfere with binding of an anti-PD-1 antibody molecule, e.g., an anti-PD-1 antibody molecule provided herein, to a target, e.g., human PD-1. The interference with binding can be direct or indirect (e.g., through an allosteric modulation of the antibody molecule or the target). The extent to which an antibody molecule is able to interfere with the binding of another antibody molecule to the target, and therefore whether it can be said to compete, can be determined using a competition binding assay, for example, a FACS assay, an ELISA or BIACORE assay. In some embodiments, a competition binding assay is a quantitative competition assay. In some embodiments, a first anti-PD-1 antibody molecule is said to compete for binding to the target with a second anti-PD-1 antibody molecule when the binding of the first antibody molecule to the target is reduced by 10% or more, e.g., 20% or more, 30% or more, 40% or more, 50% or more, 55% or more, 60% or more, 65% or more, 70% or more, 75% or more, 80% or more, 85% or more, 90% or more, 95% or more, 98% or more, 99% or more in a competition binding assay (e.g., a competition assay described herein).

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

An "effectively human" protein is a protein that does not evoke a neutralizing antibody response, e.g., the human anti-murine antibody (HAMA) response. HAMA can be problematic in a number of circumstances, e.g., if the antibody molecule is administered repeatedly, e.g., in treatment of a chronic or recurrent disease condition. A HAMA response can make repeated antibody administration potentially ineffective because of an increased antibody clearance from the serum (see, e.g., Saleh et al., Cancer Immunol. Immunother., 32:180-190 (1990)) and also because of potential allergic reactions (see, e.g., LoBuglio et al., Hybridoma, 5:5117-5123 (1986)).

The antibody molecule can be a polyclonal or a monoclonal antibody. In other embodiments, the antibody can be recombinantly produced, e.g., produced by phage display or by combinatorial methods.

Phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. *International Publication No. WO 90/02809;* Fuchs et al. (1991) *Bio/Technology* 9:1370-1372; Hay et al. (1992) *Hum Antibody Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In one embodiment, the antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 Year *Immunol* 7:33-40; Tuaillon et al. 1993 *PNAS* 90:3720-3724; Bruggeman et al. 1991 *Eur J Immunol* 21:1323-1326).

An antibody can be one in which the variable region, or a portion thereof, e.g., the CDRs, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

A humanized or CDR-grafted antibody will have at least one or two but generally all three recipient CDRs (of heavy and or light immunoglobulin chains) replaced with a donor CDR. The antibody may be replaced with at least a portion of a non-human CDR or only some of the CDRs may be replaced with non-human CDRs. It is only necessary to replace the number of CDRs required for binding of the humanized antibody to PD-1. Preferably, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art (see e.g., Morrison, S. L., 1985, *Science* 229:1202-1207, by Oi et al., 1986, *BioTechniques* 4:214, and by Queen et al. U.S. Pat. Nos. 5,585,089, 5,693,761 and 5,693,762, the contents of all of which are hereby incorporated by reference).

Humanized or CDR-grafted antibodies can be produced by CDR-grafting or CDR substitution, wherein one, two, or all CDRs of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Criteria for selecting amino acids from the donor are described in U.S. Pat. No. 5,585,089, e.g., columns 12-16 of U.S. Pat. No. 5,585,089, e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

The antibody molecule can be a single chain antibody. A single-chain antibody (scFV) may be engineered (see, for example, Colcher, D. et al. (1999) *Ann N Y Acad Sci* 880:263-80; and Reiter, Y. (1996) *Clin Cancer Res* 2:245-52). The single chain antibody can be dimerized or multimerized to generate multivalent antibodies having specificities for different epitopes of the same target protein.

In yet other embodiments, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In one embodiment the antibody has: effector function; and can fix complement. In other embodiments the antibody does not; recruit effector cells; or fix complement. In another embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. Nos. 5,624,821 and 5,648,260, the contents of all of which are hereby incorporated by reference). Similar type of alterations could be described which if applied to the murine, or other species immunoglobulin would reduce or eliminate these functions.

An antibody molecule can be derivatized or linked to another functional molecule (e.g., another peptide or protein). As used herein, a "derivatized" antibody molecule is one that has been modified. Methods of derivatization include but are not limited to the addition of a fluorescent moiety, a radionucleotide, a toxin, an enzyme or an affinity ligand such as biotin. Accordingly, the antibody molecules of the invention are intended to include derivatized and otherwise modified forms of the antibodies described herein, including immunoadhesion molecules. For example, an antibody molecule can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate association of the antibody or antibody portion with another molecule (such as a streptavidin core region or a polyhistidine tag).

One type of derivatized antibody molecule is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody molecule of the invention may be derivatized (or labeled) to include fluorescent compounds, various enzymes, prosthetic groups, luminescent materials, bioluminescent materials, fluorescent emitting metal atoms, e.g., europium (Eu), and other anthanides, and radioactive materials (described below). Exemplary fluorescent detectable agents include fluorescein, fluorescein isothiocyanate, rhodamine, 5dimethylamine-1-napthalenesulfonyl chloride, phycoerythrin and the like. An antibody may also be derivatized with detectable enzymes, such as alkaline phosphatase, horseradish peroxidase, β-galactosidase, acetylcholinesterase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody molecule may also be derivatized with a prosthetic group (e.g., streptavidin/biotin and avidin/biotin). For example, an antibody may be derivatized with biotin, and detected through indirect measurement of avidin or streptavidin binding. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of bioluminescent materials include luciferase, luciferin, and aequorin.

Labeled antibody molecule can be used, for example, diagnostically and/or experimentally in a number of contexts, including (i) to isolate a predetermined antigen by standard techniques, such as affinity chromatography or immunoprecipitation; (ii) to detect a predetermined antigen (e.g., in a cellular lysate or cell supernatant) in order to evaluate the abundance and pattern of expression of the protein; (iii) to monitor protein levels in tissue as part of a clinical testing procedure, e.g., to determine the efficacy of a given treatment regimen.

An antibody molecules may be conjugated to another molecular entity, typically a label or a therapeutic (e.g., a cytotoxic or cytostatic) agent or moiety. Radioactive isotopes can be used in diagnostic or therapeutic applications.

The invention provides radiolabeled antibody molecules and methods of labeling the same. In one embodiment, a method of labeling an antibody molecule is disclosed. The method includes contacting an antibody molecule, with a chelating agent, to thereby produce a conjugated antibody.

As is discussed above, the antibody molecule can be conjugated to a therapeutic agent. Therapeutically active radioisotopes have already been mentioned. Examples of other therapeutic agents include taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see e.g., U.S. Pat. No. 5,208,020), CC-1065 (see e.g., U.S. Pat. Nos. 5,475,092, 5,585,499, 5,846, 545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclinies (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

In one aspect, the invention features a method of providing a target binding molecule that specifically binds to a target disclosed herein, e.g., PD-1 receptor. For example, the target binding molecule is an antibody molecule. The method includes: providing a target protein that comprises at least a portion of non-human protein, the portion being homologous to (at least 70, 75, 80, 85, 87, 90, 92, 94, 95, 96, 97, 98% identical to) a corresponding portion of a human target protein, but differing by at least one amino acid (e.g., at least one, two, three, four, five, six, seven, eight, or nine amino acids); obtaining an antibody molecule that specifically binds to the antigen; and evaluating efficacy of the binding agent in modulating activity of the target protein.

The method can further include administering the binding agent (e.g., antibody molecule) or a derivative (e.g., a humanized antibody molecule) to a human subject.

Multispecific Antibody Molecules

In certain embodiments, the antibody molecule is a multi-specific (e.g., a bispecific or a trispecific) antibody molecule. Protocols for generating bispecific or heterodimeric antibody molecules are known in the art; including but not limited to, for example, the "knob in a hole" approach described in, e.g., U.S. Pat. No. 5,731,168; the electrostatic steering Fc pairing as described in, e.g., WO 09/089004, WO 06/106905 and WO 2010/129304; Strand Exchange Engineered Domains (SEED) heterodimer formation as described in, e.g., WO 07/110205; Fab arm exchange as described in, e.g., WO 08/119353, WO 2011/131746, and WO 2013/060867; double antibody conjugate, e.g., by antibody cross-linking to generate a bi-specific structure using a heterobifunctional reagent having an amine-reactive group and a sulfhydryl reactive group as described in, e.g., U.S. Pat. No. 4,433,059; bispecific antibody determinants generated by recombining half antibodies (heavy-light chain pairs or Fabs) from different antibodies through cycle of reduction and oxidation of disulfide bonds between the two heavy chains, as described in, e.g., U.S. Pat. No. 4,444,878; trifunctional antibodies, e.g., three Fab' fragments cross-linked through sulfhydryl reactive groups, as described in, e.g., U.S. Pat. No. 5,273,743; biosynthetic binding proteins, e.g., pair of scFvs cross-linked through C-terminal tails preferably through disulfide or amine-reactive chemical cross-linking, as described in, e.g., U.S. Pat. No. 5,534,254; bifunctional antibodies, e.g., Fab fragments with different binding specificities dimerized through leucine zippers (e.g., c-fos and c-jun) that have replaced the constant domain, as described in, e.g., U.S. Pat. No. 5,582,996; bispecific and oligospecific mono- and oligovalent receptors, e.g., VH-CH1 regions of two antibodies (two Fab fragments) linked through a polypeptide spacer between the CH1 region of one antibody and the VH region of the other antibody typically with associated light chains, as described in, e.g., U.S. Pat. No. 5,591,828; bispecific DNA-antibody conjugates, e.g., crosslinking of antibodies or Fab fragments through a double stranded piece of DNA, as described in, e.g., U.S. Pat. No. 5,635,602; bispecific fusion proteins, e.g., an expression construct containing two scFvs with a hydrophilic helical peptide linker between them and a full constant region, as described in, e.g., U.S. Pat. No. 5,637,481; multivalent and multispecific binding proteins, e.g., dimer of polypeptides having first domain with binding region of Ig heavy chain variable region, and second domain with binding region of Ig light chain variable region, generally termed diabodies (higher order structures are also disclosed creating bispecific, trispecific, or tetraspecific molecules, as described in, e.g., U.S. Pat. No. 5,837,242; minibody constructs with linked VL and VH chains further connected with peptide spacers to an antibody hinge region and CH3 region, which can be dimerized to form bispecific/multivalent molecules, as described in, e.g., U.S. Pat. No. 5,837,821; VH and VL domains linked with a short peptide linker (e.g., 5 or 10 amino acids) or no linker at all in either orientation, which can form dimers to form bispecific diabodies; trimers and tetramers, as described in, e.g., U.S. Pat. No. 5,844,094; String of VH domains (or VL domains in family members) connected by peptide linkages with crosslinkable groups at the C-terminus further associated with VL domains to form a series of FVs (or scFvs), as described in, e.g., U.S. Pat. No. 5,864,019; and single chain binding polypeptides with both a VH and a VL domain linked through a peptide linker are combined into multivalent structures through non-covalent or chemical crosslinking to form, e.g., homobivalent, heterobivalent, trivalent, and tetravalent structures using both scFV or diabody type format, as described in, e.g., U.S. Pat. No. 5,869,620. Additional exemplary multispecific and bispecific molecules and methods of making the same are found, for example, in U.S. Pat. Nos. 5,910,573, 5,932,448, 5,959,083, 5,989,830, 6,005,079, 6,239,259, 6,294,353, 6,333,396, 6,476,198, 6,511,663, 6,670,453, 6,743,896, 6,809,185, 6,833,441, 7,129,330, 7,183,076, 7,521,056, 7,527,787, 7,534,866, 7,612,181, US2002/004587A1, US2002/076406A1, US2002/103345A1, US2003/207346A1, US2003/211078A1, US2004/219643A1, US2004/220388A1, US2004/242847A1, US2005/003403A1, US2005/004352A1, US2005/069552A1, US2005/079170A1, US2005/100543A1, US2005/136049A1, US2005/136051A1, US2005/163782A1, US2005/266425A1, US2006/083747A1, US2006/120960A1, US2006/204493A1, US2006/263367A1, US2007/004909A1, US2007/087381A1, US2007/128150A1, US2007/141049A1, US2007/154901A1, US2007/274985A1, US2008/050370A1, US2008/069820A1, US2008/152645A1, US2008/171855A1, US2008/241884A1, US2008/254512A1, US2008/260738A1, US2009/130106A1, US2009/148905A1, US2009/155275A1, US2009/162359A1, US2009/162360A1, US2009/175851A1, US2009/175867A1, US2009/232811A1, US2009/234105A1, US2009/263392A1, US2009/274649A1, EP346087A2, WO00/06605A2, WO02/072635A2, WO04/081051A1, WO06/020258A2, WO2007/044887A2, WO2007/095338A2, WO2007/137760A2, WO2008/119353A1, WO2009/021754A2, WO2009/068630A1, WO91/03493A1, WO93/23537A1, WO94/09131A1, WO94/12625A2, WO95/09917A1, WO96/37621A2, WO99/64460A1. The contents of the above-referenced applications are incorporated herein by reference in their entireties.

In other embodiments, the anti-PD-1 antibody molecule (e.g., a monospecific, bispecific, or multispecific antibody molecule) is covalently linked, e.g., fused, to another partner e.g., a protein e.g., one, two or more cytokines, e.g., as a fusion molecule for example a fusion protein. In other embodiments, the fusion molecule comprises one or more proteins, e.g., one, two or more cytokines. In one embodiment, the cytokine is an interleukin (IL) chosen from one, two, three or more of IL-1, IL-2, IL-12, IL-15 or IL-21. In one embodiment, a bispecific antibody molecule has a first binding specificity to a first target (e.g., to PD-1), a second binding specificity to a second target (e.g., LAG-3 or TIM-3), and is optionally linked to an interleukin (e.g., IL-12) domain e.g., full length IL-12 or a portion thereof.

A "fusion protein" and a "fusion polypeptide" refer to a polypeptide having at least two portions covalently linked together, where each of the portions is a polypeptide having a different property. The property may be a biological property, such as activity in vitro or in vivo. The property can also be simple chemical or physical property, such as binding to a target molecule, catalysis of a reaction, etc. The two portions can be linked directly by a single peptide bond or through a peptide linker, but are in reading frame with each other.

This invention provides an isolated nucleic acid molecule encoding the above antibody molecule, vectors and host cells thereof. The nucleic acid molecule includes but is not limited to RNA, genomic DNA and cDNA.

Exemplary Agents Used in the Combinations

Described herein are methods and compositions that include a combination of one or more of: (i) an agent that enhances antigen (e.g., tumor antigen) presentation; (ii) an agent that enhances an effector cell response (e.g., B cell and/or T cell activation and/or mobilization); or (iii) an agent that decreases tumor immunosuppression, thereby treating the disorder, e.g., the hyperproliferative condition or disorder (e.g., the cancer). In some embodiments, the combination includes a PD-1 inhibitor (e.g., an anti-PD-1 antibody molecule as described herein). Exemplary agents that can be used in these combinations are provided herein.

Exemplary STING Agonists

In an embodiment, the combination includes a STING agonist. In some embodiments, the combination is used to treat a cancer, e.g., a cancer described herein e.g., a solid tumor (e.g., a breast cancer, a squamous cell carcinoma, a melanoma, an ovarian cancer, a fallopian tube carcinoma, a peritoneal carcinoma, a soft tissue sarcoma, an esophageal cancer, a head and neck cancer, an endometrial cancer, a cervical cancer, or a basal cell carcinoma), e.g., a hematologic malignancy (e.g., a leukemia (e.g., a chronic lymphocytic leukemia (CLL), or a lymphoma (e.g., a marginal zone B-cell lymphoma, a small lymphocytic lymphoma, a follicular lymphoma, Hodgkin lymphoma, non-Hodgkin lymphoma)). In some embodiments, the cancer is chosen from a head and neck cancer (e.g., a head and neck squamous cell carcinoma (HNSCC), a skin cancer (e.g., melanoma), a lung cancer (e.g., a non-small cell lung cancer (NSCLC)), or a breast cancer (e.g., a triple negative breast cancer (TNBC)).

In some embodiments, the STING agonist is cyclic dinucleotide, e.g., a cyclic dinucleotide comprising purine or pyrimidine nucleobases (e.g., adenosine, guanine, uracil, thymine, or cytosine nucleobases). In some embodiments, the nucleobases of the cyclic dinucleotide comprise the same nucleobase or different nucleobases.

In some embodiments, the STING agonist comprises an adenosine or a guanosine nucleobase. In some embodiments, the STING agonist comprises one adenosine nucleobase and one guanosine nucleobase. In some embodiments, the STING agonist comprises two adenosine nucleobases or two guanosine nucleobases.

In some embodiments, the STING agonist comprises a modified cyclic dinucleotide, e.g., comprising a modified nucleobase, a modified ribose, or a modified phosphate linkage. In some embodiments, the modified cyclic dinucleotide comprises a modified phosphate linkage, e.g., a thiophosphate.

In some embodiments, the STING agonist comprises a cyclic dinucleotide (e.g., a modified cyclic dinucleotide) with 2',5' or 3',5' phosphate linkages. In some embodiments, the STING agonist comprises a cyclic dinucleotide (e.g., a modified cyclic dinucleotide) with Rp or Sp stereochemistry around the phosphate linkages.

Figure 4:
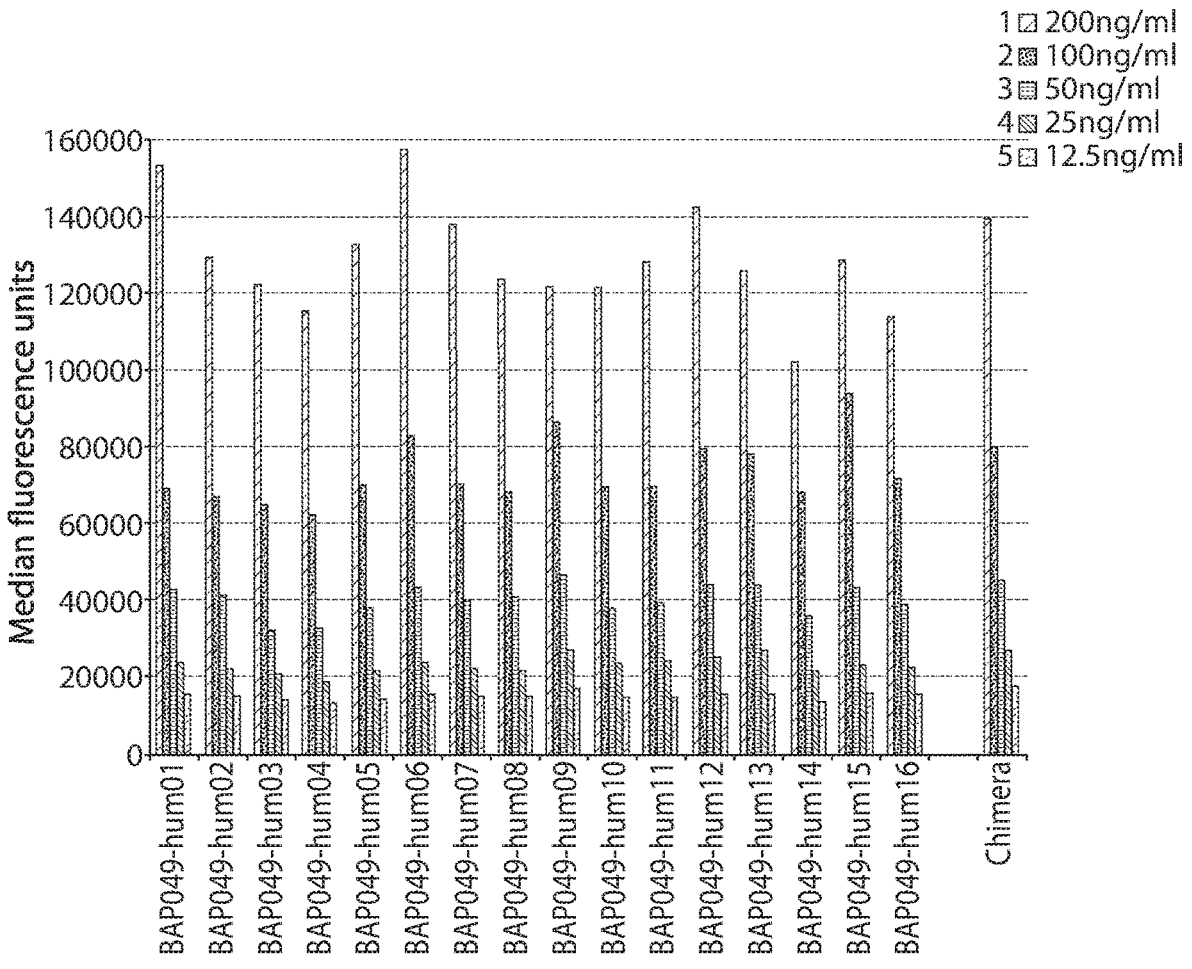
FIG. 4 is a bar graph showing the results of FACS binding analysis for the sixteen humanized BAP049 clones (BAP049-hum01 to BAP049-hum16). The antibody concentrations are 200, 100, 50, 25 and 12.5 ng/ml from the leftmost bar to the rightmost bar for each tested mAb.
Figure 6A:
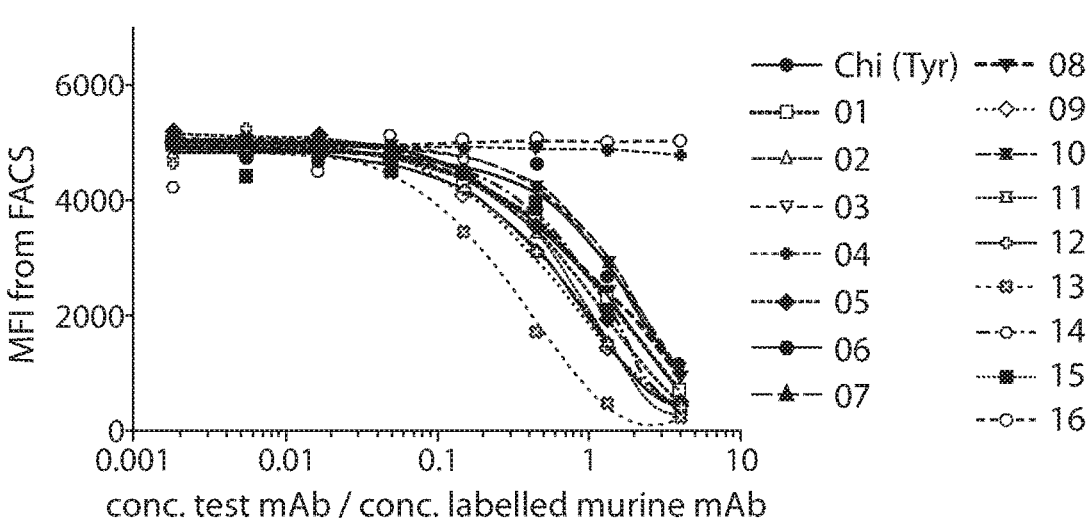
FIG. 6A-6B depicts the binding affinity and specificity of humanized BAP049 mAbs measured in a competition binding assay using a constant concentration of Alexa 488-labeled murine mAb BAP049, serial dilutions of the test antibodies, and PD-1-expressing 300.19 cells. Experiment was performed twice, and the results are shown in FIGS. 6A and 6B, respectively.
Figure 6B:
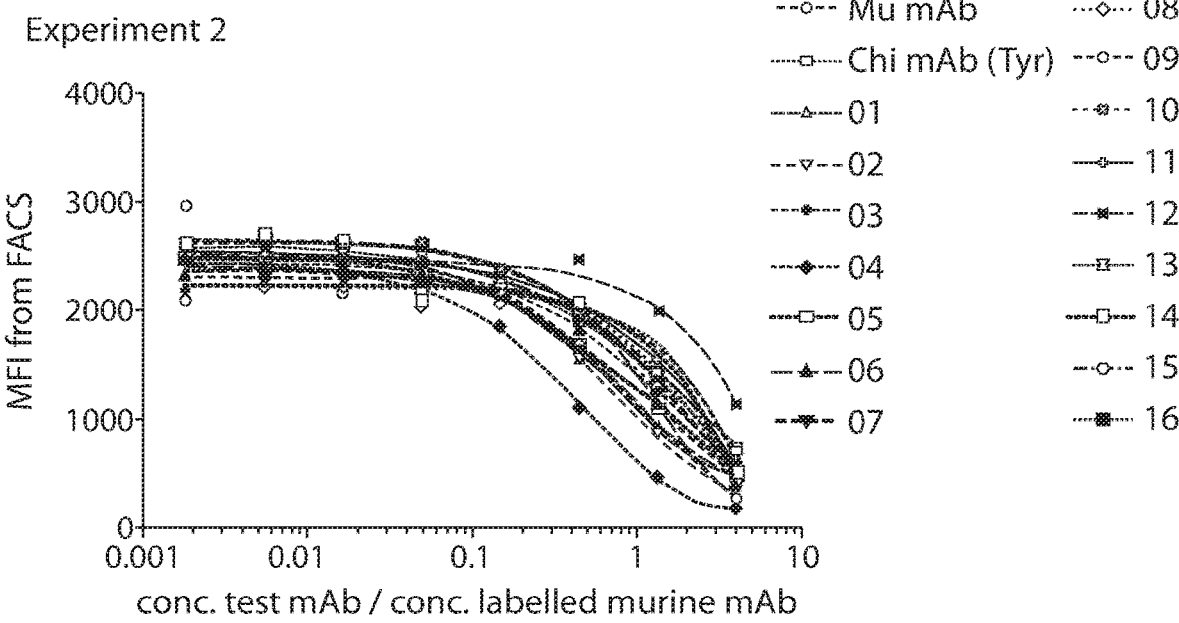
Figure 8A:
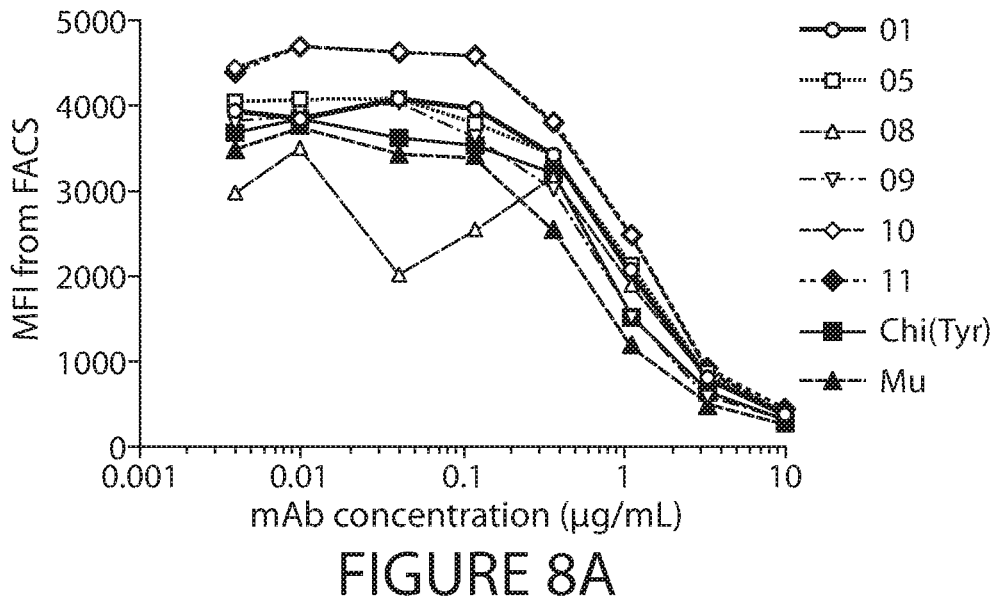
FIGS. 8A-8B depict blocking of ligand binding to PD-1 by selected humanized BAP049 clones. Blocking of PD-L1-Ig and PD-L2-Ig binding to PD-1 is shown in FIG. 8A. Blocking of PD-L2-Ig binding to PD-1 is shown in FIG. 8B. BAP049-hum01, BAP049-hum05, BAP049-hum08, BAP049-hum09, BAP049-hum10, and BAP049-hum11 were evaluated. Murine mAb BAP049 and chimeric mAb having Tyr at position 102 of the light chain variable region were also included in the analyses.
Figure 8B:
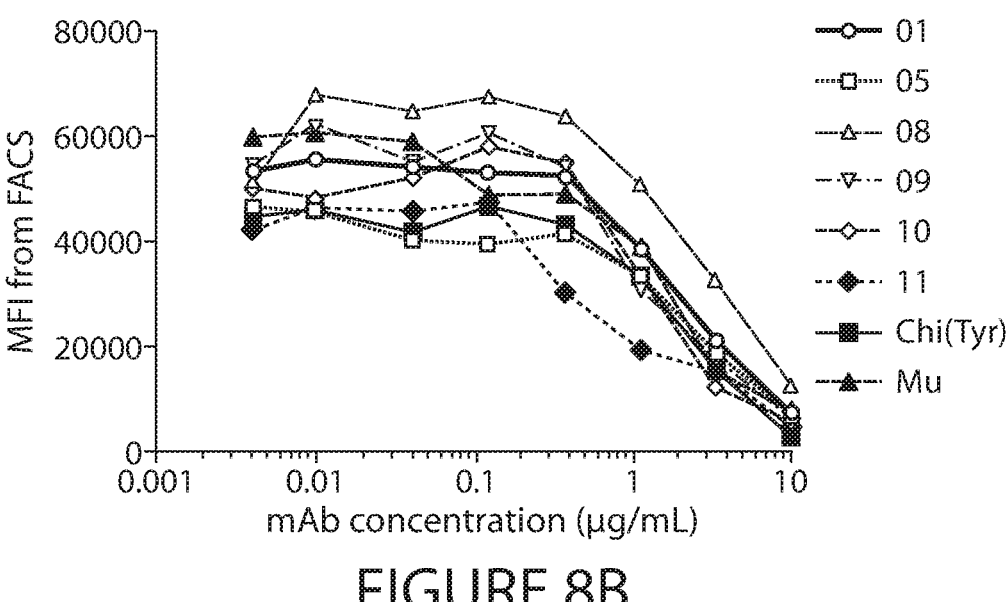
Figure 11:
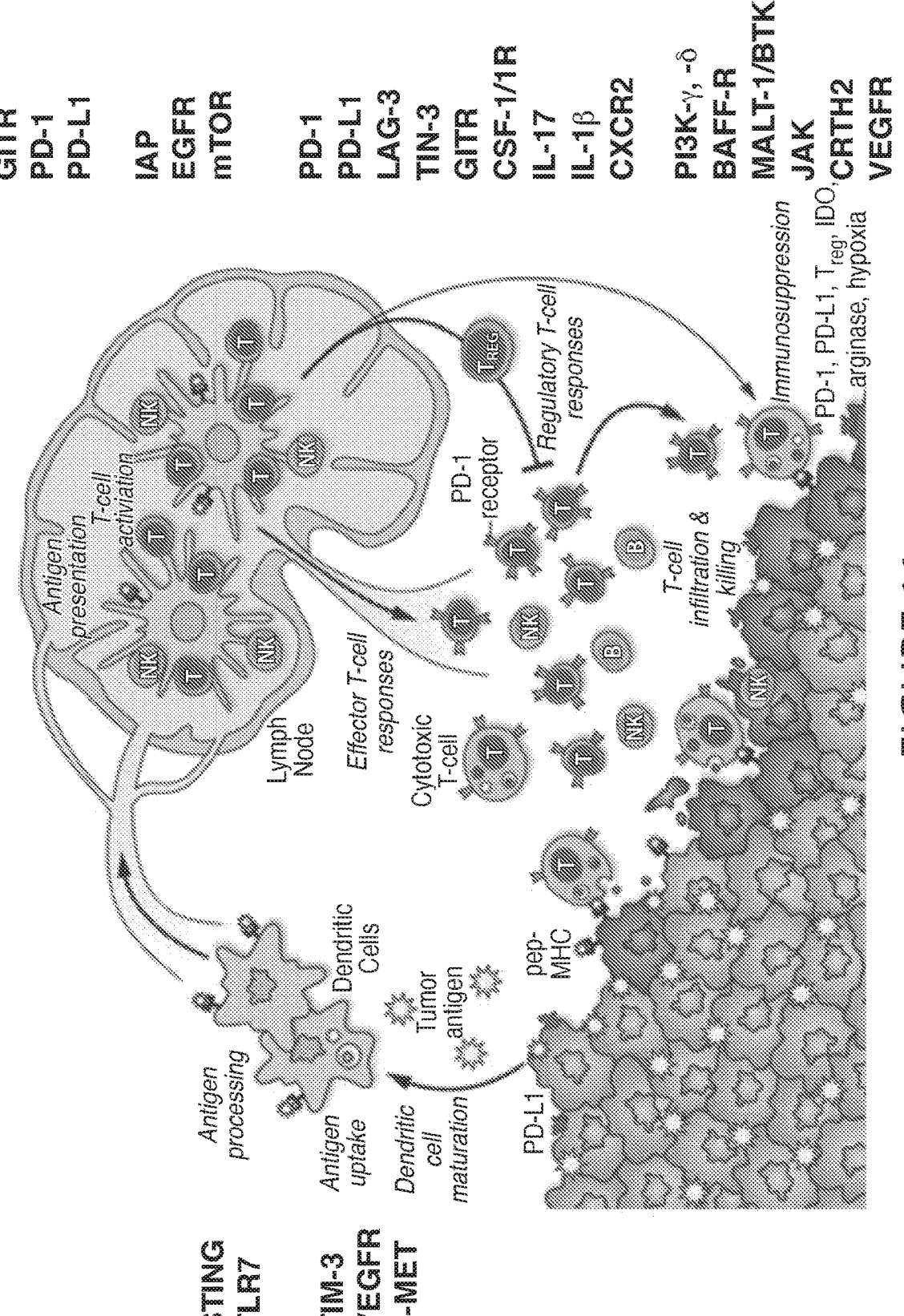
FIG. 11 is a schematic diagram that outlines the antigen processing and presentation, effector cell responses and immunosuppression pathways targeted by the combination therapies disclosed herein.

In some embodiments, the STING agonist is Rp,Rp dithio 2',3' c-di-AMP (e.g., Rp,Rp-dithio c-[A(2',5')pA(3',5')p]), or a cyclic dinucleotide analog thereof. In some embodiments, the STING agonist is a compound depicted in U.S. Patent Publication No. US2015/0056224 (e.g., a compound in FIG. 2c, e.g., compound 21 or compound 22). In some embodiments, the STING agonist is c-[G(2',5')pG(3',5')p], a dithio ribose O-substituted derivative thereof, or a compound depicted in FIG. 4 of PCT Publication Nos. WO 2014/189805 and WO 2014/189806. In some embodiments, the STING agonist is c-[A(2',5')pA(3',5')p] or a dithio ribose O-substituted derivative thereof, or is a compound depicted in FIG. 5 of PCT Publication Nos. WO 2014/189805 and WO 2014/189806. In some embodiments, the STING agonist is c-[G(2',5')pA(3',5')p], or a dithio ribose O-substituted derivative thereof, or is a compound depicted in FIG. 5 of PCT Publication Nos. WO 2014/189805 and WO 2014/189806. In some embodiments, the STING agonist is 2'-0-propargyl-cyclic-[A(2',5')pA(3',5')p] (2'-0-propargyl-ML-CDA) or a compound depicted in FIG. 7 of PCT Publication No. WO 2014/189806.

Other exemplary STING agonists are disclosed, e.g., in PCT Publication Nos. WO 2014/189805 and WO 2014/189806, and U.S. Publication No. 2015/0056225.

Exemplary TLR Agonists

In an embodiment, a combination described herein includes a Toll-like receptor (TLR) agonist. In some embodiments, the combination is used to treat a cancer, e.g., a cancer described herein, e.g., a solid tumor (e.g., a breast cancer, a squamous cell carcinoma, a melanoma, an ovarian cancer, a fallopian tube carcinoma, a peritoneal carcinoma, a soft tissue sarcoma, an esophageal cancer, a head and neck cancer, an endometrial cancer, a cervical cancer, or a basal cell carcinoma), e.g., a hematologic malignancy (e.g., a leukemia (e.g., a chronic lymphocytic leukemia (CLL), or a lymphoma (e.g., a marginal zone B-cell lymphoma, a small lymphocytic lymphoma, a follicular lymphoma, Hodgkin lymphoma, non-Hodgkin lymphoma)).

TLRs are a family of pattern recognition receptors that were initially identified as sensors of the innate immune system that recognize microbial pathogens. In humans, the TLRs include TLR-1, TLR-2, TLR-3, TLR-4, TLR-5, TLR-6, TLR-7, TLR-8, TLR-9, and TLR-10. TLR-1, -2, -4, -5, and -6, are expressed on the surface of cells and TLR-3, -7/8, and -9 are expressed with the ER compartment. Human dendritic cell subsets can be identified on the basis of distinct TLR expression patterns. The myeloid or "conventional" subset of human dendritic cells express TLRs 1-8 and the plasmacytoid subset of dendritic cells express only TLR-7 and TLR-9. Ligand binding to TLRs invokes a cascade of intra-cellular signaling pathways that induce the production of factors involved in inflammation and immunity Upon stimulation, the myeloid subset and the plasmacytoid subset of human dendritic cells result in antigen-specific CD4+ and CD8+ T cell priming and activation of NK cells and T-cells, respectively.

In some embodiments, the TLR agonist is chosen from one or more of a TLR-1 agonist, a TLR-2 agonist, a TLR-3 agonist, a TLR-4 agonist, a TLR-5 agonist, a TLR-6 agonist, a TLR-7 agonist, a TLR-8 agonist, a TLR-9 agonist, a TLR-10 agonist, a TLR-1/2 agonist, a TLR-2/6 agonist, or a TLR-7/8 agonist. In one embodiment, the TLR agonist is a TLR7 agonist.

In some embodiments, the TLR agonist is imiquimod or 3-(2-Methylpropyl)-3,5,8-triazatricyclo[7.4.0.02,6]trideca-1(9),2(6),4,7,10,12-hexaen-7-amine. Imiquimod or 3-(2-Methylpropyl)-3,5,8-triazatricyclo[7.4.0.02,6]trideca-1(9),2(6),4,7,10,12-hexaen-7-amine can bind to and activate TLR-7 and/or TLR-8.

In some embodiments, the TLR agonist is 852A. 852A is disclosed, e.g., in Inglefield et al. *J Interferon Cytokine Res.* 2008; 28(4):253-63. 852A can bind to and activate TLR-7 and/or TLR-8. In some embodiments, the TLR agonist is Bacille Calmette-Guérin (BCG). BCG can bind to and activate TLR-9.

In some embodiments, the TLR agonist is EMD 120108. EMD 120108 is a synthetic oligonucleotide containing phosphorothioate oligodeoxynucleotide. EMD 1201081 can bind to and activate TLR-9, e.g., in monocytes/macrophages, plasmacytoid dendritic cells (DCs) and B cells, initiating immune signaling pathways, activating B cells and inducing T-helper cell cytokine production.

In some embodiments, the TLR agonist is IMO-2055. IMO-2055 is a synthetic oligonucleotide containing unmethylated CpG dinucleotides. Mimicking unmethylated CpG sequences in bacterial DNA, IMO-2055 can bind to and activate TLR-9, e.g., in monocytes/macrophages, plasmacytoid dendritic cells (DCs) and B cells, initiating immune signaling pathways and activating B cells and DCs and inducing T-helper cell cytokine production.

Other exemplary TLR agonists that can be used in the combination include, e.g., TLR-1/2 agonists (e.g., Pam3Cys), TLR-2 agonists (e.g., CFA, MALP2, Pam2Cys, FSL-1, or Hib-OMPC), TLR-3 agonists (e.g., polyribosinic:polyribocytidic acid (Poly I:C), polyadenosine-polyuridylic acid (poly AU), polyinosinic-polycytidylic acid stabilized with poly-L-lysine and carboxymethylcellulose (Hiltonol®)), TLR-4 agonists (e.g., monophosphoryl lipid A (MPL), LPS, sialyl-Tn (STn)), TLR-5 agonists (e.g., bacterial flagellin), TLR-7 agonists (e.g., imiquimod), TLR-7/8 agonists (e.g., resiquimod or loxoribine), and TLR-9 agonists (e.g., unmethylated CpG dinucleotide (CpG-ODN)).

In another embodiment, the TLR agonist is used in combination with a GITR agonist, e.g., as described in WO2004060319, and International Publication No. WO2014012479.

Exemplary VEGFR Inhibitors

In one embodiment, a combination described herein includes a vascular endothelial growth factor (VEGF) receptor inhibitor (e.g., an inhibitor of one or more of VEGFR (e.g., VEGFR-1, VEGFR-2, VEGFR-3) or VEGF). In some embodiments, the combination is used to treat a cancer, e.g., a cancer described herein, e.g., a solid tumor (e.g., a melanoma, a breast cancer, a colon cancer, an esophageal cancer, a gastrointestinal stromal tumor (GIST), a kidney cancer (e.g., a renal cell cancer), a liver cancer, a non-small cell lung cancer (NSCLC), an ovarian cancer, a pancreatic cancer, a prostate cancer, or a stomach cancer), e.g., a hematologic malignancy (e.g., a lymphoma).

In some embodiments, the VEGFR inhibitor is vatalanib succinate (Compound A47) or a compound disclosed in EP 296122.

In some embodiment, the VEGFR inhibitor is an inhibitor of one or more of VEGFR-2, PDGFRbeta, KIT or Raf kinase C, 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37) or a compound disclosed in PCT Publication No. WO 2007/030377.

Other exemplary VEGFR pathway inhibitors that can be used in the combinations disclosed herein include, e.g., bevacizumab (AVASTIN®), axitinib (INLYTA®); brivanib alaninate (BMS-582664, (S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate); sorafenib (NEXAVAR®); pazopanib (VOTRIENT®); sunitinib malate (SUTENT®); cediranib (AZD2171, CAS 288383-20-1); vargatef (BIBF1120, CAS 928326-83-4); Foretinib (GSK1363089); telatinib (BAY57-9352, CAS 332012-40-5); apatinib (YN968D1, CAS 811803-05-1); imatinib (GLEEVEC®); ponatinib (AP24534, CAS 943319-70-8); tivozanib (AV951, CAS 475108-18-0); regorafenib (BAY73-4506, CAS 755037-03-7); vatalanib dihydrochloride (PTK787, CAS 212141-51-0); brivanib (BMS-540215, CAS 649735-46-6); vandetanib (CAPRELSA® or AZD6474); motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470); dovitinib dilactic acid (TKI258, CAS 852433-84-2); linfanib (ABT869, CAS 796967-16-3); cabozantinib (XL184, CAS 849217-68-1); lestaurtinib (CAS 111358-88-4); N-[5-[[[5-(1,1-dimethylethyl)-2-oxazolyl]methyl]thio]-2-thiazolyl]-4-piperidinecarboxamide (BMS38703, CAS 345627-80-7); (3R,4R)-4-amino-1-((4-((3-methoxyphenyl)amino)pyrrolo[2,1-f][1,2,4]triazin-5-yl)methyl)piperidin-3-ol (BMS690514); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); 4-methyl-3-[[1-methyl-6-(3-pyridinyl)-1H-pyrazolo[3,4-d]pyrimidin-4-yl]amino]-N-[3-(trifluoromethyl)phenyl]-benzamide (BHG712, CAS 940310-85-0); aflibercept (EYLEA®), and endostatin (ENDOSTAR®).

Exemplary anti-VEGF antibodies that can be used in the combinations disclosed herein include, e.g., a monoclonal antibody that binds to the same epitope as the monoclonal anti-VEGF antibody A4.6.1 produced by hybridoma ATCC HB 10709; a recombinant humanized anti-VEGF monoclonal antibody generated according to Presta et al. (1997) Cancer Res. 57:4593-4599. In one embodiment, the anti-VEGF antibody is Bevacizumab (BV), also known as rhuMAb VEGF or AVASTIN®. It comprises mutated human IgG1 framework regions and antigen-binding complementarity—determining regions from the murine anti-hVEGF monoclonal antibody A.4.6.1 that blocks binding of human VEGF to its receptors. Bevacizumab and other humanized anti-VEGF antibodies are further described in U.S. Pat. No. 6,884,879 issued Feb. 26, 2005. Additional antibodies include the G6 or B20 series antibodies (e.g., G6-31, B20-4.1), as described in PCT Publication No. WO2005/012359, PCT Publication No. WO2005/044853, the contents of these patent applications are expressly incorporated herein by reference. For additional antibodies see U.S. Pat. Nos. 7,060,269, 6,582,959, 6,703,020, 6,054,297, WO98/45332, WO 96/30046, WO94/10202, EP 0666868B1, U.S. Patent Application Publication Nos. 2006/009360, 2005/0186208, 2003/0206899, 2003/0190317, 2003/0203409, and 2005/0112126; and Popkov et al, *Journal of Immunological Methods* 288: 149-164 (2004). Other antibodies include those that bind to a functional epitope on human VEGF comprising of residues F17, M1 8, D19, Y21, Y25, Q89, 191, Kl 01, El 03, and C104 or, alternatively, comprising residues F17, Y21, Q22, Y25, D63, 183 and Q89.

Exemplary c-MET Inhibitors

In one embodiment, a combination described herein includes an inhibitor of c-MET. In some embodiments, the combination is used to treat a cancer, e.g., a cancer described herein, e.g., a solid tumor (e.g., a non-small cell lung cancer, a pancreatic cancer, a liver cancer, a thyroid cancer (e.g., anaplastic thyroid carcinoma), a brain tumor (e.g., a glioblastoma), a kidney cancer (e.g., a renal cell carcinoma), or a head and neck cancer (e.g., a head and neck squamous cell carcinoma). In certain embodiments, the cancer is a liver cancer, e.g., a hepatocellular carcinoma (HCC) (e.g., a c-MET-expressing HCC).

In some embodiments, the c-MET inhibitor is Compound A17 or a compound described in U.S. Pat. Nos. 7,767,675 and 8,420,645). c-MET, a receptor tyrosine kinase overexpressed or mutated in many tumor cell types, plays key roles in tumor cell proliferation, survival, invasion, metastasis, and tumor angiogenesis. Inhibition of c-MET may induce cell death in tumor cells overexpressing c-MET protein or expressing constitutively activated c-MET protein.

In some embodiments, the c-MET inhibitor is JNJ-38877605. JNJ-38877605 is an orally available, small molecule inhibitor of c-Met. JNJ-38877605 selectively binds to c-MET, thereby inhibiting c-MET phosphorylation and disrupting c-Met signal transduction pathways.

In some embodiments, the c-Met inhibitor is AMG 208. AMG 208 is a selective small-molecule inhibitor of c-MET. AMG 208 inhibits the ligand-dependent and ligand-independent activation of c-MET, inhibiting its tyrosine kinase activity, which may result in cell growth inhibition in tumors that overexpress c-Met.

In some embodiments, the c-Met inhibitor is AMG 337. AMG 337 is an orally bioavailable inhibitor of c-Met. AMG 337 selectively binds to c-MET, thereby disrupting c-MET signal transduction pathways.

In some embodiments, the c-Met inhibitor is LY2801653. LY2801653 is an orally available, small molecule inhibitor of c-Met. LY2801653 selectively binds to c-MET, thereby inhibiting c-MET phosphorylation and disrupting c-Met signal transduction pathways.

In some embodiments, c-Met inhibitor is MSC2156119J. MSC2156119J is an orally bioavailable inhibitor of c-Met. MSC2156119J selectively binds to c-MET, which inhibits c-MET phosphorylation and disrupts c-Met-mediated signal transduction pathways.

In some embodiments, the c-MET inhibitor is capmatinib. Capmatinib is also known as INCB028060. Capmatinib is an orally bioavailable inhibitor of c-MET. Capmatinib selectively binds to c-Met, thereby inhibiting c-Met phosphorylation and disrupting c-Met signal transduction pathways.

In some embodiments, the c-MET inhibitor is crizotinib. Crizotinib is also known as PF-02341066. Crizotinib is an orally available aminopyridine-based inhibitor of the receptor tyrosine kinase anaplastic lymphoma kinase (ALK) and the c-Met/hepatocyte growth factor receptor (HGFR). Crizotinib, in an ATP-competitive manner, binds to and inhibits ALK kinase and ALK fusion proteins. In addition, crizotinib inhibits c-Met kinase, and disrupts the c-Met signaling pathway. Altogether, this agent inhibits tumor cell growth.

In some embodiments, the c-MET inhibitor is golvatinib. Golvatinib is an orally bioavailable dual kinase inhibitor of c-MET and VEGFR-2 with potential antineoplastic activity. Golvatinib binds to and inhibits the activities of both c-MET and VEGFR-2, which may inhibit tumor cell growth and survival of tumor cells that overexpress these receptor tyrosine kinases.

In some embodiments, the c-MET inhibitor is tivantinib. Tivantinib is also known as ARQ 197. Tivantinib is an orally bioavailable small molecule inhibitor of c-MET. Tivantinib binds to the c-MET protein and disrupts c-Met signal transduction pathways, which may induce cell death in tumor cells overexpressing c-MET protein or expressing constitutively activated c-Met protein.

Exemplary TGFb Inhibitors

In one embodiment, a combination described herein includes a transforming growth factor beta (TGF-β) inhibitor. In some embodiments, the combination is used to treat a cancer, e.g., a cancer described herein, e.g., a solid tumor (e.g., a brain cancer (e.g., a glioma), a melanoma, a kidney cancer (e.g., a renal cell carcinoma), a pleural malignant mesothelioma (e.g., a relapsed pleural malignant mesothelioma), or a breast cancer (e.g., a metastatic breast cancer)). In certain embodiments, the cancer is chosen from a colorectal cancer (e.g., a microsatelliate stable colorectal cancer (MSS CRC), a liver cancer (e.g., a hepatocellular carcinoma), a lung cancer (e.g., a non-small cell lung cancer (HSCLC)), a breast cancer (e.g., a triple negative breast cancer (TNBC)), a TGFb-expressing cancer, a pancreatic cancer, a prostate cancer, or a renal cancer (e.g., a renal cell carcinoma).

TGF-β belongs to a large family of structurally-related cytokines including, e.g., bone morphogenetic proteins (BMPs), growth and differentiation factors, activins and inhibins. In some embodiments, the TGF-β inhibitors described herein can bind and/or inhibit one or more isoforms of TGF-β (e.g., one, two, or all of TGF-β1, TGF-β2, or TGF-β3).

Under normal conditions, TGF-β maintains homeostasis and limits the growth of epithelial, endothelial, neuronal and hematopoietic cell lineages, e.g., through the induction of anti-proliferative and apoptotic responses. Canonical and non-canonical signaling pathways are involved in cellular responses to TGF-β. Activation of the TGF-β/Smad canonical pathway can mediate the anti-proliferative effects of TGF-β. The non-canonical TGF-β pathway can activate additional intra-cellular pathways, e.g., mitogen-activated protein kinases (MAPK), phosphatidylinositol 3 kinase/Protein Kinase B, Rho-like GTPases (Tian et al. *Cell Signal.* 2011; 23(6):951-62; Blobe et al. *N Engl J Med.* 2000; 342(18):1350-8), thus modulating epithelial to mesenchymal transition (EMT) and/or cell motility.

Alterations of TGF-β signaling pathway are associated with human diseases, e.g., cancers, cardio-vascular diseases, fibrosis, reproductive disorders, and wound healing. Without wishing to be bound by theory, it is believed that in some embodiments, the role of TGF-β in cancer is dependent on the disease setting (e.g., tumor stage and genetic alteration) and/or cellular context. For example, in late stages of cancer, TGF-β can modulate a cancer-related process, e.g., by promoting tumor growth (e.g., inducing EMT), blocking anti-tumor immune responses, increasing tumor-associated fibrosis, or enhancing angiogenesis (Wakefield and Hill *Nat Rev Cancer.* 2013; 13(5):328-41). In certain embodiments, a combination comprising a TGF-β inhibitor described herein is used to treat a cancer in a late stage, a metastatic cancer, or an advanced cancer.

Preclinical evidence indicates that TGF-β plays an important role in immune regulation (Wojtowicz-Praga *Invest New Drugs.* 2003; 21(1):21-32; Yang et al. *Trends Immunol.* 2010; 31(6):220-7). TGF-β can down-regulate the host-immune response via several mechanisms, e.g., shift of the T-helper balance toward Th2 immune phenotype; inhibition of anti-tumoral Th1 type response and M1-type macrophages; suppression of cytotoxic CD8+ T lymphocytes (CTL), NK lymphocytes and dendritic cell functions, generation of CD4+CD25+ T-regulatory cells; or promotion of M2-type macrophages with pro-tumoral activity mediated by secretion of immunosuppressive cytokines (e.g., IL10 or VEGF), pro-inflammatory cytokines (e.g., IL6, TNFα, or IL1) and generation of reactive oxygen species (ROS) with genotoxic activity (Yang et al. *Trends Immunol.* 2010; 31(6): 220-7; Truty and Urrutia *Pancreatology.* 2007; 7(5-6):423-35; Achyut et al *Gastroenterology.* 2011; 141(4):1167-78).

In some embodiments, the TGF-β inhibitor is fresolimumab (CAS Registry Number: 948564-73-6). Fresolimumab is also known as GC1008. Fresolimumab is a human monoclonal antibody that binds to and inhibits TGF-beta isoforms 1, 2 and 3.

The heavy chain of fresolimumab has the amino acid sequence of: QVQLVQSGAEVKKPGSSVKVSCK-ASGYTFSSNVISWVRQAPGQGLEWMGGVIPIVDI-ANYA QRFKGRVTITADESTSTTYMELSSLRSED-TAVYYCASTLGLVLDAMDYWGQGTLVTVSSAST KGPSVFPLAPCSRSTSESTAALGCLVKDYF- PEPVTVSWNSGALTSGVHTFPAVLQSSGLYSLS
SVVTVPSSSLGTKTYTCNVDHKPSNTKVDKRVESKY-
GPPCPSCPAPEFLGGPSVFLFPPKPKD TLMISRTPE-
VTCVVVDVSQEDPE-
VQFNWYVDGVEVHNAKTKPREEQFNSTYRVVSVLT
VLH
QDWLNGKEYKCKVSNKGLPSSIEKTISKAKGQPREP
QVYTLPPSQEEMTKNQVSLTCLVKGF YPSDIA-
VEWESNGQPENNYKTTPPVLDSDGSFFLY-
SRLTVDKSRWQEGNVFSCSVMHEALHN
HYTQKSLSLSLGK (SEQ ID NO: 238). The light chain of
fresolimumab has the amino acid sequence of:
ETVLTQSPGTLSLSPGERATLSCRASQSLGSSY-
LAWYQQKPGQAPRLLIYGASSRAPGIPDRFS
GSGSGTDFTLTISRLEPEDFAVYYCQQYAD-
SPITFGQGTRLEIKRTVAAPSVFIFPPSDEQLKSG
TASVVCLLNNFYPREAKVQWKVD-
NALQSGNSQESVTEQDSKDSTYSLSSTLTL-
SKADYEKH KVYACEVTHQGLSSPVTKSFNRGEC
(SEQ ID NO: 239).

Fresolimumab is disclosed, e.g., in WO 2006/086469,
U.S. Pat. Nos. 8,383,780, and 8,591,901.

In some embodiments, the TGF-β inhibitor is XOMA
089. XOMA 089 is also known as XPA.42.089. XOMA 089
is a fully human monoclonal antibody that specifically binds
and neutralizes TGF-beta 1 and 2 ligands.

The heavy chain variable region of XOMA 089 has the
amino acid sequence of: QVQLVQS-
GAEVKKPGSSVKVSCK-
ASGGTFSSYAISWVRQAPGQGLEWMGGIIPIFGTAN-
YAQ
KFQGRVTITADESTSTAYMELSSLRSEDTAVYYCAR-
GLWEVRALPSVYWGQGTLVTVSS (SEQ ID NO: 240)
(disclosed as SEQ ID NO: 6 in WO 2012/167143). The light
chain variable region of XOMA 089 has the amino acid
sequence of: SYELTQPPSVSVAPGQTARITCGANDIG-
SKSVHWYQQKAGQAPVLVVSEDIIRPSGIPERISGS
NSGNTATLTISRVEAGDEADYYCQVW-
DRDSDQYVFGTGTKVTVLG (SEQ ID NO: 241) (dis-
closed as SEQ ID NO: 8 in WO 2012/167143).

XOMA 089 binds with high affinity to the human TGF-β
isoforms. Generally, XOMA 089 binds with high affinity to
TGF-β1 and TGF-β2, and to a lesser extent to TGF-β3. In
Biacore assays, the $K_D$ of XOMA 089 on human TGF-β is
14.6 pM for TGF-β1, 67.3 pM for TGF-β2, and 948 pM for
TGF-β3. Given the high affinity binding to all three TGF-β
isoforms, in certain embodiments, XOMA 089 is expected to
bind to TGF-β1, 2 and 3 at a dose of XOMA 089 as
described herein. XOMA 089 cross-reacts with rodent and
cynomolgus monkey TGF-β and shows functional activity
in vitro and in vivo, making rodent and cynomolgus monkey
relevant species for toxicology studies.

In certain embodiments, the combination includes an
inhibitor of PD-1 (e.g., an anti-PD-1 antibody molecule
described herein) and a TGF-β inhibitor (e.g., a TGF-β
inhibitor described herein).

Without wishing to be bound by theory, it is believed that
in some embodiments, resistance to PD-1 immunotherapy is
associated with the presence of a transcriptional signature
which includes, e.g., genes connected to TGF-β signaling
and TGF-β-dependent processes, e.g., wound healing or
angiogenesis (Hugo et al. *Cell.* 2016; 165(1):35-44). In
some embodiments, TGF-β blockade extends the therapeu-
tic window of a therapy that inhibits the PD-1/PD-L1 axis.
TGF-β inhibitors can affect the clinical benefits of PD-1
immunotherapy, e.g., by modulating tumor microenviron-
ment, e.g., vasculogenesis, fibrosis, or factors that affect the
recruitment of effector T cells (Yang et al. *Trends Immunol.*

2010; 31(6):220-7; Wakefield and Hill *Nat Rev Cancer.*
2013; 13(5):328-41; Truty and Urrutia *Pancreatology.* 2007;
7(5-6):423-35).

Without wishing to be bound by theory, it is also believed
that in some embodiments, a number of elements of the
anti-tumor immunity cycle express both PD-1 and TGF-β
receptors, and PD-1 and TGF-β receptors are likely to
propagate non-redundant cellular signals. For example, in
mouse models of autochthonous prostate cancer, the use of
either a dominant-negative form of TGFBRII, or abrogation
of TGF-β production in T cells delays tumor growth
(Donkor et al. *Immunity.* 2011; 35(1):123-34; Diener et al.
*Lab Invest.* 2009; 89(2):142-51). Studies in the transgenic
adenocarcinoma of the mouse prostate (TRAMP) mice
showed that blocking TGF-β signaling in adoptively trans-
ferred T cells increases their persistence and antitumor
activity (Chou et al. *J Immunol.* 2012; 189(8):3936-46). The
antitumor activity of the transferred T cells may decrease
over time, partially due to PD-1 upregulation in tumor-
infiltrating lymphocytes, supporting a combination of PD-1
and TGF-β inhibition as described herein. The use of neu-
tralizing antibodies against either PD-1 or TGF-β can also
affect Tregs, given their high expression levels of PD-1 and
their responsiveness to TGF-β stimulation (Riella et al. *Am
J Transplant.* 2012; 12(10):2575-87), supporting a combi-
nation of PD-1 and TGF-β inhibition to treat cancer, e.g., by
enhancing the modulation of Tregs differentiation and func-
tion.

Without wishing to be bound by theory, it is believed that
cancers can use TGF-β to escape immune surveillance to
facilitate tumor growth and metastatic progression. For
example, in certain advanced cancers, high levels of TGF-β
are associated with tumor aggressiveness and poor progno-
sis, and TGF-β pathway can promote one or more of cancer
cell motility, invasion, EMT, or a stem cell phenotype.
Immune regulation mediated by cancer cells and leukocyte
populations (e.g., through a variety of cell-expressed or
secreted molecules, e.g., IL-10 or TGF-β) may limit the
response to checkpoint inhibitors as monotherapy in certain
patients. In certain embodiments, a combined inhibition of
TGF-β with a checkpoint inhibitor (e.g., an inhibitor of PD-1
described herein) is used to treat a cancer that does not
respond, or responds poorly, to a checkpoint inhibitor (e.g.,
anti-PD-1) monotherapy, e.g., a pancreatic cancer or a
colorectal cancer (e.g., a microsatellite stable colorectal
cancer (MSS-CRC)). In other embodiments, a combined
inhibition of TGF-β with a checkpoint inhibitor (e.g., an
inhibitor of PD-1 described herein) is used to treat a cancer
that shows a high level of effector T cell infiltration, e.g., a
lung cancer (e.g., a non-small cell lung cancer), a breast
cancer (e.g., a triple negative breast cancer), a liver cancer
(e.g., a hepatocellular carcinoma), a prostate cancer, or a
renal cancer (e.g., a clear cell renal cell carcinoma). In some
embodiments, the combination of a TGF-β inhibitor and an
inhibitor of PD-1 results in a synergistic effect.

In one embodiment, the TGF-β inhibitor, XOMA 089, or
a compound disclosed in PCT Publication No. WO 2012/
167143, is administered at a dose between 0.1 mg/kg and 20
mg/kg, e.g., between 0.1 mg/kg and 15 mg/kg, between 0.1
mg/kg and 12 mg/kg, between 0.3 mg/kg and 6 mg/kg,
between 1 mg/kg and 3 mg/kg, between 0.1 mg/kg and 1
mg/kg, between 0.1 mg/kg and 0.5 mg/kg, between 0.1
mg/kg and 0.3 mg/kg, between 0.3 mg/kg and 3 mg/kg,
between 0.3 mg/kg and 1 mg/kg, between 3 mg/kg and 6
mg/kg, or between 6 mg/kg and 12 mg/kg, e.g., at a dose of
about 0.1 mg/kg, 0.3 mg/kg, 0.5 mg/kg, 1 mg/kg, 3 mg/kg,
6 mg/kg, 12 mg/kg, or 15 mg/kg, e.g., once every week, once every two weeks, once every three weeks, once every four weeks, or once every six weeks.

In one embodiment, the TGF-β inhibitor, XOMA 089, or a compound disclosed in PCT Publication No. WO 2012/167143, is administered at a dose between 0.1 mg/kg and 15 mg/kg (e.g., between 0.3 mg/kg and 12 mg/kg or between 1 mg/kg and 6 mg, e.g., about 0.1 mg/kg, 0.3 mg/kg, 1 mg/kg, 3 mg/kg, 6 mg/kg, 12 mg/kg, or 15 mg/kg), e.g., once every three weeks. For example, the TGF-β inhibitor, XOMA 089, or a compound disclosed in PCT Publication No. WO 2012/167143, can be administered at a dose between 0.1 mg/kg and 1 mg/kg (e.g., between 0.1 mg/kg and 1 mg/kg, e.g., 0.3 mg/kg), e.g., once every three weeks. In one embodiment, the TGF-β inhibitor, XOMA 089, or a compound disclosed in PCT Publication No. WO 2012/167143, is administered intravenously.

In one embodiment, the combination includes a TGF-β inhibitor, XOMA 089, or a compound disclosed in PCT Publication No. WO 2012/167143, and an inhibitor of PD-1 (e.g., an anti-PD-1 antibody described herein).

In one embodiment, the TGF-β inhibitor, XOMA 089, or a compound disclosed in PCT Publication No. WO 2012/167143, is administered at a dose between 0.1 mg/kg and 15 mg/kg (e.g., between 0.3 mg/kg and 12 mg/kg or between 1 mg/kg and 6 mg, e.g., about 0.1 mg/kg, 0.3 mg/kg, 1 mg/kg, 3 mg/kg, 6 mg/kg, 12 mg/kg, or 15 mg/kg), e.g., once every three weeks, e.g., intravenously, and the inhibitor of PD-1 (e.g., the anti-PD-1 antibody molecule) is administered at a dose between 50 mg and 500 mg (e.g., between 100 mg and 400 mg, e.g., at a dose of about 100 mg, 200 mg, 300 mg, or 400 mg), e.g., once every 3 weeks or once every 4 weeks, e.g., by intravenous infusion. In some embodiments, the inhibitor of PD-1 (e.g., the anti-PD-1 antibody molecule) is administered at a dose between 100 mg and 300 mg (e.g., at a dose of about 100 mg, 200 mg, or 300 mg), e.g., once every 3 weeks, e.g., by intravenous infusion.

In some embodiments, the TGF-β inhibitor, XOMA 089, or a compound disclosed in PCT Publication No. WO 2012/167143, is administered at a dose of about 0.1 mg/kg or 0.3 mg/kg, e.g., once every 3 weeks, e.g., by intravenous infusion, and the inhibitor of PD-1 (e.g., the anti-PD-1 antibody molecule) is administered at a dose of about 100 mg, e.g., once every 3 weeks, e.g., by intravenous infusion. In some embodiments, the TGF-β inhibitor, XOMA 089, or a compound disclosed in PCT Publication No. WO 2012/167143, is administered at a dose of about 0.3 mg/kg, e.g., once every 3 weeks, e.g., by intravenous infusion, and the inhibitor of PD-1 (e.g., the anti-PD-1 antibody molecule) is administered at a dose of about 100 mg or 300 mg, e.g., once every 3 weeks, e.g., by intravenous infusion. In some embodiments, the TGF-β inhibitor, XOMA 089, or a compound disclosed in PCT Publication No. WO 2012/167143, is administered at a dose of about 1 mg/kg, 3 mg/kg, 6 mg/kg, 12 mg/kg, or 15 mg/kg, e.g., once every 3 weeks, e.g., by intravenous infusion, and the inhibitor of PD-1 (e.g., the anti-PD-1 antibody molecule) is administered at a dose of about 300 mg, e.g., once every 3 weeks, e.g., by intravenous infusion.

In some embodiments, the TGF-β inhibitor, XOMA 089, or a compound disclosed in PCT Publication No. WO 2012/167143, is administered at a dose between 0.1 mg and 0.2 mg (e.g., about 0.1 mg/kg), e.g., once every three weeks, e.g., by intravenous infusion, and the inhibitor of PD-1 (e.g., the anti-PD-1 antibody molecule) is administered at a dose between 50 mg and 200 mg (e.g., about 100 mg), e.g., once every three weeks, e.g., by intravenous infusion.

In some embodiments, the TGF-β inhibitor, XOMA 089, or a compound disclosed in PCT Publication No. WO 2012/167143, is administered at a dose between 0.2 mg and 0.5 mg (e.g., about 0.3 mg/kg), e.g., once every three weeks, e.g., by intravenous infusion, and the inhibitor of PD-1 (e.g., the anti-PD-1 antibody molecule) is administered at a dose between 50 mg and 200 mg (e.g., about 100 mg), e.g., once every three weeks, e.g., by intravenous infusion.

In some embodiments, the TGF-β inhibitor, XOMA 089, or a compound disclosed in PCT Publication No. WO 2012/167143, is administered at a dose between 0.2 mg and 0.5 mg (e.g., about 0.3 mg/kg), e.g., once every three weeks, e.g., by intravenous infusion, and the inhibitor of PD-1 (e.g., the anti-PD-1 antibody molecule) is administered at a between 200 mg and 400 mg (e.g., about 300 mg), e.g., once every three weeks, e.g., by intravenous infusion.

In some embodiments, the TGF-β inhibitor, XOMA 089, or a compound disclosed in PCT Publication No. WO 2012/167143, is administered at a dose between 0.5 mg and 2 mg (e.g., about 1 mg/kg), e.g., once every three weeks, e.g., by intravenous infusion, and the inhibitor of PD-1 (e.g., the anti-PD-1 antibody molecule) is administered at a between 200 mg and 400 mg (e.g., about 300 mg), e.g., once every three weeks, e.g., by intravenous infusion.

In some embodiments, the TGF-β inhibitor, XOMA 089, or a compound disclosed in PCT Publication No. WO 2012/167143, is administered at a dose between 2 mg and 5 mg (e.g., about 3 mg/kg), e.g., once every three weeks, e.g., by intravenous infusion, and the inhibitor of PD-1 (e.g., the anti-PD-1 antibody molecule) is administered at a between 200 mg and 400 mg (e.g., about 300 mg), e.g., once every three weeks, e.g., by intravenous infusion.

In some embodiments, the TGF-β inhibitor, XOMA 089, or a compound disclosed in PCT Publication No. WO 2012/167143, is administered at a dose between 5 mg and 10 mg (e.g., about 6 mg/kg), e.g., once every three weeks, e.g., by intravenous infusion, and the inhibitor of PD-1 (e.g., the anti-PD-1 antibody molecule) is administered at a between 200 mg and 400 mg (e.g., about 300 mg), e.g., once every three weeks, e.g., by intravenous infusion.

In some embodiments, the TGF-β inhibitor, XOMA 089, or a compound disclosed in PCT Publication No. WO 2012/167143, is administered at a dose between 10 mg and 15 mg (e.g., about 12 mg/kg), e.g., once every three weeks, e.g., by intravenous infusion, and the inhibitor of PD-1 (e.g., the anti-PD-1 antibody molecule) is administered at a between 200 mg and 400 mg (e.g., about 300 mg), e.g., once every three weeks, e.g., by intravenous infusion.

In some embodiments, the TGF-β inhibitor, XOMA 089, or a compound disclosed in PCT Publication No. WO 2012/167143, is administered at a dose between 10 mg and 20 mg (e.g., about 15 mg/kg), e.g., once every three weeks, e.g., by intravenous infusion, and the inhibitor of PD-1 (e.g., the anti-PD-1 antibody molecule) is administered at a between 200 mg and 400 mg (e.g., about 300 mg), e.g., once every three weeks, e.g., by intravenous infusion.

In some embodiments, the TGF-β inhibitor, XOMA 089, or a compound disclosed in PCT Publication No. WO 2012/167143, is administered before the inhibitor of PD-1 (e.g., the anti-PD-1 antibody molecule) is administered. In other embodiments, the TGF-β inhibitor, XOMA 089, or a compound disclosed in PCT Publication No. WO 2012/167143, is administered after the inhibitor of PD-1 (e.g., the anti-PD-1 antibody molecule) is administered. In certain embodiments, the TGF-β inhibitor, XOMA 089, or a compound disclosed in PCT Publication No. WO 2012/167143, and the inhibitor of PD-1 (e.g., the anti-PD-1 antibody molecule), are administered separately with at least a 30-minute (e.g., at least 1, 1.5, or 2 hours) break between the two administrations.

In one embodiment, the TGF-β inhibitor, XOMA 089, or a compound disclosed in PCT Publication No. WO 2012/167143, is administered in combination with an inhibitor of PD-1 (e.g., an anti-PD-1 antibody molecule) to treat a pancreatic cancer, a colorectal cancer (e.g., a microsatellite stable colorectal cancer (MSS-CRC)), a lung cancer (e.g., a non-small cell lung cancer), a breast cancer (e.g., a triple negative breast cancer), a liver cancer (e.g., a hepatocellular carcinoma), a prostate cancer, or a renal cancer (e.g., a clear cell renal cell carcinoma).

Exemplary IDO/TDO Inhibitors

In one embodiment, a combination described herein includes an inhibitor of indoleamine 2,3-dioxygenase (IDO) and/or tryptophan 2,3-dioxygenase (TDO). In some embodiments, the combination is used to treat a cancer, e.g., a cancer described herein, e.g., a solid tumor (e.g., melanoma, non-small cell lung cancer, colon cancer, squamous cell head and neck cancer, ovarian cancer, peritoneal cancer, fallopian tube cancer, breast cancer (e.g., metastatic or HER2-negative breast cancer)), e.g., a hematologic malignancy (e.g., a lymphoma, e.g., a non-Hodgkin's lymphoma or a Hodgkin's lymphoma (e.g., a diffuse large B-cell lymphoma (DLBCL))).

In some embodiments, the IDO/TDO inhibitor is chosen from (4E)-4-[(3-chloro-4-fluoroanilino)-nitrosomethylidene]-1,2,5-oxadiazol-3-amine (also known as INCB24360), indoximod (1-methyl-D-tryptophan), or α-cyclohexyl-5H-Imidazo[5,1-a]isoindole-5-ethanol (also known as NLG919).

In some embodiments, the IDO/TDO inhibitor is epacadostat (CAS Registry Number: 1204669-58-8). Epacadostat is also known as INCB24360 or INCB024360 (Incyte). Epacadostat is a potent and selective indoleamine 2,3-dioxygenase (IDO1) inhibitor with IC50 of 10 nM, highly selective over other related enzymes such as IDO2 or tryptophan 2,3-dioxygenase (TDO).

In some embodiments, the IDO/TDO inhibitor is indoximod (New Link Genetics). Indoximod, the D isomer of 1-methyl-tryptophan, is an orally administered small-molecule indoleamine 2,3-dioxygenase (IDO) pathway inhibitor that disrupts the mechanisms by which tumors evade immune-mediated destruction.

In some embodiments, the IDO/TDO inhibitor is NLG919 (New Link Genetics). NLG919 is a potent IDO (indoleamine-(2,3)-dioxygenase) pathway inhibitor with Ki/EC50 of 7 nM/75 nM in cell-free assays.

In some embodiments, the IDO/TDO inhibitor is F001287 (Flexus/BMS). F001287 is a small molecule inhibitor of indoleamine 2,3-dioxygenase 1 (IDO1).

Exemplary A2AR Antagonists

In one embodiment, a combination described herein includes an adenosine Ata receptor (A2aR) antagonist (e.g., an inhibitor of A2aR pathway, e.g., an adenosine inhibitor, e.g., an inhibitor of A2aR or CD-73). In some embodiments, the combination is used to treat a cancer, e.g., a cancer described herein. In certain embodiments, the cancer is a lung cancer, e.g., a non-small cell lung cancer (NSCLC).

In some embodiments, the A2aR antagonist is istradefylline (CAS Registry Number: 155270-99-8). Istradefylline is also known as KW-6002 or 8-[(E)-2-(3,4-dimethoxyphenyl)vinyl]-1,3-diethyl-7-methyl-3,7-dihydro-1H-purine-2,6-dione. Istradefylline is disclosed, e.g., in LeWitt et al. (2008) *Annals of Neurology* 63 (3): 295-302).

In some embodiments, the A2aR antagonist is tozadenant (Biotie). Tozadenant is also known as SYN115 or 4-hydroxy-N-(4-methoxy-7-morpholin-4-yl-1,3-benzothiazol-2-yl)-4-methylpiperidine-1-carboxamide. Tozadenant blocks the effect of endogenous adenosine at the Ata receptors, resulting in the potentiation of the effect of dopamine at the D2 receptor and inhibition of the effect of glutamate at the mGluR5 receptor. In some embodiments, the A2aR antagonist is preladenant (CAS Registry Number: 377727-87-2). Preladenant is also known as SCH 420814 or 2-(2-Furanyl)-7-[2-[4-[4-(2-methoxyethoxy)phenyl]-1-piperazinyl]ethyl]7H-pyrazolo[4,3-e][1,2,4]triazolo[1,5-c]pyrimidine-5-amine Preladenant was developed as a drug that acted as a potent and selective antagonist at the adenosine A2A receptor.

In some embodiments, the A2aR antagonist is vipadenan. Vipadenan is also known as BIIB014, V2006, or 3-[(4-amino-3-methylphenyl)methyl]-7-(furan-2-yl)triazolo[4,5-d]pyrimidin-5-amine. In some embodiments, the A2aR antagonist is PBF-509 (Palobiofarma). In some embodiments, the A2aR antagonist, e.g., PBF-509 is administered at a daily dose of about 80 mg, 160 mg, or 240 mg.

Other exemplary A2aR antagonists include, e.g., ATL-444, MSX-3, SCH-58261, SCH-412,348, SCH-442,416, VER-6623, VER-6947, VER-7835, CGS-15943, or ZM-241,385.

In some embodiments, the A2aR antagonist is an A2aR pathway antagonist (e.g., a CD-73 inhibitor, e.g., an anti-CD73 antibody) is MEDI9447. MEDI9447 is a monoclonal antibody specific for CD73. Targeting the extracellular production of adenosine by CD73 may reduce the immunosuppressive effects of adenosine. MEDI9447 was reported to have a range of activities, e.g., inhibition of CD73 ecto-nucleotidase activity, relief from AMP-mediated lymphocyte suppression, and inhibition of syngeneic tumor growth. MEDI9447 can drive changes in both myeloid and lymphoid infiltrating leukocyte populations within the tumor microenvironment. These changes include, e.g., increases in CD8 effector cells and activated macrophages, as well as a reduction in the proportions of myeloid-derived suppressor cells (MDSC) and regulatory T lymphocytes.

Exemplary Oncolytic Viruses

In some embodiments, a combination as described herein includes an oncolytic virus. In embodiments, oncolytic viruses are capable of selectively replicating in and triggering the death of or slowing the growth of a cancer cell. In some cases, oncolytic viruses have no effect or a minimal effect on non-cancer cells. In some embodiments, the combination is used to treat a cancer, e.g., a cancer described herein. In certain embodiments, the cancer is a brain cancer, e.g., a glioblastoma (GBM). An oncolytic virus includes, but is not limited to, an oncolytic adenovirus, oncolytic Herpes Simplex Viruses, oncolytic retrovirus, oncolytic parvovirus, oncolytic vaccinia virus, oncolytic Sindbis virus, oncolytic influenza virus, or oncolytic RNA virus (e.g., oncolytic reovirus, oncolytic Newcastle Disease Virus (NDV), oncolytic measles virus, or oncolytic vesicular stomatitis virus (VSV)).

In some embodiments, the oncolytic virus is a recombinant herpes virus, e.g., a herpes simplex virus (HSV) that comprises a gene encoding GM-CSF. Without wishing to be bound by theory, it is believed that in some embodiments, insertion of GM-CSF gene can enhance an anti-tumor immune response, e.g., by recruiting and stimulating dendritic cells to tumor site. Other modifications can be made to the virus, e.g., to attenuate the virus and/or to increase selectivity for cancer cells. In some embodiments, the recombinant herpes virus lacks a functional ICP34.5 gene, a functional ICP47 gene, or both. In some embodiments, deletion of ICP34.5 gene prevents HSV infection of non-tumor cells or provides tumor-selective replication. In some embodiments, deletion of ICP47 gene allows for or increases antigen presentation. Deletion of ICP47 can cause increased expression of the HSV US11 gene and allows US11 to be expressed as an immediate early and not a late gene. This may further enhance the degree of viral replication and oncolysis of tumor cells. In certain embodiments, HSV-1 strain JS1 is used, e.g., to improve tumor cell killing ability compared with other HSV-1 strains. In certain embodiments, the recombinant herpes virus is talimogene laherparepvec (T-VEC). T-VEC is based on herpes simplex virus type 1 (HSV-1) modified to include a gene that codes for human GM-CSF. Talimogene laherparepvec is described, e.g., in International Application Publication No. WO 2014/036412. In certain embodiments, the combination is used to treat a melanoma, a head and neck cancer, a pancreatic cancer, a breast cancer, a colorectal cancer, or a renal cancer (e.g., a renal cell carcinoma), In some embodiments, the oncolytic virus is recombinant herpes virus, e.g., a neuroattenuated, replication-restricted herpes simplex virus type 1 (HSV-1). In some embodiments, the recombinant herpes virus is ICP34.5 gene-deleted. In some embodiments, the recombinant herpes virus is not capable of replication in non-divising cells. In some embodiments, the recombinant herpes virus is engineered from wild-type strain 17. In certain embodiments, the recombinant herpes virus is HSV1716 (SEPREHVIR®). Without wishing to be bound by theory, it is believed that in some embodiments, upon intratumoral injection, oncolytic HSV1716 replicates in, and lyses dividing cells such as tumor cells. HSV1716 is described, e.g., in International Application Publication No. WO 2003/068809. In certain embodiments, the combination is used to treat a glioma (e.g., a high grade glioma), a head and neck cancer (e.g., a squamous cell carcinoma of head and neck), a melanoma, a liver cancer (e.g., a hepatocellular carcinoma), a pleural mesothelioma, or a non-CNS pediatric cancer.

In some embodiments, the oncolytic virus is a vaccinia virus. In some embodiments, the vaccinia virus includes a gene that activate cytotoxic T cell production (e.g., a TIR-domain-containing adapter-inducing interferon-β (TRIF) gene), a gene that decreases immune blockade (e.g., a hydroxyprostaglandin dehydrogenase 15-(NAD) (HPGD) gene), or both. In some embodiments, the surface of the vaccinia virus is deglycosylated. In some embodiments, the vaccinia virus has one or more (e.g., two, three or all) of the properties chosen from cancer lysis, immune adaptation, T cell stimulation, or removal of immune inhibition. In some embodiments, the vaccinia virus is engineered from strain Western Reserve. In certain embodiments, the oncolytic virus is WO-12 (Western Oncolytics Ltd., US). In some embodiments, the combination is used to treat a solid tumor.

In some embodiments, the oncolytic virus is a recombinant poliovirus, e.g., a live attenuated, nonpathogenic oncolytic virus in which the internal ribosomal entry site (IRES) is replaced with a heterologous IRES, e.g., to reduce or avoid neurovirulence. In some embodiments, the heterologous IRES is an IRES from human rhinovirus type 2 (HRV2). In some embodiments, the recombinant poliovirus is oncolytic poliovirus PVS-RIPO (also known as PVSRIPO). PVS-RIPO is a genetically modified nonpathogenic version of the oral poliovirus Sabin type 1 where the internal ribosomal entry site (IRES) on the poliovirus is replaced with the IRES from human rhinovirus type 2

(HRV2). Without wishing to be bound by theory, it is believed that in some embodiments, PVS-RIPO preferentially propagates in susceptible, nonneuronal cells (e.g., glioblastoma multiforme (GBM)) due to the heterologous HRV2 in this recombinant virus. Upon intratumoral administration of PVS-RIPO, the poliovirus can be selectively taken up by and replicates in tumor cells expressing CD155 (poliovirus receptor, PVR or NECL5) eventually causing tumor cell lysis. CD155, an oncofetal cell adhesion molecule and tumor antigen, is ectopically expressed in certain cancers, such as GMB, and plays a role in tumor cell migration, invasion, and metastasis. PVS-RIPO is described, e.g., in International Application Publication No. WO 2014/081937. In some embodiments, the combination is used to treat a solid tumor, e.g., a solid tumor expressing CD155. In other embodiments, the combination is used to treat a brain cancer, e.g., a glioblastoma.

In some embodiments, the oncolytic virus is a virus, e.g., recombinant oncolytic virus, described in US2010/0178684 A1, which is incorporated herein by reference in its entirety. In some embodiments, a recombinant oncolytic virus comprises, or comprises a nucleic acid sequence (e.g., heterologous nucleic acid sequence) encoding, an inhibitor of an immune or inflammatory response, e.g., as described in US2010/0178684 A1, incorporated herein by reference in its entirety. In embodiments, the recombinant oncolytic virus, e.g., oncolytic NDV, comprises, or comprises a nucleic acid sequence encoding, a pro-apoptotic protein (e.g., apoptin), a cytokine (e.g., GM-CSF, CSF, interferon-gamma, interleukin-2 (IL-2), tumor necrosis factor-alpha), an immunoglobulin (e.g., an antibody against ED-B fibronectin), a tumor associated antigen, a bispecific adapter protein (e.g., bispecific antibody or antibody fragment directed against NDV HN protein and a T cell co-stimulatory receptor, such as CD3 or CD28; or a fusion protein between human IL-2 and single chain antibody directed against NDV HN protein). See, e.g., Zamarin et al. Future Microbiol. 7.3(2012): 347-67, incorporated herein by reference in its entirety. In some embodiments, the oncolytic virus is a chimeric oncolytic NDV described in U.S. Pat. No. 8,591,881 B2, US 2012/0122185 A1, or US 2014/0271677 A1, each of which is incorporated herein by reference in their entireties.

In some embodiments, the oncolytic virus comprises a conditionally replicative adenovirus (CRAd), which is designed to replicate exclusively in cancer cells. See, e.g., Alemany et al. *Nature Biotechnol.* 18(2000):723-27. In some embodiments, an oncolytic adenovirus comprises one described in Table 1 on page 725 of Alemany et al., incorporated herein by reference in its entirety.

Exemplary oncolytic viruses include but are not limited to the following:

Group B Oncolytic Adenovirus (ColoAd1) (PsiOxus Therapeutics Ltd.) (see, e.g., Clinical Trial Identifier: NCT02053220);

ONCOS-102 (previously called CGTG-102), which is an adenovirus comprising granulocyte-macrophage colony stimulating factor (GM-CSF) (Oncos Therapeutics) (see, e.g., Clinical Trial Identifier: NCT01598129);

VCN-01, which is a genetically modified oncolytic human adenovirus encoding human PH20 hyaluronidase (VCN Biosciences, S.L.) (see, e.g., Clinical Trial Identifiers: NCT02045602 and NCT02045589);

Conditionally Replicative Adenovirus ICOVIR-5, which is a virus derived from wild-type human adenovirus serotype 5 (Had5) that has been modified to selectively replicate in cancer cells with a deregulated retinoblastoma/E2F pathway (Institut Catala d'Oncologia) (see, e.g., Clinical Trial Identifier: NCT01864759);

Celyvir, which comprises bone marrow-derived autologous mesenchymal stem cells (MSCs) infected with ICOVIR5, an oncolytic adenovirus (Hospital Infantil Universitario Niño Jesús, Madrid, Spain/Ramon Alemany) (see, e.g., Clinical Trial Identifier: NCT01844661);

CG0070, which is a conditionally replicating oncolytic serotype 5 adenovirus (Ad5) in which human E2F-1 promoter drives expression of the essential E1a viral genes, thereby restricting viral replication and cytotoxicity to Rb pathway-defective tumor cells (Cold Genesys, Inc.) (see, e.g., Clinical Trial Identifier: NCT02143804); or DNX-2401 (formerly named Delta-24-RGD), which is an adenovirus that has been engineered to replicate selectively in retinoblastoma (Rb)-pathway deficient cells and to infect cells that express certain RGD-binding integrins more efficiently (Clinica Universidad de Navarra, Universidad de Navarra/DNAtrix, Inc.) (see, e.g., Clinical Trial Identifier: NCT01956734).

In some embodiments, an oncolytic virus described herein is administering by injection, e.g., subcutaneous, intra-arterial, intravenous, intramuscular, intrathecal, or intraperitoneal injection. In embodiments, an oncolytic virus described herein is administered intratumorally, transdermally, transmucosally, orally, intranasally, or via pulmonary administration.

Exemplary Vaccines, e.g., Scaffold Vaccines

In one embodiment, a combination described herein includes a vaccine, e.g., a scaffold vaccine. In some embodiments, the combination is used to treat a cancer, e.g., a cancer described herein.

Cancer vaccines are disclosed, e.g., in PCT Publication Nos. WO 2007/070660 and WO 2012/167230, EP 1960009 B1, U.S. Pat. Nos. 8,067,237 and 8,932,583, and U.S. Publication No. US 2011/0020216. The components that can be used within cancer vaccines (e.g., implantable scaffold materials) are disclosed, e.g., in PCT Publication Nos. WO 2009/102465 and WO 2013/106852. Methods that can be used for administration of cancer vaccines are disclosed, e.g., in PCT Publication Nos. WO 2013/158673, WO 2012/048165, and WO 2012/149358.

In some embodiments, the cancer vaccine includes a macroporous scaffold comprising (i) cells or a cell recruitment composition, and (ii) a deployment signal capable of inducing or promoting migration of cells, and (iii) a bioactive composition coated or seeded onto/into the scaffold, which causes cells recruited into the scaffold be modified. Migration of the modified cells can be promoted by the open, interconnected macropores and the deployment signal.

In some embodiments, the cancer vaccine induces an endogenous immune response to a cancer target via administration of a porous scaffold bearing a recruitment composition and a target antigen composition, wherein an endogenous antigen presenting cell is recruited into the scaffold to encounter antigen and where said cell resides until a deployment signal induces egress to a lymph node tissue outside the scaffold, thereby stimulating an endogenous immune response to said cancer target.

In some embodiments, the cancer vaccine is used to remove a target cell from a mammal using a scaffold composition.

In some embodiments, an in situ cancer vaccine is generated via recruitment of cancer cells to an implanted scaffold and destruction of the cells using a cytotoxic agent.

In some embodiments, a cytosine-guanosine oligonucleotide (CpG-ODN) is used as a component of a scaffold, which can effectively reprogram and deploy dendritic cells recruited to the scaffold, and generate an effective anti-tumor response.

In some embodiments, polyinosine-polycytidylic acid (poly I:C) and/or CpG ODN are used to exert a synergistic effect on tumor inhibition.

In some embodiments, porous rods comprising an immune cell recruitment compound (e.g. GM-CSF) and an immune cell activation compound (e.g. CpG ODN), and optionally comprising an antigen such as a tumor lysate, are used, e.g., to elicit an immune response to a vaccine antigen. In some embodiments, pores that facilitate recruitment or release of cells are formed in situ within hydrogels following hydrogel injection. In some embodiments, injectable shape memory porous hydrogel polymer is used for administration.

In other embodiments, the combinations disclosed herein include a cancer or tumor vaccine. Non-limiting examples of tumor vaccines that can be used include peptides of melanoma antigens, such as peptides of gp100, MAGE antigens, Trp-2, MART1 and/or tyrosinase, tumor cells transfected to express the cytokine GM-CSF, DNA-based vaccines, RNA-based vaccines, and viral transduction-based vaccines. The cancer vaccine may be prophylactic or therapeutic.

Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, Cancer: Principles and Practice of Oncology. Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) Proc. Natl. Acad. Sci. U.S.A. 90: 3539-43).

The combinations disclosed herein, e.g., PD-1 blockade, can be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al. (1994) Science 266: 2011-2013). (These somatic tissues may be protected from immune attack by various means). Tumor antigen may also be "neo-antigens" expressed in cancer cells because of somatic mutations that alter protein sequence or create fusion proteins between two unrelated sequences (e.g., bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV and HCV), Kaposi's Herpes Sarcoma Virus (KHSV), and Epstein-Barr virus (EBV). Another form of tumor specific antigen which may be used in conjunction with PD-1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) *Science* 269: 1585-1588; Tamura, Y. et al. (1997) *Science* 278:117-120).

Dendritic cells (DC) are potent antigen presenting cells that can be used to prime antigen-specific responses. DC's can be produced ex vivo and loaded with various protein and peptide antigens as well as tumor cell extracts (Nestle, F. et al. (1998) *Nature Medicine* 4: 328-332). DCs may also be transduced by genetic means to express these tumor antigens as well. DCs have also been fused directly to tumor cells for the purposes of immunization (Kugler, A. et al. (2000) *Nature Medicine* 6:332-336). As a method of vaccination, DC immunization may be effectively combined with other agent, e.g., PD-1 blockade, to activate more potent anti-tumor responses.

Exemplary Bispecific T-Cell Engagers

In one embodiment, a combination described herein includes a bispecific T-cell engager. In some embodiments, the combination is used to treat a cancer, e.g., a cancer described herein, e.g., a solid tumor (e.g., a gastrointestinal cancer, a melanoma, or a lung cancer) or a hematologic malignancy (e.g., a lymphoma (e.g., non-Hodgkin's lymphoma) or a leukemia (e.g., an acute lymphoblastic leukemia).

Bi-specific T-cell engagers (BITE®) are a class of artificial bispecific monoclonal antibodies that can direct a host's immune system, e.g., the T cells' cytotoxic activity, against cancer cells. Bi-specific T-cell engagers can form a link between T cells and tumor cells, which causes T cells to exert cytotoxic activity on tumor cells by producing proteins like perforin and granzymes, independently of the presence of MHC I or co-stimulatory molecules. These proteins enter tumor cells and initiate the cell's apoptosis. This action mimics physiological processes observed during T cell attacks against tumor cells.

In some embodiments, the bi-specific T-cell engager is a fusion protein comprising two single-chain variable fragments (scFvs) of different antibodies. In some embodiments, one of the scFvs binds to T cells, e.g., via the CD3 receptor, and the other to a tumor cell, e.g., via a tumor specific molecule.

In some embodiments, the bi-specific T-cell engager is a bispecific antibody molecule of NKG2A and CD138, or a bispecific antibody molecule of CD3 and TCR. In some embodiments, the bispecific T-cell engager is a bispecific antibody molecule that binds to CD3 and a tumor antigen (e.g., EGFR, PSCA, PSMA, EpCAM, HER2 among others).

In some embodiments, the bi-specific T-cell engager is blinatumomab (CAS Registry Number: 853426-35-4). Blinatumomab is also known as MT103. Blinatumomab specifically targets a CD3 site for T cells and a CD19 site for B cells.

In some embodiments, the bi-specific T-cell engager is MT110. MT110 is a single-chain antibody that targets EpCAM and CD3. MT110 is disclosed, e.g., in Amann et al. *J Immunother.* 2009; 32(5):452-64.

In some embodiments, the bi-specific T-cell engager targets melanoma-associated chondroitin sulfate proteoglycan (MCSP). In some embodiments, the bi-specific T-cell engager targets CD33. In some embodiments the bi-specific T-cell engager comprises trastuzumab (targeting HER2/neu), cetuximab, or panitumumab (both targeting the EGF receptor), a functional fragment thereof. In some embodiments, the bi-specific T-cell engager targets CD66e and EphA2.

Exemplary GITR Agonist

In one embodiment, a combination described herein includes a GITR agonist. In some embodiments, the combination is used to treat a cancer, e.g., a cancer described herein, e.g., a solid tumor or a hematologic malignancy. In some embodiments, the cancer is chosen from a forkhead box P3 (FoxP3)-expressing cancer, a head and neck cancer (e.g., a head and neck squamous cell carcinoma (HNSCC)), or a lung cancer (e.g., a non-small cell lung cancer (NSCLC)).

In certain embodiments, the GITR agonist is an anti-GITR antibody molecule. Exemplary anti-GITR antibody molecules are described, e.g., in International Application Publication No. WO 2016/057846 (e.g., Mab7). In some embodiments, the anti-GITR antibody molecule comprises an HCDR1 sequence of GFSLSSY (SEQ ID NO: 301) (disclosed as SEQ ID NO: 84 of WO 2016/057846), an HCDR2 sequence of WGGGG (SEQ ID NO: 302) (disclosed as SEQ ID NO: 80 of WO 2016/057846), an HCDR3 sequence of HAYGHDGGFAMDY (SEQ ID NO: 303) (disclosed as SEQ ID NO: 29 of WO 2016/057846), an LCDR1 of SESVSSN (SEQ ID NO: 304) (disclosed as SEQ ID NO: 85 of WO 2016/057846), an LCDR2 of GAS (SEQ ID NO: 305) (disclosed as SEQ ID NO: 82 of WO 2016/057846), and an LCDR3 of SYSYPF (SEQ ID NO: 306) (disclosed as SEQ ID NO: 83 of WO 2016/057846), all according to Chothia CDR definition. In other embodiments, the anti-GITR antibody molecule comprises an HCDR1 sequence of SYGVD (SEQ ID NO: 307) (disclosed as SEQ ID NO: 22 of WO 2016/057846), an HCDR2 sequence of VIWGGGGTYYASSLMG (SEQ ID NO: 308) (disclosed as SEQ ID NO: 25 of WO 2016/057846), an HCDR3 sequence of HAYGHDGGFAMDY (SEQ ID NO: 303) (disclosed as SEQ ID NO: 29 of WO 2016/057846), an LCDR1 of RASESVSSNVA (SEQ ID NO: 309) (disclosed as SEQ ID NO: 30 of WO 2016/057846), an LCDR2 of GASNRAT (SEQ ID NO: 310) (disclosed as SEQ ID NO: 33 of WO 2016/057846), and an LCDR3 of GQSYSYPFT (SEQ ID NO: 311) (disclosed as SEQ ID NO: 34 of WO 2016/057846), all according to Kabat CDR definition.

In some embodiments, the anti-GITR antibody molecule comprises a heavy chain variable region (VH) amino acid sequence of EVQLVESGGGLVQSGGSLRLS-CAASGFSLSSSYGVDWVRQAPGK-GLEWVGVIWGGGGTYYA SSLMGRFTISRDNSKNT-LYLQMNSLRAEDTAVYYCARHAYGHDGGFAMDYW GQGTLVTVS S (SEQ ID NO: 312) (disclosed as SEQ ID NO: 99 of WO 2016/057846). In some embodiments, the anti-GITR antibody molecule comprises a light chain variable region (VL) amino acid sequence of EIVMTQSPATLSVSPGERATLSCRASESVSSN-VAWYQQRPGQAPRLLIYGASNRATGIPARFS GSGSGTDFTLTISRLEPEDFAVYYCGQSYS-YPFTFGQGTKLEIK (SEQ ID NO: 313) (disclosed as SEQ ID NO: 7 of WO 2016/057846).

In some embodiments, the anti-GITR antibody molecule comprises a heavy chain (HC) amino acid sequence of: EVQLVESGGGLVQSGGSLRLS-CAASGFSLSSSYGVDWVRQAPGK-GLEWVGVIWGGGGTYYA SSLMGRFTISRDNSKNT-LYLQMNSLRAEDTAVYYCARHAYGHDGGFAMDYW GQGTLVTVS SASTKGPSVFPLAPSSKSTSGGTAAL-GCLVKDYFPEPVTVSWNSGALTSGVHTFPAVLQSSGL YSLSSVVTVPSSSLGTQTYICNVNHKPSNTKVDKRVE-PKSCDKTHTCPPCPAPELLGGPSVFLF PPKPKDTLMISRTPEVTCVVVDVSHEDPE-VKFNWYVDGVEVHNAKTKPREEQYNSTYRVVS VLTVLHQDWLNGKEYKCKVSNKALPA-PIEKTISKAKGQPREPQVYTLPPSREEMTKNQVSLT CLVKGFYPSDIAVEWESNGQPEN-
NYKTTPPVLDSDGSFFLYSK-
LTVDKSRWQQGNVFSCSV MHEALHNHYTQKSLSL-
SPGK (SEQ ID NO: 314) (disclosed as SEQ ID NO: 100 of
WO 2016/057846). In some embodiments, the anti-GITR
antibody molecule comprises a light chain (LC) amino acid
sequence of EIVMTQSPATLSVSPGERATLSCRAS-
ESVSSNVAWYQQRPGQAPRLLIYGASNRATGIPARFS
GSGSGTDFTLTISRLEPEDFAVYYCGQSYS-
YPFTFGQGTKLEIKRTVAAPSVFIFPPSDEQLKSG
TASVVCLLNNFYPREAKVQWKVD-
NALQSGNSQESVTEQDSKDSTYSLSSTLTL-
SKADYEKH KVYACEVTHQGLSSPVTKSFNRGEC
(SEQ ID NO: 315) (disclosed as SEQ ID NO: 66 of WO
2016/057846).

Exemplary GITR agonists include, e.g., GITR fusion
proteins and anti-GITR antibodies (e.g., bivalent anti-GITR
antibodies), such as, a GITR fusion protein described in U.S.
Pat. No. 6,111,090, European Patent No.: 0920505B1, U.S.
Pat. No. 8,586,023, PCT Publication Nos.: WO 2010/
003118 and 2011/090754, or an anti-GITR antibody
described, e.g., in U.S. Pat. No. 7,025,962, European Patent
No.: 1947183B1, U.S. Pat. Nos. 7,812,135, 8,388,967,
8,591,886, European Patent No.: EP 1866339, PCT Publi-
cation No. WO 2011/028683, U.S. Pat. No. 8,709,424, PCT
Publication No. WO 2013/039954, International Publication
No. WO2013/039954, U.S. Publication No.: US2014/
0072566, International Publication No. WO2015/026684,
PCT Publication No. WO2005/007190, PCT Publication
No. WO 2007/133822, PCT Publication No. WO2005/
055808, PCT Publication No. WO 99/40196, PCT Publica-
tion No. WO 2001/03720, PCT Publication No. WO99/
20758, U.S. Pat. No. 6,689,607, PCT Publication No.
WO2006/083289, PCT Publication No. WO 2005/115451,
U.S. Pat. No. 7,618,632, PCT Publication No. WO 2011/
051726, International Publication No. WO2004/060319,
and International Publication No. WO2014/012479.

In one embodiment, the GITR agonist is used in combi-
nation with a PD-1 inhibitor, e.g., as described in WO2015/
026684.

In another embodiment, the GITR agonist is used in
combination with a TLR agonist, e.g., as described in
WO2004/060319, and International Publication No.
WO2014/012479.

Exemplary PD-1 Inhibitors

PD-1 is a CD28/CTLA-4 family member expressed, e.g.,
on activated CD4+ and CD8+ T cells, $T_{regs}$, and B cells. It
negatively regulates effector T cell signaling and function.
PD-1 is induced on tumor-infiltrating T cells, and can result
in functional exhaustion or dysfunction (Keir et al. (2008)
Annu. Rev. Immunol. 26:677-704; Pardoll et al. (2012) Nat
Rev Cancer 12(4):252-64). PD-1 delivers a coinhibitory
signal upon binding to either of its two ligands, Programmed
Death-Ligand 1 (PD-L1) or Programmed Death-Ligand 2
(PD-L2). PD-L1 is expressed on a number of cell types,
including T cells, natural killer (NK) cells, macrophages,
dendritic cells (DCs), B cells, epithelial cells, vascular
endothelial cells, as well as many types of tumors. High
expression of PD-L1 on murine and human tumors has been
linked to poor clinical outcomes in a variety of cancers (Keir
et al. (2008) Annu. Rev. Immunol. 26:677-704; Pardoll et al.
(2012) Nat Rev Cancer 12(4):252-64). PD-L2 is expressed
on dendritic cells, macrophages, and some tumors. Blockade
of the PD-1 pathway has been pre-clinically and clinically
validated for cancer immunotherapy. Both preclinical and
clinical studies have demonstrated that anti-PD-1 blockade
can restore activity of effector T cells and results in robust anti-tumor response. For example, blockade of PD-1 path-
way can restore exhausted/dysfunctional effector T cell
function (e.g., proliferation, IFN-γ secretion, or cytolytic
function) and/or inhibit $T_{reg}$ cell function (Keir et al. (2008)
Annu. Rev. Immunol. 26:677-704; Pardon et al. (2012) Nat
Rev Cancer 12(4):252-64). Blockade of the PD-1 pathway
can be effected with an antibody, an antigen binding frag-
ment thereof, an immunoadhesin, a fusion protein, or oli-
gopeptide of PD-1, PD-L1 and/or PD-L2.

As used herein, the term "Programmed Death 1" or
"PD-1" include isoforms, mammalian, e.g., human PD-1,
species homologs of human PD-1, and analogs comprising
at least one common epitope with PD-1. The amino acid
sequence of PD-1, e.g., human PD-1, is known in the art,
e.g., Shinohara T et al. (1994) Genomics 23(3):704-6; Finger
L R, et al. Gene (1997) 197(1-2):177-87.

The anti-PD-1 antibody molecules described herein can
be used alone or in combination with one or more additional
agents described herein in accordance with a method
described herein. In certain embodiments, the combinations
described herein include a PD-1 inhibitor, e.g., an anti-PD-1
antibody molecule (e.g., humanized antibody molecules) as
described herein.

In some embodiments, the anti-PD-1 antibody molecule
(e.g., an isolated or recombinant antibody molecule) has one
or more of the following properties:

(i) binds to PD-1, e.g., human PD-1, with high affinity,
    e.g., with an affinity constant of at least about $10^7$ $M^{-1}$,
    typically about $10^8$ $M^{-1}$, and more typically, about $10^9$
    $M^{-1}$ to $10^{10}$ $M^{-1}$ or stronger;

(ii) does not substantially bind to CD28, CTLA-4, ICOS
    or BTLA;

(iii) inhibits or reduces binding of PD-1 to a PD-1 ligand,
    e.g., PD-L1 or PD-L2, or both;

(iv) binds specifically to an epitope on PD-1, e.g., the
    same or similar epitope as the epitope recognized by
    murine monoclonal antibody BAP049 or a chimeric
    antibody BAP049, e.g., BAP049-chi or BAP049-chi-Y;

(v) shows the same or similar binding affinity or speci-
    ficity, or both, as any of BAP049-hum01, BAP049-
    hum02, BAP049-hum03, BAP049-hum04, BAP049-
    hum05, BAP049-hum06, BAP049-hum07, BAP049-
    hum08, BAP049-hum09, BAP049-hum10, BAP049-
    hum11, BAP049-hum12, BAP049-hum13, BAP049-
    hum14, BAP049-hum15, BAP049-hum16, BAP049-
    Clone-A, BAP049-Clone-B, BAP049-Clone-C,
    BAP049-Clone-D, or BAP049-Clone-E;

(vi) shows the same or similar binding affinity or speci-
    ficity, or both, as an antibody molecule (e.g., a heavy
    chain variable region and light chain variable region)
    described in Table 1;

(vii) shows the same or similar binding affinity or speci-
    ficity, or both, as an antibody molecule (e.g., a heavy
    chain variable region and light chain variable region)
    having an amino acid sequence shown in Table 1;

(viii) shows the same or similar binding affinity or speci-
    ficity, or both, as an antibody molecule (e.g., a heavy
    chain variable region and light chain variable region)
    encoded by the nucleotide sequence shown in Table 1;

(ix) inhibits, e.g., competitively inhibits, the binding of a
    second antibody molecule to PD-1, wherein the second
    antibody molecule is an antibody molecule described
    herein, e.g., an antibody molecule chosen from, e.g.,
    any of BAP049-hum01, BAP049-hum02, BAP049-
    hum03, BAP049-hum04, BAP049-hum05, BAP049-
    hum06, BAP049-hum07, BAP049-hum08, BAP049-
    hum09, BAP049-hum10, BAP049-hum11, BAP049- hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E;

(x) binds the same or an overlapping epitope with a second antibody molecule to PD-1, wherein the second antibody molecule is an antibody molecule described herein, e.g., an antibody molecule chosen from, e.g., any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E;

(xi) competes for binding, and/or binds the same epitope, with a second antibody molecule to PD-1, wherein the second antibody molecule is an antibody molecule described herein, e.g., an antibody molecule chosen from, e.g., any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E;

(xii) has one or more biological properties of an antibody molecule described herein, e.g., an antibody molecule chosen from, e.g., any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E;

(xiii) has one or more pharmacokinetic properties of an antibody molecule described herein, e.g., an antibody molecule chosen from, e.g., any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E;

(xiv) inhibits one or more activities of PD-1, e.g., results in one or more of: an increase in tumor infiltrating lymphocytes, an increase in T-cell receptor mediated proliferation, or a decrease in immune evasion by cancerous cells;

(xv) binds human PD-1 and is cross-reactive with cynomolgus PD-1;

(xvi) binds to one or more residues within the C strand, CC' loop, C' strand, or FG loop of PD-1, or a combination two, three or all of the C strand, CC' loop, C' strand or FG loop of PD-1, e.g., wherein the binding is assayed using ELISA or Biacore; or (xvii) has a VL region that contributes more to binding to PD-1 than a VH region.

In some embodiments, the antibody molecule binds to PD-1 with high affinity, e.g., with a $K_D$ that is about the same, or at least about 10%, 20%, 30%, 40%, 50%, 60%, 70%, 80% or 90% higher or lower than the $K_D$ of a murine or chimeric anti-PD-1 antibody molecule, e.g., a murine or chimeric anti-PD-1 antibody molecule described herein. In some embodiments, the $K_D$ of the murine or chimeric anti-PD-1 antibody molecule is less than about 0.4, 0.3, 0.2, 0.1, or 0.05 nM, e.g., measured by a Biacore method. In some embodiments, the $K_D$ of the murine or chimeric anti-PD-1 antibody molecule is less than about 0.2 nM, e.g., about 0.135 nM. In other embodiments, the $K_D$ of the murine or chimeric anti PD-1 antibody molecule is less than about 10, 5, 3, 2, or 1 nM, e.g., measured by binding on cells expressing PD-1 (e.g., 300.19 cells). In some embodiments, the $K_D$ of the murine or chimeric anti PD-1 antibody molecule is less than about 5 nM, e.g., about 4.60 nM (or about 0.69 μg/mL).

In some embodiments, the anti-PD-1 antibody molecule binds to PD-1 with a $K_{off}$ slower than $1\times10^{-4}$, $5\times10^{-5}$, or $1\times10^{-5}$ $s^{-1}$, e.g., about $1.65\times10^{-5}$ $s^{-1}$. In some embodiments, the anti-PD-1 antibody molecule binds to PD-1 with a $K_{on}$ faster than $1\times10^4$, $5\times10^4$, $1\times10^5$, or $5\times10^5 M^{-1}s^{-1}$, e.g., about $1.23\times10^5$ $M^{-1}s^{-1}$.

In some embodiments, the expression level of the antibody molecule is higher, e.g., at least about 0.5, 1, 2, 3, 4, 5, 6, 7, 8, 9 or 10-fold higher, than the expression level of a murine or chimeric antibody molecule, e.g., a murine or chimeric anti-PD-1 antibody molecule described herein. In some embodiments, the antibody molecule is expressed in CHO cells.

In some embodiments, the anti-PD-1 antibody molecule reduces one or more PD-1-associated activities with an $IC_{50}$ (concentration at 50% inhibition) that is about the same or lower, e.g., at least about 10%, 20%, 30%, 40%, 50%, 60%, 70%, 80% or 90% lower, than the $IC_{50}$ of a murine or chimeric anti-PD-1 antibody molecule, e.g., a murine or chimeric anti-PD-1 antibody molecule described herein. In some embodiments, the $IC_{50}$ of the murine or chimeric anti-PD-1 antibody molecule is less than about 6, 5, 4, 3, 2, or 1 nM, e.g., measured by binding on cells expressing PD-1 (e.g., 300.19 cells). In some embodiments, the $IC_{50}$ of the murine or chimeric anti-PD-1 antibody molecule is less than about 4 nM, e.g., about 3.40 nM (or about 0.51 μg/mL). In some embodiments, the PD-1-associated activity reduced is the binding of PD-L1 and/or PD-L2 to PD-1. In some embodiments, the anti-PD-1 antibody molecule binds to peripheral blood mononucleated cells (PBMCs) activated by Staphylococcal enterotoxin B (SEB). In other embodiments, the anti-PD-1 antibody molecule increases the expression of IL-2 on whole blood activated by SEB. For example, the anti-PD-1 antibody increases the expression of IL-2 by at least about 2, 3, 4, or 5-fold, compared to the expression of IL-2 when an isotype control (e.g., IgG4) is used.

In some embodiments, the anti-PD-1 antibody molecule has improved stability, e.g., at least about 0.5, 1, 2, 3, 4, 5, 6, 7, 8, 9 or 10-fold more stable in vivo or in vitro, than a murine or chimeric anti-PD-1 antibody molecule, e.g., a murine or chimeric anti-PD-1 antibody molecule described herein.

In one embodiment, the anti PD-1 antibody molecule is a humanized antibody molecule and has a risk score based on T cell epitope analysis of 300 to 700, 400 to 650, 450 to 600, or a risk score as described herein.

In another embodiment, the anti-PD-1 antibody molecule comprises at least one antigen-binding region, e.g., a variable region or an antigen-binding fragment thereof, from an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-1 antibody molecule comprises at least one, two, three or four variable regions from an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-1 antibody molecule comprises at least one or two heavy chain variable regions from an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-1 antibody molecule comprises at least one or two light chain variable regions from an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-1 antibody molecule includes a heavy chain constant region for an IgG4, e.g., a human IgG4. In one embodiment, the human IgG4 includes a substitution at position 228 according to EU numbering (e.g., a Ser to Pro substitution). In still another embodiment, the anti-PD-1 antibody molecule includes a heavy chain constant region for an IgG1, e.g., a human IgG1. In one embodiment, the human IgG1 includes a substitution at position 297 according to EU numbering (e.g., an Asn to Ala substitution). In one embodiment, the human IgG1 includes a substitution at position 265 according to EU numbering, a substitution at position 329 according to EU numbering, or both (e.g., an Asp to Ala substitution at position 265 and/or a Pro to Ala substitution at position 329). In one embodiment, the human IgG1 includes a substitution at position 234 according to EU numbering, a substitution at position 235 according to EU numbering, or both (e.g., a Leu to Ala substitution at position 234 and/or a Leu to Ala substitution at position 235). In one embodiment, the heavy chain constant region comprises an amino sequence set forth in Table 3, or a sequence substantially identical (e.g., at least 80%, 85%, 90%, 92%, 95%, 97%, 98%, 99% or higher identical) thereto.

In yet another embodiment, the anti-PD-1 antibody molecule includes a kappa light chain constant region, e.g., a human kappa light chain constant region. In one embodiment, the light chain constant region comprises an amino sequence set forth in Table 3, or a sequence substantially identical (e.g., at least 80%, 85%, 90%, 92%, 95%, 97%, 98%, 99% or higher identical) thereto.

In another embodiment, the anti-PD-1 antibody molecule includes a heavy chain constant region for an IgG4, e.g., a human IgG4, and a kappa light chain constant region, e.g., a human kappa light chain constant region, e.g., a heavy and light chain constant region comprising an amino sequence set forth in Table 3, or a sequence substantially identical (e.g., at least 80%, 85%, 90%, 92%, 95%, 97%, 98%, 99% or higher identical) thereto. In one embodiment, the human IgG4 includes a substitution at position 228 according to EU numbering (e.g., a Ser to Pro substitution). In yet another embodiment, the anti-PD-1 antibody molecule includes a heavy chain constant region for an IgG1, e.g., a human IgG1, and a kappa light chain constant region, e.g., a human kappa light chain constant region, e.g., a heavy and light chain constant region comprising an amino sequence set forth in Table 3, or a sequence substantially identical (e.g., at least 80%, 85%, 90%, 92%, 95%, 97%, 98%, 99% or higher identical) thereto. In one embodiment, the human IgG1 includes a substitution at position 297 according to EU numbering (e.g., an Asn to Ala substitution). In one embodiment, the human IgG1 includes a substitution at position 265 according to EU numbering, a substitution at position 329 according to EU numbering, or both (e.g., an Asp to Ala substitution at position 265 and/or a Pro to Ala substitution at position 329). In one embodiment, the human IgG1 includes a substitution at position 234 according to EU numbering, a substitution at position 235 according to EU numbering, or both (e.g., a Leu to Ala substitution at position 234 and/or a Leu to Ala substitution at position 235).

In another embodiment, the anti-PD-1 antibody molecule includes a heavy chain variable domain and a constant region, a light chain variable domain and a constant region, or both, comprising the amino acid sequence of BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences. The anti-PD-1 antibody molecule, optionally, comprises a leader sequence from a heavy chain, a light chain, or both, as shown in Table 4; or a sequence substantially identical thereto.

In yet another embodiment, the anti-PD-1 antibody molecule includes at least one, two, or three complementarity determining regions (CDRs) from a heavy chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-1 antibody molecule includes at least one, two, or three CDRs (or collectively all of the CDRs) from a heavy chain variable region comprising an amino acid sequence shown in Table 1, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In yet another embodiment, the anti-PD-1 antibody molecule includes at least one, two, or three CDRs from a light chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequence.

In yet another embodiment, the anti-PD-1 antibody molecule includes at least one, two, or three CDRs (or collectively all of the CDRs) from a light chain variable region comprising an amino acid sequence shown in Table 1, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1. In certain embodiments, the anti-PD-1 antibody molecule includes a substitution in a light chain CDR, e.g., one or more substitutions in a CDR1, CDR2 and/or CDR3 of the light chain. In one embodiment, the anti-PD-1 antibody molecule includes a substitution in the light chain CDR3 at position 102 of the light variable region, e.g., a substitution of a cysteine to tyrosine, or a cysteine to serine residue, at position 102 of the light variable region according to Table 1 (e.g., SEQ ID NO: 16 or 24 for murine or chimeric, unmodified; or any of SEQ ID NOs: 34, 42, 46, 54, 58, 62, 66, 70, 74, or 78 for a modified sequence).

In another embodiment, the anti-PD-1 antibody molecule includes at least one, two, three, four, five or six CDRs (or collectively all of the CDRs) from a heavy and light chain variable region comprising an amino acid sequence shown in Table 1, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In one embodiment, the anti-PD-1 antibody molecule includes all six CDRs from an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1, or closely related CDRs, e.g., CDRs which are identical or which have at least one amino acid alteration, but not more than two, three or four alterations (e.g., substitutions, deletions, or insertions, e.g., conservative substitutions). In one embodiment, the anti-PD-1 antibody molecule may include any CDR described herein. In certain embodiments, the anti-PD-1 antibody molecule includes a substitution in a light chain CDR, e.g., one or more substitutions in a CDR1, CDR2 and/or CDR3 of the light chain. In one embodiment, the anti-PD-1 antibody molecule includes a substitution in the light chain CDR3 at position 102 of the light variable region, e.g., a substitution of a cysteine to tyrosine, or a cysteine to serine residue, at position 102 of the light variable region according to Table 1 (e.g., SEQ ID NO: 16 or 24 for murine or chimeric, unmodified; or any of SEQ ID NOs: 34, 42, 46, 54, 58, 62, 66, 70, 74, or 78 for a modified sequence).

In another embodiment, the anti-PD-1 antibody molecule includes at least one, two, or three CDRs according to Kabat et al. (e.g., at least one, two, or three CDRs according to the Kabat definition as set out in Table 1) from a heavy chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat et al. shown in Table 1.

In another embodiment, the anti-PD-1 antibody molecule includes at least one, two, or three CDRs according to Kabat et al. (e.g., at least one, two, or three CDRs according to the Kabat definition as set out in Table 1) from a light chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat et al. shown in Table 1.

In yet another embodiment, the anti-PD-1 antibody molecule includes at least one, two, three, four, five, or six CDRs according to Kabat et al. (e.g., at least one, two, three, four, five, or six CDRs according to the Kabat definition as set out in Table 1) from the heavy and light chain variable regions of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, three, four, five, or six CDRs according to Kabat et al. shown in Table 1.

In yet another embodiment, the anti-PD-1 antibody molecule includes all six CDRs according to Kabat et al. (e.g., all six CDRs according to the Kabat definition as set out in Table 1) from the heavy and light chain variable regions of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to all six CDRs according to Kabat et al. shown in Table 1. In one embodiment, the anti-PD-1 antibody molecule may include any CDR described herein.

In another embodiment, the anti-PD-1 antibody molecule includes at least one, two, or three Chothia hypervariable loops (e.g., at least one, two, or three hypervariable loops according to the Chothia definition as set out in Table 1) from a heavy chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or at least the amino acids from those hypervariable loops that contact PD-1; or which have at least one amino acid alteration, but not more than two, three or four alterations (e.g., substitutions, deletions, or insertions, e.g., conservative substitutions) relative to one, two, or three hypervariable loops according to Chothia et al. shown in Table 1.

In another embodiment, the anti-PD-1 antibody molecule includes at least one, two, or three Chothia hypervariable loops (e.g., at least one, two, or three hypervariable loops according to the Chothia definition as set out in Table 1) of a light chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or at least the amino acids from those hypervariable loops that contact PD-1; or which have at least one amino acid alteration, but not more than two, three or four alterations (e.g., substitutions, deletions, or insertions, e.g., conservative substitutions) relative to one, two, or three hypervariable loops according to Chothia et al. shown in Table 1.

In yet another embodiment, the anti-PD-1 antibody molecule includes at least one, two, three, four, five, or six hypervariable loops (e.g., at least one, two, three, four, five, or six hypervariable loops according to the Chothia definition as set out in Table 1) from the heavy and light chain variable regions of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or at least the amino acids from those hypervariable loops that contact PD-1; or which have at least one amino acid alteration, but not more than two, three or four alterations (e.g., substitutions, deletions, or insertions, e.g., conservative substitutions) relative to one, two, three, four, five or six hypervariable loops according to Chothia et al. shown in Table 1.

In one embodiment, the anti-PD-1 antibody molecule includes all six hypervariable loops (e.g., all six hypervariable loops according to the Chothia definition as set out in Table 1) of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E, or closely related hypervariable loops, e.g., hypervariable loops which are identical or which have at least one amino acid alteration, but not more than two, three or four alterations (e.g., substitutions, deletions, or insertions, e.g., conservative substitutions); or which have at least one amino acid alteration, but not more than two, three or four alterations (e.g., substitutions, deletions, or insertions, e.g., conservative substitutions) relative to all six hypervariable loops according to Chothia et al. shown in Table 1. In one embodiment, the anti-PD-1 antibody molecule may include any hypervariable loop described herein.

In still another embodiment, the anti-PD-1 antibody molecule includes at least one, two, or three hypervariable loops that have the same canonical structures as the corresponding hypervariable loop of an antibody described herein, e.g., an antibody chosen from any of BAP049-hum01, BAP049-hum02, BAP049-hum03, BAP049-hum04, BAP049- hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E, e.g., the same canonical structures as at least loop 1 and/or loop 2 of the heavy and/or light chain variable domains of an antibody described herein. See, e.g., Chothia et al., (1992) *J. Mol. Biol.* 227:799-817; Tomlinson et al., (1992) *J. Mol. Biol.* 227:776-798 for descriptions of hypervariable loop canonical structures. These structures can be determined by inspection of the tables described in these references.

In certain embodiments, the anti-PD-1 antibody molecule includes a combination of CDRs or hypervariable loops defined according to the Kabat et al. and Chothia et al.

In one embodiment, the anti-PD-1 antibody molecule includes at least one, two or three CDRs or hypervariable loops from a heavy chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E, according to the Kabat and Chothia definition (e.g., at least one, two, or three CDRs or hypervariable loops according to the Kabat and Chothia definition as set out in Table 1); or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs or hypervariable loops according to Kabat and/or Chothia shown in Table 1.

For example, the anti-PD-1 antibody molecule can include VH CDR1 according to Kabat et al. or VH hypervariable loop 1 according to Chothia et al., or a combination thereof, e.g., as shown in Table 1. In one embodiment, the combination of Kabat and Chothia CDR of VH CDR1 comprises the amino acid sequence GYTFTTYWMH (SEQ ID NO: 224), or an amino acid sequence substantially identical thereto (e.g., having at least one amino acid alteration, but not more than two, three or four alterations (e.g., substitutions, deletions, or insertions, e.g., conservative substitutions)). The anti-PD-1 antibody molecule can further include, e.g., VH CDRs 2-3 according to Kabat et al. and VL CDRs 1-3 according to Kabat et al., e.g., as shown in Table 1. Accordingly, in some embodiments, framework regions are defined based on a combination of CDRs defined according to Kabat et al. and hypervariable loops defined according to Chothia et al. For example, the anti-PD-1 antibody molecule can include VH FR1 defined based on VH hypervariable loop 1 according to Chothia et al. and VH FR2 defined based on VH CDRs 1-2 according to Kabat et al., e.g., as shown in Table 1. The anti-PD-1 antibody molecule can further include, e.g., VH FRs 3-4 defined based on VH CDRs 2-3 according to Kabat et al. and VL FRs 1-4 defined based on VL CDRs 1-3 according to Kabat et al.

The anti-PD-1 antibody molecule can contain any combination of CDRs or hypervariable loops according to the Kabat and Chothia definitions. In one embodiment, the anti-PD-1 antibody molecule includes at least one, two or three CDRs from a light chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E, according to the Kabat and Chothia definition (e.g., at least one, two, or three CDRs according to the Kabat and Chothia definition as set out in Table 1).

In an embodiment, e.g., an embodiment comprising a variable region, a CDR (e.g., Chothia CDR or Kabat CDR), or other sequence referred to herein, e.g., in Table 1, the antibody molecule is a monospecific antibody molecule, a bispecific antibody molecule, or is an antibody molecule that comprises an antigen binding fragment of an antibody, e.g., a half antibody or antigen binding fragment of a half antibody. In certain embodiments the antibody molecule is a bispecific antibody molecule having a first binding specificity for PD-1 and a second binding specificity for TIM-3, LAG-3, CEACAM (e.g., CEACAM-1 and/or CEACAM-5), PD-L1 or PD-L2.

In one embodiment, the anti-PD-1 antibody molecule includes:

(a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 33;

(b) a VH comprising a VHCDR1 amino acid sequence chosen from SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32;

(c) a VH comprising a VHCDR1 amino acid sequence of SEQ ID NO: 224, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33; or (d) a VH comprising a VHCDR1 amino acid sequence of SEQ ID NO: 224; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32.

In one embodiment, the anti-PD-1 antibody molecule comprises a VH comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33.

In one embodiment, the anti-PD-1 antibody molecule comprises a VH comprising a VHCDR1 amino acid sequence of SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32.

In one embodiment, the anti-PD-1 antibody molecule comprises a VH comprising a VHCDR1 amino acid sequence of SEQ ID NO: 224, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33.

In one embodiment, the anti-PD-1 antibody molecule comprises a VH comprising a VHCDR1 amino acid sequence of SEQ ID NO: 224; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32.

In one embodiment, the antibody molecule is a humanized antibody molecule. In another embodiment, the antibody molecule is a monospecific antibody molecule. In yet another embodiment, the antibody molecule is a bispecific antibody molecule.

In one embodiment, the anti-PD-1 antibody molecule includes:

(i) a heavy chain variable region (VH) including a VHCDR1 amino acid sequence chosen from SEQ ID NO: 1, SEQ ID NO: 4 or SEQ ID NO: 224; a VHCDR2 amino acid sequence of SEQ ID NO: 2; and a VHCDR3 amino acid sequence of SEQ ID NO: 3; and (ii) a light chain variable region (VL) including a VLCDR1 amino acid sequence of SEQ ID NO: 10, a VLCDR2 amino acid sequence of SEQ ID NO: 11, and a VLCDR3 amino acid sequence of SEQ ID NO: 32.

In another embodiment, the anti-PD-1 antibody molecule includes:

(i) a heavy chain variable region (VH) including a VHCDR1 amino acid sequence chosen from SEQ ID NO: 1, SEQ ID NO: 4 or SEQ ID NO: 224; a VHCDR2 amino acid sequence of SEQ ID NO: 5, and a VHCDR3 amino acid sequence of SEQ ID NO: 3; and (ii) a light chain variable region (VL) including a VLCDR1 amino acid sequence of SEQ ID NO: 13, a VLCDR2 amino acid sequence of SEQ ID NO: 14, and a VLCDR3 amino acid sequence of SEQ ID NO: 33.

In one embodiment, the anti-PD-1 antibody molecule comprises the VHCDR1 amino acid sequence of SEQ ID NO: 1. In another embodiment, the anti-PD-1 antibody molecule comprises the VHCDR1 amino acid sequence of SEQ ID NO: 4. In yet another embodiment, the anti-PD-1 antibody molecule comprises the VHCDR1 amino acid sequence of SEQ ID NO: 224.

In one embodiment, the light or the heavy chain variable framework (e.g., the region encompassing at least FR1, FR2, FR3, and optionally FR4) of the anti-PD-1 antibody molecule can be chosen from: (a) a light or heavy chain variable framework including at least 80%, 85%, 87% 90%, 92%, 93%, 95%, 97%, 98%, or preferably 100% of the amino acid residues from a human light or heavy chain variable framework, e.g., a light or heavy chain variable framework residue from a human mature antibody, a human germline sequence, or a human consensus sequence; (b) a light or heavy chain variable framework including from 20% to 80%, 40% to 60%, 60% to 90%, or 70% to 95% of the amino acid residues from a human light or heavy chain variable framework, e.g., a light or heavy chain variable framework residue from a human mature antibody, a human germline sequence, or a human consensus sequence; (c) a non-human framework (e.g., a rodent framework); or (d) a non-human framework that has been modified, e.g., to remove antigenic or cytotoxic determinants, e.g., deimmunized, or partially humanized. In one embodiment, the light or heavy chain variable framework region (particularly FR1, FR2 and/or FR3) includes a light or heavy chain variable framework sequence at least 70, 75, 80, 85, 87, 88, 90, 92, 94, 95, 96, 97, 98, 99% identical or identical to the frameworks of a VL or VH segment of a human germline gene.

In certain embodiments, the anti-PD-1 antibody molecule comprises a heavy chain variable domain having at least one, two, three, four, five, six, seven, ten, fifteen, twenty or more changes, e.g., amino acid substitutions or deletions, from an amino acid sequence of BAP049-chi-HC, e.g., the amino acid sequence of the FR region in the entire variable region, e.g., shown in FIGS. 9A-9B, or SEQ ID NO: 18, 20, 22 or 30. In one embodiment, the anti-PD-1 antibody molecule comprises a heavy chain variable domain having one or more of: E at position 1, V at position 5, A at position 9, V at position 11, K at position 12, K at position 13, E at position 16, L at position 18, R at position 19, I or V at position 20, G at position 24, I at position 37, A or S at position 40, T at position 41, S at position 42, R at position 43, M or L at position 48, V or F at position 68, T at position 69, I at position 70, S at position 71, A or R at position 72, K or N at position 74, T or K at position 76, S or N at position 77, L at position 79, L at position 81, E or Q at position 82, M at position 83, S or N at position 84, R at position 87, A at position 88, or T at position 91 of amino acid sequence of BAP049-chi-HC, e.g., the amino acid sequence of the FR in the entire variable region, e.g., shown in FIGS. 9A-9B, or SEQ ID NO: 18, 20, 22 or 30.

Alternatively, or in combination with the heavy chain substitutions of BAP049-chi-HC described herein, the anti-PD-1 antibody molecule comprises a light chain variable domain having at least one, two, three, four, five, six, seven, ten, fifteen, twenty or more amino acid changes, e.g., amino acid substitutions or deletions, from an amino acid sequence of BAP049-chi-LC, e.g., the amino acid sequence shown in FIGS. 10A-10B, or SEQ ID NO: 24 or 26. In one embodiment, the anti-PD-1 antibody molecule comprises a heavy chain variable domain having one or more of: E at position 1, V at position 2, Q at position 3, L at position 4, T at position 7, D or L or A at position 9, F or T at position 10, Q at position 11, S or P at position 12, L or A at position 13, S at position 14, P or L or V at position 15, K at position 16, Q or D at position 17, R at position 18, A at position 19, S at position 20, I or L at position 21, T at position 22, L at position 43, K at position 48, A or S at position 49, R or Q at position 51, Y at position 55, I at position 64, S or P at position 66, S at position 69, Y at position 73, G at position 74, E at position 76, F at position 79, N at position 82, N at position 83, L or I at position 84, E at position 85, S or P at position 86, D at position 87, A or F or I at position 89, T or Y at position 91, F at position 93, or Y at position 102 of the amino acid sequence of BAP049-chi-LC, e.g., the amino acid sequence shown in FIGS. 10A-10B, or SEQ ID NO: 24 or 26.

In other embodiments, the anti-PD-1 antibody molecule includes one, two, three, or four heavy chain framework regions (e.g., a VHFW amino acid sequence shown in Table 2, or encoded by the nucleotide sequence shown in Table 2), or a sequence substantially identical thereto.

In yet other embodiments, the anti-PD-1 antibody molecule includes one, two, three, or four light chain framework regions (e.g., a VLFW amino acid sequence shown in Table 2, or encoded by the nucleotide sequence shown in Table 2), or a sequence substantially identical thereto.

In other embodiments, the anti-PD-1 antibody molecule includes one, two, three, or four heavy chain framework regions (e.g., a VHFW amino acid sequence shown in Table 2, or encoded by the nucleotide sequence shown in Table 2), or a sequence substantially identical thereto; and one, two, three, or four light chain framework regions (e.g., a VLFW amino acid sequence shown in Table 2, or encoded by the nucleotide sequence shown in Table 2), or a sequence substantially identical thereto.

In some embodiments, the anti-PD-1 antibody molecule comprises the heavy chain framework region 1 (VHFW1) of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum15, BAP049-hum16, BAP049-Clone-A, BAP049-Clone-B, BAP049-Clone-C, BAP049-Clone-D, or BAP049-Clone-E (e.g., SEQ ID NO: 147). In some embodiments, the antibody molecule comprises the heavy chain framework region 1 (VHFW1) of BAP049-hum14 or BAP049-hum15 (e.g., SEQ ID NO: 151).

In some embodiments, the anti-PD-1 antibody molecule comprises the heavy chain framework region 2 (VHFW2) of BAP049-hum01, BAP049-hum02, BAP049-hum05, BAP049-hum06, BAP049-hum07, BAP049-hum09, BAP049-hum11, BAP049-hum12, BAP049-hum13, BAP049-Clone-A, BAP049-Clone-B, BAP049-Clone-C, or BAP049-Clone-E (e.g., SEQ ID NO: 153). In some embodiments, the antibody molecule comprises the heavy chain framework region 2 (VHFW2) of BAP049-hum03, BAP049-hum04, BAP049-hum08, BAP049-hum10, BAP049-hum14, BAP049-hum15, or BAP049-Clone-D (e.g., SEQ ID NO: 157). In some embodiments, the antibody molecule comprises the heavy chain framework region 2 (VHFW2) of BAP049-hum16 (e.g., SEQ ID NO: 160).

In some embodiments, the anti-PD-1 antibody molecule comprises the heavy chain framework region 3 (VHFW3) of BAP049-hum01, BAP049-hum02, BAP049-hum05, BAP049-hum06, BAP049-hum07, BAP049-hum09, BAP049-hum11, BAP049-hum12, BAP049-hum13, BAP049-Clone-A, BAP049-Clone-B, BAP049-Clone-C, or BAP049-Clone-E (e.g., SEQ ID NO: 162). In some embodiments, the antibody molecule comprises the heavy chain framework region 3 (VHFW3) of BAP049-hum03, BAP049-hum04, BAP049-hum08, BAP049-hum10, BAP049-hum14, BAP049-hum15, BAP049-hum16, or BAP049-Clone-D (e.g., SEQ ID NO: 166).

In some embodiments, the anti-PD-1 antibody molecule comprises the heavy chain framework region 4 (VHFW4) of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E (e.g., SEQ ID NO: 169).

In some embodiments, the anti-PD-1 antibody molecule comprises the light chain framework region 1 (VLFW1) of BAP049-hum08, BAP049-hum09, BAP049-hum15, BAP049-hum16, or BAP049-Clone-C (e.g., SEQ ID NO:

174). In some embodiments, the antibody molecule comprises the light chain framework region 1 (VLFW1) of BAP049-hum01, BAP049-hum04, BAP049-hum05, BAP049-hum07, BAP049-hum10, BAP049-hum11, BAP049-hum14, BAP049-Clone-A, BAP049-Clone-B, BAP049-Clone-D, or BAP049-Clone-E (e.g., SEQ ID NO: 177). In some embodiments, the antibody molecule comprises the light chain framework region 1 (VLFW1) of BAP049-hum06 (e.g., SEQ ID NO: 181). In some embodiments, the antibody molecule comprises the light chain framework region 1 (VLFW1) of BAP049-hum13 (e.g., SEQ ID NO: 183). In some embodiments, the antibody molecule comprises the light chain framework region 1 (VLFW1) of BAP049-hum02, BAP049-hum03, or BAP049-hum12 (e.g., SEQ ID NO: 185).

In some embodiments, the anti-PD-1 antibody molecule comprises the light chain framework region 2 (VLFW2) of BAP049-hum01, BAP049-hum02, BAP049-hum03, BAP049-hum06, BAP049-hum08, BAP049-hum09, BAP049-hum10, BAP049-hum11, BAP049-hum14, BAP049-hum15, BAP049-hum16, BAP049-Clone-A, BAP049-Clone-B, BAP049-Clone-D, or BAP049-Clone-E (e.g., SEQ ID NO: 187). In some embodiments, the antibody molecule comprises the light chain framework region 2 (VLFW2) of BAP049-hum04, BAP049-hum05, BAP049-hum07, BAP049-hum13, or BAP049-Clone-C (e.g., SEQ ID NO: 191). In some embodiments, the antibody molecule comprises the light chain framework region 2 (VLFW2) of BAP049-hum12 (e.g., SEQ ID NO: 194).

In some embodiments, the anti-PD-1 antibody molecule comprises the light chain framework region 3 (VLFW3) of BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-C, BAP049-Clone-D, or BAP049-Clone-E (e.g., SEQ ID NO: 196). In some embodiments, the antibody molecule comprises the light chain framework region 3 (VLFW3) of BAP049-hum02 or BAP049-hum03 (e.g., SEQ ID NO: 200). In some embodiments, the antibody molecule comprises the light chain framework region 3 (VLFW3) of BAP049-hum01 or BAP049-Clone-A (e.g., SEQ ID NO: 202). In some embodiments, the antibody molecule comprises the light chain framework region 3 (VLFW3) of BAP049-hum04, BAP049-hum05, or BAP049-Clone-B (e.g., SEQ ID NO: 205).

In some embodiments, the anti-PD-1 antibody molecule comprises the light chain framework region 4 (VLFW4) of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E (e.g., SEQ ID NO: 208).

In some embodiments, the anti-PD-1 antibody molecule comprises the heavy chain framework regions 1-3 of BAP049-hum01, BAP049-hum02, BAP049-hum05, BAP049-hum06, BAP-hum07, BAP049-hum09, BAP049-hum11, BAP049-hum12, BAP049-hum13, BAP049-Clone-A, BAP049-Clone-B, BAP049-Clone-C, or BAP049-Clone-E (e.g., SEQ ID NO: 147 (VHFW1), SEQ ID NO: 153 (VHFW2), and SEQ ID NO: 162 (VHFW3)). In some embodiments, the antibody molecule comprises the heavy chain framework regions 1-3 of BAP049-hum03, BAP049-hum04, BAP049-hum08, BAP049-hum10, or BAP049-

Clone-D (e.g., SEQ ID NO: 147 (VHFW1), SEQ ID NO: 157 (VHFW2), and SEQ ID NO: 166 (VHFW3)). In some embodiments, the antibody molecule comprises the heavy chain framework regions 1-3 of BAP049-hum14 or BAP049-hum15 (e.g., SEQ ID NO: 151 (VHFW1), SEQ ID NO: 157 (VHFW2), and SEQ ID NO: 166 (VHFW3)). In some embodiments, the antibody molecule comprises the heavy chain framework regions 1-3 of BAP049-hum16 (e.g., SEQ ID NO: 147 (VHFW1), SEQ ID NO: 160 (VHFW2), and SEQ ID NO: 166 (VHFW3)). In some embodiments, the antibody molecule further comprises the heavy chain framework region 4 (VHFW4) of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E (e.g., SEQ ID NO: 169).

In some embodiments, the anti-PD-1 antibody molecule comprises the light chain framework regions 1-3 of BAP049-hum01 or BAP049-Clone-A (e.g., SEQ ID NO: 177 (VLFW1), SEQ ID NO: 187 (VLFW2), and SEQ ID NO: 202 (VLFW3)). In some embodiments, the antibody molecule comprises the light chain framework regions 1-3 of BAP049-hum02 or BAP049-hum03 (e.g., SEQ ID NO: 185 (VLFW1), SEQ ID NO: 187 (VLFW2), and SEQ ID NO: 200 (VLFW3)). In some embodiments, the antibody molecule comprises the light chain framework regions 1-3 of BAP049-hum04, BAP049-hum05, or BAP049-Clone-B (e.g., SEQ ID NO: 177 (VLFW1), SEQ ID NO: 191 (VLFW2), and SEQ ID NO: 205 (VLFW3)). In some embodiments, the antibody molecule comprises the light chain framework regions 1-3 of BAP049-hum06 (e.g., SEQ ID NO: 181 (VLFW1), SEQ ID NO: 187 (VLFW2), and SEQ ID NO: 196 (VLFW3)). In some embodiments, the antibody molecule comprises the light chain framework regions 1-3 of BAP049-hum07 (e.g., SEQ ID NO: 177 (VLFW1), SEQ ID NO: 191 (VLFW2), and SEQ ID NO: 196 (VLFW3)). In some embodiments, the antibody molecule comprises the light chain framework regions 1-3 of BAP049-hum08, BAP049-hum09, BAP049-hum15, BAP049-hum16, or BAP049-Clone-C (e.g., SEQ ID NO: 174 (VLFW1), SEQ ID NO: 187 (VLFW2), and SEQ ID NO: 196 (VLFW3)). In some embodiments, the antibody molecule comprises the light chain framework regions 1-3 of BAP049-hum10, BAP049-hum11, BAP049-hum14, BAP049-Clone-D, or BAP049-Clone-E (e.g., SEQ ID NO: 177 (VLFW1), SEQ ID NO: 187 (VLFW2), and SEQ ID NO: 196 (VLFW3)). In some embodiments, the antibody molecule comprises the light chain framework regions 1-3 of BAP049-hum12 (e.g., SEQ ID NO: 185 (VLFW1), SEQ ID NO: 194 (VLFW2), and SEQ ID NO: 196 (VLFW3)). In some embodiments, the antibody molecule comprises the light chain framework regions 1-3 of BAP049-hum13 (e.g., SEQ ID NO: 183 (VLFW1), SEQ ID NO: 191 (VLFW2), and SEQ ID NO: 196 (VLFW3)). In some embodiments, the antibody molecule further comprises the light chain framework region 4 (VLFW4) of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E (e.g., SEQ ID NO: 208).

In some embodiments, the anti-PD-1 antibody molecule comprises the heavy chain framework regions 1-3 of BAP049-hum01 or BAP049-Clone-A (e.g., SEQ ID NO: 147 (VHFW1), SEQ ID NO: 153 (VHFW2), and SEQ ID NO: 162 (VHFW3)) and the light chain framework regions 1-3 of BAP049-hum01 or BAP049-Clone-A (e.g., SEQ ID NO: 177 (VLFW1), SEQ ID NO: 187 (VLFW2), and SEQ ID NO: 202 (VLFW3)).

In some embodiments, the anti-PD-1 antibody molecule comprises the heavy chain framework regions 1-3 of BAP049-hum02 (e.g., SEQ ID NO: 147 (VHFW1), SEQ ID NO: 153 (VHFW2), and SEQ ID NO: 162 (VHFW3)) and the light chain framework regions 1-3 of BAP049-hum02 (e.g., SEQ ID NO: 185 (VLFW1), SEQ ID NO: 187 (VLFW2), and SEQ ID NO: 200 (VLFW3)).

In some embodiments, the anti-PD-1 antibody molecule comprises the heavy chain framework regions 1-3 of BAP049-hum03 (e.g., SEQ ID NO: 147 (VHFW1), SEQ ID NO: 157 (VHFW2), and SEQ ID NO: 166 (VHFW3)) and the light chain framework regions 1-3 of BAP049-hum03 (e.g., SEQ ID NO: 185 (VLFW1), SEQ ID NO: 187 (VLFW2), and SEQ ID NO: 200 (VLFW3)).

In some embodiments, the anti-PD-1 antibody molecule comprises the heavy chain framework regions 1-3 of BAP049-hum04 (e.g., SEQ ID NO: 147 (VHFW1), SEQ ID NO: 157 (VHFW2), and SEQ ID NO: 166 (VHFW3)) and the light chain framework regions 1-3 of BAP049-hum04 (e.g., SEQ ID NO: 177 (VLFW1), SEQ ID NO: 191 (VLFW2), and SEQ ID NO: 205 (VLFW3)).

In some embodiments, the anti-PD-1 antibody molecule comprises the heavy chain framework regions 1-3 of BAP049-hum05 or BAP049-Clone-B (e.g., SEQ ID NO: 147 (VHFW1), SEQ ID NO: 153 (VHFW2), and SEQ ID NO: 162 (VHFW3)) and the light chain framework regions 1-3 of BAP049-hum05 or BAP049-Clone-B (e.g., SEQ ID NO: 177 (VLFW1), SEQ ID NO: 191 (VLFW2), and SEQ ID NO: 205 (VLFW3)).

In some embodiments, the anti-PD-1 antibody molecule comprises the heavy chain framework regions 1-3 of BAP049-hum06 (e.g., SEQ ID NO: 147 (VHFW1), SEQ ID NO: 153 (VHFW2), and SEQ ID NO: 162 (VHFW3)) and the light chain framework regions 1-3 of BAP049-hum06 (e.g., SEQ ID NO: 181 (VLFW1), SEQ ID NO: 187 (VLFW2), and SEQ ID NO: 196 (VLFW3)).

In some embodiments, the anti-PD-1 antibody molecule comprises the heavy chain framework regions 1-3 of BAP049-hum07 (e.g., SEQ ID NO: 147 (VHFW1), SEQ ID NO: 153 (VHFW2), and SEQ ID NO: 162 (VHFW3)) and the light chain framework regions 1-3 of BAP049-hum07 (e.g., SEQ ID NO: 177 (VLFW1), SEQ ID NO: 191 (VLFW2), and SEQ ID NO: 196 (VLFW3)).

In some embodiments, the anti-PD-1 antibody molecule comprises the heavy chain framework regions 1-3 of BAP049-hum08 (e.g., SEQ ID NO: 147 (VHFW1), SEQ ID NO: 157 (VHFW2), and SEQ ID NO: 166 (VHFW3)) and the light chain framework regions 1-3 of BAP049-hum08 (e.g., SEQ ID NO: 174 (VLFW1), SEQ ID NO: 187 (VLFW2), and SEQ ID NO: 196 (VLFW3)).

In some embodiments, the anti-PD-1 antibody molecule comprises the heavy chain framework regions 1-3 of BAP049-hum09 or BAP049-Clone-C (e.g., SEQ ID NO: 147 (VHFW1), SEQ ID NO: 153 (VHFW2), and SEQ ID NO: 162 (VHFW3)) and the light chain framework regions 1-3 of BAP049-hum09 or BAP049-Clone-C (e.g., SEQ ID NO: 174 (VLFW1), SEQ ID NO: 187 (VLFW2), and SEQ ID NO: 196 (VLFW3)).

In some embodiments, the anti-PD-1 antibody molecule comprises the heavy chain framework regions 1-3 of BAP049-hum10 or BAP049-Clone-D (e.g., SEQ ID NO: 147 (VHFW1), SEQ ID NO: 157 (VHFW2), and SEQ ID NO: 166 (VHFW3)) and the light chain framework regions 1-3 of BAP049-hum10 or BAP049-Clone-D (e.g., SEQ ID NO: 177 (VLFW1), SEQ ID NO: 187 (VLFW2), and SEQ ID NO: 196 (VLFW3)).

In some embodiments, the anti-PD-1 antibody molecule comprises the heavy chain framework regions 1-3 of BAP049-hum11 or BAP049-Clone-E (e.g., SEQ ID NO: 147 (VHFW1), SEQ ID NO: 153 (VHFW2), and SEQ ID NO: 162 (VHFW3)) and the light chain framework regions 1-3 of BAP049-hum11 or BAP049-Clone-E (e.g., SEQ ID NO: 177 (VLFW1), SEQ ID NO: 187 (VLFW2), and SEQ ID NO: 196 (VLFW3)).

In some embodiments, the anti-PD-1 antibody molecule comprises the heavy chain framework regions 1-3 of BAP049-hum12 (e.g., SEQ ID NO: 147 (VHFW1), SEQ ID NO: 153 (VHFW2), and SEQ ID NO: 162 (VHFW3)) and the light chain framework regions 1-3 of BAP049-hum12 (e.g., SEQ ID NO: 185 (VLFW1), SEQ ID NO: 194 (VLFW2), and SEQ ID NO: 196 (VLFW3)).

In some embodiments, the anti-PD-1 antibody molecule comprises the heavy chain framework regions 1-3 of BAP049-hum13 (e.g., SEQ ID NO: 147 (VHFW1), SEQ ID NO: 153 (VHFW2), and SEQ ID NO: 162 (VHFW3)) and the light chain framework regions 1-3 of BAP049-hum13 (e.g., SEQ ID NO: 183 (VLFW1), SEQ ID NO: 191 (VLFW2), and SEQ ID NO: 196 (VLFW3)).

In some embodiments, the anti-PD-1 antibody molecule comprises the heavy chain framework regions 1-3 of BAP049-hum14 (e.g., SEQ ID NO: 151 (VHFW1), SEQ ID NO: 157 (VHFW2), and SEQ ID NO: 166 (VHFW3)) and the light chain framework regions 1-3 of BAP049-hum14 (e.g., SEQ ID NO: 177 (VLFW1), SEQ ID NO: 187 (VLFW2), and SEQ ID NO: 196 (VLFW3)).

In some embodiments, the anti-PD-1 antibody molecule comprises the heavy chain framework regions 1-3 of BAP049-hum15 (e.g., SEQ ID NO: 151 (VHFW1), SEQ ID NO: 157 (VHFW2), and SEQ ID NO: 166 (VHFW3)) and the light chain framework regions 1-3 of BAP049-hum15 (e.g., SEQ ID NO: 174 (VLFW1), SEQ ID NO: 187 (VLFW2), and SEQ ID NO: 196 (VLFW3)).

In some embodiments, the anti-PD-1 antibody molecule comprises the heavy chain framework regions 1-3 of BAP049-hum16 (e.g., SEQ ID NO: 147 (VHFW1), SEQ ID NO: 160 (VHFW2), and SEQ ID NO: 166 (VHFW3)) and the light chain framework regions 1-3 of BAP049-hum16 (e.g., SEQ ID NO: 174 (VLFW1), SEQ ID NO: 187 (VLFW2), and SEQ ID NO: 196 (VLFW3)).

In some embodiments, the anti-PD-1 antibody molecule further comprises the heavy chain framework region 4 (VHFW4) of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E (e.g., SEQ ID NO: 169) and the light chain framework region 4 (VLFW4) of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E (e.g., SEQ ID NO: 208).

In some embodiments, the anti-PD-1 antibody molecule comprises a heavy chain framework region having a combination of framework regions FW1, FW2 and FW3 as shown in FIG. 5 or 7. In other embodiment, the antibody molecule comprises a light chain framework region having a combination of framework regions FW1, FW2 and FW3 as shown in FIG. 5 or 7. In yet other embodiments, the antibody molecule comprises a heavy chain framework region having a combination of framework regions FW1, FW2 and FW3 as shown in FIG. 5 or 7, and a light chain framework region having a combination of framework regions FW1, FW2 and FW3 as shown in FIG. 5 or 7.

In one embodiment, the heavy or light chain variable domain, or both, of the anti-PD-1 antibody molecule includes an amino acid sequence, which is substantially identical to an amino acid disclosed herein, e.g., at least 80%, 85%, 90%, 92%, 95%, 97%, 98%, 99% or higher identical to a variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-Clone-A, BAP049-Clone-B, BAP049-Clone-C, BAP049-Clone-D, or BAP049-Clone-E; or as described in Table 1, or encoded by the nucleotide sequence in Table 1; or which differs at least 1 or 5 residues, but less than 40, 30, 20, or 10 residues, from a variable region of an antibody described herein.

In one embodiment, the heavy or light chain variable region, or both, of the anti-PD-1 antibody molecule includes an amino acid sequence encoded by a nucleic acid sequence described herein or a nucleic acid that hybridizes to a nucleic acid sequence described herein (e.g., a nucleic acid sequence as shown in Tables 1 and 2) or its complement, e.g., under low stringency, medium stringency, or high stringency, or other hybridization condition described herein.

In another embodiment, the anti-PD-1 antibody molecule comprises at least one, two, three, or four antigen-binding regions, e.g., variable regions, having an amino acid sequence as set forth in Table 1, or a sequence substantially identical thereto (e.g., a sequence at least about 85%, 90%, 95%, 99% or more identical thereto, or which differs by no more than 1, 2, 5, 10, or 15 amino acid residues from the sequences shown in Table 1. In another embodiment, the anti-PD-1 antibody molecule includes a VH and/or VL domain encoded by a nucleic acid having a nucleotide sequence as set forth in Table 1, or a sequence substantially identical thereto (e.g., a sequence at least about 85%, 90%, 95%, 99% or more identical thereto, or which differs by no more than 3, 6, 15, 30, or 45 nucleotides from the sequences shown in Table 1.

In yet another embodiment, the anti-PD-1 antibody molecule comprises at least one, two, or three CDRs from a heavy chain variable region having an amino acid sequence as set forth in Table 1, or a sequence substantially homologous thereto (e.g., a sequence at least about 85%, 90%, 95%, 99% or more identical thereto, and/or having one, two, three or more substitutions, insertions or deletions, e.g., conserved substitutions). In yet another embodiment, the anti-PD-1 antibody molecule comprises at least one, two, or three CDRs from a light chain variable region having an amino acid sequence as set forth in Table 1, or a sequence substantially homologous thereto (e.g., a sequence at least about 85%, 90%, 95%, 99% or more identical thereto, and/or having one, two, three or more substitutions, insertions or deletions, e.g., conserved substitutions). In yet another embodiment, the anti-PD-1 antibody molecule comprises at least one, two, three, four, five or six CDRs from heavy and light chain variable regions having an amino acid sequence as set forth in Table 1), or a sequence substantially homologous thereto (e.g., a sequence at least about 85%, 90%, 95%, 99% or more identical thereto, and/or having one, two, three or more substitutions, insertions or deletions, e.g., conserved substitutions).

In one embodiment, the anti-PD-1 antibody molecule comprises at least one, two, or three CDRs and/or hypervariable loops from a heavy chain variable region having an amino acid sequence of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E, as summarized in Table 1, or a sequence substantially identical thereto (e.g., a sequence at least about 85%, 90%, 95%, 99% or more identical thereto, and/or having one, two, three or more substitutions, insertions or deletions, e.g., conserved substitutions). In another embodiment, the anti-PD-1 antibody molecule comprises at least one, two, or three CDRs and/or hypervariable loops from a light chain variable region having an amino acid sequence of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E, as summarized in Table 1, or a sequence substantially identical thereto (e.g., a sequence at least about 85%, 90%, 95%, 99% or more identical thereto, and/or having one, two, three or more substitutions, insertions or deletions, e.g., conserved substitutions). In one embodiment, the anti-PD-1 antibody molecule comprises all six CDRs and/or hypervariable loops described herein, e.g., described in Table 1.

In one embodiment, the anti-PD-1 antibody molecule has a variable region that is identical in sequence, or which differs by 1, 2, 3, or 4 amino acids from a variable region described herein (e.g., an FR region disclosed herein).

In one embodiment, the anti-PD-1 antibody molecule is a full antibody or fragment thereof (e.g., a Fab, F(ab')$_2$, Fv, or a single chain Fv fragment (scFv)). In certain embodiments, the anti-PD-1 antibody molecule is a monoclonal antibody or an antibody with single specificity. The anti-PD-1 antibody molecule can also be a humanized, chimeric, camelid, shark, or an in vitro-generated antibody molecule. In one embodiment, the anti-PD-1 antibody molecule thereof is a humanized antibody molecule. The heavy and light chains of the anti-PD-1 antibody molecule can be full-length (e.g., an antibody can include at least one, and preferably two, complete heavy chains, and at least one, and preferably two, complete light chains) or can include an antigen-binding fragment (e.g., a Fab, F(ab')$_2$, Fv, a single chain Fv fragment, a single domain antibody, a diabody (dAb), a bivalent antibody, or bispecific antibody or fragment thereof, a single domain variant thereof, or a camelid antibody).

In yet other embodiments, the anti-PD-1 antibody molecule has a heavy chain constant region (Fc) chosen from, e.g., the heavy chain constant regions of IgG1, IgG2, IgG3, IgG4, IgM, IgA1, IgA2, IgD, and IgE; particularly, chosen from, e.g., the heavy chain constant regions of IgG1, IgG2, IgG3, and IgG4, more particularly, the heavy chain constant region of IgG1 or IgG2 (e.g., human IgG1, IgG2 or IgG4). In one embodiment, the heavy chain constant region is human IgG1. In another embodiment, the anti-PD-1 antibody molecule has a light chain constant region chosen from, e.g., the light chain constant regions of kappa or lambda, preferably kappa (e.g., human kappa). In one embodiment, the constant region is altered, e.g., mutated, to modify the properties of the anti-PD-1 antibody molecule (e.g., to increase or decrease one or more of: Fc receptor binding, antibody glycosylation, the number of cysteine residues, effector cell function, or complement function). For example, the constant region is mutated at positions 296 (M to Y), 298 (S to T), 300 (T to E), 477 (H to K) and 478 (N to F) to alter Fc receptor binding (e.g., the mutated positions correspond to positions 132 (M to Y), 134 (S to T), 136 (T to E), 313 (H to K) and 314 (N to F) of SEQ ID NOs: 212 or 214; or positions 135 (M to Y), 137 (S to T), 139 (T to E), 316 (H to K) and 317 (N to F) of SEQ ID NOs: 215, 216, 217 or 218). In another embodiment, the heavy chain constant region of an IgG4, e.g., a human IgG4, is mutated at position 228 according to EU numbering (e.g., S to P), e.g., as shown in Table 3. In certain embodiments, the anti-PD-1 antibody molecules comprises a human IgG4 mutated at position 228 according to EU numbering (e.g., S to P), e.g., as shown in Table 3; and a kappa light chain constant region, e.g., as shown in Table 3. In still another embodiment, the heavy chain constant region of an IgG1, e.g., a human IgG1, is mutated at one or more of position 297 according to EU numbering (e.g., N to A), position 265 according to EU numbering (e.g., D to A), position 329 according to EU numbering (e.g., P to A), position 234 according to EU numbering (e.g., L to A), or position 235 according to EU numbering (e.g., L to A), e.g., as shown in Table 3. In certain embodiments, the anti-PD-1 antibody molecules comprises a human IgG1 mutated at one or more of the aforesaid positions, e.g., as shown in Table 3; and a kappa light chain constant region, e.g., as shown in Table 3.

In one embodiment, the anti-PD-1 antibody molecule is isolated or recombinant.

In one embodiment, the anti-PD-1 antibody molecule is a humanized antibody molecule.

In one embodiment, the anti-PD-1 antibody molecule has a risk score based on T cell epitope analysis of less than 700, 600, 500, 400 or less.

In one embodiment, the anti-PD-1 antibody molecule is a humanized antibody molecule and has a risk score based on T cell epitope analysis of 300 to 700, 400 to 650, 450 to 600, or a risk score as described herein.

In one embodiment, the anti-PD-1 antibody molecule includes:

(a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 33;

(b) a VH comprising a VHCDR1 amino acid sequence chosen from SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32;

(c) a VH comprising a VHCDR1 amino acid sequence of SEQ ID NO: 224, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33; or (d) a VH comprising a VHCDR1 amino acid sequence of SEQ ID NO: 224; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32.

In certain embodiments, the anti-PD-1 antibody molecule comprises:

(i) a heavy chain variable region (VH) comprising a VHCDR1 amino acid sequence chosen from SEQ ID NO: 1, SEQ ID NO: 4 or SEQ ID NO: 224; a VHCDR2 amino acid sequence of SEQ ID NO: 2; and a VHCDR3 amino acid sequence of SEQ ID NO: 3; and (ii) a light chain variable region (VL) comprising a VLCDR1 amino acid sequence of SEQ ID NO: 10, a VLCDR2 amino acid sequence of SEQ ID NO: 11, and a VLCDR3 amino acid sequence of SEQ ID NO: 32.

In other embodiments, the anti-PD-1 antibody molecule comprises:

(i) a heavy chain variable region (VH) comprising a VHCDR1 amino acid sequence chosen from SEQ ID NO: 1, SEQ ID NO: 4 or SEQ ID NO: 224; a VHCDR2 amino acid sequence of SEQ ID NO: 5, and a VHCDR3 amino acid sequence of SEQ ID NO: 3; and (ii) a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 33.

In embodiments of the aforesaid antibody molecules, the VHCDR1 comprises the amino acid sequence of SEQ ID NO: 1. In other embodiments, the VHCDR1 comprises the amino acid sequence of SEQ ID NO: 4. In yet other embodiments, the VHCDR1 amino acid sequence of SEQ ID NO: 224.

In embodiments, the aforesaid antibody molecules have a heavy chain variable region comprising at least one framework (FW) region comprising the amino acid sequence of any of SEQ ID NOs: 147, 151, 153, 157, 160, 162, 166, or 169, or an amino acid sequence at least 90% identical thereto, or having no more than two amino acid substitutions, insertions or deletions compared to the amino acid sequence of any of SEQ ID NOs: 147, 151, 153, 157, 160, 162, 166, or 169.

In other embodiments, the aforesaid antibody molecules have a heavy chain variable region comprising at least one framework region comprising the amino acid sequence of any of SEQ ID NOs: 147, 151, 153, 157, 160, 162, 166, or 169.

In yet other embodiments, the aforesaid antibody molecules have a heavy chain variable region comprising at least two, three, or four framework regions comprising the amino acid sequences of any of SEQ ID NOs: 147, 151, 153, 157, 160, 162, 166, or 169.

In other embodiments, the aforesaid antibody molecules comprise a VHFW1 amino acid sequence of SEQ ID NO:

147 or 151, a VHFW2 amino acid sequence of SEQ ID NO: 153, 157, or 160, and a VHFW3 amino acid sequence of SEQ ID NO: 162 or 166, and, optionally, further comprising a VHFW4 amino acid sequence of SEQ ID NO: 169.

In other embodiments, the aforesaid antibody molecules have a light chain variable region comprising at least one framework region comprising the amino acid sequence of any of SEQ ID NOs: 174, 177, 181, 183, 185, 187, 191, 194, 196, 200, 202, 205, or 208, or an amino acid sequence at least 90% identical thereto, or having no more than two amino acid substitutions, insertions or deletions compared to the amino acid sequence of any of 174, 177, 181, 183, 185, 187, 191, 194, 196, 200, 202, 205, or 208.

In other embodiments, the aforesaid antibody molecules have a light chain variable region comprising at least one framework region comprising the amino acid sequence of any of SEQ ID NOs: 174, 177, 181, 183, 185, 187, 191, 194, 196, 200, 202, 205, or 208.

In other embodiments, the aforesaid antibody molecules have a light chain variable region comprising at least two, three, or four framework regions comprising the amino acid sequences of any of SEQ ID NOs: 174, 177, 181, 183, 185, 187, 191, 194, 196, 200, 202, 205, or 208.

In other embodiments, the aforesaid antibody molecules comprise a VLFW1 amino acid sequence of SEQ ID NO: 174, 177, 181, 183, or 185, a VLFW2 amino acid sequence of SEQ ID NO: 187, 191, or 194, and a VLFW3 amino acid sequence of SEQ ID NO: 196, 200, 202, or 205, and, optionally, further comprising a VLFW4 amino acid sequence of SEQ ID NO: 208.

In other embodiments, the aforesaid antibodies comprise a heavy chain variable domain comprising an amino acid sequence at least 85% identical to any of SEQ ID NOs: 38, 50, 82, or 86.

In other embodiments, the aforesaid antibody molecules comprise a heavy chain variable domain comprising the amino acid sequence of SEQ ID NO: 38, 50, 82, or 86.

In other embodiments, the aforesaid antibody molecules comprise a light chain variable domain comprising an amino acid sequence at least 85% identical to any of SEQ ID NOs: 42, 46, 54, 58, 62, 66, 70, 74, or 78.

In other embodiments, the aforesaid antibody molecules comprise a light chain variable domain comprising the amino acid sequence of SEQ ID NO: 42, 46, 54, 58, 62, 66, 70, 74, or 78.

In other embodiments, the aforesaid antibody molecules comprise a heavy chain variable domain comprising the amino acid sequence of SEQ ID NO: 38.

In other embodiments, the aforesaid antibody molecules comprise a heavy chain comprising the amino acid sequence of SEQ ID NO: 40.

In other embodiments, the aforesaid antibody molecules comprise a heavy chain comprising the amino acid sequence of SEQ ID NO: 91.

In other embodiments, the aforesaid antibody molecules comprise a heavy chain variable domain comprising the amino acid sequence of SEQ ID NO: 50.

In other embodiments, the aforesaid antibody molecules comprise a heavy chain comprising the amino acid sequence of SEQ ID NO: 52 or SEQ ID NO: 102.

In other embodiments, the aforesaid antibody molecules comprise a heavy chain variable domain comprising the amino acid sequence of SEQ ID NO: 82.

In other embodiments, the aforesaid antibody molecules comprise a heavy chain comprising the amino acid sequence of SEQ ID NO: 84.

In other embodiments, the aforesaid antibody molecules comprise a heavy chain variable domain comprising the amino acid sequence of SEQ ID NO: 86.

In other embodiments, the aforesaid antibody molecules comprise a heavy chain comprising the amino acid sequence of SEQ ID NO: 88.

In other embodiments, the aforesaid antibody molecules comprise a light chain variable domain comprising the amino acid sequence of SEQ ID NO: 42.

In other embodiments, the aforesaid antibody molecules comprise a light chain comprising the amino acid sequence of SEQ ID NO: 44.

In other embodiments, the aforesaid antibody molecules comprise a light chain variable domain comprising the amino acid sequence of SEQ ID NO: 46.

In other embodiments, the aforesaid antibody molecules comprise a light chain comprising the amino acid sequence of SEQ ID NO: 48.

In other embodiments, the aforesaid antibody molecules comprise a light chain variable domain comprising the amino acid sequence of SEQ ID NO: 54.

In other embodiments, the aforesaid antibody molecules comprise a light chain comprising the amino acid sequence of SEQ ID NO: 56.

In other embodiments, the aforesaid antibody molecules comprise a light chain variable domain comprising the amino acid sequence of SEQ ID NO: 58.

In other embodiments, the aforesaid antibody molecules comprise a light chain comprising the amino acid sequence of SEQ ID NO: 60.

In other embodiments, the aforesaid antibody molecules comprise a light chain variable domain comprising the amino acid sequence of SEQ ID NO: 62.

In other embodiments, the aforesaid antibodies comprise a light chain comprising the amino acid sequence of SEQ ID NO: 64.

In other embodiments, the aforesaid antibody molecules comprise a light chain variable domain comprising the amino acid sequence of SEQ ID NO: 66.

In other embodiments, the aforesaid antibody molecules comprise a light chain comprising the amino acid sequence of SEQ ID NO: 68.

In other embodiments, the aforesaid antibody molecules comprise a light chain variable domain comprising the amino acid sequence of SEQ ID NO: 70.

In other embodiments, the aforesaid antibody molecules comprise a light chain comprising the amino acid sequence of SEQ ID NO: 72.

In other embodiments, the aforesaid antibody molecules comprise a light chain variable domain comprising the amino acid sequence of SEQ ID NO: 74.

In other embodiments, the aforesaid antibody molecules comprise a light chain comprising the amino acid sequence of SEQ ID NO: 76.

In other embodiments, the aforesaid antibody molecules comprise a light chain variable domain comprising the amino acid sequence of SEQ ID NO: 78.

In other embodiments, the aforesaid antibody molecules comprise a light chain comprising the amino acid sequence of SEQ ID NO: 80.

In other embodiments, the aforesaid antibody molecules comprise a heavy chain variable domain comprising the amino acid sequence of SEQ ID NO: 38 and a light chain variable domain comprising the amino acid sequence of SEQ ID NO: 42.

In other embodiments, the aforesaid antibody molecules comprise a heavy chain variable domain comprising the amino acid sequence of SEQ ID NO: 38 and a light chain variable domain comprising the amino acid sequence of SEQ ID NO: 66.

In other embodiments, the aforesaid antibody molecules comprise a heavy chain variable domain comprising the amino acid sequence of SEQ ID NO: 38 and a light chain variable domain comprising the amino acid sequence of SEQ ID NO: 70.

In other embodiments, the aforesaid antibody molecules comprise a heavy chain variable domain comprising the amino acid sequence of SEQ ID NO: 50 and a light chain variable domain comprising the amino acid sequence of SEQ ID NO: 70.

In other embodiments, the aforesaid antibody molecules comprise a heavy chain variable domain comprising the amino acid sequence of SEQ ID NO: 38 and a light chain variable domain comprising the amino acid sequence of SEQ ID NO: 46.

In other embodiments, the aforesaid antibody molecules comprise a heavy chain variable domain comprising the amino acid sequence of SEQ ID NO: 50 and a light chain variable domain comprising the amino acid sequence of SEQ ID NO: 46.

In other embodiments, the aforesaid antibody molecules comprise a heavy chain variable domain comprising the amino acid sequence of SEQ ID NO: 50 and a light chain variable domain comprising the amino acid sequence of SEQ ID NO: 54.

In other embodiments, the aforesaid antibody molecules comprise a heavy chain variable domain comprising the amino acid sequence of SEQ ID NO: 38 and a light chain variable domain comprising the amino acid sequence of SEQ ID NO: 54.

In other embodiments, the aforesaid antibody molecules comprise a heavy chain variable domain comprising the amino acid sequence of SEQ ID NO: 38 and a light chain variable domain comprising the amino acid sequence of SEQ ID NO: 58.

In other embodiments, the aforesaid antibody molecules comprise a heavy chain variable domain comprising the amino acid sequence of SEQ ID NO: 38 and a light chain variable domain comprising the amino acid sequence of SEQ ID NO: 62.

In other embodiments, the aforesaid antibody molecules comprise a heavy chain variable domain comprising the amino acid sequence of SEQ ID NO: 50 and a light chain variable domain comprising the amino acid sequence of SEQ ID NO: 66.

In other embodiments, the aforesaid antibody molecules comprise a heavy chain variable domain comprising the amino acid sequence of SEQ ID NO: 38 and a light chain variable domain comprising the amino acid sequence of SEQ ID NO: 74.

In other embodiments, the aforesaid antibody molecules comprise a heavy chain variable domain comprising the amino acid sequence of SEQ ID NO: 38 and a light chain variable domain comprising the amino acid sequence of SEQ ID NO: 78.

In other embodiments, the aforesaid antibody molecules comprise a heavy chain variable domain comprising the amino acid sequence of SEQ ID NO: 82 and a light chain variable domain comprising the amino acid sequence of SEQ ID NO: 70.

In other embodiments, the aforesaid antibody molecules comprise a heavy chain variable domain comprising the amino acid sequence of SEQ ID NO: 82 and a light chain variable domain comprising the amino acid sequence of SEQ ID NO: 66.

In other embodiments, the aforesaid antibody molecules comprise a heavy chain variable domain comprising the amino acid sequence of SEQ ID NO: 86 and a light chain variable domain comprising the amino acid sequence of SEQ ID NO: 66.

In other embodiments, the aforesaid antibody molecules comprise a heavy chain comprising the amino acid sequence of SEQ ID NO: 91 and a light chain comprising the amino acid sequence of SEQ ID NO: 44.

In other embodiments, the aforesaid antibody molecules comprise a heavy chain comprising the amino acid sequence of SEQ ID NO: 91 and a light chain comprising the amino acid sequence of SEQ ID NO: 56.

In other embodiments, the aforesaid antibody molecules comprise a heavy chain comprising the amino acid sequence of SEQ ID NO: 91 and a light chain comprising the amino acid sequence of SEQ ID NO: 68.

In other embodiments, the aforesaid antibody molecules comprise a heavy chain comprising the amino acid sequence of SEQ ID NO: 91 and a light chain comprising the amino acid sequence of SEQ ID NO: 72.

In other embodiments, the aforesaid antibody molecules comprise a heavy chain comprising the amino acid sequence of SEQ ID NO: 102 and a light chain comprising the amino acid sequence of SEQ ID NO: 72.

In other embodiments, the aforesaid antibody molecules comprise a heavy chain comprising the amino acid sequence of SEQ ID NO: 40 and a light chain comprising the amino acid sequence of SEQ ID NO: 44.

In other embodiments, the aforesaid antibody molecules comprise a heavy chain comprising the amino acid sequence of SEQ ID NO: 40 and a light chain comprising the amino acid sequence of SEQ ID NO: 48.

In other embodiments, the aforesaid antibody molecules comprise a heavy chain comprising the amino acid sequence of SEQ ID NO: 52 and a light chain comprising the amino acid sequence of SEQ ID NO: 48.

In other embodiments, the aforesaid antibody molecules comprise a heavy chain comprising the amino acid sequence of SEQ ID NO: 52 and a light chain comprising the amino acid sequence of SEQ ID NO: 56.

In other embodiments, the aforesaid antibody molecules comprise a heavy chain comprising the amino acid sequence of SEQ ID NO: 40 and a light chain comprising the amino acid sequence of SEQ ID NO: 56.

In other embodiments, the aforesaid antibodies comprise a heavy chain comprising the amino acid sequence of SEQ ID NO: 40 and a light chain comprising the amino acid sequence of SEQ ID NO: 60.

In other embodiments, the aforesaid antibody molecules comprise a heavy chain comprising the amino acid sequence of SEQ ID NO: 40 and a light chain comprising the amino acid sequence of SEQ ID NO: 64.

In other embodiments, the aforesaid antibody molecules comprise a heavy chain comprising the amino acid sequence of SEQ ID NO: 52 and a light chain comprising the amino acid sequence of SEQ ID NO: 68.

In other embodiments, the aforesaid antibody molecules comprise a heavy chain comprising the amino acid sequence of SEQ ID NO: 40 and a light chain comprising the amino acid sequence of SEQ ID NO: 68.

In other embodiments, the aforesaid antibody molecules comprise a heavy chain comprising the amino acid sequence of SEQ ID NO: 52 and a light chain comprising the amino acid sequence of SEQ ID NO: 72.

In other embodiments, the aforesaid antibody molecules comprise a heavy chain comprising the amino acid sequence of SEQ ID NO: 40 and a light chain comprising the amino acid sequence of SEQ ID NO: 72.

In other embodiments, the aforesaid antibody molecules comprise a heavy chain comprising the amino acid sequence of SEQ ID NO: 40 and a light chain comprising the amino acid sequence of SEQ ID NO: 76.

In other embodiments, the aforesaid antibody molecules comprise a heavy chain comprising the amino acid sequence of SEQ ID NO: 40 and a light chain comprising the amino acid sequence of SEQ ID NO: 80.

In other embodiments, the aforesaid antibody molecules comprise a heavy chain comprising the amino acid sequence of SEQ ID NO: 84 and a light chain comprising the amino acid sequence of SEQ ID NO: 72.

In other embodiments, the aforesaid antibodies comprise a heavy chain comprising the amino acid sequence of SEQ ID NO: 84 and a light chain comprising the amino acid sequence of SEQ ID NO: 68.

In other embodiments, the aforesaid antibody molecules comprise a heavy chain comprising the amino acid sequence of SEQ ID NO: 88 and a light chain comprising the amino acid sequence of SEQ ID NO: 68.

In other embodiments, the aforesaid antibody molecules are chosen from a Fab, F(ab')2, Fv, or a single chain Fv fragment (scFv).

In other embodiments, the aforesaid antibody molecules comprise a heavy chain constant region selected from IgG1, IgG2, IgG3, and IgG4.

In other embodiments, the aforesaid antibody molecules comprise a light chain constant region chosen from the light chain constant regions of kappa or lambda.

In other embodiments, the aforesaid antibody molecules comprise a human IgG4 heavy chain constant region with a mutation at position 228 according to EU numbering or position 108 of SEQ ID NO: 212 or 214 and a kappa light chain constant region.

In other embodiments, the aforesaid antibody molecules comprise a human IgG4 heavy chain constant region with a Serine to Proline mutation at position 228 according to EU numbering or position 108 of SEQ ID NO: 212 or 214 and a kappa light chain constant region.

In other embodiments, the aforesaid antibody molecules comprise a human IgG1 heavy chain constant region with an Asparagine to Alanine mutation at position 297 according to EU numbering or position 180 of SEQ ID NO: 216 and a kappa light chain constant region.

In other embodiments, the aforesaid antibody molecules comprise a human IgG1 heavy chain constant region with an Aspartate to Alanine mutation at position 265 according to EU numbering or position 148 of SEQ ID NO: 217, and Proline to Alanine mutation at position 329 according to EU numbering or position 212 of SEQ ID NO: 217 and a kappa light chain constant region.

In other embodiments, the aforesaid antibody molecules comprise a human IgG1 heavy chain constant region with a Leucine to Alanine mutation at position 234 according to EU numbering or position 117 of SEQ ID NO: 218, and Leucine to Alanine mutation at position 235 according to EU numbering or position 118 of SEQ ID NO: 218 and a kappa light chain constant region.

In other embodiments, the aforesaid antibody molecules are capable of binding to human PD-1 with a dissociation constant ($K_D$) of less than about 0.2 nM.

In some embodiments, the aforesaid antibody molecules bind to human PD-1 with a $K_D$ of less than about 0.2 nM, 0.15 nM, 0.1 nM, 0.05 nM, or 0.02 nM, e.g., about 0.13 nM to 0.03 nM, e.g., about 0.077 nM to 0.088 nM, e.g., about 0.083 nM, e.g., as measured by a Biacore method.

In other embodiments, the aforesaid antibody molecules bind to cynomolgus PD-1 with a $K_D$ of less than about 0.2 nM, 0.15 nM, 0.1 nM, 0.05 nM, or 0.02 nM, e.g., about 0.11 nM to 0.08 nM, e.g., about 0.093 nM, e.g., as measured by a Biacore method.

In certain embodiments, the aforesaid antibody molecules bind to both human PD-1 and cynomolgus PD-1 with similar $K_D$, e.g., in the nM range, e.g., as measured by a Biacore method. In some embodiments, the aforesaid antibody molecules bind to a human PD-1-Ig fusion protein with a $K_D$ of less than about 0.1 nM, 0.075 nM, 0.05 nM, 0.025 nM, or 0.01 nM, e.g., about 0.04 nM, e.g., as measured by ELISA.

In some embodiments, the aforesaid antibody molecules bind to Jurkat cells that express human PD-1 (e.g., human PD-1-transfected Jurkat cells) with a $K_D$ of less than about 0.1 nM, 0.075 nM, 0.05 nM, 0.025 nM, or 0.01 nM, e.g., about 0.06 nM, e.g., as measured by FACS analysis.

In some embodiments, the aforesaid antibody molecules bind to cynomolgus T cells with a $K_D$ of less than about 1 nM, 0.75 nM, 0.5 nM, 0.25 nM, or 0.1 nM, e.g., about 0.4 nM, e.g., as measured by FACS analysis.

In some embodiments, the aforesaid antibody molecules bind to cells that express cynomolgus PD-1 (e.g., cells transfected with cynomolgus PD-1) with a $K_D$ of less than about 1 nM, 0.75 nM, 0.5 nM, 0.25 nM, or 0.01 nM, e.g., about 0.6 nM, e.g., as measured by FACS analysis.

In certain embodiments, the aforesaid antibody molecules are not cross-reactive with mouse or rat PD-1. In other embodiments, the aforesaid antibodies are cross-reactive with rhesus PD-1. For example, the cross-reactivity can be measured by a Biacore method or a binding assay using cells that expresses PD-1 (e.g., human PD-1-expressing 300.19 cells). In other embodiments, the aforesaid antibody molecules bind an extracellular Ig-like domain of PD-1.

In other embodiments, the aforesaid antibody molecules are capable of reducing binding of PD-1 to PD-L1, PD-L2, or both, or a cell that expresses PD-L1, PD-L2, or both. In some embodiments, the aforesaid antibody molecules reduce (e.g., block) PD-L1 binding to a cell that expresses PD-1 (e.g., human PD-1-expressing 300.19 cells) with an IC50 of less than about 1.5 nM, 1 nM, 0.8 nM, 0.6 nM, 0.4 nM, 0.2 nM, or 0.1 nM, e.g., between about 0.79 nM and about 1.09 nM, e.g., about 0.94 nM, or about 0.78 nM or less, e.g., about 0.3 nM. In some embodiments, the aforesaid antibodies reduce (e.g., block) PD-L2 binding to a cell that expresses PD-1 (e.g., human PD-1-expressing 300.19 cells) with an IC50 of less than about 2 nM, 1.5 nM, 1 nM, 0.5 nM, or 0.2 nM, e.g., between about 1.05 nM and about 1.55 nM, or about 1.3 nM or less, e.g., about 0.9 nM.

In other embodiments, the aforesaid antibody molecules are capable of enhancing an antigen-specific T cell response.

In embodiments, the antibody molecule is a monospecific antibody molecule or a bispecific antibody molecule. In embodiments, the antibody molecule has a first binding specificity for PD-1 and a second binding specificity for TIM-3, LAG-3, CEACAM (e.g., CEACAM-1, CEACAM-3, and/or CEACAM-5), PD-L1 or PD-L2. In embodiments, the antibody molecule comprises an antigen binding fragment of an antibody, e.g., a half antibody or antigen binding fragment of a half antibody.

In some embodiments, the aforesaid antibody molecules increase the expression of IL-2 from cells activated by Staphylococcal enterotoxin B (SEB) (e.g., at 25 μg/mL) by at least about 2, 3, 4, 5-fold, e.g., about 2 to 3-fold, e.g., about 2 to 2.6-fold, e.g., about 2.3-fold, compared to the expression of IL-2 when an isotype control (e.g., IgG4) is used, e.g., as measured in a SEB T cell activation assay or a human whole blood ex vivo assay.

In some embodiments, the aforesaid antibody molecules increase the expression of IFN-γ from T cells stimulated by anti-CD3 (e.g., at 0.1 μg/mL) by at least about 2, 3, 4, 5-fold, e.g., about 1.2 to 3.4-fold, e.g., about 2.3-fold, compared to the expression of IFN-γ when an isotype control (e.g., IgG4) is used, e.g., as measured in an IFN-γ activity assay.

In some embodiments, the aforesaid antibody molecules increase the expression of IFN-γ from T cells activated by SEB (e.g., at 3 pg/mL) by at least about 2, 3, 4, 5-fold, e.g., about 0.5 to 4.5-fold, e.g., about 2.5-fold, compared to the expression of IFN-γ when an isotype control (e.g., IgG4) is used, e.g., as measured in an IFN-γ activity assay.

In some embodiments, the aforesaid antibody molecules increase the expression of IFN-γ from T cells activated with an CMV peptide by at least about 2, 3, 4, 5-fold, e.g., about 2 to 3.6-fold, e.g., about 2.8-fold, compared to the expression of IFN-γ when an isotype control (e.g., IgG4) is used, e.g., as measured in an IFN-γ activity assay.

In some embodiments, the aforesaid antibody molecules increase the proliferation of $CD8^+$ T cells activated with an CMV peptide by at least about 1, 2, 3, 4, 5-fold, e.g., about 1.5-fold, compared to the proliferation of $CD8^+$ T cells when an isotype control (e.g., IgG4) is used, e.g., as measured by the percentage of CD8+ T cells that passed through at least n (e.g., n=2 or 4) cell divisions.

In certain embodiments, the aforesaid antibody molecules has a Cmax between about 100 μg/mL and about 500 μg/mL, between about 150 μg/mL and about 450 μg/mL, between about 250 μg/mL and about 350 μg/mL, or between about 200 μg/mL and about 400 μg/mL, e.g., about 292.5 μg/mL, e.g., as measured in monkey.

In certain embodiments, the aforesaid antibody molecules has a $T_{112}$ between about 250 hours and about 650 hours, between about 300 hours and about 600 hours, between about 350 hours and about 550 hours, or between about 400 hours and about 500 hours, e.g., about 465.5 hours, e.g., as measured in monkey.

In some embodiments, the aforesaid antibody molecules bind to PD-1 with a Kd slower than $5\times10^{-4}$, $1\times10^{-4}$, $5\times10^{-5}$, or $1\times10^{-5}$ $s^{-1}$, e.g., about $2.13\times10^{-4}$ $s^{-1}$, e.g., as measured by a Biacore method. In some embodiments, the aforesaid antibody molecules bind to PD-1 with a Ka faster than $1\times10^4$, $5\times10^4$, $1\times10^5$, or $5\times10^5$ $M^{-1}$ $s^{-1}$, e.g., about $2.78\times10^5$ $M^{-1}$ $s^{-1}$, e.g., as measured by a Biacore method.

In some embodiments, the aforesaid anti-PD-1 antibody molecules bind to one or more residues within the C strand, CC' loop, C' strand and FG loop of PD-1. The domain structure of PD-1 is described, e.g., in Cheng et al., "Structure and Interactions of the Human Programmed Cell Death 1 Receptor" *J. Biol. Chem.* 2013, 288:11771-11785. As described in Cheng et. al., the C strand comprises residues F43-M50, the CC' loop comprises S51-N54, the C' strand comprises residues Q55-F62, and the FG loop comprises residues L1084114 (amino acid numbering according to Chang et al. supra). Accordingly, in some embodiments, an anti-PD-1 antibody as described herein binds to at least one residue in one or more of the ranges F43-M50, S51-N54, Q55-F62, and L1084114 of PD-1. In some embodiments, an anti-PD-1 antibody as described herein binds to at least one residue in two, three, or all four of the ranges F43-M50, S51-N54, Q55-F62, and L108-1114 of PD-1. In some embodiments, the anti-PD-1 antibody binds to a residue in PD-1 that is also part of a binding site for one or both of PD-L1 and PD-L2.

In another aspect, the invention provides an isolated nucleic acid molecule encoding any of the aforesaid antibody molecules, vectors and host cells thereof.

An isolated nucleic acid encoding the antibody heavy chain variable region or light chain variable region, or both, of any the aforesaid antibody molecules is also provided.

In one embodiment, the isolated nucleic acid encodes heavy chain CDRs 1-3, wherein said nucleic acid comprises a nucleotide sequence of SEQ ID NO: 108-112, 223, 122-126, 133-137, or 144-146.

In another embodiment, the isolated nucleic acid encodes light chain CDRs 1-3, wherein said nucleic acid comprises a nucleotide sequence of SEQ ID NO: 113-120, 127-132, or 138-143.

In other embodiments, the aforesaid nucleic acid further comprises a nucleotide sequence encoding a heavy chain variable domain, wherein said nucleotide sequence is at least 85% identical to any of SEQ ID NO: 39, 51, 83, 87, 90, 95, or 101.

In other embodiments, the aforesaid nucleic acid further comprises a nucleotide sequence encoding a heavy chain variable domain, wherein said nucleotide sequence comprises any of SEQ ID NO: 39, 51, 83, 87, 90, 95, or 101.

In other embodiments, the aforesaid nucleic acid further comprises a nucleotide sequence encoding a heavy chain, wherein said nucleotide sequence is at least 85% identical to any of SEQ ID NO: 41, 53, 85, 89, 92, 96, or 103.

In other embodiments, the aforesaid nucleic acid further comprises a nucleotide sequence encoding a heavy chain, wherein said nucleotide sequence comprises any of SEQ ID NO: 41, 53, 85, 89, 92, 96, or 103.

In other embodiments, the aforesaid nucleic acid further comprises a nucleotide sequence encoding a light chain variable domain, wherein said nucleotide sequence is at least 85% identical to any of SEQ ID NO: 43, 47, 55, 59, 63, 67, 71, 75, 79, 93, 97, 99, 104, or 106.

In other embodiments, the aforesaid nucleic acid further comprises a nucleotide sequence encoding a light chain variable domain, wherein said nucleotide sequence comprises any of SEQ ID NO: 43, 47, 55, 59, 63, 67, 71, 75, 79, 93, 97, 99, 104, or 106.

In other embodiments, the aforesaid nucleic acid further comprises a nucleotide sequence encoding a light chain, wherein said nucleotide sequence is at least 85% identical to any of SEQ ID NO: 45, 49, 57, 61, 65, 69, 73, 77, 81, 94, 98, 100, 105 or 107.

In other embodiments, the aforesaid nucleic acid further comprises a nucleotide sequence encoding a light chain, wherein said nucleotide sequence comprises any of SEQ ID NO: 45, 49, 57, 61, 65, 69, 73, 77, 81, 94, 98, 100, 105 or 107.

In certain embodiments, one or more expression vectors and host cells comprising the aforesaid nucleic acids are provided.

A method of producing an antibody molecule or fragment thereof, comprising culturing the host cell as described herein under conditions suitable for gene expression is also provided.

In one aspect, the invention features a method of providing an antibody molecule described herein. The method includes: providing a PD-1 antigen (e.g., an antigen comprising at least a portion of a PD-1 epitope); obtaining an antibody molecule that specifically binds to the PD-1 polypeptide; and evaluating if the antibody molecule specifically binds to the PD-1 polypeptide, or evaluating efficacy of the antibody molecule in modulating, e.g., inhibiting, the activity of the PD-1. The method can further include administering the antibody molecule to a subject, e.g., a human or non-human animal.

In another aspect, the invention provides, compositions, e.g., pharmaceutical compositions, which include a pharmaceutically acceptable carrier, excipient or stabilizer, and at least one of the therapeutic agents, e.g., anti-PD-1 antibody molecules described herein. In one embodiment, the composition, e.g., the pharmaceutical composition, includes a combination of the antibody molecule and one or more agents, e.g., a therapeutic agent or other antibody molecule, as described herein. In one embodiment, the antibody molecule is conjugated to a label or a therapeutic agent.

Additional Inhibitors of PD-1 and Other Immune Checkpoint Molecules

In some embodiments, the PD-1 inhibitor is an inhibitor, e.g., an anti-PD-1 antibody molecule, other than the anti-PD-1 antibody molecule of Table 1. In certain embodiments, the PD-1 inhibitor comprises an anti-PD-1 antibody molecule of Table 1 and an anti-PD-1 antibody molecule other than the antibody molecule of Table 1. In other embodiments, the PD-1 inhibitor is an anti-PD-1 antibody chosen from Nivolumab, Pembrolizumab or Pidilizumab.

In some embodiments, the anti-PD-1 antibody is Nivolumab. Alternative names for Nivolumab include MDX-1106, MDX-1106-04, ONO-4538, or BMS-936558. In some embodiments, the anti-PD-1 antibody is Nivolumab (CAS Registry Number: 946414-94-4). Nivolumab is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449 and WO2006/121168. In one embodiment, the inhibitor of PD-1 is Nivolumab, and having a sequence disclosed herein (or a sequence substantially identical or similar thereto, e.g., a sequence at least 85%, 90%, 95% identical or higher to the sequence specified).

The heavy and light chain amino acid sequences of Nivolumab are as follows:

```
Heavy chain
                              (SEQ ID NO: 242)
QVQLVESGGGVVQPGRSLRLDCKASGITFSNSGMHWVRQAPGKGLEWVAV

IWYDGSKRYYADSVKGRFTISRDNSKNTLFLQMNSLRAEDTAVYYCATND

DYWGQGTLVTVSSASTKGPSVFPLAPCSRSTSESTAALGCLVKDYFPEPV

TVSWNSGALTSGVHTFPAVLQSSGLYSLSSVVTVPSSSLGTKTYTCNVDH

KPSNTKVDKRVESKYGPPCPPCPAPEFLGGPSVFLFPPKPKDTLMISRTP

EVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLY

SRLTVDKSRWQEGNVFSCSVMHEALHNHYTQKSLSLSLGK

Light chain
                              (SEQ ID NO: 243)
EIVLTQSPATLSLSPGERATLSCRASQSVSSYLAWYQQKPGQAPRLLIYD

ASNRATGIPARFSGSGSGTDFTLTISSLEPEDFAVYYCQQSSNWPRTFGQ

GTKVEIKRTVAAPSVFIFPPSDEQLKSGTASVVCLLNNFYPREAKVQWKV
```

-continued

```
DNALQSGNSQESVTEQDSKDSTYSLSSTLTLSKADYEKHKVYACEVTHQG

LSSPVTKSFNRGEC
```

In some embodiments, the anti-PD-1 antibody is Pembrolizumab. Pembrolizumab (also referred to as Lambrolizumab, MK-3475, MK03475, SCH-900475 or KEYTRUDA®; Merck) is a humanized IgG4 monoclonal antibody that binds to PD-1. Pembrolizumab and other humanized anti-PD-1 antibodies are disclosed in Hamid, O. et al. (2013) *New England Journal of Medicine* 369 (2): 134-44, U.S. Pat. No. 8,354,509 and WO2009/114335. The heavy and light chain amino acid sequences of Pembrolizumab are as follows:

Exemplary PD-L1 or PD-L2 Inhibitors

In one embodiment, a combination described herein includes a PD-L1 or PD-L2 inhibitor. In some embodiments, the combination is used to treat a cancer, e.g., a cancer described herein, e.g., a solid tumor or a hematologic malignancy. In some embodiments, the cancer is a thyroid cancer (e.g., an anaplastic thyroid cancer), an endometrial cancer, a lymphoma, a lung cancer (e.g., a non-small cell lung cancer), a breast cancer (e.g., a triple negative breast cancer), or an MSI-high cancer. In some embodiments, the PD-L1 inhibitor is an anti-PD-L1 antibody or fragment thereof.

In an embodiment, the anti-PD-L1 antibody or fragment thereof is an anti-PD-L1 antibody molecule disclosed in U.S. Patent Application Publication No. 2016/0108123

```
Heavy chain
                                             (SEQ ID NO: 244)
QVQLVQSGVE VKKPGASVKV SCKASGYTFT NYYMYWVRQA PGQGLEWMGG     50

INPSNGGTNF NEKFKNRVTL TTDSSTTTAY MELKSLQFDD TAVYYCARRD    100

YRFDMGFDYW GQGTTVTVSS ASTKGPSVFP LAPCSRSTSE STAALGCLVK    150

DYFPEPVTVS WNSGALTSGV HTFPAVLQSS GLYSLSSVVT VPSSSLGTKT    200

YTCNVDHKPS NTKVDKRVES KYGPPCPPCP APEFLGGPSV FLFPPKPKDT    250

LMISRTPEVT CVVVDVSQED PEVQFNWYVD GVEVHNAKTK PREEQFNSTY    300

RVVSVLTVLH QDWLNGKEYK CKVSNKGLPS SIEKTISKAK GQPREPQVYT    350

LPPSQEEMTK NQVSLTCLVK GFYPSDIAVE WESNGQPENN YKTTPPVLDS    400

DGSFFLYSRL TVDKSRWQEG NVFSCSVMHE ALHNHYTQKS LSLSLGK      447

Ligh chain
                                             (SEQ ID NO: 245)
EIVLTQSPAT LSLSPGERAT LSCRASKGVS TSGYSYLHWY QQKPGQAPRL     50

LIYLASYLES GVPARFSGSG SGTDFTLTIS SLEPEDFAVY YCQHSRDLPL    100

TFGGGTKVEI KRTVAAPSVF IFPPSDEQLK SGTASVVCLL NNFYPREAKV    150

QWKVDNALQS GNSQESVTEQ DSKDSTYSLS STLTLSKADY EKHKVYACEV    200

THQGLSSPVT KSFNRGEC                                       218'
```

In one embodiment, the inhibitor of PD-1 is Pembrolizumab disclosed in, e.g., U.S. Pat. No. 8,354,509 and WO 2009/114335, and having a sequence disclosed herein (or a sequence substantially identical or similar thereto, e.g., a sequence at least 85%, 90%, 95% identical or higher to the sequence specified).

In some embodiments, the anti-PD-1 antibody is Pidilizumab. Pidilizumab (CT-011; Cure Tech) is a humanized IgG1k monoclonal antibody that binds to PD-1. Pidilizumab and other humanized anti-PD-1 monoclonal antibodies are disclosed in WO2009/101611.

Other anti-PD-1 antibodies include AMP 514 (Amplimmune), among others, e.g., anti-PD-1 antibodies disclosed in U.S. Pat. No. 8,609,089, US 2010028330, and/or US 20120114649. Additional exemplary anti-PD-1 antibodies also include, e.g., REGN2810, BGB-108, and BGB-A317.

In some embodiments, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 inhibitor is AMP-224 (B7-DCIg; Amplimmune; e.g., disclosed in WO2010/027827 and WO2011/066342), is a PD-L2 Fc fusion soluble receptor that blocks the interaction between PD-1 and B7-H1.

(U.S. Ser. No. 14/881,888), entitled "Antibody Molecules to PD-L1 and Uses Thereof," incorporated by reference in its entirety.

In one embodiment, the anti-PD-L1 antibody molecule includes at least one or two heavy chain variable domain (optionally including a constant region), at least one or two light chain variable domain (optionally including a constant region), or both, comprising the amino acid sequence of any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O; or as described in Table 1 of US 2016/0108123, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-L1 antibody molecule includes at least one, two, or three complementarity determining regions (CDRs) from a heavy chain variable region and/or a light chain variable region of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-0; or as described in Table 1 of US 2016/0108123, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-L1 antibody molecule includes at least one, two, or three CDRs (or collectively all of the CDRs) from a heavy chain variable region comprising an amino acid sequence shown in Table 1 of US 2016/0108123, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In yet another embodiment, the anti-PD-L1 antibody molecule includes at least one, two, or three CDRs (or collectively all of the CDRs) from a light chain variable region comprising an amino acid sequence shown in Table 1 of US 2016/0108123, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1. In certain embodiments, the anti-PD-L1 antibody molecule includes a substitution in a light chain CDR, e.g., one or more substitutions in a CDR1, CDR2 and/or CDR3 of the light chain.

In another embodiment, the anti-PD-L1 antibody molecule includes at least one, two, three, four, five or six CDRs (or collectively all of the CDRs) from a heavy and light chain variable region comprising an amino acid sequence shown in Table 1, or encoded by a nucleotide sequence shown in Table 1 of US 2016/0108123. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In one embodiment, the anti-PD-L1 antibody molecule includes:

(i) a heavy chain variable region (VH) including a VHCDR1 amino acid sequence chosen from SEQ ID NO: 1, SEQ ID NO: 4 or SEQ ID NO: 195; a VHCDR2 amino acid sequence of SEQ ID NO: 2; and a VHCDR3 amino acid sequence of SEQ ID NO: 3, each disclosed in Table 1 of US 2016/0108123; and (ii) a light chain variable region (VL) including a VLCDR1 amino acid sequence of SEQ ID NO: 9, a VLCDR2 amino acid sequence of SEQ ID NO: 10, and a VLCDR3 amino acid sequence of SEQ ID NO: 11, each disclosed in Table 1 of US 2016/0108123.

In another embodiment, the anti-PD-L1 antibody molecule includes:

(i) a heavy chain variable region (VH) including a VHCDR1 amino acid sequence chosen from SEQ ID NO: 1, SEQ ID NO: 4 or SEQ ID NO: 195; a VHCDR2 amino acid sequence of SEQ ID NO: 5, and a VHCDR3 amino acid sequence of SEQ ID NO: 3, each disclosed in Table 1 of US 2016/0108123; and (ii) a light chain variable region (VL) including a VLCDR1 amino acid sequence of SEQ ID NO: 12, a VLCDR2 amino acid sequence of SEQ ID NO: 13, and a VLCDR3 amino acid sequence of SEQ ID NO: 14, each disclosed in Table 1 of US 2016/0108123.

In one embodiment, the anti-PD-L1 antibody molecule comprises the VHCDR1 amino acid sequence of SEQ ID NO: 1 disclosed in Table 1 of US 2016/0108123. In another embodiment, the anti-PD-L1 antibody molecule comprises the VHCDR1 amino acid sequence of SEQ ID NO: 4 disclosed in Table 1 of US 2016/0108123. In yet another embodiment, the anti-PD-L1 antibody molecule comprises the VHCDR1 amino acid sequence of SEQ ID NO: 195, each disclosed in Table 1 of US 2016/0108123.

In one embodiment, the anti-PD-L1 antibody molecule comprises the VH amino acid sequence of EVQLVQS-GAEVKKPGATVKISCKVSGYTFT-SYWMYWVRQARGQRLEWIGRIDPNSGSTKYN EKFKNRFTISRDNSKNTLYLQMNSLRAEDTAVYY-CARDYRKGLYAMDYWGQGTTVTVSS (SEQ ID NO: 316) or SEQ ID NO: 78 of US 2016/0108123, and the VL amino acid sequence of AIQLTQSPSSL-SASVGDRVTITCKASQDVGTA-VAWYLQKPGQSPQLLIYWASTRHTGVPSRFS GSGSGTDFTFTISSLEAEDAATYYCQQYNSY-PLTFGQGTKVEIK (SEQ ID NO: 317) or SEQ ID NO: 82 of US 2016/0108123, each disclosed in Table 1 of US 2016/0108123. In one embodiment, the anti-PD-L1 antibody molecule comprises the VH amino acid sequence of EVQLVQSGAEVKKPGATVKISCKVSGYTFT-SYWMYWVRQATGQGLEWMGRIDPNSGSTKY NEKFKNRVTITADKSTSTAYMELSSLRSEDTAVYY-CARDYRKGLYAMDYWGQGTTVTVSS (SEQ ID NO: 318) or SEQ ID NO: 30 of US 2016/0108123, and the VL amino acid sequence of DVVMTQSPLSLPVTLGQPASIS-CKASQDVGTAVAWYQQKPGQAPRLLIYWAST-RHTGVPSRF SGSGSGTEFTLTISSLQPDDFA-TYYCQQYNSYPLTFGQGTKVEIK (SEQ ID NO: 319) or SEQ ID NO: 66 of US 2016/0108123, each disclosed in Table 1 of US 2016/0108123.

In one embodiment, the anti-PD-L1 antibody molecule comprises the heavy chain amino acid sequence of SEQ ID NO: 80 of US 2016/0108123, and the light chain amino acid sequence of SEQ ID NO: 84 of US 2016/0108123, each disclosed in Table 1 of US 2016/0108123. In one embodiment, the anti-PD-L1 antibody molecule comprises the heavy chain amino acid sequence of SEQ ID NO: 96 of US 2016/0108123, and the light chain amino acid sequence of SEQ ID NO: 68 of US 2016/0108123, each disclosed in Table 1 of US 2016/0108123.

A PD-L1 inhibitor (e.g., an anti-PD-L1 antibody molecule described herein) or a composition described herein can be formulated into a formulation (e.g., a dose formulation or dosage form) suitable for administration (e.g., intravenous administration) to a subject as described herein.

In certain embodiments, the formulation is a liquid formulation. In other embodiments, the formulation is a lyophilized formulation, e.g., lyophilized or dried from a liquid formulation. In other embodiments, the formulation is a reconstituted formulation, e.g., reconstituted from a lyophilized formulation.

In some embodiments, the formulation comprises the PD-L1 inhibitor (e.g., the anti-PD-L1 antibody molecule) and a buffering agent.

In some embodiments, the formulation comprises a PD-L1 inhibitor (e.g., an anti-PD-L1 antibody molecule) present at a concentration of 10 to 500 mg/mL, e.g., 25 to 250 mg/mL, 50 to 150 mg/mL, 50 to 100 mg/mL, or 100 to 200 mg/mL, e.g., 50 mg/mL, 100 mg/mL, 150 mg/mL, or 200 mg/mL. In certain embodiments, the PD-1 inhibitor (e.g., the anti-PD-1 antibody molecule) is present at a concentration of 50 to 150 mg/mL, e.g., 100 mg/mL. In some embodiments, the formulation has a pH of 5 to 6 (e.g., 5.5). In certain embodiments, the formulation is for intravenous infusion, e.g., following dilution. In some embodiments, the formulation comprises one or more pharmaceutically acceptable excipients.

In some embodiments, the formulation comprises a buffering agent comprising histidine (e.g., a histidine buffer). In some embodiments, the formulation comprises L-histidine, L-histidine hydrochloride monohydrate, or both. In certain embodiments, the buffering agent (e.g., histidine buffer) is present at a concentration of 1 mM to 20 mM, e.g., 2 mM to 15 mM, 3 mM to 10 mM, 4 mM to 9 mM, 5 mM to 8 mM, or 6 mM to 7 mM, e.g., 1 mM, 2 mM, 3 mM, 4 mM, 5 mM, 6 mM, 6.7 mM, 7 mM, 8 mM, 9 mM, 10 mM, 11 mM, 12 mM, 13 mM, 14 mM, 15 mM, 16 mM, 17 mM, 18 mM, 19 mM, or 20 mM.

In some embodiments, the formulation further comprises a carbohydrate. In certain embodiments, the carbohydrate is sucrose. In some embodiments, the carbohydrate (e.g., sucrose) is present at a concentration of 50 mM to 150 mM, e.g., 25 mM to 150 mM, 50 mM to 100 mM, 60 mM to 90 mM, 70 mM to 80 mM, or 70 mM to 75 mM, e.g., 25 mM, 50 mM, 60 mM, 70 mM, 73.3 mM, 80 mM, 90 mM, 100 mM, or 150 mM.

In some embodiments, the formulation further comprises a surfactant. In certain embodiments, the surfactant is polysorbate 20. In some embodiments, the surfactant or polysorbate 20) is present at a concentration of 0.005% to 0.025% (w/w), e.g., 0.0075% to 0.02% or 0.01% to 0.015% (w/w), e.g., 0.005%, 0.0075%, 0.01%, 0.013%, 0.015%, or 0.02% (w/w).

In some embodiments, the formulation comprises an inhibitor of PD-L1 (e.g., an anti-PD-L1 antibody molecule), a histidine buffer, a carbohydrate, and a surfactant. In certain embodiments, the formulation comprises an inhibitor of PD-L1 (e.g., an anti-PD-L1 antibody molecule), and one or more (e.g., two, three, or all) of L-histidine, L-histidine hydrochloride monohydrate, sucrose, or polysorbate 20, e.g., at a pH of 5 to 6. In certain embodiments, the formulation comprises an inhibitor of PD-L1 (e.g., an anti-PD-L1 antibody molecule), L-histidine, L-histidine hydrochloride monohydrate, sucrose, and polysorbate 20, e.g., at a pH of 5 to 6.

A formulation described herein can be stored in a container. In certain embodiments, 50 mg to 150 mg, e.g., 80 mg to 120 mg, 90 mg to 110 mg, 100 mg to 120 mg, 100 mg to 110 mg, 110 mg to 120 mg, or 110 mg to 130 mg, of the PD-L1 inhibitor (e.g., the anti-PD-L1 antibody molecule), is present in the container (e.g., vial).

Other exemplary buffering agents that can be used in the formulation described herein include, but are not limited to, an arginine buffer, a citrate buffer, or a phosphate buffer. Other exemplary carbohydrates that can be used in the formulation described herein include, but are not limited to, trehalose, mannitol, sorbitol, or a combination thereof. The formulation described herein may also contain a tonicity agent, e.g., sodium chloride, and/or a stabilizing agent, e.g., an amino acid (e.g., glycine, arginine, methionine, or a combination thereof).

In one embodiment, the combination includes an inhibitor of PD-L1 or an antibody molecule disclosed in US 2016/0108123, and an inhibitor of PD-1 (e.g., an anti-PD-1 antibody described herein).

The combination of a PD-1 inhibitor (e.g., an anti-PD-1 antibody molecule described herein) and a PD-L1 inhibitor (e.g., an anti-PD-L1 antibody molecule described herein) has been tested in an MC38 murine model of colon adenocarcinoma. A surrogate anti-mouse PD-1 antibody, RMP1-14 was used in the study. Co-administration of RMP1-14 and the anti-PD-L1 antibody molecule resulted in enhanced anti-tumor activity relative to both single agents in this model. For example, the anti-PD-L1 antibody molecule and RMP1-14 in combination resulted in 4/10 animals with complete responses as well as 3/10 animals demonstrating partial responses. The combination therapy resulted in non-significant enhancement of the median time to end point to 46 days, which was 21 days longer than animals treated with isotype and over 20 days longer than either antibody alone.

In some embodiments, the inhibitor of PD-1 (e.g., the anti-PD-1 antibody molecule) binds PD-1 and inhibits its interaction with PD-L1, PD-L2, or both. In some embodiments, the inhibitor of PD-L1 (e.g., the anti-PD-L1 antibody molecule) binds PD-L1 and inhibits its interaction with PD-1, B7.1, or both. PD-1 and PD-L1 mediate overlapping but also distinct functions on the T-cell. Both receptors can deliver negative signals to the T-cell when engaged. PD-L1 can mediate an immunosuppressive function through its interaction with B7.1, e.g., blocking the ability of B7.1 to activate T-cells through binding to CD28 and further dampening the generation of an immune response (Butte et al. *Immunity*. 2007; 27(1):111-22). Without wishing to be bound by theory, it is believed that in some embodiments, a combined inhibition of PD-L1 and PD-1 can result in a non-redundant and/or complementary anti-cancer immunity (Dong et al. *Nat Med*. 2002; 8(8):793-800; Yamazaki et al *J Immunol*. 2002; 169(10):5538-45; Taube et al. *Sci Transl Med*. 2012; 4(127):127ra37). In some embodiments, a combination of an inhibitor of PD-1 (e.g., an anti-PD-1 antibody molecule described herein) and an inhibitor of PD-L1 (e.g., an anti-PD-L1 antibody molecule described herein) increases activation of T cells, compared to the inhibitor of PD-1 or the inhibitor of PD-L1 alone. In some embodiments, a combination of an inhibitor of PD-1 (e.g., an anti-PD-1 antibody molecule described herein) and an inhibitor of PD-L1 (e.g., an anti-PD-L1 antibody molecule described herein) has a synergistic anti-cancer activity.

In one embodiment, the PD-L1 inhibitor or an anti-PD-L1 antibody molecule disclosed in US 2016/0108123, is administered at a dose (e.g., a flat dose) between 10 mg and 2000 mg, e.g., between 20 mg and 1600 mg, between 40 mg and 1200 mg, between 80 mg and 800 mg, between 100 mg and 600 mg, between 200 mg and 300 mg, between 20 mg and 100 mg, between 40 mg and 200 mg, between 100 mg and 400 mg, between 200 mg and 600 mg, between 800 mg and 1200 mg, or between 1200 mg and 1600 mg, e.g., at a dose (e.g., a flat dose) of about 10 mg, 20 mg, 40 mg, 80 mg, 100 mg, 150 mg, 200 mg, 240 mg, 300 mg, 400 mg, 500 mg, 600 mg, 800 mg, 1000 mg, 1200 mg, 1600 mg, or 2000 mg, e.g., once every three weeks, once every four weeks, or once every six weeks.

In one embodiment, the PD-L1 inhibitor or an anti-PD-L1 antibody molecule disclosed in US 2016/0108123, is administered at a dose between 20 mg and 1200 mg (e.g., between 80 mg and 800 mg, e.g., about 20 mg, 80 mg, 240 mg, 800 mg, or 1200 mg), e.g., once every three weeks or once every six weeks. For example, the PD-L1 inhibitor or an anti-PD- L1 antibody molecule disclosed in US 2016/0108123 can be administered at a dose between 10 mg and 100 mg (e.g., between 20 mg and 80 mg, e.g., 20 mg, 40 mg, or 80 mg), e.g., once every three weeks or once every six weeks. In one embodiment, the PD-L1 inhibitor or an anti-PD-L1 antibody molecule disclosed in US 2016/0108123, is administered by intravenous infusion.

In one embodiment, the PD-L1 inhibitor or an anti-PD-L1 antibody molecule disclosed in US 2016/0108123, is administered at a dose between 10 mg and 100 mg (e.g., between 20 mg and 80 mg, e.g., 20 mg, 40 mg, or 80 mg), e.g., once every three weeks or once every six weeks, e.g., by intravenous infusion, and the PD-1 inhibitor (e.g., the anti-PD-1 antibody molecule) is administered at a dose between 50 mg and 500 mg (e.g., between 100 mg and 400 mg, e.g., at a dose of about 100 mg, 200 mg, 300 mg, or 400 mg), e.g., once every 3 weeks or once every 4 weeks, e.g., by intravenous infusion. In some embodiments, the inhibitor of PD-1 (e.g., the anti-PD-1 antibody molecule) is administered at a dose between 100 mg and 300 mg (e.g., at a dose of about 100 mg, 200 mg, or 300 mg), e.g., once every 3 weeks, e.g., by intravenous infusion. In some embodiments, the PD-L1 inhibitor or an anti-PD-L1 antibody molecule disclosed in US 2016/0108123, is administered at a dose of about 20 mg, e.g., once every three weeks, and the inhibitor of PD-1 (e.g., the anti-PD-1 antibody molecule) is administered at a dose of about 100 mg or 300 mg, e.g., once every three weeks. In some embodiments, the PD-L1 inhibitor or an anti-PD-L1 antibody molecule disclosed in US 2016/0108123, is administered at a dose of about 20 mg, 80 mg, 240 mg, 800 mg, or 1200 mg, e.g., once every three weeks, and the inhibitor of PD-1 (e.g., the anti-PD-1 antibody molecule) is administered at a dose of about 300 mg, e.g., once every three weeks.

In one embodiment, the PD-L1 inhibitor or an anti-PD-L1 antibody molecule disclosed in US 2016/0108123, is administered at a dose between 10 mg and 50 mg (e.g., about 20 mg), e.g., once every three weeks or once every six weeks, e.g., by intravenous infusion, and the PD-1 inhibitor (e.g., the anti-PD-1 antibody molecule) is administered at a dose between 50 mg and 200 mg (e.g., about 100 mg), e.g., once every 3 weeks, e.g., by intravenous infusion.

In one embodiment, the PD-L1 inhibitor or an anti-PD-L1 antibody molecule disclosed in US 2016/0108123, is administered at a dose between 10 mg and 50 mg (e.g., about 20 mg), e.g., once every three weeks or once every six weeks, e.g., by intravenous infusion, and the PD-1 inhibitor (e.g., the anti-PD-1 antibody molecule) is administered at a dose between 200 mg and 400 mg (e.g., about 300 mg), e.g., once every 3 weeks, e.g., by intravenous infusion.

In one embodiment, the PD-L1 inhibitor or an anti-PD-L1 antibody molecule disclosed in US 2016/0108123, is administered at a dose between 50 mg and 100 mg (e.g., about 80 mg), e.g., once every three weeks or once every six weeks, e.g., by intravenous infusion, and the PD-1 inhibitor (e.g., the anti-PD-1 antibody molecule) is administered at a dose between 200 mg and 400 mg (e.g., about 300 mg), e.g., once every 3 weeks, e.g., by intravenous infusion.

In one embodiment, the PD-L1 inhibitor or an anti-PD-L1 antibody molecule disclosed in US 2016/0108123, is administered at a dose between 200 mg and 300 mg (e.g., about 240 mg), e.g., once every three weeks or once every six weeks, e.g., by intravenous infusion, and the PD-1 inhibitor (e.g., the anti-PD-1 antibody molecule) is administered at a dose between 200 mg and 400 mg (e.g., about 300 mg), e.g., once every 3 weeks, e.g., by intravenous infusion.

In one embodiment, the PD-L1 inhibitor or an anti-PD-L1 antibody molecule disclosed in US 2016/0108123, is administered at a dose between 500 mg and 1000 mg (e.g., about 800 mg), e.g., once every three weeks or once every six weeks, e.g., by intravenous infusion, and the PD-1 inhibitor (e.g., the anti-PD-1 antibody molecule) is administered at a dose between 200 mg and 400 mg (e.g., about 300 mg), e.g., once every 3 weeks, e.g., by intravenous infusion.

In one embodiment, the PD-L1 inhibitor or an anti-PD-L1 antibody molecule disclosed in US 2016/0108123, is administered at a dose between 1000 mg and 1500 mg (e.g., about 1200 mg), e.g., once every three weeks or once every six weeks, e.g., by intravenous infusion, and the PD-1 inhibitor (e.g., the anti-PD-1 antibody molecule) is administered at a dose between 200 mg and 400 mg (e.g., about 300 mg), e.g., once every 3 weeks, e.g., by intravenous infusion.

In some embodiments, the PD-L1 inhibitor or an anti-PD-L1 antibody molecule disclosed in US 2016/0108123 is administered before the PD-1 inhibitor (e.g., the anti-PD-1 antibody molecule) is administered. For example, the PD-L1 inhibitor or an anti-PD-L1 antibody molecule disclosed in US 2016/0108123 can be administered first and followed by a dextrose solution flush for about 1 hour before starting administration of the PD-1 inhibitor (e.g., the anti-PD-1 antibody molecule). In some embodiments, the PD-L1 inhibitor or an anti-PD-L1 antibody molecule disclosed in US 2016/0108123 is administered after the PD-1 inhibitor (e.g., the anti-PD-1 antibody molecule) is administered.

In one embodiment, the PD-L1 inhibitor or an anti-PD-L1 antibody molecule disclosed in US 2016/0108123, is administered in combination with an inhibitor of PD-1 (e.g., an anti-PD-1 antibody molecule) to treat a solid tumor, e.g., a lung cancer (e.g., a non-small cell lung cancer), a breast cancer (e.g., a triple negative breast cancer), a uterine cancer (e.g., an endometrial carcinoma), or a thyroid cancer (e.g., an anaplastic thyroid carcinoma).

In some embodiments, the PD-L1 inhibitor is an antibody molecule. In some embodiments, the anti-PD-L1 inhibitor is chosen from YW243.55.S70, MPDL3280A, MEDI-4736, MSB-0010718C, or MDX-1105.

In some embodiments, the anti-PD-L1 antibody is MSB0010718C. MSB0010718C (also referred to as A09-246-2; Merck Serono) is a monoclonal antibody that binds to PD-L1. Pembrolizumab and other humanized anti-PD-L1 antibodies are disclosed in WO2013/079174, and having a sequence disclosed herein (or a sequence substantially identical or similar thereto, e.g., a sequence at least 85%, 90%, 95% identical or higher to the sequence specified). The heavy and light chain amino acid sequences of MSB0010718C include at least the following:

```
Heavy chain (SEQ ID NO: 24 as disclosed in
WO2013/079174)
                                (SEQ ID NO: 246)
EVQLLESGGGLVQPGGSLRLSCAASGFTFSSYIMMWVRQAPGKGLEWVSS

IYPSGGITFYADKGRFTISRDNSKNTLYLQMNSLRAEDTAVYYCARIKLG

TVTTVDYWGQGTLVTVSS

Light chain (SEQ ID NO: 25 as disclosed in
WO2013/079174)
                                (SEQ ID NO: 247)
QSALTQPASVSGSPGQSITISCTGTSSDVGGYNYVSWYQQHPGKAPKLMI

YDVSNRPSGVSNRFSGSKSGNTASLTISGLQAEDEADYYCSSYTSSSTRV

FGTGTKVTVL
```

In one embodiment, the PD-L1 inhibitor is YW243.55.S70. The YW243.55.S70 antibody is an anti-PD-L1 antibody described in WO 2010/077634 (heavy and light chain variable region sequences shown in SEQ ID NOs. 20 and 21, respectively), and having a sequence disclosed therein (or a sequence substantially identical or similar thereto, e.g., a sequence at least 85%, 90%, 95% identical or higher to the sequence specified).

In one embodiment, the PD-L1 inhibitor is MDX-1105. MDX-1105, also known as BMS-936559, is an anti-PD-L1 antibody described in WO2007/005874, and having a sequence disclosed therein (or a sequence substantially identical or similar thereto, e.g., a sequence at least 85%, 90%, 95% identical or higher to the sequence specified).

In one embodiment, the PD-L1 inhibitor is MDPL3280A (Genentech/Roche). MDPL3280A is a human Fc optimized IgG1 monoclonal antibody that binds to PD-L1. MDPL3280A and other human monoclonal antibodies to PD-L1 are disclosed in U.S. Pat. No. 7,943,743, PCT Publication No. WO 2013/019906, and U.S Publication No.: 2012/0039906. For example, MDPL3280A (also known as atezolizumab or RO5541267) can include a heavy chain variable region comprising the amino acid sequence of SEQ ID NO: 24, as disclosed in WO 2013/019906, and a light chain variable region comprising the amino acid sequence of SEQ ID NO: 21, as disclosed in WO 2013/019906 (or a sequence substantially identical or similar thereto, e.g., a sequence at least 85%, 90%, 95% identical or higher to the sequence specified).

In one embodiment, the PD-L1 inhibitor is MEDI-4736 (also known as durvalumab). MEDI-4736 is described in WO 2011/066389 and WO 2015/036499. For example, MEDI-4736 can include a light chain variable region comprising the amino acid sequence of SEQ ID NO: 1, as disclosed in WO 2015/036499, and a heavy chain variable region comprising the amino acid sequence of SEQ ID NO:2, as disclosed in WO 2015/036499 (or a sequence substantially identical or similar thereto, e.g., a sequence at least 85%, 90%, 95% identical or higher to the sequence specified).

In other embodiments, the PD-L2 inhibitor is AMP-224. AMP-224 is a PD-L2 Fc fusion soluble receptor that blocks the interaction between PD-1 and B7-H1 (B7-DCIg; Amplimmune; e.g., disclosed in WO2010/027827 and WO2011/066342).

Exemplary LAG-3 Inhibitors

In one embodiment, a combination described herein includes a LAG-3 inhibitor. In some embodiments, the combination is used to treat a cancer, e.g., a cancer described herein, e.g., a solid tumor or a hematologic malignancy. In some embodiments, the cancer is a lung cancer (e.g., a non-small cell lung cancer), a skin cancer (e.g., a melanoma), or a renal cancer (e.g., a renal cell carcinoma). In certain embodiments, the LAG-3 inhibitor is an anti-LAG-3 antibody or fragment thereof.

In one embodiment, the anti-LAG-3 antibody or fragment thereof is an anti-LAG-3 antibody molecule as described in US 2015/0259420, entitled "Antibody Molecules to LAG-3 and Uses Thereof," incorporated by reference in its entirety.

In one embodiment, the anti-LAG-3 antibody molecule includes at least one, two, three, four, five or six CDRs (or collectively all of the CDRs) from a heavy and light chain variable region (e.g., at least one, two, or three CDRs from a heavy chain variable region, at least one, two, or three CDRs from a light chain variable region, or both) from an antibody chosen from any of BAP050-hum01, BAP050-hum02, BAP050-hum03, BAP050-hum04, BAP050- hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; as described in Table 1 of US 2015/0259420; or encoded by the nucleotide sequence in Table 1; or a sequence substantially identical (e.g., at least 80%, 85%, 90%, 92%, 95%, 97%, 98%, 99% or higher identical) to any of the aforesaid sequences, or closely related CDRs, e.g., CDRs which are identical or which have at least one amino acid alteration, but not more than two, three or four alterations (e.g., substitutions, deletions, or insertions, e.g., conservative substitutions).

In yet another embodiment, the anti-LAG-3 antibody molecule comprises at least one, two, three or four variable regions (e.g., at least one or two heavy chain variable regions (optionally including a constant region), at least one or two light chain variable regions (optionally including a constant region), or both) from an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1 of US 2015/0259420; or encoded by the nucleotide sequence in Tables 1; or a sequence substantially identical (e.g., at least 80%, 85%, 90%, 92%, 95%, 97%, 98%, 99% or higher identical) to any of the aforesaid sequences.

In yet another embodiment, the anti-LAG-3 antibody molecule includes at least one, two, or three CDRs (or collectively all of the CDRs) from a heavy chain variable region comprising an amino acid sequence shown in Table 1 of US 2015/0259420, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In yet another embodiment, the anti-LAG-3 antibody molecule includes at least one, two, or three CDRs (or collectively all of the CDRs) from a light chain variable region comprising an amino acid sequence shown in Table 1 of US 2015/0259420, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1. In certain embodiments, the anti-PD-L1 antibody molecule includes a substitution in a light chain CDR, e.g., one or more substitutions in a CDR1, CDR2 and/or CDR3 of the light chain.

In another embodiment, the anti-LAG-3 antibody molecule includes at least one, two, three, four, five or six CDRs (or collectively all of the CDRs) from a heavy and light chain variable region comprising an amino acid sequence shown in Table 1, or encoded by a nucleotide sequence shown in Table 1 of US 2015/0259420. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In one embodiment, the anti-LAG-3 antibody molecule includes:

(i) a heavy chain variable region (VH) including a VHCDR1 amino acid sequence chosen from SEQ ID NO: 1, SEQ ID NO: 4 or SEQ ID NO: 286; a VHCDR2 amino acid sequence of SEQ ID NO: 2; and a VHCDR3 amino acid sequence of SEQ ID NO: 3, each disclosed in Table 1 of US 2015/0259420; and (ii) a light chain variable region (VL) including a VLCDR1 amino acid sequence of SEQ ID NO: 10, a VLCDR2 amino acid sequence of SEQ ID NO: 11, and a VLCDR3 amino acid sequence of SEQ ID NO: 12, each disclosed in Table 1 of US 2015/0259420.

In another embodiment, the anti-LAG-3 antibody molecule includes:

(i) a heavy chain variable region (VH) including a VHCDR1 amino acid sequence chosen from SEQ ID NO: 1, SEQ ID NO: 4 or SEQ ID NO: 286; a VHCDR2 amino acid sequence of SEQ ID NO: 5, and a VHCDR3 amino acid sequence of SEQ ID NO: 3, each disclosed in Table 1 of US 2015/0259420; and (ii) a light chain variable region (VL) including a VLCDR1 amino acid sequence of SEQ ID NO: 13, a VLCDR2 amino acid sequence of SEQ ID NO: 14, and a VLCDR3 amino acid sequence of SEQ ID NO: 15, each disclosed in Table 1 of US 2015/0259420.

In one embodiment, the anti-LAG-3 antibody molecule comprises the VHCDR1 amino acid sequence of SEQ ID NO: 1. In another embodiment, the anti-LAG-3 antibody molecule comprises the VHCDR1 amino acid sequence of SEQ ID NO: 4. In yet another embodiment, the anti-LAG-3 antibody molecule comprises the VHCDR1 amino acid sequence of SEQ ID NO: 286, each disclosed in Table 1 of US 2015/0259420.

In some embodiments, the anti-LAG-3 antibody molecule comprises a VH comprising the amino acid sequence of QVQLVQSGAEVKKPGASVKVSCK-ASGFTLTNYGMNWVRQARGQRLEWIGWINTDT-GEPTY ADDFKGRFVFSLDTSVSTAYLQISSLKAED-TAVYYCARNPPYYYGTNNAEAMDYWGQGTTV TVSS (SEQ ID NO: 320) or SEQ ID NO: 104 of US 2015/0259420, and a VL comprising the amino acid sequence of DIQMTQSPSSLSASVGDRVTITCSSSQDIS-NYLNWYLQKPGQSPQLLIYYTSTLHLGVPSRFSG SGSGTEFTLTISSLQPDDFA-TYYCQQYYNLPWTFGQGTKVEIK (SEQ ID NO: 321) or SEQ ID NO: 56 of US 2015/0259420, each disclosed in Table 1 of US 2015/0259420. In some embodiments, the anti-LAG-3 antibody molecule comprises a VH comprising the amino acid sequence of QVQLVQSGAEVKKP-GASVKVSCKASGFTLTNYGMNWVRQAPGQ-GLEWMGWINTDTGEPT YADDFKGRFVFSLDTSVSTAYLQISSLKAEDTAVYY-CARNPPYYYGTNNAEAMDYWGQGTT VTVSS (SEQ ID NO: 322) or SEQ ID NO: 108 of US 2015/0259420, and a VL comprising the amino acid sequence of DIQMTQSPSSLSASVGDRVTITCSSSQDIS-NYLNWYQQKPGKAPKLLIYYTSTLHLGIPPRFSGS GYGTDFTLTIN-NIESEDAAYYFCQQYYNLPWTFGQGTKVEIK (SEQ ID NO: 323) or SEQ ID NO: 36 of US 2015/0259420, each disclosed in Table 1 of US 2015/0259420.

In some embodiments, the anti-LAG-3 antibody molecule comprises a heavy chain comprising the amino acid sequence of SEQ ID NO: 122 of US 2015/0259420, and a light chain comprising the amino acid sequence of SEQ ID NO: 58 of US 2015/0259420, each disclosed in Table 1 of US 2015/0259420. In some embodiments, the anti-LAG-3 antibody molecule comprises a heavy chain comprising the amino acid sequence of SEQ ID NO: 134 of US 2015/0259420 and a light chain comprising the amino acid sequence of SEQ ID NO: 38 of US 2015/0259420, each disclosed in Table 1 of US 2015/0259420.

In some embodiments, the anti-LAG-3 antibody is BMS-986016. BMS-986016 (also referred to as BMS986016; Bristol-Myers Squibb) is a monoclonal antibody that binds to LAG-3. BMS-986016 and other humanized anti-LAG-3 antibodies are disclosed in US 2011/0150892, WO2010/019570, and WO2014/008218.

Exemplary TIM-3 Inhibitors

In one embodiment, a combination described herein includes a TIM-3 inhibitor. In some embodiments, the combination is used to treat a cancer, e.g., a cancer described herein, e.g., a solid tumor or a hematologic malignancy. In some embodiments, the cancer is a lung cancer (e.g., a non-small cell lung cancer), a skin cancer (e.g., a melanoma), or a renal cancer (e.g., a renal cell carcinoma). In other embodiments, the cancer is other than a non-small cell lung cancer, a melanoma, and a renal cell carcinoma. In some embodiments, the TIM-3 inhibitor is an anti-TIM-3 antibody or fragment thereof.

In one embodiment, the anti-TIM-3 antibody or fragment thereof is an anti-TIM-3 antibody molecule as described in US 2015/0218274, entitled "Antibody Molecules to TIM-3 and Uses Thereof," incorporated by reference in its entirety.

In one embodiment, the anti-TIM-3 antibody molecule includes at least one, two, three, four, five or six CDRs (or collectively all of the CDRs) from a heavy and light chain variable region (e.g., at least one, two, or three CDRs from a heavy chain variable region, at least one, two, or three CDRs from a light chain variable region, or both) from an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4 of US 2015/0218274; or encoded by the nucleotide sequence in Tables 1-4; or a sequence substantially identical (e.g., at least 80%, 85%, 90%, 92%, 95%, 97%, 98%, 99% or higher identical) to any of the aforesaid sequences, or closely related CDRs, e.g., CDRs which are identical or which have at least one amino acid alteration, but not more than two, three or four alterations (e.g., substitutions, deletions, or insertions, e.g., conservative substitutions).

In yet another embodiment, the anti-TIM-3 antibody molecule comprises at least one, two, three or four variable regions (e.g., at least one or two heavy chain variable regions (optionally including a constant region), at least one or two light chain variable regions (optionally including a constant region), or both) from an antibody described herein, e.g., an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4 of US 2015/0218274; or encoded by the nucleotide sequence in Tables 1-4; or a sequence substantially identical (e.g., at least 80%, 85%, 90%, 92%, 95%, 97%, 98%, 99% or higher identical) to any of the aforesaid sequences.

In yet another embodiment, the anti-TIM-3 antibody molecule includes at least one, two, or three CDRs (or collectively all of the CDRs) from a heavy chain variable region comprising an amino acid sequence shown in Tables 1-4 of US 2015/0218274, or encoded by a nucleotide sequence shown in Tables 1-4. In one embodiment, one or more of the CDRs (or collectively all of the CDRs) have one, two, three, four, five, six or more changes, e.g., amino acid substitutions or deletions, relative to the amino acid sequence shown in Tables 1-4, or encoded by a nucleotide sequence shown in Table 1-4.

In yet another embodiment, the anti-TIM-3 antibody molecule includes at least one, two, or three CDRs (or collectively all of the CDRs) from a light chain variable region comprising an amino acid sequence shown in Tables 1-4 of US 2015/0218274, or encoded by a nucleotide sequence shown in Tables 1-4. In one embodiment, one or more of the CDRs (or collectively all of the CDRs) have one, two, three, four, five, six or more changes, e.g., amino acid substitutions or deletions, relative to the amino acid sequence shown in Tables 1-4, or encoded by a nucleotide sequence shown in Tables 1-4. In certain embodiments, the anti-TIM-3 antibody molecule includes a substitution in a light chain CDR, e.g., one or more substitutions in a CDR1, CDR2 and/or CDR3 of the light chain.

In another embodiment, the anti-TIM-3 antibody molecule includes at least one, two, three, four, five or six CDRs (or collectively all of the CDRs) from a heavy and light chain variable region comprising an amino acid sequence shown in Tables 1-4 of US 2015/0218274, or encoded by a nucleotide sequence shown in Tables 1-4. In one embodiment, one or more of the CDRs (or collectively all of the CDRs) have one, two, three, four, five, six or more changes, e.g., amino acid substitutions or deletions, relative to the amino acid sequence shown in Tables 1-4, or encoded by a nucleotide sequence shown in Tables 1-4.

In one embodiment, the anti-TIM-3 antibody molecule includes:

(a) a heavy chain variable region (VH) comprising a VHCDR1 amino acid sequence chosen from SEQ ID NO: 9; a VHCDR2 amino acid sequence of SEQ ID NO: 10; and a VHCDR3 amino acid sequence of SEQ ID NO: 5; and a light chain variable region (VL) comprising a VLCDR1 amino acid sequence of SEQ ID NO: 12, a VLCDR2 amino acid sequence of SEQ ID NO: 13, and a VLCDR3 amino acid sequence of SEQ ID NO: 14, each disclosed in Tables 1-4 of US 2015/0218274;

(b) a VH comprising a VHCDR1 amino acid sequence chosen from SEQ ID NO: 3; a VHCDR2 amino acid sequence of SEQ ID NO: 4; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8, each disclosed in Tables 1-4 of US 2015/0218274;

(c) a VH comprising a VHCDR1 amino acid sequence chosen from SEQ ID NO: 9; a VHCDR2 amino acid sequence of SEQ ID NO: 25; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14, each disclosed in Tables 1-4 of US 2015/0218274;

(d) a VH comprising a VHCDR1 amino acid sequence chosen from SEQ ID NO: 3; a VHCDR2 amino acid sequence of SEQ ID NO: 24; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8, each disclosed in Tables 1-4 of US 2015/0218274;

(e) a VH comprising a VHCDR1 amino acid sequence chosen from SEQ ID NO: 9; a VHCDR2 amino acid sequence of SEQ ID NO: 31; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14, each disclosed in Tables 1-4 of US 2015/0218274; or (f) a VH comprising a VHCDR1 amino acid sequence chosen from SEQ ID NO: 3; a VHCDR2 amino acid sequence of SEQ ID NO: 30; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8, each disclosed in Tables 1-4 of US 2015/0218274.

In some embodiments, the anti-TIM-3 antibody molecule comprises a VH comprising the amino acid sequence of QVQLVQSGAEVKKPGASVKVSCKASGYTFTSYN-MHWVRQAPGQGLEWIGDIYPGQGDTSY NQKFKGRATMTADKSTSTVYMELSSLRSEDTAVYY-CARVGGAFPMDYWGQGTLVTVSS (SEQ ID NO: 324) or SEQ ID NO: 32 of US 2015/0218274, and a VL comprising the amino acid sequence of DIVLTQSPD-SLAVSLGERATINCRASESVEYYGT-SLMQWYQQKPGQPPKLLIYAASNVESGVP DRFSGSGSGTDFTLTISSLQAEDVAVYYCQQSRKDP-STFGGGTKVEIK (SEQ ID NO: 325) or SEQ ID NO: 20 of US 2015/0218274, each disclosed in Table 1 of US 2015/0218274. In some embodiments, the anti-TIM-3 antibody molecule comprises a VH comprising the amino acid sequence of QVQLVQSGAEVKKPGSSVKVSCK-ASGYTFTSYNMHWVRQAPGQ-GLEWMGDIYPGNGDTSY NQKFKGRVTITADKST-STVYMELSSLRSEDTAVYYCARVGGAFPMDYWGQG TTVTVSS (SEQ ID NO: 326) or SEQ ID NO: 52 of US 2015/0218274, and a VL comprising the amino acid sequence of AIQLTQSPSSLSASVGDRVTITCRASES-VEYYGTSLMQWYQQKPGKAPKLLIYAASNVESGVP SRFSGSGSGTDFTLTISSLQPEDFATYFCQQSRKDP- STFGGGTKVEIK (SEQ ID NO: 327) or SEQ ID NO: 64 of US 2015/0218274, each disclosed in Table 1 of US 2015/0218274.

In some embodiments, the anti-TIM-3 antibody molecule comprises a heavy chain comprising the amino acid sequence of SEQ ID NO: 34 of US 2015/0218274, and a light chain comprising the amino acid sequence of SEQ ID NO: 22 of US 2015/0218274, each disclosed in Table 1 of US 2015/0218274. In some embodiments, the anti-TIM-3 antibody molecule comprises a heavy chain comprising the amino acid sequence of SEQ ID NO: 54 of US 2015/0218274, and a light chain comprising the amino acid sequence of SEQ ID NO: 66 of US 2015/0218274, each disclosed in Table 1 of US 2015/0218274.

Exemplary anti-TIM-3 antibodies are also disclosed in U.S. Pat. No. 8,552,156, WO 2011/155607, EP 2581113 and U.S Publication No. 2014/044728.

In one embodiment, a combination described herein includes an inhibitor of TIM-3 (e.g., an anti-TIM-3 antibody molecule described herein) and a chemotherapeutic agent (e.g., a hypomethylating agent, e.g., decitabine). In some embodiments, the inhibitor of TIM-3 (e.g., an anti-TIM-3 antibody molecule disclosed in U.S. Patent Application Publication No. 2015/0218274) is administered at a dose between 10 mg and 1000 mg (e.g., between 20 mg and 800 mg, between 80 mg and 400 mg, e.g., at a dose of 240 mg), e.g., once every 2 weeks, e.g., intravenously. In some embodiments, the inhibitor of TIM-3 (e.g., an anti-TIM-3 antibody molecule disclosed in U.S. Patent Application Publication No. 2015/0218274) is stored in the form of liquid (e.g., in a vial) for intravenous infusion. In some embodiments, the chemotherapeutic agent (e.g., a hypomethylating agent, e.g., decitabine) is administered at a dose between 5 mg/m$^2$ and 50 mg/m$^2$ (e.g., between 10 mg/m$^2$ and 30 mg/m$^2$ (e.g., at a dose of 20 mg/m$^2$), e.g., daily, e.g., for 1, 2, 3, 4, 5, 6, 7, 8, or more days, e.g., intravenously. For example, the inhibitor of TIM-3 (e.g., an anti-TIM-3 antibody molecule disclosed in U.S. Patent Application Publication No. 2015/0218274) can be administered on Days 8 and 22 of a 28-day cycle, and the chemotherapeutic agent (e.g., a hypomethylating agent, e.g., decitabine) can be administered on Days 1, 2, 3, 4, and 5 of the 28-day cycle. In some embodiments, the chemotherapeutic agent (e.g., a hypomethylating agent, e.g., decitabine) is administered by intravenous infusion over a period of 30 minutes to 2 hours, e.g., 1 hour.

In one embodiment, the combination further includes an inhibitor of PD-1 (e.g., an anti-PD-1 antibody molecule described herein). In some embodiments, the inhibitor of PD-1 (e.g., the anti-PD-1 antibody molecule), is administered at a dose between 200 mg and 600 mg (e.g., between 300 mg and 500 mg, e.g., at a dose of 400 mg), e.g., once every 4 weeks, e.g., intravenously. For example, the inhibitor of PD-1 (e.g., an anti-PD-1 antibody molecule described herein) can be administered on Day 8 of the 28-day cycle. In some embodiments, the inhibitor of PD-1 (e.g., the anti-PD-1 antibody molecule) is stored in the form of lyophilisate (e.g., in a vial) for intravenous infusion. In some embodiments, when used in combination with the inhibitor of PD-1 (e.g., an anti-PD-1 antibody molecule described herein), the inhibitor of TIM-3 (e.g., an anti-TIM-3 antibody molecule disclosed in U.S. Patent Application Publication No. 2015/0218274) is administered at a dose between 20 mg and 400 mg (e.g., between 40 mg and 200 mg or between 50 mg and 100 mg, e.g., at a dose of 80 mg), e.g., once every 2 weeks, e.g., intravenously.

In certain embodiments, the inhibitor of PD-1 (e.g., an anti-PD-1 antibody molecule described herein) and the inhibitor of TIM-3 (e.g., an anti-TIM-3 antibody molecule disclosed in U.S. Patent Application Publication No. 2015/0218274) are administered on the same day. In some embodiments, the inhibitor of TIM-3 (e.g., an anti-TIM-3 antibody molecule disclosed in U.S. Patent Application Publication No. 2015/0218274) is administered before the inhibitor of PD-1 (e.g., an anti-PD-1 antibody molecule described herein) is administered. In some embodiments, the inhibitor of TIM-3 (e.g., an anti-TIM-3 antibody molecule disclosed in U.S. Patent Application Publication No. 2015/0218274) is administered first and followed by a saline or dextrose solution flush, e.g., for about 1 hour, before starting administration of the inhibitor of PD-1 (e.g., an anti-PD-1 antibody molecule described herein). In other embodiments, the inhibitor of TIM-3 (e.g., an anti-TIM-3 antibody molecule disclosed in U.S. Patent Application Publication No. 2015/0218274) is administered after the inhibitor of PD-1 (e.g., an anti-PD-1 antibody molecule described herein) is administered. In certain embodiments, the inhibitor of PD-1 (e.g., an anti-PD-1 antibody molecule described herein) and the inhibitor of TIM-3 (e.g., an anti-TIM-3 antibody molecule disclosed in U.S. Patent Application Publication No. 2015/0218274) are administered on different days.

In some embodiments, the inhibitor of PD-1 (e.g., an anti-PD-1 antibody molecule described herein), the inhibitor of TIM-3 (e.g., an anti-TIM-3 antibody molecule disclosed in U.S. Patent Application Publication No. 2015/0218274), or both, is administered via intravenous infusion over a period of 30 minutes to 2 hours, e.g., about 1 hour.

In some embodiments, the combination is used to treat a cancer, e.g., a cancer described herein, e.g., a hematological cancer, e.g., a leukemia (e.g., an acute myeloid leukemia (AML)), or a myelodysplastic syndrome (MDS). In certain embodiments, the cancer is a leukemia, e.g., a relapsed or refractory AML, or a de novo AML (e.g., an AML unfit for standard of care). In other embodiments, the cancer is an MDS, e.g., a high risk MDS.

Exemplary CTLA-4 Inhibitors

In one embodiment, a combination described herein includes a CTLA-4 inhibitor. In some embodiments, the combination is used to treat a cancer, e.g., a cancer described herein, e.g., a solid tumor or a hematologic malignancy.

Exemplary anti-CTLA-4 antibodies include Tremelimumab (IgG2 monoclonal antibody available from Pfizer, formerly known as ticilimumab, CP-675,206); and Ipilimumab (CTLA-4 antibody, also known as MDX-010, CAS No. 477202-00-9).

In one embodiment, the combination includes an anti-PD-1 antibody molecule, e.g., as described herein, and an anti-CTLA-4 antibody, e.g., ipilimumab. Exemplary doses that can be use include a dose of anti-PD-1 antibody molecule of about 1 to 10 mg/kg, e.g., 3 mg/kg, and a dose of an anti-CTLA-4 antibody, e.g., ipilimumab, of about 3 mg/kg.

Other exemplary anti-CTLA-4 antibodies are disclosed, e.g., in U.S. Pat. No. 5,811,097.

Exemplary IAP Inhibitors

In one embodiment, a combination described herein includes an inhibitor of Inhibitor of Apoptosis Protein (IAP). In some embodiments, the combination is used to treat a cancer, e.g., a cancer described herein, e.g., a solid tumor (e.g., a colorectal cancer (CRC), a lung cancer (e.g., a non-small cell lung cancer (NSCLC)), a breast cancer (e.g., a triple negative breast cancer (TNBC)), an ovarian cancer, or a pancreatic cancer), e.g., a hematologic malignancy (e.g., a multiple myeloma).

In some embodiments, the IAP inhibitor is (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003.

In some embodiments, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, is an oral small molecule SMAC-mimetic that binds to the BIR3 domain of CIAP1, XIAP, and optionally CIAP2. The CIAP1 and CIAP2 proteins are components of TNF death receptor family protein complexes. Without wishing to be bound by theory, it is believed that in some embodiments, binding of the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, can activate an E3 ligase function of CIAP1, induce ubiquitination and proteosomal degradation of CIAP1, and/or activate NF-κB signaling downstream of the receptors (Gyrd-Hansen M, Meier P (2010) *Nat. Rev. Cancer* p. 561-74). In some embodiments, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, is used for increasing antitumor immunity in a subject. For example, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, can enhance human and mouse T cell proliferation and function in vitro after co-stimulation, and/or response to prophylactic and therapeutic antitumor vaccines in vivo, e.g., through activation of NF-κB (Dougan et al. (2010) *J. Exp. Med.* p. 2195-206). NF-κB activity is involved in cross-priming of T cells during immunogenic cell death in response to release of danger-associated inflammatory molecules (Yatim et al. (2015) *Science* p. 328-34), indicating a mechanism for enhancing T cell function and anti-tumor immunity. As another example, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, can protect monocyte-derived dendritic cells from apoptosis, e.g., similar to CD40 ligation (Knights et al. (2013) *Cancer Immunol. Immunother.* p. 321-35).

In some embodiments, the combination described herein includes an IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, and an inhibitor of an immune checkpoint molecule, e.g., an inhibitor of PD-1 (e.g., an anti-PD-1 antibody molecule).

Without wishing to be bound by theory, it is believed that in some embodiments, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, is an orally available small molecule that activates NF-kB signaling downstream of TNF receptor family members. NF-κB is a master regulator of transcription in immune cells, and also acts in tumor cells directly (Perkins (2012) *Nat. Rev. Cancer* p. 121-32). Preclinical data suggest that NF-κB activity is required for cross-priming of CD8+ T lymphocytes undergoing immunogenic cell death (Yatim et al. (2015) *Science* p. 328-34). Compound A21 stimulated proliferation of T lymphocytes, induced IFNgamma, and suppressed production of IL-10 in vitro. Clinical studies with Compound A21 demonstrated induction of circulating cytokines including TNFalpha, IL-8, IL-10 and CCL2 (Infante et al. (2014) *J. Clin. Oncol.* p. 3103-10). Clinical data suggest that Compound A21 increased the rate of pathological complete response of TNBC to treatment with paclitaxel. In some embodiments, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, enhances, or is used to enhance, an anti-tumor activity of the inhibitor of an immune checkpoint molecule, e.g., the inhibitor of PD-1 (e.g., an anti-PD-1 antibody molecule).

In some embodiments, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, and the inhibitor of an immune checkpoint molecule, e.g., an inhibitor of PD-1 (e.g., an anti-PD-1 antibody molecule), each is administered at a dose and/or on a time schedule, that in combination, achieves a desired anti-tumor activity.

Without wishing to be bound by theory, it is believed that doses for the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, equal to or lower than 1800 mg are active, e.g., based on pharmacodynamic data. For example, in paired skin biopsies of two patients treated at 320 mg, both showed degradation of CIAP1, the protein targeted by Compound A21; skin biopsies collected from patients treated at lower doses (160 mg and below) showed less consistent pharmacodynamic activity (Infante et al. (2014) *J. Clin. Oncol.* p. 3103-10). In some embodiments, doses higher than 900 mg are not required for clinical efficacy. In certain situations, a dose of Compound A21 at 1800 mg was poorly tolerated when given in combination with paclitaxel. Accordingly, in one embodiment, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, is administered at a dose between of 300 mg and 900 mg, e.g., once a week. In some embodiments, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, is administered less frequently than once a week, e.g., is administered once every two weeks, once every three weeks, or once every four weeks.

In some embodiments, the IAP inhibitor, e.g., (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003, is administered at a dose of approximately 1800 mg or less, e.g., once weekly.

In some embodiments, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, is administered at a dose between 160 mg and 1800 mg, between 200 mg and 1200 mg, between 300 mg and 900 mg, between 400 mg and 800 mg, or between 500 mg and 700 mg, e.g., at a dose of 300 mg, 400 mg, 500 mg, 600 mg, 700 mg, 800 mg, or 900 mg, e.g., once a week, once every two weeks, once every three weeks, or once every four weeks.

In certain embodiments, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, is administered at a dose of between about 200 mg and about 400 mg, e.g., about 300 mg, once weekly. In other embodiments, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, is administered at a dose of between about 800 mg and about 1000 mg, e.g., about 900 mg, once a week. In some embodiments, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, is administered at a dose of between about 200 mg and about 400 mg, e.g., about 300 mg, once every four weeks.

In certain embodiments, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, is administered orally.

In some embodiments, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, is administered in combination with a PD-1 inhibitor (e.g., an anti-PD-1 antibody molecule). In one embodiment, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, is administered at a dose between 200 mg and 400 mg (e.g., at a dose of 300 mg), e.g., once a week, e.g., orally, and the PD-1 inhibitor (e.g., the anti-PD-1 antibody molecule) is administered at a dose between 300 mg and 500 mg (e.g., at a dose of 400 mg), e.g., once every 4 weeks, e.g., by intravenous infusion.

In certain embodiments, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, is administered in combination with the PD-1 inhibitor (e.g., the anti-PD-1 antibody molecule) to treat a colorectal cancer, a lung cancer (e.g., a non-small cell lung cancer (NSCLC)), or a breast cancer (e.g., a triple-negative breast cancer (e.g., NTBC)).

Exemplary EGFR Inhibitors

In one embodiment, a combination described herein includes an inhibitor of Epidermal Growth Factor Receptor (EGFR). In some embodiments, the combination is used to treat a cancer, e.g., a cancer described herein, e.g., a solid tumor (e.g., a lung cancer (e.g., a non-small cell lung cancer), a pancreatic cancer, a breast cancer (e.g., a triple negative breast cancer (TNBC)), or a colon cancer). In certain embodiments, the cancer is chosen from a colorectal cancer (e.g., a microsatellite stable colorectal cancer (MSS CRC)), a lung cancer (e.g., a non-small cell lung cancer), or a breast cancer (e.g., a triple negative lung cancer (TNBC)).

In some embodiments, the EGFR inhibitor is (R,E)-N-(7-chloro-1-(1-(4-(dimethylamino)but-2-enoyl)azepan-3-yl)-1H-benzo[d]imidazol-2-yl)-2-methylisonicotinamide (Compound A40) or a compound disclosed in PCT Publication No. WO 2013/184757.

In some embodiments, the EGFR inhibitor, e.g., (R,E)-N-(7-chloro-1-(1-(4-(dimethylamino)but-2-enoyl)azepan-3-yl)-1H-benzo[d]imidazol-2-yl)-2-methylisonicotinamide (Compound A40) or a compound disclosed in PCT Publication No. WO 2013/184757, is administered at a dose of 150-250 mg, e.g., per day. In some embodiments, the EGFR inhibitor, e.g., (R,E)-N-(7-chloro-1-(1-(4-(dimethylamino)but-2-enoyl)azepan-3-yl)-1H-benzo[d]imidazol-2-yl)-2-methylisonicotinamide (Compound A40) or a compound disclosed in PCT Publication No. WO 2013/184757, is administered at a dose of about 150, 200, or 250 mg, or about 150-200 or 200-250 mg.

In some embodiments, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, is a covalent, irreversible tyrosine kinase inhibitor. In certain embodiments, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757 inhibits activating EGFR mutations (L858R, ex19del). In other embodiments, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757 does not inhibit, or does not substantially inhibit, wild-type (wt) EGFR. Compound A40 has shown efficacy in EGFR mutant NSCLC patients. In some embodiments, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757 also inhibits one or more kinases in the TEC family of kinases. The Tec family kinases include, e.g., ITK, BMX, TEC, RLK, and BTK, and are central in the propagation of T-cell receptor and chemokine receptor signaling (Schwartzberg et al. (2005) *Nat. Rev. Immunol*. p. 284-95). For example, Compound A40 can inhibit ITK with a biochemical IC50 of 1.3 nM. ITK is a critical enzyme for the survival of Th2 cells and its inhibition results in a shift in the balance between Th2 and Th1 cells. Combined treatment, in vivo, with the ITK inhibitor ibrutinib or Compound A40, and anti-PD-L1 antibody results in superior efficacy compared with either single agent in several models.

In some embodiments, the combination described herein includes an EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, and an inhibitor of an immune checkpoint molecule, e.g., an inhibitor of PD-1 (e.g., an anti-PD-1 antibody molecule).

The combination of ITK inhibition (with ibrutinib) and checkpoint inhibition is more effective than either single agent in numerous syngeneic mouse models, e.g., those which express ITK but not BTK. In certain embodiments, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, inhibits ITK. The synergistic effect of ITK inhibition and checkpoint blockade has been tested in mouse allografts using mouse cancer cell lines (A20, CT26 and 4T1) (Sagiv-Barfi et al. (2015) *Blood*. p. 2079-86). The combination of anti-PD-L1 antibody and ibrutinib (an ITK inhibitor) was shown to be significantly more efficacious than either single agent in all three models. In these experiments, the treatment effect was prolonged despite the dosing of ibrutinib for only 8 days, and a total of 5 doses of anti-PD-L1 antibody. Approximately half of the CT26 tumor bearing mice treated with this combination were cured (no mice treated with either single agent were cured). Rechallenge of these mice with CT26 tumor inoculum demonstrated long term anti-tumor memory specific for this cell line (Sagiv-Barfi et al. (2015) *Blood*. p. 2079-86). Furthermore, tumor specific T-cells were found in the blood and spleen of mice treated with ibrutinib and anti-PD-L1 antibody. A similar experiment was performed using Compound A40 in the A20 lymphoma model (see e.g., Example 4). The combination of either Compound A40 and anti-PD-L1 antibody or ibrutinib and anti-PD-L1 antibody was more effective than a single agent. Compound A40 and ibrutinib were dosed for only ten days, and a total of 5 doses of anti-PD-L1 antibody were given. Compound A40 and ibrutinib were only dosed transiently and the effects of Compound A40 plus anti-PD-L1 antibody and ibrutinib plus anti-PD-L1 antibody on survival extended beyond 60 days. Combination of anti-PD-L1 antibody and Compound A40 resulted in tumor regression in mice bearing A20 lymphoma allografts. Accordingly, in some embodiments, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757 enhances, or is used to enhance an antitumor effect of an inhibitor of PD-1 (e.g., an anti-PD-1 antibody molecule).

In some embodiments, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, and the inhibitor of an immune checkpoint molecule, e.g., an inhibitor of PD-1 (e.g., an anti-PD-1 antibody molecule), each is administered at a dose and/or on a time schedule, that in combination, achieves a desired anti-tumor activity.

In one embodiment, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, is administered at a dose between 5 mg and 100 mg, e.g., between 10 mg and 75 mg, between 15 mg and 50 mg, between 20 mg and 30 mg, between 10 mg and 40 mg, between 10 mg and 25 mg, or between 25 mg and 40 mg, e.g., at a dose of 5 mg, 10 mg, 15 mg, 20 mg, 25 mg, 30 mg, 35 mg, 40 mg, 45 mg, 50 mg, 60 mg, 70 mg, 80 mg, 90 mg, or 100 mg, e.g., twice a day, once a day, once every two days, once every three days, or once a week.

In one embodiment, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, is administered at a dose between 10 mg and 50 mg (e.g., 25 mg), e.g., once a day. In some embodiments, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, is administered orally. In one embodiment, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, is administered at a dose between 10 mg and 50 mg (e.g., 25 mg), e.g., once a day, e.g., orally, and the PD-1 inhibitor (e.g., the anti-PD-1 antibody molecule) is administered at a dose between 300 mg and 500 mg (e.g., at a dose of 400 mg), e.g., once every 4 weeks, e.g., by intravenous infusion. In some embodiments, the combination is administered in one or more dosing cycles, e.g., one or more 28-day dosing cycles. In certain embodiments, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, is administered on day 1 to day 10 of a first dosing cycle. In certain embodiments, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, is not administered on day 11 to day 28 of a first dosing cycle, or in any subsequent dosing cycle(s).

In some embodiments, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, is administered in combination with an inhibitor of PD-1 (e.g., an anti-PD-1 antibody molecule) to treat a colorectal cancer (CRC) (e.g., an MSS-CRC), a lung cancer (e.g., a non-small cell lung cancer (NSCLC)), or a breast cancer (e.g., a triple negative breast cancer (TNBC)).

In some embodiments, the EGFR inhibitor is chosen from one of more of erlotinib, gefitinib, cetuximab, panitumumab, necitumumab, PF-00299804, nimotuzumab, or RO5083945.

Exemplary mTOR Inhibitors

In one embodiment, a combination described herein includes an inhibitor of target of rapamycin (mTOR). In some embodiments, the combination is used to treat a cancer, e.g., a cancer described herein, e.g., a solid tumor (e.g., a prostate cancer, a breast cancer, a brain cancer, a bladder cancer, a pancreatic cancer, a renal cancer, or a liver cancer, a lung cancer (e.g., a small cell lung cancer or a non-small cell lung cancer), a respiratory/thoracic cancer, a sarcoma, a bone cancer, a non-small cell lung cancer, an endocrine cancer, an astrocytoma, a cervical cancer, a neurologic cancer, a gastric cancer, or a melanoma), e.g., a hematologic malignancy (e.g., a leukemia (e.g., lymphocytic leukemia), e.g., a lymphoma, or e.g., a multiple myeloma). In certain embodiments, the cancer is chosen from a colorectal cancer (e.g., a microsatellite stable colorectal cancer (MSS CRC)), a lung cancer (e.g., a non-small cell lung cancer), or a breast cancer (e.g., a triple negative lung cancer (TNBC)).

In some embodiments, the mTOR inhibitor is dactolisib (Compound A4) or 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound disclosed in PCT Publication No. WO 2006/122806.

In some embodiments, the mTOR inhibitor is everolimus (also known as AFINITOR®; Compound A36) or a compound disclosed in PCT Publication No. WO 2014/085318.

In some embodiments, the mTOR inhibitor, everolimus (Compound A36), or a compound disclosed in PCT Publication No. WO 2014/085318, inhibits mammalian target of rapamycin (mTOR), a serine-threonine kinase, downstream of the PI3K/AKT pathway. The mTOR pathway is dysregulated in several human cancers. Without wising to be bound by theory, it is believed that in some embodiments, the mTOR inhibitor, everolimus (Compound A36), or a compound disclosed in PCT Publication No. WO 2014/085318, binds to an intracellular protein, FKBP-12, resulting in an inhibitory complex formation with mTOR complex 1 (mTORC1) and thus inhibition of mTOR kinase activity. Everolimus (Compound A36) can reduce the activity of S6 ribosomal protein kinase (S6K1) and/or eukaryotic initiation factor 4E-binding protein (4E-BP1), downstream effectors of mTOR, involved in protein synthesis. S6K1 is a substrate of mTORC1 and phosphorylates the activation domain 1 of the estrogen receptor which results in ligand-independent activation of the receptor. In addition, everolimus (Compound A36) can inhibit the expression of hypoxia-inducible factor (e.g., HIF-1) and/or reduce the expression of vascular endothelial growth factor (VEGF). Inhibition of mTOR by everolimus (Compound A36) has been shown to reduce cell proliferation, angiogenesis, and glucose uptake in in vitro and/or in vivo studies. Constitutive activation of the PI3K/Akt/mTOR pathway can contribute to endocrine resistance in breast cancer. In vitro studies show that estrogen-dependent and HER2+ breast cancer cells are sensitive to the inhibitory effects of everolimus (Compound A36), and that combination treatment with everolimus and Akt, HER2, or aromatase inhibitors enhances the anti-tumor activity of everolimus (Compound A36) in a synergistic manner. Two regulators of mTORC1 signaling are the oncogene suppressors tuberin-sclerosis complexes 1 and 2 (TSC1, TSC2). Loss or inactivation of either TSC1 or TSC2 leads to activation of downstream signaling. In TSC, a genetic disorder, inactivating mutations in either the TSC1 or the TSC2 gene lead to hamartoma formation throughout the body.

In some embodiments, the combination described herein includes the mTOR inhibitor, everolimus (Compound A36), or a compound disclosed in PCT Publication No. WO 2014/085318, and an inhibitor of an immune checkpoint molecule, e.g., an inhibitor of PD-1 (e.g., an anti-PD-1 antibody molecule).

Everolimus (Compound A36) has been used in clinics as a direct antitumor agent at the dose of 10 mg daily to repress mTOR activity in tumor cells, and as an immunosuppressant in patients requiring solid organ transplants at 1.5-2.0 mg daily to suppress T lymphocyte function. Without wishing to be bound by theory, it is believed that in some embodiments, at these doses and schedules everolimus (Compound A36) would be expected to impair an effective anti-tumor response. Immunosenescence is a decline in immune function that occurs in the elderly and includes a decreased response to vaccination, including influenza vaccination. The decline in immune function with age includes an increase in PD-1-positive "exhausted" T lymphocytes that have a diminished response to stimulation with antigen (Lages et al. (2010) *Aging Cell* 9, 785-798). Clinical data suggest a dose of 5 mg per week can be immunostimulatory, reducing the percentage of PD-1-positive CD4+ and CD8+ lymphocytes compared to placebo treatment and enhancing the response to an influenza vaccine in elderly subjects (Mannick et al. (2014) *Sci. Transl. Med.* Vol. 6, Issue 268, pp. 268ra179). In certain embodiments, an immunostimulatory dose of the mTOR inhibitor, everolimus (Compound A36), or a compound disclosed in PCT Publication No. WO 2014/085318, enhances, or is used to enhance, the antitumor activity of an inhibitor of PD-1 (e.g., an anti-PD-1 antibody molecule).

In some embodiments, the mTOR inhibitor, everolimus (Compound A36), or a compound disclosed in PCT Publication No. WO 2014/085318, and the inhibitor of an immune checkpoint molecule, e.g., an inhibitor of PD-1 (e.g., an anti-PD-1 antibody molecule), each is administered at a dose and/or on a time schedule, that in combination, achieves a desired anti-tumor activity.

In some embodiments, the dose of everolimus (Compound A36) approved for adult cancer indications (e.g. breast cancer (e.g., TNBC), renal cell carcinoma and neuroendocrine tumors (e.g., atypical pulmonary carcinoid tumor) is 10 mg daily. Without wishing to be bound by theory, it is believed that in some embodiments, modeling and simulation based on mTOR-mediated phosphorylation of its downstream target S6 kinase (S6K) predicted that a 20 mg weekly dosing regimen inhibited mTOR-mediated S6K phosphorylation almost completely, a 5 mg weekly dosing regimen inhibited S6K phosphorylation by more than 50%, and a 0.5 mg daily dosing regimen inhibited S6K phosphorylation by about 38% over the dosing interval (Mannick et al. (2014) *Sci. Transl. Med.* Vol. 6, Issue 268, pp. 268ra179; Tanaka (2008) *J. Clin. Oncol.* p. 1596-602). Accordingly, in certain embodiments, the mTOR inhibitor, everolimus (Compound A36), or a compound disclosed in PCT Publication No. WO 2014/085318, is administered at a dose of 5 mg once weekly (QW), e.g., in combination with an inhibitor of PD-1 (e.g., an anti-PD-1 antibody molecule). In other embodiments, a dose of 0.5 mg once daily (QD) may also be used, e.g., when the dose of 5 mg once weekly (QW) is not well tolerated. In some embodiments, the mTOR inhibitor, everolimus (Compound A36), or a compound disclosed in PCT Publication No. WO 2014/085318 is administered at a dose 5 mg or less once a week.

In some embodiments, the mTOR inhibitor, e.g., everolimus (Compound A36) or a compound disclosed in PCT Publication No. WO 2014/085318, is administered at a dose of about 2.5-20 mg/day. In one embodiment, the TOR inhibitor, e.g., everolimus (Compound A36) or a compound disclosed in PCT Publication No. WO 2014/085318, is administered at a dose of about 2.5, 5, 10, or 20 mg/day, e.g., about 2.5-5, 5-10, or 10-20 mg/day.

In one embodiment, the mTOR inhibitor, Everolimus (Compound A36), or a compound disclosed in PCT Publication No. WO 2014/085318, is administered at a dose between 1 mg and 10 mg, between 2 mg and 8 mg, between 3 mg and 7 mg, or between 4 mg and 6 mg, e.g., at a dose of 1 mg, 2 mg, 3 mg, 4 mg, 5 mg, 6 mg, 7 mg, 8 mg, 9 mg, or 10 mg, e.g., once weekly, once every two weeks, once every three weeks, or once every four weeks. In one embodiment, the mTOR inhibitor, Everolimus (Compound A36), or a compound disclosed in PCT Publication No. WO 2014/085318, is administered at a dose of between 4 mg and 6 mg, e.g., 5 mg, e.g., once weekly.

In another embodiment, the mTOR inhibitor, Everolimus (Compound A36), or a compound disclosed in PCT Publication No. WO 2014/085318, is administered at a dose between 0.1 mg and 1 mg, between 0.2 mg and 0.8 mg, between 0.3 mg and 0.7 mg, or between 0.4 mg and 0.6 mg, e.g., 0.1 mg, 0.2 mg, 0.3 mg, 0.4 mg, 0.5 mg, 0.6 mg, 0.7 mg, 0.8 mg, 0.9 mg, or 1 mg, e.g., once daily or once weekly.

In some embodiments, the mTOR inhibitor, Everolimus (Compound A36), or a compound disclosed in PCT Publication No. WO 2014/085318, is administered orally.

In some embodiments, the mTOR inhibitor, Everolimus (Compound A36), or a compound disclosed in PCT Publication No. WO 2014/085318, is administered at a dose between 2 mg and 8 mg (e.g., at a dose of 5 mg), e.g., once a week, e.g., orally, and the PD-1 inhibitor (e.g., the anti-PD-1 antibody molecule) is administered at a dose between 300 mg and 500 mg (e.g., at a dose of 400 mg), e.g., once every 4 weeks, e.g., by intravenous infusion.

In some embodiments, the mTOR inhibitor, Everolimus (Compound A36), or a compound disclosed in PCT Publication No. WO 2014/085318, is administered in combination with the PD-1 inhibitor (e.g., the anti-PD-1 antibody molecule) to treat a colorectal cancer, a lung cancer (e.g., a non-small cell lung cancer (NSCLC)), or a breast cancer (e.g., a triple negative breast cancer (NTBC)).

In some embodiments, the mTOR inhibitor is chosen from one or more of rapamycin, temsirolimus (TORISEL®), AZD8055, BEZ235, BGT226, XL765, PF-4691502, GDC0980, SF1126, OSI-027, GSK1059615, KU-0063794, WYE-354, Palomid 529 (P529), PF-04691502, or PKI-587. ridaforolimus (formally known as deferolimus, (1R,2R,4S)-4-[(2R)-2 [(1R,9S,12S,15R,16E,18R,19R,21R, 23S,24E, 26E,28Z,30S,32S,35R)-1,18-dihydroxy-19,30-dimethoxy-15,17,21,23, 29,35-hexamethyl-2,3,10,14,20-pentaoxo-11, 36-dioxa-4-azatricyclo[30.3.1.04,9] hexatriaconta-16,24,26, 28-tetraen-12-yl]propyl]-2-methoxycyclohexyl dimethylphosphinate, also known as AP23573 and MK8669, and described in PCT Publication No. WO 03/064383); everolimus (AFINITOR® or RAD001); rapamycin (AY22989, SIROLIMUS®); simapimod (CAS Registry Number: 164301-51-3); (5-{2,4-Bis[(3S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502, CAS Registry Number: 1013101-36-4); N2-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine (SEQ ID NO: 237) inner salt (SF1126, CAS Registry Number: 936487-67-1), or XL765 (SAR245409).

Other exemplary mTOR Inhibitors include, but are not limited to, temsirolimus; ridaforolimus (1R,2R,4S)-4-[(2R)-2 [(1R,9S,12S,15R,16E,18R,19R,21R, 23S,24E,26E, 28Z,30S,32S,35R)-1,18-dihydroxy-19,30-dimethoxy-15, 17,21,23, 29,35-hexamethyl-2,3,10,14,20-pentaoxo-11,36-dioxa-4-azatricyclo[30.3.1.0$^{4.9}$] hexatriaconta-16,24,26,28-tetraen-12-yl]propyl]-2-methoxycyclohexyl dimethylphosphinate, also known as AP23573 and MK8669; everolimus (RAD001); rapamycin (AY22989); simapimod; (5-{2,4-bis[(3S)-3-methylmorpholin-4-yl] pyrido[2,3-d]pyrimidin-7-yl}-2-methoxyphenyl)methanol (AZD8055); 2-mmino-8-[trans-4-(2-hydroxyethoxy)cyclohexyl]-6-(6-methoxy-3-pyridinyl)-4-methyl-pyrido[2,3-d] pyrimidin-7(8H)-one (PF04691502); and N$^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine-(SEQ ID NO: 237), inner salt (SF1126); and XL765.

Exemplary IL-15 Agonists

In one embodiment, a combination described herein includes an interleukin-15 (IL-15) agonist. In some embodiments, the combination is used to treat a cancer, e.g., a cancer described herein, e.g., a solid tumor (e.g., a refractory solid tumor), (e.g., a melanoma (e.g., a metastatic or advanced melanoma), a kidney cancer (e.g., a renal cell cancer), a non-small cell lung cancer, a squamous cell head and neck cancer, or a bladder cancer (e.g., a non-muscle invasive bladder cancer)), e.g., a hematologic malignancy (e.g., a leukemia, e.g., an acute myelogenous leukemia (e.g., a refractory or relapsed acute myelogenous leukemia), e.g., a lymphoma, e.g., a non-Hodgkin lymphoma (e.g., a relapsed/refractory indolent B cell non-Hodgkin lymphoma), e.g., or a multiple myeloma (e.g., a relapsed or refractory multiple myeloma)). In certain embodiments, the cancer is a solid tumor.

IL-15, secreted by mononuclear phagocytes (and some other cell types) following viral infection, regulates T and natural killer cell activation and proliferation. This cytokine induces activation of transcription activators STAT3, STATS, and STAT6 via JAK kinase signal transduction pathways in mast cells, T cells, and dendritic epidermal T cells. IL-15 and interleukin-2 (IL-2) are structurally similar and share many biological activities; both may bind to common hematopoietin receptor subunits, negatively regulating each other's activity. CD8+ memory T cell number can be regulated by a balance between IL-15 and IL-2.

In some embodiments, the IL-15 agonist is a recombinant human IL-15 (rhIL-15), e.g., CYP0150 (Cytune). CYP0150 is a recombinant protein consisting of a human IL-15 linked to the Sushi+ domain of the human alpha chain receptor (transpresentation).

CYP0150 is disclosed, e.g., in PCT Publication No. WO 2007/046006. CYP0150 has the amino acid sequence of: MAPRRARGCRTLGLPALLLLLLLRP-PATRGDYKDDDDKIEGRITCPPPMSVEHADIWVKSYS LYSRERYICNSGFKRKAGTSSLTECVLNKATN-VAHWTTPSLKCIRDPALVHQRPAPPSGGSGG GGSGGGGSGGGGSLQNWVNVISDLKKIEDLIQSMHI-DATLYTESDVHPSCKVTAMKCFLLELQ VISLESG-DASIHDTVENLIILANNSLSSNGNVTESGCKE-CEELEEKNIKEFLQSFVHIVQMFINTS (SEQ ID NO: 248) (disclosed as SEQ ID NO: 60 in WO 2007/046006) or MDSKGSSQKAGSRLLLLLVVSNLLLCQGVVST-TRDYKDDDDKIEGRNWVNVISDLKKIEDLI QSMHI-DATLYTESDVHPSCKVTAMKCFLLELQVISLESG-DASIHDTVENLIILANNSLSSNGNV TESGCKECEELEEKNIKEFLQSFVHIVQM-FINTSSGGGSGGGGSGGGGSGGGGSGGGGSLQITC PPPMSVEHADIWVKSYSLYSRERYICNSGFKRK-AGTSSLTECVLNKATNVAHWTTPSLKCIR DPALVHQRPAPP (SEQ ID NO: 249) (disclosed as SEQ ID NO: 62 in WO 2007/046006).

In some embodiments, the IL-15 agonist is ALT-803 (Altor BioScience). ALT-803 is an IL-15N72D:IL-15RaSu/Fc soluble complex, produced from a high-yield recombinant mammalian cell line that co-expresses IL-15N72D and IL-15RaSu/Fc fusion protein. The IL-15 mutant (N72D) has enhanced IL-15 biological activity (Zhu et al. 2009, *J Immunol.* 183:3598). The IL-15N72D mutant and the soluble domain of IL-15Rα can form stable heterodimeric complexes in solution and this complex exhibits increased biological activity (approximately 25-fold more active) compared to the non-complexed IL-15. ALT-803 is disclosed, e.g., in PCT Publication No. WO 2012/040323 and U.S. Pat. No. 8,507,222.

In some embodiments, the IL-15 agonist is hetIL-15 (Admune). HetIL-15 is a heterodimeric human IL-15 (IL-15/sIL-15Ra). HetIL-15 is disclosed, e.g., in PCT Publication Nos. WO 2009/002562 and WO 2014/066527.

Exemplary CD40 Agonists

In one embodiment, the combination includes a CD40 agonist. In some embodiments, the combination is used to treat a cancer, e.g., a cancer described herein, e.g., a solid tumor (e.g., a lung cancer, an esophageal carcinoma, a melanoma, or a renal cell carcinoma), e.g., a hematologic malignancy (e.g., a leukemia (e.g., a chronic lymphocytic leukemia (CLL)), e.g., a lymphoma (e.g., a non-Hodgkin's lymphoma), or a multiple myeloma).

In one embodiment, the CD40 agonist is ADC-1013 (Alligator/BioInvent). ADC-1013 is a fully human IgG agonistic monoclonal antibody against human CD40. CD40, an integral membrane protein found on the surface of B lymphocytes, is a member of the tumor necrosis factor receptor superfamily and is highly expressed in a number of cancers such as B-cell malignancies. CD40 agonists, e.g., anti-CD40 antibodies, are able to substitute effectively for T cell helper activity (Ridge, J. et al. (1998) *Nature* 393: 474-478).

ADC-1013 is disclosed, e.g., in PCT Publication No. WO 2015/091853. ADC-1013 clones include, e.g., 1136/1137, 1132/1133, 1148/1149, 1140/1135, 1134/1135, 1107/1108, 1142/1135, 1146/1147, and 1150/1151.

The heavy chain variable region of 1132/1133 has the amino acid sequence of: EVQLLESGGGLVQPGGSLRLS-CAASGFTFSSYAMSWVRQAPGKGLEWVS-GIGSYGGGTYYA DSVKGRFTISRDNSKNT-LYLQMNSLRAEDTAVYYCARYVNFGMDYWGQGTL VTVSS (SEQ ID NO: 250) (disclosed as SEQ ID NO: 65 in WO 2015/091853). The light chain variable region of 1132/1133 has the amino acid sequence of: DIQMTQSPSSL-SASVGDRVTITCRASQSISSYLNWYQQKPGKAPKLLI-YAASSLQSGVPSRFSG SGSGTDFTLTISSLQPEDFA-TYYCQQYGRNPPTFGQGTKLEIK (SEQ ID NO: 251) (disclosed as SEQ ID NO: 66 in WO 2015/091853). The heavy chain CDR1 of 1132/1133 has the amino acid sequence of: GFTFSSYA (SEQ ID NO: 252) (disclosed as SEQ ID NO: 13 in WO 2015/091853). The heavy chain CDR2 of 1132/1133 has the amino acid sequence of: IGSYGGGT (SEQ ID NO: 253) (disclosed as SEQ ID NO: 14 in WO 2015/091853). The heavy chain CDR3 of 1132/ 1133 has the amino acid sequence of: ARYVNFGMDY (SEQ ID NO: 254) (disclosed as SEQ ID NO: 15 in WO 2015/091853). The light chain CDR1 of 1132/1133 has the amino acid sequence of: QSISSY (SEQ ID NO: 255) (disclosed as SEQ ID NO: 16 in WO 2015/091853). The light chain CDR2 of 1132/1133 has the amino acid sequence of: AAS (SEQ ID NO: 256) (disclosed as SEQ ID NO: 17 in WO 2015/091853). The light chain CDR3 of 1132/1133 has the amino acid sequence of: QQYGRNPPT (SEQ ID NO: 257) (disclosed as SEQ ID NO: 18 in WO 2015/091853).

The heavy chain variable region of 1107/1108 has the amino acid sequence of: EVQLLESGGGLVQPGGSLRLS-CAASGFTFSSYAMSWVRQAPGKGLEWVSAISGSGG-STYYA DSVKGRFTISRDNSKNTLYLQMNSLRAED-TAVYYCARRVWGFDYWGQGTLVTVSS (SEQ ID NO: 258) (disclosed as SEQ ID NO: 79 in WO 2015/091853). The light chain variable region of 1107/1108 has the amino acid sequence of: DIQMTQSPSSLSASVGDRVTIT-CRASQSISSYLNWYQQKPGKAPKLLI-YAASSLQSGVPSRFSG SGSGT DFTLTISSLQPEDFA-TYYCQQYGVYPFTFGQGTKLEIK (SEQ ID NO: 259) (disclosed as SEQ ID NO: 80 in WO 2015/091853).

The heavy chain CDR1 of 1107/1108 has the amino acid sequence of: GFTFSSYA (SEQ ID NO: 252) (disclosed as SEQ ID NO: 55 in WO 2015/091853). The heavy chain CDR2 of 1107/1108 has the amino acid sequence of: ISGSGGST (SEQ ID NO: 260) (disclosed as SEQ ID NO: 56 in WO 2015/091853). The heavy chain CDR3 of 1107/ 1108 has the amino acid sequence of: ARRVWGFDY (SEQ ID NO: 261) (disclosed as SEQ ID NO: 57 in WO 2015/ 091853). The light chain CDR1 of 1107/1108 has the amino acid sequence of: QSISSY (SEQ ID NO: 255) (disclosed as SEQ ID NO: 58 in WO 2015/091853). The light chain CDR2 of 1107/1108 has the amino acid sequence of: AAS (SEQ ID NO: 256) (disclosed as SEQ ID NO: 59 in WO 2015/091853). The light chain CDR3 of 1107/1108 has the amino acid sequence of: QQYGVYPFT (SEQ ID NO: 262) (disclosed as SEQ ID NO: 60 in WO 2015/091853).

In some embodiments, the CD40 agonist is ISF35. ISF35 is a chimeric CD154. ISF is disclosed in PCT Publication Nos. WO 2003/099340 and WO 2008/070743.

In some embodiments, the CD40 agonist is dacetuzumab. Dacetuzumab is also known as SGN-40 or huS2C6. Dacetuzumab is a humanized monoclonal antibody that targets CD40. Dacetuzumab is disclosed, e.g., in Advani et al. *J Clin Oncol.* 2009; 27(26):4371-7; and Khubchandani et al. *Curr Opin Investig Drugs.* 2009; 10(6):579-87.

In some embodiments, the CD40 agonist is lucatumumab (CAS Registry Number: 903512-50-5). Lucatumumab is also known as CHIR-12.12 or HCD-122. Lucatumumab binds to and inhibits CD40, thereby inhibiting CD40 ligand-induced cell proliferation and triggering cell lysis via anti-body-dependent cellular cytotoxicity (ADCC) in cells over-expressing CD40. Lucatumumab is disclosed, e.g., in Tai et al. *Cancer Res.* 2005; 65(13):5898-906.

Anti-CD40 antibodies are able to substitute effectively for T cell helper activity (Ridge, J. et al. (1998) Nature 393: 474-478) and can be used in conjunction with PD-1 anti-bodies (Ito, N. et al. (2000) Immunobiology 201 (5) 527-40). Exemplary OX40 Agonists In one embodiment, a combination described herein includes an OX40 agonist. In some embodiments, the combination is used to treat a cancer, e.g., a cancer described herein, e.g., a solid tumor (e.g., a breast cancer, a melanoma, a head and neck cancer, or a prostate cancer), e.g., a hematologic malignancy (e.g., a lymphoma (e.g., a B-cell lymphoma)).

OX40, also known as CD134, is a cell surface glycopro-tein and member of the tumor necrosis factor (TNF) receptor superfamily, is expressed on T-lymphocytes and provides a co-stimulatory signal for the proliferation and survival of activated T-cells. OX40 activation can induce proliferation of effector T-lymphocytes, which promotes an immune response against the tumor cells that express tumor-associ-ated antigens (TAAs).

In some embodiments, the OX40 agonist is chosen from mAb 106-222, humanized 106-222 (Hu106), mAb 119-122, or humanized 119-122 (Hu119).

MAb 106-222, humanized 106-222 (Hu106), mAb 119-122, and humanized 119-122 (Hu119) are disclosed, e.g., in PCT Publication No. WO 2012/027328 and U.S. Pat. No. 9,006,399. The amino acid sequence of the heavy chain variable region of mAb 106-222 is disclosed as SEQ ID NO: 4 in WO 2012/027328. The amino acid sequence of the light chain variable region of mAb 106-222 is disclosed as SEQ ID NO: 10 in WO 2012/027328. The amino acid sequence of the heavy chain variable region of humanized 106-222 (Hu106) is disclosed as SEQ ID NO: 5 in WO 2012/027328. The amino acid sequence of the light chain variable region of humanized 106-222 (Hu106) is disclosed as SEQ ID NO: 11 in WO 2012/027328. The amino acid sequence of the heavy chain variable region of mAb 119-122 is disclosed as SEQ ID NO: 16 in WO 2012/027328. The amino acid sequence of the light chain variable region of mAb 119-122 is disclosed as SEQ ID NO: 22 in WO 2012/027328. The amino acid sequence of the heavy chain variable region of humanized 119-122 (Hu119) is disclosed as SEQ ID NO: 17 in WO 2012/027328. The amino acid sequence of the light chain variable region of humanized 119-122 (Hu119) is disclosed as SEQ ID NO: 23 in WO 2012/027328.

In some embodiments, the OX40 agonist is a humanized monoclonal antibody disclosed in U.S. Pat. No. 7,959,925 and PCT Publication No. WO 2006/121810.

In some embodiments, the OX40 agonist is chosen from MEDI6469, MEDI0562, or MEDI6383. MEDI6469 is a murine monoclonal antibody against OX40. MEDI0562 is a humanized monoclonal antibody against OX40. MEDI6383 is a monoclonal antibody against OX40.

In some embodiments, the OX40 agonist, e.g., MEDI6469, is administered intravenously at a dose of approximately 0.4 mg/kg, e.g., every other day.

Other exemplary anti-OX-40 antibodies are disclosed, e.g., in Weinberg, A. et al. (2000) *Immunol* 164: 2160-2169.
Exemplary CD27 Agonists In one embodiment, a combination described herein includes a CD27 agonist. In some embodiments, the combination is used to treat a cancer, e.g., a cancer described herein, e.g., a solid tumor (e.g., a melanoma, a renal cell carcinoma, a hormone-refractory prostate adenocarcinoma, an ovarian cancer, a breast cancer, a colorectal adenocarcinoma, or a non-small cell lung cancer), e.g., a hematologic malignancy (e.g., a lymphoma (e.g., a Hodgkin's lymphoma, a Burkett's lymphoma, a mantle cell lymphoma, a primary lymphoma of the central nervous system, or a marginal zone B-cell lymphoma), or a leukemia (e.g., a chronic lymphocytic leukemia (CLL)).

In one embodiment, the CD27 agonist is Varlilumab (CAS Registry Number: 1393344-72-3). Varlilumab is also known as CDX-1127 (Celldex) or 1F5. Varlilumab is a fully human monoclonal antibody (mAb) that targets CD27, molecule in the activation pathway of lymphocytes. CDX-1127 is an agonist anti-CD27 mAb that can activate human T cells in the context of T cell receptor stimulation and therefore mediate anti-tumor effects. CDX-1127 can also provide direct therapeutic effects against tumors with CD27 expression.

Varlilumab is disclosed, e.g., in Vitale et al., *Clin Cancer Res.* 2012; 18(14):3812-21, WO 2008/051424, and U.S. Pat. No. 8,481,029.

In one embodiment, the CD27 agonist is BION-1402 (BioNovion). BION-1402 is also known as hCD27.15. BION-1402 is an anti-human CD27 monoclonal antibody. BION-1402 can stimulate the proliferation and/or survival of CD27+ cells. BION-1402 can activate human CD27 more effectively than its ligand CD70, which results in a significantly increased effect on proliferation of CD8+ and CD4+ T-cells.

BION-1402 is disclosed, e.g., as hCD27.15 in WO 2012/004367. This antibody is produced by hybridoma hCD27.15, which was deposited with the ATCC in on Jun. 2, 2010 under number PTA-11008. The heavy chain variable region of hCD27.15 has the amino acid sequence of: EVRLQQSGADLVKPGASVKLSCASG-FIIKATYMHWVRQRPEQGLEWIGRIDPANGE KY DPKFQVKAITADTSSSTAYLQLNSLTSDDTAVYY-CARYAWYFDVWGAGTTVTVSSAKTTPP XVYPXXPGS (SEQ ID NO: 263) (disclosed as SEQ ID NO: 3 in WO 2012/004367). The light chain variable region of hCD27.15 has the amino acid sequence of: DIQMTQSPASLSASVGDTVTITCRASENIYSF-LAWYHQKQGRSPQLLVYHAKTLAEGVPSRFS GSGSGTQFSLKINSLQAE-DFGSYYCQHYYGSPLTFGAGTKLEVKRADAAPTVSI FPPSSEELSL (SEQ ID NO: 264) (disclosed as SEQ ID NO: 4 in WO 2012/004367). The heavy chain CDR1 of hCD27.15 has the amino acid sequence of: GFIIKATYMH (SEQ ID NO: 265) (disclosed as SEQ ID NO: 5 in WO 2012/004367). The heavy chain CDR2 of hCD27.15 has the amino acid sequence of: RIDPANGETKYDPKFQV (SEQ ID NO: 266) (disclosed as SEQ ID NO: 6 in WO 2012/004367). The heavy chain CDR3 of hCD27.15 has the amino acid sequence of: YAWYFDV (SEQ ID NO: 267) (disclosed as SEQ ID NO: 7 in WO 2012/004367). The light chain CDR1 of hCD27.15 has the amino acid sequence of: RASENIYSFLA (SEQ ID NO: 268) (disclosed as SEQ ID NO: 8 in WO 2012/004367). The light chain CDR2 of hCD27.15 has the amino acid sequence of: HAKTLAE (SEQ ID NO: 269) (disclosed as SEQ ID NO: 9 in WO 2012/004367). The light chain CDR3 of hCD27.15 has the amino acid sequence of: QHYYGSPLT (SEQ ID NO: 270) (disclosed as SEQ ID NO: 10 in WO 2012/004367).
Exemplary CSF-1/1R Binding Agents In one embodiment, a combination described herein includes a CSF-1/1R binding agent. In some embodiments, the combination is used to treat a cancer, e.g., a cancer described herein, e.g., a solid tumor (e.g., a prostate cancer, a breast cancer, or pigmented villonodular synovitis (PVNS)).

In some embodiments, the CSF-1/1R binding agent is an inhibitor of macrophage colony-stimulating factor (M-CSF). M-CSF is also sometimes known as CSF-1.

In another embodiment, the CSF-1/1R binding agent is a CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224. In some embodiments, the cancer is chosen from a brain cancer (e.g., glioblastoma multiforme (GBM)), a pancreatic cancer, or a breast cancer (e.g., a triple-negative breast cancer (TNBC)).

In some embodiments, the CSF-1/1R binding agent (e.g., a CSF-1R tyrosine kinase inhibitor), 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered at a dose between 50 mg and 1500 mg, e.g., between 75 mg and 1000 mg, between 100 mg and 900 mg, between 200 mg and 800 mg, between 300 mg and 700 mg, between 400 mg and 600 mg, between 100 mg and 700 mg, between 100 mg and 500 mg, between 100 mg and 300 mg, between 700 mg and 900 mg, between 500 mg and 900 mg, between 300 mg and 900 mg, between 75 mg and 150 mg, between 100 mg and 200 mg, between 200 mg and 400 mg, between 500 mg and 700 mg, or between 800 mg and 1000 mg, e.g., at a dose of 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1000 mg. In certain embodiments, the CSF-1/1R binding agent (e.g., a CSF-1R tyrosine kinase inhibitor), 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered daily, e.g., according to a 7 days on/7 days off schedule. In other embodiments, the CSF-1/1R binding agent (e.g., a CSF-1R tyrosine kinase inhibitor), 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered twice a week, once a week, once every two weeks, once every three weeks, or once every four weeks.

In some embodiments, the CSF-1/1R binding agent (e.g., a CSF-1R tyrosine kinase inhibitor), 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered at a dose of between 50 mg and 150 mg, e.g., about 100 mg, e.g., daily, e.g., according to a 7 days on/7 days off schedule. In other embodiments, the CSF-1/1R binding agent (e.g., a CSF-1R tyrosine kinase inhibitor), 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered at a dose of between 100 mg and 200 mg, e.g., about 150 mg, e.g., daily, e.g., according to a 7 days on/7 days off schedule. In other embodiments, the CSF-1/1R binding agent (e.g., a CSF-1R tyrosine kinase inhibitor), 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered at a dose of between 200 mg and 400 mg, e.g., about 300 mg, e.g., daily, e.g., according to a 7 days on/7 days off schedule. In other embodiments, the CSF-1/1R binding agent (e.g., a CSF-1R tyrosine kinase inhibitor), 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered at a dose of between 500 mg and 700 mg, e.g., about 600 mg, e.g., daily, e.g., according to a 7 days on/7 days off schedule. In other embodiments, the CSF-1/1R binding agent (e.g., a CSF-1R tyrosine kinase inhibitor), 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered at a dose of between 800 mg and 1000 mg, e.g., about 900 mg, e.g., daily, e.g., according to a 7 days on/7 days off schedule.

In some embodiments, the CSF-1/1R binding agent (e.g., a CSF-1R tyrosine kinase inhibitor), 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered at a dose of between 50 mg and 150 mg, e.g., about 100 mg, once a week. In other embodiments, the CSF-1/1R binding agent (e.g., a CSF-1R tyrosine kinase inhibitor), 4-((2-(((1R, 2R)-2-hydroxycyclohexyl)amino)benzo[d]thiazol-6-yl) oxy)-N-methylpicolinamide (Compound A15), or a compound disclosed in PCT Publication No. WO 2005/073224, is administered at a dose of between 100 mg and 200 mg, e.g., about 150 mg, once a week. In other embodiments, the CSF-1/1R binding agent (e.g., a CSF-1R tyrosine kinase inhibitor), 4-((2-(((1R,2R)-2-hydroxycyclohexyl)amino) benzo[d]thiazol-6-yl)oxy)-N-methylpicolinamide (Compound A15), or a compound disclosed in PCT Publication No. WO 2005/073224, is administered at a dose of between 200 mg and 400 mg, e.g., about 300 mg, once a week. In other embodiments, the CSF-1/1R binding agent (e.g., a CSF-1R tyrosine kinase inhibitor), 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered at a dose of between 500 mg and 700 mg, e.g., about 600 mg, once a week. In other embodiments, the CSF-1/1R binding agent (e.g., a CSF-1R tyrosine kinase inhibitor), 4-((2-(((1R, 2R)-2-hydroxycyclohexyl)amino)benzo[d]thiazol-6-yl) oxy)-N-methylpicolinamide (Compound A15), or a compound disclosed in PCT Publication No. WO 2005/073224, is administered at a dose of between 800 mg and 1000 mg, e.g., about 900 mg, once a week.

In some embodiments, the CSF-1/1R binding agent (e.g., a CSF-1R tyrosine kinase inhibitor), 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered orally.

In some embodiments, the CSF-1/1R binding agent (e.g., a CSF-1R tyrosine kinase inhibitor), 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered in combination with a PD-1 inhibitor (e.g., an anti-PD-1 antibody molecule). In one embodiment, the CSF-1/1R binding agent (e.g., a CSF-1R tyrosine kinase inhibitor), 4-((2-(((1R, 2R)-2-hydroxycyclohexyl)amino)benzo[d]thiazol-6-yl) oxy)-N-methylpicolinamide (Compound A15), or a compound disclosed in PCT Publication No. WO 2005/073224, is administered at a dose between 50 mg and 150 mg (e.g., about 100 mg), e.g., daily (e.g., according to a 7 days on/7 days off schedule) or once a week, e.g., orally, and the PD-1 inhibitor (e.g., the anti-PD-1 antibody molecule) is administered at a dose between 300 mg and 500 mg (e.g., at a dose of 400 mg), e.g., once every 4 weeks, or at a dose between 200 mg and 400 mg (e.g., at a dose of 300 mg), e.g., once every 3 weeks, e.g., by intravenous infusion. In another embodiment, the CSF-1/1R binding agent (e.g., a CSF-1R tyrosine kinase inhibitor), 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered at a dose between 100 mg and 200 mg (e.g., about 150 mg), e.g., daily (e.g., according to a 7 days on/7 days off schedule) or once a week, e.g., orally, and the PD-1 inhibitor (e.g., the anti-PD-1 antibody molecule) is administered at a dose between 300 mg and 500 mg (e.g., at a dose of 400 mg), e.g., once every 4 weeks, or at a dose between 200 mg and 400 mg (e.g., at a dose of 300 mg), e.g., once every 3 weeks, e.g., by intravenous infusion. In another embodiment, the CSF-1/1R binding agent (e.g., a CSF-1R tyrosine kinase inhibitor), 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered at a dose between 200 mg and 400 mg (e.g., about 300 mg), e.g., daily (e.g., according to a 7 days on/7 days off schedule) or once a week, e.g., orally, and the PD-1 inhibitor (e.g., the anti-PD-1 antibody molecule) is administered at a dose between 300 mg and 500 mg (e.g., at a dose of 400 mg), e.g., once every 4 weeks, or at a dose between 200 mg and 400 mg (e.g., at a dose of 300 mg), e.g., once every 3 weeks, e.g., by intravenous infusion. In another embodiment, the CSF-1/1R binding agent (e.g., a CSF-1R tyrosine kinase inhibitor), 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered at a dose between 500 mg and 700 mg (e.g., about 600 mg), e.g., daily (e.g., according to a 7 days on/7 days off schedule) or once a week, e.g., orally, and the PD-1 inhibitor (e.g., the anti-PD-1 antibody molecule) is administered at a dose between 300 mg and 500 mg (e.g., at a dose of 400 mg), e.g., once every 4 weeks, or at a dose between 200 mg and 400 mg (e.g., at a dose of 300 mg), e.g., once every 3 weeks, e.g., by intravenous infusion. In another embodiment, the CSF-1/1R binding agent (e.g., a CSF-1R tyrosine kinase inhibitor), 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered at a dose between 800 mg and 1000 mg (e.g., about 900 mg), e.g., daily (e.g., according to a 7 days on/7 days off schedule) or once a week, e.g., orally, and the PD-1 inhibitor (e.g., the anti-PD-1 antibody molecule) is administered at a dose between 300 mg and 500 mg (e.g., at a dose of 400 mg), e.g., once every 4 weeks, or at a dose between 200 mg and 400 mg (e.g., at a dose of 300 mg), e.g., once every 3 weeks, e.g., by intravenous infusion.

In certain embodiments, the CSF-1/1R binding agent (e.g., a CSF-1R tyrosine kinase inhibitor), 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered in combination with the PD-1 inhibitor (e.g., the anti-PD-1 antibody molecule) to treat a caner, e.g., a solid tumor (e.g., an advanced solid tumor), e.g., a brain cancer (e.g., glioblastoma multiforme (GBM), e.g., recurrent glioblastoma), a breast cancer (e.g., a triple-negative breast cancer (e.g., NTBC)), or a pancreatic cancer (e.g., advanced pancreatic cancer).

In some embodiments, the CSF-1/1R binding agent is an M-CSF inhibitor, Compound A33, or a binding agent to CSF-1 disclosed in PCT Publication No. WO 2004/045532 or PCT Publication No WO 2005/068503 including RX1 or 5H4 (e.g., an antibody molecule or Fab fragment against M-CSF). In some embodiments, the cancer is chosen from an endometrial cancer, a skin cancer (e.g., melanoma), a pancreatic cancer, or a breast cancer (e.g., a triple negative breast cancer (TNBC)).

In some embodiments, the CSF-1/1R binding agent, e.g., an M-CSF inhibitor, Compound A33, or a compound disclosed in PCT Publication No. WO 2004/045532 (e.g., an antibody molecule or Fab fragment against M-CSF), is administered at an average dose of about 10 mg/kg. In some embodiments, the CSF-1/1R binding agent is a CSF1R inhibitor or 4-(2-((1R, 2R)-2-hydroxycyclohexylamino)ben-zothiazol-6-yloxy)-N-methylpicolinamide. 4-(2-((1R, 2R)-2-hydroxycyclohexylamino)benzothiazol-6-yloxy)-N-methylpicolinamide is disclosed as example 157 at page 117 of PCT Publication No. WO 2007/121484.

In some embodiments, the CSF-1/1R binding agent is pexidartinib (CAS Registry Number 1029044-16-3). Pexidrtinib is also known as PLX3397 or 5-((5-chloro-1H-pyrrolo[2,3-b]pyridin-3-yl)methyl)-N-06-(trifluoromethyl) pyridin-3-yl)methyl)pyridin-2-amine. Pexidartinib is a small-molecule receptor tyrosine kinase (RTK) inhibitor of KIT, CSF1R and FLT3. FLT3, CSF1R and FLT3 are over-expressed or mutated in many cancer cell types and play major roles in tumor cell proliferation and metastasis. PLX3397 can bind to and inhibit phosphorylation of stem cell factor receptor (KIT), colony-stimulating factor-1 receptor (CSF1R) and FMS-like tyrosine kinase 3 (FLT3), which may result in the inhibition of tumor cell proliferation and down-modulation of macrophages, osteoclasts and mast cells involved in the osteolytic metastatic disease. In some embodiments, the CSF-1/1R binding agent, e.g., pexidart-inib, is used in combination with a PD-1 inhibitor, e.g., an anti-PD-1 antibody molecule described herein.

In some embodiments, the CSF-1/1R binding agent is emactuzumab. Emactuzumab is also known as RG7155 or RO5509554. Emactuzumab is a humanized IgG1 mAb targeting CSF1R. In some embodiments, the CSF-1/1R binding agent, e.g., pexidartinib, is used in combination with a PD-L1 inhibitor, e.g., an anti-PD-L1 antibody molecule described herein.

In some embodiments, the CSF-1/1R binding agent is FPA008. FPA008 is a humanized mAb that inhibits CSF1R. In some embodiments, the CSF-1/1R binding agent, e.g., FPA008, is used in combination with a PD-1 inhibitor, e.g., an anti-PD-1 antibody molecule described herein.

Exemplary IL-17 Inhibitors

In one embodiment, a combination described herein includes an interleukine-17 (IL-17) inhibitor. In some embodiments, the combination is used to treat a cancer, e.g., a cancer described herein, e.g., a solid tumor, e.g., breast cancer (e.g., a triple negative breast cancer (TNBC), lung cancer (e.g., a non-small cell lung cancer (NSCLC), or colon cancer. In certain embodiments, the cancer is chosen from a colorectal cancer (e.g., a microsatellite stable colorectal cancer (MSS CRC)), a lung cancer (e.g., a non-small cell lung cancer), or a breast cancer (e.g., a triple negative lung cancer (TNBC)).

In some embodiments, the IL-17 inhibitor is secukinumab (CAS Registry Numbers: 875356-43-7 (heavy chain) and 875356-44-8 (light chain)). Secukinumab is also known as AIN457 and COSENTYX®. Secukinumab is a recombinant human monoclonal IgG1/κ antibody that binds specifically to IL-17A. It is expressed in a recombinant Chinese Hamster Ovary (CHO) cell line.

Secukinumab is described, e.g., in WO 2006/013107, U.S. Pat. Nos. 7,807,155, 8,119,131, 8,617,552, and EP 1776142. The heavy chain variable region of secukinumab has the amino acid sequence of: EVQLVESGG-GLVQPGGSLRLSCAASGFTFSNYWMNWVRQAPGK-GLEWVAAINQDGSEKYY VGSVKGRFTISRDNAKNS-LYLQMNSLRVEDTAVYYCVRDYYDILTDYYIHYWYF DLWGRG TLVTVSS (SEQ ID NO: 271) (disclosed as SEQ ID NO: 8 in WO 2006/013107). The light chain variable region of secukinumab has the amino acid sequence of: EIVLTQSPGTLSLSPGERATLSCRASQSVSSSY-LAWYQQKPGQAPRLLIYGASSRATGIPDRFS GSGSGTDFTLTISRLEPED-FAVYYCQQYGSSPCTFGQGTRLEIKR (SEQ ID NO: 298) (disclosed as SEQ ID NO: 10 in WO 2006/013107). The heavy chain CDR1 of secukinumab has the amino acid sequence of NYWMN (SEQ ID NO: 272) (disclosed as SEQ ID NO: 1 in WO 2006/013107). The heavy chain CDR2 of secukinumab has the amino acid sequence of AINQDGSEKYYVGSVKG (SEQ ID NO: 273) (disclosed as SEQ ID NO: 2 in WO 2006/013107). The heavy chain CDR3 of secukinumab has the amino acid sequence of DYYDILTDYYIHYWYFDL (SEQ ID NO: 274) (disclosed as SEQ ID NO: 3 in WO 2006/013107). The light chain CDR1 of secukinumab has the amino acid sequence of RASQSVSSSYLA (SEQ ID NO: 275) (disclosed as SEQ ID NO: 4 in WO 2006/013107). The light chain CDR2 of secukinumab has the amino acid sequence of GASSRAT (SEQ ID NO: 276) (disclosed as SEQ ID NO: 5 in WO 2006/013107). The light chain CDR3 of secukinumab has the amino acid sequence of GASSRAT (SEQ ID NO: 299) (disclosed as SEQ ID NO: 6 in WO 2006/013107).

In some embodiments, the IL-17 inhibitor is CJM112. CJM112 is also known as XAB4. CJM112 is a fully human monoclonal antibody (e.g., of the IgG1/K isotype) that targets IL-17A.

CJM112 is disclosed, e.g., in WO 2014/122613. acid sequence of: EVQLVESGGGDLVQPGGSLRLS-CAASGFTFSSYWMSWVRQAPGKGLEWVAN-IKQDGSEKYY VDSVKGRFTISRDNAKNS-LYLQMNSLRAEDTAVYYCARDRGSLYYWGQGTLVT VSSASTKG PSVFPLAPSSKSTSGGTAALGCLVKDYF-PEPVTVSWNSGALTSGVHTFPAVLQSSGLYSLSSV VTVPSSSLGTQTYICNVNHKPSNTKVDKRVE-PKSCDKTHTCPPCPAPELLGGPSVFLFPPKPK DTLMISRTPEVTCVVVDVSHEDPE-VKFNWYVDGVEVHNAKTKPREEQYN-STYRVVSVLTVL HQDWLNGKEYKCKVSNKALPA- PIEKTISKAKGQPREPQVYTLPPSREEMTKNQVSLTC
LVKG FYPSDIAVEWESNGQPEN-
NYKTTPPVLDSDGSFFLYSK-
LTVDKSRWQQGNVFSCSVMHEALH NHYTQKSLSL-
SPGK (SEQ ID NO: 277) (disclosed as SEQ ID NO: 14 in
WO 2014/122613). The light chain of CJM112 has the
amino acid sequence of: AIQLTQSPSSLSASVGDRVTIT-
CRPSQGINWELAWYQQKPGKAPKLLIYDAS-
SLEQGVPSRFSG SGSGTDFTLTISSLQPEDFA-
TYYCQQFNSYPLTFGGGTKVEIKRTVAAPSVFIFPPSD-
EQLKSGT
ASVVCLLNNFYPREAKVQWKVD-
NALQSGNSQESVTEQDSKDSTYSLSSTLTL-
SKADYEKHK VYACEVTHQGLSSPVTKSFNRGEC
(SEQ ID NO: 278) (disclosed as SEQ ID NO: 44 in WO
2014/122613).

CJM112 can bind to human, cynomolgus, mouse and rat
IL-17A and neutralize the bioactivity of these cytokines in
vitro and in vivo. IL-17A, a member of the IL-17 family, is
a major proinflammatory cytokine that has been indicated to
play important roles in many immune mediated conditions,
such as psoriasis and cancers (Witowski et al. (2004) *Cell
Mol. Life Sci.* p. 567-79; Miossec and Kolls (2012) *Nat. Rev.
Drug Discov.* p. 763-76). Without wishing to be bound by
theory, it is believed that in some embodiments, an IL-17
inhibitor, e.g., an anti-IL17 antibody, can enhance PD-1-
mediated response, e.g., by blocking IL-17 mediated expan-
sion of T-cell-suppressive neutrophils and/or reducing
metastasis (Coffelt et al. (2015) *Nature* p. 345-8).

In some embodiments, the combination described herein
includes an IL-17 inhibitor, CJM112, or a compound dis-
closed in WO 2006/013107, and an inhibitor of an immune
checkpoint molecule, e.g., an inhibitor of PD-1 (e.g., an
anti-PD-1 antibody molecule).

IL-17 is an important mediator of innate immunity and
chronic inflammatory response. For example, by effecting
increased chemokine production in various tissues, IL-17 is
central in the pathophysiology of autoimmune disease (Isail-
ovic et al. (2015) *J. Autoimmun.* p. 1-11). IL-17 is secreted
primarily by CD4+ Th17 as well as by γδ T cells, CD8+ T
cells, neutrophils and eosinophils, and it recruits monocytes
and neutrophils to the site of inflammation (Alshaker and
Matalka (2011) Cancer Cell Int. p. 11-33). The role of Th17
cell infiltrate in tumors has been studied in various cancers
and in many settings correlates with poor prognosis (Zeng et
al. (2015) *Int. J. Clin. Exp. Med.* p. 10515-36). Th17 cells,
and specifically IL-17, have both antitumor and pro-tumor
roles. In some settings, IL-17 promotes tumor vasculariza-
tion, cell proliferation, tumorigenesis, metastasis, and/or the
recruitment of macrophage derived suppressor cells to the
tumor microenvironment (Yang et al. (2014) *Mediators
Inflamm.* p. 014:623759). There is a role for targeting IL-17
in the treatment of malignancy (Zou and Restifo (2010) *Nat.
Rev. Immunol.* p. 246-56). In certain embodiments, the IL-17
inhibitor, CJM112, or a compound disclosed in WO 2006/
013107, enhances, or is used to enhance, PD-1 mediated
response, e.g., by blocking IL-17 mediated expansion of
T-cell-suppressive neutrophils and/or reducing metastasis.

In some embodiments, the IL-17 inhibitor, CJM112, or a
compound disclosed in WO 2006/013107, and the inhibitor
of an immune checkpoint molecule, e.g., an inhibitor of
PD-1 (e.g., an anti-PD-1 antibody molecule), each is admin-
istered at a dose and/or on a time schedule, that in combi-
nation, achieves a desired anti-tumor activity.

In one embodiment, the IL-17 inhibitor, CJM112, or a
compound disclosed in WO 2006/013107, is administered at
dose between 5 mg and 100 mg, e.g., between 10 mg and 75 mg, between 15 mg and 50 mg, between 20 mg and 30 mg,
between 10 mg and 25 mg, or between 25 mg and 40 mg,
e.g., at a dose of 5 mg, 10 mg, 15 mg, 20 mg, 25 mg, 30 mg,
35 mg, 40 mg, 45 mg, 50 mg, 60 mg, 70 mg, 80 mg, 90 mg,
or 100 mg, e.g., once every two weeks, every four weeks,
once every six weeks, or once every eight weeks, e.g.,
intravenously.

In one embodiment, the IL-17 inhibitor, CJM112, or a
compound disclosed in WO 2006/013107, is administered at
a dose between 20 mg and 30 mg (e.g., 25 mg), e.g., once
every four weeks. In some embodiments, the IL-17 inhibitor,
CJM112, or a compound disclosed in WO 2006/013107, is
administered intravenously. In one embodiment, the IL-17
inhibitor, CJM112, or a compound disclosed in WO 2006/
013107, is administered at a dose between 20 mg and 30 mg
(e.g., 25 mg), e.g., once every four weeks, e.g., by intrave-
nous infusion, and the PD-1 inhibitor (e.g., the anti-PD-1
antibody molecule) is administered at a dose between 300
mg and 500 mg (e.g., at a dose of 400 mg), e.g., once every
4 weeks, e.g., by intravenous infusion.

In one embodiment, the IL-17 inhibitor, CJM112, or a
compound disclosed in WO 2006/013107, is administered at
dose between 5 mg and 750 mg, e.g., between 10 mg and
500 mg, between 15 mg and 450 mg, between 20 mg and
400 mg, between 25 and 350 mg, between 50 mg and 300
mg, between 75 mg and 250 mg, between 100 mg and 200
mg, between 25 mg and 75 mg, or between 40 mg and 60
mg, e.g., at a dose of 5 mg, 10 mg, 15 mg, 20 mg, 30 mg,
40 mg, 50 mg, 70 mg, 80 mg, 90 mg, 100 mg, 150 mg, 200
mg, 250 mg, 300 mg, 350 mg, 400 mg, 450 mg, or 500 mg,
e.g., once every two weeks, every four weeks, once every six
weeks, or once every eight weeks, e.g., subcutaneously.

In one embodiment, the IL-17 inhibitor, CJM112, or a
compound disclosed in WO 2006/013107, is administered at
a dose between 40 mg and 60 mg (e.g., 50 mg), e.g., once
every four weeks. In some embodiments, the IL-17 inhibitor,
CJM112, or a compound disclosed in WO 2006/013107, is
administered subcutaneously. In one embodiment, the IL-17
inhibitor, CJM112, or a compound disclosed in WO 2006/
013107, is administered at a dose between 40 mg and 60 mg
(e.g., 50 mg), e.g., once every four weeks, e.g., by subcu-
taneous injection, and the PD-1 inhibitor (e.g., the anti-PD-1
antibody molecule) is administered at a dose between 300
mg and 500 mg (e.g., at a dose of 400 mg), e.g., once every
4 weeks, e.g., by intravenous infusion.

In one embodiment, the IL-17 inhibitor, CJM112, or a
compound disclosed in WO 2006/013107, is administered in
combination with the PD-1 inhibitor (e.g., the anti-PD-1
antibody molecule) to treat a colorectal cancer (CRC), a lung
cancer (e.g., non-small cell lung cancer (NSCLC)), or a
breast cancer (e.g., a triple negative breast cancer (TNBC)).

In some embodiments, the IL-17 inhibitor is ixekizumab
(CAS Registry Number: 1143503-69-8). Ixekizumab is also
known as LY2439821. Ixekizumab is a humanized IgG4
monoclonal antibody that targets IL-17A.

Ixekizumab is described, e.g., in WO 2007/070750, U.S.
Pat. Nos. 7,838,638, and 8,110,191. The Heavy chain vari-
able region of ixekizumab has the amino acid sequence of:
QVQLVQSGAEVKKPGSSVKVSCK-
ASGYSFTDYHIHWVRQAPGQ-
GLEWMGVINPMYGTTDY NQRFKGRVTITADEST-
STAYMELSSLRSEDTAVYYCARYDYFTGTGVYWGQ
GTLVTVSS (SEQ ID NO: 279) (disclosed as SEQ ID NO:
118 in WO 2007/070750). The light chain variable region of
ixekizumab has the amino acid sequence of:
DIVMTQTPLSLSVTPGQPASISCRSSRSLVHSRGN-
TYLHWYLQKPGQSPQLLIYKVSNRFIGVP DRFSGSGSGTDFTLKISRVEAEDVGVYYCSQSTH-
LPFTFGQGTKLEIK (SEQ ID NO: 280) (disclosed as SEQ
ID NO: 241 in WO 2007/070750).

In some embodiments, the IL-17 inhibitor is brodalumab
(CAS Registry Number: 1174395-19-7). Brodalumab is also
known as AMG 827 or AM-14. Brodalumab binds to the
interleukin-17 receptor A (IL-17RA) and prevents IL-17
from activating the receptor.

Brodalumab is disclosed, e.g., in WO 2008/054603, U.S.
Pat. Nos. 7,767,206, 7,786,284, 7,833,527, 7,939,070,
8,435,518, 8,545,842, 8,790,648, and 9,073,999. The heavy
chain CDR1 of brodalumab has the amino acid sequence of
RYGIS (SEQ ID NO: 281) (as disclosed as SEQ ID NO: 146
in WO 2008/054603). The heavy chain CDR2 of
brodalumab has the amino acid sequence of WIS-
TYSGNTNYAQKLQG (SEQ ID NO: 282) (as disclosed as
SEQ ID NO: 147 in WO 2008/054603). The heavy chain
CDR3 of brodalumab has the amino acid sequence of
RQLYFDY (SEQ ID NO: 283) (as disclosed as SEQ ID NO:
148 in WO 2008/054603). The light chain CDR1 of
brodalumab has the amino acid sequence of
RASQSVSSNLA (SEQ ID NO: 284) (as disclosed as SEQ
ID NO: 224 in WO 2008/054603). The heavy chain CDR2
of brodalumab has the amino acid sequence of DASTRAT
(SEQ ID NO: 285) (as disclosed as SEQ ID NO: 225 in WO
2008/054603). The heavy chain CDR3 of brodalumab has
the amino acid sequence of QQYDNWPLT (SEQ ID NO:
286) (as disclosed as SEQ ID NO: 226 in WO 2008/054603).
Exemplary IL-1β Inhibitors In one embodiment, a combination described herein
includes an interleukine-1 beta (IL-1β) inhibitor. In some
embodiments, the combination is used to treat a cancer, e.g.,
a cancer described herein, e.g., a hematologic malignancy
(e.g., a lymphoma (e.g., Hodgkin lymphoma), a leukemia
(e.g., an acute or chronic leukemia), or a multiple myeloma)
or a solid tumor (e.g., a colorectal cancer (CLC), a lung
cancer (e.g., a non-small cell lung cancer (NSCLC)), or a
breast cancer (e.g., a triple-negative breast cancer (TNBC)).
In certain embodiments, the cancer is chosen from a col-
orectal cancer (e.g., a microsatellite stable colorectal cancer
(MSS CRC), a lung cancer (e.g., a non-small cell lung
cancer), or a breast cancer (e.g., a triple negative lung cancer
(TNBC)).

In some embodiments, the IL-1β inhibitor is
canakinumab. Canakinumab is also known as ACZ885 or
ILARIS®. Canakinumab is a human monoclonal IgG1/κ
antibody that neutralizes the bioactivity of human IL-1β.

Canakinumab is disclosed, e.g., in WO 2002/16436, U.S.
Pat. No. 7,446,175, and EP 1313769. The heavy chain
variable region of canakinumab has the amino acid sequence
of: MEFGLSWVFLVALLRGVQCQVQLVES-
GGGVVQPGRSLRLSCAASGFTFSVYGMNWVRQAP
GKGLEWVAIIWYDGDNQYYADSVKGRFTIS-
RDNSKNTLYLQMNGLRAEDTAVYYCARDLR
TGPFDYWGQGTLVTVSS (SEQ ID NO: 287) (disclosed
as SEQ ID NO: 1 in U.S. Pat. No. 7,446,175). The light
chain variable region of canakinumab has the amino acid
sequence of: MLPSQLIGFLLLWVPASR-
GEIVLTQSPDFQSVTPKEKVTIT-
CRASQSIGSSLHWYQQKPDQSPK
LLIKYASQSFSGVPSRFSGSGSGTDFTLTINSLEAE-
DAAAYYCHQSSSLPFTFGPGTKVDIK (SEQ ID NO:
288) (disclosed as SEQ ID NO: 2 in U.S. Pat. No. 7,446,
175).

Canakinumab has been used, e.g., for the treatment of
Cryopyrin Associated Periodic Syndromes (CAPS), in
adults and children, for the treatment of systemic juvenile idiopathic arthritis (SJIA), for the symptomatic treatment of
acute gouty arthritis attacks in adults, and for other IL-1β
driven inflammatory diseases. Without wishing to be bound
by theory, it is believed that in some embodiments, IL-1β
inhibitors, e.g., canakinumab, can increase anti-tumor
immune response, e.g., by blocking one or more functions of
IL-1β including, e.g., recruitment of immunosuppressive
neutrophils to the tumor microenvironment, stimulation of
tumor angiogenesis, and/or promotion of metastasis (Din-
arello (2010) *Eur. J. Immunol.* p. 599-606), In some embodi-
ments, the combination described herein includes an IL-1β
inhibitor, canakinumab, or a compound disclosed in WO
2002/16436, and an inhibitor of an immune checkpoint
molecule, e.g., an inhibitor of PD-1 (e.g., an anti-PD-1
antibody molecule).

IL-1 is a secreted pleotropic cytokine with a central role
in inflammation and immune response. Increases in IL-1 are
observed in multiple clinical settings including cancer (Apte
et al. (2006) *Cancer Metastasis Rev.* p. 387-408; Dinarello
(2010) *Eur. J. Immunol.* p. 599-606). IL-1β is elevated in
lung, breast and colorectal cancer (Voronov et al. (2014)
*Front Physiol.* p. 114) and is associated with poor prognosis
(Apte et al. (2000) *Adv. Exp. Med. Biol.* p. 277-88). Without
wishing to be bound by theory, it is believed that in some
embodiments, secreted IL-1(3, derived from the tumor
microenvironment and by malignant cells, promotes tumor
cell proliferation, increases invasiveness and dampens anti-
tumor immune response, in part by recruiting inhibitory
neutrophils (Apte et al. (2006) *Cancer Metastasis Rev.* p.
387-408; Miller et al. (2007) *J. Immunol.* p. 6933-42).
Experimental data indicate that inhibition of IL-1β results in
a decrease in tumor burden and metastasis (Voronov et al.
(2003) *Proc. Natl. Acad. Sci. U.S.A.* p. 2645-50).
Canakinumab can bind IL-1β and inhibit IL-1-mediated
signaling. Accordingly, in certain embodiments, an IL-1β
inhibitor, e.g., canakinumab, enhances, or is used to
enhance, an immune-mediated anti-tumor effect of an
inhibitor of PD-1 (e.g., an anti-PD-1 antibody molecule).

In some embodiments, the IL-1β inhibitor, canakinumab,
or a compound disclosed in WO 2002/16436, and the
inhibitor of an immune checkpoint molecule, e.g., an inhibi-
tor of PD-1 (e.g., an anti-PD-1 antibody molecule), each is
administered at a dose and/or on a time schedule, that in
combination, achieves a desired anti-tumor activity.

In one embodiment, the IL-1β inhibitor, canakinumab, or
a compound disclosed in WO 2002/16436, is administered at
a dose between 25 mg and 200 mg, e.g., between 50 mg and
150 mg, between 80 mg and 120 mg, between 140 mg and
160 mg, between 40 mg and 60 mg, between 80 mg and 100
mg, between 50 mg and 100 mg, or between 100 mg and 150
mg, e.g., at a dose of 30 mg, 40 mg, 50 mg, 60 mg, 70 mg,
80 mg, 90 mg, 100 mg, 110 mg, 120 mg, 130 mg, 140 mg,
150 mg, 160 mg, 170 mg, 180 mg, 190 mg, or 200 mg, e.g.,
once every four weeks, once every six weeks, once every
eight weeks, once every ten weeks, or once every twelve
weeks.

In one embodiment, the IL-1β inhibitor, canakinumab, or
a compound disclosed in WO 2002/16436, is administered at
a dose between 80 mg and 120 mg (e.g., at a dose of 100
mg), e.g., once every eight weeks. In some embodiments,
the IL-1β inhibitor, canakinumab, or a compound disclosed
in WO 2002/16436, is administered is administered subcu-
taneously, e.g., in the abdomen or thigh. In one embodiment,
the IL-1β inhibitor, e.g., canakinumab, is administered at a
dose between 80 mg and 120 mg (e.g., at a dose of 100 mg),
e.g., once every eight weeks, e.g., by subcutaneous injection,
and the PD-1 inhibitor (e.g., the anti-PD-1 antibody molecule) is administered at a dose between 300 mg and 500 mg (e.g., at a dose of 400 mg), e.g., once every 4 weeks, e.g., by intravenous infusion.

In some embodiments, the IL-1β inhibitor, canakinumab, or a compound disclosed in WO 2002/16436, is administered in combination with the PD-1 inhibitor (e.g., the anti-PD-1 antibody molecule) to treat a colorectal cancer (e.g., MSS CRC), a lung cancer (e.g., a non-small cell lung cancer (NSCLC), or a breast cancer (e.g., a triple negative breast cancer (TNBC)).

Exemplary CXCR2 Inhibitors

In one embodiment, a combination described herein includes an inhibitor of chemokine (C-X-C motif) receptor 2 (CXCR2) inhibitor. In some embodiments, the combination is used to treat a cancer, e.g., a cancer described herein, e.g., a solid tumor, e.g., a breast cancer, a metastatic sarcoma, a pancreatic cancer, a melanoma, a renal cell carcinoma (RCC), a non-small cell lung cancer (NSCLC), or a pediatric tumor (e.g., a rhabdomyosarcoma).

In some embodiments, the CXCR2 inhibitor is danirixin (CAS Registry Number: 954126-98-8). Danirixin is also known as GSK1325756 or 1-(4-chloro-2-hydroxy-3-piperidin-3-ylsulfonylphenyl)-3-(3-fluoro-2-methylphenyl)urea. Danirixin is disclosed, e.g., in Miller et al. *Eur J Drug Metab Pharmacokinet* (2014) 39:173-181; and Miller et al. *BMC Pharmacology and Toxicology* (2015), 16:18.

In some embodiments, the CXCR2 inhibitor is reparixin (CAS Registry Number: 266359-83-5). Reparixin is also known as repertaxin or (2R)-2-[4-(2-methylpropyl)phenyl]-N-methylsulfonylpropanamide. Reparixin is a non-competitive allosteric inhibitor of CXCR1/2. Reparixin is disclosed, e.g., in Zarbock et al. *British Journal of Pharmacology* (2008), 1-8.

In some embodiments, the CXCR2 inhibitor is navarixin. Navarixin is also known as MK-7123, SCH 527123, PS291822, or 2-hydroxy-N,N-dimethyl-3-[[2-[[(1R)-1-(5-methylfuran-2-yl)propyl]amino]-3,4-dioxocyclobuten-1-yl]amino]benzamide Navarixin is disclosed, e.g., in Ning et al. *Mol Cancer Ther.* 2012; 11(6):1353-64.

Exemplary PI3K-γ, -δ Inhibitors

In one embodiment, a combination described herein includes an inhibitor of phosphatidylinositol-4,5-bisphosphate 3-kinase (PI3K), e.g., phosphatidylinositol-4,5-bisphosphate 3-kinase gamma and/or delta (PI3K-γ,δ). In some embodiments, the combination is used to treat a cancer, e.g., a cancer described herein, e.g., a solid tumor (e.g., a prostate cancer, a breast cancer, a brain cancer, a bladder cancer, a pancreatic cancer, a renal cancer, a solid tumor, a liver cancer, a non-small cell lung cancer, an endocrine cancer, an ovarian cancer, a melanoma, a female reproductive system cancer, a digestive/gastrointestinal cancer, a glioblastoma multiforme, a head and neck cancer, or a colon cancer), e.g., a hematologic malignancy (e.g., a leukemia (e.g., a lymphocytic leukemia, e.g., chronic lymphocytic leukemia (CLL) (e.g., relapsed CLL)),e.g., a lymphoma (e.g., non-Hodgkin lymphoma (e.g., relapsed follicular B-cell non-Hodgkin lymphoma (FL) or relapsed small lymphocytic lymphoma (SLL)), or e.g., a multiple myeloma).

In some embodiments, the PI3K inhibitor is an inhibitor of delta and gamma isoforms of PI3K. Exemplary PI3K inhibitors that can be used in combination are described in, e.g., WO 2010/036380, WO 2010/006086, WO 09/114870, WO 05/113556, GSK 2126458, GDC-0980, GDC-0941, Sanofi XL147, XL756, XL147, PF-46915032, BKM 120, CAL-101, CAL 263, SF1126, PX-886, and a dual PI3K inhibitor (e.g., Novartis BEZ235).

In some embodiments, the PI3K-γ,δ inhibitor is idelalisib (CAS Registry Number: 870281-82-6). Idelalisib is also known as ZYDELIG®, GS-1101, CAL-101, or 5-Fluoro-3-phenyl-2-[(1S)-1-(7H-purin-6-ylamino)propyl]-4(3H)-quinazolinone. Idelalisib blocks P1106, the delta isoform of PI3K. Idelalisib is disclosed, e.g., in Wu et al. *Journal of Hematology & Oncology* (2013) 6: 36.

In some embodiments, the PI3K-γ,δ inhibitor is dactolisib (Compound A4) or 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound disclosed in PCT Publication No. WO 2006/122806.

In some embodiments, the PI3K-γ,δ inhibitor is buparlisib (Compound A6) or a compound disclosed in PCT Publication No. WO 2007/084786.

In one embodiment, the PI3K-γ,δ inhibitor, e.g., buparlisib (Compound A6) or a compound disclosed in PCT Publication No. WO 2007/084786, is administered at a dose of about 100 mg (e.g., per day).

Other exemplary PI3K-γ,δ inhibitors that can be used in the combination include, e.g., pictilisib (GDC-0941), LY294002, pilaralisib (XL147), PI-3065, PI-103, VS-5584 (SB2343), CZC24832, duvelisib (IPI-145, INK1197), TG100-115, CAY10505, GSK1059615, PF-04691502, AS-605240, voxtalisib (SAR245409, XL765), IC-87114, omipalisib (GSK2126458, GSK458), TG100713, gedatolisib (PF-05212384, PKI-587), PKI-402, XL147 analogue, PIK-90, PIK-293, PIK-294, 3-Methyladenine (3-MA), AS-252424, AS-604850, or apitolisib (GDC-0980, RG7422).

In some embodiments, the PI3K inhibitor is Compound A8 or a compound described in PCT Publication No. WO2010/029082.

In some embodiments, the PI3K inhibitor is a pan-PI3K inhibitor, (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13) or a compound disclosed in PCT Publication No. WO2013/124826.

Exemplary PI3K-γ, -δ inhibitors include, but are not limited to, duvelisib and idelalisib. Idelalisib (also called GS-1101 or CAL-101; Gilead) is a small molecule that blocks the delta isoform of PI3K. The structure of idelalisib (5-Fluoro-3-phenyl-2-[(1S)-1-(7H-purin-6-ylamino)propyl]-4(3H)-quinazolinone) is shown below.

Duvelisib (also called IPI-145; Infinity Pharmaceuticals and Abbvie) is a small molecule that blocks PI3K-δ,γ. The structure of duvelisib (8-Chloro-2-phenyl-3-[(1S)-1-(9H-purin-6-ylamino)ethyl]-1(2H)-isoquinolinone) is shown below.

In one embodiment, the inhibitor is a dual phosphatidylinositol 3-kinase (PI3K) and mTOR inhibitor selected from 2-Amino-8-[trans-4-(2-hydroxyethoxy)cyclohexyl]-6-(6-methoxy-3-pyridinyl)-4-methyl-pyrido[2,3-c]pyrimidin-7(8H)-one (PF-04691502); N-[4-[[4-(Dimethylamino)-1-piperidinyl]carbonyl]phenyl]-N'-[4-(4,6-di-4-morpholinyl-1,3,5-triazin-2-yl)phenyl]urea (PF-05212384, PKI-587); 2-Methyl-2-{4-[3-methyl-2-oxo-8-(quinolin-3-yl)-2,3-dihydro-1H-imidazo[4,5-c]quinolin-1-yl]phenyl}propanenitrile (BEZ-235); apitolisib (GDC-0980, RG7422); 2,4-Difluoro-N-{2-(methyloxy)-5-[4-(4-pyridazinyl)-6-quinolinyl]-3-pyridinyl}benzenesulfonamide (GSK2126458); 8-(6-methoxypyridin-3-yl)-3-methyl-1-(4-(piperazin-1-yl)-3-(trifluoromethyl)phenyl)-1H-imidazo[4,5-c]quinolin-2(3H)-one Maleic acid (NVP-BGT226); 3-[4-(4-Morpholinylpyrido[3',2':4,5]furo[3,2-d]pyrimidin-2-yl]phenol (PI-103); 5-(9-isopropyl-8-methyl-2-morpholino-9H-purin-6-yl)pyrimidin-2-amine (VS-5584, SB2343); or N-[2-[(3,5-Dimethoxyphenyl)amino]quinoxalin-3-yl]-4-[(4-methyl-3-methoxyphenyl)carbonyl]aminophenylsulfonamide (XL765).

Exemplary BAFF-R Inhibitors

In one embodiment, a combination described herein includes a B-cell-activating factor receptor (BAFF-R) inhibitor. In some embodiments, the combination is used to treat a cancer, e.g., a cancer described herein, e.g., a hematologic malignancy, e.g., a leukemia (e.g., chronic lymphocytic leukemia (CLL), e.g., relapsed or refractory chronic lymphocytic leukemia).

In one embodiment, the BAFF-R inhibitor is VAY736. VAY736 is a fully human combinatorial antibody library (HuCAL)-derived monoclonal antibody targeting BAFF-R. BAFF-R, also known as tumor necrosis factor receptor superfamily member 13C, is overexpressed in certain tumor cell types and autoimmune diseases. VAY736 has both anti-inflammatory and antineoplastic activities. In cancer cells, BAFF-R plays a key role in B-cell proliferation and survival. VAY736 targets and binds to BAFF-R, which inhibits both BAFF/BAFF-R interaction and BAFF-R-mediated signaling. This may decrease cell growth in tumor cells expressing BAFF-R.

VAY736 is disclosed, e.g., in U.S. Pat. No. 8,106,163. The heavy chain CDR1 of VAY736 has the amino acid sequence of GDSVSSNSAAWG (SEQ ID NO: 289) (disclosed as SEQ ID NO: 3 in U.S. Pat. No. 8,106,163). The heavy chain CDR2 of VAY736 has the amino acid sequence of RIYYRSKWYNSYAVSVKS (SEQ ID NO: 290) (disclosed as SEQ ID NO: 10 in U.S. Pat. No. 8,106,163). The heavy chain CDR3 of VAY736 has the amino acid sequence of YDWVPKIGVFDS (SEQ ID NO: 300) (disclosed as SEQ ID NO: 17 in U.S. Pat. No. 8,106,163). The light chain CDR1 of VAY736 has the amino acid sequence of RASQFISSSYLS (SEQ ID NO: 291) (disclosed as SEQ ID NO: 24 in U.S. Pat. No. 8,106,163). The light chain CDR2 of VAY736 has the amino acid sequence of LLIYGSSSRAT (SEQ ID NO: 292) (disclosed as SEQ ID NO: 31 in U.S. Pat. No. 8,106,163). The light chain CDR3 of VAY736 has the amino acid sequence of QQLYSSPM (SEQ ID NO: 293) (disclosed as SEQ ID NO: 38 in U.S. Pat. No. 8,106,163). The heavy chain variable region of VAY736 has the amino acid sequence of: QVQLQQSGPGLVKPSQTLSLTCAIS-GDSVSSNSAAWGWIRQSPGRGLEWLGRIYYR-SKWYNS YAVSVKSRITINPDTSKNQFSLQLNSVT-PEDTAVYYCARYDWVPKIGVFDSWGQGTLVTVSS (SEQ ID NO: 294) (disclosed as SEQ ID NO: 52 in U.S. Pat. No. 8,106,163). The light chain variable region of VAY736 has the amino acid sequence of: DIVLTQSPATLSLSPGER-ATLSCRASQFISS-SYLSWYQQKPGQAPRLLIYGSSSRATGVPARFSG SGSGTDFTLTISSLEPED-FAVYYCQQLYSSPMTFGQGTKVEIKRT (SEQ ID NO: 295) (disclosed as SEQ ID NO: 45 in U.S. Pat. No. 8,106, 163). The heavy chain of VAY736 has the amino acid sequence of: QVQLQQSGPGLVKPSQTLSLTCAIS-GDSVSSNSAAWGWIRQSPGRGLEWLGRIYYR-SKWYNS YAVSVKSRITINPDTSKNQFSLQLNSVT-PEDTAVYYCARYDWVPKIGVFDSWGQGTLVTVSS ASTKGPSVFPLAPSSKSTSGGTAALGCLVKDYF-PEPVTVSWNSGALTSGVHTFPAVLQSSGLY SLSSVVTVPSSSLGTQTYICNVNHKPSNTKVDKRVE-PKSCDKTHTCPPCPAPELLGGPSVFLFP PKPKDTLMISRTPEVTCVVVDVSHEDPE-VKFNWYVDGVEVHNAKTKPREEQYNSTYRVVSV LTVLHQDWLNGKEYKCKVSNKALPAPIEKTIS KAKGQPREPQVYTLPPSREEMTKNQVSLTC LVKGFYPSDIAVEWESNGQPEN-NYKTTPPVLDSDGSFFLYSK-LTVDKSRWQQGNVFSCSVM HEALHNHYTQKSLSL-SPGK (SEQ ID NO: 296) (disclosed as SEQ ID NO: 75 in U.S. Pat. No. 8,106,163). The light chain variable region of VAY736 has the amino acid sequence of: DIVLTQSPATLSLSPGERATLSCRASQFISS-SYLSWYQQKPGQAPRLLIYGSSSRATGVPARFSG SGSGTDFTLTISSLEPED-FAVYYCQQLYSSPMTFGQGTKVEIKRTVAAPSVFIFP PSDEQLKSGT ASVVCLLNNFYPREAKVQWKVD-NALQSGNSQESVTEQDSKDSTYSLSSTLTL-SKADYEKHK VYACEVTHQGLSSPVTKSFNRGEC (SEQ ID NO: 297) (disclosed as SEQ ID NO: 71 in U.S. Pat. No. 8,106,163).

Exemplary MALT-1/BTK Inhibitors

In one embodiment, a combination described herein includes an inhibitor of MALT-1 and/or BTK. In some embodiments, the combination is used to treat a cancer, e.g., a cancer described herein.

Exemplary MALT-1/BTK inhibitors include, but are not limited to, (S)-1-(6-(2H-1,2,3-triazol-2-yl)-5-(trifluoromethyl)pyridin-3-yl)-3-(2-chloro-7-(1-methoxyethyl)pyrazolo[1,5-a]pyrimidin-6-yl)urea, (S)-1-(2-chloro-7-(1-methoxyethyl)pyrazolo[1,5-a]pyrimidin-6-yl)-3-(2-(trifluoromethyl)pyridin-4-yl)urea, (S)-1-(2-chloro-7-(1-methoxyethyl)pyrazolo[1,5-a]pyrimidin-6-yl)-3-(1-methyl-2-oxo-5-(trifluoromethyl)-1,2-dihydropyridin-3-yl)urea, (R)-1-(6-(2H-1,2,3-triazol-2-yl)-5-(trifluoromethyl)pyridin-3-yl)-3-(2-chloro-7-(1-methoxy-2-methylpropyl)pyrazolo[1,5-a]pyrimidin-6-yl)urea, (R)-1-(5-chloro-6-(2H-1,2,3-triazol-2-yl)pyridin-3-yl)-3-(2-chloro-7-(1-methoxy-2-methylpropyl)pyrazolo[1,5-a]pyrimidin-6-yl)urea, (S)-1-(7-(1-methoxyethyl)-2-methylpyrazolo[1,5-a]pyrimidin-6-yl)-3-(2-(trifluoromethyl)pyridin-4-yl)urea, (S)-1-(2-fluoro-7-

(1-methoxyethyl)pyrazolo[1,5-a]pyrimidin-6-yl)-3-(2-(trifluoromethyl)pyridin-4-yl)urea, and (S)-1-(2-chloro-7-(1-methoxyethyl)pyrazolo[1,5-a]pyrimidin-6-yl)-3-(5-cyanopyridin-3-yl)urea.

Exemplary BTK inhibitors include, but are not limited to, ibrutinib (PCI-32765); GDC-0834; RN-486; CGI-560; CGI-1764; HM-71224; CC-292; ONO-4059; CNX-774; or LFM-A13. In one embodiment, the BTK inhibitor does not reduce or inhibit the kinase activity of interleukin-2-inducible kinase (ITK), e.g., is selected from GDC-0834; RN-486; CGI-560; CGI-1764; HM-71224; CC-292; ONO-4059; CNX-774; or LFM-A13.

In one embodiment, the kinase inhibitor is a BTK inhibitor, e.g., ibrutinib (PCI-32765). The structure of ibrutinib (1-[(3R)-3-[4-Amino-3-(4-phenoxyphenyl)-1H-pyrazolo[3,4-d]pyrimidin-1-yl]piperidin-1-yl]prop-2-en-1-one) is shown below.

In other embodiments, the BTK inhibitor is a BTK inhibitor described in International Application WO/2015/079417, which is herein incorporated by reference in its entirety. For instance, in some embodiments, the BTK inhibitor is a compound of formula (I) or a pharmaceutically acceptable salt thereof;

(I)

wherein,

R1 is hydrogen, C1-C6 alkyl optionally substituted by hydroxy;

R2 is hydrogen or halogen;

R3 is hydrogen or halogen;

R4 is hydrogen;

R5 is hydrogen or halogen;

or R4 and R5 are attached to each other and stand for a bond, —CH2-, —CH2-CH2-, —CH═CH—, —CH═CH—CH2-; —CH2-CH═CH—; or —CH2-CH2-CH2-;

R6 and R7 stand independently from each other for H, C1-C6 alkyl optionally substituted by hydroxyl, C3-C6 cycloalkyl optionally substituted by halogen or hydroxy, or halogen;

R8, R9, R, R', R10 and R11 independently from each other stand for H, or C1-C6 alkyl optionally substituted by C1-C6 alkoxy; or any two of R8, R9, R, R', R10 and R11 together with the carbon atom to which they are bound may form a 3-6 membered saturated carbocyclic ring;

R12 is hydrogen or C1-C6 alkyl optionally substituted by halogen or C1-C6 alkoxy;

or R12 and any one of R8, R9, R, R', R10 or R11 together with the atoms to which they are bound may form a 4, 5, 6 or 7 membered azacyclic ring, which ring may optionally be substituted by halogen, cyano, hydroxyl, C1-C6 alkyl or C1-C6 alkoxy;

n is 0 or 1; and

R13 is C2-C6 alkenyl optionally substituted by C1-C6 alkyl, C1-C6 alkoxy or N,N-di-C1-C6 alkyl amino; C2-C6 alkynyl optionally substituted by C1-C6 alkyl or C1-C6 alkoxy; or C2-C6 alkylenyl oxide optionally substituted by C1-C6 alkyl.

In some embodiments, the BTK inhibitor of Formula I is chosen from: N-(3-(5-((1-Acryloylazetidin-3-yl)oxy)-6-aminopyrimidin-4-yl)-5-fluoro-2-methylphenyl)-4-cyclo-propyl-2-fluorobenzamide; (E)-N-(3-(6-Amino-5-((1-(but-2-enoyl)azetidin-3-yl)oxy)pyrimidin-4-yl)-5-fluoro-2-methylphenyl)-4-cyclopropyl-2-fluorobenzamide; N-(3-(6-Amino-5-((1-propioloylazetidin-3-yl)oxy)pyrimidin-4-yl)-5-fluoro-2-methylphenyl)-4-cyclopropyl-2-fluorobenzamide; N-(3-(6-Amino-5-((1-(but-2-ynoyl)azetidin-3-yl)oxy)pyrimidin-4-yl)-5-fluoro-2-methylphenyl)-4-cyclopropyl-2-fluorobenzamide; N-(3-(5-((1-Acryloylpiperidin-4-yl)oxy)-6-aminopyrimidin-4-yl)-5-fluoro-2-methylphenyl)-4-cyclopropyl-2-fluorobenzamide; N-(3-(6-Amino-5-(2-(N-methylacrylamido)ethoxy)pyrimi-din-4-yl)-5-fluoro-2-methylphenyl)-4-cyclopropyl-2-fluo-robenzamide; (E)-N-(3-(6-Amino-5-(2-(N-methylbut-2-enamido)ethoxy)pyrimidin-4-yl)-5-fluoro-2-methylphenyl)-4-cyclopropyl-2-fluorobenzamide; N-(3-(6-Amino-5-(2-(N-methylpropiolamido)ethoxy)pyrimidin-4-yl)-5-fluoro-2-methylphenyl)-4-cyclopropyl-2-fluorobenzamide; (E)-N-(3-(6-Amino-5-(2-(4-methoxy-N-methylbut-2-enamido)ethoxy)pyrimidin-4-yl)-5-fluoro-2-methylphenyl)-4-cyclopropyl-2-fluorobenzamide; N-(3-(6-Amino-5-(2-(N-methylbut-2-ynamido)ethoxy)pyrimidin-4-yl)-5-fluoro-2-methylphenyl)-4-cyclopropyl-2-fluorobenzamide; N-(2-((4-Amino-6-(3-(4-cyclopropyl-2-fluorobenzamido)-5-fluoro-2-methylphenyl)pyrimidin-5-yl)oxy)ethyl)-N-methyloxirane-2-carboxamide; N-(2-((4-Amino-6-(3-(6-cyclopropyl-8-fluoro-1-oxoisoquinolin-2(1H)-yl)phenyl)pyrimidin-5-yl)oxy)ethyl)-N-methylacrylamide; N-(3-(5-(2-Acrylamidoethoxy)-6-aminopyrimidin-4-yl)-5-fluoro-2-methylphenyl)-4-cyclopropyl-2-fluorobenzamide; N-(3-(6-Amino-5-(2-(N-ethylacrylamido)ethoxy)pyrimidin-4-yl)-5-fluoro-2-methylphenyl)-4-cyclopropyl-2-fluorobenzamide; N-(3-(6-Amino-5-(2-(N-(2-fluoroethyl)acrylamido)ethoxy)pyrimidin-4-yl)-5-fluoro-2-methylphenyl)-4-cyclopropyl-2-fluorobenzamide; N-(3-(5-((1-Acrylamidocyclopropyl)methoxy)-6-aminopyrimidin-4-yl)-5-fluoro-2-methylphenyl)-4-cyclopropyl-2-fluorobenzamide; (S)—N-(3-(5-(2-Acrylamidopropoxy)-6-aminopyrimidin-4-yl)-5-fluoro-2-methylphenyl)-4-cyclopropyl-2-fluorobenzamide; (S)—N-(3-(6-Amino-5-(2-(but-2-ynamido)propoxy)pyrimi-din-4-yl)-5-fluoro-2-methylphenyl)-4-cyclopropyl-2-fluo-robenzamide; (S)—N-(3-(6-Amino-5-(2-(N-methylacrylamido)propoxy)pyrimidin-4-yl)-5-fluoro-2-methylphenyl)-4-cyclopropyl-2-fluorobenzamide; (S)—N-(3-(6-Amino-5-(2-(N-methylbut-2-ynamido)propoxy)pyrimidin-4-yl)-5-fluoro-2-methylphenyl)-4-cyclopropyl-2-fluorobenzamide; N-(3-(6-Amino-5-(3-(N-methylacrylamido)propoxy)py-rimidin-4-yl)-5-fluoro-2-methylphenyl)-4-cyclopropyl-2-fluorobenzamide; (S)—N-(3-(5-((1-Acryloylpyrrolidin-2-yl)methoxy)-6-aminopyrimidin-4-yl)-5-fluoro-2-methylphenyl)-4-cyclopropyl-2-fluorobenzamide; (S)—N-(3-(6-Amino-5-((1-(but-2-ynoyl)pyrrolidin-2-yl)methoxy)pyrimidin-4-yl)-5-fluoro-2-methylphenyl)-4-cyclopropyl-2-fluorobenzamide; (S)-2-(3-(5-((1-Acryloylpyrrolidin-2-yl)methoxy)-6-aminopyrimidin-4-yl)-5-fluoro-2-(hydroxymethyl)phenyl)-6-cyclopropyl-3,4-dihydroisoquinolin-1(2H)-one; N-(2-((4-Amino-6-(3-(6-cyclopropyl-1-oxo-3,4-dihydroisoquinolin-2(1H)-yl)-5-fluoro-2-(hydroxymethyl)phenyl)pyrimidin-5-yl)oxy)ethyl)-N-methylacrylamide; N-(3-(5-(((2S,4R)-1-Acryloyl-4-methoxypyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4R)-1-(but-2-ynoyl)-4-methoxypyrrolidin-2-yl)methoxy)pyrimidin-4-yl)-5-fluoro-2-methylphenyl)-4-cyclopropyl-2-fluorobenzamide; 2-(3-(5-(((2S,4R)-1-Acryloyl-4-methoxypyrrolidin-2-yl)methoxy)-6-aminopyrimidin-4-yl)-5-fluoro-2-(hydroxymethyl)phenyl)-6-cyclopropyl-3,4-dihydroisoquinolin-1(2H)-one; N-(3-(5-(((2S,4S)-1-Acryloyl-4-methoxypyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4S)-1-(but-2-ynoyl)-4-methoxypyrrolidin-2-yl)methoxy)pyrimidin-4-yl)-5-fluoro-2-methylphenyl)-4-cyclopropyl-2-fluorobenzamide; N-(3-(5-(((2S,4R)-1-Acryloyl-4-fluoropyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4R)-1-(but-2-ynoyl)-4-fluoropyrrolidin-2-yl)methoxy)pyrimidin-4-yl)-5-fluoro-2-methylphenyl)-4-cyclopropyl-2-fluorobenzamide; (S)—N-(3-(5-((1-Acryloylazetidin-2-yl)methoxy)-6-aminopyrimidin-4-yl)-5-fluoro-2-methylphenyl)-4-cyclopropyl-2-fluorobenzamide; (S)—N-(3-(6-Amino-5-((1-propioloylazetidin-2-yl)methoxy)pyrimidin-4-yl)-5-fluoro-2-methylphenyl)-4-cyclopropyl-2-fluorobenzamide; (S)-2-(3-(5-((1-Acryloylazetidin-2-yl)methoxy)-6-aminopyrimidin-4-yl)-5-fluoro-2-(hydroxymethyl)phenyl)-6-cyclopropyl-3,4-dihydroisoquinolin-1(2H)-one; (R)—N-(3-(5-((1-Acryloylazetidin-2-yl)methoxy)-6-aminopyrimidin-4-yl)-5-fluoro-2-methylphenyl)-4-cyclopropyl-2-fluorobenzamide; (R)—N-(3-(5-((1-Acryloylpiperidin-3-yl)methoxy)-6-aminopyrimidin-4-yl)-5-fluoro-2-methylphenyl)-4-cyclopropyl-2-fluorobenzamide; N-(3-(5-(((2R,3S)-1-Acryloyl-3-methoxypyrrolidin-2-yl)methoxy)-6-aminopyrimidin-4-yl)-5-fluoro-2-methylphenyl)-4-cyclopropyl-2-fluorobenzamide; N-(3-(5-(((2S,4R)-1-Acryloyl-4-cyanopyrrolidin-2-yl)methoxy)-6-aminopyrimidin-4-yl)-5-fluoro-2-methylphenyl)-4-cyclopropyl-2-fluorobenzamide; or N-(3-(5-(((2S,4S)-1-Acryloyl-4-cyanopyrrolidin-2-yl)methoxy)-6-aminopyrimidin-4-yl)-5-fluoro-2-methylphenyl)-4-cyclopropyl-2-fluorobenzamide.

Unless otherwise provided, the chemical terms used above in describing the BTK inhibitor of Formula I are used according to their meanings as set out in International Application WO/2015/079417, which is herein incorporated by reference in its entirety.

Exemplary JAK Inhibitors

In one embodiment, a combination described herein includes an inhibitor of Janus kinase (JAK). In some embodiments, the combination is used to treat a cancer, e.g., a cancer described herein, e.g., a solid tumor (e.g., a colon cancer, a prostate cancer, a lung cancer, a breast cancer, or a pancreatic cancer), e.g., a hematologic malignancy (e.g., a leukemia (e.g., a myeloid leukemia or a lymphocytic leukemia), e.g., a lymphoma (e.g., a non-Hodgkin lymphoma), or a multiple myeloma.

In some embodiments, the JAK inhibitor is 2-fluoro-N-methyl-4-(7-(quinolin-6-ylmethyl)imidazo[1,2-b][1,2,4]tri-azin-2-yl)benzamide (Compound A17), or a dihydrochloric salt thereof, or a compound disclosed in PCT Publication No. WO 2007/070514.

In some embodiments, the JAK inhibitor, e.g., 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514, is administered at a dose of about 400-600 mg (e.g., per day), e.g., about 400, 500, or 600 mg, or about 400-500 or 500-600 mg.

In some embodiment, the JAK inhibitor is ruxolitinib phosphate (also known as JAKAFI; Compound A18) or a compound disclosed in PCT Publication No. WO 2007/070514.

In one embodiment, the JAK inhibitor, e.g., ruxolitinib phosphate (also known as JAKAFI; Compound A18) or a compound disclosed in PCT Publication No. WO 2007/070514, is administered at a dose of about 15-25 mg, e.g., twice daily. In some embodiments, the dose is about 15, 20, or 25 mg, or about 15-20 or 20-25 mg.

Exemplary CRTH2 Inhibitors

In one embodiment, a combination described herein includes an inhibitor of chemoattractant receptor homologous to the T helper 2 cell (CRTH2). In some embodiments, the combination is used to treat a cancer, e.g., a cancer described herein.

In some embodiments, the CRTH2 inhibitor is QAV680 (CAS Registry Number: 872365-16-7). QAV680 is also known as fevipiprant and 2-[2-methyl-1-[(4-methylsulfo-nylphenyl)methyl]pyrrolo[2,3-b]pyridin-3-yl]acetic acid. QAV680 is disclosed, e.g., in Sandham et al. *Bioorg Med Chem.* 2013; 21(21):6582-91. QAW039 is also known as [1-(4-Methanesulfonyl-2-trifluoromethyl-benzyl)-2-methyl-1H-pyrrolo[2,3-b]pyridin-3-yl]-acetic acid. QAW039 is disclosed, e.g. in Sykes et al. European Respiratory Journal Sep. 1, 2014 vol. 44 no. Suppl 58 P4074.

In some embodiments, the CRTH2 inhibitor is QAW039 (CAS Number: 872365-14-5).

Other CRTH2 inhibitors that can be used in the combination include, e.g., AZD1981, ARRY-502, setipiprant (ACT-453859), and ACT-129968.

Exemplary PFKFB3 Inhibitors

In one embodiment, a combination described herein includes an inhibitor of 6-phosphofructo-2-kinase/fructose-2,6-biphosphatase 3 (PFKFB3). In some embodiments, the combination is used to treat a cancer, e.g., a cancer described herein, e.g., a solid tumor (e.g., an advanced solid tumor), e.g., an ovarian cancer, a fallopian tube cancer, a colorectal cancer (CRC), a leukemia, a lung cancer, a prostate cancer, a breast cancer, or a pancreas cancer. In some embodiments, the cancer is an ovarian cancer (e.g., a recurrent ovarian cancer), a fallopian tube cancer, or a colorectal cancer (e.g., a metastatic colorectal cancer). Without wishing to be bound by theory, it is believed that in some embodiments, PFKFB3-driven glycolysis can regulate vessel branching in cancer, and endothelial cells can rely on glycolysis for ATP production and metastatic potential. In some embodiments, the combination is used to treat a cancer with high angiogenic activity. In other embodiments, the combination is used to treat a cancer enriched in Th17 cells. In other embodiments, the combination is used to treat a cancer unresponsive or moderately responsive to an anti-PD-1 or anti-PD-L1 monotherapy.

In some embodiments, the PFKFB3 inhibitor is PFK-158. PFK-158 is also known as ACT-PFK-158 or (E)-1-(pyridin-4-yl)-3-(7-(trifluoromethyl)quinolin-2-yl)-prop-2-en-1-one (Cas Number 1462249-75-7). PFK-158 is a derivative of 3-(3-pyridinyl)-1-[4-pyridinyl]-2-propen-1-one (3PO). PFKFB3, which catalyzes the conversion of fructose-6-phosphate to fructose-2,6-bisphosphate, is highly expressed and active in human cancer cells and plays a key role in increasing both glycolytic flux in and proliferation of cancer cells. In some embodiments, PFKFB3 is expressed (e.g., overexpressed compared to a normal tissue) in a cancer chosen from a leukemia, a colon cancer, a lung cancer, a prostate cancer, an ovarian cancer, a fallopian tube cancer, a breast cancer, or a pancreas cancer. PFKFB3 inhibitors, e.g., PFK-158, can bind to and inhibit the activity of PFKFB3, which leads to the inhibition of both the glycolytic pathway in and glucose uptake by cancer cells. This prevents the production of macromolecules and energy that causes the enhanced cellular proliferation in cancer cells as compared to that of normal, healthy cells. Depriving cancer cells of nutrients and energy leads to the inhibition of cancer cell growth. In some embodiments, a PFKFB3 inhibitor, e.g., PFK-158, inhibits glucose uptake by a cancer cell. In other embodiments, a PFKFB3 inhibitor, e.g., PFK-158, reduces pathological angiogenesis. For example, PFK-158 can reduce [18]FDG uptake in xenografted tumors and exhibit antitumor activity in low leukocyte count (LLC) mice. PFK-158 is disclosed, e.g., at page 5 of WO 2013/148228.

In some embodiments, the PFKFB3 inhibitor has the following structure:

In some embodiments, the combination described herein is used to treat an ovarian cancer. Ovarian cancer is generally known as an immune responsive disease (Zhang et al. N Engl J Med. 2003; 348(3):203-13). For example, improved overall survival was observed in patients with higher frequencies of intraepithelial CD8+ T cells compared with patients with lower CD8+ T cell frequencies (median survival 55 months versus 26 months; hazard ratio=0.33; P<0.001) (Sato et al. Proc Natl Acad Sci USA. 2005; 102(51):18538-43). In some embodiments, increased Treg frequency can be used as predictors of poor survival (Curiel et al. Nat Med. 2004; 10(9):942-9). Without wishing to be bound by theory, it is believed that in some embodiments, high tumor antigen load can result in progressive loss of one or more effector functions of antigen-specific T cells, e.g., leading to T cell exhaustion. Patients with ovarian cancer, e.g., advanced ovarian cancer, can be selected for immunotherapy, e.g., a combination therapy described herein, at least in part, because of the small disease burden after initial therapy and high risk for recurrence.

In some embodiments, the combination further includes an IDO inhibitor (e.g., an IDO inhibitor described herein). In other embodiments, the combination further includes a CD-27 agonist (e.g., a CD-27 agonist described herein). In other embodiments, the combination further includes an anti-CTLA-4 antibody (e.g., an anti-CTLA-4 antibody described herein, e.g., ipilimumab). In other embodiments, the combination further includes a PARP inhibitor (e.g., a PARP described herein, e.g., ipilimumab). In other embodiments, the combination further includes a chemotherapy (e.g., a chemotherapy described herein, e.g., paclitaxel). In other embodiments, the combination further includes a CSF-1R inhibitor (e.g., a CSF-1R inhibitor described herein).

In some embodiments, the combination described herein is used to treat a colorectal cancer. Colorectal cancer (CRC) is generally considered as an inflammation-driven cancer. Metastatic, or stage IV colon cancers, have a 5-year relative survival rate of about 11%. Without wishing to be bound by theory, it is believed that in some embodiments, human CRC development is linked to the interleukin-23 (IL-23)-IL-17 pathway (Grivennikov et al., Nature. 2012; 491(7423):254-8). IL-17 is associated with poor prognosis and promotes angiogenesis via stimulating VEGF production of cancer cells in CRC. Activated gdT17 cells also secreted other cytokines including IL-8, TNF-α, and GM-CSF, which chemoattract MDSCs in the tumor and sustain their immunosuppressive activity. Th17 cell expression signatures in CRC have been shown to be associated with poor survival (Grivennikov et al., Nature. 2012; 491(7423):254-8; Zou and Restifo, Nat Rev Immunol. 2010; 10(4):248-56). CRC is often sensitive to VEGF inhibition, but it has been shown that an IL-17-mediated paracrine network promotes tumor resistance to anti-angiogenic therapy (Chung et al. Nat Med. 2013; 19(9):1114-23). IL-17 induced recruitment of CD11b+Gr1+ myeloid cells to the tumor microenvironment can promote VEGF-independent tumor growth.

In some embodiments, the combination is used to treat a subject having a microsatellite stable (MSS) colorectal cancer. In certain embodiments, subject does not respond or responds poorly to a checkpoint inhibitor monotherapy. In other embodiments, the combination is used to treat a subject having a microsatellite instable (MSI) colorectal cancer. In certain embodiments, the subject has an MSI colorectal cancer or a stage IV colorectal cancer. In certain embodiments, the subject responds to checkpoint inhibitor therapy.

In some embodiments, the combination further includes a chemotherapy, e.g., a chemotherapy described herein. In some embodiments, the combination further includes 5-FU, folinic acid, or both. Alternatively, or in combination, the combination further includes oxaliplatin. Alternatively, or in combination, in other embodiments, the combination further includes irinotecan. In certain embodiments, the combination further includes FOLFOX or FOLFIRI. In some embodiments, the combination further includes an angiogenesis inhibitor (e.g., bevacizumab).

In some embodiments, the PFKFB3 inhibitor, PFK-158, or a compound disclosed in PCT Publication No. WO 2013/148228, is administered in combination with a PD-1 inhibitor (e.g., an anti-PD-1 antibody molecule). In some embodiments, the PFKFB3 inhibitor, PFK-158, or a compound disclosed in PCT Publication No. WO 2013/148228, is administered intravenously. In some embodiments, the PD-1 inhibitor (e.g., the anti-PD-1 antibody molecule) is administered at a dose between 300 mg and 500 mg (e.g., at a dose of 400 mg), e.g., once every 4 weeks, e.g., by intravenous infusion. In other embodiments, the PD-1 inhibitor (e.g., the anti-PD-1 antibody molecule) is administered at a dose between 200 mg and 400 mg (e.g., at a dose of 300 mg), e.g., once every 3 weeks, e.g., by intravenous infusion. In certain embodiments, the combination is used to treat a cancer described herein, e.g., an ovarian cancer, a fallopian tube cancer (e.g., a papillary serous adenocarcinoma), or a colorectal cancer. In some embodiments, the combination is used to treat a subject who responds poorly or has failed chemotherapy (e.g., a platinum-based chemotherapy or a chemotherapy with 5FU).

Exemplary Chemotherapies

In one embodiment, a combination described herein includes a chemotherapeutic agent. In some embodiments, the combination is used to treat a cancer, e.g., a cancer described herein, e.g., a breast cancer, a lung cancer (e.g., a non-small cell lung cancer (NSCLC)), a nasopharyngeal cancer, or a pancreatic cancer. In some embodiments, the cancer is a breast cancer, e.g., a metastatic breast cancer, e.g., a HER2-negative breast cancer (e.g., a triple negative breast cancer (TNBC) or a HR+ breast cancer resistant to an endocrine therapy). In some embodiments, the lung cancer (e.g., a non-small cell lung cancer) is a squamous NSCLC or a non-squamous NSCLC. In certain embodiments, the combination is used to treat a nasopharyngeal cancer.

In some embodiments, the chemotherapeutic agent is paclitaxel, e.g., a protein-bound paclitaxel, also known as nanoparticle albumin-bound paclitaxel or nab-paclitaxel (ABRAXANE®). In some embodiments, paclitaxel has the following structure:

Paclitaxel is also known as (2α,4α,5β,7β,10β,13α)-4,10-Bis(acetyloxy)-13-{[(2R,3S)-3-(benzoylamino)-2-hydroxy-3-phenylpropanoyl]oxy}-1,7-dihydroxy-9-oxo-5,20-epoxy-tax-11-en-2-yl benzoate.

Nab-paclitaxel is a nanoparticle albumin-bound paclitaxel that differs from traditional paclitaxel which is formulated with Kolliphor EL (formerly Cremophor EL). This solvent free formulation was designed to improve the therapeutic index of paclitaxel, in particular to reduce toxicities such as hypersensitivity reactions (which allows obviating the antihistamine and steroid premedication) while potentially increasing the paclitaxel intake in cancer cells (Ibrahim et al. *Clin Cancer Res.* 2002; 8(5):1038-44). The solvent vehicle used for traditional paclitaxel may also affects drug delivery to the tumor, limiting its clinical effectiveness (ten Tije et al. *Clin Pharmacokinet.* 2003; 42(7):665-85) and leading to a more than dose-proportional increase in systemic drug exposure over a narrow dose range that is most likely explained by the entrapment of paclitaxel in solvent micelles (Gianni et al. *J Clin Oncol.* 1995; 13(1):180-90; van Tellingen et al. *Br J Cancer.* 1999; 81(2):330-5; Sparreboom et al. *Cancer Res.* 1999; 59(7):1454-7). Compared with traditional paclitaxel, nab-paclitaxel yields a 10-fold higher mean maximal concentration of free paclitaxel and in addition, nab-paclitaxel is transported more rapidly across endothelial cell layers and exhibits greater tissue penetration and slower elimination of paclitaxel. According to preclinical models, increased intratumoral delivery and retention result in 33% higher intratumoral drug concentrations (Desai et al. *Clin Cancer Res.* 2006; 12(4):1317-24. Erratum in: *Clin Cancer Res.* 2006; 12(12):3869).

While not wishing to be bound by theory, it is believed that in some embodiments, nab-paclitaxel is a microtubule inhibitor that promotes the assembly of microtubules from tubulin dimers and stabilizes microtubules by preventing depolymerization. This stability results in the inhibition of the normal dynamic reorganization of the microtubule network that is important for vital interphase and mitotic cellular functions.

In some embodiments, nab-paclitaxel can be used as monotherapy, with a recommended dose of 260 mg/m$^2$ every 3 weeks, for the treatment of patients with metastatic breast cancer, e.g., after failure of first line chemotherapy for metastatic disease or relapse within 6 months of adjuvant chemotherapy (prior therapy should have included an anthracycline unless clinically contraindicated). The results of a phase III trial that demonstrated significantly improved ORR (33 vs 19%; P=0.001) and TTP (23.0 vs 16.9 weeks; HR=0.75; P=0.006) in patients treated in first and second line or beyond with nab-paclitaxel compared with patients who received traditional paclitaxel 175 mg/m$^2$ every 3 weeks (Gradishar et al. *J Clin Oncol.* 2005; 23(31):7794-803).

In certain embodiments, a weekly regimen (Day 1, 8, 15 every 4 weeks) of nab-paclitaxel can be used. Two different weekly doses (100 mg/m$^2$ and 150 mg/m2 qw3/4) were compared in a randomized phase II trial with nab-paclitaxel 300 mg/m$^2$ every 3 weeks (q3w) and docetaxel 100 mg/m$^2$ q3w in the first-line setting (Gradishar et al. *J Clin Oncol.* 2009; 27(22):3611-9. Erratum in: *J Clin Oncol.* 2011; 29(19):2739; Gradishar et al. *Clin Breast Cancer.* 2012; 12(5):313-21). In some embodiments, the 150 mg/m$^2$ qw3/4 dosing is used, e.g., for patients who need a rapid tumor response. In other embodiments, the 100 mg/m$^2$ qw3/4 dose is used, e.g., due to the more manageable safety profile.

The pharmacokinetics of total paclitaxel following 30 and 180-minute infusions of nab-paclitaxel at dose levels of 80 to 375 mg/m$^2$ were determined in clinical studies. Dose levels of mg/m$^2$ refer to mg of paclitaxel in nab-paclitaxel. Following intravenous administration of nab-paclitaxel, paclitaxel plasma concentrations declined in a biphasic manner, with an initial rapid decline representing distribution to the peripheral compartment and a slower second phase representing drug elimination. The drug exposure (AUCs) was dose proportional within the 80 to 300 mg/m$^2$ range, and the pharmacokinetics of paclitaxel for nab-paclitaxel were independent of the duration of intravenous administration. The mean total clearance ranges from 13 to 30 L/h/m$^2$, and the mean terminal half-life ranges from 13 to 27 hours.

In some embodiments, the combination described herein is used to treat a breast cancer, e.g., a metastatic breast cancer or a HER2-negative breast cancer (e.g., a triple negative breast cancer). While not wishing to be bound by theory, it is believed that in some embodiments, the use of steroids in combination with anti-PD-1 compounds may be antagonistic and nab-paclitaxel presents an advantage over other taxanes, at least in part, because premedication with corticosteroids is not needed.

In some embodiments, the combination is used to treat a subject having a triple negative breast cancer or an HR+ breast cancer disease after failing an endocrine therapy. In other embodiments, the combination is used to treat a taxane naïve patient or a patient having at least 1 year of disease-free survival after their use in the adjuvant setting. In certain embodiments, the combination is used to treat a subject who is eligible for a first line chemotherapy.

In breast cancer the interaction of the immune system with tumor cells and tumor microenvironment can play an important role, e.g., in the TNBC and HER2+ subtypes. Breast cancers in general, and particularly the TNBC sub-types, frequently contain tumor-infiltrating lymphocytes (TIL) in the stroma and are associated with high PD-L1 expression (in up to 50% of tumors). While not wishing to be bound by theory, it is believed that in some embodiments, cytotoxic chemotherapies can enhance the immune priming, T cell trafficking, and/or immune effector phases of the cancer-immunity cycle while also increasing the antigenic-ity, immunogenicity and susceptibility to immune killing of cancer cells, increasing the potential for response to check-point inhibitors.

In some embodiments, the combination is used to treat a subject, who has developed, or is at risk of developing, resistant to an anti-PD-1 or anti-PD-L1 therapy. For example, preclinical and clinical evidence shows that sev-eral cytotoxic and targeted anticancer therapies can help to circumvent certain potential mechanisms of resistance to PD-L1/PD-1 inhibition (e.g., defect in cancer antigen-spe-cific T cell activation or lack of immune cell infiltration in tumors) by enhancing T cell trafficking and infiltration into the tumor bed (Zitvogel et al 2013). Several cytotoxic drugs (including paclitaxel) can also directly impact dendritic cell (DC) phenotype and function, promoting their maturation and proinflammatory cytokine secretion and upregulating their antigen-presenting functions (e.g., expression of MHC class II molecules on their surface), resulting in augmented CD8+ T cell priming and enhanced cytotoxic activity (Pfannenstiel et al. *Cell Immunol.* 2010; 263(1):79-87). It has also been suggested that chemotherapy may stimulate in tumor cells their antigenicity (by inducing somatic muta-tions and upregulating multiple surface molecules on tumor cells acting as new antigens), immunogenicity (by secreting cell death-associated molecules (CDAMs)) and susceptibil-ity to immune attack (by expression of costimulatory mol-ecules such as B7-1 on the surface of malignant cells or downregulation of immunosuppressive molecules such as PD-L1 and PD-L2) (Hodge et al. *Int J Cancer.* 2013; 133(3):624-36). In preclinical in vivo models, chemotherapy treatment with platinum or taxanes synergizes with anti-PD-L1 and induces durable anti-tumour responses associated with an increased number of tumor-infiltrating CD8+ T cells (Giaccone et al. 2015, Adams et al. 2015, Liu et al. 2015). In the clinical setting an increased tumor PD-L1 expression and infiltration of CD8+ T cells have been observed in patients undergoing serial biopsies in a Phase 1b study testing the combination of a PD-L1 inhibitor (atezolizumab) and chemotherapy in NSCLC (Camidge et al. 2015). Devel-opment of new intratumoral immune cell infiltrates was also observed after neoadjuvant paclitaxel therapy for early breast cancer, with the clinical and pathologic response directly correlating with the tumor immune cell infiltration (Demaria et al. *Clin Cancer Res.* 2001; 7(10):3025-30).

In certain embodiments, the combination is used to treat a subject who has shown immune infiltration, e.g., contain-ing tumor-infiltrating lymphocytes (TILs) in the cancer. In other embodiments, the subject is selected for the treatment based, at least in part, on the presence of TILs in the cancer. For example, more than 70% of breast cancers contain tumor-infiltrating lymphocytes in the stroma, and preclinical data suggest that in most breast cancers the local immune microenvironment plays a role in the control of cancer progression. Several studies have shown that immune infil-tration in breast cancer correlates with better prognosis and with greater response to chemotherapy (Denkert et al. *J Clin Oncol.* 2010; 28(1):105-13; Loi et al. *Oncoimmunology.* 2013; 2(7):e24720.). For TNBC, approximately 15% of tumors show high degree of lymphocytic infiltration at diagnosis and the majority (65%-80%) harbor low to mod-erate level of immune cells (Ruffell et al. *Proc Natl Acad Sci USA.* 2012; 109(8):2796-801; García-Teijido et al. *Clin Med Insights Oncol.* 2016; 10(Suppl 1):31-9). Gene expression profiling also demonstrated an association between expres-sion of immunomodulatory genes and better clinical out-comes in TNBC (Desmedt et al. *J Clin Oncol.* 2016; 34(16):1872-81). In 2 different studies, one in TNBC speci-mens and the other in all breast cancer types, PD-L1 expression was high (19% in the TNBC samples and 44% in the all BC types samples) and associated with greater CD8+ T-cell infiltrate than PD-L1-tumors in the TNBC samples (Mittendorf et al. *Cancer Immunol Res.* 2014; 2(4):361-70., Ghebeh et al. *Neoplasia.* 2006; 8(3):190-8). In addition, TBNC appear to exhibit a genetic instability with high mutation rate that could also result in increased immuno-genic neo-antigens and anti-tumor T-cell infiltration (Wang et al. *Ann Oncol.* 2015; 26(3):523-8). In HER2-positive breast cancer, TIL and immune signatures are also associ-ated with better prognosis (Salgado et al. *JAMA Oncol.* 2015; 1(4):448-54). HER2-positive breast cancer is also a highly proliferating breast cancer subtype with an increased level of genomic instability. The overexpression of HER2 itself can act as a tumor-associated antigen, triggering the immune system. In highly proliferative HR+ cancers (lumi-nal B), immune cells can predict for better prognosis (Bian-chini et al. *J Clin Oncol.* 2010; 28(28):4316-23. Erratum in: *J Clin Oncol.* 2010; 28(32):4868. *J Clin Oncol.* 2012; 30(6):679). In HR+ breast cancer the interaction between tumor cells and the immune milieu may rely on different mechanisms than in other breast cancer subtypes, involving the modulation of the tumor microenvironment by mutual interplays of endocrine factors, pro-inflammatory status and immune cells (Dieci et al. *Cancer Treat Rev.* 2016; 46:9-19).

In some embodiments, the chemotherapeutid agent, e.g., nab-paclitaxel, and the inhibitor of an immune checkpoint molecule, e.g., an inhibitor of PD-1 (e.g., an anti-PD-1 antibody molecule), each is administered at a dose and/or on a time schedule, that in combination, achieves a desired anti-tumor activity.

In one embodiment, the chemotherapeutid agent, e.g., nab-paclitaxel, is administered at dose between 25 mg/m$^2$ and 300 mg/m$^2$, e.g., between 25 mg/m$^2$ and 250 mg/m$^2$, between 50 mg/m$^2$ and 200 mg/m$^2$, between 100 mg/m$^2$ and 150 mg/m$^2$, between 75 mg/m$^2$ and 125 mg/m$^2$, between 125 mg/m$^2$ and 175 mg/m$^2$, between 50 mg/m$^2$ and 100 mg/m$^2$, between 100 mg/m$^2$ and 200 mg/m$^2$, or between 200 mg/m$^2$ and 250 mg/m$^2$, e.g., at a dose of 50 mg/m$^2$, 75 mg/m$^2$, 100 mg/m$^2$, 125 mg/m$^2$, 150 mg/m$^2$, 175 mg/m$^2$, 200 mg/m$^2$, 220 mg/m$^2$, or 260 mg/m$^2$, e.g., three times (e.g., weekly) during a period of four weeks, e.g., weekly at Day 1, Day 8, and Day 15 every four weeks (qw3/4), e.g., intravenously.

In one embodiment, the chemotherapeutid agent, e.g., nab-paclitaxel, is administered at a dose between 50 mg/m$^2$ and 150 mg/m$^2$ (e.g., 100 mg/m$^2$), e.g., weekly at Day 1, Day 8, and Day 15 every four weeks (qw3/4). In some embodiments, the chemotherapeutid agent, e.g., nab-paclitaxel, is administered intravenously. In one embodiment, the chemotherapeutid agent, e.g., nab-paclitaxel, is administered at a dose between 50 mg/m$^2$ and 150 mg/m$^2$ (e.g., 100 mg/m$^2$), e.g., weekly at Day 1, Day 8, and Day 15 every four weeks (qw3/4), e.g., by intravenous infusion, and the PD-1 inhibitor (e.g., the anti-PD-1 antibody molecule) is administered at a dose between 300 mg and 500 mg (e.g., at a dose of 400 mg), e.g., once every 4 weeks or once every 8 weeks, e.g., by intravenous infusion. In some embodiments, the infusion of the chemotherapeutid agent, e.g., nab-paclitaxel, starts after (e.g., at least 30 minutes, 45 minutes, 60 minutes, 75 minutes, 90 minutes, or 120 minutes after) the end of the infusion of the PD-1 inhibitor (e.g., the anti-PD-1 antibody molecule). For example, the chemotherapeutic agent, e.g., nab-paclitaxel, and/or the PD-1 inhibitor (e.g., anti-PD-1 antibody molecule), can be administered as a 30 to 120 minutes (e.g., 30 minutes) intravenous infusion. In an embodiment, a treatment cycle is 28 days or 56 days (e.g., 28 days).

In certain embodiments, the chemotherapeutic agent comprises cisplatin, permetrexed, or both. Cisplatin is also known as cisplatinum, platamin, neoplatin, cismaplat, or cis-diamminedichloridoplatinum(II) (CDDP). Permetrxed is also known as (S)-2-(4-(2-(2-amino-4-oxo-4,7-dihydro-3H-pyrrolo[2,3-d]pyrimidin-5-yl)ethyl)benzamido)pentanedioic acid. In some embodiments, the combination is used to treat a cancer, e.g., a cancer described herein. In certain embodiments, the cancer is a lung cancer, e.g., a non-small cell lung cancer (NSCLC). In some embodiments, the NSCLC is a non-squamous NSCLC. In certain embodiments, the cancer is a nasopharyngeal cancer.

In certain embodiments, the chemotherapeutic agent comprises paclitaxel, carboplatin, or both. Carboplatin is also known as cis-diammine(cyclobutane-1,1-dicarboxylate-O, O')platinum(II). In some embodiments, the combination is used to treat a cancer, e.g., a cancer described herein. In certain embodiments, the cancer is a lung cancer, e.g., a non-small cell lung cancer (NSCLC). In some embodiments, the NSCLC is a squamous NSCLC. In certain embodiments, the cancer is a nasopharyngeal cancer.

Other exemplary chemotherapeutic agents that can be used in the combination include, but are not limited to, an alkylating agent (e.g., a bifunctional alkylator (e.g., cyclophosphamide, a mechlorethamine, chlorambucil, or melphalan), a monofunctional alkylator (a dacarbazine(DTIC), nitrosoureas, temozolomide(oral dacarbazine)), an anthracycline (e.g., daunorubicin, doxorubicin, epirubicin, idarubicin, mitoxantrone, or valrubicin), a cytoskeletal disruptors (taxane) (e.g., paclitaxel, docetaxel, abraxane, or taxotere), an epothilone, a histone deacetylase inhibitor (e.g., vorinostat or romidepsin), an inhibitor of topoisomerase I (e.g., irinotecan or topotecan), an inhibitor of topoisomerase II (e.g., etoposide, teniposide, or tafluposide), or a kinase inhibitors (e.g., bortezomib, erlotinib, gefitinib, imatinib, vemurafenib, vismodegib), a nucleotide analog or precursor analog (e.g., azacitidine, azathioprine, capecitabine, cytarabine, doxifluridine, fluorouracil, gemcitabine, hydroxyurea, mercaptopurine, methotrexate, tioguanine (thioguanine)), a peptide antibiotic (e.g., bleomycin or actinomycin), a platinum-based agent (e.g., carboplatin, cisplatin, or oxaliplatin), a retinoid (e.g., tretinoin, alitretinoin, bexarotene), or a *vinca* alkaloid or derivative (e.g., vinblastine, vincristine, vindesine, or vinorelbine).

In some embodiments, the combination further comprises an inhibitor of angiogenesis, an EGFR inhibitor, a PARP inhibitor (e.g., BSI-201), an antibody-drug conjugate (e.g., targeting GPNMB (e.g., glembatumumab vedotin (CDX- 011)), sacituzumab govitecan (IMMU-132)), a Frizzled receptor inhibitor (e.g., vanticumab), a PD-L1 inhibitor (e.g., atezolizumab), a surgery, a radiation therapy, or a combination thereof.

In one embodiment, a combination described herein includes a chemotherapeutic agent (e.g., a hypomethylating agent, e.g., decitabine). In one embodiment, the combination described herein further includes an inhibitor of an immune checkpoint molecule, e.g., an inhibitor of PD-1 (e.g., an anti-PD-1 antibody molecule described herein), an inhibitor of TIM-3 (e.g., an anti-TIM-3 antibody molecule described herein), or both. In some embodiments, the combination is used to treat a cancer, e.g., a cancer described herein, e.g., a hematological cancer, e.g., a leukemia (e.g., an acute myeloid leukemia (AML)), or a myelodysplastic syndrome (MDS). In certain embodiments, the cancer is a leukemia, e.g., a relapsed or refractory AML, or a de novo AML (e.g., an AML unfit for standard of care). In other embodiments, the cancer is an MDS, e.g., a high risk MDS.

In some embodiments, the chemotherapeutic agent is a hypomethylating agent. A hypomethylating agent (or demethylating agent) is an agent that inhibits DNA methylation. In certain embodiments, a hypomethylating agent blocks the activity of DNA methyltransferase (i.e., DNA methyltransferase inhibitor/DNMT inhibitor). Exemplary hypomethylating agents that can be used in a combination described herein include decitabine and azacitidine.

In some embodiments, the chemotherapeutic agent is decitabine. Decitabine (also known as 5-aza-2'-deoxycytidine or DACOGEN®) is a cytidine deoxynucleoside analogue. It can selectively inhibit DNA methyltransferases at low doses. Inhibition of DNA methyltransferases by decitabine can result in gene promoter hypomethylation, which can lead to reactivation of tumor suppressor genes, or induction of cellular differentiation or cellular senescence followed by programmed cell death. Decitabine is indicated for the treatment of adult patients aged 65 years and above with newly diagnosed de novo or secondary AML, according to the WHO classification, who are not candidates for standard induction chemotherapy. The use of decitabine was studied in patients with newly diagnosed de novo or secondary AML according to the WHO classification (Malik and Cashen. *Cancer Manag Res.* 2014; 6: 53-61). The median Overall Survival (OS) in the intent-to-treat population was 7.7 months in patients treated with decitabine. The complete remission rate (CR+ complete remission with incomplete platelet recovery (CRp)) was 17.8% (Lübbert et al. *J Clin Oncol.* 2011; 29(15):1987-96). Decitabine is indicated for treatment of patients with MDS, e.g., previously treated and untreated, de novo and secondary MDS of all French-American-British subtypes and intermediate-1, intermediate-2, and high-risk International Prognostic Scoring System groups in the U.S.

In some embodiments, the combination is used to treat an acute myeloid leukemia (AML). AML is a clonal neoplasm of the hematopoietic system that is characterized, e.g., by the proliferation of abnormal myeloid blast cells in the bone marrow. The proliferation of abnormal myeloid blast cells can interfere with normal hematopoiesis, which leads to an accumulation of dysfunctional, immature myeloid cells in the marrow and peripheral blood. In some embodiments, a diagnosis of AML is made when myeloid blasts make up ≥20% of the nucleated cells in a bone marrow aspirate. These leukemic blasts can inhibit normal hematopoietic stem and progenitor cells and impact the appearance of mature, differentiated hematopoietic cells in the peripheral blood. Clinical symptoms can include, e.g., anemia, neutropenia, or thrombocytopenia, which can result in life threatening infection and bleeding. AML may arise in the setting of prior myelodysplastic syndrome ("secondary AML") or prior cytotoxic chemotherapy ("therapy-related AML").

Long-term disease control can be achieved in patients with good prognostic features, e.g., young age and favorable cytogenetics. Patients under 60 without significant medical comorbidities can initially be treated with intensive myeloablative induction chemotherapy that typically includes an anthracycline and cytarabine. The goal of this therapy is to achieve, e.g., a complete remission (CR) with fewer than 5% blast cells in the setting of normal hematopoiesis, which can be accomplished more than 65% of the time in this patient population. Post-remission consolidation therapy with chemotherapy or either autologous or allogeneic hematopoietic stem cell transplantation can subsequently be given to increase the durability of remission. There are fairly high rates of AML relapse for which there are limited effective treatment options. Older patients typically fare even worse, achieving much lower and less durable response rates and experiencing more complications with treatment. For this older population who cannot tolerate intensive therapies, options are limited, and no effective standard approach exists. Treatment options include, e.g., low dose cytarabine or hypomethylating agents such as 5-azacitadine or decitabine. There is need for more effective therapeutic modalities to improve the survival of AML patients, e.g., elderly patients with AML, and those with relapsed or refractory disease.

Myelodysplastic syndrome (MDS) is a heterogeneous group of chronic myeloid disorders that involve persistent peripheral blood cytopenias and an increased prevalence of leukemic transformation. Clinical characteristics are variable and diagnosis is typically made on the basis of morphologic and cytogenetic abnormalities in hematopoietic cells in the bone marrow and peripheral blood. Prognosis in MDS can be determined by the Revised International Prognostic Scoring System (rIPSS), which is based upon cytogenetics, marrow blast percentage, and cytopenias clinical data. Patients are grouped into five risk categories based on total scores from these prognostic factors (Greenberg et al. *J Natl Compr Canc Netw.* 2013; 11(7):838-74). Patients diagnosed with high and very high risk MDS according to the rIPSS, have high rates of transformation to AML and poor prognosis. Hypomethylating agents are considered a standard of care for MDS treatment (NCCN Guidelines for Patients®, Myelodysplastic Syndromes, Version 1.2016, National Comprehensive Cancer Network).

Without wishing to be bound by theory, it is believed that in some embodiments, anti-tumor immunity can be used to treat AML and improve outcomes for patients with the disease, e.g., based on anti-leukemic activity seen with allogeneic hematopoietic stem cell transplant and donor lymphocyte infusions. There is evidence of a suppressive immune microenvironment in AML with elevated PD-L1 expression in leukemic blasts. Preclinical evidence in a mouse model of AML indicates that disease progression is associated with increased PD-1 expression on CD8-positive T-cells, and that treatment with anti-PD-1 or anti-PD-L1 antibodies decreases AML burden and improves survival in these models of the disease. In patients there is evidence of increased expression of PD-L1 in a subset of patients with AML/MDS that further increases at progression.

In addition to activation of the PD-1/PD-L1 pathway, there is evidence that AML stem cells co-express the immune checkpoint TIM-3. TIM-3 can cooperate with the PD-1/PD-L1 pathway to suppress tumor recognition by cytotoxic T cells. TIM-3 is a unique AML stem cell antigen that is present in leukemic blasts but not normal hematopoietic stem cells, and anti-TIM3 antibody treatment has shown efficacy in reducing leukemic burden in a mouse model of AML (Kikushige et al. *Cell Stem Cell.* 2010; 7(6):708-17). There is also evidence in MDS that treatment with the standard of care hypomethylating agent decitabine increases PD-1 expression in T-cells, underscoring its role in immunomodulation.

Without wishing to be bound by theory, it is believed that in some embodiments, chemotherapeutic agents (e.g., hypomethylating agents, e.g., decitabine) may induce increased expression of immune checkpoints (e.g., PD-1, TIM-3, or both) that may allow for immune evasion and lead to therapeutic resistance. Without wishing to be bound by theory, it is also believed that in some embodiments, AML and MDS co-overexpress the immune checkpoint receptors PD-1 and TIM-3, which cooperate to inhibit immune recognition by cytotoxic T cells. Preclinical evidence suggests that the concurrent blockade of PD-1 and TIM-3 promotes greater activation of T-cells than either therapy alone (Sakuishi et al. *J Exp Med.* 2010; 207(10):2187-94, Ngiow et al. *Cancer Res.* 2011; 71(10):3540-51) and synergistically inhibits tumor growth in experimental cancer models (Anderson et al. *Cancer Immunol Res.* 2014; 2(5):393-8, Ngiow et al. *Cancer Res.* 2011; 71(10):3540-51). In some embodiments, the combination described herein optimizes the approach to checkpoint inhibition for AML and MDS, e.g., by considering treatment-induced immunomodulation and co-inhibitory pathways.

In other embodiments, the combination includes an inhibitor of an immune checkpoint molecule, e.g., an inhibitor of PD-1 (e.g., an anti-PD-1 antibody molecule described herein), and a chemotherapeutic agent (e.g., a hypomethylating agent, e.g., decitabine). In some embodiments, the inhibitor of an immune checkpoint molecule, e.g., the inhibitor of PD-1 (e.g., the anti-PD-1 antibody molecule), is administered at a dose between 200 mg and 600 mg (e.g., between 300 mg and 500 mg, e.g., at a dose of 400 mg), e.g., once every 4 weeks, e.g., intravenously. In some embodiments, the chemotherapeutic agent (e.g., a hypomethylating agent, e.g., decitabine) is administered at a dose between 5 mg/m$^2$ and 50 mg/m$^2$ (e.g., between 10 mg/m$^2$ and 30 mg/m$^2$, e.g., at a dose of 20 mg/m$^2$), e.g., daily, e.g., for 1, 2, 3, 4, 5, 6, 7, 8, or more days, e.g., intravenously. In an embodiment, the inhibitor of an immune checkpoint molecule, e.g., the inhibitor of PD-1 (e.g., the anti-PD-1 antibody molecule), is administered on day 8 of a 28-day cycle, and the chemotherapeutic agent (e.g., a hypomethylating agent, e.g., decitabine) is at days 1, 2, 3, 4, and 5 of the 28-day cycle.

In other embodiments, the combination includes an inhibitor of an immune checkpoint molecule, e.g., an inhibitor of TIM-3 or an anti-TIM-3 antibody molecule disclosed in U.S. Patent Application Publication No. 2015/0218274, and a chemotherapeutic agent (e.g., a hypomethylating agent, e.g., decitabine). In some embodiments, the inhibitor of an immune checkpoint molecule, e.g., the inhibitor of TIM-3 or an anti-TIM-3 antibody molecule disclosed in U.S. Patent Application Publication No. 2015/0218274, is administered at a dose between 10 mg and 1000 mg (e.g., between 20 mg and 800 mg, between 80 mg and 400 mg, e.g., at a dose of 240 mg), e.g., once every 2 weeks, e.g., intravenously. In some embodiments, the chemotherapeutic agent (e.g., a hypomethylating agent, e.g., decitabine) is administered at a dose between 5 mg/m$^2$ and 50 mg/m$^2$ (e.g., between 10 mg/m$^2$ and 30 mg/m$^2$ (e.g., at a dose of 20 mg/m²), e.g., daily, e.g., for 1, 2, 3, 4, 5, 6, 7, 8, or more days, e.g., intravenously. In an embodiment, the inhibitor of an immune checkpoint molecule, e.g., the inhibitor of TIM-3 or an anti-TIM-3 antibody molecule disclosed in U.S. Patent Application Publication No. 2015/0218274, is administered on days 8 and 22 of a 28-day cycle, and the chemotherapeutic agent (e.g., a hypomethylating agent, e.g., decitabine) is on days 1, 2, 3, 4, and 5 of the 28-day cycle.

In other embodiments, the combination includes an inhibitor of PD-1 (e.g., an anti-PD-1 antibody molecule described herein), an inhibitor of TIM-3 (e.g., an anti-TIM-3 antibody molecule disclosed in U.S. Patent Application Publication No. 2015/0218274), and a chemotherapeutic agent (e.g., a hypomethylating agent, e.g., decitabine). In some embodiments, the inhibitor of PD-1 (e.g., the anti-PD-1 antibody molecule), is administered at a dose between 200 mg and 600 mg (e.g., at a dose of 400 mg), e.g., once every 4 weeks, e.g., intravenously. In some embodiments, the inhibitor of TIM-3 (e.g., an anti-TIM-3 antibody molecule disclosed in U.S. Patent Application Publication No. 2015/0218274) is administered at a dose between 10 mg and 800 mg (e.g., between 20 mg and 400 mg, between 40 mg and 200 mg or between 50 mg and 100 mg, e.g., at a dose of 80 mg), e.g., once every 2 weeks, e.g., intravenously. In some embodiments, the chemotherapeutic agent (e.g., a hypomethylating agent, e.g., decitabine) is administered at a dose between 5 mg/m² and 50 mg/m² (e.g., between 10 mg/m² and 30 mg/m² (e.g., at a dose of 20 mg/m²), e.g., daily, e.g., for 1, 2, 3, 4, 5, 6, 7, 8, or more days, e.g., intravenously. In an embodiment, the inhibitor of PD-1 (e.g., the anti-PD-1 antibody molecule) is administered on day 8 of a 28-day cycle, the inhibitor of TIM-3 (e.g., an anti-TIM-3 antibody molecule disclosed in U.S. Patent Application Publication No. 2015/0218274) is administered on days 8 and 22 of the 28-day cycle, and the chemotherapeutic agent (e.g., a hypomethylating agent, e.g., decitabine) is on days 1, 2, 3, 4, and 5 of the 28-day cycle.

In certain embodiments, the inhibitor of PD-1 (e.g., an anti-PD-1 antibody molecule described herein) and the inhibitor of TIM-3 (e.g., an anti-TIM-3 antibody molecule disclosed in U.S. Patent Application Publication No. 2015/0218274) are administered on the same day. In certain embodiments, the inhibitor of PD-1 (e.g., an anti-PD-1 antibody molecule described herein) and the inhibitor of TIM-3 (e.g., an anti-TIM-3 antibody molecule disclosed in U.S. Patent Application Publication No. 2015/0218274) are administered on different days. In some embodiments, the inhibitor of TIM-3 (e.g., an anti-TIM-3 antibody molecule disclosed in U.S. Patent Application Publication No. 2015/0218274) is administered, e.g., on the same day, before the inhibitor of PD-1 (e.g., an anti-PD-1 antibody molecule described herein) is administered. In other embodiments, the inhibitor of TIM-3 (e.g., an anti-TIM-3 antibody molecule disclosed in U.S. Patent Application Publication No. 2015/0218274) is administered, e.g., on the same day, after the inhibitor of PD-1 (e.g., an anti-PD-1 antibody molecule described herein) is administered. In certain embodiments, a saline or dextrose solution flush, e.g., for about 1 hour, can be performed between administration of the inhibitor of PD-1 (e.g., an anti-PD-1 antibody molecule described herein) and administration of the inhibitor of TIM-3 (e.g., an anti-TIM-3 antibody molecule disclosed in U.S. Patent Application Publication No. 2015/0218274). In some embodiments, the inhibitor of PD-1 (e.g., an anti-PD-1 antibody molecule described herein), the inhibitor of TIM-3 (e.g., an anti-TIM-3 antibody molecule disclosed in U.S. Patent Application Publication No. 2015/0218274), or both, is administered via intravenous infusion over a period of 30 minutes to 2 hours, e.g., about 1 hour. The inhibitor of PD-1 (e.g., an anti-PD-1 antibody molecule described herein), and the inhibitor of TIM-3 (e.g., an anti-TIM-3 antibody molecule disclosed in U.S. Patent Application Publication No. 2015/0218274), can be stored in the form of liquid or lyophilisate. In some embodiments, the inhibitor of PD-1 (e.g., an anti-PD-1 antibody molecule described herein) is stored in the form of lyophilisate, and the inhibitor of TIM-3 (e.g., an anti-TIM-3 antibody molecule disclosed in U.S. Patent Application Publication No. 2015/0218274) is stored in the form of liquid.

The combination including the chemotherapeutic agent (e.g., a hypomethylating agent (also sometimes known as demethylating agent), e.g., decitabine), and one or both of the inhibitor of PD-1 (e.g., an anti-PD-1 antibody molecule described herein) or the inhibitor of TIM-3 (e.g., an anti-TIM-3 antibody molecule disclosed in U.S. Patent Application Publication No. 2015/0218274), can be used on combination with an additional therapy, e.g., for treating a cancer, e.g., a cancer therapy described herein. Exemplary additional therapies include, but are not limited to, arsenic trioxide (trisenox), all-trans retinoic acid (ATRA), a stem cell or bone marrow transplant, a second chemotherapeutic agent (e.g., azacitidine, cytarabine, daunorubicin, idarubicin, or lenalidomide), or a radiation therapy.

Exemplary BRAF and MEK Inhibitors

In one embodiment, a combination described herein includes an inhibitor of BRAF. In some embodiments, the combination is used to treat a cancer, e.g., a cancer described herein, e.g., a skin cancer (e.g., a melanoma). Without wishing to be bound by theory, it is believed that in some embodiments, the mitogen-activated protein kinase (MAPK) pathway is aberrantly activated in a number of human cancers, e.g., by a mutation in BRAF kinase, which have been found in almost 50% of metastatic melanomas. In some embodiments, the combination is used to treat a cancer having a BRAF mutation, e.g., a BRAF mutation described herein. In some embodiments, the combination is used to treat a melanoma, e.g., an unresectable or metastatic melanoma. In some embodiments, the combination is used to treat a melanoma in a subject, wherein the melanoma has a BRAF mutation (e.g., a BRAF V600 mutation) and the subject has an elevated level of lactate dehydrogenase (LDH) compared to a reference LDH level.

In some embodiments, the BRAF inhibitor is dabrafenib. Dabrafenib is also known as GSK2118436, N-{3-[5-(2-aminopyrimidin-4-yl)-2-tert-butyl-1,3-thiazol-4-yl]-2-fluorophenyl}-2,6-difluorobenzenesulfonamide, or TAFINLAR® (CAS Number 1195765-45-7). Dabrafenib is an orally bioavailable, potent and selective RAF kinase inhibitor of human wild-type BRAF and CRAF enzymes, as well as the mutant forms of the BRAF enzyme, e.g., BRAF V600E, BRAF V600K, and BRAF V600D. The mode of action of dabrafenib is consistent with competitive inhibition of ATP binding. In certain embodiments, the combination is used to treat a subject who has been determined to have a cancer (e.g., a melanoma) having a BRAF mutation, e.g., a BRAF mutation described herein (e.g., a BRAF V600 mutation). In other embodiments, the combination is used to treat a cancer (e.g., a melanoma) other than a wild-type BRAF cancer (e.g., wild-type BRAF melanoma).

In some embodiments, the BRAF inhibitor or dabrafenib is administered at a dose between 50 mg and 300 mg (e.g., between 100 mg and 200 mg), e.g., twice a day. In certain embodiments, the BRAF inhibitor or dabrafenib is administered at a dose between 100 mg and 200 mg (e.g., at a dose of about 150 mg), e.g., twice a day. For example, the second dose of the BRAF inhibitor or dabrafenib can be administered about 12 hours after administration of the first dose. In some embodiments, the BRAF inhibitor or dabrafenib is administered at a total daily dose between 100 mg and 600 mg (e.g., between 200 mg and 400 mg). In certain embodiments, the BRAF inhibitor or dabrafenib is administered at a total daily dose between 200 mg and 400 mg (e.g., at a total daily dose of about 300 mg). In some embodiments, the BRAF inhibitor of dabrafenib is administered orally.

In one embodiment, a combination described herein includes an inhibitor of MEK. In some embodiments, the combination is used to treat a cancer, e.g., a cancer described herein, e.g., a skin cancer (e.g., a melanoma). Without wishing to be bound by theory, it is believed that when MEK, a member of the MAPK signaling cascade, is inhibited, cell proliferation can be blocked and apoptosis can be induced. In some embodiments, the combination is used to treat a melanoma, e.g., an unresectable or metastatic melanoma. In some embodiments, the combination is used to treat a melanoma in a subject, wherein the melanoma has a BRAF mutation (e.g., a BRAF V600 mutation) and the subject has an elevated level of lactate dehydrogenase (LDH) compared to a reference LDH level.

In some embodiments, the MEK inhibitor is trametinib. Trametinib is also known as GSK1120212, JTP-74057, TMT212, N-(3-{3-cyclopropyl-5-[(2-fluoro-4-iodophenyl) amino]-6,8-dimethyl-2,4,7-trioxo-3,4,6,7-tetrahydropyrido [4,3-d]pyrimidin-1(2H)-yl}phenyl)acetamide, or Mekinist (CAS Number 871700-17-3). Without wishing to be bound by theory, it is believed that in some embodiments, trametinib is a reversible and highly selective allosteric inhibitor of MEK1 and MEK2. MEK proteins are critical components of the MAPK pathway which is commonly hyperactivated in tumor cells such as melanoma cells. Oncogenic mutations in both BRAF and RAS can signal through MEK1 or MEK2.

In some embodiments, the MEK inhibitor or trametinib is administered at a dose between 0.5 mg and 4 mg (e.g., between 1 mg and 3 mg), e.g., once a day. In certain embodiments, the MEK inhibitor or trametinib is administered at a dose between 1 mg and 3 mg (e.g., at a dose of about 2 mg), e.g., once a day. In some embodiments, the MEK inhibitor or trametinib is administered orally.

In one embodiment, a combination described herein includes an inhibitor of BRAF and an inhibitor of MEK.

In vitro and in vivo preclinical data indicated increased anti-tumor activity by the combination of a BRAF-inhibitor (e.g., dabrafenib) and a MEK inhibitor (e.g., trametinib). For example, the combination of dabrafenib and trametinib has demonstrated enhanced anti-proliferative activity against a panel of BRAF-mutant cell lines in vitro, suggesting a synergistic effect of dabrafenib and trametinib in addressing primary resistance to each single agent. The combination was effective in inhibiting the growth of dabrafenib-resistant BRAF-mutant melanoma cell clones indicating the potential ability of the combination therapy to overcome acquired resistance. This cell-line data are comparable to in vitro results of other experimental BRAF- and MEK-inhibitor combinations (Corcoran et al. *Sci Signal.* 2010; 3(149):ra84; Emery et al. *Proc Natl Acad Sci USA.* 2009; 106(48):20411-6).

As another example, the combination of dabrafenib and trametinib demonstrated improved activity in mouse xenograft models of BRAF-mutant melanoma compared to either single agent. In skin toxicity studies performed in rats, the addition of trametinib to dabrafenib prevented the development of proliferative skin lesions observed following treatment with dabrafenib alone. These results suggest that the addition of a MEK inhibitor to a BRAF inhibitor can suppress the proliferative signals in normal skin cells which can lead to the development of hyperproliferative skin lesions including, e.g., keratoacanthomas and cutaneous squamous-cell carcinomas frequently observed in clinical trials involving BRAF-inhibitors (Flaherty et al. *Curr Opin Oncol.* 2010; 22(3):178-83; Chapman et al. *Expert Opin Investig Drugs.* 2011; 20(2):209-20; Robert et al. *Curr Opin Oncol.* 2011; 23(2):177-82). Similar results have been observed with another combination of BRAF and MEK inhibitors (Carnahan et al. *Mol Cancer Ther.* 2010; 9(8): 2399-410).

In some embodiments, the BRAF inhibitor or dabrafenib is administered at a dose between 50 mg and 300 mg (e.g., between 100 mg and 200 mg), e.g., twice a day, e.g., orally, and the MEK inhibitor or trametinib is administered at a dose between 0.5 mg and 4 mg (e.g., between 1 mg and 3 mg), e.g., once a day, e.g., orally. In certain embodiments, the BRAF inhibitor or dabrafenib is administered at a dose between 100 mg and 200 mg (e.g., at a dose of about 150 mg), twice a day, orally, and the MEK inhibitor or trametinib is administered at a dose between 1 mg and 3 mg (e.g., at a dose of about 2 mg), once a day, orally. For example, the first dose of the BRAF inhibitor or dabrafenib can be administered at the same time as the MEK inhibitor or dabrafenib, and the second dose of the BRAF inhibitor or dabrafenib can be administered about 12 hours after administration of the first dose. In some embodiments, the BRAF inhibitor or dabrafenib is administered at a total daily dose between 100 mg and 600 mg (e.g., between 200 mg and 400 mg), e.g., orally, and the MEK inhibitor or trametinib is administered at a dose between 0.5 mg and 4 mg (e.g., between 1 mg and 3 mg), e.g., once a day, e.g., orally. In certain embodiments, the BRAF inhibitor or dabrafenib is administered at a total daily dose between 200 mg and 400 mg (e.g., at a total daily dose of about 300 mg), e.g., orally, and the MEK inhibitor or trametinib is administered at a dose between 1 mg and 3 mg (e.g., at a dose of about 2 mg), e.g., once a day, e.g., orally.

In certain embodiments, the combination includes an inhibitor of PD-1 (e.g., an anti-PD-1 antibody molecule, and (i) an inhibitor of BRAF or dabrafenib, (ii) an inhibitor of MEK or trametinib, or (iii) both (i) and (ii). Without wishing to be bound by theory, it is believed that use of an inhibitor of an immune checkpoint molecule, e.g., an inhibitor of PD-1 or PD-L1, in combination with an inhibitor of BRAF (e.g., dabrafenib), an inhibitor of MEK (e.g., trametinib), or both, can improve a response (e.g., a more rapid response, a more durable response, a higher response rate, or a more complete response) caused by inhibition of BRAF and/or MEK.

The following observations, at least in part, support a combinatorial or synergistic effect of a targeted therapy (e.g., a BRAF targeted therapy, a MEK targeted therapy, or both) with an immune checkpoint inhibitor (e.g., an inhibitor of PD-1, e.g., an anti-PD-1 antibody molecule). For example, oncogenic BRAF can lead to immune escape in melanoma (Sumimoto et al. *J Exp Med.* 2006; 203(7):1651-6). Blocking BRAF activity leads to increased expression of melanoma differentiation antigens in vitro (Kono et al. *Mol Cancer Res.* 2006; 4(10):779-92), e.g., through release of transcriptional repression and subsequent expression of MITF targets, e.g., MART-1, gp100, TRP-1 and TRP-2 (Boni et al. *Cancer Res.* 2010; 70(13):5213-9). The effect of MAPK pathway inhibition on T cell activation and signaling was also studied in vitro. While BRAF inhibitors did not show adverse effects on T cell function and may even augment their function through paradoxical signaling through RAS-GTP (Callahan et al. *Cancer Immunol Res.* 2014; 2(1):70-9), MEK inhibitors showed dose-dependent inhibition T cell function in vitro (Boni et al. *Cancer Res.* 2010; 70(13):5213-9; Vella et al. *Cancer Immunol Res.* 2014; 2(4):351-60). The in vivo antitumor effect of trametinib was further explored in a murine immunocompetent BALB/C syngeneic CT26 tumor model. In this study, trametinib monotherapy increased CD4$^+$ tumor infiltrating lymphocytes (TILs) and did not negatively affect the prevalence of CD8$^+$ TILs. The combination of trametinib with murine anti-PD-1 resulted in an effective antitumor response in the KRAS-mutant CT26 colorectal tumor syngeneic mouse model (Liu et al. *Clin Cancer Res.* 2015; 21(7):1639-51).

As another example, an immune biomarker analysis was performed in tumor samples from 16 patients with metastatic melanoma treated with vemurafenib or dabrafenib plus trametinib. In this analysis, BRAF inhibition was associated with increased melanoma antigen expression (e.g., MART, TYRP-1, TYRP-2, gp100), significantly increased CD8$^+$ TILs, decreased expression of immunosuppressive cytokines in the tumor microenvironment, and increased markers of T cell toxicity but also increased T cell exhaustion marker (e.g., TIM-3, PD-1). It was also observed that the antigen expression and CD8$^+$ TILs were decreased at time of melanoma disease progression but could be restored through combined BRAF and MEK inhibition (Frederick et al. *Clin Cancer Res.* 2013; 19(5):1225-31; Wilmott et al. *Clin Cancer Res.* 2012; 18(5):1386-94).

Without wishing to be bound by theory, it is believed that in some embodiments, use of an inhibitor of BRAF (e.g., dabrafenib) or an inhibitor of MEK (e.g., trametinib), alone or in combination, can benefit the response to an immunotherapeutic agent, e.g., by altering the immune microenvironment (Schilling et al. *Ann Oncol.* 2014; 25(3):747-53; Liu et al. *Clin Cancer Res.* 2015; 1; 21(7):1639-51; Kakavand et al. *Clin Cancer Res.* 2015; 21(14):3140-8).

In certain embodiments, the inhibitor of PD-1 (e.g., an anti-PD-1 antibody molecule) is administered at a dose between 200 mg and 600 mg, e.g., between 300 mg and 500 mg (e.g., at a dose of 400 mg) once every four weeks or once every eight weeks. Population pharmacokinetic (PK) analysis of an anti-PD-1 antibody molecule described herein indicated that the changes in exposure due to patient weight differences are minimal across the anticipated weight range of 30 to 150 kg for the patient population, which supports selection of a flat dosing scheme. A flat dose of about 400 mg once every four weeks or about 300 mg once every three weeks is expected to achieve a mean steady-state Ctrough value higher than the ex vivo EC50 for antigen-stimulated IL-2 production, a translational biomarker for PD-1 blockade (Patnaik et al. *Clin Cancer Res.* 2015; 21(19):4286-93). Based, at least in part, on the safety profile observed and the expected Ctrough values, a dose of about 400 mg once every four weeks is expected to be a safe and efficacious dose. While not wishing to be bound by theory, it is believed that in some embodiments, an increase of the interval between administrations of the anti-PD-1 antibody molecule (e.g., to eight weeks or more) can make the combination more tolerable. Given the long half-life of the anti-PD-1 antibody molecule described herein, the Ctrough values at week 8 are expected to be above the ex vivo EC50 for antigen-stimulated IL-2 production.

In certain embodiments, the inhibitor of PD-1 (e.g., an anti-PD-1 antibody molecule) is administered at a dose between 300 mg and 500 mg (e.g., at a dose of 400 mg) once every four weeks, e.g., intravenously, e.g., over a period of 15 to 120 minutes (e.g., about 30 minutes). In other embodiments, the inhibitor of PD-1 (e.g., an anti-PD-1 antibody molecule) is administered at a dose between 300 mg and 500 mg (e.g., at a dose of 400 mg) once every eight weeks, e.g., intravenously, e.g., over a period of 15 to 120 minutes (e.g., about 30 minutes). In some embodiments, the dose may be interrupted up to 12 weeks, e.g., up to 8 weeks or up to 4 weeks.

In some embodiments, the inhibitor of PD-1 (e.g., an anti-PD-1 antibody molecule) is administered to the subject as a formulation described herein. In certain embodiments, the formulation is a lyophilized formulation. In other embodiments, the formulation is a reconstituted formulation, e.g., reconstituted from a lyophilized formulation. In other embodiments, the formulation is a liquid formulation. In certain embodiments, the inhibitor of PD-1 (e.g., an anti-PD-1 antibody molecule) is reconstituted using sterile water for injection.

In some embodiments, the inhibitor of PD-1 (e.g., an anti-PD-1 antibody molecule) is administered at a dose between 300 mg and 500 mg (e.g., at a dose of 400 mg), e.g., once every four weeks, e.g., intravenously, and (i) the BRAF inhibitor or dabrafenib is administered at a dose between 50 mg and 300 mg (e.g., between 100 mg and 200 mg, e.g., at a dose of 150 mg), e.g., twice a day, e.g., orally, or at a total daily dose between 100 mg and 600 mg (e.g., between 200 mg and 400 mg, e.g., at a total daily dose of 300 mg), e.g., orally, (ii) the MEK inhibitor or trametinib is administered at a dose between 0.5 mg and 4 mg (e.g., between 1 mg and 3 mg, e.g., at a dose of 2 mg), e.g., once a day, e.g., orally; or (iii) both (i) and (ii).

In certain embodiments, the combination includes an inhibitor of PD-1 (e.g., an anti-PD-1 antibody molecule, an inhibitor of BRAF or dabrafenib, and an inhibitor of MEK or trametinib. In some embodiments, the inhibitor of PD-1 (e.g., an anti-PD-1 antibody molecule) is administered at a dose between 300 mg and 500 mg (e.g., at a dose of 400 mg), e.g., once every four weeks, e.g., intravenously; the BRAF inhibitor or dabrafenib is administered at a dose between 50 mg and 300 mg (e.g., between 100 mg and 200 mg, e.g., at a dose of 150 mg), e.g., twice a day, e.g., orally, or at a total daily dose between 100 mg and 600 mg (e.g., between 200 mg and 400 mg, e.g., at a total daily dose of 300 mg), e.g., orally; and the MEK inhibitor or trametinib is administered at a dose between 0.5 mg and 4 mg (e.g., between 1 mg and 3 mg, e.g., at a dose of 2 mg), e.g., once a day, e.g., orally.

In some embodiments, the administration of the inhibitor of PD-1 (e.g., an anti-PD-1 antibody molecule) starts on the same day as the administration of the BRAF inhibitor or dabrafenib, the MEK inhibitor or trametinib, or both. In other embodiments, the inhibitor of PD-1 (e.g., an anti-PD-1 antibody molecule) is administered after the BRAF inhibitor or dabrafenib, the MEK inhibitor or trametinib, or both, has been administered for about four weeks or more. For example, the administration of the inhibitor of PD-1 (e.g., an anti-PD-1 antibody molecule) can start on Day 29, when the administration of BRAF inhibitor or dabrafenib, the MEK inhibitor or trametinib, or both, starts on Day 1. As an example, the BRAF inhibitor or dabrafenib can be administered twice a day per the dosing regimen for Days 1-28 of 28-day cycle, and the MEK inhibitor or trametinib can be administered per the dosing regimen for Days 1-28 of a 28-day cycle.

In some embodiments, the inhibitor of PD-1 (e.g., an anti-PD-1 antibody molecule) is administered at a dose between 300 mg and 500 mg (e.g., at a dose of 400 mg), e.g., once every eight weeks, e.g., intravenously, and (i) the BRAF inhibitor or dabrafenib is administered at a dose between 50 mg and 300 mg (e.g., between 100 mg and 200 mg, e.g., at a dose of 150 mg), e.g., twice a day, e.g., orally, or at a total daily dose between 100 mg and 600 mg (e.g., between 200 mg and 400 mg, e.g., at a total daily dose of 300 mg), e.g., orally, (ii) the MEK inhibitor or trametinib is administered at a dose between 0.5 mg and 4 mg (e.g., between 1 mg and 3 mg, e.g., at a dose of 2 mg), e.g., once a day, e.g., orally; or (iii) both (i) and (ii).

In certain embodiments, the combination includes an inhibitor of PD-1 (e.g., an anti-PD-1 antibody molecule, an inhibitor of BRAF or dabrafenib, and an inhibitor of MEK or trametinib. In some embodiments, the inhibitor of PD-1 (e.g., an anti-PD-1 antibody molecule) is administered at a dose between 300 mg and 500 mg (e.g., at a dose of 400 mg), e.g., once every eight weeks, e.g., intravenously; the BRAF inhibitor or dabrafenib is administered at a dose between 50 mg and 300 mg (e.g., between 100 mg and 200 mg, e.g., at a dose of 150 mg), e.g., twice a day, e.g., orally, or at a total daily dose between 100 mg and 600 mg (e.g., between 200 mg and 400 mg, e.g., at a total daily dose of 300 mg), e.g., orally; and the MEK inhibitor or trametinib is administered at a dose between 0.5 mg and 4 mg (e.g., between 1 mg and 3 mg, e.g., at a dose of 2 mg), e.g., once a day, e.g., orally.

In certain embodiments, the combination is used to treat a cancer, e.g., a melanoma, with an elevated level (e.g., serum level) of LDH, e.g., compared to a reference LDH level, e.g., the level of LDH in a normal subject. While without wishing to be bound by theory, it is believed that in some embodiments, serum LDH is an independent prognostic factor in melanoma, and correlates with a poor prognosis as evidenced by decreased survival in patients with advanced melanoma when compared to patients with LDH levels within the normal range. Studies also showed that elevated LDH was a negative predictor of response to therapy and other efficacy outcomes (Sirott et al. *Cancer.* 1993; 72(10):3091-8; Eton et al. *J Clin Oncol.* 1998; 16(3): 1103-11; Balch et al. *J Clin Oncol.* 2001; 19(16):3622-34). Patient population with elevated LDH level represents an area of unmet medical need that warrants use of a treatment option (e.g., a combination therapy) described herein. In certain embodiments, the cancer, e.g., a melanoma, further has a BRAF V600 mutation.

In some embodiments, the LDH level in the subject is at least 2, 3, 4, or 5 fold higher than a reference level, e.g., a reference level described herein. In some embodiments, the LDH level at baseline is between 1× upper limit of normal (ULN) and 2×ULN. In other embodiments, the LDH level at baseline is greater than 2×ULN, e.g., greater than 3×ULN, 4×ULN, or 5×ULN. In some embodiments, the LDH level is greater than about 100 to 350 (e.g., about 105 to 333) IU/L (international units per liter). In some embodiments, the level of LDH is determined in serum. Tests for determining LDH level are described, e.g., in Ferri F F, ed. Ferri's Clinical Advisor 2014. Philadelphia: Pa: Elsevier Mosby; 2014: Section IV—Laboratory tests and interpretation of results. In certain embodiments, the subject has an ECOG performance score chosen from 0, 1, or 2. Methods for determining an ECOG performance score is described, e.g., in Oken et al. *Am J Clin Oncol.* 1982; 5: 649-655.

In certain embodiments, the combination is used to treat a cancer (e.g., a melanoma) having a BRAF mutation, e.g., a BRAF mutation described herein. In certain embodiments, the BRAF mutation is a V600 mutation. In certain embodiments, the BRAF mutation is located in the activation segment of the kinase domain. In other embodiments, the BRAF mutation result in increased kinase activity, and optionally, are transforming in vitro. In some embodiments, the BRAF mutation is chosen from a V600E mutation, a V600K mutation, or a V600D mutation. In certain embodiments, the BRAF mutation is a V600E mutation. In other embodiments, the combination is used to treat a cancer (e.g., a melanoma) other than a wild-type BRAF cancer (e.g., wild-type BRAF melanoma). In certain embodiments, the BRAF mutation is a mutation that is sensitive or responsive to an inhibitor of BRAF, an inhibitor of MEK, or both.

Exemplary BRAF mutations include, but are not limited to, BRAF c.1779_1780 delTGinsGA (D594N), BRAF c.1780G>C (D594H), BRAF c.1780G>A (D594N), BRAF c.1781A>G (D594G), BRAF c.1781A>T (D594V), BRAF c.1782T>A (D594E), BRAF c.1782T>G (D594E), BRAF c.1789C>G (L597V), BRAF c.1789_1790 delCTinsTC (L597S), BRAF c.1790T>A (L597Q), BRAF c.1790T>G (L597R), BRAF c.1798G>A (V600M), BRAF c.1798_1799 delGTinsAA (V600K), BRAF c.1798_1799 delGTinsAG (V600R), BRAF c.1799T>A (V600E), BRAF c.1799T>G (V600G), BRAF c.1799_1800 delTGinsAT (V600D), BRAF c.1799_1800 delTGinsAA (V600E), or BRAF c.1801A>G (K601E). Other exemplary BRAF mutations also include a BRAF fusion, e.g., as described in Botton et al. *Pigment Cell Melanoma Res.* 2013; 26(6):845-51; Hutchinson et al. *Clin Cancer Res.* 2013; 19(24):6696-702).

In some embodiments, the inhibitor of PD-1 is an anti-PD-L1 antibody molecule.

Other exemplary inhibitors of BRAF that can be used in the combination described herein include, but are not limited to, vemurafenib (also known as RG7204 or PLX4032), GDC-0879, PLX-4720, sorafenib, or LGX818.

Other exemplary inhibitors of MEK that can be used in the combination described herein include, but are not limited to, cobimetinib (also known as XL518), binimetinib (also known as MEK162), selumetinib, PD-325901, CI-1040, PD035901, or TAK-733.

In some embodiments, the combination described herein is used further in combination with surgery, a chemotherapeutic agent, a radiation therapy, an immunotherapy (e.g., an anti-CTLA-4 antibody molecule, an anti-PD-L1 antibody molecule, an interferon, an interleukin (e.g., IL-2), or a TNF therapy), or a targeted therapy (e.g., an oncolytic virus, or an angiogenesis inhibitor).

Pharmaceutical Compositions and Kits

In another aspect, the present invention provides compositions, e.g., pharmaceutically acceptable compositions, which include an antibody molecule described herein, formulated together with a pharmaceutically acceptable carrier. As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, spinal or epidermal administration (e.g. by injection or infusion).

The compositions of this invention may be in a variety of forms. These include, for example, liquid, semi-solid and solid dosage forms, such as liquid solutions (e.g., injectable and infusible solutions), dispersions or suspensions, liposomes and suppositories. The preferred form depends on the intended mode of administration and therapeutic application. Typical preferred compositions are in the form of injectable or infusible solutions. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Therapeutic compositions typically should be sterile and stable under the conditions of manufacture and storage. The composition can be formulated as a solution, microemulsion, dispersion, liposome, or other ordered structure suitable to high antibody concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

A PD-1 inhibitor (e.g., anti-PD-1 antibody molecule) or a composition described herein can be formulated into a formulation (e.g., a dose formulation or dosage form) suitable for administration (e.g., intravenous administration) to a subject as described herein.

In certain embodiments, the formulation is a drug substance formulation. In other embodiments, the formulation is a lyophilized formulation, e.g., lyophilized or dried from a drug substance formulation. In other embodiments, the formulation is a reconstituted formulation, e.g., reconstituted from a lyophilized formulation. In other embodiments, the formulation is a liquid formulation.

In some embodiments, the formulation is a drug substance formulation. In some embodiments, the formulation (e.g., drug substance formulation) comprises the PD-1 inhibitor (e.g., the anti-PD-1 antibody molecule) and a buffering agent.

In some embodiments, the formulation (e.g., drug substance formulation) comprises a PD-1 inhibitor (e.g., an anti-PD-1 antibody molecule) present at a concentration of 10 to 50 mg/mL, e.g., 15 to 50 mg/mL, 20 to 45 mg/mL, 25 to 40 mg/mL, 30 to 35 mg/mL, 25 to 35 mg/mL, or 30 to 40 mg/mL, e.g., 15 mg/mL, 20 mg/mL, 25 mg/mL, 30 mg/mL, 33.3 mg/mL, 35 mg/mL, 40 mg/mL, 45 mg/mL, or 50 mg/mL. In certain embodiments, the PD-1 inhibitor (e.g., the anti-PD-1 antibody molecule) is present at a concentration of 30 to 35 mg/mL, e.g., 33.3 mg/mL.

In some embodiments, the formulation (e.g., drug substance formulation) comprises a buffering agent comprising histidine (e.g., a histidine buffer). In certain embodiments, the buffering agent (e.g., histidine buffer) is present at a concentration of 1 mM to 20 mM, e.g., 2 mM to 15 mM, 3 mM to 10 mM, 4 mM to 9 mM, 5 mM to 8 mM, or 6 mM to 7 mM, e.g., 1 mM, 2 mM, 3 mM, 4 mM, 5 mM, 6 mM, 6.7 mM, 7 mM, 8 mM, 9 mM, 10 mM, 11 mM, 12 mM, 13 mM, 14 mM, 15 mM, 16 mM, 17 mM, 18 mM, 19 mM, or 20 mM. In some embodiments, the buffering agent (e.g., histidine buffer) is present at a concentration of 6 mM to 7 mM, e.g., 6.7 mM. In other embodiments, the buffering agent (e.g., a histidine buffer) has a pH of 4 to 7, e.g., 5 to 6, e.g., 5, 5.5, or 6. In some embodiments, the buffering agent (e.g., histidine buffer) has a pH of 5 to 6, e.g., 5.5. In certain embodiments, the buffering agent comprises histidine at a concentration of 6 mM to 7 mM (e.g., 6.7 mM) and has a pH of 5 to 6 (e.g., 5.5).

In some embodiments, the formulation (e.g., drug substance formulation) comprises a PD-1 inhibitor (e.g., an anti-PD-1 antibody molecule) present at a concentration of 30 to 35 mg/mL, e.g., 33.3 mg/mL; and a buffering agent that comprises histidine at a concentration of 6 mM to 7 mM (e.g., 6.7 mM) and has a pH of 5 to 6 (e.g., 5.5).

In some embodiments, the formulation (e.g., drug substance formulation) further comprises a carbohydrate. In certain embodiments, the carbohydrate is sucrose. In some embodiments, the carbohydrate (e.g., sucrose) is present at a concentration of 50 mM to 150 mM, e.g., 25 mM to 150 mM, 50 mM to 100 mM, 60 mM to 90 mM, 70 mM to 80 mM, or 70 mM to 75 mM, e.g., 25 mM, 50 mM, 60 mM, 70 mM, 73.3 mM, 80 mM, 90 mM, 100 mM, or 150 mM. In some embodiments, the formulation comprises a carbohydrate or sucrose present at a concentration of 70 mM to 75 mM, e.g., 73.3 mM.

In some embodiments, the formulation (e.g., drug substance formulation) comprises a PD-1 inhibitor (e.g., an anti-PD-1 antibody molecule) present at a concentration of 30 to 35 mg/mL, e.g., 33.3 mg/mL; a buffering agent that comprises histidine at a concentration of 6 mM to 7 mM (e.g., 6.7 mM) and has a pH of 5 to 6 (e.g., 5.5); and a carbohydrate or sucrose present at a concentration of 70 mM to 75 mM, e.g., 73.3 mM.

In some embodiments, the formulation (e.g., drug substance formulation) further comprises a surfactant. In certain embodiments, the surfactant is polysorbate 20. In some embodiments, the surfactant or polysorbate 20) is present at a concentration of 0.005% to 0.025% (w/w), e.g., 0.0075% to 0.02% or 0.01% to 0.015% (w/w), e.g., 0.005%, 0.0075%, 0.01%, 0.013%, 0.015%, or 0.02% (w/w). In some embodiments, the formulation comprises a surfactant or polysorbate 20 present at a concentration of 0.01% to 0.015%, e.g., 0.013% (w/w).

In some embodiments, the formulation (e.g., drug substance formulation) comprises a PD-1 inhibitor (e.g., an anti-PD-1 antibody molecule) present at a concentration of 30 to 35 mg/mL, e.g., 33.3 mg/mL; a buffering agent that comprises histidine at a concentration of 6 mM to 7 mM (e.g., 6.7 mM) and has a pH of 5 to 6 (e.g., 5.5); and a surfactant or polysorbate 20 present at a concentration of 0.01% to 0.015%, e.g., 0.013% (w/w).

In some embodiments, the formulation (e.g., drug substance formulation) comprises a PD-1 inhibitor (e.g., an anti-PD-1 antibody molecule) present at a concentration of 30 to 35 mg/mL, e.g., 33.3 mg/mL; a buffering agent that comprises histidine at a concentration of 6 mM to 7 mM (e.g., 6.7 mM) and has a pH of 5 to 6 (e.g., 5.5); a carbohydrate or sucrose present at a concentration of 70 mM to 75 mM, e.g., 73.3 mM; and a surfactant or polysorbate 20 present at a concentration of 0.01% to 0.015%, e.g., 0.013% (w/w).

In some embodiments, the formulation (e.g., drug substance formulation) comprises a PD-1 inhibitor (e.g., an anti-PD-1 antibody molecule) present at a concentration of 33.3 mg/mL; a buffering agent that comprises histidine at a concentration of 6.7 mM and has a pH of 5.5; sucrose present at a concentration of 73.3 mM; and polysorbate 20 present at a concentration of 0.013% (w/w).

In some embodiments, the formulation is a lyophilized formulation. In certain embodiments, the lyophilized formulation is lyophilized from a drug substance formulation described herein. For example, 2 to 5 mL, e.g., 3 to 4 mL, e.g., 3.6 mL, of the drug substance formulation described herein can be filled per container (e.g., vial) and lyophilized.

In certain embodiments, the formulation is a reconstituted formulation. For example, a reconstituted formulation can be prepared by dissolving a lyophilized formulation in a diluent such that the protein is dispersed in the reconstituted formulation. In some embodiments, the lyophilized formulation is reconstituted with 0.5 mL to 2 mL, e.g., 1 mL, of water or buffer for injection. In certain embodiments, the lyophilized formulation is reconstituted with 1 mL of water for injection, e.g., at a clinical site.

In some embodiments, the formulation (e.g., reconstituted formulation) comprises the PD-1 inhibitor (e.g., the anti-PD-1 antibody molecule) and a buffering agent.

In some embodiments, the formulation (e.g., reconstituted formulation) comprises a PD-1 inhibitor (e.g., an anti-PD-1 antibody molecule) present at a concentration of 20 mg/mL to 200 mg/mL, e.g., 50 mg/mL to 150 mg/mL, 80 mg/mL to 120 mg/mL, or 90 mg/mL to 110 mg/mL, e.g., 50 mg/mL, 60 mg/mL, 70 mg/mL, 80 mg/mL, 90 mg/mL, 100 mg/mL, 110 mg/mL, 120 mg/mL, 130 mg/mL, 140 mg/mL, 150 mg/mL, 160 mg/mL, 170 mg/mL, 180 mg/mL, 190 mg/mL, or 200 mg/mL. In certain embodiments, the PD-1 inhibitor (e.g., the anti-PD-1 antibody molecule) is present at a concentration of 80 to 120 mg/mL, e.g., 100 mg/mL.

In some embodiments, the formulation (e.g., reconstituted formulation) comprises a buffering agent comprising histidine (e.g., a histidine buffer). In certain embodiments, the buffering agent (e.g., histidine buffer) is present at a concentration of 5 mM to 100 mM, e.g., 10 mM to 50 mM, 15 mM to 25 mM, e.g., 5 mM, 10 mM, 20 mM, 30 mM, 40 mM, 50 mM, 60 mM, 70 mM, 80 mM, 90 mM, or 100 mM. In some embodiments, the buffering agent (e.g., histidine buffer) is present at a concentration of 15 mM to 25 mM, e.g., 20 mM. In other embodiments, the buffering agent (e.g., a histidine buffer) has a pH of 4 to 7, e.g., 5 to 6, e.g., 5, 5.5 or 6. In some embodiments, the buffering agent (e.g., histidine buffer) has a pH of 5 to 6, e.g., 5.5. In certain embodiments, the buffering agent comprises histidine at a concentration of 15 mM to 25 mM (e.g., 20 mM) and has a pH of 5 to 6 (e.g., 5.5).

In some embodiments, the formulation (e.g., reconstituted formulation) comprises a PD-1 inhibitor (e.g., an anti-PD-1 antibody molecule) present at a concentration of 80 to 120 mg/mL, e.g., 100 mg/mL; and a buffering agent that comprises histidine at a concentration of 6 mM to 7 mM (e.g., 6.7 mM) and has a pH of 5 to 6 (e.g., 5.5).

In some embodiments, the formulation (e.g., reconstituted formulation) further comprises a carbohydrate. In certain embodiments, the carbohydrate is sucrose. In some embodiments, the carbohydrate (e.g., sucrose) is present at a concentration of 100 mM to 500 mM, e.g., 150 mM to 400 mM, 175 mM to 300 mM, or 200 mM to 250 mM, e.g., 150 mM, 160 mM, 170 mM, 180 mM, 190 mM, 200 mM, 210 mM, 220 mM, 230 mM, 240 mM, 250 mM, 260 mM, 270 mM, 280 mM, 290 mM, or 300 mM. In some embodiments, the formulation comprises a carbohydrate or sucrose present at a concentration of 200 mM to 250 mM, e.g., 220 mM.

In some embodiments, the formulation (e.g., reconstituted formulation) comprises a PD-1 inhibitor (e.g., an anti-PD-1 antibody molecule) present at a concentration of 80 to 120 mg/mL, e.g., 100 mg/mL; and a buffering agent that comprises histidine at a concentration of 6 mM to 7 mM (e.g., 6.7 mM) and has a pH of 5 to 6 (e.g., 5.5); and a carbohydrate or sucrose present at a concentration of 200 mM to 250 mM, e.g., 220 mM.

In some embodiments, the formulation (e.g., reconstituted formulation) further comprises a surfactant. In certain embodiments, the surfactant is polysorbate 20. In some embodiments, the surfactant or polysorbate 20 is present at a concentration of 0.01% to 0.1% (w/w), e.g., 0.02% to 0.08%, 0.025% to 0.06% or 0.03% to 0.05% (w/w), e.g., 0.01%, 0.025%, 0.03%, 0.04%, 0.05%, 0.06%, 0.07%, 0.08%, 0.09%, or 0.1% (w/w). In some embodiments, the formulation comprises a surfactant or polysorbate 20 present at a concentration of 0.03% to 0.05%, e.g., 0.04% (w/w).

In some embodiments, the formulation (e.g., reconstituted formulation) comprises a PD-1 inhibitor (e.g., an anti-PD-1 antibody molecule) present at a concentration of 80 to 120 mg/mL, e.g., 100 mg/mL; and a buffering agent that comprises histidine at a concentration of 6 mM to 7 mM (e.g., 6.7 mM) and has a pH of 5 to 6 (e.g., 5.5); and a surfactant or polysorbate 20 present at a concentration of 0.03% to 0.05%, e.g., 0.04% (w/w).

In some embodiments, the formulation (e.g., reconstituted formulation) comprises a PD-1 inhibitor (e.g., an anti-PD-1 antibody molecule) present at a concentration of 80 to 120 mg/mL, e.g., 100 mg/mL; and a buffering agent that comprises histidine at a concentration of 6 mM to 7 mM (e.g., 6.7 mM) and has a pH of 5 to 6 (e.g., 5.5); a carbohydrate or sucrose present at a concentration of 200 mM to 250 mM, e.g., 220 mM; and a surfactant or polysorbate 20 present at a concentration of 0.03% to 0.05%, e.g., 0.04% (w/w).

In some embodiments, the formulation (e.g., reconstituted formulation) comprises a PD-1 inhibitor (e.g., an anti-PD-1 antibody molecule) present at a concentration of 100 mg/mL; and a buffering agent that comprises histidine at a concentration of 6.7 mM and has a pH of 5.5; sucrose present at a concentration of 220 mM; and polysorbate 20 present at a concentration of 0.04% (w/w).

In some embodiments, the formulation is reconstituted such that an extractable volume of at least 1 mL (e.g., at least 1.5 mL, 2 mL, 2.5 mL, or 3 mL) of the reconstituted formulation can be withdrawn from the container (e.g., vial) containing the reconstituted formulation. In certain embodiments, the formulation is reconstituted and/or extracted from the container (e.g., vial) at a clinical site. In certain embodiments, the formulation (e.g., reconstituted formulation) is injected to an infusion bag, e.g., within 1 hour (e.g., within 45 minutes, 30 minutes, or 15 minutes) before the infusion starts to the patient.

In certain embodiments, the formulation is a liquid formulation. In some embodiments, the liquid formulation is prepared by diluting a drug substance formulation described herein. For example, a drug substance formulation can be diluted, e.g., with 10 to 30 mg/mL (e.g., 25 mg/mL) of a solution comprising one or more excipients (e.g., concentrated excipients). In some embodiments, the solution comprises one, two, or all of histidine, sucrose, or polysorbate 20. In certain embodiments, the solution comprises the same excipient(s) as the drug substance formulation. Exemplary excipients include, but are not limited to, an amino acid (e.g., histidine), a carbohydrate (e.g., sucrose), or a surfactant (e.g., polysorbate 20). In certain embodiments, the liquid formulation is not a reconstituted lyophilized formulation. In other embodiments, the liquid formulation is a reconstituted lyophilized formulation. In some embodiments, the formulation is stored as a liquid. In other embodiments, the formulation is prepared as a liquid and then is dried, e.g., by lyophilization or spray-drying, prior to storage.

In some embodiments, the formulation (e.g., liquid formulation) comprises a PD-1 inhibitor (e.g., an anti-PD-1 antibody molecule) present at a concentration of 5 mg/mL to 50 mg/mL, e.g., 10 mg/mL to 40 mg/mL, 15 mg/mL to 35 mg/mL, or 20 mg/mL to 30 mg/mL, e.g., 5 mg/mL, 10 mg/mL, 15 mg/mL, 20 mg/mL, 25 mg/mL, 30 mg/mL, 35 mg/mL, 40 mg/mL, 45 mg/mL, or 50 mg/mL. In certain embodiments, the PD-1 inhibitor (e.g., the anti-PD-1 antibody molecule) is present at a concentration of 20 to 30 mg/mL, e.g., 25 mg/mL.

In some embodiments, the formulation (e.g., liquid formulation) comprises a buffering agent comprising histidine (e.g., a histidine buffer). In certain embodiments, the buffering agent (e.g., histidine buffer) is present at a concentration of 5 mM to 100 mM, e.g., 10 mM to 50 mM, 15 mM to 25 mM, e.g., 5 mM, 10 mM, 20 mM, 30 mM, 40 mM, 50 mM, 60 mM, 70 mM, 80 mM, 90 mM, or 100 mM. In some embodiments, the buffering agent (e.g., histidine buffer) is present at a concentration of 15 mM to 25 mM, e.g., 20 mM. In other embodiments, the buffering agent (e.g., a histidine buffer) has a pH of 4 to 7, e.g., 5 to 6, e.g., 5, 5.5 or 6. In some embodiments, the buffering agent (e.g., histidine buffer) has a pH of 5 to 6, e.g., 5.5. In certain embodiments, the buffering agent comprises histidine at a concentration of 15 mM to 25 mM (e.g., 20 mM) and has a pH of 5 to 6 (e.g., 5.5).

In some embodiments, the formulation (e.g., liquid formulation) comprises a PD-1 inhibitor (e.g., an anti-PD-1 antibody molecule) present at a concentration of 20 to 30 mg/mL, e.g., 25 mg/mL; and a buffering agent that comprises histidine at a concentration of 6 mM to 7 mM (e.g., 6.7 mM) and has a pH of 5 to 6 (e.g., 5.5).

In some embodiments, the formulation (e.g., liquid formulation) further comprises a carbohydrate. In certain embodiments, the carbohydrate is sucrose. In some embodiments, the carbohydrate (e.g., sucrose) is present at a concentration of 100 mM to 500 mM, e.g., 150 mM to 400 mM, 175 mM to 300 mM, or 200 mM to 250 mM, e.g., 150 mM, 160 mM, 170 mM, 180 mM, 190 mM, 200 mM, 210 mM, 220 mM, 230 mM, 240 mM, 250 mM, 260 mM, 270 mM, 280 mM, 290 mM, or 300 mM. In some embodiments, the formulation comprises a carbohydrate or sucrose present at a concentration of 200 mM to 250 mM, e.g., 220 mM.

In some embodiments, the formulation (e.g., liquid formulation) comprises a PD-1 inhibitor (e.g., an anti-PD-1 antibody molecule) present at a concentration of 20 to 30 mg/mL, e.g., 25 mg/mL; and a buffering agent that comprises histidine at a concentration of 6 mM to 7 mM (e.g., 6.7 mM) and has a pH of 5 to 6 (e.g., 5.5); and a carbohydrate or sucrose present at a concentration of 200 mM to 250 mM, e.g., 220 mM.

In some embodiments, the formulation (e.g., liquid formulation) further comprises a surfactant. In certain embodiments, the surfactant is polysorbate 20. In some embodiments, the surfactant or polysorbate 20 is present at a concentration of 0.01% to 0.1% (w/w), e.g., 0.02% to 0.08%, 0.025% to 0.06% or 0.03% to 0.05% (w/w), e.g., 0.01%, 0.025%, 0.03%, 0.04%, 0.05%, 0.06%, 0.07%, 0.08%, 0.09%, or 0.1% (w/w). In some embodiments, the formulation comprises a surfactant or polysorbate 20 present at a concentration of 0.03% to 0.05%, e.g., 0.04% (w/w).

In some embodiments, the formulation (e.g., liquid formulation) comprises a PD-1 inhibitor (e.g., an anti-PD-1 antibody molecule) present at a concentration of 20 to 30 mg/mL, e.g., 25 mg/mL; and a buffering agent that comprises histidine at a concentration of 6 mM to 7 mM (e.g., 6.7 mM) and has a pH of 5 to 6 (e.g., 5.5); and a surfactant or polysorbate 20 present at a concentration of 0.03% to 0.05%, e.g., 0.04% (w/w).

In some embodiments, the formulation (e.g., liquid d formulation) comprises a PD-1 inhibitor (e.g., an anti-PD-1 antibody molecule) present at a concentration of 20 to 30 mg/mL, e.g., 25 mg/mL; and a buffering agent that comprises histidine at a concentration of 6 mM to 7 mM (e.g., 6.7 mM) and has a pH of 5 to 6 (e.g., 5.5); a carbohydrate or sucrose present at a concentration of 200 mM to 250 mM, e.g., 220 mM; and a surfactant or polysorbate 20 present at a concentration of 0.03% to 0.05%, e.g., 0.04% (w/w).

In some embodiments, the formulation (e.g., liquid formulation) comprises a PD-1 inhibitor (e.g., an anti-PD-1 antibody molecule) present at a concentration of 25 mg/mL; and a buffering agent that comprises histidine at a concentration of 6.7 mM and has a pH of 5.5; sucrose present at a concentration of 220 mM; and polysorbate 20 present at a concentration of 0.04% (w/w).

In certain embodiments, 1 mL to 10 mL (e.g., 2 mL to 8 mL, 3 mL to 7 mL, or 4 mL to 5 mL, e.g., 3 mL, 4 mL, 4.3 mL, 4.5 mL, 5 mL, or 6 mL) of the liquid formulation is filled per container (e.g., vial). In other embodiments, the liquid formulation is filled into a container (e.g., vial) such that an extractable volume of at least 2 mL (e.g., at least 3 mL, at least 4 mL, or at least 5 mL) of the liquid formulation can be withdrawn per container (e.g., vial). In certain embodiments, the liquid formulation is diluted from the drug substance formulation and/or extracted from the container (e.g., vial) at a clinical site. In certain embodiments, the formulation (e.g., liquid formulation) is injected to an infusion bag, e.g., within 1 hour (e.g., within 45 minutes, 30 minutes, or 15 minutes) before the infusion starts to the patient.

A formulation described herein can be stored in a container. The container used for any of the formulations described herein can include, e.g., a vial, and optionally, a stopper, a cap, or both. In certain embodiments, the vial is a glass vial, e.g., a 6R white glass vial. In other embodiments, the stopper is a rubber stopper, e.g., a grey rubber stopper. In other embodiments, the cap is a flip-off cap, e.g., an aluminum flip-off cap. In some embodiments, the container comprises a 6R white glass vial, a grey rubber stopper, and an aluminum flip-off cap. In some embodiments, the container (e.g., vial) is for a single-use container. In certain embodiments, 50 mg to 150 mg, e.g., 80 mg to 120 mg, 90 mg to 110 mg, 100 mg to 120 mg, 100 mg to 110 mg, 110 mg to 120 mg, or 110 mg to 130 mg, of the PD-1 inhibitor (e.g., the anti-PD-1 antibody molecule), is present in the container (e.g., vial).

Other exemplary buffering agents that can be used in the formulation described herein include, but are not limited to, an arginine buffer, a citrate buffer, or a phosphate buffer. Other exemplary carbohydrates that can be used in the formulation described herein include, but are not limited to, trehalose, mannitol, sorbitol, or a combination thereof. The formulation described herein may also contain a tonicity agent, e.g., sodium chloride, and/or a stabilizing agent, e.g., an amino acid (e.g., glycine, arginine, methionine, or a combination thereof).

The antibody molecules can be administered by a variety of methods known in the art, although for many therapeutic applications, the preferred route/mode of administration is intravenous injection or infusion. For example, the antibody molecules can be administered by intravenous infusion at a rate of more than 20 mg/min, e.g., 20-40 mg/min, and typically greater than or equal to 40 mg/min to reach a dose of about 35 to 440 mg/m$^2$, typically about 70 to 310 mg/m$^2$, and more typically, about 110 to 130 mg/m$^2$. In embodiments, the antibody molecules can be administered by intravenous infusion at a rate of less than 10 mg/min; preferably less than or equal to 5 mg/min to reach a dose of about 1 to 100 mg/m$^2$, preferably about 5 to 50 mg/m$^2$, about 7 to 25 mg/m$^2$ and more preferably, about 10 mg/m$^2$. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody molecule can be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation. Therapeutic compositions can also be administered with medical devices known in the art.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody molecule is 0.1-30 mg/kg, more preferably 1-25 mg/kg. Dosages and therapeutic regimens of the anti-PD-1 antibody molecule can be determined by a skilled artisan. In certain embodiments, the anti-PD-1 antibody molecule is administered by injection (e.g., subcutaneously or intravenously) at a dose of about 1 to 40 mg/kg, e.g., 1 to 30 mg/kg, e.g., about 5 to 25 mg/kg, about 10 to 20 mg/kg, about 1 to 5 mg/kg, 1 to 10 mg/kg, 5 to 15 mg/kg, 10 to 20 mg/kg, 15 to 25 mg/kg, or about 3 mg/kg. The dosing schedule can vary from e.g., once a week to once every 2, 3, or 4 weeks. In one embodiment, the anti-PD-1 antibody molecule is administered at a dose from about 10 to 20 mg/kg every other week.

As another example, non-limiting range for a therapeutically or prophylactically effective amount of an antibody molecule is 200-500 mg, more preferably 300-400 mg/kg. Dosages and therapeutic regimens of the anti-PD-1 antibody molecule can be determined by a skilled artisan. In certain embodiments, the anti-PD-1 antibody molecule is administered by injection (e.g., subcutaneously or intravenously) at a dose (e.g., a flat dose) of about 200 mg to 500 mg, e.g., about 250 mg to 450 mg, about 300 mg to 400 mg, about 250 mg to 350 mg, about 350 mg to 450 mg, or about 300 mg or about 400 mg. The dosing schedule (e.g., flat dosing schedule) can vary from e.g., once a week to once every 2, 3, 4, 5, or 6 weeks. In one embodiment the anti-PD-1 antibody molecule is administered at a dose from about 300 mg to 400 mg once every three or once every four weeks. In one embodiment, the anti-PD-1 antibody molecule is administered at a dose from about 300 mg once every three weeks. In one embodiment, the anti-PD-1 antibody molecule is administered at a dose from about 400 mg once every four weeks. In one embodiment, the anti-PD-1 antibody molecule is administered at a dose from about 300 mg once every four weeks. In one embodiment, the anti-PD-1 antibody molecule is administered at a dose from about 400 mg once every three weeks. While not wishing to be bound by theory, in some embodiments, flat or fixed dosing can be beneficial to patients, for example, to save drug supply and to reduce pharmacy errors.

In some embodiments, the clearance (CL) of the anti-PD-1 antibody molecule is from about 6 to 16 mL/h, e.g., about 7 to 15 mL/h, about 8 to 14 mL/h, about 9 to 12 mL/h, or about 10 to 11 mL/h, e.g., about 8.9 mL/h, 10.9 mL/h, or 13.2 mL/h.

In some embodiments, the exponent of weight on CL of the anti-PD-1 antibody molecule is from about 0.4 to 0.7, about 0.5 to 0.6, or 0.7 or less, e.g., 0.6 or less, or about 0.54.

In some embodiments, the volume of distribution at steady state (Vss) of the anti-PD-1 antibody molecule is from about 5 to 10 V, e.g., about 6 to 9 V, about 7 to 8 V, or about 6.5 to 7.5 V, e.g., about 7.2 V.

In some embodiments, the half-life of the anti-PD-1 antibody molecule is from about 10 to 30 days, e.g., about 15 to 25 days, about 17 to 22 days, about 19 to 24 days, or about 18 to 22 days, e.g., about 20 days.

In some embodiments, the Cmin (e.g., for a 80 kg patient) of the anti-PD-1 antibody molecule is at least about 0.4 μg/mL, e.g., at least about 3.6 μg/mL, e.g., from about 20 to 50 μg/mL, e.g., about 22 to 42 μg/mL, about 26 to 47 μg/mL, about 22 to 26 μg/mL, about 42 to 47 μg/mL, about 25 to 35 μg/mL, about 32 to 38 μg/mL, e.g., about 31 μg/mL or about 35 μg/mL. In one embodiment, the Cmin is determined in a patient receiving the anti-PD-1 antibody molecule at a dose of about 400 mg once every four weeks. In another embodiment, the Cmin is determined in a patient receiving the anti-PD-1 antibody molecule at a dose of about 300 mg once every three weeks. In some embodiments, the Cmin is at least about 50-fold higher, e.g., at least about 60-fold, 65-fold, 70-fold, 75-fold, 80-fold, 85-fold, 90-fold, 95-fold, or 100-fold, e.g., at least about 77-fold, higher than the EC50 of the anti-PD-1 antibody molecule, e.g., as determined based on IL-2 change in an SEB ex-vivo assay. In other embodiments, the Cmin is at least 5-fold higher, e.g., at least 6-fold, 7-fold, 8-fold, 9-fold, or 10-fold, e.g., at least about 8.6-fold, higher than the EC90 of the anti-PD-1 antibody molecule, e.g., as determined based on IL-2 change in an SEB ex-vivo assay.

The antibody molecule can be administered by intravenous infusion at a rate of more than 20 mg/min, e.g., 20-40 mg/min, and typically greater than or equal to 40 mg/min to reach a dose of about 35 to 440 mg/m$^2$, typically about 70 to 310 mg/m$^2$, and more typically, about 110 to 130 mg/m$^2$. In embodiments, the infusion rate of about 110 to 130 mg/m$^2$ achieves a level of about 3 mg/kg. In other embodiments, the antibody molecule can be administered by intravenous infusion at a rate of less than 10 mg/min, e.g., less than or equal to 5 mg/min to reach a dose of about 1 to 100 mg/m$^2$, e.g., about 5 to 50 mg/m$^2$, about 7 to 25 mg/m$^2$, or, about 10 mg/m$^2$. In some embodiments, the antibody is infused over a period of about 30 min. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the modified antibody or antibody fragment may vary according to factors such as the disease state, age, sex, and weight of the individual, and the ability of the antibody or antibody portion to elicit a desired response in the individual. A therapeutically effective amount is also one in which any toxic or detrimental effects of the modified antibody or antibody fragment is outweighed by the therapeutically beneficial effects. A "therapeutically effective dosage" preferably inhibits a measurable parameter, e.g., tumor growth rate by at least about 20%, more preferably by at least about 40%, even more preferably by at least about 60%, and still more preferably by at least about 80% relative to untreated subjects. The ability of a compound to inhibit a measurable parameter, e.g., cancer, can be evaluated in an animal model system predictive of efficacy in human tumors. Alternatively, this property of a composition can be evaluated by examining the ability of the compound to inhibit, such inhibition in vitro by assays known to the skilled practitioner.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Also within the scope of the invention is a kit comprising an antibody molecule described herein. The kit can include one or more other elements including: instructions for use; other reagents, e.g., a label, a therapeutic agent, or an agent useful for chelating, or otherwise coupling, an antibody to a label or therapeutic agent, or a radioprotective composition;

devices or other materials for preparing the antibody for administration; pharmaceutically acceptable carriers; and devices or other materials for administration to a subject.

Uses of the Combination Therapies

The combinations, e.g., the anti-PD-1 antibody molecules disclosed herein, have in vitro and in vivo diagnostic, as well as therapeutic and prophylactic utilities. For example, these molecules can be administered to cells in culture, in vitro or ex vivo, or to a subject, e.g., a human subject, to treat, prevent, and/or diagnose a variety of disorders, such as cancers and infectious disorders.

Accordingly, in one aspect, the invention provides a method of modifying an immune response in a subject comprising administering to the subject the combination described herein, such that the immune response in the subject is modified. In one embodiment, the immune response is enhanced, stimulated or up-regulated.

As used herein, the term "subject" is intended to include human and non-human animals. In one embodiment, the subject is a human subject, e.g., a human patient having a disorder or condition characterized by abnormal PD-1 functioning. The term "non-human animals" includes mammals and non-mammals, such as non-human primates. In one embodiment, the subject is a human. In one embodiment, the subject is a human patient in need of enhancement of an immune response. In one embodiment, the subject is immunocompromised, e.g., the subject is undergoing, or has undergone a chemotherapeutic or radiation therapy. Alternatively, or in combination, the subject is, or is at risk of being, immunocompromised as a result of an infection. The methods and compositions described herein are suitable for treating human patients having a disorder that can be treated by augmenting the T-cell mediated immune response. For example, the methods and compositions described herein can enhance a number of immune activities. In one embodiment, the subject has increased number or activity of tumour-infiltrating T lymphocytes (TILs). In another embodiment, the subject has increased expression or activity of interferon-gamma (IFN-γ). In yet another embodiment, the subject has decreased PD-L1 expression or activity.

Therapeutic Uses

Blockade of PD-1 can enhance an immune response to cancerous cells in a subject. The ligand for PD-1, PD-L1, is not expressed in normal human cells, but is abundant in a variety of human cancers (Dong et al. (2002) *Nat Med* 8:787-9). The interaction between PD-1 and PD-L1 can result in a decrease in tumor infiltrating lymphocytes, a decrease in T-cell receptor mediated proliferation, and/or immune evasion by the cancerous cells (Dong et al. (2003) *J Mol Med* 81:281-7; Blank et al. (2005) *Cancer Immunol. Immunother.* 54:307-314; Konishi et al. (2004) *Clin. Cancer Res.* 10:5094-100). Immune suppression can be reversed by inhibiting the local interaction of PD-1 to PD-L1; the effect is additive when the interaction of PD-1 to PD-L2 is blocked as well (Iwai et al. (2002) *PNAS* 99:12293-7; Brown et al. (2003) *J. Immunol.* 170:1257-66). Thus, inhibition of PD-1 can result in augmenting an immune response.

In one aspect, the invention relates to treatment of a subject in vivo using an anti-PD-1 antibody molecule such that growth of cancerous tumors is inhibited or reduced. An anti-PD-1 antibody may be used alone to inhibit the growth of cancerous tumors. Alternatively, an anti-PD-1 antibody may be used in combination with one or more of: a standard of care treatment (e.g., for cancers or infectious disorders), another antibody or antigen-binding fragment thereof, an immunomodulator (e.g., an activator of a costimulatory molecule or an inhibitor of an inhibitory molecule); a vaccine, e.g., a therapeutic cancer vaccine; or other forms of cellular immunotherapy, as described below.

Accordingly, in one embodiment, the invention provides a method of inhibiting growth of tumor cells in a subject, comprising administering to the subject a therapeutically effective amount of an anti-PD-1 antibody molecule described herein.

In one embodiment, the methods are suitable for the treatment of cancer in vivo. To achieve antigen-specific enhancement of immunity, the anti-PD-1 antibody molecule can be administered together with an antigen of interest. When antibodies to PD-1 are administered in combination with one or more agents, the combination can be administered in either order or simultaneously.

In another aspect, a method of treating a subject, e.g., reducing or ameliorating, a hyperproliferative condition or disorder (e.g., a cancer), e.g., solid tumor, a hematological cancer, soft tissue tumor, or a metastatic lesion, in a subject is provided. The method includes administering to the subject one or more of the combinations disclosed herein.

As used herein, the term "cancer" is meant to include all types of cancerous growths or oncogenic processes, metastatic tissues or malignantly transformed cells, tissues, or organs, irrespective of histopathologic type or stage of invasiveness. Examples of cancerous disorders include, but are not limited to, solid tumors, hematological cancers, soft tissue tumors, and metastatic lesions. Examples of solid tumors include malignancies, e.g., sarcomas, and carcinomas (including adenocarcinomas and squamous cell carcinomas), of the various organ systems, such as those affecting liver, lung, breast, lymphoid, gastrointestinal (e.g., colon), genitourinary tract (e.g., renal, urothelial cells), prostate and pharynx. Adenocarcinomas include malignancies such as most colon cancers, rectal cancer, renal-cell carcinoma, liver cancer, non-small cell carcinoma of the lung, cancer of the small intestine and cancer of the esophagus. Squamous cell carcinomas include malignancies, e.g., in the lung, esophagus, skin, head and neck region, oral cavity, anus, and cervix. In one embodiment, the cancer is a melanoma, e.g., an advanced stage melanoma. Metastatic lesions of the aforementioned cancers can also be treated or prevented using the methods and compositions of the invention.

Exemplary cancers whose growth can be inhibited using the antibodies molecules disclosed herein include cancers typically responsive to immunotherapy. Non-limiting examples of preferred cancers for treatment include melanoma (e.g., metastatic malignant melanoma), renal cancer (e.g., clear cell carcinoma), prostate cancer (e.g., hormone refractory prostate adenocarcinoma), breast cancer, colon cancer and lung cancer (e.g., non-small cell lung cancer). Additionally, refractory or recurrent malignancies can be treated using the antibody molecules described herein.

Examples of other cancers that can be treated include bone cancer, pancreatic cancer, skin cancer, cancer of the head or neck, cutaneous or intraocular malignant melanoma, uterine cancer, ovarian cancer, rectal cancer, anal cancer, gastro-esophageal, stomach cancer, liposarcoma, testicular cancer, uterine cancer, carcinoma of the fallopian tubes, carcinoma of the endometrium, carcinoma of the cervix, carcinoma of the vagina, carcinoma of the vulva, Merkel cell cancer, Hodgkin lymphoma, non-Hodgkin lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, multiple myeloma, myelodisplastic syndromes, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos (e.g., mesothelioma), and combinations of said cancers. In certain embodiments, the cancer is a skin cancer, e.g., a Merkel cell carcinoma or a melanoma. In one embodiment, the cancer is a Merkel cell carcinoma. In other embodiments, the cancer is a melanoma. In other embodiments, the cancer is a breast cancer, e.g., a triple negative breast cancer (TNBC) or a HER2-negative breast cancer. In other embodiments, the cancer is kidney cancer, e.g., a renal cell carcinoma (e.g., clear cell renal cell carcinoma (CCRCC) or a non-clear cell renal cell carcinoma (nccRCC)). In other embodiments, the cancer is a thyroid cancer, e.g., an anaplastic thyroid carcinoma (ATC). In other embodiments, the cancer is a neuroendocrine tumor (NET), e.g., an atypical pulmonary carcinoid tumor or an NET in pancreas, gastrointestinal (GI) tract, or lung. In certain embodiments, the cancer is a lung cancer, e.g., a non-small cell lung cancer (NSCLC) (e.g., a squamous NSCLC or a non-squamous NSCLC). In certain embodiments, the cancer is a leukemia (e.g., an acute myeloid leukemia (AML), e.g., a relapsed or refractory AML or a de novo AML). In certain embodiments, the cancer is a myelodysplastic syndrome (MDS) (e.g., a high risk MDS).

In some embodiments, the cancer is chosen from a lung cancer, a squamous cell lung cancer, a melanoma, a renal cancer, a liver cancer, a myeloma, a prostate cancer, a breast cancer, an ER+ breast cancer, an IM-TN breast cancer, a colorectal cancer, a colorectal cancer with high microsatellite instability, an EBV+ gastric cancer, a pancreatic cancer, a thyroid cancer, a hematological cancer, a non-Hodgkin's lymphoma, or a leukemia, or a metastatic lesion of the cancer. In some embodiments, the cancer is chosen from a non-small cell lung cancer (NSCLC), a NSCLC adenocarcinoma, a NSCLC squamous cell carcinoma, a hepatocellular carcinoma.

Treatment of metastatic cancers, e.g., metastatic cancers that express PD-L1 (Iwai et al. (2005) *Int. Immunol.* 17:133-144) can be effected using the antibody molecules described herein. In one embodiment, the cancer expresses an elevated level of PD-L1, IFNγ and/or CD8.

While not wishing to be bound by theory, in some embodiments, a patient is more likely to respond to treatment with an immunomodulator (optionally in combination with one or more agents as described herein) if the patient has a cancer that highly expresses PD-L1, and/or the cancer is infiltrated by anti-tumor immune cells, e.g., TILs. The anti-tumor immune cells may be positive for CD8, PD-L1, and/or IFN-γ; thus levels of CD8, PD-L1, and/or IFN-γ can serve as a readout for levels of TILs in the microenvironment. In certain embodiments, the cancer microenvironment is referred to as triple-positive for PD-L1/CD8/IFN-γ.

Accordingly, in certain aspects, this application provides methods of determining whether a tumor sample is positive for one or more of PD-L1, CD8, and IFN-γ, and if the tumor sample is positive for one or more, e.g., two, or all three, of the markers, then administering to the patient a therapeutically effective amount of an anti-PD-1 antibody molecule, optionally in combination with one or more other immunomodulators or anti-cancer agents.

In the following indications, a large fraction of patients are triple-positive for PD-L1/CD8/IFN-γ: Lung cancer (squamous); lung cancer (adenocarcinoma); head and neck cancer; stomach cancer; NSCLC; HNSCC; gastric cancers (e.g., MSIhi and/or EBV+); CRC (e.g., MSIhi); nasopharyngeal cancer (NPC); cervical cancer (e.g., squamous); thyroid cancer e.g., papillary thyroid, e.g., anaplastic thyroid carcinoma; skin cancer (e.g., Merkel cell carcinoma or melanoma); breast cancer (e.g., TN breast cancer); and DLBCL (Diffuse Large B-Cell Lymphoma). In breast cancer generally and in colon cancer generally, a moderate fraction of patients is triple-positive for PD-L1/CD8/IFN-γ. In the following indications, a small fraction of patients are triple-positive for PD-L1/CD8/IFN-γ: ER+ breast cancer, and pancreatic cancer. These findings are discussed further in Example 4. Regardless of whether a large or small fraction of patients is triple-positive for these markers, screening the patients for these markers allows one to identify a fraction of patients that has an especially high likelihood of responding favorably to therapy with a PD-1 antibody (e.g., a blocking PD-1 antibody), optionally in combination with one or more other immunomodulators (e.g., an anti-TIM-3 antibody molecule, an anti-LAG-3 antibody molecule, or an anti-PD-L1 antibody molecule) and/or anti-cancer agents, e.g., those listed in Table 7 and disclosed in the publications listed in Table 7.

In some embodiments, the cancer sample is classified as triple-positive for PD-L1/CD8/IFN-γ. This measurement can roughly be broken down into two thresholds: whether an individual cell is classified as positive, and whether the sample as a whole is classified as positive. First, one can measure, within an individual cell, the level of PD-L1, CD8, and/or IFN-γ. In some embodiments, a cell that is positive for one or more of these markers is a cell that has a higher level of the marker compared to a control cell or a reference value. For example, in some embodiments, a high level of PD-L1 in a given cell is a level higher than the level of PD-L1 in a corresponding non-cancerous tissue in the patient. As another example, in some embodiments, a high level of CD8 or IFN-γ in a given cell is a level of that protein typically seen in a TIL. Second, one can also measure the percentage of cells in the sample that are positive for PD-L1, CD8, and/or IFN-γ. (It is not necessary for a single cell to express all three markers.) In some embodiments, a triple positive sample is one that has a high percentage of cells, e.g., higher than a reference value or higher than a control sample, that are positive for these markers.

In other embodiments, one can measure the levels of PD-L1, CD8, and/or IFN-γ overall in the sample. In this case, a high level of CD8 or IFN-γ in the sample can be the level of that protein typically seen in a tumor infiltrated with TIL. Similarly, a high level of PD-L1 can be the level of that protein typically seen in a tumor sample, e.g., a tumor microenvironment.

The identification of subsets of patients that are triple-positive for PD-L1/CD8/IFN-γ, as shown in Example 4 herein, reveals certain sub-populations of patients that are likely to be responsive to PD-1 antibody therapy. For instance, many IM-TN (immunomodulatory, triple negative) breast cancer patients are triple-positive for PD-L1/CD8/IFN-γ. IM-TN breast cancer is described in, e.g., Brian D. Lehmann et al., "Identification of human triple-negative breast cancer subtypes and preclinical models for selection of targeted therapies", *J Clin Invest*. Jul. 1, 2011; 121(7): 2750-2767. Triple-negative breast cancers are those that do not express estrogen receptor (ER), progesterone receptor (PR) and Her2/neu. These cancers are difficult to treat because they are typically not responsive to agents that target ER, PR, and Her2/neu. Triple-negative breast cancers can be further subdivided into different classes, one of which is immunomodulatory. As described in Lehmann et al., IM-TN breast cancer is enriched for factors involved in immune cell processes, for example, one or more of immune cell signaling (e.g., TH1/TH2 pathway, NK cell pathway, B cell receptor signaling pathway, DC pathway, and T cell receptor signaling), cytokine signaling (e.g., cytokine pathway, IL-12 pathway, and IL-7 pathway), antigen processing and presentation, signaling through core immune signal transduction pathways (e.g., NFKB, TNF, and JAK/STAT signaling), genes involved in T-cell function, immune transcription, interferon (IFN) response and antigen processing. Accordingly, in some embodiments, the cancer treated is a cancer that is, or is determined to be, positive for one or more marker of IM-TN breast cancer, e.g., a factor that promotes one or more of immune cell signaling (e.g., TH1/TH2 pathway, NK cell pathway, B cell receptor signaling pathway, DC pathway, and T cell receptor signaling), cytokine signaling (e.g., cytokine pathway, IL-12 pathway, and IL-7 pathway), antigen processing and presentation, signaling through core immune signal transduction pathways (e.g., NFKB, TNF, and JAK/STAT signaling), genes involved in T-cell function, immune transcription, interferon (IFN) response and antigen processing.

As another example, it is shown herein that a subset of colon cancer patients having high MSI (microsatellite instability) is also triple-positive for PD-L1/CD8/IFN-γ. Accordingly, in some embodiments, a PD-1 antibody, e.g., a PD-1 antibody as described herein, (optionally in combination with one or more immunomodulators such as a LAG-3 antibody, TIM-3 antibody, or PD-L1 antibody, and one or more anti-cancer agents, e.g., an anti-cancer agent described in Table 7 or in a publication in Table 7) is administered to a patient who has, or who is identified as having, colon cancer with high MSI, thereby treating the cancer. In some embodiments, a cell with high MSI is a cell having MSI at a level higher than a reference value or a control cell, e.g., a non-cancerous cell of the same tissue type as the cancer.

As another example, it is shown herein that a subset of gastric cancer patients having high MSI, and/or which is EBV+, is also triple-positive for PD-L1/CD8/IFN-γ. Accordingly, in some embodiments, a PD-1 antibody, e.g., a PD-1 antibody as described herein, (optionally in combination with one or more immunomodulators such as a LAG-3 antibody, TIM-3 antibody, or PD-L1 antibody, and one or more anti-cancer agents, e.g., an anti-cancer agent described in Table 7 or in a publication in Table 7) is administered to a patient who has, or who is identified as having, gastric cancer with high MSI and/or EBV+, thereby treating the cancer. In some embodiments, a cell with high MSI is a cell having MSI at a level higher than a reference value or a control cell, e.g., a non-cancerous cell of the same tissue type as the cancer.

Additionally disclosed herein are methods of assaying a cancer for PD-L1, and then treating the cancer with a PD-1 antibody. As described in Example 5 herein, a cancer sample can be assayed for PD-L1 protein levels or mRNA levels. A sample having levels of PD-L1 (protein or mRNA) higher than a reference value or a control cell (e.g., a non-cancerous cell) can be classified as PD-L1 positive. Accordingly, in some embodiments, a PD-1 antibody, e.g., a PD-1 antibody as described herein, (optionally in combination with one or more anti-cancer agents) is administered to a patient who has, or who is identified as having, a cancer that is PD-L1 positive. The cancer may be, e.g., non-small cell lung (NSCLC) adenocarcinoma (ACA), NSCLC squamous cell carcinoma (SCC), or hepatocellular carcinoma (HCC).

In some embodiments, the methods herein involve using an anti-PD-1 antibody, e.g., an anti-PD-1 antibody as described herein, e.g., as a monotherapy, for treating a cancer that is (or is identified as being) positive for PD-L1. In some embodiments, the cancer is colorectal cancer (e.g., MSI-high), gastric cancer (e.g., MSI-high and/or EBV+), NPC, cervical cancer, breast cancer (e.g., TN breast cancer), and ovarian cancer. In some embodiments, the cancer is NSCLC, melanoma, or HNSCC. In some embodiments, the anti-PD-1 antibody is administered at a dose of, e.g., 1, 3, 10, or 20 mg/kg. In other embodiments, the anti-PD-1 antibody molecule is administered at a dose of, e.g., 200, 250, 300, 350, 400, 450, or 500 mg. In one embodiment, anti-PD-1 antibody molecule is administered at a dose of 250 mg to 450 mg, e.g., 250 mg, 300 mg, 350 mg, 400 mg or 450 mg.

Based on, e.g., Example 4 herein, it was found that certain gastric cancers that are triple-positive for PD-L1/CD8/IFN-γ are also positive for PIK3CA. Accordingly, in some embodiments, a cancer can be treated with an anti-PD-1 antibody molecule (optionally in combination with one or more immunomodulators, e.g., an anti-LAG-3 antibody molecule, an anti-TIM-3 antibody molecule, or an anti-PD-L1 antibody molecule) and an agent that inhibits PIK3CA. Exemplary agents in this category are described in Stein RC (September 2001). "Prospects for phosphoinositide 3-kinase inhibition as a cancer treatment". Endocrine-related *Cancer* 8 (3): 237-48 and Marone R, Cmiljanovic V, Giese B, Wymann M P (January 2008). "Targeting phosphoinositide 3-kinase: moving towards therapy". *Biochimica et Biophysica Acta* 1784 (1): 159-85.

Based on, e.g., Example 4 herein, CRC, e.g., a patient that has (or is identified as having) MSI-high CRC may be treated with a PD-1 antibody, optionally in combination with a therapeutic that targets one or more of LAG-3, RNF43, and BRAF. For instance, these cancers may be treated with a PD-1 antibody, optionally in combination with one or more therapeutics that target one or more of LAG-3, PD-1, RNF43, and BRAF. In embodiments, the one or more therapeutics include an immunomodulators such as an anti-LAG-3 antibody molecule, and an anti-cancer agent described in Table 7 or a publication listed in Table 7. LAG-3 inhibitors, e.g., antibodies, are described herein. RNF43 can be inhibited, e.g., with an antibody, small molecule (e.g., 2-(2',3-dimethyl-[2,4'-bipyridin]-5-yl)-N-(5-(pyrazin-2-yl)pyridin-2-yl)acetamide (Compound A28)), siRNA, or a Rspo ligand or derivative thereof. BRAF inhibitors (e.g., vemurafenib or dabrafenib) are described herein.

Based on, e.g., Example 4 herein, a patient that has (or is identified as having) a squamous cell lung cancer may be treated with a PD-1 antibody molecule in combination with a therapeutic that targets LAG-3, e.g., a LAG-3 antibody molecule, and optionally with one or more anti-cancer agents, e.g., an anti-cancer agent described in Table 7 or in a publication in Table 7.

In some embodiments, a subject that has (or is identified as having) a squamous cell lung cancer may be treated with a PD-1 antibody, optionally in combination with a therapeutic that targets TIM-3, e.g., a TIM-3 antibody. TIM-3 inhibitors, e.g., antibodies, are described herein.

Based on, e.g., Example 4 herein, a patient that has (or is identified as having) a thyroid cancer (e.g., anaplastic thyroid carcinoma) may be treated with a PD-1 antibody molecule, optionally in combination with a therapeutic that targets BRAF, and optionally in combination with one or more immunomodulators, e.g., an anti-LAG-3 antibody molecule, an anti-TIM-3 antibody molecule, and an anti-PD-L1 antibody molecule. BRAF inhibitors (e.g., vemurafenib or dabrafenib) are described herein, e.g., in Table 7 and the publications listed in Table 7.

In some embodiments, the therapies here can be used to treat a patient that has (or is identified as having) a cancer associated with an infection, e.g., a viral or bacterial infection. Exemplary cancers include cervical cancer, anal cancer, HPV-associated head and neck squamous cell cancer, HPV-associated esophageal papillomas, HHV6-associated lymphomas, EBV-associated lymphomas (including Burkitt lymphoma), Gastric MALT lymphoma, other infection-associated MALT lymphomas, HCC, and Kaposi's sarcoma.

In other embodiments, the cancer is a hematological malignancy or cancer including but is not limited to a leukemia or a lymphoma. For example, the anti-PD-1 antibody molecule can be used to treat cancers and malignancies including, but not limited to, e.g., acute leukemias including but not limited to, e.g., B-cell acute lymphoid leukemia ("BALL"), T-cell acute lymphoid leukemia ("TALL"), acute lymphoid leukemia (ALL); one or more chronic leukemias including but not limited to, e.g., chronic myelogenous leukemia (CML), chronic lymphocytic leukemia (CLL); additional hematologic cancers or hematologic conditions including, but not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like.

In one embodiment, the cancer is chosen from a lung cancer (e.g., a non-small cell lung cancer (NSCLC) (e.g., a NSCLC with squamous and/or non-squamous histology, or a NSCLC adenocarcinoma)), a melanoma (e.g., an advanced melanoma), a renal cancer (e.g., a renal cell carcinoma, e.g., clear cell renal cell carcinoma), a liver cancer, a myeloma (e.g., a multiple myeloma), a prostate cancer, a breast cancer (e.g., a breast cancer that does not express one, two or all of estrogen receptor, progesterone receptor, or Her2/neu, e.g., a triple negative breast cancer), a colorectal cancer, a pancreatic cancer, a head and neck cancer (e.g., head and neck squamous cell carcinoma (HNSCC), anal cancer, gastroesophageal cancer, thyroid cancer (e.g., anaplastic thyroid carcinoma), cervical cancer, a lymphoproliferative disease (e.g., a post-transplant lymphoproliferative disease) or a hematological cancer, T-cell lymphoma, a non-Hodgkin's lymphoma, or a leukemia (e.g., a myeloid leukemia).

In another embodiment, the cancer is chosen form a carcinoma (e.g., advanced or metastatic carcinoma), melanoma or a lung carcinoma, e.g., a non-small cell lung carcinoma.

In one embodiment, the cancer is a lung cancer, e.g., a non-small cell lung cancer.

In another embodiment, the cancer is a hepatocarcinoma, e.g., an advanced hepatocarcinoma, with or without a viral infection, e.g., a chronic viral hepatitis.

In another embodiment, the cancer is a prostate cancer, e.g., an advanced prostate cancer.

In yet another embodiment, the cancer is a myeloma, e.g., multiple myeloma.

In yet another embodiment, the cancer is a renal cancer, e.g., a renal cell carcinoma (RCC) (e.g., a metastatic RCC, a non-clear cell renal cell carcinoma (nccRCC), or a clear cell renal cell carcinoma).

In one embodiment, the cancer is a melanoma, e.g., an advanced melanoma. In one embodiment, the cancer is an advanced or unresectable melanoma that does not respond to other therapies. In other embodiments, the cancer is a melanoma with a BRAF mutation (e.g., a BRAF V600 mutation). In some embodiments, the cancer (e.g., melanoma) is present in a subject having an elevated level of LDH in serum, compared to a reference serum LDH level. In yet other embodiments, the anti-PD-1 antibody molecule is administered after treatment with an anti-CTLA-4 antibody (e.g., ipilimumab) with or without a BRAF inhibitor (e.g., vemurafenib or dabrafenib). In one embodiment, the anti-PD-1 antibody molecule is administered with a BRAF inhibitor. For example, the anti-PD-1 antibody molecule can be administered at a dose between 200 mg and 600 mg (e.g., at a dose of 400 mg), e.g., once every 4 weeks or once every 8 weeks, e.g., intravenously, and the BRAF inhibitor or dabrafenib, can be administered at a dose between 50 mg and 250 mg (e.g., at a dose of 150 mg) twice a day, e.g., orally. In one embodiment, the combination further includes a MEK inhibitor or trametinib.

In one embodiment, the cancer is a colorectal cancer (CRC). Colorectal cancer is the third most common cancer in the world, with approximately 1.4 million people diagnosed in 2012, and the fourth most common cause of death from cancer, with 694,000 deaths (World Cancer Report 2014). Outcomes for patients with CRC are linked to the immune infiltrate in tumors, suggesting CRC can benefit from therapies that stimulate an immune response (Fridman et al. 2011 *Cancer Res.* p. 5601-5). Without wishing to be bound by theory, it is believed that in some embodiments, combination therapies can be more effective in treating colorectal cancer, e.g., outside the mismatch repair-deficient sub-population, when monotherapies are less effective (Kroemer et al. (2015) *OncoImmunology* 4:7, e1058597-1-3). For example, a combination of an inhibitor of PD-1 (e.g., an anti-PD-1 antibody molecule) and a second therapeutic agent described herein, can increase the response rate and/or durability of response, compared to a monotherapy (e.g., the inhibitor of PD-1 alone, or the second therapeutic agent alone).

In another embodiment, the cancer is a lung cancer, e.g., a non-small cell lung cancer (NSCLC). Lung cancer is the most common cancer in the world with approximately 1.8 million new cases in 2012, and the most common cause of death from cancer, with 1.6 million deaths (World Cancer Report 2014). Of these cases, approximately 85% are non-small cell lung cancer (NSCLC). Inhibitors of the PD-1/PD-L1 interaction are used for treating NSCLC. The response rate to these agents in an unselected patient population is approximately 20% after failure of first-line therapy (Gettinger and Herbst (2014) *Cancer J.* p. 281-9; Brahmer et al. (2012) *N. Engl. J. Med.* p. 123-35; Topalian et al. (2012) *N. Engl. J. Med.* p. 2443-54; Herbst et al. (2014) *Nature* p. 563-7; Borghaei et al. (2015)*N. Engl. J. Med.* p. 1627-39). In some embodiments, selection for expression of PD-L1 in tumors can enrich for response to PD-1/PD-L1 inhibitors. Without wishing to be bound by theory, it is believed that in some embodiments, combination therapies may be more effective in treating lung cancer (e.g., NSCLC), compared to monotherapies. For example, a combination of an inhibitor of PD-1 (e.g., an anti-PD-1 antibody molecule) and a second therapeutic agent described herein, can increase the response rate and/or durability of response (e.g., to broaden activity, deepen responses, and/or lead to more durable responses), compared to a monotherapy (e.g., the inhibitor of PD-1 alone, or the second therapeutic agent alone).

Breast cancer is the second most common cancer in the world with approximately 1.7 million new cases in 2012 and the fifth most common cause of death from cancer, with approximately 521,000 deaths (World Cancer Report). Of these cases, approximately 15% are triple-negative, which do not express the estrogen receptor (ER), progesterone receptor (PR) or HER2. As such, these patients generally do not benefit from targeted therapies available to patients with other breast cancer subtypes. Triple-negative breast cancer (TNBC) is an aggressive disease and outcomes after therapy are poor (Foulkes et al. (2010) *N. Engl. J. Med.* p. 1938-48). Recent data suggest that inhibitors of PD-1 are active in some patients, with responses reported in five of 27 patients treated with pembrolizumab with metastatic TNBC in the Keynote-012 study (Buisseret et al. (2015) *Annals of Oncology* 26(suppl_3): p. 6-9). Without wishing to be bound by theory, it is believed that in some embodiments, combination therapies may be more effective in treating breast cancer (e.g., TNBC), compared to monotherapies. For example, a combination of an inhibitor of PD-1 (e.g., an anti-PD-1 antibody molecule) and a second therapeutic agent described herein, can increase the response rate and/or durability of response (e.g., to increase the proportion of patients who respond to the treatment), compared to a monotherapy (e.g., the inhibitor of PD-1 alone, or the second therapeutic agent alone).

Methods and compositions disclosed herein are useful for treating metastatic lesions associated with the aforementioned cancers.

Combination Therapies

Exemplary non-limiting combinations and uses of the anti-PD-1 antibody molecules are disclosed in U.S. Patent Application Publication No. 2015/0210769 (U.S. Ser. No. 14/604,415), entitled "Antibody Molecules to PD-1 and Uses Thereof," incorporated by reference in its entirety.

In certain embodiments, the combination includes an anti-PD-1 antibody molecule in combination with a modulator of a costimulatory molecule or an inhibitory molecule, e.g., a co-inhibitory ligand or receptor.

In one embodiment, the anti-PD-1 antibody molecule is administered in combination with a modulator, e.g., agonist, of a costimulatory molecule. In one embodiment, the agonist of the costimulatory molecule is chosen from an agonist (e.g., an agonistic antibody or antigen-binding fragment thereof, or soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In another embodiment, the anti-PD-1 antibody molecule is used in combination with a costimulatory molecule, e.g., an agonist associated with a positive signal that includes a costimulatory domain of CD28, CD27, ICOS and GITR.

In one embodiment, the anti-PD-1 antibody molecule is administered in combination with an inhibitor of an inhibitory molecule of an immune checkpoint molecule. It will be understood by those of ordinary skill in the art, that the term "immune checkpoints" means a group of molecules on the cell surface of CD4 and CD8 T cells. These molecules can effectively serve as "brakes" to down-modulate or inhibit an anti-tumor immune response. Immune checkpoint molecules include, but are not limited to, Programmed Death 1 (PD-1), Cytotoxic T-Lymphocyte Antigen 4 (CTLA-4), B7H1, B7H4, OX-40, CD137, CD40, LAG-3 and TIM-3, which directly inhibit immune cells. Immunotherapeutic agents which can act as immune checkpoint inhibitors useful in the methods of the present invention, include, but are not limited to, inhibitors of PD-L1, PD-L2, CTLA-4, TIM-3, LAG-3, VISTA, BTLA, TIGIT, LAIR1, CD160, 2B4, CEACAM (e.g., CEACAM-1 and/or CEACAM-5), and/or TGF beta.

In one embodiment, the inhibitor is a soluble ligand (e.g., a CTLA-4-Ig or a TIM-3-Ig), or an antibody or antibody fragment that binds to PD-L1, PD-L2 or CTLA-4. For example, the anti-PD-1 antibody molecule can be administered in combination with an anti-CTLA-4 antibody, e.g., ipilimumab, for example, to treat a cancer (e.g., a cancer chosen from: a melanoma, e.g., a metastatic melanoma; a lung cancer, e.g., a non-small cell lung carcinoma; or a prostate cancer). Exemplary anti-CTLA-4 antibodies include Tremelimumab (IgG2 monoclonal antibody available from Pfizer, formerly known as ticilimumab, CP-675, 206); and Ipilimumab (CTLA-4 antibody, also known as MDX-010, CAS No. 477202-00-9). In one embodiment, the anti-PD-1 antibody molecule is administered after treatment, e.g., after treatment of a melanoma, with an anti-CTLA-4 antibody (e.g., ipilimumab) with or without a BRAF inhibitor (e.g., vemurafenib or dabrafenib). Exemplary doses that can be use include a dose of anti-PD-1 antibody molecule of about 1 to 10 mg/kg, e.g., 3 mg/kg, or 200 to 500 mg, e.g., 300 mg or 400 mg), and a dose of an anti-CTLA-4 antibody, e.g., ipilimumab, of about 3 mg/kg.

Immune inhibitory molecules, e.g., PD-1 and LAG-3, can regulate, e.g., synergistically regulate, T-cell function to promote tumoral immune escape. In another embodiment, the anti-PD-1 antibody molecule is administered in combination with an anti-LAG-3 antibody or an antigen-binding fragment thereof. In another embodiment, the anti-PD-1 antibody molecule is administered in combination with an anti-TIM-3 antibody or antigen-binding fragment thereof. In yet other embodiments, the anti-PD-1 antibody molecule is administered in combination with an anti-LAG-3 antibody and an anti-TIM-3 antibody, or antigen-binding fragments thereof. The combination of antibodies recited herein can be administered separately, e.g., as separate antibodies, or linked, e.g., as a bispecific or trispecific antibody molecule. In another embodiment, the anti-PD-1 antibody molecule is administered in combination with a CEACAM inhibitor (e.g., CEACAM-1, CEACAM-3, and/or CEACAM-5 inhibitor), e.g., an anti-CEACAM antibody molecule. In another embodiment, the anti-PD-1 antibody molecule is administered in combination with a CEACAM-1 inhibitor, e.g., an anti-CEACAM-1 antibody molecule. In another embodiment, the anti-PD-1 antibody molecule is administered in combination with a CEACAM-5 inhibitor, e.g., an anti-CEACAM-5 antibody molecule. In one embodiment, a bispecific antibody that includes an anti-PD-1 antibody molecule and an anti-TIM-3 or anti-LAG-3 antibody, or antigen-binding fragment thereof, is administered. In certain embodiments, the combination of antibodies recited herein is used to treat a cancer, e.g., a cancer as described herein (e.g., a solid tumor). The efficacy of the aforesaid combinations can be tested in animal models known in the art. For example, the animal models to test the synergistic effect of anti-PD-1 and anti-LAG-3 are described, e.g., in Woo et al. (2012) *Cancer Res.* 72(4):917-27.

In one embodiment, the inhibitor of CEACAM (e.g., CEACAM-1 and/or CEACAM-5) is an anti-CEACAM antibody molecule. Without wishing to be bound by theory, CEACAM-1 has been described as a ligand and partner of TIM-3 (see e.g., WO 2014/022332). Synergistic in vivo effect of the combination of anti-TIM-3 and anti-CEACAM-1 antibodies have been detected in xenograft cancer models (see e.g., WO 2014/022332). Tumors are believed to use CEACAM-1 or CEACAM-5 to inhibit the immune system, as described in, e.g., Markel et al. *J Immunol.* 2002 Mar. 15; 168(6):2803-10; Markel et al. *J Immunol.* 2006 Nov. 1; 177(9):6062-71; Markel et al. *Immunology.* 2009 February; 126(2): 186-200; Markel et al. *Cancer Immunol Immunother.* 2010 February; 59(2):215-30; Ortenberg et al. *Mol Cancer Ther.* 2012 June; 11(6):1300-10; Stern et al. *J Immunol.* 2005 Jun. 1; 174(11):6692-701; Zheng et al. *PLoS One.* 2010 Sep. 2; 5(9). pii: e12529. Thus, CEACAM inhibitors can be used with the other immunomodulators described herein (e.g., anti-PD-1 or anti-TIM-3 inhibitors) to enhance an immune response against a cancer, e.g., melanoma, lung cancer (e.g., NSCLC), bladder, colon or ovarian cancer, or other cancers as described herein. In one embodiment, the inhibitor of CEACAM is an anti-CEACAM-1 antibody as described in WO 2010/125571, WO 2013/82366 and WO 2014/022332, e.g., a monoclonal antibody 34B1, 26H7, and 5F4 or a recombinant form thereof, as described in, e.g., US 2004/0047858, U.S. Pat. No. 7,132,255 and WO 99/52552. In other embodiments, the anti-CEACAM antibody is an anti-CEACAM-1 and/or anti-CEACAM-5 antibody molecule as described in, e.g., WO 2010/125571, WO 2013/054331 and US 2014/0271618.

In some embodiments, the PD-1 and LAG-3 immune inhibitory molecules (e.g., antibody molecules) are administered in combination with each other, e.g., to treat cancer. In some embodiments, the patient is a patient who progressed (e.g., experienced tumor growth) during therapy with a PD-1 inhibitor (e.g., an antibody molecule as described herein) and/or a PD-L1 inhibitor (e.g., antibody molecule). In some embodiments, therapy with the PD-1 antibody molecule and/or PD-L1 antibody molecule is continued, and a LAG-3 immune inhibitory molecule (e.g., antibody) is added to the therapy.

In some embodiments, the PD-1 and TIM-3 immune inhibitory molecules (e.g., antibody molecules) are administered in combination with each other, e.g., to treat cancer. In some embodiments, the patient is a patient who progressed (e.g., experienced tumor growth) during therapy with a PD-1 inhibitor (e.g., an antibody molecule as described herein) and/or a PD-L1 inhibitor (e.g., antibody molecule). In some embodiments, therapy with the PD-1 antibody molecule and/or PD-L1 antibody molecule is continued, and a TIM-3 immune inhibitory molecule (e.g., antibody) is added to the therapy.

In other embodiments, the anti-PD-1 antibody molecule is administered in combination with a cytokine, e.g., interleukin-21, interleukin-2, interleukin-12, or interleukin-15. In certain embodiments, the combination of anti-PD-1 antibody molecule and cytokine described herein is used to treat a cancer, e.g., a cancer as described herein (e.g., a solid tumor or melanoma).

Exemplary immunomodulators that can be used in combination with anti-PD-1 antibody molecules include, but are not limited to, e.g., afutuzumab (available from Roche®); pegfilgrastim (Neulasta®); lenalidomide (CC-5013, Revlimid®); thalidomide (Thalomid®), actimid (CC4047); and cytokines, e.g., IL-21 or IRX-2 (mixture of human cytokines including interleukin 1, interleukin 2, and interferon γ, CAS 951209-71-5, available from IRX Therapeutics).

In yet other embodiments, the anti-PD-1 antibody molecule is used in combination with an indoleamine-pyrrole 2,3-dioxygenase (IDO) inhibitor (e.g., INCB24360) in a subject with advanced or metastatic cancer (e.g., a patient with metastic and recurrent NSCL cancer).

In other embodiments, the combinations disclosed herein, e.g., the combination comprising an anti-PD-1 antibody molecule, are administered to a subject in conjunction with (e.g., before, simultaneously or following) one or more of: bone marrow transplantation, T cell ablative therapy using chemotherapy agents such as, fludarabine, external-beam radiation therapy (XRT), cyclophosphamide, and/or antibodies such as OKT3 or CAMPATH. In one embodiment, the combinations, e.g., the combinations comprising an anti-PD-1 antibody molecule, are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive the combinations. In an additional embodiment, the combinations are administered before or following surgery.

Another example of a combination is an anti-PD-1 antibody in combination with decarbazine for the treatment of melanoma. Other combination therapies that may result in synergy with PD-1 blockade through cell death are radiation, surgery, and hormone deprivation. Each of these protocols creates a source of tumor antigen in the host. Angiogenesis inhibitors may also be combined with PD-1 blockade. Inhibition of angiogenesis leads to tumor cell death which may feed tumor antigen into host antigen presentation pathways.

Combinations that include PD-1 blocking antibodies can also be used in combination with bispecific antibodies. Bispecific antibodies can be used to target two separate antigens. For example anti-Fc receptor/anti-tumor antigen (e.g., Her-2/neu) bispecific antibodies have been used to target macrophages to sites of tumor. This targeting may more effectively activate tumor specific responses. The T cell arm of these responses would be augmented by the use of PD-1 blockade. Alternatively, antigen may be delivered directly to DCs by the use of bispecific antibodies which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al. (1986) *J. Exp. Med.* 163: 1037-1050), IL-10 (Howard, M. & O'Garra, A. (1992) *Immunology Today* 13: 198-200), and Fas ligand (Hahne, M. et al. (1996) *Science* 274: 1363-1365). Compositions disclosed herein that include anti-PD-1 antibodies can counteract the effects of the immunosuppressive agent and favor tumor immune responses by the host.

Other antibodies which may be used to activate host immune responsiveness can be used in the combinations herein further in combination with an anti-PD-1 antibody molecule, e.g., an anti-PD-1 antibody molecule as described herein. These include molecules on the surface of dendritic cells which activate DC function and antigen presentation. Anti-CD40 antibodies are able to substitute effectively for T cell helper activity (Ridge, J. et al. (1998) *Nature* 393: 474-478) and can be used in conjunction with PD-1 antibodies (Ito, N. et al. (2000) *Immunobiology* 201 (5) 527-40). Antibodies to T cell costimulatory molecules such as CTLA-4 (e.g., U.S. Pat. No. 5,811,097), OX-40 (Weinberg, A. et al. (2000) *Immunol* 164: 2160-2169), 4-1BB (Melero, I. et al. (1997) *Nature Medicine* 3: 682-685 (1997), and ICOS (Hutloff, A. et al. (1999) *Nature* 397: 262-266) may also provide for increased levels of T cell activation.

Additional exemplary standard of care treatments are described in the section entitled "Combination Therapies" in U.S. Patent Application Publication No. 2015/0210769 (U.S. Ser. No. 14/604,415), entitled "Antibody Molecules to PD-1 and Uses Thereof," incorporated by reference in its entirety, and below.

In all of the methods described herein, PD-1 blockade can be combined with other forms of immunotherapy such as cytokine treatment (e.g., interferons, GM-CSF, G-CSF, IL-2, IL-21), or bispecific antibody therapy, which provides for enhanced presentation of tumor antigens (see e.g., Holliger (1993) *Proc. Natl. Acad. Sci. USA* 90:6444-6448; Poljak (1994) *Structure* 2:1121-1123).

Methods of administering the antibody molecules are known in the art and are described below. Suitable dosages of the molecules used will depend on the age and weight of the subject and the particular drug used. Dosages and therapeutic regimens of the anti-PD-1 antibody molecule can be determined by a skilled artisan. In certain embodiments, the anti-PD-1 antibody molecule is administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg. In some embodiments, the anti-PD-1 antibody molecule is administered at a dose of about 1 mg/kg, about 3 mg/kg, about 5 mg/kg, about 10 mg/kg, about 20 mg/kg, about 30 mg/kg, or about 40 mg/kg. In some embodiments, the anti-PD-1 antibody molecule is administered at a dose of about 1-3 mg/kg, or about 3-10 mg/kg. In some embodiments, the anti-PD-1 antibody molecule is administered at a dose of about 0.5-2, 2-4, 2-5, 5-15, or 5-20 mg/kg. The dosing schedule can vary from e.g., once a week to once every 2, 3, or 4 weeks. In one embodiment, the anti-PD-1 antibody molecule is administered at a dose from about 10 to 20 mg/kg every other week. In another embodiment, the anti-PD-1 antibody molecule is administered at a dose of about 1 mg/kg once every two weeks, about 3 mg/kg once every two weeks, 10 mg/kg once every two weeks, 3 mg/kg once every four weeks, or 5 mg/kg once every four weeks.

In other embodiments, the anti-PD-1 antibody molecule is administered by injection (e.g., subcutaneously or intravenously) at a dose (e.g., a flat dose) of about 200 mg to 500 mg, e.g., about 250 mg to 450 mg, about 300 mg to 400 mg, about 250 mg to 350 mg, about 350 mg to 450 mg, or about 300 mg or about 400 mg. In some embodiments, the anti-PD-1 antibody molecule is administered at a dose of about 200 mg, 250 mg, 300 mg, 350 mg, 400 mg, 450 mg, or 500 mg. In some embodiments, the anti-PD-1 antibody molecule is administered at a dose of about 250-450 mg, or about 300-400 mg. In some embodiments, the anti-PD-1 antibody molecule is administered at a dose of about 200-300 mg, 250-350 mg, 300-400 mg, 350-450 mg, or 400-500 mg. The dosing schedule can vary from e.g., once a week to once every 2, 3, 4, 5, or 6 weeks. In one embodiment the anti-PD-1 antibody molecule is administered at a dose from about 300 mg to 400 mg once every three or once every four weeks. In one embodiment, the anti-PD-1 antibody molecule is administered at a dose from about 300 mg once every three weeks. In one embodiment, the anti-PD-1 antibody molecule is administered at a dose from about 400 mg once every four weeks. In one embodiment, the anti-PD-1 antibody molecule is administered at a dose from about 300 mg once every four weeks. In one embodiment, the anti-PD-1 antibody molecule is administered at a dose from about 400 mg once every three weeks.

The antibody molecules can be used in unconjugated forms or conjugated to a second agent, e.g., a cytotoxic drug, radioisotope, or a protein, e.g., a protein toxin or a viral protein. This method includes: administering the antibody molecule, alone or conjugated to a cytotoxic drug, to a subject requiring such treatment. The antibody molecules can be used to deliver a variety of therapeutic agents, e.g., a cytotoxic moiety, e.g., a therapeutic drug, a radioisotope, molecules of plant, fungal, or bacterial origin, or biological proteins (e.g., protein toxins) or particles (e.g., a recombinant viral particles, e.g., via a viral coat protein), or mixtures thereof.

Additional Combination Therapies

The combinations disclosed herein, e.g., the combination comprising PD-1 blocking agents, may also be combined with a standard cancer treatment, e.g., chemotherapeutic regimes. In these instances, it may be possible to reduce the dose of chemotherapeutic reagent administered (Mokyr, M. et al. (1998) *Cancer Research* 58: 5301-5304). In certain embodiments, the methods and compositions described herein are administered in combination with one or more of other antibody molecules, chemotherapy, other anti-cancer therapy (e.g., targeted anti-cancer therapies, or oncolytic drugs), cytotoxic agents, immune-based therapies (e.g., cytokines), surgical and/or radiation procedures. Exemplary cytotoxic agents that can be administered in combination with include antimicrotubule agents, topoisomerase inhibitors, anti-metabolites, mitotic inhibitors, alkylating agents, anthracyclines, vinca alkaloids, intercalating agents, agents capable of interfering with a signal transduction pathway, agents that promote apoptosis, proteosome inhibitors, and radiation (e.g., local or whole body irradiation).

Alternatively, or in combination with the aforesaid combinations, the methods and compositions described herein can be administered in combination with one or more of: an immunomodulator (e.g., an activator of a costimulatory molecule or an inhibitor of an inhibitory molecule); a vaccine, e.g., a therapeutic cancer vaccine; or other forms of cellular immunotherapy.

Exemplary combinations, e.g., combinations comprising anti-PD-1 antibody molecules and standard of care for cancer, are disclosed in U.S. Patent Application Publication No. 2015/0210769 (U.S. Ser. No. 14/604,415), entitled "Antibody Molecules to PD-1 and Uses Thereof," incorporated by reference in its entirety, including, but not limited to, alkylating agents, anthracyclines, *vinca* alkaloids, proteosome inhibitors, and tyrosine kinase inhibitors (e.g., a receptor tyrosine kinase (RTK) inhibitor).

Exemplary tyrosine kinase inhibitor include, but are not limited to, an epidermal growth factor (EGF) pathway inhibitor (e.g., an epidermal growth factor receptor (EGFR) inhibitor), a vascular endothelial growth factor (VEGF) pathway inhibitor (e.g., a vascular endothelial growth factor receptor (VEGFR) inhibitor (e.g., a VEGFR-1 inhibitor, a VEGFR-2 inhibitor, a VEGFR-3 inhibitor)), a platelet derived growth factor (PDGF) pathway inhibitor (e.g., a platelet derived growth factor receptor (PDGFR) inhibitor (e.g., a PDGFR-β inhibitor)), a RAF-1 inhibitor, a KIT inhibitor and a RET inhibitor. Selected tyrosine kinase inhibitors are chosen from sunitinib, erlotinib, gefitinib, or sorafenib. Sorafinib is also known as 4-[4-[[4-chloro-3-(trifluoromethyl)phenyl]carbamoylamino]phenoxy]-N-methyl-pyridine-2-carboxamide. In certain embodiments, the combination includes sorafenib, e.g., to treat a cancer described herein, e.g., a liver cancer (e.g., a hepatocellular carcinoma).

In certain embodiments, combinations include Vascular Endothelial Growth Factor (VEGF) receptor inhibitors, e.g., a VEGFR inhibitor as described herein.

In some embodiments, the combination includes a PI3K inhibitor, e.g., a PI3K inhibitor as described herein.

In some embodiments, the combination includes an mTOR inhibitor, e.g., an mTOR inhibitor as described herein.

In some embodiments, the combination includes a BRAF inhibitor, e.g., GSK2118436, RG7204, PLX4032, GDC-0879, PLX4720, and sorafenib tosylate (Bay 43-9006). In some embodiments, the combination includes a RAF inhibitor, e.g., debrafinib or N-{3-[5-(2-aminopyrimidin-4-yl)-2-tert-butyl-1,3-thiazol-4-yl]-2-fluorophenyl}-2,6-difluorobenzenesulfonamide.

In some embodiments, the combination includes a MEK inhibitor. In some embodiments, the cancer treated with the combination is chosen from a melanoma, a colorectal cancer, a non-small cell lung cancer, an ovarian cancer, a breast cancer (e.g., a triple negative breast cancer (TNBC), a prostate cancer, a pancreatic cancer, a hematological malignancy or a renal cell carcinoma. In certain embodiments, the cancer includes a BRAF mutation (e.g., a BRAF V600E mutation), a BRAF wildtype, a KRAS wildtype or an activating KRAS mutation. The cancer may be at an early, intermediate or late stage. In one embodiment, the cancer treated with the combination is an unresectable or metastatic melanoma, e.g., having a BRAFV600 mutation. In certain embodiments, the cancer is chosen from a colorectal cancer (e.g., a microsatellite stable colorectal cancer (MSS CRC), a lung cancer (e.g., a non-small cell lung cancer), or a breast cancer (e.g., a triple negative lung cancer (TNBC)).

Any MEK inhibitor can be used in combination including, but not limited to, ARRY-142886, G02442104 (also known as GSK1120212), RDEA436, RDEA119/BAY 869766, AS703026, G00039805 (also known as AZD-6244 or selumetinib), BIX 02188, BIX 02189, CI-1040 (PD-184352), PD0325901, PD98059, U0126, GDC-0973 (Methanone, [3,4-difluoro-2-[(2-fluoro-4-iodophenyl)amino]phenyl][3-hydroxy-3-(25)-2-piperidinyl-1-azetidinyl]-), G-38963, G02443714 (also known as AS703206), or a pharmaceutically acceptable salt or solvate thereof. Additional examples of MEK inhibitors are disclosed in WO 2013/019906, WO 03/077914, WO 2005/121142, WO 2007/04415, WO 2008/024725 and WO 2009/085983, the contents of which are incorporated herein by reference.

In some embodiments, the MEK inhibitor is trametinib or N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H)-yl}phenyl)acetamide.

In some embodiments, the MEK inhibitor or trametinib is a reversible and highly selective allosteric inhibitor of MEK1 and MEK2. MEK proteins are important components of the MAPK pathway which is commonly hyperactivated in tumor cells. Oncogenic mutations in both BRAF (a member of the RAF kinases) and RAS signal through MEK1 or MEK2. Without wishing to be bound by theory, it is believed that in some embodiments, a MEK inhibitor, e.g., trametinib, can increase CD4+ and CD8+ tumor infiltrating lymphocytes (TILs) and/or increase the efficacy of a PD-1 inhibitor (Liu et al. (2014) *Clin. Cancer Res.* p. 462-8).

In some embodiments, the combination described herein includes a MEK inhibitor or trametinib, and an inhibitor of an immune checkpoint molecule, e.g., an inhibitor of PD-1 (e.g., an anti-PD-1 antibody molecule).

MAPK pathway signaling is important for tumor growth (Downward (2003) *Nat. Rev. Cancer.* p. 11-22) and trametinib is efficacious as monotherapy and in combination with dabrafenib for the treatment of BRAFV600 mutant melanoma. Trametinib achieves MEK inhibition in tumor cells at exposures achieved at the approved dose of 2 mg p.o. once a day (QD) (Infante et al. (2012) *Lancet Oncol.* p. 773-81). Pre-clinical data in the CT26 mouse syngeneic model demonstrates that the combination of trametinib and anti-PD-L1 antibody results in increased TILs, decreased tumor growth and prolongation of survival (Liu et al. (2015) *Clin. Cancer Res.* p. 1639-51). The immunomodulatory effects of trametinib in combination with checkpoint inhibitor antibodies have been investigated in the CT26 murine syngeneic model in vivo. For example, trametinib increases the numbers of tumor infiltrating lymphocytes (TILs), and trametinib potentiates the anti-tumor effects of anti-PD-1 antibody, anti-PD-L1 antibody, and anti-CTLA-4 antibody treatment. Using this model, mice were treated with control, trametinib, anti-PD-1 antibody or the combination of trametinib and anti-PD-1 antibody for seven days and then the tumors were harvested. Treatment with either trametinib or trametinib and anti-PD-1 antibody for seven days resulted in significant increases of CD4+ T cells in tumor tissue. Only treatment with the combination of trametinib and anti-PD-1 antibody resulted in significant increases in CD8+ T cells. In addition, in the CT26 murine model, the combination of trametinib and anti-PD-1 antibody was more effective in inhibiting tumor growth than either single agent. Treatment with the combination also prolonged survival. The schedule of drug administration can be important. Tumor growth was inhibited when trametinib and anti-PD-1 antibody were administered concurrently, or when trametinib was first given as single agent for 7 days prior to combination treatment. Tumor growth was not inhibited when the antibody was given first followed by combination therapy, indicating that the schedule of drug administration can be important. In some embodiments, the MEK inhibitor or trametinib enhances, or is used to enhance, an anti-tumor effect of the inhibitor of PD-1 (e.g., the anti-PD-1 antibody molecule).

In some embodiments, the MEK inhibitor or trametinib, and the inhibitor of an immune checkpoint molecule, e.g., an inhibitor of PD-1 (e.g., an anti-PD-1 antibody molecule), each is administered at a dose and/or on a time schedule, that in combination, achieves a desired anti-tumor activity.

In one embodiment, the MEK inhibitor or trametinib is administered at a dose between 0.2 mg and 5 mg, e.g., between 0.3 mg and 4 mg, between 0.4 mg and 3 mg, between 0.5 mg and 2 mg, between 1 mg and 1.5 mg, between 1.5 mg and 2 mg, or between 0.4 mg and 0.6 mg, e.g., at a dose of 0.2 mg, 0.5 mg, 1 mg, 1.5 mg, 2 mg, 2.5 mg, 3 mg, 4 mg, or 5 mg, e.g., twice a day, once a day, once every two days, once every three days, or once a week.

In one embodiment, the MEK inhibitor or trametinib is administered at a dose between 0.4 mg and 0.6 mg (e.g., at a dose of 0.5 mg) once a day. In another embodiment, the MEK inhibitor or trametinib is administered at a dose between 1 mg and 3 mg (e.g., at a dose of 2 mg) once a day. In some embodiments, the MEK inhibitor or trametinib, is administered is administered orally. In one embodiment, the MEK inhibitor or trametinib is administered at a dose between 0.4 mg and 0.6 mg (e.g., at a dose of 0.5 mg), e.g., once a day, e.g., orally, and the PD-1 inhibitor (e.g., the anti-PD-1 antibody molecule) is administered at a dose between 300 mg and 500 mg (e.g., a dose of 400 mg), e.g., once every 4 weeks, e.g., by intravenous infusion. In one embodiment, the MEK inhibitor or trametinib is administered at a dose between 1 mg and 3 mg (e.g., at a dose of 2 mg), e.g., once a day, e.g., orally, and the PD-1 inhibitor (e.g., the anti-PD-1 antibody molecule) is administered at a dose between 300 mg and 500 mg (e.g., a dose of 400 mg), e.g., once every 4 weeks or once every 8 weeks, e.g., by intravenous infusion.

In one embodiment, the MEK inhibitor or trametinib, is administered in combination with the PD-1 inhibitor (e.g., the anti-PD-1 antibody molecule) to treat a melanoma (e.g., a metastatic or unresectable melanoma), a colorectal cancer (CRC), a lung cancer (e.g., non-small cell lung cancer (NSCLC)), or a breast cancer (e.g., a triple negative breast cancer (TNBC)). In certain embodiments, the melanoma has a BRAF mutation, e.g., a BRAF V600 mutation. In some embodiments, the combination further includes a BRAF inhibitor, e.g., dabrafenib. In some embodiments, the combination is used to treat a subject having an elevated level of LDH in serum, compared to a reference serum LDH level.

In some embodiments, the combination includes a JAK2 inhibitor, e.g., CEP-701, INCB18424, CP-690550 (tasocitinib).

In some embodiments, the combination includes paclitaxel or a paclitaxel agent, e.g., TAXOL®, protein-bound paclitaxel (e.g., ABRAXANE®).

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy.

The combinations disclosed can be administered in combination with one or more of the existing modalities for treating cancers, including, but not limited to: surgery; radiation therapy (e.g., external-beam therapy which involves three dimensional, conformal radiation therapy where the field of radiation is designed, local radiation (e.g., radiation directed to a preselected target or organ), or focused radiation). Focused radiation can be selected from the group consisting of stereotactic radiosurgery, fractionated stereotactic radiosurgery, and intensity-modulated radiation therapy. The focused radiation can have a radiation source selected from the group consisting of a particle beam (proton), cobalt-60 (photon), and a linear accelerator (x-ray), e.g., as described in WO 2012/177624.

In certain embodiments, the combinations include an antibody against a Killer-cell Immunoglobulin-like Receptors (also referred to herein as an "anti-KIR antibody"), a pan-KIR antibody, an anti-NKG2D antibody, and an anti-MICA antibody. In certain embodiments, the combination of anti-PD-1 antibody molecule and anti-KIR antibody, pan-KIR antibody, or an anti-NKG2D antibody described herein is used to treat a cancer, e.g., a cancer as described herein (e.g., a solid tumor, e.g., an advanced solid tumor).

In one embodiment, the combination includes a cellular immunotherapy (e.g., Provenge (e.g., Sipuleucel)), and optionally in combination with cyclophosphamide. In certain embodiments, the combination of anti-PD-1 antibody molecule, Provenge and/or cyclophosphamide is used to treat a cancer, e.g., a cancer as described herein (e.g., a prostate cancer, e.g., an advanced prostate cancer).

In another embodiment, the combination includes a vaccine, e.g., a dendritic cell renal carcinoma (DC-RCC) vaccine. In certain embodiments, the combination of anti-PD-1 antibody molecule and the DC-RCC vaccine is used to treat a cancer, e.g., a cancer as described herein (e.g., a renal carcinoma, e.g., metastatic renal cell carcinoma (RCC) or clear cell renal cell carcinoma (CCRCC)).

In yet another embodiment, the anti-PD-1 antibody molecule, alone or in combination with another immunomodulator (e.g., an anti-LAG-3, anti-PD-L1 or anti-TIM-3 antibody molecule), is administered in combination with chemotherapy, and/or immunotherapy. For example, the anti-PD-1 antibody molecule can be used to treat a myeloma, alone or in combination with one or more of: chemotherapy or other anti-cancer agents (e.g., thalidomide analogs, e.g., lenalidomide), an anti-TIM-3 antibody, tumor antigen-pulsed dendritic cells, fusions (e.g., electrofusions) of tumor cells and dendritic cells, or vaccination with immunoglobulin idiotype produced by malignant plasma cells. In one embodiment, the anti-PD-1 antibody molecule is used in combination with an anti-TIM-3 antibody to treat a myeloma, e.g., a multiple myeloma.

In one embodiment, the anti-PD-1 antibody molecule, alone or in combination with another immunomodulator (e.g., an anti-LAG-3, anti-PD-L1 or anti-TIM-3 antibody molecule), is used in combination with chemotherapy to treat a lung cancer, e.g., non-small cell lung cancer. In one embodiment, the anti-PD-1 antibody molecule is used with platinum doublet therapy to treat lung cancer.

In yet another embodiment, the anti-PD-1 antibody molecule, alone or in combination with another immunomodulator (e.g., an anti-LAG-3, anti-PD-L1 or anti-TIM-3 antibody molecule), is used to treat a renal cancer, e.g., renal cell carcinoma (RCC) (e.g., clear cell renal cell carcinoma (CCRCC), a non-clear cell renal cell carcinoma (nccRCC), or metastatic RCC. The anti-PD-1 antibody molecule can be administered in combination with one or more of: an immune-based strategy (e.g., interleukin-2 or interferon-α), a targeted agent (e.g., a VEGF inhibitor such as a monoclonal antibody to VEGF); a VEGF tyrosine kinase inhibitor such as sunitinib, sorafenib, axitinib and pazopanib; an RNAi inhibitor), or an inhibitor of a downstream mediator of VEGF signaling, e.g., an inhibitor of the mammalian target of rapamycin (mTOR), e.g., everolimus and temsirolimus. In certain embodiments, the combination includes sorafenib, e.g., to treat a cancer described herein, e.g., a liver cancer (e.g., a hepatocellular carcinoma).

An example of suitable therapeutics for use in combination with the anti-PD-1 antibody molecules described herein, alone or in combination with another immunomodulator (e.g., an anti-LAG-3, anti-PD-L1 or anti-TIM-3 antibody molecule), for treatment of pancreatic cancer includes, but is not limited to, a chemotherapeutic agent, e.g., paclitaxel or a paclitaxel agent (e.g., a paclitaxel formulation such as TAXOL, an albumin-stabilized nanoparticle paclitaxel formulation (e.g., ABRAXANE) or a liposomal paclitaxel formulation); gemcitabine (e.g., gemcitabine alone or in combination with AXP107-11); other chemotherapeutic agents such as oxaliplatin, 5-fluorouracil, capecitabine, rubitecan, epirubicin hydrochloride, NC-6004, cisplatin, docetaxel (e.g., TAXOTERE), mitomycin C, ifosfamide; interferon; tyrosine kinase inhibitor (e.g., EGFR inhibitor (e.g., erlotinib, panitumumab, cetuximab, nimotuzumab); HER2/neu receptor inhibitor (e.g., trastuzumab); dual kinase inhibitor (e.g., bosutinib, saracatinib, lapatinib, vandetanib); multikinase inhibitor (e.g., sorafenib, sunitinib, XL184, pazopanib); VEGF inhibitor (e.g., bevacizumab, AV-951, brivanib); radioimmunotherapy (e.g., XR303); cancer vaccine (e.g., GVAX, survivin peptide); COX-2 inhibitor (e.g., celecoxib); IGF-1 receptor inhibitor (e.g., AMG 479, MK-0646); mTOR inhibitor (e.g., everolimus, temsirolimus); IL-6 inhibitor (e.g., CNTO 328); cyclin-dependent kinase inhibitor (e.g., P276-00, UCN-01); Altered Energy Metabolism-Directed (AEMD) compound (e.g., CPI-613); HDAC inhibitor (e.g., vorinostat); TRAIL receptor 2 (TR-2) agonist (e.g., conatumumab); MEK inhibitor (e.g., AS703026, selumetinib, GSK1120212); Raf/MEK dual kinase inhibitor (e.g., RO5126766); Notch signaling inhibitor (e.g., MK0752); monoclonal antibody-antibody fusion protein (e.g., L19IL2); curcumin; HSP90 inhibitor (e.g., tanespimycin, STA-9090); rIL-2; denileukin diftitox; topoisomerase 1 inhibitor (e.g., irinotecan, PEP02); statin (e.g., simvastatin); Factor VIIa inhibitor (e.g., PCI-27483); AKT inhibitor (e.g., RX-0201); hypoxia-activated prodrug (e.g., TH-302); metformin hydrochloride, gamma-secretase inhibitor (e.g., RO4929097); ribonucleotide reductase inhibitor (e.g., 3-AP); immunotoxin (e.g., HuC242-DM4); PARD inhibitor (e.g., KU-0059436, veliparib); CTLA-4 inhibitor (e.g., CP-675,206, ipilimumab); AdV-tk therapy; proteasome inhibitor (e.g., bortezomib (Velcade), NPI-0052); thiazolidinedione (e.g., pioglitazone); NPC-1C; Aurora kinase inhibitor (e.g., R763/AS703569), CTGF inhibitor (e.g., FG-3019); siG12D LODER; and radiation therapy (e.g., tomotherapy, stereotactic radiation, proton therapy), surgery, and a combination thereof. In certain embodiments, a combination of paclitaxel or a paclitaxel agent, and gemcitabine can be used with the anti-PD-1 antibody molecules described herein.

An example of suitable therapeutics for use in combination with the anti-PD-1 antibody molecules, alone or in combination with another immunomodulator (e.g., an anti-LAG-3, anti-PD-L1 or anti-TIM-3 antibody molecule), for treatment of small cell lung cancer includes, but is not limited to, a chemotherapeutic agent, e.g., etoposide, carboplatin, cisplatin, oxaliplatin, irinotecan, topotecan, gemcitabine, liposomal SN-38, bendamustine, temozolomide, belotecan, NK012, FR901228, flavopiridol); tyrosine kinase inhibitor (e.g., EGFR inhibitor (e.g., erlotinib, gefitinib, cetuximab, panitumumab); multikinase inhibitor (e.g., sorafenib, sunitinib); VEGF inhibitor (e.g., bevacizumab, vandetanib); cancer vaccine (e.g., GVAX); Bcl-2 inhibitor (e.g., oblimersen sodium, ABT-263); proteasome inhibitor (e.g., bortezomib (Velcade), NPI-0052), paclitaxel or a paclitaxel agent; docetaxel; IGF-1 receptor inhibitor (e.g., AMG 479); HGF/SF inhibitor (e.g., AMG 102, MK-0646); chloroquine; Aurora kinase inhibitor (e.g., MLN8237); radioimmunotherapy (e.g., TF2); HSP90 inhibitor (e.g., tanespimycin, STA-9090); mTOR inhibitor (e.g., everolimus); Ep-CAM-/CD3-bispecific antibody (e.g., MT110); CK-2 inhibitor (e.g., CX-4945); HDAC inhibitor (e.g., belinostat); SMO antagonist (e.g., BMS 833923); peptide cancer vaccine, and radiation therapy (e.g., intensity-modulated radiation therapy (IMRT), hypofractionated radiotherapy, hypoxia-guided radiotherapy), surgery, and combinations thereof.

An example of suitable therapeutics for use in combination with the anti-PD-1 antibody molecules, alone or in combination with another immunomodulator (e.g., an anti-LAG-3, anti-PD-L1 or anti-TIM-3 antibody molecule), for treatment of non-small cell lung cancer includes, but is not limited to, a chemotherapeutic agent, e.g., vinorelbine, cisplatin, docetaxel, pemetrexed disodium, etoposide, gemcitabine, carboplatin, liposomal SN-38, TLK286, temozolomide, topotecan, pemetrexed disodium, azacitidine, irinotecan, tegafur-gimeracil-oteracil potassium, sapacitabine; tyrosine kinase inhibitor (e.g., EGFR inhibitor (e.g., erlotinib, gefitinib, cetuximab, panitumumab, necitumumab, PF-00299804, nimotuzumab, RO5083945), MET inhibitor (e.g., PF-02341066, ARQ 197), PI3K kinase inhibitor (e.g., XL147, GDC-0941), Raf/MEK dual kinase inhibitor (e.g., RO5126766), PI3K/mTOR dual kinase inhibitor (e.g., XL765), SRC inhibitor (e.g., dasatinib), dual inhibitor (e.g., BIBW 2992, GSK1363089, ZD6474, AZD0530, AG-013736, lapatinib, MEHD7945A, linifanib), multikinase inhibitor (e.g., sorafenib, sunitinib, pazopanib, AMG 706, XL184, MGCD265, BMS-690514, R935788), VEGF inhibitor (e.g., endostar, endostatin, bevacizumab, cediranib, BIBF 1120, axitinib, tivozanib, AZD2171), cancer vaccine (e.g., BLP25 liposome vaccine, GVAX, recombinant DNA and adenovirus expressing L523S protein), Bcl-2 inhibitor (e.g., oblimersen sodium), proteasome inhibitor (e.g., bortezomib, carfilzomib, NPI-0052, MLN9708), paclitaxel or a paclitaxel agent, docetaxel, IGF-1 receptor inhibitor (e.g., cixutumumab, MK-0646, OSI 906, CP-751,871, BIIB022), hydroxychloroquine, HSP90 inhibitor (e.g., tanespimycin, STA-9090, AUY922, XL888), mTOR inhibitor (e.g., everolimus, temsirolimus, ridaforolimus), Ep-CAM-/CD3-bispecific antibody (e.g., MT110), CK-2 inhibitor (e.g., CX-4945), HDAC inhibitor (e.g., MS 275, LBH589, vorinostat, valproic acid, FR901228), DHFR inhibitor (e.g., pralatrexate), retinoid (e.g., bexarotene, tretinoin), antibody-drug conjugate (e.g., SGN-15), bisphosphonate (e.g., zoledronic acid), cancer vaccine (e.g., belagenpumatucel-L), low molecular weight heparin (LMWH) (e.g., tinzaparin, enoxaparin), GSK1572932A, melatonin, talactoferrin, dimesna, topoisomerase inhibitor (e.g., amrubicin, etoposide, karenitecin), nelfinavir, cilengitide, ErbB3 inhibitor (e.g., MM-121, U3-1287), survivin inhibitor (e.g., YM155, LY2181308), eribulin mesylate, COX-2 inhibitor (e.g., celecoxib), pegfilgrastim, Polo-like kinase 1 inhibitor (e.g., BI 6727), TRAIL receptor 2 (TR-2) agonist (e.g., CS-1008), CNGRC peptide (SEQ ID NO: 225)-TNF alpha conjugate, dichloroacetate (DCA), HGF inhibitor (e.g., SCH 900105), SAR240550, PPAR-gamma agonist (e.g., CS-7017), gamma-secretase inhibitor (e.g., RO4929097), epigenetic therapy (e.g., 5-azacitidine), nitroglycerin, MEK inhibitor (e.g., AZD6244), cyclin-dependent kinase inhibitor (e.g., UCN-01), cholesterol-Fus1, antitubulin agent (e.g., E7389), farnesyl-OH-transferase inhibitor (e.g., lonafarnib), immunotoxin (e.g., BB-10901, SS1 (dsFv) PE38), fondaparinux, vascular-disrupting agent (e.g., AVE8062), PD-L1 inhibitor (e.g., MDX-1105, MDX-1106), beta-glucan, NGR-hTNF, EMD 521873, MEK inhibitor (e.g., GSK1120212), epothilone analog (e.g., ixabepilone), kinesin-spindle inhibitor (e.g., 4SC-205), telomere targeting agent (e.g., KML-001), P70 pathway inhibitor (e.g., LY2584702), AKT inhibitor (e.g., MK-2206), angiogenesis inhibitor (e.g., lenalidomide), Notch signaling inhibitor (e.g., OMP-21M18), radiation therapy, surgery, and combinations thereof.

An example of suitable therapeutics for use in combination with the anti-PD-1 antibody molecules, alone or in combination with another immunomodulator (e.g., an anti-LAG-3, anti-PD-L1 or anti-TIM-3 antibody molecule), for treatment of ovarian cancer includes, but is not limited to, a chemotherapeutic agent (e.g., paclitaxel or a paclitaxel agent; docetaxel; carboplatin; gemcitabine; doxorubicin; topotecan; cisplatin; irinotecan, TLK286, ifosfamide, olaparib, oxaliplatin, melphalan, pemetrexed disodium, SJG-136, cyclophosphamide, etoposide, decitabine); ghrelin antagonist (e.g., AEZS-130), immunotherapy (e.g., APC8024, oregovomab, OPT-821), tyrosine kinase inhibitor (e.g., EGFR inhibitor (e.g., erlotinib), dual inhibitor (e.g., E7080), multikinase inhibitor (e.g., AZD0530, JI-101, sorafenib, sunitinib, pazopanib), ON 01910.Na), VEGF inhibitor (e.g., bevacizumab, BIBF 1120, cediranib, AZD2171), PDGFR inhibitor (e.g., IMC-3G3), paclitaxel, topoisomerase inhibitor (e.g., karenitecin, Irinotecan), HDAC inhibitor (e.g., valproate, vorinostat), folate receptor inhibitor (e.g., farletuzumab), angiopoietin inhibitor (e.g., AMG 386), epothilone analog (e.g., ixabepilone), proteasome inhibitor (e.g., carfilzomib), IGF-1 receptor inhibitor (e.g., OSI 906, AMG 479), PARP inhibitor (e.g., veliparib, AG014699, iniparib, MK-4827), Aurora kinase inhibitor (e.g., MLN8237, ENMD-2076), angiogenesis inhibitor (e.g., lenalidomide), DHFR inhibitor (e.g., pralatrexate), radioimmunotherapeutic agent (e.g., Hu3S193), statin (e.g., lovastatin), topoisomerase 1 inhibitor (e.g., NKTR-102), cancer vaccine (e.g., p53 synthetic long peptides vaccine, autologous OC-DC vaccine), mTOR inhibitor (e.g., temsirolimus, everolimus), BCR/ABL inhibitor (e.g., imatinib), ET-A receptor antagonist (e.g., ZD4054), TRAIL receptor 2 (TR-2) agonist (e.g., CS-1008), HGF/SF inhibitor (e.g., AMG 102), EGEN-001, Polo-like kinase 1 inhibitor (e.g., BI 6727), gamma-secretase inhibitor (e.g., RO4929097), Wee-1 inhibitor (e.g., MK-1775), antitubulin agent (e.g., vinorelbine, E7389), immunotoxin (e.g., denileukin diftitox), SB-485232, vascular-disrupting agent (e.g., AVE8062), integrin inhibitor (e.g., EMD 525797), kinesin-spindle inhibitor (e.g., 4SC-205), revlimid, HER2 inhibitor (e.g., MGAH22), ErrB3 inhibitor (e.g., MM-121), radiation therapy; and combinations thereof.

In one exemplary embodiment, the anti-PD-1 antibody molecule, alone or in combination with another immunomodulator (e.g., an anti-LAG-3, anti-PD-L1 or anti-TIM-3 antibody molecule), is used to treat a myeloma, alone or in combination with one or more of: chemotherapy or other anti-cancer agents (e.g., thalidomide analogs, e.g., lenalidomide), HSCT (Cook, R. (2008) *J Manag Care Pharm.* 14(7 Suppl):19-25), an anti-TIM-3 antibody (Hallett, W H D et al. (2011) *J of American Society for Blood and Marrow Transplantation* 17(8):1133-145), tumor antigen-pulsed dendritic cells, fusions (e.g., electrofusions) of tumor cells and dendritic cells, or vaccination with immunoglobulin idiotype produced by malignant plasma cells (reviewed in Yi, Q. (2009) *Cancer J.* 15(6):502-10).

In yet another embodiment, the anti-PD-1 antibody molecule, alone or in combination with another immunomodulator (e.g., an anti-LAG-3, anti-PD-L1 or anti-TIM-3 antibody molecule), is used to treat a renal cancer, e.g., a renal cell carcinoma (RCC), a non-clear cell renal cell carcinoma, or a metastatic RCC. The anti-PD-1 antibody molecule can be administered in combination with one or more of: an immune-based strategy (e.g., interleukin-2 or interferon-α), a targeted agent (e.g., a VEGF inhibitor such as a monoclonal antibody to VEGF, e.g., bevacizumab (Rini, B. I. et al. (2010) *J. Clin. Oncol.* 28(13):2137-2143)); a VEGF tyrosine kinase inhibitor such as sunitinib, sorafenib, axitinib and pazopanib (reviewed in Pal. S. K. et al. (2014) *Clin. Advances in Hematology & Oncology* 12(2):90-99)); an RNAi inhibitor), or an inhibitor of a downstream mediator of VEGF signaling, e.g., an inhibitor of the mammalian target of rapamycin (mTOR), e.g., everolimus and temsirolimus (Hudes, G. et al. (2007) *N. Engl. J. Med.* 356(22): 2271-2281, Motzer, R. J. et al. (2008) *Lancet* 372: 449-456).

An example of suitable therapeutics for use in the combinations described herein, e.g., the combinations with the anti-PD-1 antibody molecules described herein, alone or in combination with another immunomodulator (e.g., an anti-LAG-3, anti-PD-L1 or anti-TIM-3 antibody molecule), for treatment of chronic myelogenous leukemia (AML) according to the invention includes, but is not limited to, a chemotherapeutic (e.g., cytarabine, hydroxyurea, clofarabine, melphalan, thiotepa, fludarabine, busulfan, etoposide, cordycepin, pentostatin, capecitabine, azacitidine, cyclophosphamide, cladribine, topotecan), tyrosine kinase inhibitor (e.g., BCR/ABL inhibitor (e.g., imatinib, nilotinib), ON 01910.Na, dual inhibitor (e.g., dasatinib, bosutinib), multikinase inhibitor (e.g., DCC-2036, ponatinib, sorafenib, sunitinib, RGB-286638)), interferon alfa, steroids, apoptotic agent (e.g., omacetaxine mepesuccinat), immunotherapy (e.g., allogeneic CD4+ memory Th1-like T cells/microparticle-bound anti-CD3/anti-CD28, autologous cytokine induced killer cells (CIK), AHN-12), CD52 targeting agent (e.g., alemtuzumab), HSP90 inhibitor (e.g., tanespimycin, STA-9090, AUY922, XL888), mTOR inhibitor (e.g., everolimus), SMO antagonist (e.g., BMS 833923), ribonucleotide reductase inhibitor (e.g., 3-AP), JAK-2 inhibitor (e.g., INCB018424), Hydroxychloroquine, retinoid (e.g., fenretinide), cyclin-dependent kinase inhibitor (e.g., UCN-01), HDAC inhibitor (e.g., belinostat, vorinostat, JNJ-26481585), PARP inhibitor (e.g., veliparib), MDM2 antagonist (e.g., RO5045337), Aurora B kinase inhibitor (e.g., TAK-901), radioimmunotherapy (e.g., actinium-225-labeled anti-CD33 antibody HuM195), Hedgehog inhibitor (e.g., PF-04449913), STAT3 inhibitor (e.g., OPB-31121), KB004, cancer vaccine (e.g., AG858), bone marrow transplantation, stem cell transplantation, radiation therapy, and combinations thereof.

An example of suitable therapeutics for use in the combinations described herein, e.g., the combinations with the anti-PD-1 antibody molecules described herein, alone or in combination with another immunomodulator (e.g., an anti-LAG-3, anti-PD-L1 or anti-TIM-3 antibody molecule), for treatment of chronic lymphocytic leukemia (CLL) includes, but is not limited to, a chemotherapeutic agent (e.g., fludarabine, cyclophosphamide, doxorubicin, vincristine, chlorambucil, bendamustine, chlorambucil, busulfan, gemcitabine, melphalan, pentostatin, mitoxantrone, 5-azacytidine, pemetrexed disodium), tyrosine kinase inhibitor (e.g., EGFR inhibitor (e.g., erlotinib), BTK inhibitor (e.g., PCI-32765), multikinase inhibitor (e.g., MGCD265, RGB-286638), CD-20 targeting agent (e.g., rituximab, ofatumumab, RO5072759, LFB-R603), CD52 targeting agent (e.g., alemtuzumab), prednisolone, darbepoetin alfa, lenalidomide, Bcl-2 inhibitor (e.g., ABT-263), immunotherapy (e.g., allogeneic CD4+ memory Th1-like T cells/microparticle-bound anti-CD3/anti-CD28, autologous cytokine induced killer cells (CIK)), HDAC inhibitor (e.g., vorinostat, valproic acid, LBH589, JNJ-26481585, AR-42), XIAP inhibitor (e.g., AEG35156), CD-74 targeting agent (e.g., milatuzumab), mTOR inhibitor (e.g., everolimus), AT-101, immunotoxin (e.g., CAT-8015, anti-Tac(Fv)-PE38 (LMB-2)), CD37 targeting agent (e.g., TRU-016), radioimmunotherapy (e.g., 131-tositumomab), hydroxychloroquine, perifosine, SRC inhibitor (e.g., dasatinib), thalidomide, PI3K delta inhibitor (e.g., CAL-101), retinoid (e.g., fenretinide), MDM2 antagonist (e.g., RO5045337), plerixafor, Aurora kinase inhibitor (e.g., MLN8237, TAK-901), proteasome inhibitor (e.g., bortezomib), CD-19 targeting agent (e.g., MEDI-551, MOR208), MEK inhibitor (e.g., ABT-348), JAK-2 inhibitor (e.g., INCB018424), hypoxia-activated prodrug (e.g., TH-302), paclitaxel or a paclitaxel agent, HSP90 inhibitor, AKT inhibitor (e.g., MK2206), HMG-CoA inhibitor (e.g., simvastatin), GNKG186, radiation therapy, bone marrow transplantation, stem cell transplantation, and a combination thereof.

An example of suitable therapeutics for use in the combinations described herein, e.g., the combinations with the anti-PD-1 antibody molecules described herein, alone or in combination with another immunomodulator (e.g., an anti- LAG-3, anti-PD-L1 or anti-TIM-3 antibody molecule), for treatment of acute lymphocytic leukemia (ALL) includes, but is not limited to, a chemotherapeutic agent (e.g., prednisolone, dexamethasone, vincristine, asparaginase, daunorubicin, cyclophosphamide, cytarabine, etoposide, thioguanine, mercaptopurine, clofarabine, liposomal annamycin, busulfan, etoposide, capecitabine, decitabine, azacitidine, topotecan, temozolomide), tyrosine kinase inhibitor (e.g., BCR/ABL inhibitor (e.g., imatinib, nilotinib), ON 01910.Na, multikinase inhibitor (e.g., sorafenib)), CD-20 targeting agent (e.g., rituximab), CD52 targeting agent (e.g., alemtuzumab), HSP90 inhibitor (e.g., STA-9090), mTOR inhibitor (e.g., everolimus, rapamycin), JAK-2 inhibitor (e.g., INCB018424), HER2/neu receptor inhibitor (e.g., trastuzumab), proteasome inhibitor (e.g., bortezomib), methotrexate, asp araginase, CD-22 targeting agent (e.g., epratuzumab, inotuzumab), immunotherapy (e.g., autologous cytokine induced killer cells (CIK), AHN-12), blinatumomab, cyclin-dependent kinase inhibitor (e.g., UCN-01), CD45 targeting agent (e.g., BC8), MDM2 antagonist (e.g., RO5045337), immunotoxin (e.g., CAT-8015, DT2219ARL), HDAC inhibitor (e.g., JNJ-26481585), JVRS-100, paclitaxel or a paclitaxel agent, STAT3 inhibitor (e.g., OPB-31121), PARP inhibitor (e.g., veliparib), EZN-2285, radiation therapy, steroid, bone marrow transplantation, stem cell transplantation, or a combination thereof.

An example of suitable therapeutics for use in the combinations described herein, e.g., the combinations with the anti-PD-1 antibody molecules described herein, alone or in combination with another immunomodulator (e.g., an anti-LAG-3, anti-PD-L1 or anti-TIM-3 antibody molecule), for treatment of acute myeloid leukemia (AML) includes, but is not limited to, a chemotherapeutic agent (e.g., cytarabine, daunorubicin, idarubicin, clofarabine, decitabine, vosaroxin, azacitidine, clofarabine, ribavirin, CPX-351, treosulfan, elacytarabine, azacitidine), tyrosine kinase inhibitor (e.g., BCR/ABL inhibitor (e.g., imatinib, nilotinib), ON 01910.Na, multikinase inhibitor (e.g., midostaurin, SU 11248, quizartinib, sorafinib)), immunotoxin (e.g., gemtuzumab ozogamicin), DT388IL3 fusion protein, HDAC inhibitor (e.g., vorinostat, LBH589), plerixafor, mTOR inhibitor (e.g., everolimus), SRC inhibitor (e.g., dasatinib), HSP90 inhibitor (e.g., STA-9090), retinoid (e.g., bexarotene, Aurora kinase inhibitor (e.g., CD-22 BI 811283), JAK-2 inhibitor (e.g., INCB018424), Polo-like kinase inhibitor (e.g., BI 6727), cenersen, CD45 targeting agent (e.g., BC8), cyclin-dependent kinase inhibitor (e.g., UCN-01), MDM2 antagonist (e.g., RO5045337), mTOR inhibitor (e.g., everolimus), LY573636-sodium, ZRx-101, MLN4924, lenalidomide, immunotherapy (e.g., AHN-12), histamine dihydrochloride, radiation therapy, bone marrow transplantation, stem cell transplantation, and a combination thereof.

An example of suitable therapeutics for use in the combinations described herein, e.g., the combinations with the anti-PD-1 antibody molecules described herein, alone or in combination with another immunomodulator (e.g., an anti-LAG-3, anti-PD-L1 or anti-TIM-3 antibody molecule), for treatment of multiple myeloma (MM) includes, but is not limited to, a chemotherapeutic agent (e.g., melphalan, amifostine, cyclophosphamide, doxorubicin, clofarabine, bendamustine, fludarabine, adriamycin, SyB L-0501), thalidomide, lenalidomide, dexamethasone, prednisone, pomalidomide, proteasome inhibitor (e.g., bortezomib, carfilzomib, MLN9708), cancer vaccine (e.g., GVAX), CD-40 targeting agent (e.g., SGN-40, CHIR-12.12), perifosine, zoledronic acid, Immunotherapy (e.g., MAGE-A3, NY-ESO-1, HuMax-CD38), HDAC inhibitor (e.g., vorinostat, LBH589, AR-42), aplidin, cycline-dependent kinase inhibitor (e.g., PD-0332991, dinaciclib), arsenic trioxide, CB3304, HSP90 inhibitor (e.g., KW-2478), tyrosine kinase inhibitor (e.g., EGFR inhibitor (e.g., cetuximab), multikinase inhibitor (e.g., AT9283)), VEGF inhibitor (e.g., bevacizumab), plerixafor, MEK inhibitor (e.g., AZD6244), IPH2101, atorvastatin, immunotoxin (e.g., BB-10901), NPI-0052, radioimmunotherapeutic (e.g., yttrium Y 90 ibritumomab tiuxetan), STAT3 inhibitor (e.g., OPB-31121), MLN4924, Aurora kinase inhibitor (e.g., ENMD-2076), IMGN901, ACE-041, CK-2 inhibitor (e.g., CX-4945), radiation therapy, bone marrow transplantation, stem cell transplantation, and a combination thereof.

An example of suitable therapeutics for use in the combinations described herein, e.g., the combinations with the anti-PD-1 antibody molecules described herein, alone or in combination with another immunomodulator (e.g., an anti-LAG-3, anti-PD-L1 or anti-TIM-3 antibody molecule), for treatment of prostate cancer includes, but is not limited to, a chemotherapeutic agent (e.g., docetaxel, carboplatin, fludarabine), abiraterone, hormonal therapy (e.g., flutamide, bicalutamide, nilutamide, cyproterone acetate, ketoconazole, aminoglutethimide, abarelix, degarelix, leuprolide, goserelin, triptorelin, buserelin), tyrosine kinase inhibitor (e.g., dual kinase inhibitor (e.g., lapatanib), multikinase inhibitor (e.g., sorafenib, sunitinib)), VEGF inhibitor (e.g., bevacizumab), TAK-700, cancer vaccine (e.g., BPX-101, PEP223), lenalidomide, TOK-001, IGF-1 receptor inhibitor (e.g., cixutumumab), TRC105, Aurora A kinase inhibitor (e.g., MLN8237), proteasome inhibitor (e.g., bortezomib), OGX-011, radioimmunotherapy (e.g., HuJ591-GS), HDAC inhibitor (e.g., valproic acid, SB939, LBH589), hydroxychloroquine, mTOR inhibitor (e.g., everolimus), dovitinib lactate, diindolylmethane, efavirenz, OGX-427, genistein, IMC-3G3, bafetinib, CP-675,206, radiation therapy, surgery, or a combination thereof.

An example of suitable therapeutics for use in the combinations described herein, e.g., the combinations with the anti-PD-1 antibody molecules described herein, alone or in combination with another immunomodulator (e.g., an anti-LAG-3, anti-PD-L1 or anti-TIM-3 antibody molecule), for treatment of HNSCC includes, but is not limited to, one or both of Compound A8 as described herein (or a compound described in PCT Publication No. WO2010/029082) and cetuximab (e.g., Erbitux, marketed by BMS). In some embodiments, the therapeutic (e.g., the Compound A8 or compound related to A8) is a PI3K modulator, e.g., a PI3K inhibitor. In some embodiments, the therapeutic (e.g., cetuximab) modulates, e.g., inhibits, EGFR. In some embodiments, the cancer has, or is identified as having, elevated levels or activity of PI3K or EGFR compared to a control cell or reference value.

An example of suitable therapeutics for use in the combinations described herein, e.g., the combinations with the anti-PD-1 antibody molecules described herein, alone or in combination with another immunomodulator (e.g., an anti-LAG-3, anti-PD-L1 or anti-TIM-3 antibody molecule), for treatment of gastric cancer, e.g., MSI-high and/or EBV+ gastric cancer, includes, but is not limited to, Compound A8 as described herein (or a compound described in PCT Publication No. WO2010/029082). In some embodiments, the therapeutic (e.g., the Compound A8 or compound related to A8) is a PI3K modulator, e.g., a PI3K inhibitor. In some embodiments, the cancer has, or is identified as having, elevated levels or activity of PI3K compared to a control cell or reference value.

An example of suitable therapeutics for use in the combinations described herein, e.g., the combinations with the anti-PD-1 antibody molecules described herein, alone or in combination with another immunomodulator (e.g., an anti-LAG-3, anti-PD-L1 or anti-TIM-3 antibody molecule), for treatment of gastric cancer, e.g., MSI-high and/or RNF43-inactivated gastric cancer, includes, but is not limited to, Compound A28 as described herein (or a compound described in PCT Publication No. WO2010/101849). In some embodiments, the therapeutic (e.g., the Compound A28 or compound related to A28) is a modulator, e.g., inhibitor, of porcupine. In some embodiments, the cancer has, or is identified as having, elevated levels or activity of porcupine compared to a control cell or reference value.

An example of suitable therapeutics for use in the combinations described herein, e.g., the combinations with the anti-PD-1 antibody molecules described herein, alone or in combination with another immunomodulator (e.g., an anti-LAG-3, anti-PD-L1 or anti-TIM-3 antibody molecule), for treatment of GI stromal tumor (GIST), includes, but is not limited to, Compound A16 as described herein (or a compound described in PCT Publication No. WO1999/003854). In some embodiments, the therapeutic (e.g., the Compound A16 or compound related to A16) is a modulator, e.g., inhibitor, of a tyrosine kinase. In some embodiments, the cancer has, or is determined to have, elevated levels or activity of a tyrosine kinase compared to a control cell or reference value.

An example of suitable therapeutics for use in the combinations described herein, e.g., the combinations with the anti-PD-1 antibody molecules described herein, alone or in combination with another immunomodulator (e.g., an anti-LAG-3, anti-PD-L1 or anti-TIM-3 antibody molecule), for treatment of NSCLC, e.g., squamous or adenocarcinoma, includes, but is not limited to, one or both of Compound A17 as described herein (or a compound described in U.S. Pat. Nos. 7,767,675 and 8,420,645) and Compound A23 as described herein (or a compound described in PCT Publication No. WO2003/077914). In some embodiments, the compound (e.g., the Compound A17 or compound related to A17) modulates, e.g., inhibits, c-MET. In some embodiments, the compound (e.g., the Compound A23 or compound related to A23) modulates, e.g., inhibits, Alk. In some embodiments, the cancer has, or is determined to have, elevated levels or activity of one or both of c-MET or Alk compared to a control cell or reference value. In some embodiments, the cancer has, or is identified as having, a mutation in EGFR.

An example of suitable therapeutics for use in the combinations described herein, e.g., the combinations with the anti-PD-1 antibody molecules described herein, alone or in combination with another immunomodulator (e.g., an anti-LAG-3, anti-PD-L1 or anti-TIM-3 antibody molecule), for treatment of melanoma (e.g., NRAS melanoma) includes, but is not limited to, one or both of Compound A24 as described herein (or a compound described in U.S. Pat. Nos. 8,415,355 and 8,685,980) and Compound A34 as described herein (or a compound described in PCT Publication No. WO2003/077914). In some embodiments, the compound (e.g., the Compound A24 or compound related to A24) modulates, e.g., inhibits, one or more of JAK and CDK4/6. In some embodiments, the compound (e.g., the Compound A34 or compound related to A34) modulates, e.g., inhibits, MEK. In some embodiments, the cancer has, or is identified as having, elevated levels or activity of one or more of JAK, CDK4/6, and MEK compared to a control cell or reference value.

An example of suitable therapeutics for use in the combinations described herein, e.g., the combinations with the anti-PD-1 antibody molecules described herein, alone or in combination with another immunomodulator (e.g., an anti-LAG-3, anti-PD-L1 or anti-TIM-3 antibody molecule), for treatment of melanoma (e.g., NRAS melanoma) includes, but is not limited to, one or both of Compound A29 as described herein (or a compound described in PCT Publication No. WO2011/025927) and Compound A34 as described herein (or a compound described in PCT Publication No. WO2003/077914). In some embodiments, the compound (e.g., the Compound A29 or compound related to A29) modulates, e.g., inhibits, BRAF. In some embodiments, the compound (e.g., the Compound A34 or compound related to A34) modulates, e.g., inhibits, MEK. In some embodiments, the cancer has, or is identified as having, elevated levels or activity of one or both of BRAF and MEK compared to a control cell or reference value.

An example of suitable therapeutics for use in the combinations described herein, e.g., the combinations with the anti-PD-1 antibody molecules described herein, alone or in combination with another immunomodulator (e.g., an anti-LAG-3, anti-PD-L1 or anti-TIM-3 antibody molecule), for treatment of squamous NSCLC includes, but is not limited to, Compound A5 as described herein (or a compound described in U.S. Pat. No. 8,552,002). In some embodiments, the compound (e.g., the Compound A5 or compound related to A5) modulates, e.g., inhibits, FGFR. In some embodiments, the cancer has, or is identified as having, elevated levels or activity of FGFR compared to a control cell or reference value.

An example of suitable therapeutics for use in the combinations described herein, e.g., the combinations with the anti-PD-1 antibody molecules described herein, alone or in combination with another immunomodulator (e.g., an anti-LAG-3, anti-PD-L1 or anti-TIM-3 antibody molecule), for treatment of colorectal cancer includes, but is not limited to, one or both of Compound A29 as described herein (or a compound PCT Publication No. WO2011/025927) and cetuximab (e.g., Erbitux, marketed by BMS). In some embodiments, the therapeutic (e.g., the Compound A29 or compound related to A29) modulates, e.g., inhibits, BRAF. In some embodiments, the therapeutic (e.g., cetuximab) modulates, e.g., inhibits, EGFR. In some embodiments, the cancer has, or is identified as having, elevated levels or activity of BRAF or EGFR compared to a control cell or reference value.

This disclosure also provides a method of treating cancer with Compound A8, cetuximab, and a combination described herein, e.g., the combinations with the anti-PD-1 antibody molecules described herein, (optionally in combination with a TIM-3 antibody molecule or LAG-3 antibody molecule). In some embodiments, the patient is first treated with Compound A8 and cetuximab. This treatment continues for an amount of time, e.g., a predetermined amount of time, e.g., about 1, 2, 4, 6, 8, 10, or 12 months. Next, the PD-1 antibody molecule (optionally in combination with a TIM-3 antibody molecule or LAG-3 antibody molecule) is administered. The PD-1 antibody can optionally be administered in combination with cetuximab.

In some embodiments, the patient is first treated with all three of Compound A8, cetuximab, and a PD-1 antibody molecule (optionally in combination with a TIM-3 antibody molecule or LAG-3 antibody molecule). This treatment continues for an amount of time, e.g., a predetermined amount of time, e.g., about 6, 8, 10, or 12 months. Next, the Compound A8 and/or cetuximab can be tapered off, so that the maintenance phase involves treatment with the PD-1 antibody molecule (e.g., as a monotherapy, or in combination with a TIM-3 antibody molecule or LAG-3 antibody molecule) but not Compound A8 or cetuximab.

In other embodiments, the three compounds (Compound A8, cetuximab, and a PD-1 antibody molecule, optionally in combination with a TIM-3 antibody molecule or LAG-3 antibody molecule) are given sequentially at the outset of the treatment. For instance, Compound A8 and cetuximab can be given first, as described above. Next, the PD-1 antibody molecule (optionally in combination with a TIM-3 antibody molecule or LAG-3 antibody molecule) is added to the regimen. Next, the Compound A8 and/or cetuximab can be tapered off as described above.

Exemplary doses for the three (or more) agent regimens are as follows. The anti-PD-1 antibody molecule can be administered, e.g., at a dose of about 1 to 40 mg/kg, e.g., 1 to 30 mg/kg, e.g., about 5 to 25 mg/kg, about 10 to 20 mg/kg, about 1 to 5 mg/kg, or about 3 mg/kg. Alternatively, the anti-PD-1 antibody molecule can be administered, e.g., at a dose of about 200 to 500 mg, e.g., about 300 to 500 mg, about 200 to 400 mg, about 250 to 350 mg, or about 300 to 400 mg, or about 300 mg or about 400 mg. In one embodiment, the PD-1 antibody molecule is administered once every three weeks, e.g., at a dose of 300 mg once every three weeks. In another embodiment, the anti-PD-1 antibody molecule is administered once every four weeks, e.g., at a dose of 400 mg once every four weeks. In some embodiments, the Compound A8 is administered at a dose of approximately 200-300, 300-400, or 200-400 mg. In some embodiments, the cetuximab is administered at a 400 mg/m$^2$ initial dose as a 120-minute intravenous infusion followed by 250 mg/m$^2$ weekly infused over 60 minutes. In embodiments, one or more of the Compound A8, cetuximab, and PD-1 antibody molecule is administered at a dose that is lower than the dose at which that agent is typically administered as a monotherapy, e.g., about 0-10%, 10-20%, 20-30%, 30-40%, 40-50%, 50-60%, 60-70%, 70-80%, or 80-90% lower than the dose at which that agent is typically administered as a monotherapy. In embodiments, the one or more of the Compound A8, cetuximab, and PD-1 antibody molecule is administered at a dose that is lower than the dose of that agent recited in this paragraph, e.g., about 0-10%, 10-20%, 20-30%, 30-40%, 40-50%, 50-60%, 60-70%, 70-80%, or 80-90% lower than the dose of that agent recited in this paragraph. In certain embodiments, the concentration of the Compound A8 that is required to achieve inhibition, e.g., growth inhibition, is lower when the Compound A8 is administered in combination with one or both of the cetuximab and PD-1 antibody molecule than when the Compound A8 is administered individually. In certain embodiments, the concentration of the cetuximab that is required to achieve inhibition, e.g., growth inhibition, is lower when the cetuximab is administered in combination with one or both of the Compound A8 and PD-1 antibody molecule than when the cetuximab is administered individually. In certain embodiments, the concentration of the PD-1 antibody molecule that is required to achieve inhibition, e.g., growth inhibition, is lower when the PD-1 antibody molecule is administered in combination with one or both of the cetuximab and Compound A8 than when the PD-1 antibody molecule is administered individually.

Additionally disclosed herein is a method of treating cancer with the anti-PD-1 antibody molecules, alone or in combination with another immunomodulator (e.g., an anti-LAG-3, anti-PD-L1 or anti-TIM-3 antibody molecule), and a targeted anti-cancer agent, e.g., an agent that targets one or more proteins. In some embodiments, the anti-PD-1 antibody molecule (and optionally other immunomodulator(s)) are administered first, and the targeted anti-cancer agent is administered second. The length of time between administration of the anti-PD-1 antibody molecule and the targeted anti-cancer agent can be, e.g., 10, 20, or 30 minutes, 1, 2, 4, 6, or 12 hours, or 1, 2, 3, 4, 5, 6, or 7 days, or any span of time within this range. In certain embodiments, the anti-PD-1 antibody molecule is administered repeatedly over a period of time (e.g., 1, 2, 3, 4, 5, or 6 days, or 1, 2, 4, 8, 12, 16, or 20 weeks, or any span of time within this range) before the targeted anti-cancer agent is administered. In other embodiments, the anti-PD-1 antibody molecule and the targeted anti-cancer agent are administered at substantially the same time.

Infectious Diseases

Other methods of the invention are used to treat patients that have been exposed to particular toxins or pathogens. Accordingly, another aspect of the invention provides a method of treating an infectious disease in a subject comprising administering to the subject a combination as disclosed herein, e.g., a combination including an anti-PD-1 antibody molecule, such that the subject is treated for the infectious disease.

In the treatment of infection (e.g., acute and/or chronic), administration of the anti-PD-1 antibody molecules can be combined with conventional treatments in addition to or in lieu of stimulating natural host immune defenses to infection. Natural host immune defenses to infection include, but are not limited to inflammation, fever, antibody-mediated host defense, T-lymphocyte-mediated host defenses, including lymphokine secretion and cytotoxic T-cells (especially during viral infection), complement mediated lysis and opsonization (facilitated phagocytosis), and phagocytosis. The ability of the anti-PD-1 antibody molecules to reactivate dysfunctional T-cells would be useful to treat chronic infections, in particular those in which cell-mediated immunity is important for complete recovery.

Similar to its application to tumors as discussed above, antibody mediated PD-1 blockade can be used alone, or as an adjuvant, in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to HIV, Hepatitis (A, B, & C), Influenza, Herpes, Giardia, Malaria, *Leishmania, Staphylococcus aureus, Pseudomonas Aeruginosa*. PD-1 blockade is particularly useful against established infections by agents such as HIV that present altered antigens over the course of the infections. These novel epitopes are recognized as foreign at the time of anti-human PD-1 administration, thus provoking a strong T cell response that is not dampened by negative signals through PD-1.

Additional and Further Combination Therapies

Anti-PD-1 antibody molecules can be used in any of the combinations disclosed herein. In some embodiments, combinations with one or more further therapeutics are provided herein. Many of the combinations in this section are useful in treating cancer, but other indications are also described. In some embodiments, the anti-PD-1 antibody molecule is administered by injection (e.g., subcutaneously or intravenously) at a dose (e.g., a flat dose) of about 200 mg to 500 mg, e.g., about 300 mg to 400 mg, or about 300 mg or about 400 mg. The dosing schedule (e.g., flat dosing schedule) can vary from e.g., once a week to once every 2, 3, 4, 5, or 6 weeks. In one embodiment, the anti-PD-1 antibody molecule is administered at a dose from about 300 mg once every three weeks. In one embodiment, the anti-PD-1 antibody molecule is administered at a dose from about 400 mg once every four weeks. This section focuses on combinations of anti-PD-1 antibody molecules, optionally in combination with one or more immunomodulators (e.g., an anti-TIM-3 antibody molecule, an anti-LAG-3 antibody molecule, or an anti-PD-L1 antibody molecule), with one or more of the agents described in Table 7. In the combinations herein below, in one embodiment, the anti-PD-1 antibody molecule includes:

(a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 33;

(b) a VH comprising a VHCDR1 amino acid sequence chosen from SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32;

(c) a VH comprising a VHCDR1 amino acid sequence of SEQ ID NO: 224, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33; or (d) a VH comprising a VHCDR1 amino acid sequence of SEQ ID NO: 224; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32.

In the combinations herein below, in another embodiment, the anti-PD-1 antibody molecule comprises (i) a heavy chain variable region (VH) comprising a VHCDR1 amino acid sequence chosen from SEQ ID NO: 1, SEQ ID NO: 4, or SEQ ID NO: 224; a VHCDR2 amino acid sequence of SEQ ID NO: 2 or SEQ ID NO: 5; and a VHCDR3 amino acid sequence of SEQ ID NO: 3; and (ii) a light chain variable region (VL) comprising a VLCDR1 amino acid sequence of SEQ ID NO: 10 or SEQ ID NO: 13, a VLCDR2 amino acid sequence of SEQ ID NO: 11 or SEQ ID NO: 14, and a VLCDR3 amino acid sequence of SEQ ID NO: 32 or SEQ ID NO: 33.

In one embodiment, the combination, e.g., a combination comprising an anti-PD-1 antibody molecule as described herein, includes or is used in combination with a PKC inhibitor, Sotrastaurin (Compound A1), or a compound disclosed in PCT Publication No. WO 2005/039549, to treat a disorder, e.g., a disorder described herein. In one embodiment, the PKC inhibitor is Sotrastaurin (Compound A1) or a compound disclosed in PCT Publication No. WO 2005/039549. In one embodiment, a PD-1 antibody molecule is used in combination with Sotrastaurin (Compound A1), or a compound as described in PCT Publication No. WO 2005/039549, to treat a disorder such as a cancer, a melanoma, a non-Hodgkin lymphoma, an inflammatory bowel disease, transplant rejection, an ophthalmic disorder, or psoriasis.

In certain embodiments, Sotrastaurin (Compound A1) is administered at a dose of about 20 to 600 mg, e.g., about 200 to about 600 mg, about 50 mg to about 450 mg, about 100 mg to 400 mg, about 150 mg to 350 mg, or about 200 mg to 300 mg, e.g., about 50 mg, 100 mg, 150 mg, 200 mg, 300 mg, 400 mg, 500 mg, or 600 mg. The dosing schedule can vary from e.g., every other day to daily, twice or three times a day.

In one embodiment, the combination, e.g., a combination comprising an anti-PD-1 antibody molecule as described herein, includes or is used in combination with a BCR-ABL inhibitor, TASIGNA (Compound A2), or a compound disclosed in PCT Publication No. WO 2004/005281, to treat a disorder, e.g., a disorder described herein. In one embodiment, the BCR-ABL inhibitor is TASIGNA, or a compound disclosed in PCT Publication No. WO 2004/005281. In one embodiment, a PD-1 antibody molecule is used in combination with TASIGNA (Compound A2), or a compound as described in PCT Publication No. WO 2004/005281, to treat a disorder such as a lymphocytic leukemia, Parkinson's Disease, a neurologic cancer, a melanoma, a digestive/gastrointestinal cancer, a colorectal cancer, a myeloid leukemia, a head and neck cancer, or pulmonary hypertension.

In one embodiment, the BCR-ABL inhibitor or TASIGNA is administered at a dose of about 300 mg (e.g., twice daily, e.g., for newly diagnosed Ph+CML-CP), or about 400 mg, e.g., twice daily, e.g., for resistant or intolerant Ph+CML-CP and CML-AP). BCR-ABL inhibitor or a Compound A2 is administered at a dose of about 300-400 mg.

In another embodiment, the combination, e.g., a combination comprising an anti-PD-1 antibody molecule as described herein, includes or is used in combination with an HSP90 inhibitor, such as 5-(2,4-dihydroxy-5-isopropylphenyl)-N-ethyl-4-(4-(morpholinomethyl)phenyl)isoxazole-3-carboxamide (Compound A3), or a compound disclosed in PCT Publication No. WO 2010/060937 or WO 2004/072051, to treat a disorder, e.g., a disorder described herein. In one embodiment, the HSP90 inhibitor is 5-(2,4-dihydroxy-5-isopropylphenyl)-N-ethyl-4-(4-(morpholinomethyl)phenyl)isoxazole-3-carboxamide (Compound A3), or a compound disclosed in PCT Publication No. WO 2010/060937 or WO 2004/072051. In one embodiment, a PD-1 antibody molecule is used in combination with 5-(2,4-dihydroxy-5-isopropylphenyl)-N-ethyl-4-(4-(morpholinomethyl)phenyl)isoxazole-3-carboxamide (Compound A3), or a compound as described in PCT Publication No. WO 2010/060937 or WO 2004/072051, to treat a disorder such as a cancer, a multiple myeloma, a non-small cell lung cancer, a lymphoma, a gastric cancer, a breast cancer, a digestive/gastrointestinal cancer, a pancreatic cancer, a colorectal cancer, a solid tumor, or a hematopoiesis disorder.

In another embodiment, the combination, e.g., a combination comprising an anti-PD-1 antibody molecule as described herein, is used in combination with an inhibitor of PI3K and/or mTOR, Dactolisib (Compound A4) or 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound disclosed in PCT Publication No. WO 2006/122806, to treat a disorder, e.g., a disorder described herein. In one embodiment, the PI3K and/or mTOR inhibitor is Dactolisib (Compound A4), 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound disclosed in PCT Publication No. WO 2006/122806. In one embodiment, a PD-1 antibody molecule is used in combination with Dactolisib (Compound A4), 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound described in PCT Publication No. WO 2006/122806, to treat a disorder such as a cancer, a prostate cancer, a leukemia (e.g., lymphocytic leukemia), a breast cancer, a brain cancer, a bladder cancer, a pancreatic cancer, a renal cancer, a solid tumor, or a liver cancer.

In another embodiment, the combination, e.g., a combination comprising an anti-PD-1 antibody molecule as described herein, includes or is used in combination with an FGFR inhibitor, 3-(2,6-dichloro-3,5-dimethoxyphenyl)-1-(6-((4-(4-ethylpiperazin-1-yl)phenyl)amino)pyrimidin-4-yl)-1-methylurea (Compound A5) or a compound disclosed in U.S. Pat. No. 8,552,002, to treat a disorder, e.g., a disorder described herein. In one embodiment, the FGFR inhibitor is 3-(2,6-dichloro-3,5-dimethoxyphenyl)-1-(6-((4-(4-ethylpiperazin-1-yl)phenyl)amino)pyrimidin-4-yl)-1-methylurea (Compound A5) or a compound disclosed in U.S. Pat. No. 8,552,002. In one embodiment, a PD-1 antibody molecule is used in combination with Compound A5, or a compound as described in U.S. Pat. No. 8,552,002, to treat a disorder such as a digestive/gastrointestinal cancer, a hematological cancer, or a solid tumor.

In one embodiment, the FGFR inhibitor or 3-(2,6-dichloro-3,5-dimethoxyphenyl)-1-(6-((4-(4-ethylpiperazin-1-yl)phenyl)amino)pyrimidin-4-yl)-1-methylurea (Compound A5) is administered at a dose of about 100-125 mg (e.g., per day), e.g., about 100 mg or about 125 mg.

In another embodiment, the combination, e.g., a combination comprising an anti-PD-1 antibody molecule as described herein, includes or is used in combination with a PI3K inhibitor, Buparlisib (Compound A6), or a compound disclosed in PCT Publication No. WO 2007/084786, to treat a disorder, e.g., a disorder described herein. In one embodiment, the PI3K inhibitor is Buparlisib (Compound A6) or a compound disclosed in PCT Publication No. WO 2007/084786. In one embodiment, a PD-1 antibody molecule is used in combination with Buparlisib (Compound A6), or a compound disclosed in PCT Publication No. WO 2007/084786, to treat a disorder such as, a prostate cancer, a non-small cell lung cancer, an endocrine cancer, a leukemia, an ovarian cancer, a melanoma, a bladder cancer, a breast cancer, a female reproductive system cancer, a digestive/gastrointestinal cancer, a colorectal cancer, a glioblastoma multiforme, a solid tumor, a non-Hodgkin lymphoma, a hematopoiesis disorder, or a head and neck cancer.

In one embodiment, the PI3K inhibitor or Buparlisib (Compound A6) is administered at a dose of about 100 mg (e.g., per day).

In another embodiment, the combination, e.g., a combination comprising an anti-PD-1 antibody molecule as described herein, includes or is used in combination with an FGFR inhibitor, 8-(2,6-difluoro-3,5-dimethoxyphenyl)-N-(4-((dimethylamino)methyl)-1H-imidazol-2-yl)quinoxaline-5-carboxamide (Compound A7) or a compound disclosed in PCT Publication No. WO 2009/141386 to treat a disorder, e.g., a disorder described herein. In one embodiment, the FGFR inhibitor is 842,6-difluoro-3,5-dimethoxyphenyl)-N-(4-((dimethylamino)methyl)-1H-imidazol-2-yl)quinoxaline-5-carboxamide (Compound A7) or a compound disclosed in a PCT Publication No. WO 2009/141386. In one embodiment, the FGFR inhibitor is 8-(2,6-difluoro-3,5-dimethoxyphenyl)-N-(4-((dimethylamino)methyl)-1H-imidazol-2-yl)quinoxaline-5-carboxamide (Compound A7). In one embodiment, a PD-1 antibody molecule is used in combination with 8-(2,6-difluoro-3,5-dimethoxyphenyl)-N-

(4-((dimethylamino)methyl)-1H-imidazol-2-yl)quinoxa-line-5-carboxamide (Compound A7), or a compound disclosed in PCT Publication No. WO 2009/141386, to treat a disorder such as a cancer characterized by angiogenesis.

In one embodiment, the FGFR inhibitor or 8-(2,6-difluoro-3,5-dimethoxyphenyl)-N-(4-((dimethylamino)methyl)-1H-imidazol-2-yl)quinoxaline-5-carboxamide (Compound A7) is administered at a dose of e.g., from approximately 3 mg to approximately 5 g, more preferably from approximately 10 mg to approximately 1.5 g per person per day, optionally divided into 1 to 3 single doses which may, for example, be of the same size.

In another embodiment the combination, e.g., a combination comprising an anti-PD-1 antibody molecule as described herein, includes or is used in combination with a PI3K inhibitor, (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8) or a compound disclosed PCT Publication No. WO 2010/029082 to treat a disorder, e.g., a disorder described herein. In one embodiment, the PI3K inhibitor is (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8) or a compound disclosed PCT Publication No. WO 2010/029082. In one embodiment, a PD-1 antibody molecule is used in combination with (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8), or a compound disclosed PCT Publication No. WO 2010/029082, to treat a disorder such as a gastric cancer, a breast cancer, a pancreatic cancer, a digestive/gastrointestinal cancer, a solid tumor, and a head and neck cancer.

In one embodiment, the PI3K inhibitor or (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8) is administered at a dose of about 150-300, 200-300, 200-400, or 300-400 mg (e.g., per day), e.g., about 200, 300, or 400 mg.

In another embodiment, the combination, e.g., a combination comprising an anti-PD-1 antibody molecule as described herein, includes or is used in combination with an inhibitor of cytochrome P450 (e.g., a CYP17 inhibitor) or a compound disclosed in PCT Publication No. WO 2010/149755, to treat a disorder, e.g., a disorder described herein. In one embodiment, the cytochrome P450 inhibitor (e.g., the CYP17 inhibitor) is a compound disclosed in PCT Publication No. WO 2010/149755. In one embodiment, a PD-1 antibody molecule is used in combination with a compound disclosed in PCT Publication No. WO 2010/149755, to treat prostate cancer.

In another embodiment, the combination, e.g., a combination comprising an anti-PD-1 antibody molecule as described herein, includes or is used in combination with an HDM2 inhibitor, (S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3(4H)-one (Compound A10) or a compound disclosed in PCT Publication No. WO 2011/076786 to treat a disorder, e.g., a disorder described herein). In one embodiment, the HDM2 inhibitor is (S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3(4H)-one (Compound A10) or a compound disclosed in PCT Publication No. WO 2011/076786. In one embodiment, a PD-1 antibody molecule is used in combination with (S)-1-(4-chlorophenyl)-7-isopropoxy-6-methoxy-2-(4-(methyl(((1r,4S)-4-(4-methyl-3- oxopiperazin-1-yl)cyclohexyl)methyl)amino)phenyl)-1,2-dihydroisoquinolin-3(4H)-one (Compound A10), or a compound disclosed in PCT Publication No. WO 2011/076786, to treat a disorder such as a solid tumor.

In one embodiment, the HDM2 inhibitor or (S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3(4H)-one (Compound A10) is administered at a dose of about 400 to 700 mg, e.g., administered three times weekly, 2 weeks on and one week off. In some embodiments, the dose is about 400, 500, 600, or 700 mg; about 400-500, 500-600, or 600-700 mg, e.g., administered three times weekly.

In another embodiment, the combination, e.g., a combination comprising an anti-PD-1 antibody molecule as described herein, includes or is used in combination with an iron chelating agent, Deferasirox (also known as EXJADE; Compound A11), or a compound disclosed in PCT Publication No. WO 1997/049395 to treat a disorder, e.g., a disorder described herein. In one embodiment, the iron chelating agent is Deferasirox or a compound disclosed in PCT Publication No. WO 1997/049395. In one embodiment, the iron chelating agent is Deferasirox (Compound A11). In one embodiment, a PD-1 antibody molecule is used in combination with Deferasirox (Compound A11), or a compound disclosed in PCT Publication No. WO 1997/049395, to treat iron overload, hemochromatosis, or myelodysplasia.

In another embodiment, the combination, e.g., a combination comprising an anti-PD-1 antibody molecule as described herein, includes or is used in combination with an aromatase inhibitor, Letrozole (also known as FEMARA; Compound A12), or a compound disclosed in U.S. Pat. No. 4,978,672 to treat a disorder, e.g., a disorder described herein. In one embodiment, the aromatase inhibitor is Letrozole (Compound A12) or a compound disclosed in U.S. Pat. No. 4,978,672. In one embodiment, a PD-1 antibody molecule is used in combination with Letrozole (Compound A12), or a compound disclosed in U.S. Pat. No. 4,978,672, to treat a disorder such as a cancer, a leiomyosarcoma, an endometrium cancer, a breast cancer, a female reproductive system cancer, or a hormone deficiency.

In another embodiment, the combination, e.g., a combination comprising an anti-PD-1 antibody molecule as described herein, includes or is used in combination with a PI3K inhibitor, e.g., a pan-PI3K inhibitor, (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13) or a compound disclosed in PCT Publication No. WO2013/124826 to treat a disorder, e.g., a disorder described herein. In one embodiment, the PI3K inhibitor is (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13) or a compound disclosed in PCT Publication No. WO2013/124826. In one embodiment, a PD-1 antibody molecule is used in combination with (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13), or a compound disclosed in PCT Publication No. WO2013/124826, to treat a disorder such as a cancer or an advanced solid tumor.

In another embodiment, the combination, e.g., a combination comprising an anti-PD-1 antibody molecule as described herein, includes or is used in combination with an inhibitor of p53 and/or a p53/Mdm2 interaction, (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (Compound A14), or a compound disclosed in PCT Publication No. WO2013/111105 to treat a disorder, e.g., a disorder described herein. In one embodiment, the p53 and/or a p53/Mdm2 interaction inhibitor is (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (Compound A14) or a compound disclosed in PCT Publication No. WO2013/111105. In one embodiment, a PD-1 antibody molecule is used in combination with (S)-5-(5-chloro-1-methyl-2-oxo-1,2-dihydropyridin-3-yl)-6-(4-chlorophenyl)-2-(2,4-dime-thoxypyrimidin-5-yl)-1-isopropyl-5,6-dihydropyrrolo[3,4-d]imidazol-4(1H)-one (Compound A14), or a compound disclosed in PCT Publication No. WO2013/111105, to treat a disorder such as a cancer or a soft tissue sarcoma.

In another embodiment, the combination, e.g., a combination comprising an anti-PD-1 antibody molecule as described herein, includes or is used in combination with a CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224 to treat a disorder, e.g., a disorder described herein. In one embodiment, the CSF-1R tyrosine kinase inhibitor is 4-((2-(((1R,2R)-2-hydroxycyclohexyl)amino)benzo[d]thiazol-6-yl)oxy)-N-methylpicolinamide (Compound A15) or a compound disclosed in PCT Publication No. WO 2005/073224. In one embodiment, a PD-1 antibody molecule is used in combination with 4-((2-(((1R,2R)-2-hydroxycyclohexyl)amino)benzo[d]thiazol-6-yl)oxy)-N-methylpicolinamide (Compound A15) or a compound disclosed in PCT Publication No. WO 2005/073224, to treat a disorder such as cancer.

CSF-1-differentiated macrophages, sometimes referred to herein as M2 macrophages or tumor-associated macrophages (TAMs) when present in malignant tissues, are generally pro-tumorigenic, and can be characterized, e.g., by the expression of CSF-1R and CD163. In cancer, CSF-1-differentiated macrophages often reflect diminished tissue integrity and/or an adaptive process engaged by tumors to support growth (Noy and Pollard (2014) $Immunity;$ 41(1): 49-61). To exert their pro-tumorigenic activity, M2 macrophages produce an array of molecules, e.g., cytokines, chemokines, growth factors, hormones, matrix-remodeling proteases, and metabolites such as CSF-1 and CCL2, prostaglandin E2, and damage-associated molecular patterns such as high-mobility group box 1 protein, extracellular adenosine triphosphate, and degraded extracellular matrix components (Ruffell et al. (2012) $Trends\ Immunol;$ 33(3): 119-26; Zelenay et al. (2013) $Trends\ Immunol;$ 34(7):329-35). In vivo studies have revealed that M2-macrophages also mediate chemotherapy resistance by providing survival factors and/or activating anti-apoptotic programs in malignant cells. For example, CSF-1 neutralization enhances the response to chemotherapy in mammary carcinomas (DeNardo et al. (2011) $Cancer\ Discov.$ 1, 54-67). TAMs are associated with vascular endothelial growth factor signaling and are regulators of tumor angiogenesis (Murdoch et al. (2008) $Nat\ Rev\ Cancer;$ 8(8):618-31; Ruffell et al. (2012) $Trends\ Immunol;$ 33(3):119-26). M2 macrophages can also directly suppress CD8+ T cell proliferation in murine tumor models (DeNardo et al. (2011) $Cancer\ Discov.$ 1, 54-67; Doedens et al. (2010) $Cancer\ Res;$ 70(19):7465-75; Mova-hedi et al. (2010) $Cancer\ Res;$ 70(14):5728-39; Ruffell et al. (2014) $Cancer\ Cell;$ 26, 623-637). For example, macrophages directly suppress T cell responses through PD-L1 expression in hepatocellular and ovarian carcinomas (Kuang et al. (2009) $J\ Exp\ Med;$ 206(6):1327-37; Kryczek et al. (2006) $J\ Exp\ Med;$ 203(4):871-81).

Preclinical data indicate that TAMs can serve as a therapeutic target, at least in part, because they represent key orchestrators of various tumor-promoting processes, e.g., escape of immune surveillance. For example, the differentiation, migration and survival of TAMs can be regulated by CSF-1R upon engagement with the soluble CSF. CSF-1R is a member of the receptor protein tyrosine kinase family of growth factor receptors, which includes several known proto-oncogenes (Ries et al. (2014) $Cancer\ Cell$ 25(6):846-59). By interfering with the CSF-1R pathway, Compound A15 induced reduction and re-programming of M2-type macrophages in animal models of glioma, providing antitumor efficacy by removing/reprogramming the immuno suppressive TAMs. As monotherapy, CSF-1R inhibition alone impedes the growth of orthotopically implanted PDAC cell lines (Mitchem et al. (2013) $Cancer\ Res;$ 73(3):1128-41) and induces regression of glioblastoma multiforme (GBM) (Pyontech et al. (2013) $Nat\ Med;$ 19(10):1264-72).

Antitumor immunity within the tumor microenvironment can be suppressed by a variety of tumor infiltrating leukocytes, including Tregs, MDSCs and TAMs. TAMs and MDSCs can be found in large numbers in tumors and their immunomodulatory activity is often exerted locally within the tumor microenvironment. Without wishing to be bound by theory, it is believed that mechanisms employed by these cell types to suppress effective immunity include, e.g., secretion of cytokines such as IL-10 and TGF-β, and expression of inhibitory receptors, e.g., CTLA-4 and PD-L1. The removal of the TAMs and MDSCs which are important in generative immunosuppression provide, at least in part, the basis for combination strategies with checkpoint inhibitors such as anti-PD-1 therapy in those malignancies in which TAMs contribute to tumor pathogenesis. Accordingly, a CSF-1R inhibitor can enhance the clinical efficacy of a checkpoint inhibitor such as an anti-PD-1 antibody molecule, and/or induce clinical benefit, e.g., in patients with tumors showing high expression of TAMs (e.g., brain cancer (e.g., glioblastoma), breast cancer (e.g., TNBC), or pancreatic cancer) and in those who do not respond effectively to an anti-PD-1 antibody molecule as single agent.

Without wishing to be bound by theory, it is believed that in some embodiments, the CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, selectively inhibits a CSF-1R kinase activity. Compound A15 potently inhibits CSF-1R (IC$_{50}$ 1.2 nM) as determined in an in vitro kinase assay with recombinant CSF-1R kinase domain. The cellular activity of Compound A15 was shown by reducing the tyrosine-phosphorylated levels of CSF-1R in cells (EC$_{50}$pCSF-1R 58 nM) and a significant anti-proliferative effect on the macrophage colony-stimulating factor (M-CSF) dependent cell line MNFS-60 (EC$_{50}$ 71 nM). Biochemical and cellular kinase selectivity of Compound A15 has been shown with a kinase panel of more than 200 kinases and at the cellular level using auto-phosphorylation enzyme-linked immunosorbent assays (ELISA) and kinase transfected BaF3 proliferation assays. IC$_{50}$'s for a relevant subset of kinases, including related Class III RTKs cKit and PDGFRβ, were at least >3 μM. Compound A15 kinase selectivity has been confirmed at the cellular level as assessed by auto-phosphorylation assays (ECL ELISA assays) and BaF3 proliferation assays. Cellular EC$_{50}$'s for pPDGFRβ, BAF3-PDGFRβ and pcKit were ≥2

µM all other BaF3 cell lines were >10 µM while pCSF-1R and MCSF-dependent proliferation cellular $EC_{50}$ were <71 nM.

The biological effects of CSF-1R signaling include, e.g., the differentiation, proliferation, migration, and/or survival of the precursor macrophages and osteoclasts from the monocytic lineage. Without wishing to be bound by theory, it is believed that in some embodiments, a mechanism by which Compound A15 mediates anti-tumor activity via CSF-1R signaling is when tumor-associated macrophages (TAMs) are reduced or reprogrammed to a classically activated phagocytic macrophage (Pyonteck et al. (2013) *Nat Med;* 19(10):1264-72; Mao et al. (2016) *Clin Cancer Res.* March 8, DOI: 10.1158/1078-0432.CCR-15-1912, Epub ahead of print). Compound A15 (200 mg/kg daily) has been shown to induce regression of established tumors and increase survival in a genetic mouse model of glioblastoma, and slow the growth of proneural glioblastoma-derived xenografts (Pyonteck et al. (2013) *Nat Med;* 19(10):1264-72). In the genetic model (platelet derived growth factor B-driven, or PDG mice), efficacy of Compound A15 was accompanied by an apparent reprogramming from M2 to M1 phenotype. The clinical potential of Compound A15 (200 mg/kg daily for 10 days) has also been shown in an animal model of neuroblastoma (Mao et al. (2016) *Clin Cancer Res.* March 8, DOI: 10.1158/1078-0432.CCR-15-1912). This study showed that infiltrating CSF-1R+ myeloid cells are suppressive and predict poor clinical outcome in patients with neuroblastoma. The addition of Compound A15 recovered the potential of myeloid cells to stimulate human T cell proliferation (Mao et al. (2016) *Clin Cancer Res.* March 8, DOI: 10.1158/1078-0432.CCR-15-1912). Similarly, human primary monocytes were co-cultured with neuroblastoma cell lines and then shown to acquire strong suppressive capacity against autologous T cells. Addition of Compound A15 was able to inhibit the suppressive function of the tumor-educated monocytes on CD8+ and CD4+ T cells (Mao et al. (2016) *Clin Cancer Res.* March 8, DOI: 10.1158/1078-0432.CCR-15-1912).

As described in Example 6, Compound A15 was also tested in combination with an exemplary anti-PD-1 antibody molecule in the MC38 syngeneic colorectal cancer model, chosen based on the presence of TAMs and response to anti-PD-1 and shown to inhibit tumor growth and enhance survival as compared to anti-PD-1 antibody molecule alone.

In some embodiments, the CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered according to a non-continuous schedule. Preclinical data suggest that comparable antitumor activity can be achieved with certain non-continuous schedules. Experiments in rats and monkeys have shown transaminases elevation with continuous daily dosing. These transaminases elevations are generally transitory and a 7d on/7d off regimen can be selected to achieve a tolerable profile and TAMs depletion. In other embodiments, the CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered once a week. Preclinical data suggest that a once-a-week (Q1W) administration of Compound A15 performs at least as well as the daily dose in terms of TAMs depletion and anti-tumor activity. In certain embodiments, the dose of the CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, as used in the combination, is at least two (e.g., at least 3, 4, or 5) dose level below the highest investigated single agent dose for the CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224. In some embodiments, the CSF-1R tyrosine kinase inhibitor, 4-((2-(((1R, 2R)-2-hydroxycyclohexyl)amino)benzo[d]thiazol-6-yl) oxy)-N-methylpicolinamide (Compound A15), or a compound disclosed in PCT Publication No. WO 2005/073224, is administered at a dose between 50 mg and 1500 mg, e.g., between 75 mg and 1000 mg, between 100 mg and 900 mg, between 200 mg and 800 mg, between 300 mg and 700 mg, between 400 mg and 600 mg, between 100 mg and 700 mg, between 100 mg and 500 mg, between 100 mg and 300 mg, between 700 mg and 900 mg, between 500 mg and 900 mg, between 300 mg and 900 mg, between 75 mg and 150 mg, between 100 mg and 200 mg, between 200 mg and 400 mg, between 500 mg and 700 mg, or between 800 mg and 1000 mg, e.g., at a dose of 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1000 mg, e.g., daily (e.g., according to a 7 days on/7 days off schedule), or twice a week, once a week, once every two weeks, once every three weeks, or once every four weeks. In some embodiments, the CSF-1R tyrosine kinase inhibitor, 4-((2-(((1R,2R)-2-hydroxycyclohexyl) amino)benzo[d]thiazol-6-yl)oxy)-N-methylpicolinamide (Compound A15), or a compound disclosed in PCT Publication No. WO 2005/073224, is administered at a dose of 100 mg, 150 mg, 300 mg, 600 mg, or 900 mg. In other embodiments, the CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered daily, e.g., according to a 7 days on/7 days off schedule, or once a week. In some embodiments, the CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered at a dose of between 50 mg and 150 mg, e.g., about 100 mg, e.g., daily (e.g., according to a 7 days on/7 days off schedule). In other embodiments, the CSF-1R tyrosine kinase inhibitor, 4-((2-(((1R,2R)-2-hydroxycyclohexyl)amino) benzo[d]thiazol-6-yl)oxy)-N-methylpicolinamide (Compound A15), or a compound disclosed in PCT Publication No. WO 2005/073224, is administered at a dose of between 100 mg and 200 mg, e.g., about 150 mg, e.g., daily (e.g., according to a 7 days on/7 days off schedule). In other embodiments, the CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered at a dose of between 200 mg and 400 mg, e.g., about 300 mg, e.g., daily (according to a 7 days on/7 days off schedule). In other embodiments, the CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered at a dose of between 500 mg and 700 mg, e.g., about 600 mg, e.g., daily (e.g., according to a 7 days on/7 days off schedule). In other embodiments, the CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered at a dose of between 800 mg and 1000 mg, e.g., about 900 mg, e.g., daily (e.g., according to a 7 days on/7 days off schedule).

In some embodiments, the CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered at a dose of between 50 mg and 150 mg, e.g., about 100 mg, once a week. In other embodiments, the CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered at a dose of between 100 mg and 200 mg, e.g., about 150 mg, once a week. In other embodiments, the CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered at a dose of between 200 mg and 400 mg, e.g., about 300 mg, once a week. In other embodiments, the CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered at a dose of between 500 mg and 700 mg, e.g., about 600 mg, once a week. In other embodiments, the CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered at a dose of between 800 mg and 1000 mg, e.g., about 900 mg, once a week.

In some embodiments, the CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered in combination with a PD-1 inhibitor (e.g., an anti-PD-1 antibody molecule). In some embodiments, the PD-1 inhibitor (e.g., the anti-PD-1 antibody molecule) is administered at a dose between 300 mg and 500 mg (e.g., at a dose of 400 mg), e.g., once every 4 weeks. In other embodiments, the PD-1 inhibitor (e.g., the anti-PD-1 antibody molecule) is administered at a dose between 200 mg and 400 mg (e.g., at a dose of 300 mg), e.g., once every 3 weeks. In one embodiment, the CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered at a dose between 50 mg and 150 mg (e.g., about 100 mg), e.g., daily (e.g., according to a 7 days on/7 days off schedule) or once a week, e.g., orally, and the PD-1 inhibitor (e.g., the anti-PD-1 antibody molecule) is administered at a dose between 300 mg and 500 mg (e.g., at a dose of 400 mg), e.g., once every 4 weeks, or at a dose between 200 mg and 400 mg (e.g., at a dose of 300 mg), e.g., once every 3 weeks, e.g., by intravenous infusion. In another embodiment, the CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered at a dose between 100 mg and 200 mg (e.g., about 150 mg), e.g., daily (e.g., according to a 7 days on/7 days off schedule) or once a week, e.g., orally, and the PD-1 inhibitor (e.g., the anti-PD-1 antibody molecule) is administered at a dose between 300 mg and 500 mg (e.g., at a dose of 400 mg), e.g., once every 4 weeks, or at a dose between 200 mg and 400 mg (e.g., at a dose of 300 mg), e.g., once every 3 weeks, e.g., by intravenous infusion. In another embodiment, the CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered at a dose between between 200 mg and 400 mg (e.g., about 300 mg), e.g., daily (e.g., according to a 7 days on/7 days off schedule) or once a week, e.g., orally, and the PD-1 inhibitor (e.g., the anti-PD-1 antibody molecule) is administered at a dose between 300 mg and 500 mg (e.g., at a dose of 400 mg), e.g., once every 4 weeks, or at a dose between 200 mg and 400 mg (e.g., at a dose of 300 mg), e.g., once every 3 weeks, e.g., by intravenous infusion. In another embodiment, the CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered at a dose between 500 mg and 700 mg (e.g., about 600 mg), e.g., daily (e.g., according to a 7 days on/7 days off schedule) or once a week, e.g., orally, and the PD-1 inhibitor (e.g., the anti-PD-1 antibody molecule) is administered at a dose between 300 mg and 500 mg (e.g., at a dose of 400 mg), e.g., once every 4 weeks, or at a dose between 200 mg and 400 mg (e.g., at a dose of 300 mg), e.g., once every 3 weeks, e.g., by intravenous infusion. In another embodiment, the CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered at a dose between 800 mg and 1000 mg (e.g., about 900 mg), e.g., daily (e.g., according to a 7 days on/7 days off schedule) or once a week, e.g., orally, and the PD-1 inhibitor (e.g., the anti-PD-1 antibody molecule) is administered at a dose between 300 mg and 500 mg (e.g., at a dose of 400 mg), e.g., once every 4 weeks, or at a dose between 200 mg and 400 mg (e.g., at a dose of 300 mg), e.g., once every 3 weeks, e.g., by intravenous infusion.

In some embodiments, the CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered orally. In some embodiments, the anti-PD-1 antibody molecule is administered intravenously. In some embodiments, the anti-PD-1 antibody molecule is administered via intravenous infusion, e.g., over a period of 15 minutes to 3 hours, e.g., over a period of 30 minutes to 2 hours, e.g., over a period of 30 minutes, 1 hour, 1.5 hour, or 2 hours. In certain embodiments, the CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered prior to the administration of the anti-PD-1 antibody molecule, e.g., whilst fasting. For example, the administration of the anti-PD-1 antibody molecule can start any time after the administration of the CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224.

In certain embodiments, the CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered in combination with the PD-1 inhibitor (e.g., the anti-PD-1 antibody molecule) to treat a cancer, e.g., a solid tumor (e.g., an advanced solid tumor). Exemplary cancers that can be treated by the combination include, but are not limited to, a brain cancer (e.g., glioblastoma multiforme (GBM), e.g., recurrent glioblastoma), a breast cancer (e.g., a triple-negative breast cancer (e.g., NTBC)), or a pancreatic cancer (e.g., advanced pancreatic cancer). The common features of these cancers include, e.g., a tumor biology characterized by high levels of TAMs in the tumor microenvironment that may contribute to immune evasion and immune suppression. In some embodiments, blockade of CSF-1R in conjunction with an anti-PD-1 therapy can, e.g., promote re-programming of TAMs and/or remove immune suppression of tumor infiltrating lymphocytes (TIL).

In another embodiment, the combination, e.g., a combination comprising an anti-PD-1 antibody molecule as described herein, includes or is used in combination with an apoptosis inducer and/or an angiogenesis inhibitor, such as Imatinib mesylate (also known as GLEEVEC®; Compound A16) or a compound disclosed in PCT Publication No. WO1999/003854 to treat a disorder, e.g., a disorder described. In one embodiment, the apoptosis inducer and/or an angiogenesis inhibitor is Imatinib mesylate (Compound A16) or a compound disclosed in PCT Publication No. WO1999/003854. In one embodiment, a PD-1 antibody molecule is used in combination with Imatinib mesylate (Compound A16), or a compound disclosed in PCT Publication No. WO1999/003854, to treat a disorder such as a cancer, a multiple myeloma, a prostate cancer, a non-small cell lung cancer, a lymphoma, a gastric cancer, a melanoma, a breast cancer, a pancreatic cancer, a digestive/gastrointestinal cancer, a colorectal cancer, a glioblastoma multiforme, a liver cancer, a head and neck cancer, asthma, multiple sclerosis, allergy, Alzheimer's dementia, amyotrophic lateral sclerosis, or rheumatoid arthritis.

In certain embodiments, Imatinib mesylate (Compound A16) is administered at a dose of about 100 to 1000 mg, e.g., about 200 mg to 800 mg, about 300 mg to 700 mg, or about 400 mg to 600 mg, e.g., about 200 mg, 300 mg, 400 mg, 500 mg, 600 mg, or 700 mg. The dosing schedule can vary from e.g., every other day to daily, twice or three times a day. In one embodiment, Imatinib mesylate is administered at an oral dose from about 100 mg to 600 mg daily, e.g., about 100 mg, 200 mg, 260 mg, 300 mg, 400 mg, or 600 mg daily.

In another embodiment, the combination, e.g., a combination comprising an anti-PD-1 antibody molecule as described herein, includes or is used in combination with a JAK inhibitor, 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514, to treat a disorder, e.g., a disorder described herein. In one embodiment, the JAK inhibitor is 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514. In one embodiment, a PD-1 antibody molecule is used in combination with 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514, to treat a disorder such as colorectal cancer, myeloid leukemia, hematological cancer, autoimmune disease, non-Hodgkin lymphoma, or thrombocythemia.

In one embodiment, the JAK inhibitor or a 2-fluoro-N-methyl-4-(7-(quinolin-6-ylmethyl)imidazo[1,2-b][1,2,4]triazin-2-yl)benzamide (Compound A17), or a dihydrochloric salt thereof is administered at a dose of about 400-600 mg (e.g., per day), e.g., about 400, 500, or 600 mg, or about 400-500 or 500-600 mg.

In another embodiment, the combination, e.g., a combination comprising an anti-PD-1 antibody molecule as described herein, includes or is used in combination with a JAK inhibitor, Ruxolitinib Phosphate (also known as JAKAFI; Compound A18) or a compound disclosed in PCT Publication No. WO 2007/070514 to treat a disorder, e.g., a disorder described herein. In one embodiment, the JAK inhibitor is Ruxolitinib Phosphate (Compound A18) or a compound disclosed in PCT Publication No. WO 2007/070514. In one embodiment, a PD-1 antibody molecule is used in combination with Ruxolitinib Phosphate (Compound A18), or a compound disclosed in PCT Publication No. WO 2007/070514, to treat a disorder such as a prostate cancer, a lymphocytic leukemia, a multiple myeloma, a lymphoma, a lung cancer, a leukemia, cachexia, a breast cancer, a pancreatic cancer, rheumatoid arthritis, psoriasis, a colorectal cancer, a myeloid leukemia, a hematological cancer, an autoimmune disease, a non-Hodgkin lymphoma, or thrombocythemia.

In one embodiment, the JAK inhibitor or Ruxolitinib Phosphate (Compound A18) is administered at a dose of about 15-25 mg, e.g., twice daily. In some embodiments, the dose is about 15, 20, or 25 mg, or about 15-20 or 20-25 mg.

In another embodiment, the combination, e.g., a combination comprising an anti-PD-1 antibody molecule as described herein, includes or is used in combination with a deacetylase (DAC) inhibitor, Panobinostat (Compound A19), or a compound disclosed in PCT Publication No. WO 2014/072493 to treat a disorder, e.g., a disorder described herein. In one embodiment, the DAC inhibitor is Panobinostat (Compound A19) or a compound disclosed in PCT Publication No. WO 2014/072493. In one embodiment, a PD-1 antibody molecule is used in combination with Panobinostat (Compound A19), a compound disclosed in PCT Publication No. WO 2014/072493, to treat a disorder such as a colorectal cancer, a small cell lung cancer, a respiratory/thoracic cancer, a prostate cancer, a multiple myeloma, myelodysplastic syndrome, a bone cancer, a non-small cell lung cancer, an endocrine cancer, a lymphoma, a neurologic cancer, a leukemia, HIV/AIDS, an immune disorder, transplant rejection, a gastric cancer, a melanoma, a breast cancer (e.g., a triple negative breast cancer (TNBC)), a pancreatic cancer, a colorectal cancer, a glioblastoma multiforme, a myeloid leukemia, a hematological cancer, a renal cancer, a non-Hodgkin lymphoma, a head and neck cancer, a hematopoiesis disorders, or a liver cancer. In some embodiments, the cancer is chosen from a colorectal cancer (e.g., a microsatellite stable colorectal cancer (MSS CRC), a lung cancer (e.g., a non-small cell lung cancer), or a breast cancer (e.g., a triple negative lung cancer (TNBC)).

In some embodiments, the deacetylase (DAC) inhibitor, Panobinostat (Compound A19), or a compound disclosed in PCT Publication No. WO 2014/072493, is an inhibitor of histone deacetylases (HDACs). Without wishing to be bound by theory, it is believed that in some embodiments, the deacetylase (DAC) inhibitor, Panobinostat (Compound A19), or a compound disclosed in PCT Publication No. WO 2014/072493 belongs to a cinnamic hydroxamic acid class of compounds and is a pan-inhibitor of Class I, II, and IV histone (and non-histone) DACs (HDACs). These HDACs are epigenetic modulators and important cancer targets due to the dysregulation of these enzymes in many types of tumors. DAC enzymes also target lysine groups on various non-histone proteins such as p53, α-tubulin, Hsp90, and HIF1-α. Thus, in certain embodiments, the deacetylase (DAC) inhibitor, Panobinostat (Compound A19), or a compound disclosed in PCT Publication No. WO 2014/072493, is a pan-DAC inhibitor. The deacetylase (DAC) inhibitor, Panobinostat (Compound A19), or a compound disclosed in PCT Publication No. WO 2014/072493, can offer a multi-faceted approach for the inhibition of cancer cell proliferation and/or survival, e.g., through its effects on histone acetylation, gene expression, and/or the oncogenic function of non-histone proteins such as Hsp90. Panobinostat (Compound A19), e.g., as a pan-HDAC inhibitor, is highly effective at inhibiting the HDAC activity of the majority of class I, IIa, IIIb, and IV isoforms at low nanomolar concentrations.

In some embodiments, the combination described herein includes a deacetylase (DAC) inhibitor, Panobinostat (Compound A19), or a compound disclosed in PCT Publication No. WO 2014/072493, and an inhibitor of an immune checkpoint molecule, e.g., an inhibitor of PD-1 (e.g., an anti-PD-1 antibody molecule).

Without wishing to be bound by theory, it is believed that in some embodiments, epigenetic modifiers, such as HDAC inhibitors, can be used to enhance immunotherapy. Panobinostat (Compound A19) enhanced expression of the PD-L1 gene in melanoma cell lines, cultured melanoma biopsy material, and in tumor-bearing mice. Panobinostat (Compound A19) also modestly improved responses to treatment with a PD-1 inhibitor in mice (Woods et al. (2015) *Cancer Immunol. Res. p.* 1375-85). Clinical data indicate that epigenetic modifiers, including the combination of an HDAC inhibitor with a DNMT inhibitor, are active in some patients with NSCLC (Juergens et al. (2011) *Cancer Discov.* p. 598-607). Preclinical data indicate that immunotherapies such as PD-1 or CTLA-4 inhibitors can augment this activity (Kim et al. (2014) *Proc. Natl. Acad. Sci. U.S.A.* p. 11774-9). In some embodiments, the deacetylase (DAC) inhibitor, Panobinostat (Compound A19), or a compound disclosed in PCT Publication No. WO 2014/072493, enhances, or is used to enhance, an immunotherapy, e.g., an immunotherapy comprising an inhibitor of PD-1 (e.g., an anti-PD-1 antibody molecule), In some embodiments, the deacetylase (DAC) inhibitor, Panobinostat (Compound A19), or a compound disclosed in PCT Publication No. WO 2014/072493, and the inhibitor of an immune checkpoint molecule, e.g., an inhibitor of PD-1 (e.g., an anti-PD-1 antibody molecule), each is administered at a dose and/or on a time schedule, that in combination, achieves a desired anti-tumor activity.

In some embodiments, the approved dose for Panobinostat (Compound A19) in multiple myeloma is 20 mg every other day three times a week (TIW), two weeks on/one week off Panobinostat (Compound A19) for a 21 day cycle. In other embodiments, a less frequent administration schedule of one week on/one week off for a 28 day cycle has also been tested in patients with myeloma using doses of 30 mg-60 mg TIW. In certain embodiments, the deacetylase (DAC) inhibitor, Panobinostat (Compound A19), or a compound disclosed in PCT Publication No. WO 2014/072493, is administered at a dose of 10 mg TIW on the one week on/one week off schedule, e.g., in combination with an inhibitor of PD-1 (e.g., an anti-PD-1 antibody molecule). The dose and schedule can be increased to the regimen of 20 mg TIW, two weeks on/one week off, if feasible based on the safety and tolerability of the lower dose and less frequent schedule. If the dose of 10 mg TIW on the one week on/one week off schedule is unacceptably toxic, a lower dose or less frequent schedule can be used.

In one embodiment, the DAC inhibitor, Panobinostat (Compound A19), or a compound disclosed in PCT Publication No. WO 2014/072493 is administered at a dose of about 20 mg (e.g., per day).

In one embodiment, the DAC inhibitor, Panobinostat (Compound A19), or a compound disclosed in PCT Publication No. WO 2014/072493, is administered at a dose between 2 mg and 30 mg, between 5 mg and 20 mg, or between 10 mg and 15 mg, e.g., 2 mg, 5 mg, 10 mg, 15 mg, 20 mg, 25 mg, or 30 mg, e.g., once daily, three times in a week, or once weekly, e.g., on the schedule of one week on/one week off, one week on/three weeks off, or two weeks on/one week off. In one embodiment, the DAC inhibitor or Panobinostat (Compound A19) is administered at a dose of between 5 mg and 15 mg, e.g., about 10 mg, e.g., three times in a week, e.g., on the schedule of one week on/three weeks off or one week on/one week off. In another embodiment, the DAC inhibitor or Panobinostat (Compound A19) is administered at a dose of between 15 mg and 25 mg, e.g., 20 mg, e.g., three times in a week, e.g., on the schedule of two weeks on/three week off.

In some embodiments, the DAC inhibitor, Panobinostat (Compound A19), or a compound disclosed in PCT Publication No. WO 2014/072493, is administered orally.

In one embodiment, the DAC inhibitor, Panobinostat (Compound A19), or a compound disclosed in PCT Publication No. WO 2014/072493, is administered at a dose between 5 mg and 15 mg (e.g., at a dose of 10 mg), e.g., three times in a week (e.g., on the schedule of one week on/three weeks off or one week on/one week off), e.g., orally, and the PD-1 inhibitor (e.g., the anti-PD-1 antibody molecule) is administered at a dose between 300 mg and 500 mg (e.g., at a dose of 400 mg), e.g., once every 4 weeks, e.g., by intravenous infusion.

In one embodiment, the DAC inhibitor, Panobinostat (Compound A19), or a compound disclosed in PCT Publication No. WO 2014/072493, is administered in combination with the PD-1 inhibitor (e.g., the anti-PD-1 antibody molecule) to treat a colorectal cancer (e.g., an MSS CRC), a lung cancer (e.g., a non-small cell lung cancer (NSCLC), or a breast cancer (e.g., a triple negative breast cancer (TNBC)).

In another embodiment, the combination, e.g., a combination comprising an anti-PD-1 antibody molecule as described herein, includes or is used in combination with an inhibitor of one or more of cytochrome P450 (e.g., 11B2), aldosterone or angiogenesis, Osilodrostat (Compound A20), or a compound disclosed in PCT Publication No. WO2007/024945 to treat a disorder, e.g., a disorder described herein. In one embodiment, the inhibitor of one or more of cytochrome P450 (e.g., 11B2), aldosterone or angiogenesis is Osilodrostat (Compound A20) or a compound disclosed in PCT Publication No. WO2007/024945. In one embodiment, a PD-1 antibody molecule is used in combination with Osilodrostat (Compound A20), or a compound disclosed in PCT Publication No. WO2007/024945, to treat a disorder such as Cushing's syndrome, hypertension, or heart failure therapy.

In another embodiment, the combination, e.g., a combination comprising an anti-PD-1 antibody molecule as described herein, includes or is used in combination with a IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003 to treat a disorder, e.g., a disorder described herein. In one embodiment, the IAP inhibitor is (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003. In one embodiment, a PD-1 antibody molecule is used in combination with (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, to treat a disorder such as a multiple myeloma, a colorectal cancer (CLC), a lung cancer (e.g., non-small cell lung cancer (NSCLC), a breast cancer (e.g., a triple-negative breast cancer (TNBC)), an ovarian cancer, a pancreatic cancer, or a hematopoiesis disorder. In some embodiments, the cancer is chosen from a colorectal cancer (e.g., a microsatellite stable colorectal cancer (MSS CRC), a lung cancer (e.g., a non-small cell lung cancer), or a breast cancer (e.g., a triple negative lung cancer (TNBC)).

In some embodiments, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, is an oral small molecule SMAC-mimetic that binds to the BIR3 domain of CIAP1, XIAP, and optionally CIAP2. The CIAP1 and CIAP2 proteins are components of TNF death receptor family protein complexes. Without wishing to be bound by theory, it is believed that in some embodiments, binding of the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, can activate an E3 ligase function of CIAP1, induce ubiquitination and proteosomal degradation of CIAP1, and/or activate NF-κB signaling downstream of the receptors (Gyrd-Hansen M, Meier P (2010) Nat. Rev. Cancer p. 561-74). In some embodiments, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, is used for increasing antitumor immunity in a subject. For example, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, can enhance human and mouse T cell proliferation and function in vitro after co-stimulation, and/or response to prophylactic and therapeutic antitumor vaccines in vivo, e.g., through activation of NF-κB (Dougan et al. (2010) J. Exp. Med. p. 2195-206). NF-κB activity is involved in cross-priming of T cells during immunogenic cell death in response to release of danger-associated inflammatory molecules (Yatim et al. (2015) Science p. 328-34), indicating a mechanism for enhancing T cell function and anti-tumor immunity. As another example, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, can protect monocyte-derived dendritic cells from apoptosis, similar to CD40 ligation (Knights et al. (2013) Cancer Immunol. Immunother. p. 321-35).

In some embodiments, the combination described herein includes an IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, and an inhibitor of an immune checkpoint molecule, e.g., an inhibitor of PD-1 (e.g., an anti-PD-1 antibody molecule).

Without wishing to be bound by theory, it is believed that in some embodiments, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003, is an orally available small molecule that activates NF-kB signaling downstream of TNF receptor family members. NF-κB is a master regulator of transcription in immune cells, and also acts in tumor cells directly (Perkins (2012) Nat. Rev. Cancer p. 121-32). Preclinical data suggest that NF-κB activity is required for cross-priming of CD8+ T lymphocytes undergoing immunogenic cell death (Yatim et al. (2015) Science p. 328-34). Compound A21 stimulated proliferation of T lymphocytes, induced IFNgamma, and suppressed production of IL-10 in vitro. Clinical studies with Compound A21 demonstrated induction of circulating cytokines including TNFalpha, IL-8, IL-10 and CCL2 (Infante et al. (2014) J. Clin. Oncol. p. 3103-10). Clinical data suggest that Compound A21 increased the rate of pathological complete response of TNBC to treatment with paclitaxel. In some embodiments, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, enhances, or is used to enhance, an anti-tumor activity of the inhibitor of PD-1 (e.g., an anti-PD-1 antibody molecule).

In some embodiments, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, and the inhibitor of an immune checkpoint molecule, e.g., an inhibitor of PD-1 (e.g., an anti-PD-1 antibody molecule), each is administered at a dose and/or on a time schedule, that in combination, achieves a desired anti-tumor activity.

Without wishing to be bound by theory, it is believed that doses for the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, equal to or lower than 1800 mg are active, e.g., based on pharmacodynamic data. For example, in paired skin biopsies of two patients treated at 320 mg, both showed degradation of CIAP1, the protein targeted by Compound A21; skin biopsies collected from patients treated at lower doses (160 mg and below) showed less consistent pharmacodynamic activity (Infante et al. (2014) J. Clin. Oncol. p. 3103-10). In some embodiments, doses higher than 900 mg are not required for clinical efficacy. In certain situations, a dose of Compound A21 at 1800 mg was poorly tolerated when given in combination with paclitaxel. Accordingly, in one embodiment, the IAP inhibitor, (S)—N-0S)-1-cyclohexyl-2-0S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, is administered at a dose between of 300 mg and 900 mg, e.g., once a week. In some embodiments, the IAP inhibitor, (S)—N—((S)-1-cyclohexyl-2-0S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, is administered less frequently than once a week, e.g., is administered once every two weeks, once every three weeks, or once every four weeks.

In one embodiment, the IAP inhibitor or (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003 is administered at a dose of approximately 1800 mg or less, e.g., once weekly.

In some embodiments, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, is administered at a dose between about 160 mg and about 1800 mg, between about 200 mg and about 1200 mg, between about 300 mg and about 900 mg, between 400 mg and about 800 mg, or between about 500 mg and about 700 mg, e.g., at a dose about 300 mg, about 400 mg, about 500 mg, about 600 mg, about 700 mg, about 800 mg, or about 900 mg, e.g., once a week, once every two weeks, once every three weeks, or once every four weeks.

In certain embodiments, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, is administered at a dose of between about 200 mg and about 400 mg, e.g., about 300 mg, once weekly. In other embodiments, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, is administered at a dose of between about 800 mg and about 1000 mg, e.g., about 900 mg, once a week. In some embodiments, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, is administered at a dose of between about 200 mg and about 400 mg, e.g., about 300 mg, once every four weeks.

In certain embodiments, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, is administered orally.

In some embodiments, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, is administered in combination with a PD-1 inhibitor (e.g., an anti-PD-1 antibody molecule). In one embodiment, the IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, is administered at a dose between 200 mg and 400 mg (e.g., at a dose of 300 mg), e.g., once a week, e.g., orally, and the PD-1 inhibitor (e.g., the anti-PD-1 antibody molecule) is administered at a dose between 300 mg and 500 mg (e.g., at a dose of 400 mg), e.g., once every 4 weeks, e.g., by intravenous infusion.

In certain embodiments, the IAP inhibitor, e.g., (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003, is administered in combination with the PD-1 inhibitor (e.g., the anti-PD-1 antibody molecule) to treat colorectal cancer (e.g., MSS CRC), lung cancer (e.g., non-small cell lung cancer (NSCLC)), or breast cancer (e.g., triple-negative breast cancer (e.g., NTBC)).

In another embodiment, the combination, e.g., a combination comprising an anti-PD-1 antibody molecule as described herein, includes or is used in combination a Smoothened (SMO) inhibitor, Sonidegib phosphate (Compound A22), (R)-2-(5-(4-(6-benzyl-4,5-dimethylpyridazin-3-yl)-2-methylpiperazin-1-yl)pyrazin-2-yl)propan-2-ol (Compound A25), or a compound disclosed in PCT Publication No. WO 2007/131201 or WO 2010/007120 to treat a disorder, e.g., a disorder described herein. In one embodiment, the SMO inhibitor is Sonidegib phosphate (Compound A22), (R)-2-(5-(4-(6-benzyl-4,5-dimethylpyridazin-3-yl)-2-methylpiperazin-1-yl)pyrazin-2-yl)propan-2-ol (Compound A25), or a compound disclosed in PCT Publication No. WO 2007/131201 or WO 2010/007120. In one embodiment, a PD-1 antibody molecule is used in combination with Sonidegib phosphate (Compound A22), (R)-2-(5-(4-(6-benzyl-4,5-dimethylpyridazin-3-yl)-2-methylpiperazin-1-yl)pyrazin-2-yl)propan-2-ol (Compound A25), or a compound disclosed in PCT Publication No. WO 2007/131201 or WO 2010/007120 to treat a disorder such as a cancer, a medulloblastoma, a small cell lung cancer, a prostate cancer, a basal cell carcinoma, a pancreatic cancer, or an inflammation.

In certain embodiments, Sonidegib phosphate (Compound A22) is administered at a dose of about 20 to 500 mg, e.g., about 40 mg to 400 mg, about 50 mg to 300 mg, or about 100 mg to 200 mg, e.g., about 50 mg, 100 mg, 150 mg, 200 mg, 250 mg, or 300 mg. The dosing schedule can vary from e.g., every other day to daily, twice or three times a day.

In another embodiment, the combination, e.g., a combination comprising an anti-PD-1 antibody molecule as described herein, includes or is used in combination with an Alk inhibitor, ceritinib (also known as ZYKADIA; Compound A23) or a compound disclosed in PCT Publication No. WO 2007/131201 to treat a disorder, e.g., a disorder described herein. In one embodiment, the Alk inhibitor is ceritinib (Compound A23) or a compound disclosed in PCT Publication No. WO 2007/131201. In one embodiment, a PD-1 antibody molecule is used in combination with ceritinib (Compound A23), or a compound disclosed in PCT Publication No. WO 2007/131201, to treat a disorder such as non-small cell lung cancer or solid tumors.

In one embodiment, the Alk inhibitor or ceritinib (Compound A23) is administered at a dose of approximately 750 mg, e.g., once daily.

In another embodiment, the combination, e.g., a combination comprising an anti-PD-1 antibody molecule as described herein, includes or is used in combination with a JAK and/or CDK4/6 inhibitor, 7-cyclopentyl-N,N-dimethyl-2-((5-(piperazin-1-yl)pyridin-2-yl)amino)-7H-pyrrolo[2,3-d]pyrimidine-6-carboxamide (Compound A24), or a compound disclosed in U.S. Pat. No. 8,415,355 or U.S. Pat. No. 8,685,980 to treat a disorder, e.g., a disorder described herein. In one embodiment, the JAK and/or CDK4/6 inhibitor is 7-cyclopentyl-N,N-dimethyl-2-((5-(piperazin-1-yl)pyridin-2-yl)amino)-7H-pyrrolo[2,3-d]pyrimidine-6-carboxamide (Compound A24) or a compound disclosed in U.S. Pat. No. 8,415,355 or U.S. Pat. No. 8,685,980. In one embodiment, a PD-1 antibody molecule is used in combination with 7-cyclopentyl-N,N-dimethyl-2-((5-(piperazin-1-yl)pyridin-2-yl)amino)-7H-pyrrolo[2,3-d]pyrimidine-6-carboxamide (Compound A24), or a compound disclosed in U.S. Pat. No. 8,415,355 or U.S. Pat. No. 8,685,980, to treat a disorder such as a lymphoma, a neurologic cancer, a melanoma, a breast cancer, or a solid tumor.

In one embodiment, the JAK and/or CDK4/6 inhibitor or 7-cyclopentyl-N,N-dimethyl-2-((5-(piperazin-1-yl)pyridin- 2-yl)amino)-7H-pyrrolo[2,3-d]pyrimidine-6-carboxamide (Compound A24) is administered at a dose of approximately 200-600 mg, e.g., per day. In one embodiment, the compound is administered at a dose of about 200, 300, 400, 500, or 600 mg, or about 200-300, 300-400, 400-500, or 500-600 mg.

In another embodiment, the combination, e.g., a combination comprising an anti-PD-1 antibody molecule as described herein, includes or is used in combination a prolactin receptor (PRLR) inhibitor, a human monoclonal antibody molecule (Compound A26) as disclosed in U.S. Pat. No. 7,867,493), to treat a disorder, e.g., a disorder described herein. In one embodiment, the PRLR inhibitor is a human monoclonal antibody (Compound A26) disclosed in U.S. Pat. No. 7,867,493. In one embodiment, a PD-1 antibody molecule is used in combination with human monoclonal antibody molecule (Compound A26) described in U.S. Pat. No. 7,867,493 to treat a disorder such as, a cancer, a prostate cancer, or a breast cancer.

In another embodiment, the combination, e.g., a combination comprising an anti-PD-1 antibody molecule as described herein, includes or is used in combination with a PIM Kinase inhibitor, N-(4-((1R,3S,5S)-3-amino-5-methyl-cyclohexyl)pyridin-3-yl)-6-(2,6-difluorophenyl)-5-fluoropi-colinamide (Compound A27) or a compound disclosed in PCT Publication No. WO 2010/026124 to treat a disorder, e.g., a disorder described herein. In one embodiment, the PIM Kinase inhibitor is N-(4-((1R,3S,5S)-3-amino-5-meth-ylcyclohexyl)pyridin-3-yl)-6-(2,6-difluorophenyl)-5-fluo-ropicolinamide (Compound A27) or a compound disclosed in PCT Publication No. WO 2010/026124. In one embodiment, a PD-1 antibody molecule is used in combination with N-(4-((1R,3S,5S)-3-amino-5-methylcyclohexyl)pyridin-3-yl)-6-(2,6-difluorophenyl)-5-fluoropicolinamide (Compound A27), or a compound disclosed in PCT Publication No. WO 2010/026124, to treat a disorder such as a multiple myeloma, myelodysplastic syndrome, a myeloid leukemia, or a non-Hodgkin lymphoma.

In another embodiment, the combination, e.g., a combination comprising an anti-PD-1 antibody molecule as described herein, includes or is used in combination a Wnt signaling inhibitor, 2-(2',3-dimethyl-[2,4'-bipyridin]-5-yl)-N-(5-(pyrazin-2-yl)pyridin-2-yl)acetamide (Compound A28) or a compound disclosed in PCT publication No. WO 2010/101849 to treat a disorder, e.g., a disorder described herein. In one embodiment, the Wnt signaling inhibitor is 2-(2',3-dimethyl-[2,4'-bipyridin]-5-yl)-N-(5-(pyrazin-2-yl) pyridin-2-yl)acetamide (Compound A28) or a compound disclosed in PCT publication No. WO 2010/101849. In one embodiment, the Wnt signaling inhibitor is 242%3-dim-ethyl-[2,4'-bipyridin]-5-yl)-N-(5-(pyrazin-2-yl)pyridin-2-yl)acetamide (Compound A28). In one embodiment, a PD-1 antibody molecule is used in combination with 2-(2',3-dimethyl-[2,4'-bipyridin]-5-yl)-N-(5-(pyrazin-2-yl)pyridin-2-yl)acetamide (Compound A28), or a compound disclosed in PCT publication No. WO 2010/101849, to treat a disorder such as a solid tumor (e.g., a head and neck cancer, a squamous cell carcinoma, a breast cancer, a pancreatic cancer, or a colon cancer). In certain embodiments, the cancer is chosen from a skin cancer (e.g., a melanoma), a microsatellite instability-high (MSI-high) solid tumor, a pancreatic cancer, or a breast cancer (e.g., a triple negative breast cancer (TNBC)).

In certain embodiments, 2-(2',3-dimethyl-[2,4'-bipyri-din]-5-yl)-N-(5-(pyrazin-2-yl)pyridin-2-yl)acetamide (Compound A28) is administered at a dose of about 1 to 50 mg, e.g., about 2 mg to 45 mg, about 3 mg to 40 mg, about 5 mg to 35 mg, 5 mg to 10 mg, or about 10 mg to 30 mg, e.g., about 2 mg, 5 mg, 10 mg, 20 mg, 30 mg, or 40 mg. The dosing schedule can vary from e.g., every other day to daily, twice or three times a day.

In another embodiment, the combination, e.g., a combination comprising an anti-PD-1 antibody molecule as described herein, includes or is used in combination with a BRAF inhibitor, Encorafenib (Compound A29), or a compound disclosed in PCT Publication No. WO 2011/025927 to treat a disorder, e.g., a disorder described herein. In one embodiment, the BRAF inhibitor is Encorafenib (Compound A29) or a compound disclosed in PCT Publication No. WO 2011/025927. In one embodiment, a PD-1 antibody molecule is used in combination with Encorafenib (Compound A29), or a compound disclosed in PCT Publication No. WO 2011/025927, to treat a disorder such as a non-small cell lung cancer, a melanoma, or a colorectal cancer.

In one embodiment, the BRAF inhibitor or Encorafenib (Compound A29) is administered at a dose of about 200-300, 200-400, or 300-400 mg, e.g., per day. In one embodiment, the compound is administered at a dose of about 200, about 300 or about 400 mg.

In another embodiment, the combination, e.g., a combination comprising an anti-PD-1 antibody molecule as described herein, includes or is used in combination a CDK4/6 inhibitor, 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-car-boxamide (Compound A30), or a compound disclosed in PCT publication No. WO 2011/101409 to treat a disorder, e.g., a disorder described herein. In one embodiment, the CDK4/6 inhibitor is 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-car-boxamide (Compound A30) or a compound disclosed in PCT publication No. WO 2011/101409. In one embodiment, a PD-1 antibody molecule is used in combination with 7-cyclopentyl-N,N-dimethyl-2-((5-((1R,6S)-9-methyl-4-oxo-3,9-diazabicyclo[4.2.1]nonan-3-yl)pyridin-2-yl) amino)-7H-pyrrolo[2,3-d]pyrimidine-6-carboxamide (Compound A30), or a compound disclosed in PCT publication No. WO 2011/101409, to treat a disorder such as a cancer, a mantle cell lymphoma, a liposarcoma, a non-small cell lung cancer, a melanoma, a squamous cell esophageal cancer, or a breast cancer.

In another embodiment, the combination, e.g., a combination comprising an anti-PD-1 antibody molecule as described herein, includes or is used in combination with a HER3 inhibitor, Compound A31, or a compound disclosed in PCT Publication No. WO 2012/022814, to treat a disorder, e.g., a disorder described herein. In one embodiment, the HER3 inhibitor is Compound A31 or a compound disclosed in PCT Publication WO 2012/022814. In one embodiment, a PD-1 antibody molecule is used in combination with Compound A31, or a compound disclosed in PCT Publication WO 2012/022814, to treat a disorder such as a gastric cancer, an esophageal cancer, a head and neck cancer, a squamous cell carcinoma, a stomach cancer, a breast cancer (e.g., metastatic breast cancer), or a digestive/gastrointestinal cancer.

In some embodiments, Compound A31 is a human monoclonal antibody molecule.

In one embodiment, the HER3 inhibitor or Compound A31 is administered at a dose of about 3, 10, 20, or 40 mg/kg, e.g., once weekly (QW). In one embodiment, the compound is administered at a dose of about 3-10, 10-20, or 20-40 mg/kg.

In another embodiment, the combination, e.g., a combination comprising an anti-PD-1 antibody molecule as described herein, includes or is used in combination in an FGFR2 and/or FGFR4 inhibitor, Compound A32, or a compound disclosed in a publication PCT Publication No. WO 2014/160160 (e.g., an antibody molecule drug conjugate against an FGFR2 and/or FGFR4, e.g., mAb 12425), to treat a disorder, e.g., a disorder described herein. In one embodiment, the FGFR2 and/or FGFR4 inhibitor is Compound A32 or a compound disclosed in a publication PCT Publication No. WO 2014/160160. In one embodiment, a PD-1 antibody molecule is used in combination with Compound A32, or a compound as described in Table 7, to treat a disorder such as a cancer, a gastric cancer, a breast cancer, a rhabdomyosarcoma, a liver cancer, an adrenal cancer, a lung cancer, an esophageal cancer, a colon cancer, or an endometrial cancer.

In some embodiments, Compound A32 is an antibody molecule drug conjugate against an FGFR2 and/or FGFR4, e.g., mAb 12425.

In another embodiment, the combination, e.g., a combination comprising an anti-PD-1 antibody molecule as described herein, includes or is used in combination an M-CSF inhibitor, Compound A33, or a compound disclosed in PCT Publication No. WO 2004/045532 (e.g., an antibody molecule or Fab fragment against M-CSF), to treat a disorder, e.g., a disorder described herein. In one embodiment, the M-CSF inhibitor is Compound A33 or a compound disclosed in PCT Publication No. WO 2004/045532. In one embodiment, a PD-1 antibody molecule is used in combination with Compound A33, or a compound as described in PCT Publication No. WO 2004/045532, to treat a disorder such as a cancer, a prostate cancer, a breast cancer, or pigmented villonodular synovitis (PVNS).

In embodiments, Compound A33 is a monoclonal antibody molecule against M-CSF or a fragment (e.g., Fab fragment) thereof. In embodiments, the M-CSF inhibitor or Compound A33 is administered at an average dose of about 10 mg/kg.

In another embodiment, the combination, e.g., a combination comprising an anti-PD-1 antibody molecule as described herein, includes or is used in combination with a MEK inhibitor, Binimetinib (Compound A34), or a compound disclosed in PCT Publication No. WO 2003/077914 to treat a disorder, e.g., a disorder described herein. In one embodiment, the MEK inhibitor is Binimetinib (Compound A34), or a compound disclosed in PCT Publication No. WO 2003/077914. In one embodiment, a PD-1 antibody molecule is used in combination with Binimetinib (Compound A34), or a compound disclosed in PCT Publication No. WO 2003/077914, to treat a disorder such as a non-small cell lung cancer, a multisystem genetic disorder, a melanoma, an ovarian cancer, a digestive/gastrointestinal cancer, a rheumatoid arthritis, or a colorectal cancer.

In one embodiment, the MEK inhibitor or Binimetinib (Compound A34) is administered at a dose of about 45 mg, e.g., twice daily.

In another embodiment, the combination, e.g., a combination comprising an anti-PD-1 antibody molecule as described herein, includes or is used in combination an inhibitor of one or more of c-KIT, histamine release, Flt3 (e.g., FLK2/STK1) or PKC, Midostaurin (Compound A35) or a compound disclosed in PCT Publication No. WO 2003/037347 to treat a disorder, e.g., a disorder described herein. In one embodiment, the inhibitor is Midostaurin (Compound A35) or compound disclosed in PCT Publication No. WO 2003/037347. In one embodiment, the inhibitor of one or more of c-KIT, histamine release, Flt3 (e.g., FLK2/STK1) or PKC is Midostaurin. In one embodiment, a PD-1 antibody molecule is used in combination with Midostaurin (Compound A35), or compound disclosed in PCT Publication No. WO 2003/037347, to treat a disorder such as a cancer, a colorectal cancer, a myeloid leukemia, myelodysplastic syndrome, an age-related mascular degeration, a diabetic complication, or a dermatologic disorder.

In another embodiment, the combination, e.g., a combination comprising an anti-PD-1 antibody molecule as described herein, includes or is used in combination with a TOR inhibitor (e.g., mTOR inhibitor), Everolimus (also known as AFINITOR; Compound A36) or a Compound disclosed in PCT Publication No. WO 2014/085318 to treat a disorder, e.g., a disorder described herein). In one embodiment, the TOR inhibitor is Everolimus (Compound A36) or a Compound disclosed in PCT Publication No. WO 2014/085318. In one embodiment, a PD-1 antibody molecule is used in combination with Everolimus (Compound A36) to treat a disorder such as a colorectal cancer, an interstitial lung disease, a small cell lung cancer, a respiratory/thoracic cancer, a prostate cancer, a multiple myeloma, a sarcoma, an age-related macular degeneration, a bone cancer, tuberous sclerosis, a non-small cell lung cancer, an endocrine cancer, a lymphoma, a neurologic disorders, an astrocytoma, a cervical cancer, a neurologic cancer, a leukemia, an immune disorders, transplant rejection, a gastric cancer, a melanoma, epilepsy, a breast cancer (e.g., a triple-negative breast cancer (TNBC), or a bladder cancer. In some embodiments, the cancer is chosen from a colorectal cancer (e.g., a microsatellite stable colorectal cancer (MSS CRC), a lung cancer (e.g., a non-small cell lung cancer), or a breast cancer (e.g., a triple negative lung cancer (TNBC)).

In some embodiments, the mTOR inhibitor, everolimus (Compound A36), or a compound disclosed in PCT Publication No. WO 2014/085318, inhibits mammalian target of rapamycin (mTOR), a serine-threonine kinase, downstream of the PI3K/AKT pathway. The mTOR pathway is dysregulated in several human cancers. Without wising to be bound by theory, it is believed that in some embodiments, the mTOR inhibitor, everolimus (Compound A36), or a compound disclosed in PCT Publication No. WO 2014/085318, binds to an intracellular protein, FKBP-12, resulting in an inhibitory complex formation with mTOR complex 1 (mTORC1) and thus inhibition of mTOR kinase activity. Everolimus (Compound A36) can reduce the activity of S6 ribosomal protein kinase (S6K1) and/or eukaryotic initiation factor 4E-binding protein (4E-BP1), downstream effectors of mTOR, involved in protein synthesis. S6K1 is a substrate of mTORC1 and phosphorylates the activation domain 1 of the estrogen receptor which results in ligand-independent activation of the receptor. In addition, everolimus (Compound A36) can inhibit the expression of hypoxia-inducible factor (e.g., HIF-1) and/or reduce the expression of vascular endothelial growth factor (VEGF). Inhibition of mTOR by everolimus (Compound A36) has been shown to reduce cell proliferation, angiogenesis, and glucose uptake in in vitro and/or in vivo studies. Constitutive activation of the PI3K/Akt/mTOR pathway can contribute to endocrine resistance in breast cancer. In vitro studies show that estrogen-dependent and HER2+ breast cancer cells are sensitive to the inhibitory effects of everolimus (Compound A36), and that combination treatment with everolimus and Akt, HER2, or aromatase inhibitors enhances the anti-tumor activity of everolimus (Compound A36) in a synergistic manner. Two regulators of mTORC1 signaling are the oncogene suppressors tuberin-sclerosis complexes 1 and 2 (TSC1, TSC2).

Loss or inactivation of either TSC1 or TSC2 leads to activation of downstream signaling. In TSC, a genetic disorder, inactivating mutations in either the TSC1 or the TSC2 gene lead to hamartoma formation throughout the body.

In some embodiments, the combination described herein includes the mTOR inhibitor, everolimus (Compound A36), or a compound disclosed in PCT Publication No. WO 2014/085318, and an inhibitor of an immune checkpoint molecule, e.g., an inhibitor of PD-1 (e.g., an anti-PD-1 antibody molecule).

Everolimus (Compound A36) has been used in clinics as a direct antitumor agent at the dose of 10 mg daily to repress mTOR activity in tumor cells, and as an immunosuppressant in patients requiring solid organ transplants at 1.5-2.0 mg daily to suppress T lymphocyte function. Without wishing to be bound by theory, it is believed that in some embodiments, at these doses and schedules everolimus (Compound A36) would be expected to impair an effective anti-tumor response. Immunosenescence is a decline in immune function that occurs in the elderly and includes a decreased response to vaccination, including influenza vaccination. The decline in immune function with age includes an increase in PD-1-positive "exhausted" T lymphocytes that have a diminished response to stimulation with antigen (Lages et al. (2010) *Aging Cell* 9, 785-798). Clinical data suggest a dose of 5 mg per week can be immunostimulatory, reducing the percentage of PD-1-positive CD4+ and CD8+ lymphocytes compared to placebo treatment and enhancing the response to an influenza vaccine in elderly subjects (Mannick et al. (2014) *Sci. Transl. Med.* Vol. 6, Issue 268, pp. 268ra179). In certain embodiments, an immunostimulatory dose of the mTOR inhibitor, everolimus (Compound A36), or a compound disclosed in PCT Publication No. WO 2014/085318, enhances, or is used to enhance, the antitumor activity of an inhibitor of PD-1 (e.g., an anti-PD-1 antibody molecule).

In some embodiments, the mTOR inhibitor, everolimus (Compound A36), or a compound disclosed in PCT Publication No. WO 2014/085318, and the inhibitor of an immune checkpoint molecule, e.g., an inhibitor of PD-1 (e.g., an anti-PD-1 antibody molecule), each is administered at a dose and/or on a time schedule, that in combination, achieves a desired anti-tumor activity.

In some embodiments, the dose of everolimus (Compound A36) approved for adult cancer indications (e.g. breast cancer (e.g., TNBC), renal cell carcinoma and neuroendocrine tumors (e.g., an atypical pulmonary carcinoma tumor) is 10 mg daily. Without wishing to be bound by theory, it is believed that in some embodiments, modeling and simulation based on mTOR-mediated phosphorylation of its downstream target S6 kinase (S6K) predicted that a 20 mg weekly dosing regimen inhibited mTOR-mediated S6K phosphorylation almost completely, a 5 mg weekly dosing regimen inhibited S6K phosphorylation by more than 50%, and a 0.5 mg daily dosing regimen inhibited S6K phosphorylation by about 38% over the dosing interval (Mannick et al. (2014) *Sci. Transl. Med.* Vol. 6, Issue 268, pp. 268ra179; Tanaka (2008) *J. Clin. Oncol.* p. 1596-602). Accordingly, in certain embodiments, the mTOR inhibitor, everolimus (Compound A36), or a compound disclosed in PCT Publication No. WO 2014/085318, is administered at a dose of 5 mg once weekly (QW), e.g., in combination with an inhibitor of PD-1 (e.g., an anti-PD-1 antibody molecule). In other embodiments, a dose of 0.5 mg once daily (QD) may also be used, e.g., when the dose of 5 mg once weekly (QW) is not well tolerated. In some embodiments, the mTOR inhibitor, everolimus (Compound A36), or a compound disclosed in PCT Publication No. WO 2014/085318 is administered at a dose 5 mg or less once a week.

In one embodiment, the TOR inhibitor or Everolimus (Compound A36) administered at a dose of about 2.5-20 mg/day. In one embodiment, the compound is administered at a dose of about 2.5, 5, 10, or 20 mg/day, e.g., about 2.5-5, 5-10, or 10-20 mg/day.

In one embodiment, the mTOR inhibitor, Everolimus (Compound A36), or a compound disclosed in PCT Publication No. WO 2014/085318, is administered at a dose between 1 mg and 10 mg, between 2 mg and 8 mg, between 3 mg and 7 mg, or between 4 mg and 6 mg, e.g., at a dose of 1 mg, 2 mg, 3 mg, 4 mg, 5 mg, 6 mg, 7 mg, 8 mg, 9 mg, or 10 mg, e.g., once weekly, once every two weeks, once every three weeks, or once every four weeks. In one embodiment, the mTOR inhibitor, Everolimus (Compound A36), or a compound disclosed in PCT Publication No. WO 2014/085318, is administered at a dose of between 4 mg and 6 mg, e.g., 5 mg, e.g., once weekly.

In another embodiment, the mTOR inhibitor, Everolimus (Compound A36), or a compound disclosed in PCT Publication No. WO 2014/085318, is administered at a dose between 0.1 mg and 1 mg, between 0.2 mg and 0.8 mg, between 0.3 mg and 0.7 mg, or between 0.4 mg and 0.6 mg, e.g., 0.1 mg, 0.2 mg, 0.3 mg, 0.4 mg, 0.5 mg, 0.6 mg, 0.7 mg, 0.8 mg, 0.9 mg, or 1 mg, e.g., once daily or once weekly.

In some embodiments, the mTOR inhibitor, Everolimus (Compound A36), or a compound disclosed in PCT Publication No. WO 2014/085318, is administered orally.

In some embodiments, the mTOR inhibitor, Everolimus (Compound A36), or a compound disclosed in PCT Publication No. WO 2014/085318, is administered at a dose between 2 mg and 8 mg (e.g., at a dose of 5 mg), e.g., once a week, e.g., orally, and the PD-1 inhibitor (e.g., the anti-PD-1 antibody molecule) is administered at a dose between 300 mg and 500 mg (e.g., at a dose of 400 mg), e.g., once every 4 weeks, e.g., by intravenous infusion.

In some embodiments, the mTOR inhibitor, Everolimus (Compound A36), or a compound disclosed in PCT Publication No. WO 2014/085318, is administered in combination with the PD-1 inhibitor (e.g., the anti-PD-1 antibody molecule) to treat a colorectal cancer (e.g., an MSS CRC), a lung cancer (e.g., a non-small cell lung cancer (NSCLC)), or a breast cancer (e.g., a triple negative breast cancer (NTBC)).

In another embodiment, the combination, e.g., a combination comprising an anti-PD-1 antibody molecule as described herein, includes or is used in combination an inhibitor of one or more of VEGFR-2, PDGFRbeta, KIT or Raf kinase C, 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37) or a compound disclosed in PCT Publication No. WO 2007/030377 to treat a disorder, e.g., a disorder described herein. In one embodiment, the inhibitor of one or more of VEGFR-2, PDGFRbeta, KIT or Raf kinase C is 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37) or a compound disclosed in PCT Publication No. WO 2007/030377. In one embodiment, a PD-1 antibody molecule is used in combination with 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37), or a compound disclosed in PCT Publication No. WO 2007/030377, to treat a disorder such as a cancer, a melanoma, or a solid tumor.

In another embodiment, the combination, e.g., a combination comprising an anti-PD-1 antibody molecule as described herein, includes or is used in combination a somatostatin agonist and/or growth hormone release inhibitor, Pasireotide diaspartate (also known as SIGNIFOR; Compound A38) or a compound disclosed in PCT Publication No. WO2002/010192 or U.S. Pat. No. 7,473,761 to treat a disorder, e.g., a disorder described herein. In one embodiment, the somatostatin agonist and/or growth hormone release inhibitor is Pasireotide diaspartate (Compound A38) or a compound disclosed in PCT Publication No. WO2002/010192 or U.S. Pat. No. 7,473,761. In one embodiment, a PD-1 antibody molecule is used in combination with Pasireotide diaspartate (Compound A38), or a compound disclosed in PCT Publication No. WO2002/010192 or U.S. Pat. No. 7,473,761, to treat a disorder such as a prostate cancer, an endocrine cancer, a neurologic cancer, a neuroendocrine tumor (NET) (e.g., an atypical pulmonary carcinoid tumor), a skin cancer (e.g., a melanoma or Merkel cell carcinoma), a pancreatic cancer, a liver cancer, Cushing's syndrome, a gastrointestinal disorder, acromegaly, a liver and biliary tract disorder, or liver cirrhosis.

In another embodiment, the combination, e.g., a combination comprising an anti-PD-1 antibody molecule as described herein, includes or is used in combination a signal transduction modulator and/or angiogenesis inhibitor, Dovitinib (Compound A39) or a compound disclosed in PCT Publication No. WO 2009/115562 to treat a disorder, e.g., a disorder described herein. In one embodiment, the signal transduction modulator and/or angiogenesis inhibitor is Dovitinib (Compound A39) or a compound disclosed in PCT Publication No. WO 2009/115562. In one embodiment, a PD-1 antibody molecule is used in combination with Dovitinib (Compound A39), or a compound disclosed in PCT Publication No. WO 2009/115562, to treat a disorder such as a cancer, a respiratory/thoracic cancer, a multiple myeloma, a prostate cancer, a non-small cell lung cancer, an endocrine cancer, or a neurological genetic disorder.

In another embodiment, the combination, e.g., a combination comprising an anti-PD-1 antibody molecule as described herein, includes or is used in combination with an EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40) or a compound disclosed in PCT Publication No. WO 2013/184757 to treat a disorder, e.g., a disorder described herein. In one embodiment, the EGFR inhibitor is (R,E)-N-(7-chloro-1-(1-(4-(dimethylamino) but-2-enoyl)azepan-3-yl)-1H-benzo[d]imidazol-2-yl)-2-methylisonicotinamide (Compound A40) or a compound disclosed in PCT Publication No. WO 2013/184757. In one embodiment, a PD-1 antibody molecule is used in combination with (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, to treat a disorder such as a cancer, e.g., a solid tumor.

In some embodiments, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, is a covalent, irreversible tyrosine kinase inhibitor. In certain embodiments, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757 inhibits activating EGFR mutations (L858R, ex19del). In other embodiments, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757 does not inhibit, or does not substantially inhibit, wild-type (wt) EGFR. Compound A40) has shown efficacy in EGFR mutant NSCLC patients. In some embodiments, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757 also inhibits one or more kinases in the TEC family of kinases. The Tec family kinases include, e.g., ITK, BMX, TEC, RLK, and BTK, and are central in the propagation of T-cell receptor and chemokine receptor signaling (Schwartzberg et al. (2005) *Nat. Rev. Immunol.* p. 284-95). For example, Compound A40 can inhibit ITK with a biochemical IC50 of 1.3 nM. ITK is a critical enzyme for the survival of Th2 cells and its inhibition results in a shift in the balance between Th2 and Th1 cells. Combined treatment, in vivo, with the ITK inhibitor ibrutinib or Compound A40 and anti-PD-L1-antibody results in superior efficacy compared with either single agent in several models.

In some embodiments, the combination described herein includes an EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, and an inhibitor of an immune checkpoint molecule, e.g., an inhibitor of PD-1 (e.g., an anti-PD-1 antibody molecule).

The combination of ITK inhibition (with ibrutinib) and checkpoint inhibition is more effective than either single agent in numerous syngeneic mouse models, e.g., those which express ITK but not BTK. In certain embodiments, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, inhibits ITK. The synergistic effect of ITK inhibition and checkpoint blockade has been tested in mouse allografts using mouse cancer cell lines (A20, CT26 and 4T1) (Sagiv-Barfi et al. (2015) Blood. p. 2079-86). The combination of anti-PD-L1 antibody and ibrutinib (an ITK inhibitor) was shown to be significantly more efficacious than either single agent in all three models. In these experiments, the treatment effect was prolonged despite the dosing of ibrutinib for only 8 days, and a total of 5 doses of anti-PD-L1 antibody. Approximately half of the CT26 tumor bearing mice treated with this combination were cured (no mice treated with either single agent were cured). Rechallenge of these mice with CT26 tumor inoculum demonstrated long term anti-tumor memory specific for this cell line (Sagiv-Barfi et al. (2015) Blood. p. 2079-86). Furthermore, tumor specific T-cells were found in the blood and spleen of mice treated with ibrutinib and anti-PD-L1 antibody. To extend this observation to Compound A40, a similar experiment was performed using the A20 lymphoma model. In this study, the combination of either Compound A40 and anti-PD-L1 antibody or ibrutinib and anti-PD-L1 antibody was more effective than any single agent. Compound A40 and ibrutinib were dosed for only ten days, and a total of 5 doses of anti-PD-L1 antibody were given. The effects of Compound A40 plus anti-PD-L1 antibody and ibrutinib plus anti-PD-L1 antibody on survival extended beyond 60 days, even when Compound A40 and ibrutinib were only dosed transiently.

Combination of anti-PD-L1-antibody and Compound A40 resulted in tumor regression in mice bearing A20 lymphoma allografts. Accordingly, in some embodiments, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757 enhances, or is used to enhance an antitumor effect of an inhibitor of PD-1 (e.g., an anti-PD-1 antibody molecule).

In some embodiments, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, and the inhibitor of an immune checkpoint molecule, e.g., an inhibitor of PD-1 (e.g., an anti-PD-1 antibody molecule), each is administered at a dose and/or on a time schedule, that in combination, achieves a desired anti-tumor activity.

In one embodiment, the EGFR inhibitor or (R,E)-N-(7-chloro-1-(1-(4-(dimethylamino)but-2-enoyl)azepan-3-yl)-1H-benzo[d]imidazol-2-yl)-2-methylisonicotinamide (Compound A40) is administered at a dose of 150-250 mg, e.g., per day. In one embodiment, the compound is administered at a dose of about 150, 200, or 250 mg, or about 150-200 or 200-250 mg.

In one embodiment, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, is administered at a dose between 5 mg and 100 mg, e.g., between 10 mg and 75 mg, between 15 mg and 50 mg, between 20 mg and 30 mg, between 10 mg and 40 mg, between 10 mg and 25 mg, or between 25 mg and 40 mg, e.g., at a dose of 5 mg, 10 mg, 15 mg, 20 mg, 25 mg, 30 mg, 35 mg, 40 mg, 45 mg, 50 mg, 60 mg, 70 mg, 80 mg, 90 mg, or 100 mg, e.g., twice a day, once a day, once every two days, once every three days, or once a week.

In one embodiment, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, is administered at a dose between 10 mg and 50 mg (e.g., 25 mg) once a day. In some embodiments, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, is administered orally. In one embodiment, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, is administered at a dose between 10 mg and 50 mg (e.g., 25 mg), e.g., once a day, e.g., orally, and the PD-1 inhibitor (e.g., the anti-PD-1 antibody molecule) is administered at a dose between 300 mg and 500 mg (e.g., at a dose of 400 mg), e.g., once every 4 weeks, e.g., by intravenous infusion. In some embodiments, the combination is administered in one or more dosing cycles, e.g., one or more 28-day dosing cycles. In certain embodiments, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, is administered on day 1 to day 10 of a first dosing cycle. In certain embodiments, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, is not administered on day 11 to day 28 of a first dosing cycle, or in any subsequent dosing cycle(s).

In some embodiments, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, is administered in combination with an inhibitor of PD-1 (e.g., an anti-PD-1 antibody molecule) to treat a colorectal cancer (CRC), a lung cancer (e.g., a non-small cell lung cancer (NSCLC)), or a breast cancer (e.g., a triple negative breast cancer (TNBC)).

In another embodiment, the combination, e.g., a combination comprising an anti-PD-1 antibody molecule as described herein, includes or is used in combination an ALK inhibitor, $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42) or a compound disclosed in PCT Publication No. WO 2008/073687 to treat a disorder, e.g., a disorder described herein. In one embodiment, the ALK inhibitor is $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42) or a compound disclosed in PCT Publication No. WO 2008/073687. In one embodiment, a PD-1 antibody molecule is used in combination with $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42), or a compound disclosed in PCT Publication No. WO 2008/073687, to treat a disorder such as a cancer, an anaplastic large-cell lymphoma (ALCL), a non-small cell lung carcinoma (NSCLC), or a neuroblastoma.

In another embodiment, the combination, e.g., a combination comprising an anti-PD-1 antibody molecule as described herein, includes or is used in combination an IGF-1R inhibitor, 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-$N^2$-(2-fluoro-5-methyl-4-(1-(tetrahydro-2H-pyran-4-yl)piperidin-4-yl)phenyl)-$N^4$-(5-methyl-1H-pyrazol-3-yl)pyrimidine-2,4-diamine (Compound A44), or 5-chloro-N2-(4-(1-ethylpiperidin-4-yl)-2-fluoro-5-methylphenyl)-$N^4$-(5-methyl-1H-pyrazol-3-yl)pyrimidine-2,4-diamine (Compound A45) or a compound disclosed in PCT Publication No. WO 2010/002655 to treat a disorder, e.g., a disorder described. In one embodiment, the IGF-1R inhibitor is 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-$N^2$-(2-fluoro-5-methyl-4-(1-(tetrahydro-2H-pyran-4-yl)piperidin-4-yl)phenyl)-$N^4$-(5-methyl-1H-pyrazol-3-yl)pyrimidine-2,4-diamine (Compound A44), 5-chloro-N2-(4-(1-ethylpiperidin-4-yl)-2-fluoro-5-methylphenyl)-$N^4$-(5-methyl-1H-pyrazol-3-yl)pyrimidine-2,4-diamine (Compound A45), or a compound disclosed in PCT Publication No. WO 2010/002655. In one embodiment, a PD-1 antibody molecule is used in combination with 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-$N^2$-(2-fluoro-5-methyl-4-(1-(tetrahydro-2H-pyran-4-yl)piperidin-4-yl)phenyl)-$N^4$-(5-methyl-1H-pyrazol-3-yl)pyrimidine-2,4-diamine (Compound A44), 5-chloro-N2-(4-(1-ethylpiperidin-4-yl)-2-fluoro-5-methylphenyl)-$N^4$-(5-methyl-1H-pyrazol- 3-yl)pyrimidine-2,4-diamine (Compound A45), or a compound disclosed in PCT Publication No. WO 2010/002655, to treat a disorder such as a cancer or a sarcoma.

In another embodiment, the combination, e.g., a combination comprising an anti-PD-1 antibody molecule as described herein, includes or is used in combination a P-Glycoprotein 1 inhibitor, Valspodar (also known as AMDRAY; Compound A46) or a compound disclosed in EP 296122 to treat a disorder, e.g., a disorder described herein. In one embodiment, the P-Glycoprotein 1 inhibitor is Valspodar (Compound A46) or a compound disclosed in EP 296122. In one embodiment, a PD-1 antibody molecule is used in combination with Valspodar (Compound A46), or a compound disclosed in EP 296122, to treat a disorder such as a cancer or a drug-resistant tumor.

In another embodiment, the combination, e.g., a combination comprising an anti-PD-1 antibody molecule as described herein, includes or is used in combination one or more of a VEGFR inhibitor, Vatalanib succinate (Compound A47) or a compound disclosed in EP 296122 to treat a disorder, e.g., a disorder described herein. In one embodiment, the VEGFR inhibitor is Vatalanib succinate (Compound A47) or a compound disclosed in EP 296122. In one embodiment, a PD-1 antibody molecule is used in combination with Vatalanib succinate (Compound A47), or a compound disclosed in EP 296122, to treat cancer.

In another embodiment, the combination, e.g., a combination comprising an anti-PD-1 antibody molecule as described herein, includes or is used in combination with an IDH inhibitor or a compound disclosed in WO2014/141104 to treat a disorder, e.g., a disorder described herein. In one embodiment, the IDH inhibitor is a compound disclosed in PCT Publication No. WO2014/141104. In one embodiment, a PD-1 antibody molecule is used in combination with a compound disclosed in WO2014/141104 to treat a disorder such as a cancer.

In another embodiment, the combination, e.g., a combination comprising an anti-PD-1 antibody molecule as described herein, includes or is used in combination with a BCL-ABL inhibitor or a compound disclosed in PCT Publication No. WO2013/171639, WO2013/171640, WO2013/171641, or WO2013/171642 to treat a disorder, e.g., a disorder described herein. In one embodiment, the BCL-ABL inhibitor is a compound disclosed in PCT Publication No. WO2013/171639, WO2013/171640, WO2013/171641, or WO2013/171642. In one embodiment, a PD-1 antibody molecule is used in combination with a compound disclosed in PCT Publication No. WO2013/171639, WO2013/171640, WO2013/171641, or WO2013/171642 to treat a disorder such as a cancer.

In another embodiment, the combination, e.g., a combination comprising an anti-PD-1 antibody molecule as described herein, includes or is used in combination with a c-RAF inhibitor or a compound disclosed in PCT Publication No. WO2014/151616 to treat a disorder, e.g., a disorder described herein. In one embodiment, the c-RAF inhibitor is Compound A50 or a compound disclosed in PCT Publication No. WO2014/151616. In some embodiments, the c-RAF inhibitor or Compound A50 is a compound of formula (I):

or a pharmaceutically acceptable salt thereof, wherein:

$Z^1$ is O, S, S($=$O) or $SO_2$;

$Z^2$ is N, S or $CR^a$, where $R^a$ is H, halo, $C_{1-4}$ alkyl or $C_{1-4}$ haloalkyl;

$R^1$ is CN, halo, OH, $C_{1-4}$ alkoxy, or $C_{1-4}$ alkyl that is optionally substituted with one to three groups selected from halo, $C_{1-4}$ alkoxy, CN, and hydroxyl;

Ring B is selected from phenyl, pyridine, pyrimidine, pyrazine, pyridazine, pyridone, pyrimidone, pyrazinone, pyridazinone, and thiazole, each of which is optionally substituted with up to two groups selected from halo, OH, CN, $C_{1-4}$ alkyl, $C_{2-4}$ alkenyl, —O—($C_{1-4}$ alkyl), $NH_2$, NH—($C_{1-4}$ alkyl), —N($C_{1-4}$ alkyl)$_2$, —$SO_2R^2$, $NHSO_2R^2$, $NHC(O)R^2$, $NHCO_2R^2$, $C_{3-6}$ cycloalkyl, 5-6 membered heteroaryl, —O—$C_{3-6}$ cycloalkyl, —O-(5-6-membered heteroaryl), $C_{4-8}$ heterocycloalkyl, and —O-(4-8 membered heterocycloalkyl), where each heterocycloalkyl and heteroaryl contains up to three heteroatoms selected from N, O and S as ring members, where each $C_{1-4}$ alkyl, $C_{2-4}$ alkenyl, $C_{3-6}$ cycloalkyl, 5-6 membered heteroaryl, and 4-8 membered heterocycloalkyl is each optionally substituted with up to three groups selected from oxo, hydroxyl, halo, $C_{1-4}$ alkyl, $C_{1-4}$ haloalkyl, $C_{1-4}$ alkoxy, and —(CH$_2$)$_{1-2}$Q where Q is OH, $C_{1-4}$ alkoxy, —CN, $NH_2$, —$NHR^3$, —N($R^3$)$_2$, —$SO_2R^3$, $NHSO_2R^3$, NHC(O)O$R^3$, or NHC(O)$R^3$; each $R^2$ and $R^3$ is independently $C_{1-4}$ alkyl; and Ring B is optionally fused to a 5-6 membered aromatic or nonaromatic ring containing up to two heteroatoms selected from N, O and S, where the 5-6 membered ring can be substituted with halo, $C_{1-4}$ alkyl, $C_{1-4}$ haloalkyl, or $C_{1-4}$ alkoxy, and if the fused ring is nonaromatic the substituent options can further include oxo;

each Y is independently selected from $C_{1-4}$ alkyl, $C_{1-4}$ alkoxy, CN, halo, oxo, —(CH$_2$)$_p$OR$^4$, —(CH$_2$)p N($R^4$)$_2$, —(CH$_2$)pNHC(O)R$^4$, —(CH$_2$)$_p$NHCOO($C_{1-4}$ alkyl), and imidazole, or two Y groups on Ring A are optionally taken together to form a ring fused to or bridging Ring A, where said fused or bridging ring optionally contains a heteroatom selected from N, O and S as a ring member, and is optionally substituted with up to two groups selected from $C_{1-4}$ alkyl, $C_{1-4}$ alkoxy, CN, halo, oxo, —(CH$_2$)$_p$OR$^4$, —(CH$_2$)p N($R^4$)$_2$, —(CH$_2$)$_p$NHC(O)R$^4$, and —(CH$_2$)$_p$NHCOO($C_{1-4}$ alkyl);

each $R^4$ is independently H or $C_{1-4}$ alkyl;

each p is independently 0, 1, or 2;

q is 0, 1 or 2;

$Z^3$, $Z^4$, and $Z^5$ are independently selected from CH and N and optionally NO;

L is —C($=$O)—NR$^4$—[CY] or —NR$^4$—C($=$O)—[CY], where [CY] indicates which atom of L is attached to CY; and

CY is an aromatic ring selected from phenyl, pyridine, pyrimidine, pyrazine, pyridazine, pyridone, thiazole, isothiazole, oxazole, pyrazole, and isoxazole, wherein the ring is optionally fused to a thiophene, imidazole, oxazolone, or pyrrole ring;

and CY is substituted with up to two groups selected from halo, CN, $R^5$, $OR^5$, $SO_2R^5$, $—S(=NH)(=O)R^5$, OH, $NH_2$, $NHR^5$, and $—N(R^5)_2$, wherein each $R^5$ is independently $C_{1-4}$ alkyl, $C_{2-4}$ alkenyl, $C_{2-6}$ heterocyclyl, 5-membered heteroaryl containing up to three heteroatoms selected from N, O and S as ring members, or $C_{3-8}$ cycloalkyl, and $R^5$ is optionally substituted with up to four groups selected from oxo, halo, CN, $R^6$, OH, $OR^6$, $SO_2R^6$, $NH_2$, $NHR^6$, $N(R^6)_2$, $NHSO_2R^6$, $NHCOOR^6$, NHC $(=O)R^6$, $—CH_2OR^7$, $—CH_2N(R^7)_2$, wherein each $R^6$ is independently $C_{1-4}$ alkyl, and each $R^2$ is independently H or $C_{1-4}$ alkyl;

and two $R^4$, $R^5$, $R^6$, or $R^7$ on the same nitrogen atom can be taken together to form a 5-6 membered heterocyclic ring optionally containing an additional N, O or S as a ring member and optionally substituted with up to two groups selected from $C_{1-4}$ alkyl, oxo, halo, OH, and $C_{1-4}$ alkoxy.

In one embodiment, a PD-1 antibody molecule is used in combination with a compound disclosed in PCT Publication No. WO2014/151616 to treat a disorder such as a cancer, e.g., a cancer described herein. In certain embodiments, the cancer is a lung cancer (e.g., a non-small cell lung cancer).

In another embodiment, the combination, e.g., a combination comprising an anti-PD-1 antibody molecule as described herein, includes or is used in combination with an ERK1/2 ATP competitive inhibitor or a compound disclosed in PCT Publication No. WO2015/066188 to treat a disorder, e.g., a disorder described herein. In one embodiment, the ERK1/2 ATP competitive inhibitor is a compound disclosed in PCT Publication No. WO2015/066188. In one embodiment, a PD-1 antibody molecule is used in combination with Compound A51 or a compound disclosed in PCT Publication No. WO2015/066188 to treat a disorder such as a cancer.

In some embodiments, the combination, e.g., a combination comprising an anti-PD-1 antibody molecule as described herein, is administered in combination with one or more agents selected from, Compound A8, Compound A17, Compound A23, Compound A24, Compound A27, Compound A29, and Compound A33.

In some embodiments, the combination, e.g., a combination comprising an anti-PD-1 antibody molecule as described herein, is administered in combination with an anti-cancer agent having a known activity in an immune cell assay, e.g., in one or more of a huMLR assay, a T cell proliferation assay, and a B-cell proliferation assay. Exemplary assays are described below. Based on the assay, an IC50 for can be calculated for each test agent. In embodiments, the anti-cancer agent has an IC50 of, e.g., 0-1 μM, 1-4 μM, or greater than 4 μM, e.g., 4-10 μM or 4-20 μM. In embodiments, the second therapeutic agent is chosen from one or more of: Compound A9, Compound A16, Compound A17, Compound A21, Compound A22, Compound A25, Compound A28, Compound A48, and Compound 49.

In some embodiments, the Compound A28 (or a compound related to Compound A28) is administered at a dose of approximately 5-10 or 10-30 mg. In some embodiments, the Compound A22 (or compound related to Compound A22) is administered at a dose of about 200 mg. In some embodiments, the Compound A17 (or compound related to Compound A17) is administered at a dose of approximately 400-600 mg. In some embodiments, the Compound A16 (or compound related to Compound A16) is administered at a dose of approximately 400-600 mg PO qDay. In some embodiments, the Compound A29 (or compound related to Compound A29) is administered at a dose of approximately 200-400 or 300-400 mg. In some embodiments, the Compound A24 (or compound related to Compound A24) is administered at a dose of approximately 200-600 mg. In some embodiments, the Compound A23 (ceritinib) (or compound related to ceritinib) is administered at a dose of approximately 750 mg once daily. In some embodiments, the Compound A8 (or compound related to Compound A8) is administered at a dose of approximately 200-400 or 300-400 mg. In some embodiments, the Compound A5 (or compound related to Compound A5) is administered at a dose of approximately 100-125 mg. In some embodiments, the Compound A6 (or compound related to Compound A6) is administered at a dose of about 100 mg. In some embodiments, the Compound A1 (or compound related to Compound A1) is administered at a dose of approximately 200-300 or 200-600 mg. In some embodiments, the Compound A40 (or compound related to Compound A40) is administered at a dose of approximately 150-250 mg. In embodiments, the Compound A10 (or compound related to Compound A10) is administered at a dose of approximately 400 to 700 mg, e.g., administered three times weekly, 2 weeks on and one week off. In embodiments, the BCR-ABL inhibitor is administered at a dose of approximately 20 mg bid-80 mg bid.

Exemplary huMLR assay and B or T cell proliferation assays are provided below.

Human Mixed Lymphocyte Reaction

The Mixed Lymphocyte Reaction (MLR) is a functional assay which measures the proliferative response of lymphocytes from one individual (the responder) to lymphocytes from another individual (the stimulator). To perform an allogeneic MLR, peripheral blood mononuclear cells (PBMC) from three donors were isolated from buffy-coats of unknown HLA type (Kantonspital Blutspendezentrum from Bern and Aarau, Switzerland). The cells were prepared at 2.105 in 0.2 mL of culture medium containing RPMI 1640 GlutaMAX™ with 10% fetal calf serum (FCS), 100 U penicillin/100 μg streptomycin, 50 μM 2-Mercaptoethanol. Individual 2-way reactions were set up by mixing PBMC from two different donors at a 1:1 ratio and co-cultures were done in triplicates in flat-bottomed 96-well tissue culture plates for 6 days at 37° C., 5% CO2, in presence or not of an 8-point concentration range of test compounds. Cells were pulsed with 3H-TdR (1 μCi/0.2 mL) for the last 16 h of culture and incorporated radioactivity was used as a measure of cell proliferation. The concentration that inhibited 50% of the maximal huMLR response (IC50) was calculated for each compound. Cyclosporine was used as a positive control of huMLR inhibition.

Human B Cell Proliferation Assay

PBMC were freshly isolated by Ficoll-Paque density gradient from human blood and subjected to negative B-cell isolation. B cells were resuspended in culture medium (RPMI 1640, HEPES, 10% FCS, 50 μg/mL gentamicine, 50 μM 2-Mercaptoethanol, 1×ITS (Insulin, Transferrin and Sodium Selenite), 1× Non-Essential Amino-Acids) at a concentration of 9.104 per well in a flat-bottom 96-well culture plate. B cell stimulation was performed by human anti-IgM antibody molecule (30 ug/mL) and IL-4 (75 ng/mL) or by CD40 ligand (3 ug/mL) and IL-4 (75 ng/mL) in presence or not of a 7-point concentration range of test compounds. After 72 h of culture at 37° C., 10% CO2, cells were pulsed with 3H-TdR (1 μCi/well) for the last 6 h of culture. B cells were then harvested and the incorporation of thymidine was measured using a scintillation counter. Of each duplicate treatment, the mean was calculated and these data were plotted in XLfit 4 to determine the respective IC50 values.

Human T Cell Proliferation Assay

PBMC were freshly isolated by Ficoll-Paque density gradient from human blood and subjected to negative isolation of T cells. T cells were prepared in culture medium (RPMI 1640, HEPES, 10% FCS, 50 μg/mL gentamicine, 50 μM 2-Mercaptoethanol, 1×ITS (Insulin, Transferrin and Sodium Selenite), 1× Non-Essential Amino-Acids) at a concentration of 8.104 per well in a flat-bottom 96-well culture plate. T cell stimulation was performed by human anti-CD3 antibody molecule (10 ug/mL) or by human anti-CD3 antibody molecule (5 μg/mL) and anti-CD28 antibody molecule (1 μg/mL) in presence or not of a 7-point concentration range of test compounds. After 72 h of culture at 37° C., 10% CO2, cells were pulsed with 3H-TdR (1 μCi/well) for the last 6 h of culture. Cell proliferation was measured by the incorporation of thymidine allowing IC50 determination for each tested compound.

Contraception

In some embodiments of any of the methods disclosed herein, the subject uses contraception (e.g., a contraceptive) prior to receiving, during, or after receiving, a therapy (e.g., a combination therapy) comprising an anti-PD-1 antibody molecule described herein. Without wishing to be bound by theory, it is believed that in certain embodiments, using contraception for a period prior to receiving, during, or after receiving, the therapy (e.g., the combination therapy) may reduce or prevent the risk of embryofetal toxicity, e.g., increased abortion or premature infant death.

In certain embodiments, the method described herein comprises administering a contraceptive to a subject (e.g., a female subject) who is receiving, or has received, a therapy (e.g., a combination therapy) comprising an anti-PD-1 antibody molecule described herein. In other embodiments, a contraceptive is used in combination with a therapy (e.g., a combination therapy) comprising an anti-PD-1 antibody molecule described herein for treating a disorder described herein, e.g., a cancer described herein. In other embodiments, a contraceptive is used in combination with a therapy (e.g., a combination therapy) comprising an anti-PD-1 antibody molecule described herein to reduce or prevent the risk of embryofetal toxicity, e.g., increased abortion or premature infant death.

In some embodiments, the subject is advised, e.g., by a healthcare provider, to discontinue the therapy (e.g., the combination therapy) comprising the anti-PD-1 antibody molecule, when the subject is pregnant or known to be pregnant, or is at risk of being pregnant. In other embodiments, the subject discontinues the therapy (e.g., the combination therapy) comprising the anti-PD-1 antibody molecule, when the subject is pregnant or known to be pregnant, or is at risk of being pregnant.

In some embodiments, the duration of the period when the subject (e.g., a female subject) uses effective contraception (sometimes referred to herein as a contraception period) can be determined, at least in part, by the serum half-life (T½) of the anti-PD-1 antibody molecule. During a contraception period, the subject may have completed the therapy, or is still receiving the therapy. In certain embodiments, the contraception period comprises a period following the last dose of the therapy (e.g., the last dose of the anti-PD-1 antibody molecule). In other embodiments, the contraception period further comprises a period during which the subject is receiving the therapy (e.g., the anti-PD-1 antibody molecule).

In some embodiments, the contraception period comprises a period of 50 days or more, e.g., 60 days or more, 80 days or more, 90 days or more, 100 days or more, 110 days or more, 120 days or more, 130 days or more, 140 days or more, 150 days or more, 160 days or more, 170 days or more, 180 days or more, 190 days or more, 200 days or more, 220 days or more, 240 days or more, 260 days or more, 280 days or more, or 300 days or more, e.g., after the last dose of the anti-PD-1 antibody molecule. In certain embodiments, the contraception period comprises a period of 150 days or more, e.g., after the last dose of the anti-PD-1 antibody molecule. In certain embodiments, the contraception period comprises a period when the subject receives the anti-PD-1 antibody molecule, and a period of 150 days or more after the last dose of the anti-PD-1 antibody molecule.

In some embodiments, the contraception period is at least 2, 3, 4, 5, 6, 7, 8, 9, or 10 times of the serum half-life of the anti-PD-1 antibody molecule. In certain embodiments, the contraception period is at least 5 times of the serum half-life of the anti-PD-1 antibody molecule. In certain embodiments, the serum half-life of the anti-PD-1 antibody molecule is between 10 days and 30 days, e.g., between 15 days and 25 days, between 17 days and 23 days, or between 19 days and 21 days, e.g., 15 days or more, 16 days or more, 17 days or more, 18 days or more, 19 days or more, 20 days or more, 21 days or more, 22 days or more, or 23 days or more. In certain embodiments, the serum half-life of the anti-PD-1 antibody molecule is between 17 days and 23 days, e.g., about 19 days, 20 days, 21 days, 22 days, or 23 days.

In some embodiments, the subject uses contraception prior to receiving the therapy (e.g., the combination therapy) comprising the anti-PD-1 antibody molecule. In other embodiments, the subject uses contraception during the therapy (e.g., the combination therapy) comprising the anti-PD-1 antibody molecule. In other embodiments, the subject uses contraception after receiving the therapy (e.g., the combination therapy) comprising the anti-PD-1 antibody molecule.

In certain embodiments, the subject uses contraception during, and after receiving, the therapy (e.g., the combination therapy) comprising an anti-PD-1 antibody molecule. In other embodiments, the subject uses contraception prior to receiving, and during, the therapy (e.g., the combination therapy) comprising an anti-PD-1 antibody molecule. In other embodiments, the subject uses contraception prior to and after receiving the therapy (e.g., the combination therapy) comprising an anti-PD-1 antibody molecule. In other embodiments, the subject uses contraception prior to receiving, during, and after receiving, the therapy (e.g., the combination therapy) comprising an anti-PD-1 antibody molecule.

In some embodiments, the subject uses contraception at least 1, 3, 7, 14, or 28 days, or at least 1, 2, or 3 months, before the subject is administered the anti-PD-1 antibody molecule, e.g., before the first dose of the anti-PD-1 antibody molecule.

In other embodiments, the subject uses contraception during the therapy (e.g., the combination therapy) at least once, twice, 3 times, 4 times, 5 times, 6 times, 7 times, 8 times, 9 times, or 10 times, during the period when the subject is administered the anti-PD-1 antibody molecule, e.g., between the first and last doses of the anti-PD-1 antibody molecule.

In yet other embodiments, the subject uses contraception for a period of at least 90, 100, 110, 120, 130, 140, 150, 160, 170, 180, 190, 200, 210, 220, 230, 240, 250, 260, 270, 280, 290, or 300 days, or at least 3, 4, 5, 6, 7, 9, or 10 months, after the subject is administered the anti-PD-1 antibody molecule, e.g., after the last dose of the anti-PD-1 antibody molecule.

The subject can use various types of contraception (e.g., contraceptives). For example, the contraception can be a device, a drug, a method, or any combination thereof. Exemplary types of contraception (e.g., contraceptives) that can be used by the subject include, but are not limited to, a birth control implant (e.g., etonogestrel), a birth control patch, a birth control pill (e.g., progestin and/or estrogen), a birth control sponge (e.g., medroxyprogesterone), a birth control sponge, a birth control vagina ring, breastfeeding as birth control, a cervical cap, a condom, a diaphragm, a female condom, a fertility awareness-based method, an intrauterine device (IUD or coil), a morning-after pill (emergency contraception), an outercourse, a spermicide, sterilization for women (tubal sterilization), vasectomy, withdrawal (pull out method), or a combination thereof.

In some embodiments, the subject is a female, e.g., a female of reproductive potential. The female reproductive potential can be influenced by various factors, e.g., age, health, genetics, pathological conditions, or environmental exposures. In certain embodiments, the subject is between 15 and 50 years of age, e.g., between 18 and 45 years of age, between 20 and 40 years of age, or between 25 and 35 years of age. In some embodiments, the subject is at least 20, 25, 30, 35, 40, or 45 years of age.

Biomarkers

The invention also features methods of evaluating or monitoring the effectiveness of a therapy (e.g., a combination therapy) described herein, in a subject (e.g., a subject having a cancer, e.g., a cancer described herein). The method includes acquiring a value of effectiveness to the therapy, wherein said value is indicative of the effectiveness of the therapy.

In embodiments, the value of effectiveness to the therapy comprises a measure of one, two, three, four, five, six, seven, eight, nine or more (e.g., all) of the following:

(i) a parameter of a tumor infiltrating lymphocyte (TIL) phenotype;
(ii) a parameter of a myeloid cell population;
(iii) a parameter of a surface expression marker;
(iv) a parameter of a biomarker of an immunologic response;
(v) a parameter of a systemic cytokine modulation;
(vi) a parameter of circulating free DNA (cfDNA);
(vii) a parameter of systemic immune-modulation;
(viii) a parameter of microbiome;

(ix) a parameter of a marker of activation in a circulating immune cell; or
(x) a parameter of a circulating cytokine.

In some embodiments, the parameter of a TIL phenotype comprises the level or activity of one, two, three, four or more (e.g., all) of Hematoxylin and eosin (H&E) staining for TIL counts, CD8, FOXP3, CD4, or CD3, in the subject, e.g., in a sample from the subject (e.g., a tumor sample). In some embodiments, the parameter of a myeloid cell population comprises the level or activity of one or both of CD68 or CD163, in the subject, e.g., in a sample from the subject (e.g., a tumor sample). In some embodiments, the parameter of a surface expression marker comprises the level or activity of one, two or more (e.g., all) of PD-L1, LAG-3, or TIM-3, in the subject, e.g., in a sample from the subject (e.g., a tumor sample). In some embodiments, the parameter of a biomarker of an immunologic response comprises the level or sequence of one or more nucleic acid-based markers, in the subject, e.g., in a sample from the subject (e.g., a tumor sample). In some embodiments, the parameter of systemic cytokine modulation comprises the level or activity of one, two, three, four, five, six, seven, eight, or more (e.g., all) of IL-18, IFN-γ, ITAC (CXCL11), IL-6, IL-10, IL-4, IL-17, IL-15, or TGF-beta, in the subject, e.g., in a sample from the subject (e.g., a blood sample, e.g., a plasma sample). In some embodiments, the parameter of cfDNA comprises the sequence or level of one or more circulating tumor DNA (cfDNA) molecules, in the subject, e.g., in a sample from the subject (e.g., a blood sample, e.g., a plasma sample). In some embodiments, the parameter of systemic immune-modulation comprises phenotypic characterization of an activated immune cell, e.g., a CD3-expressing cell, a CD8-expressing cell, or both, in the subject, e.g., in a sample from the subject (e.g., a blood sample, e.g., a PBMC sample). In some embodiments, the parameter of microbiome comprises the sequence or expression level of one or more genes in the microbiome, in the subject, e.g., in a sample from the subject (e.g., a stool sample). In some embodiments, the parameter of a marker of activation in a circulating immune cell comprises the level or activity of one, two, three, four, five or more (e.g., all) of circulating CD8+, HLA-DR+Ki67+, T cells, IFN-γ, IL-18, or CXCL11 (IFN-γ induced CCK) expressing cells, in a sample (e.g., a blood sample, e.g., a plasma sample). In some embodiments, the parameter of a circulating cytokine comprises the level or activity of IL-6, in the subject, e.g., in a sample from the subject (e.g., a blood sample, e.g., a plasma sample).

In some embodiments, the evaluation or monitoring includes a biomarker analysis. For example, the effectiveness of the therapy can be evaluated or monitored at the molecular level and/or cellular level for one or more biomarkers described herein. In some embodiments, a change in the marker may relate to a clinical outcome. Exemplary biomarkers and sample collection are described in Table 8.

TABLE 8

| Exemplary biomarkers and sample collection | | | | |
|---|---|---|---|---|
| Sample Type | Visit/Time point | Volume | Marker | Purpose |
| Newly obtained tumor biopsy* | Screening (day −28 to −1) Cycle 3 Day 1-15 (Anytime between day 1 and 15; however, biopsy collection occurs post-dose) at disease progression (unscheduled)** | 3-6 passes of a core needle biopsy | H&E, CD8, FOXP3, CD4, CD3 CD68, CD163 expression PD-L1, LAG-3, TIM-3 Nucleic acid-based | Characterization of TIL phenotypes Myeloid cell populations Surface expression markers Assessing other biomarkers of |

TABLE 8-continued

| | | Exemplary biomarkers and sample collection | | |
|---|---|---|---|---|
| Sample Type | Visit/Time point | Volume | Marker | Purpose |
| | | | (DNA or RNA sequencing or quantitation) | immunologic response |
| Blood (plasma) | Screening (pre-dose) C1D1 (Post-dose) C1D15 (Post-dose) C2D1 (Post-dose) C2D15 (Post-dose) | 8 mL per time point | Systemic Cytokines (e.g. IL-18, IFN-γ, ITAC (CXCL11), IL-6, IL-10, IL-4, IL-17, IL-15, TGF-beta) | Systemic cytokine modulation |
| Blood (plasma) | Screening (pre-dose) End of Treatment (anytime) | 10 ml per time point | DNA sequencing in circulating tumor DNA (cfDNA) | Assessing cfDNA as surrogate |
| Blood (PBMC) | Screening C1D1 Post-dose C1D15 Post-dose C2D1 Post-dose C2D15 Post-dose | 8 mL per time point | Phenotypic characterization of activated immune cells (e.g. CD3, CD8) | Systemic immune-modulation |

*If a newly obtained tumor sample cannot be safely collected at study entry, an archival sample may be substituted if it has been recently obtained.
**Disease progression biopsy is to be collected at the time of progression, even if not in an initial In some embodiments, an evaluable paired tumor sample is obtained to assess the pharmacodynamic effect on the tumor microenvironment. In certain embodiments, tumor samples are obtained at screening and after approximately two cycles of therapy. In other embodiments, a tumor sample is obtained at disease progression that occurs during the treatment.

In some embodiments, an initial assessment of a hematoxylin and eosin (H&E)-stained slide for tumor infiltrating lymphocyte (TIL) counts is used to guide further IHC analysis of the tumor microenvironment, e.g., one or more of characterization by IHC of TILs (e.g., CD8, CD3, CD4, or FOXP3), a myeloid cell population (e.g., CD163 or CD68), a surface marker, e.g., LAG-3, TIM-3, or PD-L1. Other methodologies for assessing biomarkers of immunologic response, such as nucleic acid-based (DNA or RNA sequencing or quantitation) or other methods may be employed in this rapidly evolving scientific area.

The extent of tumor infiltration by immune cells including lymphocytes and macrophages, changes in regulatory T cells, and/or changes in gene expression in tumor biopsies can contribute to a decision on any benefit for a given combination.

In some embodiments, a blood sample is collected as specified in Table 8 to characterize circulating levels of cytokine in plasma and a marker of activation in circulating immune cells. Without wishing to be bound by theory, it is believed that in some embodiments, an increase in the number of one or more of circulating CD8+, HLA-DR+ Ki67+, T cells, IFN-γ, IL-18, or CXCL11 (IFN-γ induced CCK) expressing cells indicates expansion of a pre-existing primed immune response, whilst the decrease of IL-6 is indicative of reduced myeloid-derived suppressor cells (MDSC) (Herbst et al. (2016) *Lancet* 387(10027):1540-50; Tumeh et al. (2014) *Nature* p. 568-71; Powles et al. (2014) *Nature* p. 558-62). In some embodiments, a blood sample is obtained at screening and/or at end of treatment to analyze the circulating free DNA (cfDNA), e.g., to assess any correlation with a clinical outcome. Any additional markers or methods known in the art can also be utilized. In some embodiments, combination compound-specific markers is run to determine pharmacodynamic activity at the lower doses used in the therapy, which are or may be lower than previously established doses.

Nucleic Acids

The invention also features nucleic acids comprising nucleotide sequences that encode heavy and light chain variable regions and CDRs or hypervariable loops of the anti-PD-1 antibody molecules, as described herein. For example, the invention features a first and second nucleic acid encoding heavy and light chain variable regions, respectively, of an anti-PD-1 antibody molecule chosen from one or more of the antibody molecules disclosed herein. The nucleic acid can comprise a nucleotide sequence as set forth in the tables herein, or a sequence substantially identical thereto (e.g., a sequence at least about 85%, 90%, 95%, 99% or more identical thereto, or which differs by no more than 3, 6, 15, 30, or 45 nucleotides from the sequences shown in the tables herein.

In certain embodiments, the nucleic acid can comprise a nucleotide sequence encoding at least one, two, or three CDRs or hypervariable loops from a heavy chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In other embodiments, the nucleic acid can comprise a nucleotide sequence encoding at least one, two, or three CDRs or hypervariable loops from a light chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In yet another embodiment, the nucleic acid can comprise a nucleotide sequence encoding at least one, two, three, four, five, or six CDRs or hypervariable loops from heavy and light chain variable regions having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions).

In certain embodiments, the nucleic acid can comprise a nucleotide sequence encoding at least one, two, or three CDRs or hypervariable loops from a heavy chain variable region having the nucleotide sequence as set forth in the tables herein, a sequence substantially homologous thereto (e.g., a sequence at least about 85%, 90%, 95%, 99% or more identical thereto, and/or capable of hybridizing under the stringency conditions described herein). In another embodiment, the nucleic acid can comprise a nucleotide sequence encoding at least one, two, or three CDRs or hypervariable loops from a light chain variable region having the nucleotide sequence as set forth in the tables herein, or a sequence substantially homologous thereto (e.g., a sequence at least about 85%, 90%, 95%, 99% or more identical thereto, and/or capable of hybridizing under the stringency conditions described herein). In yet another embodiment, the nucleic acid can comprise a nucleotide sequence encoding at least one, two, three, four, five, or six CDRs or hypervariable loops from heavy and light chain variable regions having the nucleotide sequence as set forth in the tables herein, or a sequence substantially homologous thereto (e.g., a sequence at least about 85%, 90%, 95%, 99% or more identical thereto, and/or capable of hybridizing under the stringency conditions described herein).

In another aspect, the application features host cells and vectors containing the nucleic acids described herein. The nucleic acids may be present in a single vector or separate vectors present in the same host cell or separate host cell, as described in more detail hereinbelow.

In certain embodiments, one or more nucleic acid molecule that comprises one or both nucleotide sequences that encode heavy and light chain variable regions, CDRs, hypervariable loops, framework regions of the anti-PD-1 antibody molecules is provided. In certain embodiments, the nucleotide sequence that encodes the anti-PD-1 antibody molecule is codon optimized. For example, the invention features a first and second nucleic acid encoding heavy and light chain variable regions, respectively, of an anti-PD-1 antibody molecule chosen from one or more of, e.g., any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E, as summarized in Table 1, or a sequence substantially identical thereto. For example, the nucleic acid can comprise a nucleotide sequence as set forth in Tables 1 and 2, or a sequence substantially identical thereto (e.g., a sequence at least about 85%, 90%, 95%, 99% or more identical thereto, or which differs by no more than 3, 6, 15, 30, or 45 nucleotides from the sequences shown in Tables 1 and 2).

In other embodiments, the nucleic acid molecule comprises a nucleotide sequence that encodes a heavy chain variable domain and/or a heavy chain constant region comprising the amino acid sequence of BAP049-Clone-A, BAP049-Clone-B, BAP049-Clone-C, BAP049-Clone-D, or BAP049-Clone-E; or as described in Table 1; or the nucleotide sequence in Table 1; or a sequence substantially identical (e.g., a sequence at least about 85%, 90%, 95%, 99% or more identical) to any of the aforesaid sequences.

In other embodiments, the nucleic acid molecule comprises a nucleotide sequence that encodes a light chain variable domain and/or a light chain constant region comprising the amino acid sequence of BAP049-Clone-A, BAP049-Clone-B, BAP049-Clone-C, BAP049-Clone-D, or BAP049-Clone-E; or as described in Table 1; or the nucleotide sequence in Table 1; or a sequence substantially identical (e.g., a sequence at least about 85%, 90%, 95%, 99% or more identical) to any of the aforesaid sequences.

The aforesaid nucleotide sequences encoding the anti-PD-1 heavy and light chain variable domain and constant regions can be present in a separate nucleic acid molecule, or in the same nucleic acid molecule. In certain embodiments, the nucleic acid molecules comprise a nucleotide sequence encoding a leader sequence, e.g., a leader sequence as shown in Table 4, or a sequence substantially identical thereto.

In certain embodiments, the nucleic acid molecule comprises a nucleotide sequence encoding at least one, two, or three CDRs, or hypervariable loops, from a heavy chain variable region having an amino acid sequence as set forth in Table 1, or a sequence substantially homologous thereto (e.g., a sequence at least about 85%, 90%, 95%, 99% or more identical thereto, and/or having one, two, three or more substitutions, insertions or deletions, e.g., conserved substitutions).

In another embodiment, the nucleic acid molecule comprises a nucleotide sequence encoding at least one, two, or three CDRs, or hypervariable loops, from a light chain variable region having an amino acid sequence as set forth in Table 1, or a sequence substantially homologous thereto (e.g., a sequence at least about 85%, 90%, 95%, 99% or more identical thereto, and/or having one, two, three or more substitutions, insertions or deletions, e.g., conserved substitutions).

In yet another embodiment, the nucleic acid molecule comprises a nucleotide sequence encoding at least one, two, three, four, five, or six CDRs, or hypervariable loops, from heavy and light chain variable regions having an amino acid sequence as set forth in Table 1, or a sequence substantially homologous thereto (e.g., a sequence at least about 85%, 90%, 95%, 99% or more identical thereto, and/or having one, two, three or more substitutions, insertions or deletions, e.g., conserved substitutions).

In one embodiment, the nucleic acid molecule includes a nucleotide sequence encoding an anti-PD-1 antibody molecule that includes a substitution in the light chain CDR3 at position 102 of the light variable region, e.g., a substitution of a cysteine to tyrosine, or a cysteine to serine residue, at position 102 of the light variable region according to Table 1 (e.g., SEQ ID NO: 16 or 24 for murine or chimeric, unmodified; or any of SEQ ID NOs: 34, 42, 46, 54, 58, 62, 66, 70, 74, or 78 for a modified sequence).

In another embodiment, the nucleic acid molecule includes one or more heavy chain framework region (e.g., any of VHFW1 (type a), VHFW1 (type b), VHFW2 (type a), VHFW2 (type b), VHFW2 (type c), VHFW3 (type a), VHFW3 (type b), or VHFW4, or any combination thereof, e.g., a framework combination as described herein) for any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E, as summarized in Table 1 and 2, or a sequence substantially identical thereto. For example, the nucleic acid molecule can comprise a nucleotide sequence as set forth in Tables 1 and 2, or a sequence substantially identical thereto (e.g., a sequence at least about 85%, 90%, 95%, 99% or more identical thereto, or which differs by no more than 3, 6, 15, 30, or 45 nucleotides from the sequences shown in Tables 1 and 2).

In another embodiment, the nucleic acid molecule includes one or more light chain framework region (e.g., any of VLFW1 (type a), VLFW1 (type b), VLFW1 (type c), VLFW1 (type d), VLFW1 (type e), VLFW2 (type a), VLFW2 (type b), VLFW2 (type c), VLFW3 (type a), VLFW3 (type b), VLFW3 (type c), VLFW3 (type d), or VLFW4, or any combination thereof, e.g., a framework combination as described herein) for any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E, as summarized in Table 1 and 2, or a sequence substantially identical thereto. For example, the nucleic acid molecule can comprise a nucleotide sequence as set forth in Tables 1 and 2, or a sequence substantially identical thereto (e.g., a sequence at least about 85%, 90%, 95%, 99% or more identical thereto, or which differs by no more than 3, 6, 15, 30, or 45 nucleotides from the sequences shown in Tables 1 and 2).

In another embodiment, the nucleic acid molecule includes one or more heavy chain framework region and one or more light chain framework region as described herein. The heavy and light chain framework regions may be present in the same vector or separate vectors.

Vectors and Host Cells

In another aspect, the application features host cells and vectors containing the nucleic acids described herein. The nucleic acids may be present in a single vector or separate vectors present in the same host cell or separate host cell.

In one embodiment, the vectors comprise nucleotides encoding an antibody molecule described herein. In one embodiment, the vectors comprise the nucleotide sequences described herein. The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes may be selected by introducing one or more markers which allow for the selection of transfected host cells. The marker may provide, for example, prototropy to an auxotrophic host, biocide resistance (e.g., antibiotics), or resistance to heavy metals such as copper, or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors may be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. In the case of protoplast fusion, the cells are grown in media and screened for the appropriate activity. Methods and conditions for culturing the resulting transfected cells and for recovering the antibody molecule produced are known to those skilled in the art, and may be varied or optimized depending upon the specific expression vector and mammalian host cell employed, based upon the present description.

The invention also provides host cells comprising a nucleic acid encoding an antibody molecule as described herein.

In one embodiment, the host cells are genetically engineered to comprise nucleic acids encoding the antibody molecule.

In one embodiment, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The invention also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells.

In some embodiments, the host cell is an eukaryotic cell, e.g., a mammalian cell, an insect cell, a yeast cell, or a prokaryotic cell, e.g., E. coli. For example, the mammalian cell can be a cultured cell or a cell line. Exemplary mammalian cells include lymphocytic cell lines (e.g., NSO), Chinese hamster ovary cells (CHO), COS cells, oocyte cells, and cells from a transgenic animal, e.g., mammary epithelial cell.

TABLE 1

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

BAP049 HC

| SEQ ID NO: 1 (Kabat) | HCDR1 | TYWMH |
|---|---|---|
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |

TABLE 1-continued       TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

| SEQ ID NO: 6 | VH | QVQLQQPGSELVRPGASVKLSCKASGYTFT TYWMHWVRQRPGQGLEWIGNIYPGTGGSNF DEKFKNRTSLTVDTSSTTAYMHLASLTSED SAVYYCTRWTTGTGAYWGQGTLVTVSA |
| SEQ ID NO: 7 | DNA VH | CAGGTCCAGCTGCAGCAACCTGGGTCTGAG CTGGTGAGGCCTGGAGCTTCAGTGAAGCTG TCCTGCAAGGCGTCTGGCTACACATTCACC ACTTACTGGATGCACTGGGTGAGGCAGAGG CCTGGACAAGGCCTTGAGTGGATTGGAAAT ATTTATCCTGGTACTGGTGGTTCTAACTTC GATGAGAAGTTCAAAAACAGGACCTCACTG ACTGTAGACACATCCTCCACCACAGCCTAC ATGCACCTCGCCAGCCTGACATCTGAGGAC TCTGCGGTCTATTACTGTACAAGATGGACT ACTGGGACGGGAGCTTATTGGGGCCAAGGG ACTCTGGTCACTGTCTCTGCA |
| SEQ ID NO: 8 | VH | QVQLQQSGSELVRPGASVKLSCKASGYTFT TYWMHWVRQRPGQGLEWIGNIYPGTGGSNF DEKFKNRTSLTVDTSSTTAYMHLASLTSED SAVYYCTRWTTGTGAYWGQGTLVTVSA |
| SEQ ID NO: 9 | DNA VH | CAGGTCCAGCTGCAGCAGTCTGGGTCTGAG CTGGTGAGGCCTGGAGCTTCAGTGAAGCTG TCCTGCAAGGCGTCTGGCTACACATTCACC ACTTACTGGATGCACTGGGTGAGGCAGAGG CCTGGACAAGGCCTTGAGTGGATTGGAAAT ATTTATCCTGGTACTGGTGGTTCTAACTTC GATGAGAAGTTCAAAAACAGGACCTCACTG ACTGTAGACACATCCTCCACCACAGCCTAC ATGCACCTCGCCAGCCTGACATCTGAGGAC TCTGCGGTCTATTACTGTACAAGATGGACT ACTGGGACGGGAGCTTATTGGGGCCAAGGG ACTCTGGTCACTGTCTCTGCA |

BAP049 LC

| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 12 (Kabat) | LCDR3 | QNDYSYPCT |
| SEQ ID NO: 13 (Chothia) | LCDR1 | SQSLLDSGNQKNF |
| SEQ ID NO: 14 (Chothia) | LCDR2 | WAS |
| SEQ ID NO: 15 (Chothia) | LCDR3 | DYSYPC |
| SEQ ID NO: 16 | VL | DIVMTQSPSSLTVTAGEKVTMSCKSSQSLL DSGNQKNFLTWYQQKPGQPPKLLIFWASTR ESGVPDRFTGSGSVTDFTLTISSVQAEDLA VYYCQNDYSYPCTFGGGTKLEIK |
| SEQ ID NO: 17 | DNA VL | GACATTGTGATGACCCAGTCTCCATCCTCC CTGACTGTGACAGCAGGAGAGAAGGTCACT ATGAGCTGCAAGTCCAGTCAGAGTCTGTTA GACAGTGGAAATCAAAAGAACTTCTTGACC TGGTACCAGCAGAAACCAGGGCAGCCTCCT AAACTGTTGATCTTCTGGGCATCCACTAGG GAATCTGGGGTCCCTGATCGCTTCACAGGC |

AGTGGATCTGTAACAGATTTCACTCTCACC ATCAGCAGTGTGCAGGCTGAAGACCTGGCA GTTTATTACTGTCAGAATGATTATAGTTAT CCGTGCACGTTCGGAGGGGGGACCAAGCTG GAAATAAAA

BAP049-chi HC

| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 18 | VH | QVQLQQPGSELVRPGASVKLSCKASGYTFT TYWMHWVRQRPGQGLEWIGNIYPGTGGSNF DEKFKNRTSLTVDTSSTTAYMHLASLTSED SAVYYCTRWTTGTGAYWGQGTTVTVSS |
| SEQ ID NO: 19 | DNA VH | CAGGTCCAGCTGCAGCAGCCTGGGTCTGAG CTGGTGAGGCCTGGAGCTTCAGTGAAGCTG TCCTGCAAGGCGTCTGGCTACACATTCACC ACTTACTGGATGCACTGGGTGAGGCAGAGG CCTGGACAAGGCCTTGAGTGGATTGGAAAT ATTTATCCTGGTACTGGTGGTTCTAACTTC GATGAGAAGTTCAAAAACAGGACCTCACTG ACTGTAGACACATCCTCCACCACAGCCTAC ATGCACCTCGCCAGCCTGACATCTGAGGAC TCTGCGGTCTATTACTGTACAAGATGGACT ACTGGGACGGGAGCTTATTGGGGCCAGGGC ACCACCGTGACCGTGTCCTCC |
| SEQ ID NO: 20 | HC | QVQLQQPGSELVRPGASVKLSCKASGYTFT TYWMHWVRQRPGQGLEWIGNIYPGTGGSNF DEKFKNRTSLTVDTSSTTAYMHLASLTSED SAVYYCTRWTTGTGAYWGQGTTVTVSSAST KGPSVFPLAPCSRSTSESTAALGCLVKDYF PEPVTVSWNSGALTSGVHTFPAVLQSSGLY SLSSVVTVPSSSLGTKTYTCNVDHKPSNTK VDKRVESKYGPPCPPCPAPEFLGGPSVFLF PPKPKDTLMISRTPEVTCVVVDVSQEDPEV QFNWYVDGVEVHNAKTKPREEQFNSTYRVV SVLTVLHQDWLNGKEYKCKVSNKGLPSSIE KTISKAKGQPREPQVYTLPPSQEEMTKNQV SLTCLVKGFYPSDIAVEWESNGQPENNYKT TPPVLDSDGSFFLYSRLTVDKSRWQEGNVF SCSVMHEALHNHYTQKSLSLSLGK |
| SEQ ID NO: 21 | DNA HC | CAGGTCCAGCTGCAGCAGCCTGGGTCTGAG CTGGTGAGGCCTGGAGCTTCAGTGAAGCTG TCCTGCAAGGCGTCTGGCTACACATTCACC ACTTACTGGATGCACTGGGTGAGGCAGAGG CCTGGACAAGGCCTTGAGTGGATTGGAAAT ATTTATCCTGGTACTGGTGGTTCTAACTTC GATGAGAAGTTCAAAAACAGGACCTCACTG ACTGTAGACACATCCTCCACCACAGCCTAC ATGCACCTCGCCAGCCTGACATCTGAGGAC |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

```
                 TCTGCGGTCTATTACTGTACAAGATGGACT
                 ACTGGGACGGGAGCTTATTGGGGCCAGGGC
                 ACCACCGTGACCGTGTCCTCCGCTTCCACC
                 AAGGGCCCATCCGTCTTCCCCCTGGCGCCC
                 TGCTCCAGGAGCACCTCCGAGAGCACAGCC
                 GCCCTGGGCTGCCTGGTCAAGGACTACTTC
                 CCCGAACCGGTGACGGTGTCGTGGAACTCA
                 GGCGCCCTGACCAGCGGCGTGCACACCTTC
                 CCGGCTGTCCTACAGTCCTCAGGACTCTAC
                 TCCCTCAGCAGCGTGGTGACCGTGCCCTCC
                 AGCAGCTTGGGCACGAAGACCTACACCTGC
                 AACGTAGATCACAAGCCCAGCAACACCAAG
                 GTGGACAAGAGAGTTGAGTCCAAATATGGT
                 CCCCCATGCCCACCGTGCCCAGCACCTGAG
                 TTCCTGGGGGGACCATCAGTCTTCCTGTTC
                 CCCCCAAAACCCAAGGACACTCTCATGATC
                 TCCCGGACCCCTGAGGTCACGTGCGTGGTG
                 GTGGACGTGAGCCAGGAAGACCCCGAGGTC
                 CAGTTCAACTGGTACGTGGATGGCGTGGAG
                 GTGCATAATGCCAAGACAAAGCCGCGGGAG
                 GAGCAGTTCAACAGCACGTACCGTGTGGTC
                 AGCGTCCTCACCGTCCTGCACCAGGACTGG
                 CTGAACGGCAAGGAGTACAAGTGCAAGGTG
                 TCCAACAAAGGCCTCCCGTCCTCCATCGAG
                 AAAACCATCTCCAAAGCCAAAGGGCAGCCC
                 CGAGAGCCACAGGTGTACACCCTGCCCCCA
                 TCCCAGGAGGAGATGACCAAGAACCAGGTC
                 AGCCTGACCTGCCTGGTCAAAGGCTTCTAC
                 CCCAGCGACATCGCCGTGGAGTGGGAGAGC
                 AATGGGCAGCCGGAGAACAACTACAAGACC
                 ACGCCTCCCGTGCTGGACTCCGACGGCTCC
                 TTCTTCCTCTACAGCAGGCTAACCGTGGAC
                 AAGAGCAGGTGGCAGGAGGGGAATGTCTTC
                 TCATGCTCCGTGATGCATGAGGCTCTGCAC
                 AACCACTACACACAGAAGAGCCTCTCCCTG
                 TCTCTGGGTAAA
SEQ ID NO: 22  VH    QVQLQQSGSELVRPGASVKLSCKASGYTFT
                     TYWMHWVRQRPGQGLEWIGNIYPGTGSSNF
                     DEKFKNRTSLTVDTSSTTAYMHLASLTSED
                     SAVYYCTRWTTGTGAYWGQGTTVTVSS

SEQ ID NO: 23  DNA   CAGGTCCAGCTGCAGCAGTCTGGGTCTGAG
               VH    CTGGTGAGGCCTGGAGCTTCAGTGAAGCTG
                     TCCTGCAAGGCGTCTGGCTACACATTCACC
                     ACTTACTGGATGCACTGGGTGAGGCAGAGG
                     CCTGGACAAGGCCTTGAGTGGATTGGAAAT
                     ATTTATCCTGGTACTGGTGGTTCTAACTTC
                     GATGAGAAGTTCAAAAACAGGACCTCACTG
                     ACTGTAGACACATCCTCCACCACAGCCTAC
                     ATGCACCTCGCCAGCCTGACATCTGAGGAC
                     TCTGCGGTCTATTACTGTACAAGATGGACT
                     ACTGGGACGGGAGCTTATTGGGGCCAGGGC
                     ACCACCGTGACCGTGTCCTCC

SEQ ID NO: 30  HC    QVQLQQSGSELVRPGASVKLSCKASGYTFT
                     TYWMHWVRQRPGQGLEWIGNIYPGTGSSNF
                     DEKFKNRTSLTVDTSSTTAYMHLASLTSED
                     SAVYYCTRWTTGTGAYWGQGTTVTVSSSAST
                     KGPSVFPLAPCSRSTSESTAALGCLVKDYF
                     PEPVTVSWNSGALTSGVHTFPAVLQSSGLY
                     SLSSVVTVPSSSLGTKTYTCNVDHKPSNTK
                     VDKRVESKYGPPCPPCPAPEFLGGPSVFLF
                     PPKPKDTLMISRTPEVTCVVVDVSQEDPEV
                     QFNWYVDGVEVHNAKTKPREEQFNSTYRVV
                     SVLTVLHQDWLNGKEYKCKVSNKGLPSSIE
                     KTISKAKGQPREPQVYTLPPSQEEMTKNQV
                     SLTCLVKGFYPSDIAVEWESNGQPENNYKT
```

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

```
                     TPPVLDSDGSFFLYSRLTVDKSRWQEGNVF
                     SCSVMHEALHNHYTQKSLSLSLGK

SEQ ID NO: 31  DNA   CAGGTCCAGCTGCAGCAGTCTGGGTCTGAG
               HC    CTGGTGAGGCCTGGAGCTTCAGTGAAGCTG
                     TCCTGCAAGGCGTCTGGCTACACATTCACC
                     ACTTACTGGATGCACTGGGTGAGGCAGAGG
                     CCTGGACAAGGCCTTGAGTGGATTGGAAAT
                     ATTTATCCTGGTACTGGTGGTTCTAACTTC
                     GATGAGAAGTTCAAAAACAGGACCTCACTG
                     ACTGTAGACACATCCTCCACCACAGCCTAC
                     ATGCACCTCGCCAGCCTGACATCTGAGGAC
                     TCTGCGGTCTATTACTGTACAAGATGGACT
                     ACTGGGACGGGAGCTTATTGGGGCCAGGGC
                     ACCACCGTGACCGTGTCCTCCGCTTCCACC
                     AAGGGCCCATCCGTCTTCCCCCTGGCGCCC
                     TGCTCCAGGAGCACCTCCGAGAGCACAGCC
                     GCCCTGGGCTGCCTGGTCAAGGACTACTTC
                     CCCGAACCGGTGACGGTGTCGTGGAACTCA
                     GGCGCCCTGACCAGCGGCGTGCACACCTTC
                     CCGGCTGTCCTACAGTCCTCAGGACTCTAC
                     TCCCTCAGCAGCGTGGTGACCGTGCCCTCC
                     AGCAGCTTGGGCACGAAGACCTACACCTGC
                     AACGTAGATCACAAGCCCAGCAACACCAAG
                     GTGGACAAGAGAGTTGAGTCCAAATATGGT
                     CCCCCATGCCCACCGTGCCCAGCACCTGAG
                     TTCCTGGGGGGACCATCAGTCTTCCTGTTC
                     CCCCCAAAACCCAAGGACACTCTCATGATC
                     TCCCGGACCCCTGAGGTCACGTGCGTGGTG
                     GTGGACGTGAGCCAGGAAGACCCCGAGGTC
                     CAGTTCAACTGGTACGTGGATGGCGTGGAG
                     GTGCATAATGCCAAGACAAAGCCGCGGGAG
                     GAGCAGTTCAACAGCACGTACCGTGTGGTC
                     AGCGTCCTCACCGTCCTGCACCAGGACTGG
                     CTGAACGGCAAGGAGTACAAGTGCAAGGTG
                     TCCAACAAAGGCCTCCCGTCCTCCATCGAG
                     AAAACCATCTCCAAAGCCAAAGGGCAGCCC
                     CGAGAGCCACAGGTGTACACCCTGCCCCCA
                     TCCCAGGAGGAGATGACCAAGAACCAGGTC
                     AGCCTGACCTGCCTGGTCAAAGGCTTCTAC
                     CCCAGCGACATCGCCGTGGAGTGGGAGAGC
                     AATGGGCAGCCGGAGAACAACTACAAGACC
                     ACGCCTCCCGTGCTGGACTCCGACGGCTCC
                     TTCTTCCTCTACAGCAGGCTAACCGTGGAC
                     AAGAGCAGGTGGCAGGAGGGGAATGTCTTC
                     TCATGCTCCGTGATGCATGAGGCTCTGCAC
                     AACCACTACACACAGAAGAGCCTCTCCCTG
                     TCTCTGGGTAAA

BAP049-chi LC

SEQ ID NO: 10  LCDR1  KSSQSLLDSGNQKNFLT
(Kabat)

SEQ ID NO: 11  LCDR2  WASTRES
(Kabat)

SEQ ID NO: 12  LCDR3  QNDYSYPCT
(Kabat)

SEQ ID NO: 13  LCDR1  SQSLLDSGNQKNF
(Chothia)

SEQ ID NO: 14  LCDR2  WAS
(Chothia)

SEQ ID NO: 15  LCDR3  DYSYPC
(Chothia)
```

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

SEQ ID NO: 24  VL    DIVMTQSPSSLTVTAGEKVTMSCKSSQSLL
                     DSGNQKNFLTWYQQKPGQPPKLLIFWASTR
                     ESGVPDRFTGSGSVTDFTLTISSVQAEDLA
                     VYYCQNDYSYPCTFGQGTKVEIK

SEQ ID NO: 25  DNA   GACATTGTGATGACCCAGTCTCCATCCTCC
               VL    CTGACTGTGACAGCAGGAGAGAAGGTCACT
                     ATGAGCTGCAAGTCCAGTCAGAGTCTGTTA
                     GACAGTGGAAATCAAAAGAACTTCTTGACC
                     TGGTACCAGCAGAAACCAGGGCAGCCTCCT
                     AAACTGTTGATCTTCTGGGCATCCACTAGG
                     GAATCTGGGGTCCCTGATCGCTTCACAGGC
                     AGTGGATCTGTAACAGATTTCACTCTCACC
                     ATCAGCAGTGTGCAGGCTGAAGACCTGGCA
                     GTTTATTACTGTCAGAATGATTATAGTTAT
                     CCGTGCACGTTCGGCCAAGGGACCAAGGTG
                     GAAATCAAA

SEQ ID NO: 26  LC    DIVMTQSPSSLTVTAGEKVTMSCKSSQSLL
                     DSGNQKNFLTWYQQKPGQPPKLLIFWASTR
                     ESGVPDRFTGSGSVTDFTLTISSVQAEDLA
                     VYYCQNDYSYPCTFGQGTKVEIKRTVAAPS
                     VFIFPPSDEQLKSGTASVVCLLNNFYPREA
                     KVQWKVDNALQSGNSQESVTEQDSKDSTYS
                     LSSTLTLSKADYEKHKVYACEVTHQGLSSP
                     VTKSFNRGEC

SEQ ID NO: 27  DNA   GACATTGTGATGACCCAGTCTCCATCCTCC
               LC    CTGACTGTGACAGCAGGAGAGAAGGTCACT
                     ATGAGCTGCAAGTCCAGTCAGAGTCTGTTA
                     GACAGTGGAAATCAAAAGAACTTCTTGACC
                     TGGTACCAGCAGAAACCAGGGCAGCCTCCT
                     AAACTGTTGATCTTCTGGGCATCCACTAGG
                     GAATCTGGGGTCCCTGATCGCTTCACAGGC
                     AGTGGATCTGTAACAGATTTCACTCTCACC
                     ATCAGCAGTGTGCAGGCTGAAGACCTGGCA
                     GTTTATTACTGTCAGAATGATTATAGTTAT
                     CCGTGCACGTTCGGCCAAGGGACCAAGGTG
                     GAAATCAAACGTACGGTGGCTGCACCATCT
                     GTCTTCATCTTCCCGCCATCTGATGAGCAG
                     TTGAAATCTGGAACTGCCTCTGTTGTGTGC
                     CTGCTGAATAACTTCTATCCCAGAGAGGCC
                     AAAGTACAGTGGAAGGTGGATAACGCCCTC
                     CAATCGGGTAACTCCCAGGAGAGTGTCACA
                     GAGCAGGACAGCAAGGACAGCACCTACAGC
                     CTCAGCAGCACCCTGACGCTGAGCAAAGCA
                     GACTACGAGAAACACAAAGTCTACGCCTGC
                     GAAGTCACCCATCAGGGCCTGAGCTCGCCC
                     GTCACAAAGAGCTTCAACAGGGGAGAGTGT

BAP049-chi-Y
HC

SEQ ID NO: 1   HCDR1   TYWMH
(Kabat)

SEQ ID NO: 2   HCDR2   NIYPGTGGSNFDEKFKN
(Kabat)

SEQ ID NO: 3   HCDR3   WTTGTGAY
(Kabat)

SEQ ID NO: 4   HCDR1   GYTFTTY
(Chothia)

SEQ ID NO: 5   HCDR2   YPGTGG
(Chothia)

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

SEQ ID NO: 3    HCDR3   WTTGTGAY
(Chothia)

SEQ ID NO: 18   VH     QVQLQQPGSELVRPGASVKLSCKASGYTFT
                       TYWMHWVRQRPGQGLEWIGNIYPGTGGSNF
                       DEKFKNRTSLTVDTSSTTAYMHLASLTSED
                       SAVYYCTRWTTGTGAYWGQGTTVTVSS

SEQ ID NO: 19   DNA    CAGGTCCAGCTGCAGCAGCCTGGGTCTGAG
                VH     CTGGTGAGGCCTGGAGCTTCAGTGAAGCTG
                       TCCTGCAAGGCGTCTGGCTACACATTCACC
                       ACTTACTGGATGCACTGGGTGAGGCAGAGG
                       CCTGGACAAGGCCTTGAGTGGATTGGAAAT
                       ATTTATCCTGGTACTGGTGGTTCTAACTTC
                       GATGAGAAGTTCAAAAACAGGACCTCACTG
                       ACTGTAGACACATCCTCCACCACAGCCTAC
                       ATGCACCTCGCCAGCCTGACATCTGAGGAC
                       TCTGCGGTCTATTACTGTACAAGATGGACT
                       ACTGGGACGGGAGCTTATTGGGGCCAGGGC
                       ACCACCGTGACCGTGTCCTCC

SEQ ID NO: 20   HC     QVQLQQPGSELVRPGASVKLSCKASGYTFT
                       TYWMHWVRQRPGQGLEWIGNIYPGTGGSNF
                       DEKFKNRTSLTVDTSSTTAYMHLASLTSED
                       SAVYYCTRWTTGTGAYWGQGTTVTVSSAST
                       KGPSVFPLAPCSRSTSESTAALGCLVKDYF
                       PEPVTVSWNSGALTSGVHTFPAVLQSSGLY
                       SLSSVVTVPSSSLGTKTYTCNVDHKPSNTK
                       VDKRVESKYGPPCPPCPAPEFLGGPSVFLF
                       PPKPKDTLMISRTPEVTCVVVDVSQEDPEV
                       QFNWYVDGVEVHNAKTKPREEQFNSTYRVV
                       SVLTVLHQDWLNGKEYKCKVSNKGLPSSIE
                       KTISKAKGQPREPQVYTLPPSQEEMTKNQV
                       SLTCLVKGFYPSDIAVEWESNGQPENNYKT
                       TPPVLDSDGSFFLYSRLTVDKSRWQEGNVF
                       SCSVMHEALHNHYTQKSLSLSLGK

SEQ ID NO: 21   DNA    CAGGTCCAGCTGCAGCAGCCTGGGTCTGAG
                HC     CTGGTGAGGCCTGGAGCTTCAGTGAAGCTG
                       TCCTGCAAGGCGTCTGGCTACACATTCACC
                       ACTTACTGGATGCACTGGGTGAGGCAGAGG
                       CCTGGACAAGGCCTTGAGTGGATTGGAAAT
                       ATTTATCCTGGTACTGGTGGTTCTAACTTC
                       GATGAGAAGTTCAAAAACAGGACCTCACTG
                       ACTGTAGACACATCCTCCACCACAGCCTAC
                       ATGCACCTCGCCAGCCTGACATCTGAGGAC
                       TCTGCGGTCTATTACTGTACAAGATGGACT
                       ACTGGGACGGGAGCTTATTGGGGCCAGGGC
                       ACCACCGTGACCGTGTCCTCCGCTTCCACC
                       AAGGGCCCATCCGTCTTCCCCCTGGCGCCC
                       TGCTCCAGGAGCACCTCCGAGAGCACAGCC
                       GCCCTGGGCTGCCTGGTCAAGGACTACTTC
                       CCCGAACCGGTGACGGTGTCGTGGAACTCA
                       GGCGCCCTGACCAGCGGCGTGCACACCTTC
                       CCGGCTGTCCTACAGTCCTCAGGACTCTAC
                       TCCCTCAGCAGCGTGGTGACCGTGCCCTCC
                       AGCAGCTTGGGCACGAAGACCTACACCTGC
                       AACGTAGATCACAAGCCCAGCAACACCAAG
                       GTGGACAAGAGAGTTGAGTCCAAATATGGT
                       CCCCCATGCCCACCGTGCCCAGCACCTGAG
                       TTCCTGGGGGGACCATCAGTCTTCCTGTTC
                       CCCCCAAAACCCAAGGACACTCTCATGATC
                       TCCCGGACCCCTGAGGTCACGTGCGTGGTG
                       GTGGACGTGAGCCAGGAAGACCCCGAGGTC
                       CAGTTCAACTGGTACGTGGATGGCGTGGAG
                       GTGCATAATGCCAAGACAAAGCCGCGGGAG
                       GAGCAGTTCAACAGCACGTACCGTGTGGTC
                       AGCGTCCTCACCGTCCTGCACCAGGACTGG
                       CTGAACGGCAAGGAGTACAAGTGCAAGGTG

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

```
                TCCAACAAAGGCCTCCCGTCCTCCATCGAG
                AAAACCATCTCCAAAGCCAAAGGGCAGCCC
                CGAGAGCCACAGGTGTACACCCTGCCCCCA
                TCCCAGGAGGAGATGACCAAGAACCAGGTC
                AGCCTGACCTGCCTGGTCAAAGGCTTCTAC
                CCCAGCGACATCGCCGTGGAGTGGGAGAGC
                AATGGGCAGCCGGAGAACAACTACAAGACC
                ACGCCTCCCGTGCTGGACTCCGACGGCTCC
                TTCTTCCTCTACAGCAGGCTAACCGTGGAC
                AAGAGCAGGTGGCAGGAGGGGAATGTCTTC
                TCATGCTCCGTGATGCATGAGGCTCTGCAC
                AACCACTACACACAGAAGAGCCTCTCCCTG
                TCTCTGGGTAAA

SEQ ID NO: 22   VH   QVQLQQSGSELVRPGASVKLSCKASGYTFT
                     TYWMHWVRQRPGQGLEWIGNIYPGTGGSNF
                     DEKFKNRTSLTVDTSSTTAYMHLASLTSED
                     SAVYYCTRWTTGTGAYWGQGTTVTVSS

SEQ ID NO: 23   DNA  CAGGTCCAGCTGCAGCAGTCTGGGTCTGAG
                VH   CTGGTGAGGCCTGGAGCTTCAGTGAAGCTG
                     TCCTGCAAGGCGTCTGGCTACACATTCACC
                     ACTTACTGGATGCACTGGGTGAGGCAGAGG
                     CCTGGACAAGGCCTTGAGTGGATTGGAAAT
                     ATTTATCCTGGTACTGGTGGTTCTAACTTC
                     GATGAGAAGTTCAAAAACAGGACCTCACTG
                     ACTGTAGACACATCCTCCACCACAGCCTAC
                     ATGCACCTCGCCAGCCTGACATCTGAGGAC
                     TCTGCGGTCTATTACTGTACAAGATGGACT
                     ACTGGGACGGGAGCTTATTGGGGCCAGGGC
                     ACCACCGTGACCGTGTCCTCC

SEQ ID NO: 30   HC   QVQLQQSGSELVRPGASVKLSCKASGYTFT
                     TYWMHWVRQRPGQGLEWIGNIYPGTGGSNF
                     DEKFKNRTSLTVDTSSTTAYMHLASLTSED
                     SAVYYCTRWTTGTGAYWGQGTTVTVSSAST
                     KGPSVFPLAPCSRSTSESTAALGCLVKDYF
                     PEPVTVSWNSGALTSGVHTFPAVLQSSGLY
                     SLSSVVTVPSSSLGTKTYTCNVDHKPSNTK
                     VDKRVESKYGPPCPPCPAPEFLGGPSVFLF
                     PPKPKDTLMISRTPEVTCVVVDVSQEDPEV
                     QFNWYVDGVEVHNAKTKPREEQFNSTYRVV
                     SVLTVLHQDWLNGKEYKCKVSNKGLPSSIE
                     KTISKAKGQPREPQVYTLPPSQEEMTKNQV
                     SLTCLVKGFYPSDIAVEWESNGQPENNYKT
                     TPPVLDSDGSFFLYSRLTVDKSRWQEGNVF
                     SCSVMHEALHNHYTQKSLSLSLGK

SEQ ID NO: 31   DNA  CAGGTCCAGCTGCAGCAGTCTGGGTCTGAG
                HC   CTGGTGAGGCCTGGAGCTTCAGTGAAGCTG
                     TCCTGCAAGGCGTCTGGCTACACATTCACC
                     ACTTACTGGATGCACTGGGTGAGGCAGAGG
                     CCTGGACAAGGCCTTGAGTGGATTGGAAAT
                     ATTTATCCTGGTACTGGTGGTTCTAACTTC
                     GATGAGAAGTTCAAAAACAGGACCTCACTG
                     ACTGTAGACACATCCTCCACCACAGCCTAC
                     ATGCACCTCGCCAGCCTGACATCTGAGGAC
                     TCTGCGGTCTATTACTGTACAAGATGGACT
                     ACTGGGACGGGAGCTTATTGGGGCCAGGGC
                     ACCACCGTGACCGTGTCCTCCGCTTCCACC
                     AAGGGCCCATCCGTCTTCCCCCTGGCGCCC
                     TGCTCCAGGAGCACCTCCGAGAGCACAGCC
                     GCCCTGGGCTGCCTGGTCAAGGACTACTTC
                     CCCGAACCGGTGACGGTGTCGTGGAACTCA
                     GGCGCCCTGACCAGCGGCGTGCACACCTTC
                     CCGGCTGTCCTACAGTCCTCAGGACTCTAC
                     TCCCTCAGCAGCGTGGTGACCGTGCCCTCC
                     AGCAGCTTGGGCACGAAGACCTACACCTGC
                     AACGTAGATCACAAGCCCAGCAACACCAAG
```

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

```
                GTGGACAAGAGAGTTGAGTCCAAATATGGT
                CCCCCATGCCCACCGTGCCCAGCACCTGAG
                TTCCTGGGGGGACCATCAGTCTTCCTGTTC
                CCCCCAAAACCCAAGGACACTCTCATGATC
                TCCCGGACCCCTGAGGTCACGTGCGTGGTG
                GTGGACGTGAGCCAGGAAGACCCCGAGGTC
                CAGTTCAACTGGTACGTGGATGGCGTGGAG
                GTGCATAATGCCAAGACAAAGCCGCGGGAG
                GAGCAGTTCAACAGCACGTACCGTGTGGTC
                AGCGTCCTCACCGTCCTGCACCAGGACTGG
                CTGAACGGCAAGGAGTACAAGTGCAAGGTG
                TCCAACAAAGGCCTCCCGTCCTCCATCGAG
                AAAACCATCTCCAAAGCCAAAGGGCAGCCC
                CGAGAGCCACAGGTGTACACCCTGCCCCCA
                TCCCAGGAGGAGATGACCAAGAACCAGGTC
                AGCCTGACCTGCCTGGTCAAAGGCTTCTAC
                CCCAGCGACATCGCCGTGGAGTGGGAGAGC
                AATGGGCAGCCGGAGAACAACTACAAGACC
                ACGCCTCCCGTGCTGGACTCCGACGGCTCC
                TTCTTCCTCTACAGCAGGCTAACCGTGGAC
                AAGAGCAGGTGGCAGGAGGGGAATGTCTTC
                TCATGCTCCGTGATGCATGAGGCTCTGCAC
                AACCACTACACACAGAAGAGCCTCTCCCTG
                TCTCTGGGTAAA

BAP049-chi-Y
LC

SEQ ID NO: 10   LCDR1  KSSQSLLDSGNQKNFLT
(Kabat)

SEQ ID NO: 11   LCDR2  WASTRES
(Kabat)

SEQ ID NO: 32   LCDR3  QNDYSYPYT
(Kabat)

SEQ ID NO: 13   LCDR1  SQSLLDSGNQKNF
(Chothia)

SEQ ID NO: 14   LCDR2  WAS
(Chothia)

SEQ ID NO: 33   LCDR3  DYSYPY
(Chothia)

SEQ ID NO: 34   VL     DIVMTQSPSSLTVTAGEKVTMSCKSSQSLL
                       DSGNQKNFLTWYQQKPGQPPKLLIFWASTR
                       ESGVPDRFTGSGSVTDFTLTISSVQAEDLA
                       VYYCQNDYSYPYTFGQGTKVEIK

SEQ ID NO: 35   DNA    GACATTGTGATGACCCAGTCTCCATCCTCC
                VL     CTGACTGTGACAGCAGGAGAGAAGGTCACT
                       ATGAGCTGCAAGTCCAGTCAGAGTCTGTTA
                       GACAGTGGAAATCAAAAGAACTTCTTGACC
                       TGGTACCAGCAGAAACCAGGGCAGCCTCCT
                       AAACTGTTGATCTTCTGGGCATCCACTAGG
                       GAATCTGGGGTCCCTGATCGCTTCACAGGC
                       AGTGGATCTGTAACAGATTTCACTCTCACC
                       ATCAGCAGTGTGCAGGCTGAAGACCTGGCA
                       GTTTATTACTGTCAGAATGATTATAGTTAT
                       CCGTACACGTTCGGCCAAGGGACCAAGGTG
                       GAAATCAAA

SEQ ID NO: 36   LC     DIVMTQSPSSLTVTAGEKVTMSCKSSQSLL
                       DSGNQKNFLTWYQQKPGQPPKLLIFWASTR
                       ESGVPDRFTGSGSVTDFTLTISSVQAEDLA
                       VYYCQNDYSYPYTFGQGTKVEIKRTVAAPS
                       VFIFPPSDEQLKSGTASVVCLLNNFYPREA
```

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

|  |  |  |
|---|---|---|
|  |  | KVQWKVDNALQSGNSQESVTEQDSKDSTYS LSSTLTLSKADYEKHKVYACEVTHQGLSSP VTKSFNRGEC |
| SEQ ID NO: 37 | DNA LC | GACATTGTGATGACCCAGTCTCCATCCTCC CTGACTGTGACAGCAGGAGAGAAGGTCACT ATGAGCTGCAAGTCCAGTCAGAGTCTGTTA GACAGTGGAAATCAAAAGAACTTCTTGACC TGGTACCAGCAGAAACCAGGGCAGCCTCCT AAACTGTTGATCTTCTGGGCATCCACTAGG GAATCTGGGGTCCCTGATCGCTTCACAGGC AGTGGATCTGTAACAGATTTCACTCTCACC ATCAGCAGTGTGCAGGCTGAAGACCTGGCA GTTTATTACTGTCAGAATGATTATAGTTAT CCGTACACGTTCGGCCAAGGGACCAAGGTG GAAATCAAACGTACGGTGGCTGCACCATCT GTCTTCATCTTCCCGCCATCTGATGAGCAG TTGAAATCTGGAACTGCCTCTGTTGTGTGC CTGCTGAATAACTTCTATCCCAGAGAGGCC AAAGTACAGTGGAAGGTGGATAACGCCCTC CAATCGGGTAACTCCCAGGAGAGTGTCACA GAGCAGGACAGCAAGGACAGCACCTACAGC CTCAGCAGCACCCTGACGCTGAGCAAAGCA GACTACGAGAAACACAAAGTCTACGCCTGC GAAGTCACCCATCAGGGCCTGAGCTCGCCC GTCACAAAGAGCTTCAACAGGGGAGAGTGT |

BAP049-hum01
HC

| SEQ ID NO: 1 (Kabat) | HCDR1 | TYWMH |
|---|---|---|
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFT TYWMHWVRQATGQGLEWMGNIYPGTGGSNF DEKFKNRVTITADKSTSTAYMELSSLRSED TAVYYCTRWTTGTGAYWGQGTTVTSS |
| SEQ ID NO: 39 | DNA VH | GAAGTGCAGCTGGTGCAGTCTGGAGCAGAG GTGAAAAAGCCCGGGGAGTCTCTGAGGATC TCCTGTAAGGGTTCTGGCTACACATTCACC ACTTACTGGATGCACTGGGTGCGACAGGCC ACTGGACAAGGGCTTGAGTGGATGGGTAAT ATTTATCCTGGTACTGGTGGTTCTAACTTC GATGAGAAGTTCAAGAACAGAGTCACGATT ACCGCGGACAAATCCACGAGCACAGCCTAC ACGGCCGTGTATTACTGTACAAGATGGACT ACTGGGACGGGAGCTTATTGGGGCCAGGGC ACCACCGTGACCGTGTCCTCC |
| SEQ ID NO: 40 | HC | EVQLVQSGAEVKKPGESLRISCKGSGYTFT TYWMHWVRQATGQGLEWMGNIYPGTGGSNF DEKFKNRVTITADKSTSTAYMELSSLRSED TAVYYCTRWTTGTGAYWGQGTTVTSSAST |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

|  |  |  |
|---|---|---|
|  |  | KGPSVFPPLAPCSRSTSESTAALGCLVKDYF PEPVTVSWNSGALTSGVHTFPAVLQSSGLY SLSSVVTVPSSSLGTKTYTCNVDHKPSNTK VDKRVESKYGPPCPPCPAPEFLGGPSVFLF PPKPKDTLMISRTPEVTCVVVDVSQEDPEV QFNWYVDGVEVHNAKTKPREEQFNSTYRVV SVLTVLHQDWLNGKEYKCKVSNKGLPSSIE KTISKAKGQPREPQVYTLPPSQEEMTKNQV SLTCLVKGFYPSDIAVEWESNGQPENNYKT TPPVLDSDGSFFLYSRLTVDKSRWQEGNVF SCSVMHEALHNHYTQKSLSLSLGK |
| SEQ ID NO: 41 | DNA HC | GAAGTGCAGCTGGTGCAGTCTGGAGCAGAG GTGAAAAAGCCCGGGGAGTCTCTGAGGATC TCCTGTAAGGGTTCTGGCTACACATTCACC ACTTACTGGATGCACTGGGTGCGACAGGCC ACTGGACAAGGGCTTGAGTGGATGGGTAAT ATTTATCCTGGTACTGGTGGTTCTAACTTC GATGAGAAGTTCAAGAACAGAGTCACGATT ACCGCGGACAAATCCACGAGCACAGCCTAC ATGGAGCTGAGCAGCCTGAGATCTGAGGAC ACGGCCGTGTATTACTGTACAAGATGGACT ACTGGGACGGGAGCTTATTGGGGCCAGGGC ACCACCGTGACCGTGTCCTCCGCTTCCACC AAGGGCCCATCCGTCTTCCCCCTGGCGCCC TGCTCCAGGAGCACCTCCGAGAGCACAGCC GCCCTGGGCTGCCTGGTCAAGGACTACTTC CCCGAACCGGTGACGGTGTCGTGGAACTCA GGCGCCCTGACCAGCGGCGTGCACACCTTC CCGGCTGTCCTACAGTCCTCAGGACTCTAC TCCCTCAGCAGCGTGGTGACCGTGCCCTCC AGCAGCTTGGGCACGAAGACCTACACCTGC AACGTAGATCACAAGCCCAGCAACACCAAG GTGGACAAGAGAGTTGAGTCCAAATATGGT CCCCCATGCCCACCGTGCCCAGCACCTGAG TTCCTGGGGGGACCATCAGTCTTCCTGTTC CCCCCAAAACCCAAGGACACTCTCATGATC TCCCGGACCCCTGAGGTCACGTGCGTGGTG GTGGACGTGAGCCAGGAAGACCCCGAGGTC CAGTTCAACTGGTACGTGGATGGCGTGGAG GTGCATAATGCCAAGACAAAGCCGCGGGAG GAGCAGTTCAACAGCACGTACCGTGTGGTC AGCGTCCTCACCGTCCTGCACCAGGACTGG CTGAACGGCAAGGAGTACAAGTGCAAGGTG TCCAACAAAGGCCTCCCGTCCTCCATCGAG AAAACCATCTCCAAAGCCAAAGGGCAGCCC CGAGAGCCACAGGTGTACACCCTGCCCCCA TCCCAGGAGGAGATGACCAAGAACCAGGTC AGCCTGACCTGCCTGGTCAAAGGCTTCTAC CCCAGCGACATCGCCGTGGAGTGGGAGAGC AATGGGCAGCCGGAGAACAACTACAAGACC ACGCCTCCCGTGCTGGACTCCGACGGCTCC TTCTTCCTCTACAGCAGGCTAACCGTGGAC AAGAGCAGGTGGCAGGAGGGGAATGTCTTC TCATGCTCCGTGATGCATGAGGCTCTGCAC AACCACTACACACAGAAGAGCCTCTCCCTG TCTCTGGGTAAA |

BAP049-hum01
LC

| SEQ ID NO: 10 (Kabat) | LCDR1 | KSSQSLLDSGNQKNFLT |
|---|---|---|
| SEQ ID NO: 11 (Kabat) | LCDR2 | WASTRES |
| SEQ ID NO: 32 (Kabat) | LCDR3 | QNDYSYPYT |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

SEQ ID NO: 13  LCDR1  SQSLLDSGNQKNF
(Chothia)

SEQ ID NO: 14  LCDR2  WAS
(Chothia)

SEQ ID NO: 33  LCDR3  DYSYPY
(Chothia)

SEQ ID NO: 42  VL     EIVLTQSPATLSLSPGERATLSCKSSQSLL
                      DSGNQKNFLTWYQQKPGQAPRLLIYWASTR
                      ESGVPSRFSGSGSGTEFTLTISSLQPDDFA
                      TYYCQNDYSYPYTFGQGTKVEIK

SEQ ID NO: 43  DNA    GAAATTGTGTTGACACAGTCTCCAGCCACC
               VL     CTGTCTTTGTCTCCAGGGGAAAGAGCCACC
                      CTCTCCTGCAAGTCCAGTCAGAGTCTGTTA
                      GACAGTGGAAATCAAAAGAACTTCTTGACC
                      TGGTACCAGCAGAAACCTGGCCAGGCTCCC
                      AGGCTCCTCATCTATTGGGCATCCACTAGG
                      GAATCTGGGGTCCCATCAAGGTTCAGCGGC
                      AGTGGATCTGGGACAGAATTCACTCTCACC
                      ATCAGCAGCCTGCAGCCTGATGATTTTGCA
                      ACTTATTACTGTCAGAATGATTATAGTTAT
                      CCGTACACGTTCGGCCAAGGGACCAAGGTG
                      GAAATCAAA

SEQ ID NO: 44  LC     EIVLTQSPATLSLSPGERATLSCKSSQSLL
                      DSGNQKNFLTWYQQKPGQAPRLLIYWASTR
                      ESGVPSRFSGSGSGTEFTLTISSLQPDDFA
                      TYYCQNDYSYPYTFGQGTKVEIKRTVAAPS
                      VFIFPPSDEQLKSGTASVVCLLNNFYPREA
                      KVQWKVDNALQSGNSQESVTEQDSKDSTYS
                      LSSTLTLSKADYEKHKVYACEVTHQGLSSP
                      VTKSFNRGEC

SEQ ID NO: 45  DNA    GAAATTGTGTTGACACAGTCTCCAGCCACC
               LC     CTGTCTTTGTCTCCAGGGGAAAGAGCCACC
                      CTCTCCTGCAAGTCCAGTCAGAGTCTGTTA
                      GACAGTGGAAATCAAAAGAACTTCTTGACC
                      TGGTACCAGCAGAAACCTGGCCAGGCTCCC
                      AGGCTCCTCATCTATTGGGCATCCACTAGG
                      GAATCTGGGGTCCCATCAAGGTTCAGCGGC
                      AGTGGATCTGGGACAGAATTCACTCTCACC
                      ATCAGCAGCCTGCAGCCTGATGATTTTGCA
                      ACTTATTACTGTCAGAATGATTATAGTTAT
                      CCGTACACGTTCGGCCAAGGGACCAAGGTG
                      GAAATCAAACGTACGGTGGCTGCACCATCT
                      GTCTTCATCTTCCCGCCATCTGATGAGCAG
                      TTGAAATCTGGAACTGCCTCTGTTGTGTGC
                      CTGCTGAATAACTTCTATCCCAGAGAGGCC
                      AAAGTACAGTGGAAGGTGGATAACGCCCTC
                      CAATCGGGTAACTCCCAGGAGAGTGTCACA
                      GAGCAGGACAGCAAGGACAGCACCTACAGC
                      CTCAGCAGCACCCTGACGCTGAGCAAAGCA
                      GACTACGAGAAACACAAAGTCTACGCCTGC
                      GAAGTCACCCATCAGGGCCTGAGCTCGCCC
                      GTCACAAAGAGCTTCAACAGGGGAGAGTGT

BAP049-hum02
HC

SEQ ID NO: 1   HCDR1  TYWMH
(Kabat)

SEQ ID NO: 2   HCDR2  NIYPGTGGSNFDEKFKN
(Kabat)

SEQ ID NO: 3   HCDR3  WTTGTGAY
(Kabat)

SEQ ID NO: 4   HCDR1  GYTFTTY
(Chothia)

SEQ ID NO: 5   HCDR2  YPGTGG
(Chothia)

SEQ ID NO: 3   HCDR3  WTTGTGAY
(Chothia)

SEQ ID NO: 38  VH     EVQLVQSGAEVKKPGESLRISCKGSGYTFT
                      TYWMHWVRQATGQGLEWMGNIYPGTGGSNF
                      DEKFKNRVTITADKSTSTAYMELSSLRSED
                      TAVYYCTRWTTGTGAYWGQGTTVTVSS

SEQ ID NO: 39  DNA    GAAGTGCAGCTGGTGCAGTCTGGAGCAGAG
               VH     GTGAAAAAGCCCGGGGAGTCTCTGAGGATC
                      TCCTGTAAGGGTTCTGGCTACACATTCACC
                      ACTTACTGGATGCACTGGGTGCGACAGGCC
                      ACTGGACAAGGGCTTGAGTGGATGGGTAAT
                      ATTTATCCTGGTACTGGTGGTTCTAACTTC
                      GATGAGAAGTTCAAGAACAGAGTCACGATT
                      ACCGCGGACAAATCCACGAGCACAGCCTAC
                      ATGGAGCTGAGCAGCCTGAGATCTGAGGAC
                      ACGGCCGTGTATTACTGTACAAGATGGACT
                      ACTGGGACGGGAGCTTATTGGGGCCAGGGC
                      ACCACCGTGACCGTGTCCTCC

SEQ ID NO: 40  HC     EVQLVQSGAEVKKPGESLRISCKGSGYTFT
                      TYWMHWVRQATGQGLEWMGNIYPGTGGSNF
                      DEKFKNRVTITADKSTSTAYMELSSLRSED
                      TAVYYCTRWTTGTGAYWGQGTTVTVSSAST
                      KGPSVFPLAPCSRSTSESTAALGCLVKDYF
                      PEPVTVSWNSGALTSGVHTFPAVLQSSGLY
                      SLSSVVTVPSSSLGTKTYTCNVDHKPSNTK
                      VDKRVESKYGPPCPPCPAPEFLGGPSVFLF
                      PPKPKDTLMISRTPEVTCVVVDVSQEDPEV
                      QFNWYVDGVEVHNAKTKPREEQFNSTYRVV
                      SVLTVLHQDWLNGKEYKCKVSNKGLPSSIE
                      KTISKAKGQPREPQVYTLPPSQEEMTKNQV
                      SLTCLVKGFYPSDIAVEWESNGQPENNYKT
                      TPPVLDSDGSFFLYSRLTVDKSRWQEGNVF
                      SCSVMHEALHNHYTQKSLSLSLGK

SEQ ID NO: 41  DNA    GAAGTGCAGCTGGTGCAGTCTGGAGCAGAG
               HC     GTGAAAAAGCCCGGGGAGTCTCTGAGGATC
                      TCCTGTAAGGGTTCTGGCTACACATTCACC
                      ACTTACTGGATGCACTGGGTGCGACAGGCC
                      ACTGGACAAGGGCTTGAGTGGATGGGTAAT
                      ATTTATCCTGGTACTGGTGGTTCTAACTTC
                      GATGAGAAGTTCAAGAACAGAGTCACGATT
                      ACCGCGGACAAATCCACGAGCACAGCCTAC
                      ATGGAGCTGAGCAGCCTGAGATCTGAGGAC
                      ACGGCCGTGTATTACTGTACAAGATGGACT
                      ACTGGGACGGGAGCTTATTGGGGCCAGGGC
                      ACCACCGTGACCGTGTCCTCCGCTTCCACC
                      AAGGGCCCATCCGTCTTCCCCCTGGCGCCC
                      TGCTCCAGGAGCACCTCCGAGAGCACAGCC
                      GCCCTGGGCTGCCTGGTCAAGGACTACTTC
                      CCCGAACCGGTGACGGTGTCGTGGAACTCA
                      GGCGCCCTGACCAGCGGCGTGCACACCTTC
                      CCGGCTGTCCTACAGTCCTCAGGACTCTAC
                      TCCCTCAGCAGCGTGGTGACCGTGCCCTCC
                      AGCAGCTTGGGCACGAAGACCTACACCTGC
                      AACGTAGATCACAAGCCCAGCAACACCAAG
                      GTGGACAAGAGAGTTGAGTCCAAATATGGT
                      CCCCCATGCCCACCGTGCCCAGCACCTGAG

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

```
                     TTCCTGGGGGGGACCATCAGTCTTCCTGTTC
                     CCCCCAAAACCCAAGGACACTCTCATGATC
                     TCCCGGACCCCTGAGGTCACGTGCGTGGTG
                     GTGGACGTGAGCCAGGAAGACCCCGAGGTC
                     CAGTTCAACTGGTACGTGGATGGCGTGGAG
                     GTGCATAATGCCAAGACAAAGCCGCGGGAG
                     GAGCAGTTCAACAGCACGTACCGTGTGGTC
                     AGCGTCCTCACCGTCCTGCACCAGGACTGG
                     CTGAACGGCAAGGAGTACAAGTGCAAGGTG
                     TCCAACAAAGGCCTCCCGTCCTCCATCGAG
                     AAAACCATCTCCAAAGCCAAAGGGCAGCCC
                     CGAGAGCCACAGGTGTACACCCTGCCCCCA
                     TCCCAGGAGGAGATGACCAAGAACCAGGTC
                     AGCCTGACCTGCCTGGTCAAAGGCTTCTAC
                     CCCAGCGACATCGCCGTGGAGTGGGAGAGC
                     AATGGGCAGCCGGAGAACAACTACAAGACC
                     ACGCCTCCCGTGCTGGACTCCGACGGCTCC
                     TTCTTCCTCTACAGCAGGCTAACCGTGGAC
                     AAGAGCAGGTGGCAGGAGGGGAATGTCTTC
                     TCATGCTCCGTGATGCATGAGGCTCTGCAC
                     AACCACTACACAGAAGAGCCTCTCCCTG
                     TCTCTGGGTAAA
```

BAP049-hum02
LC

| SEQ ID NO: 10 (Kabat) | LCDR1 | KSSQSLLDSGNQKNFLT |
|---|---|---|

| SEQ ID NO: 11 (Kabat) | LCDR2 | WASTRES |
|---|---|---|

| SEQ ID NO: 32 (Kabat) | LCDR3 | QNDYSYPYT |
|---|---|---|

| SEQ ID NO: 13 (Chothia) | LCDR1 | SQSLLDSGNQKNF |
|---|---|---|

| SEQ ID NO: 14 (Chothia) | LCDR2 | WAS |
|---|---|---|

| SEQ ID NO: 33 (Chothia) | LCDR3 | DYSYPY |
|---|---|---|

| SEQ ID NO: 46 | VL | DIQMTQSPSSLSASVGDRVTITCKSSQSLL DSGNQKNFLTWYQQKPGQAPRLLIYWASTR ESGIPPRFSGSGYGTDFTLTINNIESEDAA YYFCQNDYSYPYTFGQGTKVEIK |
|---|---|---|

| SEQ ID NO: 47 | DNA VL | GACATCCAGATGACCCAGTCTCCATCCTCC CTGTCTGCATCTGTAGGAGACAGAGTCACC ATCACTTGCAAGTCCAGTCAGAGTCTGTTA GACAGTGGAAATCAAAAGAACTTCTTGACC TGGTACCAGCAGAAACCTGGCCAGGCTCCC AGGCTCCTCATCTATTGGGCATCCACTAGG GAATCTGGGATCCCACCTCGATTCAGTGGC AGCGGGTATGGAACAGATTTTACCCTCACA ATTAATAACATAGAATCTGAGGATGCTGCA TATTACTTCTGTCAGAATGATTATAGTTAT CCGTACACGTTCGGCCAAGGGACCAAGGTG GAAATCAAA |
|---|---|---|

| SEQ ID NO: 48 | LC | DIQMTQSPSSLSASVGDRVTITCKSSQSLL DSGNQKNFLTWYQQKPGQAPRLLIYWASTR ESGIPPRFSGSGYGTDFTLTINNIESEDAA YYFCQNDYSYPYTFGQGTKVEIKRTVAAPS VFIFPPSDEQLKSGTASVVCLLNNFYPREA |
|---|---|---|

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

```
                     KVQWKVDNALQSGNSQESVTEQDSKDSTYS
                     LSSTLTLSKADYEKHKVYACEVTHQGLSSP
                     VTKSFNRGEC
```

| SEQ ID NO: 49 | DNA LC | GACATCCAGATGACCCAGTCTCCATCCTCC CTGTCTGCATCTGTAGGAGACAGAGTCACC ATCACTTGCAAGTCCAGTCAGAGTCTGTTA GACAGTGGAAATCAAAAGAACTTCTTGACC TGGTACCAGCAGAAACCTGGCCAGGCTCCC AGGCTCCTCATCTATTGGGCATCCACTAGG GAATCTGGGATCCCACCTCGATTCAGTGGC AGCGGGTATGGAACAGATTTTACCCTCACA ATTAATAACATAGAATCTGAGGATGCTGCA TATTACTTCTGTCAGAATGATTATAGTTAT CCGTACACGTTCGGCCAAGGGACCAAGGTG GAAATCAAACGTACGGTGGCTGCACCATCT GTCTTCATCTTCCCGCCATCTGATGAGCAG TTGAAATCTGGAACTGCCTCTGTTGTGTGC CTGCTGAATAACTTCTATCCCAGAGAGGCC AAAGTACAGTGGAAGGTGGATAACGCCCTC CAATCGGGTAACTCCCAGGAGAGTGTCACA GAGCAGGACAGCAAGGACAGCACCTACAGC CTCAGCAGCACCCTGACGCTGAGCAAAGCA GACTACGAGAAACACAAAGTCTACGCCTGC GAAGTCACCCATCAGGGCCTGAGCTCGCCC GTCACAAAGAGCTTCAACAGGGGAGAGTGT |
|---|---|---|

BAP049-hum03
HC

| SEQ ID NO: 1 (Kabat) | HCDR1 | TYWMH |
|---|---|---|

| SEQ ID NO: 2 (Kabat) | HCDR2 | NIYPGTGGSNFDEKFKN |
|---|---|---|

| SEQ ID NO: 3 (Kabat) | HCDR3 | WTTGTGAY |
|---|---|---|

| SEQ ID NO: 4 (Chothia) | HCDR1 | GYTFTTY |
|---|---|---|

| SEQ ID NO: 5 (Chothia) | HCDR2 | YPGTGG |
|---|---|---|

| SEQ ID NO: 3 (Chothia) | HCDR3 | WTTGTGAY |
|---|---|---|

| SEQ ID NO: 50 | VH | EVQLVQSGAEVKKPGESLRISCKGSGYTFT TYWMHWIRQSPSRGLEWLGNIYPGTGGSNF DEKFKNRFTISRDNSKNTLYLQMNSLRAED TAVYYCTRWTTGTGAYWGQGTTVTVSS |
|---|---|---|

| SEQ ID NO: 51 | DNA VH | GAAGTGCAGCTGGTGCAGTCTGGAGCAGAG GTGAAAAAGCCCGGGGAGTCTCTGAGGATC TCCTGTAAGGGTTCTGGCTACACATTCACC ACTTACTGGATGCACTGGATCAGGCAGTCC CCATCGAGAGGCCTTGAGTGGCTGGGTAAT ATTTATCCTGGTACTGGTGGTTCTAACTTC GATGAGAAGTTCAAGAACAGATTCACCATC TCCAGAGACAATTCCAAGAACACGCTGTAT CTTCAAATGAACAGCCTGAGAGCCGAGGAC ACGGCCGTGTATTACTGTACAAGATGGACT ACTGGACGGGGAGCTTATTGGGGCCAGGGC ACCACCGTGACCGTGTCCTCC |
|---|---|---|

| SEQ ID NO: 52 | HC | EVQLVQSGAEVKKPGESLRISCKGSGYTFT TYWMHWIRQSPSRGLEWLGNIYPGTGGSNF DEKFKNRFTISRDNSKNTLYLQMNSLRAED |
|---|---|---|

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

```
              TAVYYCTRWTTGTGAYWGQGTTVTVSSAST
              KGPSVFPLAPCSRSTSESTAALGCLVKDYF
              PEPVTVSWNSGALTSGVHTFPAVLQSSGLY
              SLSSVVTVPSSSLGTKTYTCNVDHKPSNTK
              VDKRVESKYGPPCPPCPAPEFLGGPSVFLF
              PPKPKDTLMISRTPEVTCVVVDVSQEDPEV
              QFNWYVDGVEVHNAKTKPREEQFNSTYRVV
              SVLTVLHQDWLNGKEYKCKVSNKGLPSSIE
              KTISKAKGQPREPQVYTLPPSQEEMTKNQV
              SLTCLVKGFYPSDIAVEWESNGQPENNYKT
              TPPVLDSDGSFFLYSRLTVDKSRWQEGNVF
              SCSVMHEALHNHYTQKSLSLSLGK

SEQ ID NO: 53   DNA   GAAGTGCAGCTGGTGCAGTCTGGAGCAGAG
                HC    GTGAAAAAGCCCGGGGAGTCTCTGAGGATC
                      TCCTGTAAGGGTTCTGGCTACACATTCACC
                      ACTTACTGGATGCACTGGATCAGGCAGTCC
                      CCATCGAGAGGCCTTGAGTGGCTGGGTAAT
                      ATTTATCCTGGTACTGGTGGTTCTAACTTC
                      GATGAGAAGTTCAAGAACAGATTCACCATC
                      TCCAGAGACAATTCCAAGAACACGCTGTAT
                      CTTCAAATGAACAGCCTGAGAGCCGAGGAC
                      ACGGCCGTGTATTACTGTACAAGATGGACT
                      ACTGGGACGGGAGCTTATTGGGGCCAGGGC
                      ACCACCGTGACCGTGTCCTCCGCTTCCACC
                      AAGGGCCCATCCGTCTTCCCCCTGGCGCCC
                      TGCTCCAGGAGCACCTCCGAGAGCACAGCC
                      GCCCTGGGCTGCCTGGTCAAGGACTACTTC
                      CCCGAACCGGTGACGGTGTCGTGGAACTCA
                      GGCGCCCTGACCAGCGGCGTGCACACCTTC
                      CCGGCTGTCCTACAGTCCTCAGGACTCTAC
                      TCCCTCAGCAGCGTGGTGACCGTGCCCTCC
                      AGCAGCTTGGGCACGAAGACCTACACCTGC
                      AACGTAGATCACAAGCCCAGCAACACCAAG
                      GTGGACAAGAGAGGTTGAGTCCAAATATGGT
                      CCCCCATGCCCACCGTGCCCAGCACCTGAG
                      TTCCTGGGGGGACCATCAGTCTTCCTGTTC
                      CCCCCAAAACCCAAGGACACTCTCATGATC
                      TCCCGGACCCCTGAGGTCACGTGCGTGGTG
                      GTGGACGTGAGCCAGGAAGACCCCGAGGTC
                      CAGTTCAACTGGTACGTGGATGGCGTGGAG
                      GTGCATAATGCCAAGACAAAGCCGCGGGAG
                      GAGCAGTTCAACAGCACGTACCGTGTGGTC
                      AGCGTCCTCACCGTCCTGCACCAGGACTGG
                      CTGAACGGCAAGGAGTACAAGTGCAAGGTG
                      TCCAACAAAGGCCTCCCGTCCTCCATCGAG
                      AAAACCATCTCCAAAGCCAAAGGGCAGCCC
                      CGAGAGCCACAGGTGTACACCCTGCCCCCA
                      TCCCAGGAGGAGATGACCAAGAACCAGGTC
                      AGCCTGACCTGCCTGGTCAAAGGCTTCTAC
                      CCCAGCGACATCGCCGTGGAGTGGGAGAGC
                      AATGGGCAGCCGGAGAACAACTACAAGACC
                      ACGCCTCCCGTGCTGGACTCCGACGGCTCC
                      TTCTTCCTCTACAGCAGGCTAACCGTGGAC
                      AAGAGCAGGTGGCAGGAGGGGAATGTCTTC
                      TCATGCTCCGTGATGCATGAGGCTCTGCAC
                      AACCACTACACACAGAAGAGCCTCTCCCTG
                      TCTCTGGGTAAA

BAP049-hum03
LC

SEQ ID NO: 10   LCDR1   KSSQSLLDSGNQKNFLT
(Kabat)

SEQ ID NO: 11   LCDR2   WASTRES
(Kabat)
```

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

```
SEQ ID NO: 32   LCDR3   QNDYSYPYT
(Kabat)

SEQ ID NO: 13   LCDR1   SQSLLDSGNQKNF
(Chothia)

SEQ ID NO: 14   LCDR2   WAS
(Chothia)

SEQ ID NO: 33   LCDR3   DYSYPY
(Chothia)

SEQ ID NO: 46   VL      DIQMTQSPSSLSASVGDRVTITCKSSQSLL
                        DSGNQKNFLTWYQQKPGQAPRLLIYWASTR
                        ESGIPPRFSGSGYGTDFTLTINNIESEDAA
                        YYFCQNDYSYPYTFGQGTKVEIK

SEQ ID NO: 47   DNA     GACATCCAGATGACCCAGTCTCCATCCTCC
                VL      CTGTCTGCATCTGTAGGAGACAGAGTCACC
                        ATCACTTGCAAGTCCAGTCAGAGTCTGTTA
                        GACAGTGGAAATCAAAAGAACTTCTTGACC
                        TGGTACCAGCAGAAACCTGGCCAGGCTCCC
                        AGGCTCCTCATCTATTGGGCATCCACTAGG
                        GAATCTGGGATCCCACCTCGATTCAGTGGC
                        AGCGGGTATGGAACAGATTTTACCCTCACA
                        ATTAATAACATAGAATCTGAGGATGCTGCA
                        TATTACTTCTGTCAGAATGATTATAGTTAT
                        CCGTACACGTTCGGCCAAGGGACCAAGGTG
                        GAAATCAAA

SEQ ID NO: 48   LC      DIQMTQSPSSLSASVGDRVTITCKSSQSLL
                        DSGNQKNFLTWYQQKPGQAPRLLIYWASTR
                        ESGIPPRFSGSGYGTDFTLTINNIESEDAA
                        YYFCQNDYSYPYTFGQGTKVEIKRTVAAPS
                        VFIFPPSDEQLKSGTASVVCLLNNFYPREA
                        KVQWKVDNALQSGNSQESVTEQDSKDSTYS
                        LSSTLTLSKADYEKHKVYACEVTHQGLSSP
                        VTKSFNRGEC

SEQ ID NO: 49   DNA     GACATCCAGATGACCCAGTCTCCATCCTCC
                LC      CTGTCTGCATCTGTAGGAGACAGAGTCACC
                        ATCACTTGCAAGTCCAGTCAGAGTCTGTTA
                        GACAGTGGAAATCAAAAGAACTTCTTGACC
                        TGGTACCAGCAGAAACCTGGCCAGGCTCCC
                        AGGCTCCTCATCTATTGGGCATCCACTAGG
                        GAATCTGGGATCCCACCTCGATTCAGTGGC
                        AGCGGGTATGGAACAGATTTTACCCTCACA
                        ATTAATAACATAGAATCTGAGGATGCTGCA
                        TATTACTTCTGTCAGAATGATTATAGTTAT
                        CCGTACACGTTCGGCCAAGGGACCAAGGTG
                        GAAATCAAACGTACGGTGGCTGCACCATCT
                        GTCTTCATCTTCCCGCCATCTGATGAGCAG
                        TTGAAATCTGGAACTGCCTCTGTTGTGTGC
                        CTGCTGAATAACTTCTATCCCAGAGAGGCC
                        AAAGTACAGTGGAAGGTGGATAACGCCCTC
                        CAATCGGGTAACTCCCAGGAGAGTGTCACA
                        GAGCAGGACAGCAAGGACAGCACCTACAGC
                        CTCAGCAGCACCCTGACGCTGAGCAAAGCA
                        GACTACGAGAAACACAAAGTCTACGCCTGC
                        GAAGTCACCCATCAGGGCCTGAGCTCGCCC
                        GTCACAAAGAGCTTCAACAGGGGAGAGTGT
```

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

BAP049-hum04
HC
_____

| SEQ ID NO: 1 (Kabat) | HCDR1 | TYWMH |
|---|---|---|

| SEQ ID NO: 2 (Kabat) | HCDR2 | NIYPGTGGSNFDEKFKN |
|---|---|---|

| SEQ ID NO: 3 (Kabat) | HCDR3 | WTTGTGAY |
|---|---|---|

| SEQ ID NO: 4 (Chothia) | HCDR1 | GYTFTTY |
|---|---|---|

| SEQ ID NO: 5 (Chothia) | HCDR2 | YPGTGG |
|---|---|---|

| SEQ ID NO: 3 (Chothia) | HCDR3 | WTTGTGAY |
|---|---|---|

| SEQ ID NO: 50 | VH | EVQLVQSGAEVKKPGESLRISCKGSGYTFT TYWMHWIRQSPSRGLEWLGNIYPGTGGSNF DEKFKNRFTISRDNSKNTLYLQMNSLRAED TAVYYCTRWTTGTGAYWGQGTTVTSS |
|---|---|---|

| SEQ ID NO: 51 | DNA VH | GAAGTGCAGCTGGTGCAGTCTGGAGCAGAG GTGAAAAAGCCCGGGGAGTCTCTGAGGATC TCCTGTAAGGGTTCTGGCTACACATTCACC ACTTACTGGATGCACTGGATCAGGCAGTCC CCATCGAGAGGCCTTGAGTGGCTGGGTAAT ATTTATCCTGGTACTGGTGGTTCTAACTTC GATGAGAAGTTCAAGAACAGATTCACCATC TCCAGAGACAATTCCAAGAACACGCTGTAT CTTCAAATGAACAGCCTGAGAGCCGAGGAC ACGGCCGTGTATTACTGTACAAGATGGACT ACTGGGACGGGAGCTTATTGGGGCCAGGGC ACCACCGTGACCGTGTCCTCC |
|---|---|---|

| SEQ ID NO: 52 | HC | EVQLVQSGAEVKKPGESLRISCKGSGYTFT TYWMHWIRQSPSRGLEWLGNIYPGTGGSNF DEKFKNRFTISRDNSKNTLYLQMNSLRAED TAVYYCTRWTTGTGAYWGQGTTVTSSAST KGPSVFPLAPCSRSTSESTAALGCLVKDYF PEPVTVSWNSGALTSGVHTFPAVLQSSGLY SLSSVVTVPSSSLGTKTYTCNVDHKPSNTK VDKRVESKYGPPCPPCPAPEFLGGPSVFLF PPKPKDTLMISRTPEVTCVVVDVSQEDPEV QFNWYVDGVEVHNAKTKPREEQFNSTYRVV SVLTVLHQDWLNGKEYKCKVSNKGLPSSIE KTISKAKGQPREPQVYTLPPSQEEMTKNQV SLTCLVKGFYPSDIAVEWESNGQPENNYKT TPPVLDSDGSFFLYSRLTVDKSRWQEGNVF SCSVMHEALHNHYTQKSLSLSLGK |
|---|---|---|

| SEQ ID NO: 53 | DNA HC | GAAGTGCAGCTGGTGCAGTCTGGAGCAGAG GTGAAAAAGCCCGGGGAGTCTCTGAGGATC TCCTGTAAGGGTTCTGGCTACACATTCACC ACTTACTGGATGCACTGGATCAGGCAGTCC CCATCGAGAGGCCTTGAGTGGCTGGGTAAT ATTTATCCTGGTACTGGTGGTTCTAACTTC GATGAGAAGTTCAAGAACAGATTCACCATC TCCAGAGACAATTCCAAGAACACGCTGTAT CTTCAAATGAACAGCCTGAGAGCCGAGGAC ACGGCCGTGTATTACTGTACAAGATGGACT ACTGGGACGGGAGCTTATTGGGGCCAGGGC ACCACCGTGACCGTGTCCTCCGCTTCCACC AAGGGCCCATCCGTCTTCCCCCTGGCGCCC |
|---|---|---|

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

```
TGCTCCAGGAGCACCTCCGAGAGCACAGCC
GCCCTGGGCTGCCTGGTCAAGGACTACTTC
CCCGAACCGGTGACGGTGTCGTGGAACTCA
GGCGCCCTGACCAGCGGCGTGCACACCTTC
CCGGCTGTCCTACAGTCCTCAGGACTCTAC
TCCCTCAGCAGCGTGGTGACCGTGCCCTCC
AGCAGCTTGGGCACGAAGACCTACACCTGC
AACGTAGATCACAAGCCCAGCAACACCAAG
GTGGACAAGAGAGTTGAGTCCAAATATGGT
CCCCCATGCCCACCGTGCCCAGCACCTGAG
TTCCTGGGGGGACCATCAGTCTTCCTGTTC
CCCCCAAAACCCAAGGACACTCTCATGATC
TCCCGGACCCCTGAGGTCACGTGCGTGGTG
GTGGACGTGAGCCAGGAAGACCCCGAGGTC
CAGTTCAACTGGTACGTGGATGGCGTGGAG
GTGCATAATGCCAAGACAAAGCCGCGGGAG
GAGCAGTTCAACAGCACGTACCGTGTGGTC
AGCGTCCTCACCGTCCTGCACCAGGACTGG
CTGAACGGCAAGGAGTACAAGTGCAAGGTG
TCCAACAAAGGCCTCCCGTCCTCCATCGAG
AAAACCATCTCCAAAGCCAAAGGGCAGCCC
CGAGAGCCACAGGTGTACACCCTGCCCCCA
TCCCAGGAGGATGACCAAGAACCAGGTC
AGCCTGACCTGCCTGGTCAAAGGCTTCTAC
CCCAGCGACATCGCCGTGGAGTGGGAGAGC
AATGGGCAGCCGGAGAACAACTACAAGACC
ACGCCTCCCGTGCTGGACTCCGACGGCTCC
TTCTTCCTCTACAGCAGGCTAACCGTGGAC
AAGAGCAGGTGGCAGGAGGGGAATGTCTTC
TCATGCTCCGTGATGCATGAGGCTCTGCAC
AACCACTACACACAGAAGAGCCTCTCCCTG
TCTCTGGGTAAA
```

BAP049-hum04
LC
_____

| SEQ ID NO: 10 (Kabat) | LCDR1 | KSSQSLLDSGNQKNFLT |
|---|---|---|

| SEQ ID NO: 11 (Kabat) | LCDR2 | WASTRES |
|---|---|---|

| SEQ ID NO: 32 (Kabat) | LCDR3 | QNDYSYPYT |
|---|---|---|

| SEQ ID NO: 13 (Chothia) | LCDR1 | SQSLLDSGNQKNF |
|---|---|---|

| SEQ ID NO: 14 (Chothia) | LCDR2 | WAS |
|---|---|---|

| SEQ ID NO: 33 (Chothia) | LCDR3 | DYSYPY |
|---|---|---|

| SEQ ID NO: 54 | VL | EIVLTQSPATLSLSPGERATLSCKSSQSLL DSGNQKNFLTWYQQKPGKAPKLLIYWASTR ESGVPSRFSGSGSGTDFTFTISSLQPEDIA TYYCQNDYSYPYTFGQGTKVEIK |
|---|---|---|

| SEQ ID NO: 55 | DNA VL | GAAATTGTGTTGACACAGTCTCCAGCCACC CTGTCTTTGTCTCCAGGGGAAAGAGCCACC CTCTCCTGCAAGTCCAGTCAGAGTCTGTTA GACAGTGGAAATCAAAAGAACTTCTTGACC TGGTATCAGCAGAAACCAGGGAAAGCTCCT AAGCTCCTGATCTATTGGGCATCCACTAGG GAATCTGGGGTCCCATCAAGGTTCAGTGGA AGTGGATCTGGGACAGATTTTACTTTCACC ATCAGCAGCCTGCAGCCTGAAGATATTGCA ACATATTACTGTCAGAATGATTATAGTTAT |
|---|---|---|

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

|  |  |  |
|---|---|---|
|  |  | CCGTACACGTTCGGCCAAGGGACCAAGGTG GAAATCAAA |
| SEQ ID NO: 56 | LC | EIVLTQSPATLSLSPGERATLSCKSSQSLL DSGNQKNFLTWYQQKPGKAPKLLIYWASTR ESGVPSRFSGSGSGTDFTFTISSLQPEDIA TYYCQNDYSYPYTFGQGTKVEIKRTVAAPS VFIFPPSDEQLKSGTASVVCLLNNFYPREA KVQWKVDNALQSGNSQESVTEQDSKDSTYS LSSTLTLSKADYEKHKVYACEVTHQGLSSP VTKSFNRGEC |
| SEQ ID NO: 57 | DNA LC | GAAATTGTGTTGACACAGTCTCCAGCCACC CTGTCTTTGTCTCCAGGGGAAAGAGCCACC CTCTCCTGCAAGTCCAGTCAGAGTCTGTTA GACAGTGGAAATCAAAAGAACTTCTTGACC TGGTATCAGCAGAAACCAGGGAAAGCTCCT AAGCTCCTGATCTATTGGGCATCCACTAGG GAATCTGGGGTCCCATCAAGGTTCAGTGGA AGTGGATCTGGGACAGATTTTACTTTCACC ATCAGCAGCCTGCAGCCTGAAGATATTGCA ACATATTACTGTCAGAATGATTATAGTTAT CCGTACACGTTCGGCCAAGGGACCAAGGTG GAAATCAAACGTACGGTGGCTGCACCATCT GTCTTCATCTTCCCGCCATCTGATGAGCAG TTGAAATCTGGAACTGCCTCTGTTGTGTGC CTGCTGAATAACTTCTATCCCAGAGAGGCC AAAGTACAGTGGAAGGTGGATAACGCCCTC CAATCGGGTAACTCCCAGGAGAGTGTCACA GAGCAGGACAGCAAGGACAGCACCTACAGC CTCAGCAGCACCCTGACGCTGAGCAAAGCA GACTACGAGAAACACAAAGTCTACGCCTGC GAAGTCACCCATCAGGGCCTGAGCTCGCCC GTCACAAAGAGCTTCAACAGGGGAGAGTGT |

BAP049-hum05
HC
_____

| SEQ ID NO: 1 (Kabat) | HCDR1 | TYWMH |
|---|---|---|
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFT TYWMHWVRQATGQGLEWMGNIYPGTGGSNF DEKFKNRVTITADKSTSTAYMELSSLRSED TAVYYCTRWTTGTGAYWGQGTTVTVSS |
| SEQ ID NO: 39 | DNA VH | GAAGTGCAGCTGGTGCAGTCTGGAGCAGAG GTGAAAAAGCCCGGGGAGTCTCTGAGGATC TCCTGTAAGGGTTCTGGCTACACATTCACC ACTTACTGGATGCACTGGGTGCGACAGGCC ACTGGACAAGGGCTTGAGTGGATGGGTAAT ATTTATCCTGGTACTGGTGGTTCTAACTTC GATGAGAAGTTCAAGAACAGAGTCACGATT ACCGCGGACAAATCCACGAGCACAGCCTAC |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

|  |  |  |
|---|---|---|
|  |  | ATGGAGCTGAGCAGCCTGAGATCTGAGGAC ACGGCCGTGTATTACTGTACAAGATGGACT ACTGGGACGGGAGCTTATTGGGGCCAGGGC ACCACCGTGACCGTGTCCTCC |
| SEQ ID NO: 40 | HC | EVQLVQSGAEVKKPGESLRISCKGSGYTFT TYWMHWVRQATGQGLEWMGNIYPGTGGSNF DEKFKNRVTITADKSTSTAYMELSSLRSED TAVYYCTRWTTGTGAYWGQGTTVTVSSAST KGPSVFPLAPCSRSTSESTAALGCLVKDYF PEPVTVSWNSGALTSGVHTFPAVLQSSGLY SLSSVVTVPSSSLGTKTYTCNVDHKPSNTK VDKRVESKYGPPCPPCPAPEFLGGPSVFLF PPKPKDTLMISRTPEVTCVVVDVSQEDPEV QFNWYVDGVEVHNAKTKPREEQFNSTYRVV SVLTVLHQDWLNGKEYKCKVSNKGLPSSIE KTISKAKGQPREPQVYTLPPSQEEMTKNQV SLTCLVKGFYPSDIAVEWESNGQPENNYKT TPPVLDSDGSFFLYSRLTVDKSRWQEGNVF SCSVMHEALHNHYTQKSLSLSLGK |
| SEQ ID NO: 41 | DNA HC | GAAGTGCAGCTGGTGCAGTCTGGAGCAGAG GTGAAAAAGCCCGGGGAGTCTCTGAGGATC TCCTGTAAGGGTTCTGGCTACACATTCACC ACTTACTGGATGCACTGGGTGCGACAGGCC ACTGGACAAGGGCTTGAGTGGATGGGTAAT ATTTATCCTGGTACTGGTGGTTCTAACTTC GATGAGAAGTTCAAGAACAGAGTCACGATT ACCGCGGACAAATCCACGAGCACAGCCTAC ATGGAGCTGAGCAGCCTGAGATCTGAGGAC ACGGCCGTGTATTACTGTACAAGATGGACT ACTGGGACGGGAGCTTATTGGGGCCAGGGC ACCACCGTGACCGTGTCCTCCGCTTCCACC AAGGGCCCATCCGTCTTCCCCCTGGCGCCC TGCTCCAGGAGCACCTCCGAGAGCACAGCC GCCCTGGGCTGCCTGGTCAAGGACTACTTC CCCGAACCGGTGACGGTGTCGTGGAACTCA GGCGCCCTGACCAGCGGCGTGCACACCTTC CCGGCTGTCCTACAGTCCTCAGGACTCTAC TCCCTCAGCAGCGTGGTGACCGTGCCCTCC AGCAGCTTGGGCACGAAGACCTACACCTGC AACGTAGATCACAAGCCCAGCAACACCAAG GTGGACAAGAGAGTTGAGTCCAAATATGGT CCCCCATGCCCACCGTGCCCAGCACCTGAG TTCCTGGGGGGACCATCAGTCTTCCTGTTC CCCCCAAAACCCAAGGACACTCTCATGATC TCCCGGACCCCTGAGGTCACGTGCGTGGTG GTGGACGTGAGCCAGGAAGACCCCGAGGTC CAGTTCAACTGGTACGTGGATGGCGTGGAG GTGCATAATGCCAAGACAAAGCCGCGGGAG GAGCAGTTCAACAGCACGTACCGTGTGGTC AGCGTCCTCACCGTCCTGCACCAGGACTGG CTGAACGGCAAGGAGTACAAGTGCAAGGTG TCCAACAAAGGCCTCCCGTCCTCCATCGAG AAAACCATCTCCAAAGCCAAAGGGCAGCCC CGAGAGCCACAGGTGTACACCCTGCCCCCA TCCCAGGAGGAGATGACCAAGAACCAGGTC AGCCTGACCTGCCTGGTCAAAGGCTTCTAC CCCAGCGACATCGCCGTGGAGTGGGAGAGC AATGGGCAGCCGGAGAACAACTACAAGACC ACGCCTCCCGTGCTGGACTCCGACGGCTCC TTCTTCCTCTACAGCAGGCTAACCGTGGAC AAGAGCAGGTGGCAGGAGGGGAATGTCTTC TCATGCTCCGTGATGCATGAGGCTCTGCAC AACCACTACACACAGAAGAGCCTCTCCCTG TCTCTGGGTAAA |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

BAP049-hum05
LC

SEQ ID NO: 10   LCDR1   KSSQSLLDSGNQKNFLT
(Kabat)

SEQ ID NO: 11   LCDR2   WASTRES
(Kabat)

SEQ ID NO: 32   LCDR3   QNDYSYPYT
(Kabat)

SEQ ID NO: 13   LCDR1   SQSLLDSGNQKNF
(Chothia)

SEQ ID NO: 14   LCDR2   WAS
(Chothia)

SEQ ID NO: 33   LCDR3   DYSYPY
(Chothia)

SEQ ID NO: 54   VL   EIVLTQSPATLSLSPGERATLSCKSSQSLL
DSGNQKNFLTWYQQKPGKAPKLLIYWASTR
ESGVPSRFSGSGSGTDFTFTISSLQPEDIA
TYYCQNDYSYPYTFGQGTKVEIK

SEQ ID NO: 55   DNA   GAAATTGTGTTGACACAGTCTCCAGCCACC
VL    CTGTCTTTGTCTCCAGGGGAAAGAGCCACC
CTCTCCTGCAAGTCCAGTCAGAGTCTGTTA
GACAGTGGAAATCAAAAGAACTTCTTGACC
TGGTATCAGCAGAAACCAGGGAAAGCTCCT
AAGCTCCTGATCTATTGGGCATCCACTAGG
GAATCTGGGGTCCCATCAAGGTTCAGTGGA
AGTGGATCTGGGACAGATTTTACTTTCACC
ATCAGCAGCCTGCAGCCTGAAGATATTGCA
ACATATTACTGTCAGAATGATTATAGTTAT
CCGTACACGTTCGGCCAAGGGACCAAGGTG
GAAATCAAA

SEQ ID NO: 56   LC   EIVLTQSPATLSLSPGERATLSCKSSQSLL
DSGNQKNFLTWYQQKPGKAPKLLIYWASTR
ESGVPSRFSGSGSGTDFTFTISSLQPEDIA
TYYCQNDYSYPYTFGQGTKVEIKRTVAAPS
VFIFPPSDEQLKSGTASVVCLLNNFYPREA
KVQWKVDNALQSGNSQESVTEQDSKDSTYS
LSSTLTLSKADYEKHKVYACEVTHQGLSSP
VTKSFNRGEC

SEQ ID NO: 57   DNA   GAAATTGTGTTGACACAGTCTCCAGCCACC
LC    CTGTCTTTGTCTCCAGGGGAAAGAGCCACC
CTCTCCTGCAAGTCCAGTCAGAGTCTGTTA
GACAGTGGAAATCAAAAGAACTTCTTGACC
TGGTATCAGCAGAAACCAGGGAAAGCTCCT
AAGCTCCTGATCTATTGGGCATCCACTAGG
GAATCTGGGGTCCCATCAAGGTTCAGTGGA
AGTGGATCTGGGACAGATTTTACTTTCACC
ATCAGCAGCCTGCAGCCTGAAGATATTGCA
ACATATTACTGTCAGAATGATTATAGTTAT
CCGTACACGTTCGGCCAAGGGACCAAGGTG
GAAATCAAACGTACGGTGGCTGCACCATCT
GTCTTCATCTTCCCGCCATCTGATGAGCAG
TTGAAATCTGGAACTGCCTCTGTTGTGTGC
CTGCTGAATAACTTCTATCCCAGAGAGGCC
AAAGTACAGTGGAAGGTGGATAACGCCCTC
CAATCGGGTAACTCCCAGGAGAGTGTCACA
GAGCAGGACAGCAAGGACAGCACCTACAGC
CTCAGCAGCACCCTGACGCTGAGCAAAGCA
GACTACGAGAAACACAAAGTCTACGCCTGC

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

GAAGTCACCCATCAGGGCCTGAGCTCGCCC
GTCACAAAGAGCTTCAACAGGGGAGAGTGT

BAP049-hum06
HC

SEQ ID NO: 1   HCDR1   TYWMH
(Kabat)

SEQ ID NO: 2   HCDR2   NIYPGTGGSNFDEKFKN
(Kabat)

SEQ ID NO: 3   HCDR3   WTTGTGAY
(Kabat)

SEQ ID NO: 4   HCDR1   GYTFTTY
(Chothia)

SEQ ID NO: 5   HCDR2   YPGTGG
(Chothia)

SEQ ID NO: 3   HCDR3   WTTGTGAY
(Chothia)

SEQ ID NO: 38   VH   EVQLVQSGAEVKKPGESLRISCKGSGYTFT
TYWMHWVRQATGQGLEWMGNIYPGTGGSNF
DEKFKNRVTITADKSTSTAYMELSSLRSED
TAVYYCTRWTTGTGAYWGQGTTVTVSS

SEQ ID NO: 39   DNA   GAAGTGCAGCTGGTGCAGTCTGGAGCAGAG
VH    GTGAAAAAGCCCGGGGAGTCTCTGAGGATC
TCCTGTAAGGGTTCTGGCTACACATTCACC
ACTTACTGGATGCACTGGGTGCGACAGGCC
ACTGGACAAGGGCTTGAGTGGATGGGTAAT
ATTTATCCTGGTACTGGTGGTTCTAACTTC
GATGAGAAGTTCAAGAACAGAGTCACGATT
ACCGCGGACAAATCCACGAGCACAGCCTAC
ATGGAGCTGAGCAGCCTGAGATCTGAGGAC
ACGGCCGTGTATTACTGTACAAGATGGACT
ACTGGGACGGGAGCTTATTGGGGCCAGGGC
ACCACCGTGACCGTGTCCTCC

SEQ ID NO: 40   HC   EVQLVQSGAEVKKPGESLRISCKGSGYTFT
TYWMHWVRQATGQGLEWMGNIYPGTGGSNF
DEKFKNRVTITADKSTSTAYMELSSLRSED
TAVYYCTRWTTGTGAYWGQGTTVTVSSAST
KGPSVFPLAPCSRSTSESTAALGCLVKDYF
PEPVTVSWNSGALTSGVHTFPAVLQSSGLY
SLSSVVTVPSSSLGTKTYTCNVDHKPSNTK
VDKRVESKYGPPCPPCPAPEFLGGPSVFLF
PPKPKDTLMISRTPEVTCVVVDVSQEDPEV
QFNWYVDGVEVHNAKTKPREEQFNSTYRVV
SVLTVLHQDWLNGKEYKCKVSNKGLPSSIE
KTISKAKGQPREPQVYTLPPSQEEMTKNQV
SLTCLVKGFYPSDIAVEWESNGQPENNYKT
TPPVLDSDGSFFLYSRLTVDKSRWQEGNVF
SCSVMHEALHNHYTQKSLSLSLGK

SEQ ID NO: 41   DNA   GAAGTGCAGCTGGTGCAGTCTGGAGCAGAG
HC    GTGAAAAAGCCCGGGGAGTCTCTGAGGATC
TCCTGTAAGGGTTCTGGCTACACATTCACC
ACTTACTGGATGCACTGGGTGCGACAGGCC
ACTGGACAAGGGCTTGAGTGGATGGGTAAT
ATTTATCCTGGTACTGGTGGTTCTAACTTC
GATGAGAAGTTCAAGAACAGAGTCACGATT
ACCGCGGACAAATCCACGAGCACAGCCTAC
ATGGAGCTGAGCAGCCTGAGATCTGAGGAC
ACGGCCGTGTATTACTGTACAAGATGGACT
ACTGGGACGGGAGCTTATTGGGGCCAGGGC

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

```
                    ACCACCGTGACCGTGTCCTCCGCTTCCACC
                    AAGGGCCCATCCGTCTTCCCCCTGGCGCCC
                    TGCTCCAGGAGCACCTCCGAGAGCACAGCC
                    GCCCTGGGCTGCCTGGTCAAGGACTACTTC
                    CCCGAACCGGTGACGGTGTCGTGGAACTCA
                    GGCGCCCTGACCAGCGGCGTGCACACCTTC
                    CCGGCTGTCCTACAGTCCTCAGGACTCTAC
                    TCCCTCAGCAGCGTGGTGACCGTGCCCTCC
                    AGCAGCTTGGGCACGAAGACCTACACCTGC
                    AACGTAGATCACAAGCCCAGCAACACCAAG
                    GTGGACAAGAGAGTTGAGTCCAAATATGGT
                    CCCCCATGCCCACCGTGCCCAGCACCTGAG
                    TTCCTGGGGGGACCATCAGTCTTCCTGTTC
                    CCCCCAAAACCCAAGGACACTCTCATGATC
                    TCCCGGACCCCTGAGGTCACGTGCGTGGTG
                    GTGGACGTGAGCCAGGAAGACCCCGAGGTC
                    CAGTTCAACTGGTACGTGGATGGCGTGGAG
                    GTGCATAATGCCAAGACAAAGCCGCGGGAG
                    GAGCAGTTCAACAGCACGTACCGTGTGGTC
                    AGCGTCCTCACCGTCCTGCACCAGGACTGG
                    CTGAACGGCAAGGAGTACAAGTGCAAGGTG
                    TCCAACAAAGGCCTCCCGTCCTCCATCGAG
                    AAAACCATCTCCAAAGCCAAAGGGCAGCCC
                    CGAGAGCCACAGGTGTACACCCTGCCCCCA
                    TCCCAGGAGGAGATGACCAAGAACCAGGTC
                    AGCCTGACCTGCCTGGTCAAAGGCTTCTAC
                    CCCAGCGACATCGCCGTGGAGTGGGAGAGC
                    AATGGGCAGCCGGAGAACAACTACAAGACC
                    ACGCCTCCCGTGCTGGACTCCGACGGCTCC
                    TTCTTCCTCTACAGCAGGCTAACCGTGGAC
                    AAGAGCAGGTGGCAGGAGGGGAATGTCTTC
                    TCATGCTCCGTGATGCATGAGGCTCTGCAC
                    AACCACTACACACAGAAGAGCCTCTCCCTG
                    TCTCTGGGTAAA
```

BAP049-hum06
LC

SEQ ID NO: 10    LCDR1    KSSQSLLDSGNQKNFLT
(Kabat)

SEQ ID NO: 11    LCDR2    WASTRES
(Kabat)

SEQ ID NO: 32    LCDR3    QNDYSYPYT
(Kabat)

SEQ ID NO: 13    LCDR1    SQSLLDSGNQKNF
(Chothia)

SEQ ID NO: 14    LCDR2    WAS
(Chothia)

SEQ ID NO: 33    LCDR3    DYSYPY
(Chothia)

SEQ ID NO: 58    VL       DIVMTQTPLSLPVTPGEPASISCKSSQSLL
                          DSGNQKNFLTWYQQKPGQAPRLLIYWASTR
                          ESGVPSRFSGSGSGTDFTFTISSLEAEDAA
                          TYYCQNDYSYPYTFGQGTKVEIK

SEQ ID NO: 59    DNA      GATATTGTGATGACCCAGACTCCACTCTCC
                 VL       CTGCCCGTCACCCCTGGAGAGCCGGCCTCC
                          ATCTCCTGCAAGTCCAGTCAGAGTCTGTTA
                          GACAGTGGAAATCAAAAGAACTTCTTGACC
                          TGGTACCAGCAGAAACCTGGCCAGGCTCCC
                          AGGCTCCTCATCTATTGGGCATCCACTAGG
                          GAATCTGGGGTCCCCTCGAGGTTCAGTGGC
                          AGTGGATCTGGGACAGATTTCACCTTTACC
```

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

```
                    ATCAGTAGCCTGGAAGCTGAAGATGCTGCA
                    ACATATTACTGTCAGAATGATTATAGTTAT
                    CCGTACACGTTCGGCCAAGGGACCAAGGTG
                    GAAATCAAA
```

SEQ ID NO: 60    LC       DIVMTQTPLSLPVTPGEPASISCKSSQSLL
                          DSGNQKNFLTWYQQKPGQAPRLLIYWASTR
                          ESGVPSRFSGSGSGTDFTFTISSLEAEDAA
                          TYYCQNDYSYPYTFGQGTKVEIKRTVAAPS
                          VFIFPPSDEQLKSGTASVVCLLNNFYPREA
                          KVQWKVDNALQSGNSQESVTEQDSKDSTYS
                          LSSTLTLSKADYEKHKVYACEVTHQGLSSP
                          VTKSFNRGEC

SEQ ID NO: 61    DNA      GATATTGTGATGACCCAGACTCCACTCTCC
                 LC       CTGCCCGTCACCCCTGGAGAGCCGGCCTCC
                          ATCTCCTGCAAGTCCAGTCAGAGTCTGTTA
                          GACAGTGGAAATCAAAAGAACTTCTTGACC
                          TGGTACCAGCAGAAACCTGGCCAGGCTCCC
                          AGGCTCCTCATCTATTGGGCATCCACTAGG
                          GAATCTGGGGTCCCCTCGAGGTTCAGTGGC
                          AGTGGATCTGGGACAGATTTCACCTTTACC
                          ATCAGTAGCCTGGAAGCTGAAGATGCTGCA
                          ACATATTACTGTCAGAATGATTATAGTTAT
                          CCGTACACGTTCGGCCAAGGGACCAAGGTG
                          GAAATCAAACGTACGGTGGCTGCACCATCT
                          GTCTTCATCTTCCCGCCATCTGATGAGCAG
                          TTGAAATCTGGAACTGCCTCTGTTGTGTGC
                          CTGCTGAATAACTTCTATCCCAGAGAGGCC
                          AAAGTACAGTGGAAGGTGGATAACGCCCTC
                          CAATCGGGTAACTCCCAGGAGAGTGTCACA
                          GAGCAGGACAGCAAGGACAGCACCTACAGC
                          CTCAGCAGCACCCTGACGCTGAGCAAAGCA
                          GACTACGAGAAACACAAAGTCTACGCCTGC
                          GAAGTCACCCATCAGGGCCTGAGCTCGCCC
                          GTCACAAAGAGCTTCAACAGGGGAGAGTGT
```

BAP049-hum07
HC

SEQ ID NO: 1     HCDR1    TYWMH
(Kabat)

SEQ ID NO: 2     HCDR2    NIYPGTGGSNFDEKFKN
(Kabat)

SEQ ID NO: 3     HCDR3    WTTGTGAY
(Kabat)

SEQ ID NO: 4     HCDR1    GYTFTTY
(Chothia)

SEQ ID NO: 5     HCDR2    YPGTGG
(Chothia)

SEQ ID NO: 3     HCDR3    WTTGTGAY
(Chothia)

SEQ ID NO: 38    VH       EVQLVQSGAEVKKPGESLRISCKGSYTFT
                          TYWMHWVRQATGQGLEWMGNIYPGTGGSNF
                          DEKFKNRVTITADKSTSTAYMELSSLRSED
                          TAVYYCTRWTTGTGAYWGQGTTVTVSS

SEQ ID NO: 39    DNA      GAAGTGCAGCTGGTGCAGTCTGGAGCAGAG
                 VH       GTGAAAAAGCCCGGGGAGTCTCTGAGGATC
                          TCCTGTAAGGGTTCTGGCTACACATTCACC
                          ACTTACTGGATGCACTGGGTGCGACAGGCC
                          ACTGGACAAGGGCTTGAGTGGATGGGTAAT
                          ATTTATCCTGGTACTGGTGGTTCTAACTTC
```

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

|  |  |  |
|---|---|---|
|  |  | GATGAGAAGTTCAAGAACAGAGTCACGATT ACCGCGGACAAATCCACGAGCACAGCCTAC ATGGAGCTGAGCAGCCTGAGATCTGAGGAC ACGGCCGTGTATTACTGTACAAGATGGACT ACTGGGACGGGAGCTTATTGGGGCCAGGGC ACCACCGTGACCGTGTCCTCC |
| SEQ ID NO: 40 | HC | EVQLVQSGAEVKKPGESLRISCKGSGYTFT TYWMHWVRQATGQGLEWMGNIYPGTGGSNF DEKFKNRVTITADKSTSTAYMELSSLRSED TAVYYCTRWTTGTGAYWGQGTTVTVSSAST KGPSVFPLAPCSRSTSESTAALGCLVKDYF PEPVTVSWNSGALTSGVHTFPAVLQSSGLY SLSSVVTVPSSSLGTKTYTCNVDHKPSNTK VDKRVESKYGPPCPPCPAPEFLGGPSVFLF PPKPKDTLMISRTPEVTCVVVDVSQEDPEV QFNWYVDGVEVHNAKTKPREEQFNSTYRVV SVLTVLHQDWLNGKEYKCKVSNKGLPSSIE KTISKAKGQPREPQVYTLPPSQEEMTKNQV SLTCLVKGFYPSDIAVEWESNGQPENNYKT TPPVLDSDGSFFLYSRLTVDKSRWQEGNVF SCSVMHEALHNHYTQKSLSLSLGK |
| SEQ ID NO: 41 | DNA HC | GAAGTGCAGCTGGTGCAGTCTGGAGCAGAG GTGAAAAAGCCCGGGGAGTCTCTGAGGATC TCCTGTAAGGGTTCTGGCTACACATTCACC ACTTACTGGATGCACTGGGTGCGACAGGCC ACTGGACAAGGGCTTGAGTGGATGGGTAAT ATTTATCCTGGTACTGGTGGTTCTAACTTC GATGAGAAGTTCAAGAACAGAGTCACGATT ACCGCGGACAAATCCACGAGCACAGCCTAC ATGGAGCTGAGCAGCCTGAGATCTGAGGAC ACGGCCGTGTATTACTGTACAAGATGGACT ACTGGGACGGGAGCTTATTGGGGCCAGGGC ACCACCGTGACCGTGTCCTCCGCTTCCACC AAGGGCCCATCCGTCTTCCCCCTGGCGCCC TGCTCCAGGAGCACCTCCGAGAGCACAGCC GCCCTGGGCTGCCTGGTCAAGGACTACTTC CCCGAACCGGTGACGGTGTCGTGGAACTCA GGCGCCCTGACCAGCGGCGTGCACACCTTC CCGGCTGTCCTACAGTCCTCAGGACTCTAC TCCCTCAGCAGCGTGGTGACCGTGCCCTCC AGCAGCTTGGGCACGAAGACCTACACCTGC AACGTAGATCACAAGCCCAGCAACACCAAG GTGGACAAGAGAGTTGAGTCCAAATATGGT CCCCCATGCCCACCGTGCCCAGCACCTGAG TTCCTGGGGGGACCATCAGTCTTCCTGTTC CCCCCAAAACCCAAGGACACTCTCATGATC TCCCGGACCCCTGAGGTCACGTGCGTGGTG GTGGACGTGAGCCAGGAAGACCCCGAGGTC CAGTTCAACTGGTACGTGGATGGCGTGGAG GTGCATAATGCCAAGACAAAGCCGCGGGAG GAGCAGTTCAACAGCACGTACCGTGTGGTC AGCGTCCTCACCGTCCTGCACCAGGACTGG CTGAACGGCAAGGAGTACAAGTGCAAGGTG TCCAACAAAGGCCTCCCGTCCTCCATCGAG AAAACCATCTCCAAAGCCAAAGGGCAGCCC CGAGAGCCACAGGTGTACACCCTGCCCCCA TCCCAGGAGGAGATGACCAAGAACCAGGTC AGCCTGACCTGCCTGGTCAAAGGCTTCTAC CCCAGCGACATCGCCGTGGAGTGGGAGAGC AATGGGCAGCCGGAGAACAACTACAAGACC ACGCCTCCCGTGCTGGACTCCGACGGCTCC TTCTTCCTCTACAGCAGGCTAACCGTGGAC AAGAGCAGGTGGCAGGAGGGGAATGTCTTC TCATGCTCCGTGATGCATGAGGCTCTGCAC AACCACTACACACAGAAGAGCCTCTCCCTG TCTCTGGGTAAA |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

BAP049-hum07
LC

|  |  |  |  |
|---|---|---|---|
| SEQ ID NO: 10 (Kabat) | LCDR1 | KSSQSLLDSGNQKNFLT |  |
| SEQ ID NO: 11 (Kabat) | LCDR2 | WASTRES |  |
| SEQ ID NO: 32 (Kabat) | LCDR3 | QNDYSYPYT |  |
| SEQ ID NO: 13 (Chothia) | LCDR1 | SQSLLDSGNQKNF |  |
| SEQ ID NO: 14 (Chothia) | LCDR2 | WAS |  |
| SEQ ID NO: 33 (Chothia) | LCDR3 | DYSYPY |  |
| SEQ ID NO: 62 | VL |  | EIVLTQSPATLSLSPGERATLSCKSSQSLL DSGNQKNFLTWYQQKPGKAPKLLIYWASTR ESGVPSRFSGSGSGTDFTFTISSLEAEDAA TYYCQNDYSYPYTFGQGTKVEIK |
| SEQ ID NO: 63 | DNA VL |  | GAAATTGTGTTGACACAGTCTCCAGCCACC CTGTCTTTGTCTCCAGGGGAAAGAGCCACC CTCTCCTGCAAGTCCAGTCAGAGTCTGTTA GACAGTGGAAATCAAAAGAACTTCTTGACC TGGTATCAGCAGAAACCAGGGAAAGCTCCT AAGCTCCTGATCTATTGGGCATCCACTAGG GAATCTGGGGTCCCCTCGAGGTTCAGTGGC AGTGGATCTGGGACAGATTTCACCTTTACC ATCAGTAGCCTGGAAGCTGAAGATGCTGCA ACATATTACTGTCAGAATGATTATAGTTAT CCGTACACGTTCGGCCAAGGGACCAAGGTG GAAATCAAA |
| SEQ ID NO: 64 | LC |  | EIVLTQSPATLSLSPGERATLSCKSSQSLL DSGNQKNFLTWYQQKPGKAPKLLIYWASTR ESGVPSRFSGSGSGTDFTFTISSLEAEDAA TYYCQNDYSYPYTFGQGTKVEIKRTVAAPS VFIFPPSDEQLKSGTASVVCLLNNFYPREA KVQWKVDNALQSGNSQESVTEQDSKDSTYS LSSTLTLSKADYEKHKVYACEVTHQGLSSP VTKSFNRGEC |
| SEQ ID NO: 65 | DNA LC |  | GAAATTGTGTTGACACAGTCTCCAGCCACC CTGTCTTTGTCTCCAGGGGAAAGAGCCACC CTCTCCTGCAAGTCCAGTCAGAGTCTGTTA GACAGTGGAAATCAAAAGAACTTCTTGACC TGGTATCAGCAGAAACCAGGGAAAGCTCCT AAGCTCCTGATCTATTGGGCATCCACTAGG GAATCTGGGGTCCCCTCGAGGTTCAGTGGC AGTGGATCTGGGACAGATTTCACCTTTACC ATCAGTAGCCTGGAAGCTGAAGATGCTGCA ACATATTACTGTCAGAATGATTATAGTTAT CCGTACACGTTCGGCCAAGGGACCAAGGTG GAAATCAAACGTACGGTGGCTGCACCATCT GTCTTCATCTTCCCGCCATCTGATGAGCAG TTGAAATCTGGAACTGCCTCTGTTGTGTGC CTGCTGAATAACTTCTATCCCAGAGAGGCC AAAGTACAGTGGAAGGTGGATAACGCCCTC CAATCGGGTAACTCCCAGGAGAGTGTCACA GAGCAGGACAGCAAGGACAGCACCTACAGC CTCAGCAGCACCCTGACGCTGAGCAAAGCA |

TABLE 1-continued

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

```
                    GACTACGAGAAACACAAAGTCTACGCCTGC
                    GAAGTCACCCATCAGGGCCTGAGCTCGCCC
                    GTCACAAAGAGCTTCAACAGGGGAGAGTGT
```

BAP049-hum08
HC

| SEQ ID NO: 1 (Kabat) | HCDR1 | TYWMH |
|---|---|---|
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |

```
SEQ ID NO: 50   VH    EVQLVQSGAEVKKPGESLRISCKGSGYTFT
                      TYWMHWIRQSPSRGLEWLGNIYPGTGGSNF
                      DEKFKNRFTISRDNSKNTLYLQMNSLRAED
                      TAVYYCTRWTTGTGAYWGQGTTVTVSS

SEQ ID NO: 51   DNA   GAAGTGCAGCTGGTGCAGTCTGGAGCAGAG
                VH    GTGAAAAAGCCCGGGGAGTCTCTGAGGATC
                      TCCTGTAAGGGTTCTGGCTACACATTCACC
                      ACTTACTGGATGCACTGGATCAGGCAGTCC
                      CCATCGAGAGGCCTTGAGTGGCTGGGTAAT
                      ATTTATCCTGGTACTGGTGGTTCTAACTTC
                      GATGAGAAGTTCAAGAACAGATTCACCATC
                      TCCAGAGACAATTCCAAGAACACGCTGTAT
                      CTTCAAATGAACAGCCTGAGAGCCGAGGAC
                      ACGGCCGTGTATTACTGTACAAGATGGACT
                      ACTGGGACGGGAGCTTATTGGGGCCAGGGC
                      ACCACCGTGACCGTGTCCTCC

SEQ ID NO: 52   HC    EVQLVQSGAEVKKPGESLRISCKGSGYTFT
                      TYWMHWIRQSPSRGLEWLGNIYPGTGGSNF
                      DEKFKNRFTISRDNSKNTLYLQMNSLRAED
                      TAVYYCTRWTTGTGAYWGQGTTVTVSSAST
                      KGPSVFPLAPCSRSTSESTAALGCLVKDYF
                      PEPVTVSWNSGALTSGVHTFPAVLQSSGLY
                      SLSSVVTVPSSSLGTKTYTCNVDHKPSNTK
                      VDKRVESKYGPPCPPCPAPEFLGGPSVFLF
                      PPKPKDTLMISRTPEVTCVVVDVSQEDPEV
                      QFNWYVDGVEVHNAKTKPREEQFNSTYRVV
                      SVLTVLHQDWLNGKEYKCKVSNKGLPSSIE
                      KTISKAKGQPREPQVYTLPPSQEEMTKNQV
                      SLTCLVKGFYPSDIAVEWESNGQPENNYKT
                      TPPVLDSDGSFFLYSRLTVDKSRWQEGNVF
                      SCSVMHEALHNHYTQKSLSLSLGK

SEQ ID NO: 53   DNA   GAAGTGCAGCTGGTGCAGTCTGGAGCAGAG
                HC    GTGAAAAAGCCCGGGGAGTCTCTGAGGATC
                      TCCTGTAAGGGTTCTGGCTACACATTCACC
                      ACTTACTGGATGCACTGGATCAGGCAGTCC
                      CCATCGAGAGGCCTTGAGTGGCTGGGTAAT
                      ATTTATCCTGGTACTGGTGGTTCTAACTTC
                      GATGAGAAGTTCAAGAACAGATTCACCATC
                      TCCAGAGACAATTCCAAGAACACGCTGTAT
                      CTTCAAATGAACAGCCTGAGAGCCGAGGAC
                      ACGGCCGTGTATTACTGTACAAGATGGACT
```

```
                    ACTGGGACGGGAGCTTATTGGGGCCAGGGC
                    ACCACCGTGACCGTGTCCTCCGCTTCCACC
                    AAGGGCCCATCCGTCTTCCCCCTGGCGCCC
                    TGCTCCAGGAGCACCTCCGAGAGCACAGCC
                    GCCCTGGGCTGCCTGGTCAAGGACTACTTC
                    CCCGAACCGGTGACGGTGTCGTGGAACTCA
                    GGCGCCCTGACCAGCGGCGTGCACACCTTC
                    CCGGCTGTCCTACAGTCCTCAGGACTCTAC
                    TCCCTCAGCAGCGTGGTGACCGTGCCCTCC
                    AGCAGCTTGGGCACGAAGACCTACACCTGC
                    AACGTAGATCACAAGCCCAGCAACACCAAG
                    GTGGACAAGAGAGTTGAGTCCAAATATGGT
                    CCCCCATGCCCACCGTGCCCAGCACCTGAG
                    TTCCTGGGGGGACCATCAGTCTTCCTGTTC
                    CCCCCAAAACCCAAGGACACTCTCATGATC
                    TCCCGGACCCCTGAGGTCACGTGCGTGGTG
                    GTGGACGTGAGCCAGGAAGACCCCGAGGTC
                    CAGTTCAACTGGTACGTGGATGGCGTGGAG
                    GTGCATAATGCCAAGACAAAGCCGCGGGAG
                    GAGCAGTTCAACAGCACGTACCGTGTGGTC
                    AGCGTCCTCACCGTCCTGCACCAGGACTGG
                    CTGAACGGCAAGGAGTACAAGTGCAAGGTG
                    TCCAACAAAGGCCTCCCGTCCTCCATCGAG
                    AAAACCATCTCCAAAGCCAAAGGGCAGCCC
                    CGAGAGCCACAGGTGTACACCCTGCCCCCA
                    TCCCAGGAGGAGATGACCAAGAACCAGGTC
                    AGCCTGACCTGCCTGGTCAAAGGCTTCTAC
                    CCCAGCGACATCGCCGTGGAGTGGGAGAGC
                    AATGGGCAGCCGGAGAACAACTACAAGACC
                    ACGCCTCCCGTGCTGGACTCCGACGGCTCC
                    TTCTTCCTCTACAGCAGGCTAACCGTGGAC
                    AAGAGCAGGTGGCAGGAGGGGAATGTCTTC
                    TCATGCTCCGTGATGCATGAGGCTCTGCAC
                    AACCACTACACACAGAAGAGCCTCTCCCTG
                    TCTCTGGGTAAA
```

BAP049-hum08
LC

| SEQ ID NO: 10 (Kabat) | LCDR1 | KSSQSLLDSGNQKNFLT |
|---|---|---|
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |

```
SEQ ID NO: 66   VL    EIVLTQSPDFQSVTPKEKVTITCKSSQSLL
                      DSGNQKNFLTWYQQKPGQAPRLLIYWASTR
                      ESGVPSRFSGSGSGTDFTFTISSLEAEDAA
                      TYYCQNDYSYPYTFGQGTKVEIK

SEQ ID NO: 67   DNA   GAAATTGTGCTGACTCAGTCTCCAGACTTT
                VL    CAGTCTGTGACTCCAAAGGAGAAAGTCACC
                      ATCACCTGCAAGTCCAGTCAGAGTCTGTTA
                      GACAGTGGAAATCAAAAGAACTTCTTGACC
                      TGGTACCAGCAGAAACCTGGCCAGGCTCCC
                      AGGCTCCTCATCTATTGGGCATCCACTAGG
                      GAATCTGGGGTCCCCTCGAGGTTCAGTGGC
```

TABLE 1-continued

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

|  |  |  |
|---|---|---|
|  |  | AGTGGATCTGGGACAGATTTCACCTTTACC<br>ATCAGTAGCCTGGAAGCTGAAGATGCTGCA<br>ACATATTACTGTCAGAATGATTATAGTTAT<br>CCGTACACGTTCGGCCAAGGGACCAAGGTG<br>GAAATCAAA |
| SEQ ID NO: 68 | LC | EIVLTQSPDFQSVTPKEKVTITCKSSQSLL<br>DSGNQKNFLTWYQQKPGQAPRLLIYWASTR<br>ESGVPSRFSGSGSGTDFTFTISSLEAEDAA<br>TYYCQNDYSYPYTFGQGTKVEIKRTVAAPS<br>VFIFPPSDEQLKSGTASVVCLLNNFYPREA<br>KVQWKVDNALQSGNSQESVTEQDSKDSTYS<br>LSSTLTLSKADYEKHKVYACEVTHQGLSSP<br>VTKSFNRGEC |
| SEQ ID NO: 69 | DNA<br>LC | GAAATTGTGCTGACTCAGTCTCCAGACTTT<br>CAGTCTGTGACTCCAAAGGAGAAAGTCACC<br>ATCACCTGCAAGTCCAGTCAGAGTCTGTTA<br>GACAGTGGAAATCAAAAGAACTTCTTGACC<br>TGGTACCAGCAGAAACCTGGCCAGGCTCCC<br>AGGCTCCTCATCTATTGGGCATCCACTAGG<br>GAATCTGGGGTCCCCTCGAGGTTCAGTGGC<br>AGTGGATCTGGGACAGATTTCACCTTTACC<br>ATCAGTAGCCTGGAAGCTGAAGATGCTGCA<br>ACATATTACTGTCAGAATGATTATAGTTAT<br>CCGTACACGTTCGGCCAAGGGACCAAGGTG<br>GAAATCAAACGTACGGTGGCTGCACCATCT<br>GTCTTCATCTTCCCGCCATCTGATGAGCAG<br>TTGAAATCTGGAACTGCCTCTGTTGTGTGC<br>CTGCTGAATAACTTCTATCCCAGAGAGGCC<br>AAAGTACAGTGGAAGGTGGATAACGCCCTC<br>CAATCGGGTAACTCCCAGGAGAGTGTCACA<br>GAGCAGGACAGCAAGGACAGCACCTACAGC<br>CTCAGCAGCACCCTGACGCTGAGCAAAGCA<br>GACTACGAGAAACACAAAGTCTACGCCTGC<br>GAAGTCACCCATCAGGGCCTGAGCTCGCCC<br>GTCACAAAGAGCTTCAACAGGGGAGAGTGT |

BAP049-hum09
HC

| SEQ ID NO: 1<br>(Kabat) | HCDR1 | TYWMH |
|---|---|---|
| SEQ ID NO: 2<br>(Kabat) | HCDR2 | NIYPGTGGSNFDEKFKN |
| SEQ ID NO: 3<br>(Kabat) | HCDR3 | WTTGTGAY |
| SEQ ID NO: 4<br>(Chothia) | HCDR1 | GYTFTTY |
| SEQ ID NO: 5<br>(Chothia) | HCDR2 | YPGTGG |
| SEQ ID NO: 3<br>(Chothia) | HCDR3 | WTTGTGAY |
| SEQ ID NO: 38 | VH | EVQLVQSGAEVKKPGESLRISCKGSGYTFT<br>TYWMHWVRQATGQGLEWMGNIYPGTGGSNF<br>DEKFKNRVTITADKSTSTAYMELSSLRSED<br>TAVYYCTRWTTGTGAYWGQGTTVTVSS |
| SEQ ID NO: 39 | DNA<br>VH | GAAGTGCAGCTGGTGCAGTCTGGAGCAGAG<br>GTGAAAAAGCCCGGGGAGTCTCTGAGGATC<br>TCCTGTAAGGGTTCTGGCTACACATTCACC<br>ACTTACTGGATGCACTGGGTGCGACAGGCC<br>ACTGGACAAGGGCTTGAGTGGATGGGTAAT |

|  |  |  |
|---|---|---|
|  |  | ATTTATCCTGGTACTGGTGGTTCTAACTTC<br>GATGAGAAGTTCAAGAACAGAGTCACGATT<br>ACCGCGGACAAATCCACGAGCACAGCCTAC<br>ATGGAGCTGAGCAGCCTGAGATCTGAGGAC<br>ACGGCCGTGTATTACTGTACAAGATGGACT<br>ACTGGGACGGGGAGCTTATTGGGGCCAGGGC<br>ACCACCGTGACCGTGTCCTCC |
| SEQ ID NO: 40 | HC | EVQLVQSGAEVKKPGESLRISCKGSGYTFT<br>TYWMHWVRQATGQGLEWMGNIYPGTGGSNF<br>DEKFKNRVTITADKSTSTAYMELSSLRSED<br>TAVYYCTRWTTGTGAYWGQGTTVTVSSAST<br>KGPSVFPLAPCSRSTSESTAALGCLVKDYF<br>PEPVTVSWNSGALTSGVHTFPAVLQSSGLY<br>SLSSVVTVPSSSLGTKTYTCNVDHKPSNTK<br>VDKRVESKYGPPCPPCPAPEFLGGPSVFLF<br>PPKPKDTLMISRTPEVTCVVVDVSQEDPEV<br>QFNWYVDGVEVHNAKTKPREEQFNSTYRVV<br>SVLTVLHQDWLNGKEYKCKVSNKGLPSSIE<br>KTISKAKGQPREPQVYTLPPSQEEMTKNQV<br>SLTCLVKGFYPSDIAVEWESNGQPENNYKT<br>TPPVLDSDGSFFLYSRLTVDKSRWQEGNVF<br>SCSVMHEALHNHYTQKSLSLSLGK |
| SEQ ID NO: 41 | DNA<br>HC | GAAGTGCAGCTGGTGCAGTCTGGAGCAGAG<br>GTGAAAAAGCCCGGGGAGTCTCTGAGGATC<br>TCCTGTAAGGGTTCTGGCTACACATTCACC<br>ACTTACTGGATGCACTGGGTGCGACAGGCC<br>ACTGGACAAGGGCTTGAGTGGATGGGTAAT<br>ATTTATCCTGGTACTGGTGGTTCTAACTTC<br>GATGAGAAGTTCAAGAACAGAGTCACGATT<br>ACCGCGGACAAATCCACGAGCACAGCCTAC<br>ATGGAGCTGAGCAGCCTGAGATCTGAGGAC<br>ACGGCCGTGTATTACTGTACAAGATGGACT<br>ACTGGGACGGGGAGCTTATTGGGGCCAGGGC<br>ACCACCGTGACCGTGTCCTCCGCTTCCACC<br>AAGGGCCCATCCGTCTTCCCCCTGGCGCCC<br>TGCTCCAGGAGCACCTCCGAGAGCACAGCC<br>GCCCTGGGCTGCCTGGTCAAGGACTACTTC<br>CCCGAACCGGTGACGGTGTCGTGGAACTCA<br>GGCGCCCTGACCAGCGGCGTGCACACCTTC<br>CCGGCTGTCCTACAGTCCTCAGGACTCTAC<br>TCCCTCAGCAGCGTGGTGACCGTGCCCTCC<br>AGCAGCTTGGGCACGAAGACCTACACCTGC<br>AACGTAGATCACAAGCCCAGCAACACCAAG<br>GTGGACAAGAGAGTTGAGTCCAAATATGGT<br>CCCCCATGCCCACCGTGCCCAGCACCTGAG<br>TTCCTGGGGGGACCATCAGTCTTCCTGTTC<br>CCCCCAAAACCCAAGGACACTCTCATGATC<br>TCCCGGACCCCTGAGGTCACGTGCGTGGTG<br>GTGGACGTGAGCCAGGAAGACCCCGAGGTC<br>CAGTTCAACTGGTACGTGGATGGCGTGGAG<br>GTGCATAATGCCAAGACAAAGCCGCGGGAG<br>GAGCAGTTCAACAGCACGTACCGTGTGGTC<br>AGCGTCCTCACCGTCCTGCACCAGGACTGG<br>CTGAACGGCAAGGAGTACAAGTGCAAGGTG<br>TCCAACAAAGGCCTCCCGTCCTCCATCGAG<br>AAAACCATCTCCAAAGCCAAAGGGCAGCCC<br>CGAGAGCCACAGGTGTACACCCTGCCCCCA<br>TCCCAGGAGGAGATGACCAAGAACCAGGTC<br>AGCCTGACCTGCCTGGTCAAAGGCTTCTAC<br>CCCAGCGACATCGCCGTGGAGTGGGAGAGC<br>AATGGGCAGCCGGAGAACAACTACAAGACC<br>ACGCCTCCCGTGCTGGACTCCGACGGCTCC<br>TTCTTCCTCTACAGCAGGCTAACCGTGGAC<br>AAGAGCAGGTGGCAGGAGGGGAATGTCTTC<br>TCATGCTCCGTGATGCATGAGGCTCTGCAC<br>AACCACTACACACAGAAGAGCCTCTCCCTG<br>TCTCTGGGTAAA |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

BAP049-hum09
LC

SEQ ID NO: 10   LCDR1   KSSQSLLDSGNQKNFLT
(Kabat)

SEQ ID NO: 11   LCDR2   WASTRES
(Kabat)

SEQ ID NO: 32   LCDR3   QNDYSYPYT
(Kabat)

SEQ ID NO: 13   LCDR1   SQSLLDSGNQKNF
(Chothia)

SEQ ID NO: 14   LCDR2   WAS
(Chothia)

SEQ ID NO: 33   LCDR3   DYSYPY
(Chothia)

SEQ ID NO: 66   VL   EIVLTQSPDFQSVTPKEKVTITCKSSQSLL
DSGNQKNFLTWYQQKPGQAPRLLIYWASTR
ESGVPSRFSGSGSGTDFTFTISSLEAEDAA
TYYCQNDYSYPYTFGQGTKVEIK

SEQ ID NO: 67   DNA   GAAATTGTGCTGACTCAGTCTCCAGACTTT
             VL   CAGTCTGTGACTCCAAAGGAGAAAGTCACC
ATCACCTGCAAGTCCAGTCAGAGTCTGTTA
GACAGTGGAAATCAAAAGAACTTCTTGACC
TGGTACCAGCAGAAACCTGGCCAGGCTCCC
AGGCTCCTCATCTATTGGGCATCCACTAGG
GAATCTGGGGTCCCCTCGAGGTTCAGTGGC
AGTGGATCTGGGACAGATTTCACCTTTACC
ATCAGTAGCCTGGAAGCTGAAGATGCTGCA
ACATATTACTGTCAGAATGATTATAGTTAT
CCGTACACGTTCGGCCAAGGGACCAAGGTG
GAAATCAAA

SEQ ID NO: 68   LC   EIVLTQSPDFQSVTPKEKVTITCKSSQSLL
DSGNQKNFLTWYQQKPGQAPRLLIYWASTR
ESGVPSRFSGSGSGTDFTFTISSLEAEDAA
TYYCQNDYSYPYTFGQGTKVEIKRTVAAPS
VFIFPPSDEQLKSGTASVVCLLNNFYPREA
KVQWKVDNALQSGNSQESVTEQDSKDSTYS
LSSTLTLSKADYEKHKVYACEVTHQGLSSP
VTKSFNRGEC

SEQ ID NO: 69   DNA   GAAATTGTGCTGACTCAGTCTCCAGACTTT
             LC   CAGTCTGTGACTCCAAAGGAGAAAGTCACC
ATCACCTGCAAGTCCAGTCAGAGTCTGTTA
GACAGTGGAAATCAAAAGAACTTCTTGACC
TGGTACCAGCAGAAACCTGGCCAGGCTCCC
AGGCTCCTCATCTATTGGGCATCCACTAGG
GAATCTGGGGTCCCCTCGAGGTTCAGTGGC
AGTGGATCTGGGACAGATTTCACCTTTACC
ATCAGTAGCCTGGAAGCTGAAGATGCTGCA
ACATATTACTGTCAGAATGATTATAGTTAT
CCGTACACGTTCGGCCAAGGGACCAAGGTG
GAAATCAAACGTACGGTGGCTGCACCATCT
GTCTTCATCTTCCCGCCATCTGATGAGCAG
TTGAAATCTGGAACTGCCTCTGTTGTGTGC
CTGCTGAATAACTTCTATCCCAGAGAGGCC
AAAGTACAGTGGAAGGTGGATAACGCCCTC
CAATCGGGTAACTCCCAGGAGAGTGTCACA
GAGCAGGACAGCAAGGACAGCACCTACAGC
CTCAGCAGCACCCTGACGCTGAGCAAAGCA
GACTACGAGAAACACAAAGTCTACGCCTGC

GAAGTCACCCATCAGGGCCTGAGCTCGCCC
GTCACAAAGAGCTTCAACAGGGGAGAGTGT

BAP049-hum10
HC

SEQ ID NO: 1   HCDR1   TYWMH
(Kabat)

SEQ ID NO: 2   HCDR2   NIYPGTGGSNFDEKFKN
(Kabat)

SEQ ID NO: 3   HCDR3   WTTGTGAY
(Kabat)

SEQ ID NO: 4   HCDR1   GYTFTTY
(Chothia)

SEQ ID NO: 5   HCDR2   YPGTGG
(Chothia)

SEQ ID NO: 3   HCDR3   WTTGTGAY
(Chothia)

SEQ ID NO: 50   VH   EVQLVQSGAEVKKPGESLRISCKGSGYTFT
TYWMHWIRQSPSRGLEWLGNIYPGTGGSNF
DEKFKNRFTISRDNSKNTLYLQMNSLRAED
TAVYYCTRWTTGTGAYWGQGTTVTVSS

SEQ ID NO: 51   DNA   GAAGTGCAGCTGGTGCAGTCTGGAGCAGAG
             VH   GTGAAAAAGCCCGGGGAGTCTCTGAGGATC
TCCTGTAAGGGTTCTGGCTACACATTCACC
ACTTACTGGATGCACTGGATCAGGCAGTCC
CCATCGAGAGGCCTTGAGTGGCTGGGTAAT
ATTTATCCTGGTACTGGTGGTTCTAACTTC
GATGAGAAGTTCAAGAACAGATTCACCATC
TCCAGAGACAATTCCAAGAACACGCTGTAT
CTTCAAATGAACAGCCTGAGAGCCGAGGAC
ACGGCCGTGTATTACTGTACAAGATGGACT
ACTGGGACGGGAGCTTATTGGGGCCAGGGC
ACCACCGTGACCGTGTCCTCC

SEQ ID NO: 52   HC   EVQLVQSGAEVKKPGESLRISCKGSGYTFT
TYWMHWIRQSPSRGLEWLGNIYPGTGGSNF
DEKFKNRFTISRDNSKNTLYLQMNSLRAED
TAVYYCTRWTTGTGAYWGQGTTVTVSSAST
KGPSVFPLAPCSRSTSESTAALGCLVKDYF
PEPVTVSWNSGALTSGVHTFPAVLQSSGLY
SLSSVVTVPSSSLGTKTYTCNVDHKPSNTK
VDKRVESKYGPPCPPCPAPEFLGGPSVFLF
PPKPKDTLMISRTPEVTCVVVDVSQEDPEV
QFNWYVDGVEVHNAKTKPREEQFNSTYRVV
SVLTVLHQDWLNGKEYKCKVSNKGLPSSIE
KTISKAKGQPREPQVYTLPPSQEEMTKNQV
SLTCLVKGFYPSDIAVEWESNGQPENNYKT
TPPVLDSDGSFFLYSRLTVDKSRWQEGNVF
SCSVMHEALHNHYTQKSLSLSLGK

SEQ ID NO: 53   DNA   GAAGTGCAGCTGGTGCAGTCTGGAGCAGAG
             HC   GTGAAAAAGCCCGGGGAGTCTCTGAGGATC
TCCTGTAAGGGTTCTGGCTACACATTCACC
ACTTACTGGATGCACTGGATCAGGCAGTCC
CCATCGAGAGGCCTTGAGTGGCTGGGTAAT
ATTTATCCTGGTACTGGTGGTTCTAACTTC
GATGAGAAGTTCAAGAACAGATTCACCATC
TCCAGAGACAATTCCAAGAACACGCTGTAT
CTTCAAATGAACAGCCTGAGAGCCGAGGAC
ACGGCCGTGTATTACTGTACAAGATGGACT
ACTGGGACGGGAGCTTATTGGGGCCAGGGC

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

```
                   ACCACCGTGACCGTGTCCTCCGCTTCCACC
                   AAGGGCCCATCCGTCTTCCCCCTGGCGCCC
                   TGCTCCAGGAGCACCTCCGAGAGCACAGCC
                   GCCCTGGGCTGCCTGGTCAAGGACTACTTC
                   CCCGAACCGGTGACGGTGTCGTGGAACTCA
                   GGCGCCCTGACCAGCGGCGTGCACACCTTC
                   CCGGCTGTCCTACAGTCCTCAGGACTCTAC
                   TCCCTCAGCAGCGTGGTGACCGTGCCCTCC
                   AGCAGCTTGGGCACGAAGACCTACACCTGC
                   AACGTAGATCACAAGCCCAGCAACACCAAG
                   GTGGACAAGAGAGTTGAGTCCAAATATGGT
                   CCCCCATGCCCACCGTGCCCAGCACCTGAG
                   TTCCTGGGGGGACCATCAGTCTTCCTGTTC
                   CCCCCAAAACCCAAGGACACTCTCATGATC
                   TCCCGGACCCCTGAGGTCACGTGCGTGGTG
                   GTGGACGTGAGCCAGGAAGACCCCGAGGTC
                   CAGTTCAACTGGTACGTGGATGGCGTGGAG
                   GTGCATAATGCCAAGACAAAGCCGCGGGAG
                   GAGCAGTTCAACAGCACGTACCGTGTGGTC
                   AGCGTCCTCACCGTCCTGCACCAGGACTGG
                   CTGAACGGCAAGGAGTACAAGTGCAAGGTG
                   TCCAACAAAGGCCTCCCGTCCTCCATCGAG
                   AAAACCATCTCCAAAGCCAAAGGGCAGCCC
                   CGAGAGCCACAGGTGTACACCCTGCCCCCA
                   TCCCAGGAGGAGATGACCAAGAACCAGGTC
                   AGCCTGACCTGCCTGGTCAAAGGCTTCTAC
                   CCCAGCGACATCGCCGTGGAGTGGGAGAGC
                   AATGGGCAGCCGGAGAACAACTACAAGACC
                   ACGCCTCCCGTGCTGGACTCCGACGGCTCC
                   TTCTTCCTCTACAGCAGGCTAACCGTGGAC
                   AAGAGCAGGTGGCAGGAGGGGAATGTCTTC
                   TCATGCTCCGTGATGCATGAGGCTCTGCAC
                   AACCACTACACACAGAAGAGCCTCTCCCTG
                   TCTCTGGGTAAA
```

BAP049-hum10
LC

| | | |
|---|---|---|
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 70 | VL | EIVLTQSPATLSLSPGERATLSCKSSQSLL DSGNQKNFLTWYQQKPGQAPRLLIYWASTR ESGVPSRFSGSGSGTDFTFTISSLEAEDAA TYYCQNDYSYPYTFGQGTKVEIK |
| SEQ ID NO: 71 | DNA VL | GAAATTGTGTTGACACAGTCTCCAGCCACC CTGTCTTTGTCTCCAGGGGAAAGAGCCACC CTCTCCTGCAAGTCCAGTCAGAGTCTGTTA GACAGTGGAAATCAAAAGAACTTCTTGACC TGGTACCAGCAGAAACCTGGCCAGGCTCCC AGGCTCCTCATCTATTGGGCATCCACTAGG GAATCTGGGGTCCCCTCGAGGTTCAGTGGC AGTGGATCTGGGACAGATTTCACCTTTACC |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

```
                   ATCAGTAGCCTGGAAGCTGAAGATGCTGCA
                   ACATATTACTGTCAGAATGATTATAGTTAT
                   CCGTACACGTTCGGCCAAGGGACCAAGGTG
                   GAAATCAAA
```

| | | |
|---|---|---|
| SEQ ID NO: 72 | LC | EIVLTQSPATLSLSPGERATLSCKSSQSLL DSGNQKNFLTWYQQKPGQAPRLLIYWASTR ESGVPSRFSGSGSGTDFTFTISSLEAEDAA TYYCQNDYSYPYTFGQGTKVEIKRTVAAPS VFIFPPSDEQLKSGTASVVCLLNNFYPREA KVQWKVDNALQSGNSQESVTEQDSKDSTYS LSSTLTLSKADYEKHKVYACEVTHQGLSSP VTKSFNRGEC |
| SEQ ID NO: 73 | DNA LC | GAAATTGTGTTGACACAGTCTCCAGCCACC CTGTCTTTGTCTCCAGGGGAAAGAGCCACC CTCTCCTGCAAGTCCAGTCAGAGTCTGTTA GACAGTGGAAATCAAAAGAACTTCTTGACC TGGTACCAGCAGAAACCTGGCCAGGCTCCC AGGCTCCTCATCTATTGGGCATCCACTAGG GAATCTGGGGTCCCCTCGAGGTTCAGTGGC AGTGGATCTGGGACAGATTTCACCTTTACC ATCAGTAGCCTGGAAGCTGAAGATGCTGCA ACATATTACTGTCAGAATGATTATAGTTAT CCGTACACGTTCGGCCAAGGGACCAAGGTG GAAATCAAACGTACGGTGGCTGCACCATCT GTCTTCATCTTCCCGCCATCTGATGAGCAG TTGAAATCTGGAACTGCCTCTGTTGTGTGC CTGCTGAATAACTTCTATCCCAGAGAGGCC AAAGTACAGTGGAAGGTGGATAACGCCCTC CAATCGGGTAACTCCCAGGAGAGTGTCACA GAGCAGGACAGCAAGGACAGCACCTACAGC CTCAGCAGCACCCTGACGCTGAGCAAAGCA GACTACGAGAAACACAAAGTCTACGCCTGC GAAGTCACCCATCAGGGCCTGAGCTCGCCC GTCACAAAGAGCTTCAACAGGGGAGAGTGT |

BAP049-hum11
HC

| | | |
|---|---|---|
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFT TYWMHWVRQATGQGLEWMGNIYPGTGGSNF DEKFKNRVTITADKSTSTAYMELSSLRSED TAVYYCTRWTTGTGAYWGQGTTVTVSS |
| SEQ ID NO: 39 | DNA VH | GAAGTGCAGCTGGTGCAGTCTGGAGCAGAG GTGAAAAAGCCCGGGGAGTCTCTGAGGATC TCCTGTAAGGGTTCTGGCTACACATTCACC ACTTACTGGATGCACTGGGTGCGACAGGCC ACTGGACAAGGGCTTGAGTGGATGGGTAAT ATTTATCCTGGTACTGGTGGTTCTAACTTC |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

GATGAGAAGTTCAAGAACAGAGTCACGATT
ACCGCGGACAAATCCACGAGCACAGCCTAC
ATGGAGCTGAGCAGCCTGAGATCTGAGGAC
ACGGCCGTGTATTACTGTACAAGATGGACT
ACTGGGACGGGAGCTTATTGGGGCCAGGGC
ACCACCGTGACCGTGTCCTCC

SEQ ID NO: 40 HC
EVQLVQSGAEVKKPGESLRISCKGSGYTFT
TYWMHWVRQATGQGLEWMGNIYPGTGGSNF
DEKFKNRVTITADKSTSTAYMELSSLRSED
TAVYYCTRWTTGTGAYWGQGTTVTVSSAST
KGPSVFPLAPCSRSTSESTAALGCLVKDYF
PEPVTVSWNSGALTSGVHTFPAVLQSSGLY
SLSSVVTVPSSSLGTKTYTCNVDHKPSNTK
VDKRVESKYGPPCPPCPAPEFLGGPSVFLF
PPKPKDTLMISRTPEVTCVVVDVSQEDPEV
QFNWYVDGVEVHNAKTKPREEQFNSTYRVV
SVLTVLHQDWLNGKEYKCKVSNKGLPSSIE
KTISKAKGQPREPQVYTLPPSQEEMTKNQV
SLTCLVKGFYPSDIAVEWESNGQPENNYKT
TPPVLDSDGSFFLYSRLTVDKSRWQEGNVF
SCSVMHEALHNHYTQKSLSLSLGK

SEQ ID NO: 41 DNA
HC
GAAGTGCAGCTGGTGCAGTCTGGAGCAGAG
GTGAAAAAGCCCGGGGAGTCTCTGAGGATC
TCCTGTAAGGGTTCTGGCTACACATTCACC
ACTTACTGGATGCACTGGGTGCGACAGGCC
ACTGGACAAGGGCTTGAGTGGATGGGTAAT
ATTTATCCTGGTACTGGTGGTTCTAACTTC
GATGAGAAGTTCAAGAACAGAGTCACGATT
ACCGCGGACAAATCCACGAGCACAGCCTAC
ATGGAGCTGAGCAGCCTGAGATCTGAGGAC
ACGGCCGTGTATTACTGTACAAGATGGACT
ACTGGGACGGGAGCTTATTGGGGCCAGGGC
ACCACCGTGACCGTGTCCTCCGCTTCCACC
AAGGGCCCATCCGTCTTCCCCCTGGCGCCC
TGCTCCAGGAGCACCTCCGAGAGCACAGCC
GCCCTGGGCTGCCTGGTCAAGGACTACTTC
CCCGAACCGGTGACGGTGTCGTGGAACTCA
GGCGCCCTGACCAGCGGCGTGCACACCTTC
CCGGCTGTCCTACAGTCCTCAGGACTCTAC
TCCCTCAGCAGCGTGGTGACCGTGCCCTCC
AGCAGCTTGGGCACGAAGACCTACACCTGC
AACGTAGATCACAAGCCCAGCAACACCAAG
GTGGACAAGAGAGTTGAGTCCAAATATGGT
CCCCCATGCCCACCGTGCCCAGCACCTGAG
TTCCTGGGGGGACCATCAGTCTTCCTGTTC
CCCCCAAAACCCAAGGACACTCTCATGATC
TCCCGGACCCCTGAGGTCACGTGCGTGGTG
GTGGACGTGAGCCAGGAAGACCCCGAGGTC
CAGTTCAACTGGTACGTGGATGGCGTGGAG
GTGCATAATGCCAAGACAAAGCCGCGGGAG
GAGCAGTTCAACAGCACGTACCGTGTGGTC
AGCGTCCTCACCGTCCTGCACCAGGACTGG
CTGAACGGCAAGGAGTACAAGTGCAAGGTG
TCCAACAAAGGCCTCCCGTCCTCCATCGAG
AAAACCATCTCCAAAGCCAAAGGGCAGCCC
CGAGAGCCACAGGTGTACACCCTGCCCCCA
TCCCAGGAGGAGATGACCAAGAACCAGGTC
AGCCTGACCTGCCTGGTCAAAGGCTTCTAC
CCCAGCGACATCGCCGTGGAGTGGGAGAGC
AATGGGCAGCCGGAGAACAACTACAAGACC
ACGCCTCCCGTGCTGGACTCCGACGGCTCC
TTCTTCCTCTACAGCAGGCTAACCGTGGAC
AAGAGCAGGTGGCAGGAGGGGAATGTCTTC
TCATGCTCCGTGATGCATGAGGCTCTGCAC
AACCACTACACACAGAAGAGCCTCTCCCTG
TCTCTGGGTAAA

BAP049-hum11
LC

SEQ ID NO: 10 LCDR1 KSSQSLLDSGNQKNFLT
(Kabat)

SEQ ID NO: 11 LCDR2 WASTRES
(Kabat)

SEQ ID NO: 32 LCDR3 QNDYSYPYT
(Kabat)

SEQ ID NO: 13 LCDR1 SQSLLDSGNQKNF
(Chothia)

SEQ ID NO: 14 LCDR2 WAS
(Chothia)

SEQ ID NO: 33 LCDR3 DYSYPY
(Chothia)

SEQ ID NO: 70 VL
EIVLTQSPATLSLSPGERATLSCKSSQSLL
DSGNQKNFLTWYQQKPGQAPRLLIYWASTR
ESGVPSRFSGSGSGTDFTFTISSLEAEDAA
TYYCQNDYSYPYTFGQGTKVEIK

SEQ ID NO: 71 DNA
VL
GAAATTGTGTTGACACAGTCTCCAGCCACC
CTGTCTTTGTCTCCAGGGGAAAGAGCCACC
CTCTCCTGCAAGTCCAGTCAGAGTCTGTTA
GACAGTGGAAATCAAAAGAACTTCTTGACC
TGGTACCAGCAGAAACCTGGCCAGGCTCCC
AGGCTCCTCATCTATTGGGCATCCACTAGG
GAATCTGGGGTCCCCTCGAGGTTCAGTGGC
AGTGGATCTGGGACAGATTTCACCTTTACC
ATCAGTAGCCTGGAAGCTGAAGATGCTGCA
ACATATTACTGTCAGAATGATTATAGTTAT
CCGTACACGTTCGGCCAAGGGACCAAGGTG
GAAATCAAA

SEQ ID NO: 72 LC
EIVLTQSPATLSLSPGERATLSCKSSQSLL
DSGNQKNFLTWYQQKPGQAPRLLIYWASTR
ESGVPSRFSGSGSGTDFTFTISSLEAEDAA
TYYCQNDYSYPYTFGQGTKVEIKRTVAAPS
VFIFPPSDEQLKSGTASVVCLLNNFYPREA
KVQWKVDNALQSGNSQESVTEQDSKDSTYS
LSSTLTLSKADYEKHKVYACEVTHQGLSSP
VTKSFNRGEC

SEQ ID NO: 73 DNA
LC
GAAATTGTGTTGACACAGTCTCCAGCCACC
CTGTCTTTGTCTCCAGGGGAAAGAGCCACC
CTCTCCTGCAAGTCCAGTCAGAGTCTGTTA
GACAGTGGAAATCAAAAGAACTTCTTGACC
TGGTACCAGCAGAAACCTGGCCAGGCTCCC
AGGCTCCTCATCTATTGGGCATCCACTAGG
GAATCTGGGGTCCCCTCGAGGTTCAGTGGC
AGTGGATCTGGGACAGATTTCACCTTTACC
ATCAGTAGCCTGGAAGCTGAAGATGCTGCA
ACATATTACTGTCAGAATGATTATAGTTAT
CCGTACACGTTCGGCCAAGGGACCAAGGTG
GAAATCAAACGTACGGTGGCTGCACCATCT
GTCTTCATCTTCCCGCCATCTGATGAGCAG
TTGAAATCTGGAACTGCCTCTGTTGTGTGC
CTGCTGAATAACTTCTATCCCAGAGAGGCC
AAAGTACAGTGGAAGGTGGATAACGCCCTC
CAATCGGGTAACTCCCAGGAGAGTGTCACA
GAGCAGGACAGCAAGGACAGCACCTACAGC
CTCAGCAGCACCCTGACGCTGAGCAAAGCA

TABLE 1-continued

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

```
                    GACTACGAGAAACACAAAGTCTACGCCTGC
                    GAAGTCACCCATCAGGGCCTGAGCTCGCCC
                    GTCACAAAGAGCTTCAACAGGGGAGAGTGT
```

BAP049-hum12
HC

| SEQ ID NO: 1 (Kabat) | HCDR1 | TYWMH |
|---|---|---|
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFT TYWMHWVRQATGQGLEWMGNIYPGTGGSNF DEKFKNRVTITADKSTSTAYMELSSLRSED TAVYYCTRWTTGTGAYWGQGTTVTVSS |
| SEQ ID NO: 39 | DNA VH | GAAGTGCAGCTGGTGCAGTCTGGAGCAGAG GTGAAAAAGCCCGGGGAGTCTCTGAGGATC TCCTGTAAGGGTTCTGGCTACACATTCACC ACTTACTGGATGCACTGGGTGCGACAGGCC ACTGGACAAGGGCTTGAGTGGATGGGTAAT ATTTATCCTGGTACTGGTGGTTCTAACTTC GATGAGAAGTTCAAGAACAGAGTCACGATT ACCGCGGACAAATCCACGAGCACAGCCTAC ATGGAGCTGAGCAGCCTGAGATCTGAGGAC ACGGCCGTGTATTACTGTACAAGATGGACT ACTGGGACGGGAGCTTATTGGGGCCAGGGC ACCACCGTGACCGTGTCCTCC |
| SEQ ID NO: 40 | HC | EVQLVQSGAEVKKPGESLRISCKGSGYTFT TYWMHWVRQATGQGLEWMGNIYPGTGGSNF DEKFKNRVTITADKSTSTAYMELSSLRSED TAVYYCTRWTTGTGAYWGQGTTVTVSSAST KGPSVFPLAPCSRSTSESTAALGCLVKDYF PEPVTVSWNSGALTSGVHTFPAVLQSSGLY SLSSVVTVPSSSLGTKTYTCNVDHKPSNTK VDKRVESKYGPPCPPCPAPEFLGGPSVFLF PPKPKDTLMISRTPEVTCVVVDVSQEDPEV QFNWYVDGVEVHNAKTKPREEQFNSTYRVV SVLTVLHQDWLNGKEYKCKVSNKGLPSSIE KTISKAKGQPREPQVYTLPPSQEEMTKNQV SLTCLVKGFYPSDIAVEWESNGQPENNYKT TPPVLDSDGSFFLYSRLTVDKSRWQEGNVF SCSVMHEALHNHYTQKSLSLSLGK |
| SEQ ID NO: 41 | DNA HC | GAAGTGCAGCTGGTGCAGTCTGGAGCAGAG GTGAAAAAGCCCGGGGAGTCTCTGAGGATC TCCTGTAAGGGTTCTGGCTACACATTCACC ACTTACTGGATGCACTGGGTGCGACAGGCC ACTGGACAAGGGCTTGAGTGGATGGGTAAT ATTTATCCTGGTACTGGTGGTTCTAACTTC GATGAGAAGTTCAAGAACAGAGTCACGATT ACCGCGGACAAATCCACGAGCACAGCCTAC ATGGAGCTGAGCAGCCTGAGATCTGAGGAC ACGGCCGTGTATTACTGTACAAGATGGACT |

```
                    ACTGGGACGGGAGCTTATTGGGGCCAGGGC
                    ACCACCGTGACCGTGTCCTCCGCTTCCACC
                    AAGGGCCCATCCGTCTTCCCCCTGGCGCCC
                    TGCTCCAGGAGCACCTCCGAGAGCACAGCC
                    GCCCTGGGCTGCCTGGTCAAGGACTACTTC
                    CCCGAACCGGTGACGGTGTCGTGGAACTCA
                    GGCGCCCTGACCAGCGGCGTGCACACCTTC
                    CCGGCTGTCCTACAGTCCTCAGGACTCTAC
                    TCCCTCAGCAGCGTGGTGACCGTGCCCTCC
                    AGCAGCTTGGGCACGAAGACCTACACCTGC
                    AACGTAGATCACAAGCCCAGCAACACCAAG
                    GTGGACAAGAGAGTTGAGTCCAAATATGGT
                    CCCCCATGCCCACCGTGCCCAGCACCTGAG
                    TTCCTGGGGGGACCATCAGTCTTCCTGTTC
                    CCCCCAAAACCCAAGGACACTCTCATGATC
                    TCCCGGACCCCTGAGGTCACGTGCGTGGTG
                    GTGGACGTGAGCCAGGAAGACCCCGAGGTC
                    CAGTTCAACTGGTACGTGGATGGCGTGGAG
                    GTGCATAATGCCAAGACAAAGCCGCGGGAG
                    GAGCAGTTCAACAGCACGTACCGTGTGGTC
                    AGCGTCCTCACCGTCCTGCACCAGGACTGG
                    CTGAACGGCAAGGAGTACAAGTGCAAGGTG
                    TCCAACAAAGGCCTCCCGTCCTCCATCGAG
                    AAAACCATCTCCAAAGCCAAAGGGCAGCCC
                    CGAGAGCCACAGGTGTACACCCTGCCCCCA
                    TCCCAGGAGGAGATGACCAAGAACCAGGTC
                    AGCCTGACCTGCCTGGTCAAAGGCTTCTAC
                    CCCAGCGACATCGCCGTGGAGTGGGAGAGC
                    AATGGGCAGCCGGAGAACAACTACAAGACC
                    ACGCCTCCCGTGCTGGACTCCGACGGCTCC
                    TTCTTCCTCTACAGCAGGCTAACCGTGGAC
                    AAGAGCAGGTGGCAGGAGGGGAATGTCTTC
                    TCATGCTCCGTGATGCATGAGGCTCTGCAC
                    AACCACTACACACAGAAGAGCCTCTCCCTG
                    TCTCTGGGTAAA
```

BAP049-hum12
LC

| SEQ ID NO: 10 (Kabat) | LCDR1 | KSSQSLLDSGNQKNFLT |
|---|---|---|
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 74 | VL | DIQMTQSPSSLSASVGDRVTITCKSSQSLL DSGNQKNFLTWYLQKPGQSPQLLIYWASTR ESGVPSRFSGSGSGTDFTFTISSLEAEDAA TYYCQNDYSYPYTFGQGTKVEIK |
| SEQ ID NO: 75 | DNA VL | GACATCCAGATGACCCAGTCTCCATCCTCC CTGTCTGCATCTGTAGGAGACAGAGTCACC ATCACTTGCAAGTCCAGTCAGAGTCTGTTA GACAGTGGAAATCAAAAGAACTTCTTGACC TGGTACCTGCAGAAGCCAGGGCAGTCTCCA CAGCTCCTGATCTATTGGGCATCCACTAGG GAATCTGGGGTCCCCTCGAGGTTCAGTGGC |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

|  |  |  |
|---|---|---|
|  |  | AGTGGATCTGGGACAGATTTCACCTTTACC ATCAGTAGCCTGGAAGCTGAAGATGCTGCA ACATATTACTGTCAGAATGATTATAGTTAT CCGTACACGTTCGGCCAAGGGACCAAGGTG GAAATCAAA |
| SEQ ID NO: 76 | LC | DIQMTQSPSSLSASVGDRVTITCKSSQSLL DSGNQKNFLTWYLQKPGQSPQLLIYWASTR ESGVPSRFSGSGSGTDFTFTISSLEAEDAA TYYCQNDYSYPYTFGQGTKVEIKRTVAAPS VFIFPPSDEQLKSGTASVVCLLNNFYPREA KVQWKVDNALQSGNSQESVTEQDSKDSTYS LSSTLTLSKADYEKHKVYACEVTHQGLSSP VTKSFNRGEC |
| SEQ ID NO: 77 | DNA LC | GACATCCAGATGACCCAGTCTCCATCCTCC CTGTCTGCATCTGTAGGAGACAGAGTCACC ATCACTTGCAAGTCCAGTCAGAGTCTGTTA GACAGTGGAAATCAAAAGAACTTCTTGACC TGGTACCTGCAGAAGCCAGGGCAGTCTCCA CAGCTCCTGATCTATTGGGCATCCACTAGG GAATCTGGGGTCCCCTCGAGGTTCAGTGGC AGTGGATCTGGGACAGATTTCACCTTTACC ATCAGTAGCCTGGAAGCTGAAGATGCTGCA ACATATTACTGTCAGAATGATTATAGTTAT CCGTACACGTTCGGCCAAGGGACCAAGGTG GAAATCAAACGTACGGTGGCTGCACCATCT GTCTTCATCTTCCCGCCATCTGATGAGCAG TTGAAATCTGGAACTGCCTCTGTTGTGTGC CTGCTGAATAACTTCTATCCCAGAGAGGCC AAAGTACAGTGGAAGGTGGATAACGCCCTC CAATCGGGTAACTCCCAGGAGAGTGTCACA GAGCAGGACAGCAAGGACAGCACCTACAGC CTCAGCAGCACCCTGACGCTGAGCAAAGCA GACTACGAGAAACACAAAGTCTACGCCTGC GAAGTCACCCATCAGGGCCTGAGCTCGCCC GTCACAAAGAGCTTCAACAGGGGAGAGTGT |

BAP049-hum13 HC

| SEQ ID NO: 1 (Kabat) | HCDR1 | TYWMH |
|---|---|---|
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFT TYWMHWVRQATGQGLEWMGNIYPGTGGSNF DEKFKNRVTITADKSTSTAYMELSSLRSED TAVYYCTRWTTGTGAYWGQGTTVTVSS |
| SEQ ID NO: 39 | DNA VH | GAAGTGCAGCTGGTGCAGTCTGGAGCAGAG GTGAAAAAGCCCGGGGAGTCTCTGAGGATC TCCTGTAAGGGTTCTGGCTACACATTCACC ACTTACTGGATGCACTGGGTGCGACAGGCC ACTGGACAAGGGCTTGAGTGGATGGGTAAT |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

|  |  |  |
|---|---|---|
|  |  | ATTTATCCTGGTACTGGTGGTTCTAACTTC GATGAGAAGTTCAAGAACAGAGTCACGATT ACCGCGGACAAATCCACGAGCACAGCCTAC ATGGAGCTGAGCAGCCTGAGATCTGAGGAC ACGGCCGTGTATTACTGTACAAGATGGACT ACTGGGACGGGAGCTTATTGGGGCCAGGGC ACCACCGTGACCGTGTCCTCC |
| SEQ ID NO: 40 | HC | EVQLVQSGAEVKKPGESLRISCKGSGYTFT TYWMHWVRQATGQGLEWMGNIYPGTGGSNF DEKFKNRVTITADKSTSTAYMELSSLRSED TAVYYCTRWTTGTGAYWGQGTTVTVSSAST KGPSVFPLAPCSRSTSESTAALGCLVKDYF PEPVTVSWNSGALTSGVHTFPAVLQSSGLY SLSSVVTVPSSSLGTKTYTCNVDHKPSNTK VDKRVESKYGPPCPPCPAPEFLGGPSVFLF PPKPKDTLMISRTPEVTCVVVDVSQEDPEV QFNWYVDGVEVHNAKTKPREEQFNSTYRVV SVLTVLHQDWLNGKEYKCKVSNKGLPSSIE KTISKAKGQPREPQVYTLPPSQEEMTKNQV SLTCLVKGFYPSDIAVEWESNGQPENNYKT TPPVLDSDGSFFLYSRLTVDKSRWQEGNVF SCSVMHEALHNHYTQKSLSLSLGK |
| SEQ ID NO: 41 | DNA HC | GAAGTGCAGCTGGTGCAGTCTGGAGCAGAG GTGAAAAAGCCCGGGGAGTCTCTGAGGATC TCCTGTAAGGGTTCTGGCTACACATTCACC ACTTACTGGATGCACTGGGTGCGACAGGCC ACTGGACAAGGGCTTGAGTGGATGGGTAAT ATTTATCCTGGTACTGGTGGTTCTAACTTC GATGAGAAGTTCAAGAACAGAGTCACGATT ACCGCGGACAAATCCACGAGCACAGCCTAC ATGGAGCTGAGCAGCCTGAGATCTGAGGAC ACGGCCGTGTATTACTGTACAAGATGGACT ACTGGGACGGGAGCTTATTGGGGCCAGGGC ACCACCGTGACCGTGTCCTCCGCTTCCACC AAGGGCCCATCCGTCTTCCCCCTGGCGCCC TGCTCCAGGAGCACCTCCGAGAGCACAGCC GCCCTGGGCTGCCTGGTCAAGGACTACTTC CCCGAACCGGTGACGGTGTCGTGGAACTCA GGCGCCCTGACCAGCGGCGTGCACACCTTC CCGGCTGTCCTACAGTCCTCAGGACTCTAC TCCCTCAGCAGCGTGGTGACCGTGCCCTCC AGCAGCTTGGGCACGAAGACCTACACCTGC AACGTAGATCACAAGCCCAGCAACACCAAG GTGGACAAGAGAGTTGAGTCCAAATATGGT CCCCCATGCCCACCGTGCCCAGCACCTGAG TTCCTGGGGGGACCATCAGTCTTCCTGTTC CCCCCAAAACCCAAGGACACTCTCATGATC TCCCGGACCCCTGAGGTCACGTGCGTGGTG GTGGACGTGAGCCAGGAAGACCCCGAGGTC CAGTTCAACTGGTACGTGGATGGCGTGGAG GTGCATAATGCCAAGACAAAGCCGCGGGAG GAGCAGTTCAACAGCACGTACCGTGTGGTC AGCGTCCTCACCGTCCTGCACCAGGACTGG CTGAACGGCAAGGAGTACAAGTGCAAGGTG TCCAACAAAGGCCTCCCGTCCTCCATCGAG AAAACCATCTCCAAAGCCAAAGGGCAGCCC CGAGAGCCACAGGTGTACACCCTGCCCCCA TCCCAGGAGGAGATGACCAAGAACCAGGTC AGCCTGACCTGCCTGGTCAAAGGCTTCTAC CCCAGCGACATCGCCGTGGAGTGGGAGAGC AATGGGCAGCCGGAGAACAACTACAAGACC ACGCCTCCCGTGCTGGACTCCGACGGCTCC TTCTTCCTCTACAGCAGGCTAACCGTGGAC AAGAGCAGGTGGCAGGAGGGGAATGTCTTC TCATGCTCCGTGATGCATGAGGCTCTGCAC AACCACTACACACAGAAGAGCCTCTCCCTG TCTCTGGGTAAA |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

BAP049-hum13
LC

| SEQ ID NO: 10 (Kabat) | LCDR1 | KSSQSLLDSGNQKNFLT |
|---|---|---|
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |
| SEQ ID NO: 78 | VL | DVVMTQSPLSLPVTLGQPASISCKSSQSLL DSGNQKNFLTWYQQKPGKAPKLLIYWASTR ESGVPSRFSGSGSGTDFTFTISSLEAEDAA TYYCQNDYSYPYTFGQGTKVEIK |
| SEQ ID NO: 79 | DNA VL | GATGTTGTGATGACTCAGTCTCCACTCTCC CTGCCCGTCACCCTTGGACAGCCGGCCTCC ATCTCCTGCAAGTCCAGTCAGAGTCTGTTA GACAGTGGAAATCAAAAGAACTTCTTAACC TGGTATCAGCAGAAACCAGGGAAAGCTCCT AAGCTCCTGATCTATTGGGCATCCACTAGG GAATCTGGGGTCCCCTCGAGGTTCAGTGGC AGTGGATCTGGGACAGATTTCACCTTTACC ATCAGTAGCCTGGAAGCTGAAGATGCTGCA ACATATTACTGTCAGAATGATTATAGTTAT CCGTACACGTTCGGCCAAGGGACCAAGGTG GAAATCAAA |
| SEQ ID NO: 80 | LC | DVVMTQSPLSLPVTLGQPASISCKSSQSLL DSGNQKNFLTWYQQKPGKAPKLLIYWASTR ESGVPSRFSGSGSGTDFTFTISSLEAEDAA TYYCQNDYSYPYTFGQGTKVEIKRTVAAPS VFIFPPSDEQLKSGTASVVCLLNNFYPREA KVQWKVDNALQSGNSQESVTEQDSKDSTYS LSSTLTLSKADYEKHKVYACEVTHQGLSSP VTKSFNRGEC |
| SEQ ID NO: 81 | DNA LC | GATGTTGTGATGACTCAGTCTCCACTCTCC CTGCCCGTCACCCTTGGACAGCCGGCCTCC ATCTCCTGCAAGTCCAGTCAGAGTCTGTTA GACAGTGGAAATCAAAAGAACTTCTTAACC TGGTATCAGCAGAAACCAGGGAAAGCTCCT AAGCTCCTGATCTATTGGGCATCCACTAGG GAATCTGGGGTCCCCTCGAGGTTCAGTGGC AGTGGATCTGGGACAGATTTCACCTTTACC ATCAGTAGCCTGGAAGCTGAAGATGCTGCA ACATATTACTGTCAGAATGATTATAGTTAT CCGTACACGTTCGGCCAAGGGACCAAGGTG GAAATCAAACGTACGGTGGCTGCACCATCT GTCTTCATCTTCCCGCCATCTGATGAGCAG TTGAAATCTGGAACTGCCTCTGTTGTGTGC CTGCTGAATAACTTCTATCCCAGAGAGGCC AAAGTACAGTGGAAGGTGGATAACGCCCTC CAATCGGGTAACTCCCAGGAGAGTGTCACA GAGCAGGACAGCAAGGACAGCACCTACAGC CTCAGCAGCACCCTGACGCTGAGCAAAGCA GACTACGAGAAACACAAAGTCTACGCCTGC |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

GAAGTCACCCATCAGGGCCTGAGCTCGCCC
GTCACAAAGAGCTTCAACAGGGGAGAGTGT

BAP049-hum14
HC

| SEQ ID NO: 1 (Kabat) | HCDR1 | TYWMH |
|---|---|---|
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 82 | VH | QVQLVQSGAEVKKPGASVKVSCKASGYTFT TYWMHWIRQSPSRGLEWLGNIYPGTGGSNF DEKFKNRFTISRDNSKNTLYLQMNSLRAED TAVYYCTRWTTGTGAYWGQGTTVTVSS |
| SEQ ID NO: 83 | DNA VH | CAGGTTCAGCTGGTGCAGTCTGGAGCTGAG GTGAAGAAGCCTGGGGCCTCAGTGAAGGTC TCCTGCAAGGCTTCTGGCTACACATTCACC ACTTACTGGATGCACTGGATCAGGCAGTCC CCATCGAGAGGCCTTGAGTGGCTGGGTAAT ATTTATCCTGGTACTGGTGGTTCTAACTTC GATGAGAAGTTCAAGAACAGATTCACCATC TCCAGAGACAATTCCAAGAACACGCTGTAT CTTCAAATGAACAGCCTGAGAGCCGAGGAC ACGGCCGTGTATTACTGTACAAGATGGACT ACTGGGACGGGAGCTTACTGGGGCCAGGGC ACCACCGTGACCGTGTCCTCC |
| SEQ ID NO: 84 | HC | QVQLVQSGAEVKKPGASVKVSCKASGYTFT TYWMHWIRQSPSRGLEWLGNIYPGTGGSNF DEKFKNRFTISRDNSKNTLYLQMNSLRAED TAVYYCTRWTTGTGAYWGQGTTVTVSSAST KGPSVFPLAPCSRSTSESTAALGCLVKDYF PEPVTVSWNSGALTSGVHTFPAVLQSSGLY SLSSVVTVPSSSLGTKTYTCNVDHKPSNTK VDKRVESKYGPPCPPCPAPEFLGGPSVFLF PPKPKDTLMISRTPEVTCVVVDVSQEDPEV QFNWYVDGVEVHNAKTKPREEQFNSTYRVV SVLTVLHQDWLNGKEYKCKVSNKGLPSSIE KTISKAKGQPREPQVYTLPPSQEEMTKNQV SLTCLVKGFYPSDIAVEWESNGQPENNYKT TPPVLDSDGSFFLYSRLTVDKSRWQEGNVF SCSVMHEALHNHYTQKSLSLSLGK |
| SEQ ID NO: 85 | DNA HC | CAGGTTCAGCTGGTGCAGTCTGGAGCTGAG GTGAAGAAGCCTGGGGCCTCAGTGAAGGTC TCCTGCAAGGCTTCTGGCTACACATTCACC ACTTACTGGATGCACTGGATCAGGCAGTCC CCATCGAGAGGCCTTGAGTGGCTGGGTAAT ATTTATCCTGGTACTGGTGGTTCTAACTTC GATGAGAAGTTCAAGAACAGATTCACCATC TCCAGAGACAATTCCAAGAACACGCTGTAT CTTCAAATGAACAGCCTGAGAGCCGAGGAC ACGGCCGTGTATTACTGTACAAGATGGACT ACTGGGACGGGAGCTTACTGGGGCCAGGGC |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

ACCACCGTGACCGTGTCCTCCGCTTCCACC
AAGGGCCCATCCGTCTTCCCCCTGGCGCCC
TGCTCCAGGAGCACCTCCGAGAGCACAGCC
GCCCTGGGCTGCCTGGTCAAGGACTACTTC
CCCGAACCGGTGACGGTGTCGTGGAACTCA
GGCGCCCTGACCAGCGGCGTGCACACCTTC
CCGGCTGTCCTACAGTCCTCAGGACTCTAC
TCCCTCAGCAGCGTGGTGACCGTGCCCTCC
AGCAGCTTGGGCACGAAGACCTACACCTGC
AACGTAGATCACAAGCCCAGCAACACCAAG
GTGGACAAGAGAGTTGAGTCCAAATATGGT
CCCCCATGCCCACCGTGCCCAGCACCTGAG
TTCCTGGGGGGACCATCAGTCTTCCTGTTC
CCCCCAAAACCCAAGGACACTCTCATGATC
TCCCGGACCCCTGAGGTCACGTGCGTGGTG
GTGGACGTGAGCCAGGAAGACCCCGAGGTC
CAGTTCAACTGGTACGTGGATGGCGTGGAG
GTGCATAATGCCAAGACAAAGCCGCGGGAG
GAGCAGTTCAACAGCACGTACCGTGTGGTC
AGCGTCCTCACCGTCCTGCACCAGGACTGG
CTGAACGGCAAGGAGTACAAGTGCAAGGTG
TCCAACAAAGGCCTCCCGTCCTCCATCGAG
AAAACCATCTCCAAAGCCAAAGGGCAGCCC
CGAGAGCCACAGGTGTACACCCTGCCCCCA
TCCCAGGAGGAGATGACCAAGAACCAGGTC
AGCCTGACCTGCCTGGTCAAAGGCTTCTAC
CCCAGCGACATCGCCGTGGAGTGGGAGAGC
AATGGGCAGCCGGAGAACAACTACAAGACC
ACGCCTCCCGTGCTGGACTCCGACGGCTCC
TTCTTCCTCTACAGCAGGCTAACCGTGGAC
AAGAGCAGGTGGCAGGAGGGGAATGTCTTC
TCATGCTCCGTGATGCATGAGGCTCTGCAC
AACCACTACACACAGAAGAGCCTCTCCCTG
TCTCTGGGTAAA

BAP049-hum14
LC

SEQ ID NO: 10    LCDR1    KSSQSLLDSGNQKNFLT
(Kabat)

SEQ ID NO: 11    LCDR2    WASTRES
(Kabat)

SEQ ID NO: 32    LCDR3    QNDYSYPYT
(Kabat)

SEQ ID NO: 13    LCDR1    SQSLLDSGNQKNF
(Chothia)

SEQ ID NO: 14    LCDR2    WAS
(Chothia)

SEQ ID NO: 33    LCDR3    DYSYPY
(Chothia)

SEQ ID NO: 70    VL    EIVLTQSPATLSLSPGERATLSCKSSQSLL
                       DSGNQKNFLTWYQQKPGQAPRLLIYWASTR
                       ESGVPSRFSGSGSGTDFTFTISSLEAEDAA
                       TYYCQNDYSYPYTFGQGTKVEIK

SEQ ID NO: 71    DNA    GAAATTGTGTTGACACAGTCTCCAGCCACC
                 VL     CTGTCTTTGTCTCCAGGGGAAAGAGCCACC
                        CTCTCCTGCAAGTCCAGTCAGAGTCTGTTA
                        GACAGTGGAAATCAAAAGAACTTCTTGACC
                        TGGTACCAGCAGAAACCTGGCCAGGCTCCC
                        AGGCTCCTCATCTATTGGGCATCCACTAGG
                        GAATCTGGGGTCCCCTCGAGGTTCAGTGGC
                        AGTGGATCTGGGACAGATTTCACCTTTACC

ATCAGTAGCCTGGAAGCTGAAGATGCTGCA
ACATATTACTGTCAGAATGATTATAGTTAT
CCGTACACGTTCGGCCAAGGGACCAAGGTG
GAAATCAAA

SEQ ID NO: 72    LC    EIVLTQSPATLSLSPGERATLSCKSSQSLL
                       DSGNQKNFLTWYQQKPGQAPRLLIYWASTR
                       ESGVPSRFSGSGSGTDFTFTISSLEAEDAA
                       TYYCQNDYSYPYTFGQGTKVEIKRTVAAPS
                       VFIFPPSDEQLKSGTASVVCLLNNFYPREA
                       KVQWKVDNALQSGNSQESVTEQDSKDSTYS
                       LSSTLTLSKADYEKHKVYACEVTHQGLSSP
                       VTKSFNRGEC

SEQ ID NO: 73    DNA    GAAATTGTGTTGACACAGTCTCCAGCCACC
                 LC     CTGTCTTTGTCTCCAGGGGAAAGAGCCACC
                        CTCTCCTGCAAGTCCAGTCAGAGTCTGTTA
                        GACAGTGGAAATCAAAAGAACTTCTTGACC
                        TGGTACCAGCAGAAACCTGGCCAGGCTCCC
                        AGGCTCCTCATCTATTGGGCATCCACTAGG
                        GAATCTGGGGTCCCCTCGAGGTTCAGTGGC
                        AGTGGATCTGGGACAGATTTCACCTTTACC
                        ATCAGTAGCCTGGAAGCTGAAGATGCTGCA
                        ACATATTACTGTCAGAATGATTATAGTTAT
                        CCGTACACGTTCGGCCAAGGGACCAAGGTG
                        GAAATCAAACGTACGGTGGCTGCACCATCT
                        GTCTTCATCTTCCCGCCATCTGATGAGCAG
                        TTGAAATCTGGAACTGCCTCTGTTGTGTGC
                        CTGCTGAATAACTTCTATCCCAGAGAGGCC
                        AAAGTACAGTGGAAGGTGGATAACGCCCTC
                        CAATCGGGTAACTCCCAGGAGAGTGTCACA
                        GAGCAGGACAGCAAGGACAGCACCTACAGC
                        CTCAGCAGCACCCTGACGCTGAGCAAAGCA
                        GACTACGAGAAACACAAAGTCTACGCCTGC
                        GAAGTCACCCATCAGGGCCTGAGCTCGCCC
                        GTCACAAAGAGCTTCAACAGGGGAGAGTGT

BAP049-hum15
HC

SEQ ID NO: 1     HCDR1    TYWMH
(Kabat)

SEQ ID NO: 2     HCDR2    NIYPGTGGSNFDEKFKN
(Kabat)

SEQ ID NO: 3     HCDR3    WTTGTGAY
(Kabat)

SEQ ID NO: 4     HCDR1    GYTFTTY
(Chothia)

SEQ ID NO: 5     HCDR2    YPGTGG
(Chothia)

SEQ ID NO: 3     HCDR3    WTTGTGAY
(Chothia)

SEQ ID NO: 82    VH    QVQLVQSGAEVKKPGASVKVSCKASGYTFT
                       TYWMHWIRQSPSRGLEWLGNIYPGTGGSNF
                       DEKFKNRFTISRDNSKNTLYLQMNSLRAED
                       TAVYYCTRWTTGTGAYWGQGTTVTVSS

SEQ ID NO: 83    DNA    CAGGTTCAGCTGGTGCAGTCTGGAGCTGAG
                 VH     GTGAAGAAGCCTGGGGCCTCAGTGAAGGTC
                        TCCTGCAAGGCTTCTGGCTACACATTCACC
                        ACTTACTGGATGCACTGGATCAGGCAGTCC
                        CCATCGAGAGGCCTTGAGTGGCTGGGTAAT
                        ATTTATCCTGGTACTGGTGGTTCTAACTTC

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

```
                  GATGAGAAGTTCAAGAACAGATTCACCATC
                  TCCAGAGACAATTCCAAGAACACGCTGTAT
                  CTTCAAATGAACAGCCTGAGAGCCGAGGAC
                  ACGGCCGTGTATTACTGTACAAGATGGACT
                  ACTGGGACGGGAGCTTACTGGGGCCAGGGC
                  ACCACCGTGACCGTGTCCTCC

SEQ ID NO: 84  HC   QVQLVQSGAEVKKPGASVKVSCKASGYTFT
                  TYWMHWIRQSPSRGLEWLGNIYPGTGGSNF
                  DEKFKNRFTISRDNSKNTLYLQMNSLRAED
                  TAVYYCTRWTTGTGAYWGQGTTVTVSSAST
                  KGPSVFPLAPCSRSTSESTAALGCLVKDYF
                  PEPVTVSWNSGALTSGVHTFPAVLQSSGLY
                  SLSSVVTVPSSSLGTKTYTCNVDHKPSNTK
                  VDKRVESKYGPPCPPCPAPEFLGGPSVFLF
                  PPKPKDTLMISRTPEVTCVVVDVSQEDPEV
                  QFNWYVDGVEVHNAKTKPREEQFNSTYRVV
                  SVLTVLHQDWLNGKEYKCKVSNKGLPSSIE
                  KTISKAKGQPREPQVYTLPPSQEEMTKNQV
                  SLTCLVKGFYPSDIAVEWESNGQPENNYKT
                  TPPVLDSDGSFFLYSRLTVDKSRWQEGNVF
                  SCSVMHEALHNHYTQKSLSLSLGK

SEQ ID NO: 85  DNA  CAGGTTCAGCTGGTGCAGTCTGGAGCTGAG
               HC   GTGAAGAAGCCTGGGGCCTCAGTGAAGGTC
                  TCCTGCAAGGCTTCTGGCTACACATTCACC
                  ACTTACTGGATGCACTGGATCAGGCAGTCC
                  CCATCGAGAGGCCTTGAGTGGCTGGGTAAT
                  ATTTATCCTGGTACTGGTGGTTCTAACTTC
                  GATGAGAAGTTCAAGAACAGATTCACCATC
                  TCCAGAGACAATTCCAAGAACACGCTGTAT
                  CTTCAAATGAACAGCCTGAGAGCCGAGGAC
                  ACGGCCGTGTATTACTGTACAAGATGGACT
                  ACTGGGACGGGAGCTTACTGGGGCCAGGGC
                  ACCACCGTGACCGTGTCCTCCACC
                  AAGGGCCCATCCGTCTTCCCCCTGGCGCCC
                  TGCTCCAGGAGCACCTCCGAGAGCACAGCC
                  GCCCTGGGCTGCCTGGTCAAGGACTACTTC
                  CCCGAACCGGTGACGGTGTCGTGGAACTCA
                  GGCGCCCTGACCAGCGGCGTGCACACCTTC
                  CCGGCTGTCCTACAGTCCTCAGGACTCTAC
                  TCCCTCAGCAGCGTGGTGACCGTGCCCTCC
                  AGCAGCTTGGGCACGAAGACCTACACCTGC
                  AACGTAGATCACAAGCCCAGCAACACCAAG
                  GTGGACAAGAGAGTTGAGTCCAAATATGGT
                  CCCCCATGCCCACCGTGCCCAGCACCTGAG
                  TTCCTGGGGGGACCATCAGTCTTCCTGTTC
                  CCCCCAAAACCCAAGGACACTCTCATGATC
                  TCCCGGACCCCTGAGGTCACGTGCGTGGTG
                  GTGGACGTGAGCCAGGAAGACCCCGAGGTC
                  CAGTTCAACTGGTACGTGGATGGCGTGGAG
                  GTGCATAATGCCAAGACAAAGCCGCGGGAG
                  GAGCAGTTCAACAGCACGTACCGTGTGGTC
                  AGCGTCCTCACCGTCCTGCACCAGGACTGG
                  CTGAACGGCAAGGAGTACAAGTGCAAGGTG
                  TCCAACAAAGGCCTCCCGTCCTCCATCGAG
                  AAAACCATCTCCAAAGCCAAAGGGCAGCCC
                  CGAGAGCCACAGGTGTACACCCTGCCCCCA
                  TCCCAGGAGGAGATGACCAAGAACCAGGTC
                  AGCCTGACCTGCCTGGTCAAAGGCTTCTAC
                  CCCAGCGACATCGCCGTGGAGTGGGAGAGC
                  AATGGGCAGCCGGAGAACAACTACAAGACC
                  ACGCCTCCCGTGCTGGACTCCGACGGCTCC
                  TTCTTCCTCTACAGCAGGCTAACCGTGGAC
                  AAGAGCAGGTGGCAGGAGGGGAATGTCTTC
                  TCATGCTCCGTGATGCATGAGGCTCTGCAC
                  AACCACTACACACAGAAGAGCCTCTCCCTG
                  TCTCTGGGTAAA
```

BAP049-hum15
LC
──────────

SEQ ID NO: 10   LCDR1   KSSQSLLDSGNQKNFLT
(Kabat)

SEQ ID NO: 11   LCDR2   WASTRES
(Kabat)

SEQ ID NO: 32   LCDR3   QNDYSYPYT
(Kabat)

SEQ ID NO: 13   LCDR1   SQSLLDSGNQKNF
(Chothia)

SEQ ID NO: 14   LCDR2   WAS
(Chothia)

SEQ ID NO: 33   LCDR3   DYSYPY
(Chothia)

SEQ ID NO: 66   VL    EIVLTQSPDFQSVTPKEKVTITCKSSQSLL
                     DSGNQKNFLTWYQQKPGQAPRLLIYWASTR
                     ESGVPSRFSGSGSGTDFTFTISSLEAEDAA
                     TYYCQNDYSYPYTFGQGTKVEIK

SEQ ID NO: 67   DNA   GAAATTGTGCTGACTCAGTCTCCAGACTTT
                VL    CAGTCTGTGACTCCAAAGGAGAAAGTCACC
                     ATCACCTGCAAGTCCAGTCAGAGTCTGTTA
                     GACAGTGGAAATCAAAAGAACTTCTTGACC
                     TGGTACCAGCAGAAACCTGGCCAGGCTCCC
                     AGGCTCCTCATCTATTGGGCATCCACTAGG
                     GAATCTGGGGTCCCCTCGAGGTTCAGTGGC
                     AGTGGATCTGGGACAGATTTCACCTTTACC
                     ATCAGTAGCCTGGAAGCTGAAGATGCTGCA
                     ACATATTACTGTCAGAATGATTATAGTTAT
                     CCGTACACGTTCGGCCAAGGGACCAAGGTG
                     GAAATCAAA

SEQ ID NO: 68   LC    EIVLTQSPDFQSVTPKEKVTITCKSSQSLL
                     DSGNQKNFLTWYQQKPGQAPRLLIYWASTR
                     ESGVPSRFSGSGSGTDFTFTISSLEAEDAA
                     TYYCQNDYSYPYTFGQGTKVEIKRTVAAPS
                     VFIFPPSDEQLKSGTASVVCLLNNFYPREA
                     KVQWKVDNALQSGNSQESVTEQDSKDSTYS
                     LSSTLTLSKADYEKHKVYACEVTHQGLSSP
                     VTKSFNRGEC

SEQ ID NO: 69   DNA   GAAATTGTGCTGACTCAGTCTCCAGACTTT
                LC    CAGTCTGTGACTCCAAAGGAGAAAGTCACC
                     ATCACCTGCAAGTCCAGTCAGAGTCTGTTA
                     GACAGTGGAAATCAAAAGAACTTCTTGACC
                     TGGTACCAGCAGAAACCTGGCCAGGCTCCC
                     AGGCTCCTCATCTATTGGGCATCCACTAGG
                     GAATCTGGGGTCCCCTCGAGGTTCAGTGGC
                     AGTGGATCTGGGACAGATTTCACCTTTACC
                     ATCAGTAGCCTGGAAGCTGAAGATGCTGCA
                     ACATATTACTGTCAGAATGATTATAGTTAT
                     CCGTACACGTTCGGCCAAGGGACCAAGGTG
                     GAAATCAAACGTACGGTGGCTGCACCATCT
                     GTCTTCATCTTCCCGCCATCTGATGAGCAG
                     TTGAAATCTGGAACTGCCTCTGTTGTGTGC
                     CTGCTGAATAACTTCTATCCCAGAGAGGCC
                     AAAGTACAGTGGAAGGTGGATAACGCCCTC
                     CAATCGGGTAACTCCCAGGAGAGTGTCACA
                     GAGCAGGACAGCAAGGACAGCACCTACAGC
                     CTCAGCAGCACCCTGACGCTGAGCAAAGCA

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

```
                    GACTACGAGAAACACAAAGTCTACGCCTGC
                    GAAGTCACCCATCAGGGCCTGAGCTCGCCC
                    GTCACAAAGAGCTTCAACAGGGGAGAGTGT

BAP049-hum16
HC

SEQ ID NO: 1    HCDR1   TYWMH
(Kabat)

SEQ ID NO: 2    HCDR2   NIYPGTGGSNFDEKFKN
(Kabat)

SEQ ID NO: 3    HCDR3   WTTGTGAY
(Kabat)

SEQ ID NO: 4    HCDR1   GYTFTTY
(Chothia)

SEQ ID NO: 5    HCDR2   YPGTGG
(Chothia)

SEQ ID NO: 3    HCDR3   WTTGTGAY
(Chothia)

SEQ ID NO: 86   VH      EVQLVQSGAEVKKPGESLRISCKGSGYTFT
                        TYWMHWVRQAPGQGLEWMGNIYPGTGGSNF
                        DEKFKNRFTISRDNSKNTLYLQMNSLRAED
                        TAVYYCTRWTTGTGAYWGQGTTVTVSS

SEQ ID NO: 87   DNA     GAAGTGCAGCTGGTGCAGTCTGGAGCAGAG
                VH      GTGAAAAAGCCCGGGGAGTCTCTGAGGATC
                        TCCTGTAAGGGTTCTGGCTACACATTCACC
                        ACTTACTGGATGCACTGGGTGCGACAGGCC
                        CCTGGACAAGGGCTTGAGTGGATGGGTAAT
                        ATTTATCCTGGTACTGGTGGTTCTAACTTC
                        GATGAGAAGTTCAAGAACAGATTCACCATC
                        TCCAGAGACAATTCCAAGAACACGCTGTAT
                        CTTCAAATGAACAGCCTGAGAGCCGAGGAC
                        ACGGCCGTGTATTACTGTACAAGATGGACT
                        ACTGGGACGGGAGCTTATTGGGGCCAGGGC
                        ACCACCGTGACCGTGTCCTCC

SEQ ID NO: 88   HC      EVQLVQSGAEVKKPGESLRISCKGSGYTFT
                        TYWMHWVRQAPGQGLEWMGNIYPGTGGSNF
                        DEKFKNRFTISRDNSKNTLYLQMNSLRAED
                        TAVYYCTRWTTGTGAYWGQGTTVTVSSAST
                        KGPSVFPLAPCSRSTSESTAALGCLVKDYF
                        PEPVTVSWNSGALTSGVHTFPAVLQSSGLY
                        SLSSVVTVPSSSLGTKTYTCNVDHKPSNTK
                        VDKRVESKYGPPCPPCPAPEFLGGPSVFLF
                        PPKPKDTLMISRTPEVTCVVVDVSQEDPEV
                        QFNWYVDGVEVHNAKTKPREEQFNSTYRVV
                        SVLTVLHQDWLNGKEYKCKVSNKGLPSSIE
                        KTISKAKGQPREPQVYTLPPSQEEMTKNQV
                        SLTCLVKGFYPSDIAVEWESNGQPENNYKT
                        TPPVLDSDGSFFLYSRLTVDKSRWQEGNVF
                        SCSVMHEALHNHYTQKSLSLSLGK

SEQ ID NO: 89   DNA     GAAGTGCAGCTGGTGCAGTCTGGAGCAGAG
                HC      GTGAAAAAGCCCGGGGAGTCTCTGAGGATC
                        TCCTGTAAGGGTTCTGGCTACACATTCACC
                        ACTTACTGGATGCACTGGGTGCGACAGGCC
                        CCTGGACAAGGGCTTGAGTGGATGGGTAAT
                        ATTTATCCTGGTACTGGTGGTTCTAACTTC
                        GATGAGAAGTTCAAGAACAGATTCACCATC
                        TCCAGAGACAATTCCAAGAACACGCTGTAT
                        CTTCAAATGAACAGCCTGAGAGCCGAGGAC
                        ACGGCCGTGTATTACTGTACAAGATGGACT
```

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

```
                    ACTGGGACGGGAGCTTATTGGGGCCAGGGC
                    ACCACCGTGACCGTGTCCTCCGCTTCCACC
                    AAGGGCCCATCCGTCTTCCCCCTGGCGCCC
                    TGCTCCAGGAGCACCTCCGAGAGCACAGCC
                    GCCCTGGGCTGCCTGGTCAAGGACTACTTC
                    CCCGAACCGGTGACGGTGTCGTGGAACTCA
                    GGCGCCCTGACCAGCGGCGTGCACACCTTC
                    CCGGCTGTCCTACAGTCCTCAGGACTCTAC
                    TCCCTCAGCAGCGTGGTGACCGTGCCCTCC
                    AGCAGCTTGGGCACGAAGACCTACACCTGC
                    AACGTAGATCACAAGCCCAGCAACACCAAG
                    GTGGACAAGAGAGTTGAGTCCAAATATGGT
                    CCCCCATGCCCACCGTGCCCAGCACCTGAG
                    TTCCTGGGGGGACCATCAGTCTTCCTGTTC
                    CCCCCAAAACCCAAGGACACTCTCATGATC
                    TCCCGGACCCCTGAGGTCACGTGCGTGGTG
                    GTGGACGTGAGCCAGGAAGACCCCGAGGTC
                    CAGTTCAACTGGTACGTGGATGGCGTGGAG
                    GTGCATAATGCCAAGACAAAGCCGCGGGAG
                    GAGCAGTTCAACAGCACGTACCGTGTGGTC
                    AGCGTCCTCACCGTCCTGCACCAGGACTGG
                    CTGAACGGCAAGGAGTACAAGTGCAAGGTG
                    TCCAACAAAGGCCTCCCGTCCTCCATCGAG
                    AAAACCATCTCCAAAGCCAAAGGGCAGCCC
                    CGAGAGCCACAGGTGTACACCCTGCCCCCA
                    TCCCAGGAGGAGATGACCAAGAACCAGGTC
                    AGCCTGACCTGCCTGGTCAAAGGCTTCTAC
                    CCCAGCGACATCGCCGTGGAGTGGGAGAGC
                    AATGGGCAGCCGGAGAACAACTACAAGACC
                    ACGCCTCCCGTGCTGGACTCCGACGGCTCC
                    TTCTTCCTCTACAGCAGGCTAACCGTGGAC
                    AAGAGCAGGTGGCAGGAGGGGAATGTCTTC
                    TCATGCTCCGTGATGCATGAGGCTCTGCAC
                    AACCACTACACACAGAAGAGCCTCTCCCTG
                    TCTCTGGGTAAA

BAP049-hum16
LC

SEQ ID NO: 10   LCDR1   KSSQSLLDSGNQKNFLT
(Kabat)

SEQ ID NO: 11   LCDR2   WASTRES
(Kabat)

SEQ ID NO: 32   LCDR3   QNDYSYPYT
(Kabat)

SEQ ID NO: 13   LCDR1   SQSLLDSGNQKNF
(Chothia)

SEQ ID NO: 14   LCDR2   WAS
(Chothia)

SEQ ID NO: 33   LCDR3   DYSYPY
(Chothia)

SEQ ID NO: 66   VL      EIVLTQSPDFQSVTPKEKVTITCKSSQSLL
                        DSGNQKNFLTWYQQKPGQAPRLLIYWASTR
                        ESGVPSRFSGSGSGTDFTFTISSLEAEDAA
                        TYYCQNDYSYPYTFGQGTKVEIK

SEQ ID NO: 67   DNA     GAAATTGTGCTGACTCAGTCTCCAGACTTT
                VL      CAGTCTGTGACTCCAAAGGAGAAAGTCACC
                        ATCACCTGCAAGTCCAGTCAGAGTCTGTTA
                        GACAGTGGAAATCAAAAGAACTTCTTGACC
                        TGGTACCAGCAGAAACCTGGCCAGGCTCCC
                        AGGCTCCTCATCTATTGGGCATCCACTAGG
                        GAATCTGGGGTCCCCTCGAGGTTCAGTGGC
```

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

|  |  |  |
|---|---|---|
|  |  | AGTGGATCTGGGACAGATTTCACCTTTACC ATCAGTAGCCTGGAAGCTGAAGATGCTGCA ACATATTACTGTCAGAATGATTATAGTTAT CCGTACACGTTCGGCCAAGGGACCAAGGTG GAAATCAAA |
| SEQ ID NO: 68 | LC | EIVLTQSPDFQSVTPKEKVTITCKSSQSLL DSGNQKNFLTWYQQKPGQAPRLLIYWASTR ESGVPSRFSGSGSGTDFTFTISSLEAEDAA TYYCQNDYSYPYTFGQGTKVEIKRTVAAPS VFIFPPSDEQLKSGTASVVCLLNNFYPREA KVQWKVDNALQSGNSQESVTEQDSKDSTYS LSSTLTLSKADYEKHKVYACEVTHQGLSSP VTKSFNRGEC |
| SEQ ID NO: 69 | DNA LC | GAAATTGTGCTGACTCAGTCTCCAGACTTT CAGTCTGTGACTCCAAAGGAGAAAGTCACC ATCACCTGCAAGTCCAGTCAGAGTCTGTTA GACAGTGGAAATCAAAAGAACTTCTTGACC TGGTACCAGCAGAAACCTGGCCAGGCTCCC AGGCTCCTCATCTATTGGGCATCCACTAGG AATCTGGGGTCCCCTCGAGGTTCAGTGGC AGTGGATCTGGGACAGATTTCACCTTTACC ATCAGTAGCCTGGAAGCTGAAGATGCTGCA ACATATTACTGTCAGAATGATTATAGTTAT CCGTACACGTTCGGCCAAGGGACCAAGGTG GAAATCAAACGTACGGTGGCTGCACCATCT GTCTTCATCTTCCCGCCATCTGATGAGCAG TTGAAATCTGGAACTGCCTCTGTTGTGTGC CTGCTGAATAACTTCTATCCCAGAGAGGCC AAAGTACAGTGGAAGGTGGATAACGCCCTC CAATCGGGTAACTCCCAGGAGAGTGTCACA GAGCAGGACAGCAAGGACAGCACCTACAGC CTCAGCAGCACCCTGACGCTGAGCAAAGCA GACTACGAGAAACACAAAGTCTACGCCTGC GAAGTCACCCATCAGGGCCTGAGCTCGCCC GTCACAAAGAGCTTCAACAGGGGAGAGTGT |

BAP049-Clone-
A HC
────────────

| SEQ ID NO: 1 (Kabat) | HCDR1 | TYWMH |
|---|---|---|
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSYTFT TYWMHWVRQATGQGLEWMGNIYPGTGGSNF DEKFKNRVTITADKSTSTAYMELSSLRSED TAVYYCTRWTTGTGAYWGQGTTVTVSS |
| SEQ ID NO: 90 | DNA VH | GAAGTGCAGCTGGTGCAGTCTGGCGCCGAA GTGAAGAAGCCTGGCGAGTCCCTGCGGATC TCCTGCAAGGGCTCTGGCTACACCTTCACC ACCTACTGGATGCACTGGGTGCGACAGGCT ACCGGCCAGGGCCTGGAATGGATGGGCAAC |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

|  |  |  |
|---|---|---|
|  |  | ATCTATCCTGGCACCGGCGGCTCCAACTTC GACGAGAAGTTCAAGAACAGAGTGACCATC ACCGCCGACAAGTCCACCTCCACCGCCTAC ATGGAACTGTCCTCCCTGAGATCCGAGGAC ACCGCCGTGTACTACTGCACCCGGTGGACA ACCGGCACAGGCGCTTATTGGGGCCAGGGC ACCACAGTGACCGTGTCCTCT |
| SEQ ID NO: 91 | HC | EVQLVQSGAEVKKPGESLRISCKGSYTFT TYWMHWVRQATGQGLEWMGNIYPGTGGSNF DEKFKNRVTITADKSTSTAYMELSSLRSED TAVYYCTRWTTGTGAYWGQGTTVTVSSAST KGPSVFPLAPCSRSTSESTAALGCLVKDYF PEPVTVSWNSGALTSGVHTFPAVLQSSGLY SLSSVVTVPSSSLGTKTYTCNVDHKPSNTK VDKRVESKYGPPCPPCPAPEFLGGPSVFLF PPKPKDTLMISRTPEVTCVVVDVSQEDPEV QFNWYVDGVEVHNAKTKPREEQFNSTYRVV SVLTVLHQDWLNGKEYKCKVSNKGLPSSIE KTISKAKGQPREPQVYTLPPSQEEMTKNQV SLTCLVKGFYPSDIAVEWESNGQPENNYKT TPPVLDSDGSFFLYSRLTVDKSRWQEGNVF SCSVMHEALHNHYTQKSLSLSLG |
| SEQ ID NO: 92 | DNA HC | GAAGTGCAGCTGGTGCAGTCTGGCGCCGAA GTGAAGAAGCCTGGCGAGTCCCTGCGGATC TCCTGCAAGGGCTCTGGCTACACCTTCACC ACCTACTGGATGCACTGGGTGCGACAGGCT ACCGGCCAGGGCCTGGAATGGATGGGCAAC ATCTATCCTGGCACCGGCGGCTCCAACTTC GACGAGAAGTTCAAGAACAGAGTGACCATC ACCGCCGACAAGTCCACCTCCACCGCCTAC ATGGAACTGTCCTCCCTGAGATCCGAGGAC ACCGCCGTGTACTACTGCACCCGGTGGACA ACCGGCACAGGCGCTTATTGGGGCCAGGGC ACCACAGTGACCGTGTCCTCTGCTTCTACC AAGGGGCCCAGCGTGTTCCCCCTGGCCCCC TGCTCCAGAAGCACCAGCGAGAGCACAGCC GCCCTGGGCTGCCTGGTGAAGGACTACTTC CCCGAGCCCGTGACCGTGTCCTGGAACAGC GGAGCCCTGACCAGCGGCGTGCACACCTTC CCCGCCGTGCTGCAGAGCAGCGGCCTGTAC AGCCTGAGCAGCGTGGTGACCGTGCCCAGC AGCAGCCTGGGCACCAAGACCTACACCTGT AACGTGGACCACAAGCCCAGCAACACCAAG GTGGACAAGAGGGTGGAGAGCAAGTACGGC CCACCCTGCCCCCCCTGCCCAGCCCCCGAG TTCCTGGGCGGACCCAGCGTGTTCCTGTTC CCCCCCAAGCCCAAGGACACCCTGATGATC AGCAGAACCCCCGAGGTGACCTGTGTGGTG GTGGACGTGTCCCAGGAGGACCCCGAGGTC CAGTTCAACTGGTACGTGGACGGCGTGGAG GTGCACAACGCCAAGACCAAGCCCAGAGAG GAGCAGTTTAACAGCACCTACCGGGTGGTG TCCGTGCTGACCGTGCTGCACCAGGACTGG CTGAACGGCAAAGAGTACAAGTGTAAGGTC TCCAACAAGGGCCTGCCAAGCAGCATCGAA AAGACCATCAGCAAGGCCAAGGGCCAGCCT AGAGAGCCCCAGGTCTACACCCTGCCACCC AGCCAAGAGGAGATGACCAAGAACCAGGTG TCCCTGACCTGTCTGGTGAAGGGCTTCTAC CCAAGCGACATCGCCGTGGAGTGGGAGAGC AACGGCCAGCCCGAGAACAACTACAAGACC ACCCCCCCAGTGCTGGACAGCGACGGCAGC TTCTTCCTGTACAGCAGGCTGACCGTGGAC AAGTCCAGATGGCAGGAGGGCAACGTCTTT AGCTGCTCCGTGATGCACGAGGCCCTGCAC AACCACTACACCCAGAAGAGCCTGAGCCTG TCCCTGGGC |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

BAP049-Clone-
A LC

| | | |
|---|---|---|
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |

SEQ ID NO: 42 VL EIVLTQSPATLSLSPGERATLSCKSSQSLL
DSGNQKNFLTWYQQKPGQAPRLLIYWASTR
ESGVPSRFSGSGSGTEFTLTISSLQPDDFA
TYYCQNDYSYPYTFGQGTKVEIK

SEQ ID NO: 93 DNA GAGATCGTGCTGACCCAGTCCCCTGCCACC
VL CTGTCACTGTCTCCAGGCGAGAGAGCTACC
CTGTCCTGCAAGTCCTCCCAGTCCCTGCTG
GACTCCGGCAACCAGAAGAACTTCCTGACC
TGGTATCAGCAGAAGCCCGGCCAGGCCCCC
AGACTGCTGATCTACTGGGCCTCCACCCGG
GAATCGGCGTGCCCTCTAGATTCTCCGGC
TCCGGCTCTGGCACCGAGTTTACCCTGACC
ATCTCCAGCCTGCAGCCCGACGACTTCGCC
ACCTACTACTGCCAGAACGACTACTCCTAC
CCCTACACCTTCGGCCAGGGCACCAAGGTG
GAAATCAAG

SEQ ID NO: 44 LC EIVLTQSPATLSLSPGERATLSCKSSQSLL
DSGNQKNFLTWYQQKPGQAPRLLIYWASTR
ESGVPSRFSGSGSGTEFTLTISSLQPDDFA
TYYCQNDYSYPYTFGQGTKVEIKRTVAAPS
VFIFPPSDEQLKSGTASVVCLLNNFYPREA
KVQWKVDNALQSGNSQESVTEQDSKDSTYS
LSSTLTLSKADYEKHKVYACEVTHQGLSSP
VTKSFNRGEC

SEQ ID NO: 94 DNA GAGATCGTGCTGACCCAGTCCCCTGCCACC
LC CTGTCACTGTCTCCAGGCGAGAGAGCTACC
CTGTCCTGCAAGTCCTCCCAGTCCCTGCTG
GACTCCGGCAACCAGAAGAACTTCCTGACC
TGGTATCAGCAGAAGCCCGGCCAGGCCCCC
AGACTGCTGATCTACTGGGCCTCCACCCGG
GAATCGGCGTGCCCTCTAGATTCTCCGGC
TCCGGCTCTGGCACCGAGTTTACCCTGACC
ATCTCCAGCCTGCAGCCCGACGACTTCGCC
ACCTACTACTGCCAGAACGACTACTCCTAC
CCCTACACCTTCGGCCAGGGCACCAAGGTG
GAAATCAAGCGTACGGTGGCCGCTCCCAGC
GTGTTCATCTTCCCCCCAAGCGACGAGCAG
CTGAAGAGCGGCACCGCCAGCGTGGTGTGT
CTGCTGAACAACTTCTACCCCAGGGAGGCC
AAGGTGCAGTGGAAGGTGGACAACGCCCTG
CAGAGCGGCAACAGCCAGGAGAGCGTCACC
GAGCAGGACAGCAAGGACTCCACCTACAGC
CTGAGCAGCACCCTGACCCTGAGCAAGGCC
GACTACGAGAAGCACAAGGTGTACGCCTGT

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

GAGGTGACCCACCAGGGCCTGTCCAGCCCC
GTGACCAAGAGCTTCAACAGGGGCGAGTGC

BAP049-Clone-
B HC

| | | |
|---|---|---|
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |

SEQ ID NO: 38 VH EVQLVQSGAEVKKPGESLRISCKGSGYTFT
TYWMHWVRQATGQGLEWMGNIYPGTGGSNF
DEKFKNRVTITADKSTSTAYMELSSLRSED
TAVYYCTRWTTGTGAYWGQGTTVTVSS

SEQ ID NO: 95 DNA GAGGTGCAGCTGGTGCAGTCAGGCGCCGAA
VH GTGAAGAAGCCCGGCGAGTCACTGAGAATT
AGCTGTAAAGGTTCAGGCTACACCTTCACT
ACCTACTGGATGCACTGGGTCCGCCAGGCT
ACCGGTCAAGGCCTCGAGTGGATGGGTAAT
ATCTACCCCGGCACCGGCGGCTCTAACTTC
GACGAGAAGTTTAAGAATAGAGTGACTATC
ACCGCCGATAAGTCTACTAGCACCGCCTAT
ATGGAACTGTCTAGCCTGAGATCAGAGGAC
ACCGCCGTCTACTACTGCACTAGGTGGACT
ACCGGCACAGGCGCCTACTGGGGTCAAGGC
ACTACCGTGACCGTGTCTAGC

SEQ ID NO: 91 HC EVQLVQSGAEVKKPGESLRISCKGSGYTFT
TYWMHWVRQATGQGLEWMGNIYPGTGGSNF
DEKFKNRVTITADKSTSTAYMELSSLRSED
TAVYYCTRWTTGTGAYWGQGTTVTVSSAST
KGPSVFPLAPCSRSTSESTAALGCLVKDYF
PEPVTVSWNSGALTSGVHTFPAVLQSSGLY
SLSSVVTVPSSSLGTKTYTCNVDHKPSNTK
VDKRVESKYGPPCPPCPAPEFLGGPSVFLF
PPKPKDTLMISRTPEVTCVVVDVSQEDPEV
QFNWYVDGVEVHNAKTKPREEQFNSTYRVV
SVLTVLHQDWLNGKEYKCKVSNKGLPSSIE
KTISKAKGQPREPQVYTLPPSQEEMTKNQV
SLTCLVKGFYPSDIAVEWESNGQPENNYKT
TPPVLDSDGSFFLYSRLTVDKSRWQEGNVF
SCSVMHEALHNHYTQKSLSLSLG

SEQ ID NO: 96 DNA GAGGTGCAGCTGGTGCAGTCAGGCGCCGAA
HC GTGAAGAAGCCCGGCGAGTCACTGAGAATT
AGCTGTAAAGGTTCAGGCTACACCTTCACT
ACCTACTGGATGCACTGGGTCCGCCAGGCT
ACCGGTCAAGGCCTCGAGTGGATGGGTAAT
ATCTACCCCGGCACCGGCGGCTCTAACTTC
GACGAGAAGTTTAAGAATAGAGTGACTATC
ACCGCCGATAAGTCTACTAGCACCGCCTAT
ATGGAACTGTCTAGCCTGAGATCAGAGGAC
ACCGCCGTCTACTACTGCACTAGGTGGACT
ACCGGCACAGGCGCCTACTGGGGTCAAGGC

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

```
                    ACTACCGTGACCGTGTCTAGCGCTAGCACT
                    AAGGGCCCGTCCGTGTTCCCCCTGGCACCT
                    TGTAGCCGGAGCACTAGCGAATCCACCGCT
                    GCCCTCGGCTGCCTGGTCAAGGATTACTTC
                    CCGGAGCCCGTGACCGTGTCCTGGAACAGC
                    GGAGCCCTGACCTCCGGAGTGCACACCTTC
                    CCCGCTGTGCTGCAGAGCTCCGGGCTGTAC
                    TCGCTGTCGTCGGTGGTCACGGTGCCTTCA
                    TCTAGCCTGGGTACCAAGACCTACACTTGC
                    AACGTGGACCACAAGCCTTCCAACACTAAG
                    GTGGACAAGCGCGTCGAATCGAAGTACGGC
                    CCACCGTGCCCGCCTTGTCCCGCGCCGGAG
                    TTCCTCGGCGGTCCCTCGGTCTTTCTGTTC
                    CCACCGAAGCCCAAGGACACTTTGATGATT
                    TCCCGCACCCCTGAAGTGACATGCGTGGTC
                    GTGGACGTGTCACAGGAAGATCCGGAGGTG
                    CAGTTCAATTGGTACGTGGATGGCGTCGAG
                    GTGCACAACGCCAAAACCAAGCCGAGGGAG
                    GAGCAGTTCAACTCCACTTACCGCGTCGTG
                    TCCGTGCTGACGGTGCTGCATCAGGACTGG
                    CTGAACGGGAAGGAGTACAAGTGCAAAGTG
                    TCCAACAAGGGACTTCCTAGCTCAATCGAA
                    AAGACCATCTCGAAAGCCAAGGGACAGCCC
                    CGGGAACCCCAAGTGTATACCCTGCCACCG
                    AGCCAGGAAGAAATGACTAAGAACCAAGTC
                    TCATTGACTTGCCTTGTGAAGGGCTTCTAC
                    CCATCGGATATCGCCGTGGAATGGGAGTCC
                    AACGGCCAGCCGGAAAACAACTACAAGACC
                    ACCCCTCCGGTGCTGGACTCAGACGGATCC
                    TTCTTCCTCTACTCGCGGCTGACCGTGGAT
                    AAGAGCAGATGGCAGGAGGGAAATGTGTTC
                    AGCTGTTCTGTGATGCATGAAGCCCTGCAC
                    AACCACTACACTCAGAAGTCCCTGTCCCTC
                    TCCCTGGGA
```

BAP049-Clone-
B LC

SEQ ID NO: 10    LCDR1    KSSQSLLDSGNQKNFLT
(Kabat)

SEQ ID NO: 11    LCDR2    WASTRES
(Kabat)

SEQ ID NO: 32    LCDR3    QNDYSYPYT
(Kabat)

SEQ ID NO: 13    LCDR1    SQSLLDSGNQKNF
(Chothia)

SEQ ID NO: 14    LCDR2    WAS
(Chothia)

SEQ ID NO: 33    LCDR3    DYSYPY
(Chothia)

SEQ ID NO: 54    VL       EIVLTQSPATLSLSPGERATLSCKSSQSLL
                          DSGNQKNFLTWYQQKPGKAPKLLIYWASTR
                          ESGVPSRFSGSGSGTDFTFTISSLQPEDIA
                          TYYCQNDYSYPYTFGQGTKVEIK

SEQ ID NO: 97    DNA      GAGATGTCCTGACTCAGTCACCCGCTACC
                 VL       CTGAGCCTGAGCCCTGGCGAGCGGGCTACA
                          CTGAGCTGTAAATCTAGTCAGTCACTGCTG
                          GATAGCGGTAATCAGAAGAACTTCCTGACC
                          TGGTATCAGCAGAAGCCCGGTAAAGCCCCT
                          AAGCTGCTGATCTACTGGGCCTCTACTAGA
                          GAATCAGGCGTGCCCTCTAGGTTTAGCGGT
                          AGCGGTAGTGGCACCGACTTCACCTTCACT

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

```
                    ATCTCTAGCCTGCAGCCCGAGGATATCGCT
                    ACCTACTACTGTCAGAACGACTATAGCTAC
                    CCCTACACCTTCGGTCAAGGCACTAAGGTC
                    GAGATTAAG
```

SEQ ID NO: 56    LC       EIVLTQSPATLSLSPGERATLSCKSSQSLL
                          DSGNQKNFLTWYQQKPGKAPKLLIYWASTR
                          ESGVPSRFSGSGSGTDFTFTISSLQPEDIA
                          TYYCQNDYSYPYTFGQGTKVEIKRTVAAPS
                          VFIFPPSDEQLKSGTASVVCLLNNFYPREA
                          KVQWKVDNALQSGNSQESVTEQDSKDSTYS
                          LSSTLTLSKADYEKHKVYACEVTHQGLSSP
                          VTKSFNRGEC

SEQ ID NO: 98    DNA      GAGATCGTCCTGACTCAGTCACCCGCTACC
                 LC       CTGAGCCTGAGCCCTGGCGAGCGGGCTACA
                          CTGAGCTGTAAATCTAGTCAGTCACTGCTG
                          GATAGCGGTAATCAGAAGAACTTCCTGACC
                          TGGTATCAGCAGAAGCCCGGTAAAGCCCCT
                          AAGCTGCTGATCTACTGGGCCTCTACTAGA
                          GAATCAGGCGTGCCCTCTAGGTTTAGCGGT
                          AGCGGTAGTGGCACCGACTTCACCTTCACT
                          ATCTCTAGCCTGCAGCCCGAGGATATCGCT
                          ACCTACTACTGTCAGAACGACTATAGCTAC
                          CCCTACACCTTCGGTCAAGGCACTAAGGTC
                          GAGATTAAGCGTACGGTGGCCGCTCCCAGC
                          GTGTTCATCTTCCCCCCCAGCGACGAGCAG
                          CTGAAGAGCGGCACCGCCAGCGTGGTGTGC
                          CTGCTGAACAACTTCTACCCCCGGGAGGCC
                          AAGGTGCAGTGGAAGGTGGACAACGCCCTG
                          CAGAGCGGCAACAGCCAGGAGAGCGTCACC
                          GAGCAGGACAGCAAGGACTCCACCTACAGC
                          CTGAGCAGCACCCTGACCCTGAGCAAGGCC
                          GACTACGAGAAGCATAAGGTGTACGCCTGC
                          GAGGTGACCCACCAGGGCCTGTCCAGCCCC
                          GTGACCAAGAGCTTCAACAGGGGCGAGTGC
```

BAP049-Clone-
C HC

SEQ ID NO: 1     HCDR1    TYWMH
(Kabat)

SEQ ID NO: 2     HCDR2    NIYPGTGGSNFDEKFKN
(Kabat)

SEQ ID NO: 3     HCDR3    WTTGTGAY
(Kabat)

SEQ ID NO: 4     HCDR1    GYTFTTY
(Chothia)

SEQ ID NO: 5     HCDR2    YPGTGG
(Chothia)

SEQ ID NO: 3     HCDR3    WTTGTGAY
(Chothia)

SEQ ID NO: 38    VH       EVQLVQSGAEVKKPGESLRISCKGSGYTFT
                          TYWMHWVRQATGQGLEWMGNIYPGTGGSNF
                          DEKFKNRVTITADKSTSTAYMELSSLRSED
                          TAVYYCTRWTTGTGAYWGQGTTVTVSS

SEQ ID NO: 90    DNA      GAAGTGCAGCTGGTGCAGTCTGGCGCCGAA
                 VH       GTGAAGAAGCCTGGCGAGTCCCTGCGGATC
                          TCCTGCAAGGGCTCTGGCTACACCTTCACC
                          ACCTACTGGATGCACTGGGTGCGACAGGCT
                          ACCGGCCAGGGCCTGGAATGGATGGGCAAC
                          ATCTATCCTGGCACCGGCGGCTCCAACTTC
```

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

|  |  |  |
|---|---|---|
|  |  | GACGAGAAGTTCAAGAACAGAGTGACCATC<br>ACCGCCGACAAGTCCACCTCCACCGCCTAC<br>ATGGAACTGTCCTCCCTGAGATCCGAGGAC<br>ACCGCCGTGTACTACTGCACCCGGTGGACA<br>ACCGGCACAGGCGCTTATTGGGGCCAGGGC<br>ACCACAGTGACCGTGTCCTCT |
| SEQ ID NO: 91 | HC | EVQLVQSGAEVKKPGESLRISCKGSGYTFT<br>TYWMHWVRQATGQGLEWMGNIYPGTGGSNF<br>DEKFKNRVTITADKSTSTAYMELSSLRSED<br>TAVYYCTRWTTGTGAYWGQGTTVTVSSAST<br>KGPSVFPLAPCSRSTSESTAALGCLVKDYF<br>PEPVTVSWNSGALTSGVHTFPAVLQSSGLY<br>SLSSVVTVPSSSLGTKTYTCNVDHKPSNTK<br>VDKRVESKYGPPCPPCPAPEFLGGPSVFLF<br>PPKPKDTLMISRTPEVTCVVVDVSQEDPEV<br>QFNWYVDGVEVHNAKTKPREEQFNSTYRVV<br>SVLTVLHQDWLNGKEYKCKVSNKGLPSSIE<br>KTISKAKGQPREPQVYTLPPSQEEMTKNQV<br>SLTCLVKGFYPSDIAVEWESNGQPENNYKT<br>TPPVLDSDGSFFLYSRLTVDKSRWQEGNVF<br>SCSVMHEALHNHYTQKSLSLSLG |
| SEQ ID NO: 92 | DNA<br>HC | GAAGTGCAGCTGGTGCAGTCTGGCGCCGAA<br>GTGAAGAAGCCTGGCGAGTCCCTGCGGATC<br>TCCTGCAAGGGCTCTGGCTACACCTTCACC<br>ACCTACTGGATGCACTGGGTGCGACAGGCT<br>ACCGGCCAGGGCCTGGAATGGATGGGCAAC<br>ATCTATCCTGGCACCGGCGGCTCCAACTTC<br>GACGAGAAGTTCAAGAACAGAGTGACCATC<br>ACCGCCGACAAGTCCACCTCCACCGCCTAC<br>ATGGAACTGTCCTCCCTGAGATCCGAGGAC<br>ACCGCCGTGTACTACTGCACCCGGTGGACA<br>ACCGGCACAGGCGCTTATTGGGGCCAGGGC<br>ACCACAGTGACCGTGTCCTCTGCTTCTACC<br>AAGGGGCCCAGCGTGTTCCCCCTGGCCCCC<br>TGCTCCAGAAGCACCAGCGAGAGCACAGCC<br>GCCCTGGGCTGCCTGGTGAAGGACTACTTC<br>CCCGAGCCCGTGACCGTGTCCTGGAACAGC<br>GGAGCCCTGACCAGCGGCGTGCACACCTTC<br>CCCGCCGTGCTGCAGAGCAGCGGCCTGTAC<br>AGCCTGAGCAGCGTGGTGACCGTGCCCAGC<br>AGCAGCCTGGGCACCAAGACCTACACCTGT<br>AACGTGGACCACAAGCCCAGCAACACCAAG<br>GTGGACAAGAGGGTGGAGAGCAAGTACGGC<br>CCACCCTGCCCCCCCTGCCCAGCCCCCGAG<br>TTCCTGGGCGGACCCAGCGTGTTCCTGTTC<br>CCCCCCAAGCCCAAGGACACCCTGATGATC<br>AGCAGAACCCCCGAGGTGACCTGTGTGGTG<br>GTGGACGTGTCCCAGGAGGACCCCGAGGTC<br>CAGTTCAACTGGTACGTGGACGGCGTGGAG<br>GTGCACAACGCCAAGACCAAGCCCAGAGAG<br>GAGCAGTTTAACAGCACCTACCGGGTGGTG<br>TCCGTGCTGACCGTGCTGCACCAGGACTGG<br>CTGAACGGCAAAGAGTACAAGTGTAAGGTC<br>TCCAACAAGGGCCTGCCAAGCAGCATCGAA<br>AAGACCATCAGCAAGGCCAAGGGCCAGCCT<br>AGAGAGCCCCAGGTCTACACCCTGCCACCC<br>AGCCAAGAGGAGATGACCAAGAACCAGGTG<br>TCCCTGACCTGTCTGGTGAAGGGCTTCTAC<br>CCAAGCGACATCGCCGTGGAGTGGGAGAGC<br>AACGGCCAGCCCGAGAACAACTACAAGACC<br>ACCCCCCCAGTGCTGGACAGCGACGGCAGC<br>TTCTTCCTGTACAGCAGGCTGACCGTGGAC<br>AAGTCCAGATGGCAGGAGGGCAACGTCTTT<br>AGCTGCTCCGTGATGCACGAGGCCCTGCAC<br>AACCACTACACCCAGAAGAGCCTGAGCCTG<br>TCCCTGGGC |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

BAP049-Clone-
C LC

|  |  |  |  |
|---|---|---|---|
| SEQ ID NO: 10<br>(Kabat) | LCDR1 | KSSQSLLDSGNQKNFLT | |
| SEQ ID NO: 11<br>(Kabat) | LCDR2 | WASTRES | |
| SEQ ID NO: 32<br>(Kabat) | LCDR3 | QNDYSYPYT | |
| SEQ ID NO: 13<br>(Chothia) | LCDR1 | SQSLLDSGNQKNF | |
| SEQ ID NO: 14<br>(Chothia) | LCDR2 | WAS | |
| SEQ ID NO: 33<br>(Chothia) | LCDR3 | DYSYPY | |
| SEQ ID NO: 66 | VL | EIVLTQSPDFQSVTPKEKVTITCKSSQSLL<br>DSGNQKNFLTWYQQKPGQAPRLLIYWASTR<br>ESGVPSRFSGSGSGTDFTFTISSLEAEDAA<br>TYYCQNDYSYPYTFGQGTKVEIK | |
| SEQ ID NO: 99 | DNA<br>VL | GAGATCGTGCTGACCCAGTCCCCCGACTTC<br>CAGTCCGTGACCCCCAAAGAAAAAGTGACC<br>ATCACATGCAAGTCCTCCCAGTCCCTGCTG<br>GACTCCGGCAACCAGAAGAACTTCCTGACC<br>TGGTATCAGCAGAAGCCCGGCCAGGCCCCC<br>AGACTGCTGATCTACTGGGCCTCCACCCGG<br>GAATCTGGCGTGCCCTCTAGATTCTCCGGC<br>TCCGGCTCTGGCACCGACTTTACCTTCACC<br>ATCTCCAGCCTGGAAGCCGAGGACGCCGCC<br>ACCTACTACTGCCAGAACGACTACTCCTAC<br>CCCTACACCTTCGGCCAGGGCACCAAGGTG<br>GAAATCAAG | |
| SEQ ID NO: 68 | LC | EIVLTQSPDFQSVTPKEKVTITCKSSQSLL<br>DSGNQKNFLTWYQQKPGQAPRLLIYWASTR<br>ESGVPSRFSGSGSGTDFTFTISSLEAEDAA<br>TYYCQNDYSYPYTFGQGTKVEIKRTVAAPS<br>VFIFPPSDEQLKSGTASVVCLLNNFYPREA<br>KVQWKVDNALQSGNSQESVTEQDSKDSTYS<br>LSSTLTLSKADYEKHKVYACEVTHQGLSSP<br>VTKSFNRGEC | |
| SEQ ID NO:<br>100 | DNA<br>LC | GAGATCGTGCTGACCCAGTCCCCCGACTTC<br>CAGTCCGTGACCCCCAAAGAAAAAGTGACC<br>ATCACATGCAAGTCCTCCCAGTCCCTGCTG<br>GACTCCGGCAACCAGAAGAACTTCCTGACC<br>TGGTATCAGCAGAAGCCCGGCCAGGCCCCC<br>AGACTGCTGATCTACTGGGCCTCCACCCGG<br>GAATCTGGCGTGCCCTCTAGATTCTCCGGC<br>TCCGGCTCTGGCACCGACTTTACCTTCACC<br>ATCTCCAGCCTGGAAGCCGAGGACGCCGCC<br>ACCTACTACTGCCAGAACGACTACTCCTAC<br>CCCTACACCTTCGGCCAGGGCACCAAGGTG<br>GAAATCAAGCGTACGGTGGCCGCTCCCAGC<br>GTGTTCATCTTCCCCCCAAGCGACGAGCAG<br>CTGAAGAGCGGCACCGCCAGCGTGGTGTGT<br>CTGCTGAACAACTTCTACCCCAGGGAGGCC<br>AAGGTGCAGTGGAAGGTGGACAACGCCCTG<br>CAGAGCGGCAACAGCCAGGAGAGCGTCACC<br>GAGCAGGACAGCAAGGACTCCACCTACAGC<br>CTGAGCAGCACCCTGACCCTGAGCAAGGCC |

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

```
                    GACTACGAGAAGCACAAGGTGTACGCCTGT
                    GAGGTGACCCACCAGGGCCTGTCCAGCCCC
                    GTGACCAAGAGCTTCAACAGGGGCGAGTGC

BAP049-Clone-
D HC

SEQ ID NO: 1      HCDR1   TYWMH
(Kabat)

SEQ ID NO: 2      HCDR2   NIYPGTGGSNFDEKFKN
(Kabat)

SEQ ID NO: 3      HCDR3   WTTGTGAY
(Kabat)

SEQ ID NO: 4      HCDR1   GYTFTTY
(Chothia)

SEQ ID NO: 5      HCDR2   YPGTGG
(Chothia)

SEQ ID NO: 3      HCDR3   WTTGTGAY
(Chothia)

SEQ ID NO: 50    VH    EVQLVQSGAEVKKPGESLRISCKGSGYTFT
                       TYWMHWIRQSPSRGLEWLGNIYPGTGGSNF
                       DEKFKNRFTISRDNSKNTLYLQMNSLRAED
                       TAVYYCTRWTTGTGAYWGQGTTVTVSS

SEQ ID NO:   DNA   GAAGTGCAGCTGGTGCAGTCTGGCGCCGAA
101          VH    GTGAAGAAGCCTGGCGAGTCCCTGCGGATC
                   TCCTGCAAGGGCTCTGGCTACACCTTCACC
                   ACCTACTGGATGCACTGGATCCGGCAGTCC
                   CCCTCTAGGGGCCTGGAATGGCTGGGCAAC
                   ATCTACCCTGGCACCGGCGGCTCCAACTTC
                   GACGAGAAGTTCAAGAACAGGTTCACCATC
                   TCCCGGGACAACTCCAAGAACACCCTGTAC
                   CTGCAGATGAACTCCCTGCGGGCCGAGGAC
                   ACCGCCGTGTACTACTGTACCAGATGGACC
                   ACCGGAACCGGCGCCTATTGGGGCCAGGGC
                   ACAACAGTGACCGTGTCCTCC

SEQ ID NO:   HC    EVQLVQSGAEVKKPGESLRISCKGSGYTFT
102                TYWMHWIRQSPSRGLEWLGNIYPGTGGSNF
                   DEKFKNRFTISRDNSKNTLYLQMNSLRAED
                   TAVYYCTRWTTGTGAYWGQGTTVTVSSAST
                   KGPSVFPLAPCSRSTSESTAALGCLVKDYF
                   PEPVTVSWNSGALTSGVHTFPAVLQSSGLY
                   SLSSVVTVPSSSLGTKTYTCNVDHKPSNTK
                   VDKRVESKYGPPCPPCPAPEFLGGPSVFLF
                   PPKPKDTLMISRTPEVTCVVVDVSQEDPEV
                   QFNWYVDGVEVHNAKTKPREEQFNSTYRVV
                   SVLTVLHQDWLNGKEYKCKVSNKGLPSSIE
                   KTISKAKGQPREPQVYTLPPSQEEMTKNQV
                   SLTCLVKGFYPSDIAVEWESNGQPENNYKT
                   TPPVLDSDGSFFLYSRLTVDKSRWQEGNVF
                   SCSVMHEALHNHYTQKSLSLSLG

SEQ ID NO:   DNA   GAAGTGCAGCTGGTGCAGTCTGGCGCCGAA
103          HC    GTGAAGAAGCCTGGCGAGTCCCTGCGGATC
                   TCCTGCAAGGGCTCTGGCTACACCTTCACC
                   ACCTACTGGATGCACTGGATCCGGCAGTCC
                   CCCTCTAGGGGCCTGGAATGGCTGGGCAAC
                   ATCTACCCTGGCACCGGCGGCTCCAACTTC
                   GACGAGAAGTTCAAGAACAGGTTCACCATC
                   TCCCGGGACAACTCCAAGAACACCCTGTAC
                   CTGCAGATGAACTCCCTGCGGGCCGAGGAC
                   ACCGCCGTGTACTACTGTACCAGATGGACC
```

TABLE 1-continued

Amino acid and nucleotide sequences for murine, chimeric and humanized antibody molecules. The antibody molecules include murine mAb BAP049, chimeric mAbs BAP049-chi and BAP049-chi-Y, and humanized mAbs BAP049-hum01 to BAP049-hum16 and BAP049-Clone-A to BAP049-Clone-E. The amino acid and nucleotide sequences of the heavy and light chain CDRs, the heavy and light chain variable regions, and the heavy and light chains are shown.

```
                    ACCGGAACCGGCGCCTATTGGGGCCAGGGC
                    ACAACAGTGACCGTGTCCTCCGCTTCTACC
                    AAGGGGCCCAGCGTGTTCCCCCTGGCCCCC
                    TGCTCCAGAAGCACCAGCGAGAGCACAGCC
                    GCCCTGGGCTGCCTGGTGAAGGACTACTTC
                    CCCGAGCCCGTGACCGTGTCCTGGAACAGC
                    GGAGCCCTGACCAGCGGCGTGCACACCTTC
                    CCCGCCGTGCTGCAGAGCAGCGGCCTGTAC
                    AGCCTGAGCAGCGTGGTGACCGTGCCCAGC
                    AGCAGCCTGGGCACCAAGACCTACACCTGT
                    AACGTGGACCACAAGCCCAGCAACACCAAG
                    GTGGACAAGAGGGTGGAGAGCAAGTACGGC
                    CCACCCTGCCCCCCCTGCCCAGCCCCCGAG
                    TTCCTGGGCGGACCCAGCGTGTTCCTGTTC
                    CCCCCCAAGCCCAAGGACACCCTGATGATC
                    AGCAGAACCCCCGAGGTGACCTGTGTGGTG
                    GTGGACGTGTCCCAGGAGGACCCCGAGGTC
                    CAGTTCAACTGGTACGTGGACGGCGTGGAG
                    GTGCACAACGCCAAGACCAAGCCCAGAGAG
                    GAGCAGTTTAACAGCACCTACCGGGTGGTG
                    TCCGTGCTGACCGTGCTGCACCAGGACTGG
                    CTGAACGGCAAAGAGTACAAGTGTAAGGTC
                    TCCAACAAGGGCCTGCCAAGCAGCATCGAA
                    AAGACCATCAGCAAGGCCAAGGGCCAGCCT
                    AGAGAGCCCCAGGTCTACACCCTGCCACCC
                    AGCCAAGAGGAGATGACCAAGAACCAGGTG
                    TCCCTGACCTGTCTGGTGAAGGGCTTCTAC
                    CCAAGCGACATCGCCGTGGAGTGGGAGAGC
                    AACGGCCAGCCCGAGAACAACTACAAGACC
                    ACCCCCCCCAGTGCTGGACAGCGACGGCAGC
                    TTCTTCCTGTACAGCAGGCTGACCGTGGAC
                    AAGTCCAGATGCAGGAGGGCAACGTCTTT
                    AGCTGCTCCGTGATGCACGAGGCCCTGCAC
                    AACCACTACACCCAGAAGAGCCTGAGCCTG
                    TCCCTGGGC

BAP049-Clone-
D LC

SEQ ID NO: 10   LCDR1   KSSQSLLDSGNQKNFLT
(Kabat)

SEQ ID NO: 11   LCDR2   WASTRES
(Kabat)

SEQ ID NO: 32   LCDR3   QNDYSYPYT
(Kabat)

SEQ ID NO: 13   LCDR1   SQSLLDSGNQKNF
(Chothia)

SEQ ID NO: 14   LCDR2   WAS
(Chothia)

SEQ ID NO: 33   LCDR3   DYSYPY
(Chothia)

SEQ ID NO: 70   VL    EIVLTQSPATLSLSPGERATLSCKSSQSLL
                      DSGNQKNFLTWYQQKPGQAPRLLIYWASTR
                      ESGVPSRFSGSGSGTDFTFTISSLEAEDAA
                      TYYCQNDYSYPYTFGQGTKVEIK

SEQ ID NO:   DNA   GAGATCGTGCTGACCCAGTCCCCTGCCACC
104          VL    CTGTCACTGTCTCCAGGCGAGAGAGCTACC
                   CTGTCCTGCAAGTCCTCCCAGTCCCTGCTG
                   GACTCCGGCAACCAGAAGAACTTCCTGACC
                   TGGTATCAGCAGAAGCCCGGCCAGGCCCCC
                   AGACTGCTGATCTACTGGGCCTCCACCCGG
                   GAATCTGGCGTGCCCTCTAGATTCTCCGGC
```

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

| | | |
|---|---|---|
| | | TCCGGCTCTGGCACCGACTTTACCTTCACC ATCTCCAGCCTGGAAGCCGAGGACGCCGCC ACCTACTACTGCCAGAACGACTACTCCTAC CCCTACACCTTCGGCCAGGGCACCAAGGTG GAAATCAAG |
| SEQ ID NO: 72 | LC | EIVLTQSPATLSLSPGERATLSCKSSQSLL DSGNQKNFLTWYQQKPGQAPRLLIYWASTR ESGVPSRFSGSGSGTDFTFTISSLEAEDAA TYYCQNDYSYPYTFGQGTKVEIKRTVAAPS VFIFPPSDEQLKSGTASVVCLLNNFYPREA KVQWKVDNALQSGNSQESVTEQDSKDSTYS LSSTLTLSKADYEKHKVYACEVTHQGLSSP VTKSFNRGEC |
| SEQ ID NO: 105 | DNA LC | GAGATCGTGCTGACCCAGTCCCCTGCCACC CTGTCACTGTCTCCAGGCGAGAGAGCTACC CTGTCCTGCAAGTCCTCCCAGTCCCTGCTG GACTCCGGCAACCAGAAGAACTTCCTGACC TGGTATCAGCAGAAGCCCGGCCAGGCCCCC AGACTGCTGATCTACTGGGCCTCCACCCGG GAATCTGGCGTGCCCTCTAGATTCTCCGGC TCCGGCTCTGGCACCGACTTTACCTTCACC ATCTCCAGCCTGGAAGCCGAGGACGCCGCC ACCTACTACTGCCAGAACGACTACTCCTAC CCCTACACCTTCGGCCAGGGCACCAAGGTG GAAATCAAGCGTACGGTGGCCGCTCCCAGC GTGTTCATCTTCCCCCCAAGCGACGAGCAG CTGAAGAGCGGCACCGCCAGCGTGGTGTGT CTGCTGAACAACTTCTACCCCAGGGAGGCC AAGGTGCAGTGGAAGGTGGACAACGCCCTG CAGAGCGGCAACAGCCAGGAGAGCGTCACC GAGCAGGACAGCAAGGACTCCACCTACAGC CTGAGCAGCACCCTGACCCTGAGCAAGGCC GACTACGAGAAGCACAAGGTCTACGCCTGT GAGGTGACCCACCAGGGCCTGTCCAGCCCC GTGACCAAGAGCTTCAACAGGGGCGAGTGC |
| BAP049-Clone-E HC | | |
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 38 | VH | EVQLVQSGAEVKKPGESLRISCKGSGYTFT TYWMHWVRQATGQGLEWMGNIYPGTGGSNF DEKFKNRVTITADKSTSTAYMELSSLRSED TAVYYCTRWTTGTGAYWGQGTTVTVSS |
| SEQ ID NO: 95 | DNA VH | GAGGTGCAGCTGGTGCAGTCAGGCGCCGAA GTGAAGAAGCCCGGCGAGTCACTGAGAATT AGCTGTAAAGGTTCAGGCTACACCTTCACT ACCTACTGGATGCACTGGGTCCGCCAGGCT ACCGGTCAAGGCCTCGAGTGGATGGGTAAT |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

| | | |
|---|---|---|
| | | ATCTACCCCGGCACCGGCGGCTCTAACTTC GACGAGAAGTTTAAGAATAGAGTGACTATC ACCGCCGATAAGTCTACTAGCACCGCCTAT ATGGAACTGTCTAGCCTGAGATCAGAGGAC ACCGCCGTCTACTACTGCACTAGGTGGACT ACCGGCACAGGCGCCTACTGGGGTCAAGGC ACTACCGTGACCGTGTCTAGC |
| SEQ ID NO: 91 | HC | EVQLVQSGAEVKKPGESLRISCKGSGYTFT TYWMHWVRQATGQGLEWMGNIYPGTGGSNF DEKFKNRVTITADKSTSTAYMELSSLRSED TAVYYCTRWTTGTGAYWGQGTTVTVSSAST KGPSVFPLAPCSRSTSESTAALGCLVKDYF PEPVTVSWNSGALTSGVHTFPAVLQSSGLY SLSSVVTVPSSSLGTKTYTCNVDHKPSNTK VDKRVESKYGPPCPPCPAPEFLGGPSVFLF PPKPKDTLMISRTPEVTCVVVDVSQEDPEV QFNWYVDGVEVHNAKTKPREEQFNSTYRVV SVLTVLHQDWLNGKEYKCKVSNKGLPSSIE KTISKAKGQPREPQVYTLPPSQEEMTKNQV SLTCLVKGFYPSDIAVEWESNGQPENNYKT TPPVLDSDGSFFLYSRLTVDKSRWQEGNVF SCSVMHEALHNHYTQKSLSLSLG |
| SEQ ID NO: 96 | DNA HC | GAGGTGCAGCTGGTGCAGTCAGGCGCCGAA GTGAAGAAGCCCGGCGAGTCACTGAGAATT AGCTGTAAAGGTTCAGGCTACACCTTCACT ACCTACTGGATGCACTGGGTCCGCCAGGCT ACCGGTCAAGGCCTCGAGTGGATGGGTAAT ATCTACCCCGGCACCGGCGGCTCTAACTTC GACGAGAAGTTTAAGAATAGAGTGACTATC ACCGCCGATAAGTCTACTAGCACCGCCTAT ATGGAACTGTCTAGCCTGAGATCAGAGGAC ACCGCCGTCTACTACTGCACTAGGTGGACT ACCGGCACAGGCGCCTACTGGGGTCAAGGC ACTACCGTGACCGTGTCTAGCGCTAGCACT AAGGGCCCGTCCGTGTTCCCCCTGGCACCT TGTAGCCGGAGCACTAGCGAATCCACCGCT GCCCTCGGCTGCCTGGTCAAGGATTACTTC CCGGAGCCCGTGACCGTGTCCTGGAACAGC GGAGCCCTGACCTCCGGAGTGCACACCTTC CCCGCTGTGCTGCAGAGCTCCGGGCTGTAC TCGCTGTCGTCGGTGGTCACGGTGCCTTCA TCTAGCCTGGGTACCAAGACCTACACTTGC AACGTGGACCACAAGCCTTCCAACACTAAG GTGGACAAGCGCGTCGAATCGAAGTACGGC CCACCGTGCCCGCCTTGTCCCGCGCCGGAG TTCCTCGGCGGTCCCTCGGTCTTTCTGTTC CCACCGAAGCCCAAGGACACTTTGATGATT TCCCGCACCCCTGAAGTGACATGCGTGGTC GTGGACGTGTCACAGGAAGATCCGGAGGTG CAGTTCAATTGGTACGTGGATGGCGTCGAG GTGCACAACGCCAAAACCAAGCCGAGGGAG GAGCAGTTCAACTCCACTTACCGCGTCGTG TCCGTGCTGACGGTGCTGCATCAGGACTGG CTGAACGGGAAGGAGTACAAGTGCAAAGTG TCCAACAAGGGACTTCCTAGCTCAATCGAA AAGACCATCTCGAAAGCCAAGGGACAGCCC CGGGAACCCCAAGTGTATACCCTGCCACCG AGCCAGGAAGAAATGACTAAGAACCAAGTC TCATTGACTTGCCTTGTGAAGGGCTTCTAC CCATCGGATATCGCCGTGGAATGGGAGTCC AACGGCCAGCCGGAAAACAACTACAAGACC ACCCCTCCGGTGCTGGACTCAGACGGATCC TTCTTCCTCTACTCGCGGCTGACCGTGGAT AAGAGCAGATGGCAGGAGGGAAATGTGTTC AGCTGTTCTGTGATGCATGAAGCCCTGCAC AACCACTACACTCAGAAGTCCCTGTCCCTC TCCCTGGGA |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

BAP049-Clone-
E LC

| | | |
|---|---|---|
| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 32 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 33 (Chothia) | LCDR3 | DYSYPY |

| | | |
|---|---|---|
| SEQ ID NO: 70 | VL | EIVLTQSPATLSLSPGERATLSCKSSQSLL DSGNQKNFLTWYQQKPGQAPRLLIYWASTR ESGVPSRFSGSGSGTDFTFTISSLEAEDAA TYYCQNDYSYPYTFGQGTKVEIK |
| SEQ ID NO: 106 | DNA VL | GAGATCGTCCTGACTCAGTCACCCGCTACC CTGAGCCTGAGCCCTGGCGAGCGGGCTACA CTGAGCTGTAAATCTAGTCAGTCACTGCTG GATAGCGGTAATCAGAAGAACTTCCTGACC TGGTATCAGCAGAAGCCCGGTCAAGCCCCT AGACTGCTGATCTACTGGGCCTCTACTAGA GAATCAGGCGTGCCCTCTAGGTTTAGCGGT AGCGGTAGTGGCACCGACTTCACCTTCACT ATCTCTAGCCTGGAAGCCGAGGACGCCGCT ACCTACTACTGTCAGAACGACTATAGCTAC CCCTACACCTTCGGTCAAGGCACTAAGGTC GAGATTAAG |
| SEQ ID NO: 72 | LC | EIVLTQSPATLSLSPGERATLSCKSSQSLL DSGNQKNFLTWYQQKPGQAPRLLIYWASTR ESGVPSRFSGSGSGTDFTFTISSLEAEDAA TYYCQNDYSYPYTFGQGTKVEIKRTVAAPS VFIFPPSDEQLKSGTASVVCLLNNFYPREA KVQWKVDNALQSGNSQESVTEQDSKDSTYS LSSTLTLSKADYEKHKVYACEVTHQGLSSP VTKSFNRGEC |
| SEQ ID NO: 107 | DNA LC | GAGATCGTCCTGACTCAGTCACCCGCTACC CTGAGCCTGAGCCCTGGCGAGCGGGCTACA CTGAGCTGTAAATCTAGTCAGTCACTGCTG GATAGCGGTAATCAGAAGAACTTCCTGACC TGGTATCAGCAGAAGCCCGGTCAAGCCCCT AGACTGCTGATCTACTGGGCCTCTACTAGA GAATCAGGCGTGCCCTCTAGGTTTAGCGGT AGCGGTAGTGGCACCGACTTCACCTTCACT ATCTCTAGCCTGGAAGCCGAGGACGCCGCT ACCTACTACTGTCAGAACGACTATAGCTAC CCCTACACCTTCGGTCAAGGCACTAAGGTC GAGATTAAGCGTACGGTGGCCGCTCCCAGC GTGTTCATCTTCCCCCCCAGCGACGAGCAG CTGAAGAGCGGCACCGCCAGCGTGGTGTGC CTGCTGAACAACTTCTACCCCCGGGAGGCC AAGGTGCAGTGGAAGGTGGACAACGCCCTG CAGAGCGGCAACAGCCAGGAGAGCGTCACC GAGCAGGACAGCAAGGACTCCACCTACAGC CTGAGCAGCACCCTGACCCTGAGCAAGGCC GACTACGAGAAGCATAAGGTGTACGCCTGC |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

GAGGTGACCCACCAGGGCCTGTCCAGCCCC
GTGACCAAGAGCTTCAACAGGGGCGAGTGC

BAP049 HC

| | | |
|---|---|---|
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAAC TTCGATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |

BAP049 LC

| | | |
|---|---|---|
| SEQ ID NO: 113 (Kabat) | LCDR1 | AAGTCCAGTCAGAGTCTGTTAGACAGTGGA AATCAAAAGAACTTCTTGACC |
| SEQ ID NO: 114 (Kabat) | LCDR2 | TGGGCATCCACTAGGGAATCT |
| SEQ ID NO: 115 (Kabat) | LCDR3 | CAGAATGATTATAGTTATCCGTGCACG |
| SEQ ID NO: 116 (Chothia) | LCDR1 | AGTCAGAGTCTGTTAGACAGTGGAAATCAA AAGAACTTC |
| SEQ ID NO: 117 (Chothia) | LCDR2 | TGGGCATCC |
| SEQ ID NO: 118 (Chothia) | LCDR3 | GATTATAGTTATCCGTGC |

BAP049-chi HC

| | | |
|---|---|---|
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAAC TTCGATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

| SEQ ID NO: 110 (Chothia) | HCDR3 | TGGACTACTGGGACGGGAGCTTAT |
|---|---|---|

BAP049-chi LC

| SEQ ID NO: 113 (Kabat) | LCDR1 | AAGTCCAGTCAGAGTCTGTTAGACAGTGGA AATCAAAAGAACTTCTTGACC |
|---|---|---|
| SEQ ID NO: 114 (Kabat) | LCDR2 | TGGGCATCCACTAGGGAATCT |
| SEQ ID NO: 115 (Kabat) | LCDR3 | CAGAATGATTATAGTTATCCGTGCACG |
| SEQ ID NO: 116 (Chothia) | LCDR1 | AGTCAGAGTCTGTTAGACAGTGGAAATCAA AAGAACTTC |
| SEQ ID NO: 117 (Chothia) | LCDR2 | TGGGCATCC |
| SEQ ID NO: 118 (Chothia) | LCDR3 | GATTATAGTTATCCGTGC |

BAP049-chi Y HC

| SEQ ID NO: 108 (Kabat) | HCDR1 | ACTTACTGGATGCAC |
|---|---|---|
| SEQ ID NO: 109 (Kabat) | HCDR2 | AATATTTATCCTGGTACTGGTGGTTCTAAC TTCGATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |

BAP049-chi Y LC

| SEQ ID NO: 113 (Kabat) | LCDR1 | AAGTCCAGTCAGAGTCTGTTAGACAGTGGA AATCAAAAGAACTTCTTGACC |
|---|---|---|
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAA AAGAACTTC |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

| SEQ ID NO: 117 (Chothia) | LCDR2 | TGGGCATCC |
|---|---|---|
| SEQ ID NO: 120 (Chothia) | LCDR3 | GATTATAGTTATCCGTAC |

BAP049-hum01 HC

| SEQ ID NO: 108 (Kabat) | HCDR1 | ACTTACTGGATGCAC |
|---|---|---|
| SEQ ID NO: 109 (Kabat) | HCDR2 | AATATTTATCCTGGTACTGGTGGTTCTAAC TTCGATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |

BAP049-hum01 LC

| SEQ ID NO: 113 (Kabat) | LCDR1 | AAGTCCAGTCAGAGTCTGTTAGACAGTGGA AATCAAAAGAACTTCTTGACC |
|---|---|---|
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAA AAGAACTTC |
| SEQ ID NO: 117 (Chothia) | LCDR2 | TGGGCATCC |
| SEQ ID NO: 120 (Chothia) | LCDR3 | GATTATAGTTATCCGTAC |

BAP049-hum02 HC

| SEQ ID NO: 108 (Kabat) | HCDR1 | ACTTACTGGATGCAC |
|---|---|---|
| SEQ ID NO: 109 (Kabat) | HCDR2 | AATATTTATCCTGGTACTGGTGGTTCTAAC TTCGATGAGAAGTTCAAGAAC |
| SEQ ID NO: 110 (Kabat) | HCDR3 | TGGACTACTGGGACGGGAGCTTAT |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |

BAP049-hum02
LC

| SEQ ID NO: 113 (Kabat) | LCDR1 | AAGTCCAGTCAGAGTCTGTTAGACAGTGGA AATCAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAA AAGAACTTC |
| SEQ ID NO: 117 (Chothia) | LCDR2 | TGGGCATCC |
| SEQ ID NO: 120 (Chothia) | LCDR3 | GATTATAGTTATCCGTAC |

BAP049-hum03
HC

| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAAC TTCGATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |

BAP049-hum03
LC

| SEQ ID NO: 113 (Kabat) | LCDR1 | AAGTCCAGTCAGAGTCTGTTAGACAGTGGA AATCAAAAGAACTTCTTGACC |
| SEQ ID NO: 114 (Kabat) | LCDR2 | TGGGCATCCACTAGGGAATCT |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAA AAGAACTTC |
| SEQ ID NO: 117 (Chothia) | LCDR2 | TGGGCATCC |
| SEQ ID NO: 120 (Chothia) | LCDR3 | GATTATAGTTATCCGTAC |

BAP049-hum04
HC

| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAAC TTCGATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |

BAP049-hum04
LC

| SEQ ID NO: 113 (Kabat) | LCDR1 | AAGTCCAGTCAGAGTCTGTTAGACAGTGGA AATCAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAA AAGAACTTC |
| SEQ ID NO: 117 (Chothia) | LCDR2 | TGGGCATCC |
| SEQ ID NO: 120 (Chothia) | LCDR3 | GATTATAGTTATCCGTAC |

BAP049-hum05
HC

| SEQ ID NO: 108 (Kabat) | HCDR1 | ACTTACTGGATGCAC |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

| | | |
|---|---|---|
| SEQ ID NO: 109 (Kabat) | HCDR2 | AATATTTATCCTGGTACTGGTGGTTCTAAC TTCGATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |

BAP049-hum05
LC

| | | |
|---|---|---|
| SEQ ID NO: 113 (Kabat) | LCDR1 | AAGTCCAGTCAGAGTCTGTTAGACAGTGGA AATCAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAA AAGAACTTC |
| SEQ ID NO: 117 (Chothia) | LCDR2 | TGGGCATCC |
| SEQ ID NO: 120 (Chothia) | LCDR3 | GATTATAGTTATCCGTAC |

BAP049-hum06
HC

| | | |
|---|---|---|
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAAC TTCGATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

BAP049-hum06
LC

| | | |
|---|---|---|
| SEQ ID NO: 113 (Kabat) | LCDR1 | AAGTCCAGTCAGAGTCTGTTAGACAGTGGA AATCAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAA AAGAACTTC |
| SEQ ID NO: 117 (Chothia) | LCDR2 | TGGGCATCC |
| SEQ ID NO: 120 (Chothia) | LCDR3 | GATTATAGTTATCCGTAC |

BAP049-hum07
HC

| | | |
|---|---|---|
| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAAC TTCGATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |

BAP049-hum07
LC

| | | |
|---|---|---|
| SEQ ID NO: 113 (Kabat) | LCDR1 | AAGTCCAGTCAGAGTCTGTTAGACAGTGGA AATCAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAA AAGAACTTC |
| SEQ ID NO: 117 (Chothia) | LCDR2 | TGGGCATCC |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

| SEQ ID NO: 120 (Chothia) | LCDR3 | GATTATAGTTATCCGTAC |
|---|---|---|

BAP049-hum08
HC

| SEQ ID NO: 108 (Kabat) | HCDR1 | ACTTACTGGATGCAC |
|---|---|---|
| SEQ ID NO: 109 (Kabat) | HCDR2 | AATATTTATCCTGGTACTGGTGGTTCTAAC TTCGATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |

BAP049-hum08
LC

| SEQ ID NO: 113 (Kabat) | LCDR1 | AAGTCCAGTCAGAGTCTGTTAGACAGTGGA AATCAAAAGAACTTCTTGACC |
|---|---|---|
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAA AAGAACTTC |
| SEQ ID NO: 117 (Chothia) | LCDR2 | TGGGCATCC |
| SEQ ID NO: 120 (Chothia) | LCDR3 | GATTATAGTTATCCGTAC |

BAP049-hum09
HC

| SEQ ID NO: 108 (Kabat) | HCDR1 | ACTTACTGGATGCAC |
|---|---|---|
| SEQ ID NO: 109 (Kabat) | HCDR2 | AATATTTATCCTGGTACTGGTGGTTCTAAC TTCGATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

| SEQ ID NO: 112 (Chothia) | HCDR2 | TATCCTGGTACTGGTGGT |
|---|---|---|
| SEQ ID NO: 110 (Chothia) | HCDR3 | TGGACTACTGGGACGGGAGCTTAT |

BAP049-hum09
LC

| SEQ ID NO: 113 (Kabat) | LCDR1 | AAGTCCAGTCAGAGTCTGTTAGACAGTGGA AATCAAAAGAACTTCTTGACC |
|---|---|---|
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAA AAGAACTTC |
| SEQ ID NO: 117 (Chothia) | LCDR2 | TGGGCATCC |
| SEQ ID NO: 120 (Chothia) | LCDR3 | GATTATAGTTATCCGTAC |

BAP049-hum10
HC

| SEQ ID NO: 108 (Kabat) | HCDR1 | ACTTACTGGATGCAC |
|---|---|---|
| SEQ ID NO: 109 (Kabat) | HCDR2 | AATATTTATCCTGGTACTGGTGGTTCTAAC TTCGATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |

BAP049-hum10
LC

| SEQ ID NO: 113 (Kabat) | LCDR1 | AAGTCCAGTCAGAGTCTGTTAGACAGTGGA AATCAAAAGAACTTCTTGACC |
|---|---|---|
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

| SEQ ID NO: 116 (Chothia) | LCDR1 | AGTCAGAGTCTGTTAGACAGTGGAAATCAA AAGAACTTC |
| SEQ ID NO: 117 (Chothia) | LCDR2 | TGGGCATCC |
| SEQ ID NO: 120 (Chothia) | LCDR3 | GATTATAGTTATCCGTAC |

BAP049-hum11 HC

| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAAC TTCGATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |

BAP049-hum11 LC

| SEQ ID NO: 113 (Kabat) | LCDR1 | AAGTCCAGTCAGAGTCTGTTAGACAGTGGA AATCAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAA AAGAACTTC |
| SEQ ID NO: 117 (Chothia) | LCDR2 | TGGGCATCC |
| SEQ ID NO: 120 (Chothia) | LCDR3 | GATTATAGTTATCCGTAC |

BAP049-hum12 HC

| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAAC TTCGATGAGAAGTTCAAGAAC |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |

BAP049-hum12 LC

| SEQ ID NO: 113 (Kabat) | LCDR1 | AAGTCCAGTCAGAGTCTGTTAGACAGTGGA AATCAAAAGAACTTCTTGACC |
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAA AAGAACTTC |
| SEQ ID NO: 117 (Chothia) | LCDR2 | TGGGCATCC |
| SEQ ID NO: 120 (Chothia) | LCDR3 | GATTATAGTTATCCGTAC |

BAP049-hum13 HC

| SEQ ID NO: 108 (Kabat) | HCDR1 | ACTTACTGGATGCAC |
| SEQ ID NO: 109 (Kabat) | HCDR2 | AATATTTATCCTGGTACTGGTGGTTCTAAC TTCGATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 110 (Chothia) | HCDR3 | TGGACTACTGGGACGGGAGCTTAT |

BAP049-hum13 LC

| SEQ ID NO: 121 (Kabat) | LCDR1 | AAGTCCAGTCAGAGTCTGTTAGACAGTGGA AATCAAAAGAACTTCTTAACC |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

| SEQ ID NO: 114 (Kabat) | LCDR2 | TGGGCATCCACTAGGGAATCT |
|---|---|---|
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAA AAGAACTTC |
| SEQ ID NO: 117 (Chothia) | LCDR2 | TGGGCATCC |
| SEQ ID NO: 120 (Chothia) | LCDR3 | GATTATAGTTATCCGTAC |

BAP049-hum14
HC

| SEQ ID NO: 108 (Kabat) | HCDR1 | ACTTACTGGATGCAC |
|---|---|---|
| SEQ ID NO: 109 (Kabat) | HCDR2 | AATATTTATCCTGGTACTGGTGGTTCTAAC TTCGATGAGAAGTTCAAGAAC |
| SEQ ID NO: 223 (Kabat) | HCDR3 | TGGACTACTGGGACGGGAGCTTAC |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 223 (Chothia) | HCDR3 | TGGACTACTGGGACGGGAGCTTAC |

BAP049-hum14
LC

| SEQ ID NO: 113 (Kabat) | LCDR1 | AAGTCCAGTCAGAGTCTGTTAGACAGTGGA AATCAAAAGAACTTCTTGACC |
|---|---|---|
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAA AAGAACTTC |
| SEQ ID NO: 117 (Chothia) | LCDR2 | TGGGCATCC |
| SEQ ID NO: 120 (Chothia) | LCDR3 | GATTATAGTTATCCGTAC |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

BAP049-hum15
HC

| SEQ ID NO: 108 (Kabat) | HCDR1 | ACTTACTGGATGCAC |
|---|---|---|
| SEQ ID NO: 109 (Kabat) | HCDR2 | AATATTTATCCTGGTACTGGTGGTTCTAAC TTCGATGAGAAGTTCAAGAAC |
| SEQ ID NO: 223 (Kabat) | HCDR3 | TGGACTACTGGGACGGGAGCTTAC |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |
| SEQ ID NO: 223 (Chothia) | HCDR3 | TGGACTACTGGGACGGGAGCTTAC |

BAP049-hum15
LC

| SEQ ID NO: 113 (Kabat) | LCDR1 | AAGTCCAGTCAGAGTCTGTTAGACAGTGGA AATCAAAAGAACTTCTTGACC |
|---|---|---|
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAA AAGAACTTC |
| SEQ ID NO: 117 (Chothia) | LCDR2 | TGGGCATCC |
| SEQ ID NO: 120 (Chothia) | LCDR3 | GATTATAGTTATCCGTAC |

BAP049-hum16
HC

| SEQ ID NO: 108 (Kabat) | HCDR1 | ACTTACTGGATGCAC |
|---|---|---|
| SEQ ID NO: 109 (Kabat) | HCDR2 | AATATTTATCCTGGTACTGGTGGTTCTAAC TTCGATGAGAAGTTCAAGAAC |
| SEQ ID NO: 110 (Kabat) | HCDR3 | TGGACTACTGGGACGGGAGCTTAT |
| SEQ ID NO: 111 (Chothia) | HCDR1 | GGCTACACATTCACCACTTAC |
| SEQ ID NO: 112 (Chothia) | HCDR2 | TATCCTGGTACTGGTGGT |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

| SEQ ID NO: 110 (Chothia) | HCDR3 | TGGACTACTGGGACGGGAGCTTAT |
|---|---|---|

BAP049-hum16 LC

| SEQ ID NO: 113 (Kabat) | LCDR1 | AAGTCCAGTCAGAGTCTGTTAGACAGTGGA AATCAAAAGAACTTCTTGACC |
|---|---|---|
| SEQ ID NO: 114 (Kabat) | LCDR2 | TGGGCATCCACTAGGGAATCT |
| SEQ ID NO: 119 (Kabat) | LCDR3 | CAGAATGATTATAGTTATCCGTACACG |
| SEQ ID NO: 116 (Chothia) | LCDR1 | AGTCAGAGTCTGTTAGACAGTGGAAATCAA AAGAACTTC |
| SEQ ID NO: 117 (Chothia) | LCDR2 | TGGGCATCC |
| SEQ ID NO: 120 (Chothia) | LCDR3 | GATTATAGTTATCCGTAC |

BAP049-Clone-A HC

| SEQ ID NO: 122 (Kabat) | HCDR1 | ACCTACTGGATGCAC |
|---|---|---|
| SEQ ID NO: 123 (Kabat) | HCDR2 | AACATCTATCCTGGCACCGGCGGCTCCAAC TTCGACGAGAAGTTCAAGAAC |
| SEQ ID NO: 124 (Kabat) | HCDR3 | TGGACAACCGGCACAGGCGCTTAT |
| SEQ ID NO: 125 (Chothia) | HCDR1 | GGCTACACCTTCACCACCTAC |
| SEQ ID NO: 126 (Chothia) | HCDR2 | TATCCTGGCACCGGCGGC |
| SEQ ID NO: 124 (Chothia) | HCDR3 | TGGACAACCGGCACAGGCGCTTAT |

BAP049-Clone-A LC

| SEQ ID NO: 127 (Kabat) | LCDR1 | AAGTCCTCCCAGTCCCTGCTGGACTCCGGC AACCAGAAGAACTTCCTGACC |
|---|---|---|
| SEQ ID NO: 128 (Kabat) | LCDR2 | TGGGCCTCCACCCGGGAATCT |
| SEQ ID NO: 129 (Kabat) | LCDR3 | CAGAACGACTACTCCTACCCCTACACC |
| SEQ ID NO: 130 (Chothia) | LCDR1 | TCCCAGTCCCTGCTGGACTCCGGCAACCAG AAGAACTTC |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

| SEQ ID NO: 131 (Chothia) | LCDR2 | TGGGCCTCC |
|---|---|---|
| SEQ ID NO: 132 (Chothia) | LCDR3 | GACTACTCCTACCCCTAC |

BAP049-Clone-B HC

| SEQ ID NO: 133 (Kabat) | HCDR1 | ACCTACTGGATGCAC |
|---|---|---|
| SEQ ID NO: 134 (Kabat) | HCDR2 | AATATCTACCCCGGCACCGGCGGCTCTAAC TTCGACGAGAAGTTTAAGAAT |
| SEQ ID NO: 135 (Kabat) | HCDR3 | TGGACTACCGGCACAGGCGCCTAC |
| SEQ ID NO: 136 (Chothia) | HCDR1 | GGCTACACCTTCACTACCTAC |
| SEQ ID NO: 137 (Chothia) | HCDR2 | TACCCCGGCACCGGCGGC |
| SEQ ID NO: 135 (Chothia) | HCDR3 | TGGACTACCGGCACAGGCGCCTAC |

BAP049-Clone-B LC

| SEQ ID NO: 138 (Kabat) | LCDR1 | AAATCTAGTCAGTCACTGCTGGATAGCGGT AATCAGAAGAACTTCCTGACC |
|---|---|---|
| SEQ ID NO: 139 (Kabat) | LCDR2 | TGGGCCTCTACTAGAGAATCA |
| SEQ ID NO: 140 (Kabat) | LCDR3 | CAGAACGACTATAGCTACCCCTACACC |
| SEQ ID NO: 141 (Chothia) | LCDR1 | AGTCAGTCACTGCTGGATAGCGGTAATCAG AAGAACTTC |
| SEQ ID NO: 142 (Chothia) | LCDR2 | TGGGCCTCT |
| SEQ ID NO: 143 (Chothia) | LCDR3 | GACTATAGCTACCCCTAC |

BAP049-Clone-C HC

| SEQ ID NO: 122 (Kabat) | HCDR1 | ACCTACTGGATGCAC |
|---|---|---|
| SEQ ID NO: 123 (Kabat) | HCDR2 | AACATCTATCCTGGCACCGGCGGCTCCAAC TTCGACGAGAAGTTCAAGAAC |
| SEQ ID NO: 124 (Kabat) | HCDR3 | TGGACAACCGGCACAGGCGCTTAT |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

| SEQ ID NO: 125 (Chothia) | HCDR1 | GGCTACACCTTCACCACCTAC |
|---|---|---|
| SEQ ID NO: 126 (Chothia) | HCDR2 | TATCCTGGCACCGGCGGC |
| SEQ ID NO: 124 (Chothia) | HCDR3 | TGGACAACCGGCACAGGCGCTTAT |

BAP049-Clone-
C LC

| SEQ ID NO: 127 (Kabat) | LCDR1 | AAGTCCTCCCAGTCCCTGCTGGACTCCGGC AACCAGAAGAACTTCCTGACC |
|---|---|---|
| SEQ ID NO: 128 (Kabat) | LCDR2 | TGGGCCTCCACCCGGGAATCT |
| SEQ ID NO: 129 (Kabat) | LCDR3 | CAGAACGACTACTCCTACCCCTACACC |
| SEQ ID NO: 130 (Chothia) | LCDR1 | TCCCAGTCCCTGCTGGACTCCGGCAACCAG AAGAACTTC |
| SEQ ID NO: 131 (Chothia) | LCDR2 | TGGGCCTCC |
| SEQ ID NO: 132 (Chothia) | LCDR3 | GACTACTCCTACCCCTAC |

BAP049-Clone-
D HC

| SEQ ID NO: 122 (Kabat) | HCDR1 | ACCTACTGGATGCAC |
|---|---|---|
| SEQ ID NO: 144 (Kabat) | HCDR2 | AACATCTACCCTGGCACCGGCGGCTCCAAC TTCGACGAGAAGTTCAAGAAC |
| SEQ ID NO: 145 (Kabat) | HCDR3 | TGGACCACCGGAACCGGCGCCTAT |
| SEQ ID NO: 125 (Chothia) | HCDR1 | GGCTACACCTTCACCACCTAC |
| SEQ ID NO: 146 (Chothia) | HCDR2 | TACCCTGGCACCGGCGGC |
| SEQ ID NO: 145 (Chothia) | HCDR3 | TGGACCACCGGAACCGGCGCCTAT |

BAP049-Clone-
D LC

| SEQ ID NO: 127 (Kabat) | LCDR1 | AAGTCCTCCCAGTCCCTGCTGGACTCCGGC AACCAGAAGAACTTCCTGACC |
|---|---|---|
| SEQ ID NO: 128 (Kabat) | LCDR2 | TGGGCCTCCACCCGGGAATCT |

TABLE 1-continued

Amino acid and nucleotide sequences for murine,
chimeric and humanized antibody molecules. The
antibody molecules include murine mAb BAP049,
chimeric mAbs BAP049-chi and BAP049-chi-Y, and
humanized mAbs BAP049-hum01 to BAP049-hum16 and
BAP049-Clone-A to BAP049-Clone-E. The amino
acid and nucleotide sequences of the heavy and
light chain CDRs, the heavy and light chain
variable regions, and the heavy and light
chains are shown.

| SEQ ID NO: 129 (Kabat) | LCDR3 | CAGAACGACTACTCCTACCCCTACACC |
|---|---|---|
| SEQ ID NO: 130 (Chothia) | LCDR1 | TCCCAGTCCCTGCTGGACTCCGGCAACCAG AAGAACTTC |
| SEQ ID NO: 131 (Chothia) | LCDR2 | TGGGCCTCC |
| SEQ ID NO: 132 (Chothia) | LCDR3 | GACTACTCCTACCCCTAC |

BAP049-Clone-
E HC

| SEQ ID NO: 133 (Kabat) | HCDR1 | ACCTACTGGATGCAC |
|---|---|---|
| SEQ ID NO: 134 (Kabat) | HCDR2 | AATATCTACCCCGGCACCGGCGGCTCTAAC TTCGACGAGAAGTTTAAGAAT |
| SEQ ID NO: 135 (Kabat) | HCDR3 | TGGACTACCGGCACAGGCGCCTAC |
| SEQ ID NO: 136 (Chothia) | HCDR1 | GGCTACACCTTCACTACCTAC |
| SEQ ID NO: 137 (Chothia) | HCDR2 | TACCCCGGCACCGGCGGC |
| SEQ ID NO: 135 (Chothia) | HCDR3 | TGGACTACCGGCACAGGCGCCTAC |

BAP049-Clone-
E LC

| SEQ ID NO: 138 (Kabat) | LCDR1 | AAATCTAGTCAGTCACTGCTGGATAGCGGT AATCAGAAGAACTTCCTGACC |
|---|---|---|
| SEQ ID NO: 139 (Kabat) | LCDR2 | TGGGCCTCTACTAGAGAATCA |
| SEQ ID NO: 140 (Kabat) | LCDR3 | CAGAACGACTATAGCTACCCCTACACC |
| SEQ ID NO: 141 (Chothia) | LCDR1 | AGTCAGTCACTGCTGGATAGCGGTAATCAG AAGAACTTC |
| SEQ ID NO: 142 (Chothia) | LCDR2 | TGGGCCTCT |
| SEQ ID NO: 143 (Chothia) | LCDR3 | GACTATAGCTACCCCTAC |

TABLE 2

Amino acid and nucleotide sequences of the heavy and light chain
framework regions for humanized mAbs BAP049-hum01 to BAP049-hum16
and BAP049-Clone-A to BAP049-Clone-E

| | Amino Acid Sequence | Nucleotide Sequence |
|---|---|---|
| VHFW1 (type a) | EVQLVQSGAEVKKPGESLRISCKGS (SEQ ID NO: 147) | GAAGTGCAGCTGGTGCAGTCTGGAGCAGAGGTGAA AAAGCCCGGGGAGTCTCTGAGGATCTCCTGTAAGG GTTCT (SEQ ID NO: 148) GAAGTGCAGCTGGTGCAGTCTGGCGCCGAAGTGAA GAAGCCTGGCGAGTCCCTGCGGATCTCCTGCAAGG GCTCT (SEQ ID NO: 149) GAGGTGCAGCTGGTGCAGTCAGGCGCCGAAGTGAA GAAGCCCGGCGAGTCACTGAGAATTAGCTGTAAAG GTTCA (SEQ ID NO: 150) |
| VHFW1 (type b) | QVQLVQSGAEVKKPGASVKVSCKAS (SEQ ID NO: 151) | CAGGTTCAGCTGGTGCAGTCTGGAGCTGAGGTGAA GAAGCCTGGGGCCTCAGTGAAGGTCTCCTGCAAGG CTTCT (SEQ ID NO: 152) |
| VHFW2 (type a) | WVRQATGQGLEWMG (SEQ ID NO: 153) | TGGGTGCGACAGGCCACTGGACAAGGGCTTGAGTG GATGGGT (SEQ ID NO: 154) TGGGTGCGACAGGCTACCGGCCAGGGCCTGGAATG GATGGGC (SEQ ID NO: 155) TGGGTCCGCCAGGCTACCGGTCAAGGCCTCGAGTG GATGGGT (SEQ ID NO: 156) |
| VHFW2 (type b) | WIRQSPSRGLEWLG (SEQ ID NO: 157) | TGGATCAGGCAGTCCCCATCGAGAGGCCTTGAGTG GCTGGGT (SEQ ID NO: 158) TGGATCCGGCAGTCCCCCTCTAGGGGCCTGGAATG GCTGGGC (SEQ ID NO: 159) |
| VHFW2 (type c) | WVRQAPGQGLEWMG (SEQ ID NO: 160) | TGGGTGCGACAGGCCCCTGGACAAGGGCTTGAGTG GATGGGT (SEQ ID NO: 161) |
| VHFW3 (type a) | RVTITADKSTSTAYMELSSLRSEDT AVYYCTR (SEQ ID NO: 162) | AGAGTCACGATTACCGCGGACAAATCCACGAGCAC AGCCTACATGGAGCTGAGCAGCCTGAGATCTGAGG ACACGGCCGTGTATTACTGTACAAGA (SEQ ID NO: 163) AGAGTGACCATCACCGCCGACAAGTCCACCTCCAC CGCCTACATGGAACTGTCCTCCCTGAGATCCGAGG ACACCGCCGTGTACTACTGCACCCGG (SEQ ID NO: 164) AGAGTGACTATCACCGCCGATAAGTCTACTAGCAC CGCCTATATGGAACTGTCTAGCCTGAGATCAGAGG ACACCGCCGTCTACTACTGCACTAGG (SEQ ID NO: 165) |
| VHFW3 (type b) | RFTISRDNSKNTLYLQMNSLRAEDT AVYYCTR (SEQ ID NO: 166) | AGATTCACCATCTCCAGAGACAATTCCAAGAACAC GCTGTATCTTCAAATGAACAGCCTGAGAGCCGAGG ACACGGCCGTGTATTACTGTACAAGA (SEQ ID NO: 167) AGGTTCACCATCTCCCGGGACAACTCCAAGAACAC CCTGTACCTGCAGATGAACTCCCTGCGGGCCGAGG ACACCGCCGTGTACTACTGTACCAGA (SEQ ID NO: 168) |
| VHFW4 | WGQGTTVTVSS (SEQ ID NO: 169) | TGGGGCCAGGGCACCACCGTGACCGTGTCCTCC (SEQ ID NO: 170) TGGGGCCAGGGCACCACAGTGACCGTGTCCTCT (SEQ ID NO: 171) TGGGGTCAAGGCACTACCGTGACCGTGTCTAGC (SEQ ID NO: 172) TGGGGCCAGGGCACAACAGTGACCGTGTCCTCC (SEQ ID NO: 173) |
| VLFW1 (type a) | EIVLTQSPDFQSVTPKEKVTITC (SEQ ID NO: 174) | GAAATTGTGCTGACTCAGTCTCCAGACTTTCAGTC TGTGACTCCAAAGGAGAAAGTCACCATCACCTGC (SEQ ID NO: 175) GAGATCGTGCTGACCCAGTCCCCCGACTTCCAGTC CGTGACCCCCAAAGAAAAAGTGACCATCACATGC (SEQ ID NO: 176) |
| VLFW1 (type b) | EIVLTQSPATLSLSPGERATLSC (SEQ ID NO: 177) | GAAATTGTGTTGACACAGTCTCCAGCCACCCTGTC TTTGTCTCCAGGGGAAAGAGCCACCCTCTCCTGC (SEQ ID NO: 178) GAGATCGTGCTGACCCAGTCCCCTGCCACCCTGTC ACTGTCTCCAGGCGAGAGAGCTACCCTGTCCTGC (SEQ ID NO: 179) GAGATCGTCCTGACTCAGTCACCCGCTACCCTGAG |

TABLE 2-continued

Amino acid and nucleotide sequences of the heavy and light chain
framework regions for humanized mAbs BAP049-hum01 to BAP049-hum16
and BAP049-Clone-A to BAP049-Clone-E

| | Amino Acid Sequence | Nucleotide Sequence |
|---|---|---|
| | | CCTGAGCCCTGGCGAGCGGGCTACACTGAGCTGT (SEQ ID NO: 180) |
| VLFW1 (type c) | DIVMTQTPLSLPVTPGEPASISC (SEQ ID NO: 181) | GATATTGTGATGACCCAGACTCCACTCTCCCTGCC CGTCACCCCTGGAGAGCCGGCCTCCATCTCCTGC (SEQ ID NO: 182) |
| VLFW1 (type d) | DVVMTQSPLSLPVTLGQPASISC (SEQ ID NO: 183) | GATGTTGTGATGACTCAGTCTCCACTCTCCCTGCC CGTCACCCTTGGACAGCCGGCCTCCATCTCCTGC (SEQ ID NO: 184) |
| VLFW1 (type e) | DIQMTQSPSSLSASVGDRVTITC (SEQ ID NO: 185) | GACATCCAGATGACCCAGTCTCCATCCTCCCTGTC TGCATCTGTAGGAGACAGAGTCACCATCACTTGC (SEQ ID NO: 186) |
| VLFW2 (type a) | WYQQKPGQAPRLLIY (SEQ ID NO: 187) | TGGTACCAGCAGAAACCTGGCCAGGCTCCCAGGCT CCTCATCTAT (SEQ ID NO: 188) TGGTATCAGCAGAAGCCCGGCCAGGCCCCCAGACT GCTGATCTAC (SEQ ID NO: 189) TGGTATCAGCAGAAGCCCGGTCAAGCCCCTAGACT GCTGATCTAC (SEQ ID NO: 190) |
| VLFW2 (type b) | WYQQKPGKAPKLLIY (SEQ ID NO: 191) | TGGTATCAGCAGAAACCAGGGAAAGCTCCTAAGCT CCTGATCTAT (SEQ ID NO: 192) TGGTATCAGCAGAAGCCCGGTAAAGCCCCTAAGCT GCTGATCTAC (SEQ ID NO: 193) |
| VLFW2 (type c) | WYLQKPGQSPQLLIY (SEQ ID NO: 194) | TGGTACCTGCAGAAGCCAGGGCAGTCTCCACAGCT CCTGATCTAT (SEQ ID NO: 195) |
| VLFW3 (type a) | GVPSRFSGSGSGTDFTFTISSLEAE DAATYYC (SEQ ID NO: 196) | GGGGTCCCCTCGAGGTTCAGTGGCAGTGGATCTGG GACAGATTTCACCTTTACCATCAGTAGCCTGGAAG CTGAAGATGCTGCAACATATTACTGT (SEQ ID NO: 197) GGCGTGCCCTCTAGATTCTCCGGCTCCGGCTCTGG CACCGACTTTACCTTCACCATCTCCAGCCTGGAAG CCGAGGACGCCGCCACCTACTACTGC (SEQ ID NO: 198) GGCGTGCCCTCTAGGTTTAGCGGTAGCGGTAGTGG CACCGACTTCACCTTCACTATCTCTAGCCTGGAAG CCGAGGACGCCGCTACCTACTACTGT (SEQ ID NO: 199) |
| VLFW3 (type b) | GIPPRFSGSGYGTDFTLTINNIESE DAAYYFC (SEQ ID NO: 200) | GGGATCCCACCTCGATTCAGTGGCAGCGGGTATGG AACAGATTTTACCCTCACAATTAATAACATAGAAT CTGAGGATGCTGCATATTACTTCTGT (SEQ ID NO: 201) |
| VLFW3 (type c) | GVPSRFSGSGSGTEFTLTISSLQPD DFATYYC (SEQ ID NO: 202) | GGGGTCCCATCAAGGTTCAGCGGCAGTGGATCTGG GACAGAATTCACTCTCACCATCAGCAGCCTGCAGC CTGATGATTTTGCAACTTATTACTGT (SEQ ID NO: 203) GGCGTGCCCTCTAGATTCTCCGGCTCCGGCTCTGG CACCGAGTTTACCCTGACCATCTCCAGCCTGCAGC CCGACGACTTCGCCACCTACTACTGC (SEQ ID NO: 204) |

TABLE 2-continued

Amino acid and nucleotide sequences of the heavy and light chain
framework regions for humanized mAbs BAP049-hum01 to BAP049-hum16
and BAP049-Clone-A to BAP049-Clone-E

| | Amino Acid Sequence | Nucleotide Sequence |
|---|---|---|
| VLFW3 (type d) | GVPSRFSGSGSGTDFTFTISSLQPE DIATYYC (SEQ ID NO: 205) | GGGGTCCCATCAAGGTTCAGTGGAAGTGGATCTGG GACAGATTTTACTTTCACCATCAGCAGCCTGCAGC CTGAAGATATTGCAACATATTACTGT (SEQ ID NO: 206) GGCGTGCCCTCTAGGTTTAGCGGTAGCGGTAGTGG CACCGACTTCACCTTCACTATCTCTAGCCTGCAGC CCGAGGATATCGCTACCTACTACTGT (SEQ ID NO: 207) |
| VLFW4 | FGQGTKVEIK (SEQ ID NO: 208) | TTCGGCCAAGGGACCAAGGTGGAAATCAAA (SEQ ID NO: 209) TTCGGCCAGGGCACCAAGGTGGAAATCAAG (SEQ ID NO: 210) TTCGGTCAAGGCACTAAGGTCGAGATTAAG (SEQ ID NO: 211) |

TABLE 3

Constant region amino acid sequences of human
IgG heavy chains and human kappa light chain HC  IgG4 (S228P) mutant constant region amino
acid sequence (EU Numbering)
ASTKGPSVFP LAPCSRSTSE STAALGCLVK DYFPEPVTVS
WNSGALTSGV HTFPAVLQSS GLYSLSSVVT VPSSSLGTKT
YTCNVDHKPS NTKVDKRVES KYGPPCPPCP APEFLGGPSV
FLFPPKPKDT LMISRTPEVT CVVVDVSQED PEVQFNWYVD
GVEVHNAKTK PREEQFNSTY RVVSVLTVLH QDWLNGKEYK
CKVSNKGLPS SIEKTISKAK GQPREPQVYT LPPSQEEMTK
NQVSLTCLVK GFYPSDIAVE WESNGQPENN YKTTPPVLDS
DGSFFLYSRL TVDKSRWQEG NVFSCSVMHE ALHNHYTQKS
LSLSLGK (SEQ ID NO: 212)

LC  Human kappa constant region amino acid
sequence
RTVAAPSVFI FPPSDEQLKS GTASVVCLLN NFYPREAKVQ
WKVDNALQSG NSQESVTEQD SKDSTYSLSS TLTLSKADYE
KHKVYACEVT HQGLSSPVTK SFNRGEC
(SEQ ID NO: 213)

HC  IgG4 (S228P) mutant constant region amino
acid sequence lacing C-terminal lysine
(K) (EU Numbering)
ASTKGPSVFP LAPCSRSTSE STAALGCLVK DYFPEPVTVS
WNSGALTSGV HTFPAVLQSS GLYSLSSVVT VPSSSLGTKT
YTCNVDHKPS NTKVDKRVES KYGPPCPPCP APEFLGGPSV
FLFPPKPKDT LMISRTPEVT CVVVDVSQED PEVQFNWYVD
CVEVHNAKTK PREEQFNSTY RVVSVLTVLH QDWLNGKEYK
CKVSNKGLPS SIEKTISKAK GQPREPQVYT LPPSQEEMTK
NQVSLTCLVK GFYPSDIAVE WESNGQPENN YKTTPPVLDS
DGSFFLYSRL TVDKSRWQEG NVFSCSVMHE ALHNHYTQKS
LSLSLG (SEQ ID NO: 214)

HC  IgG1 wild type
ASTKGPSVFP LAPSSKSTSG GTAALGCLVK DYFPEPVTVS
WNSGALTSGV HTFPAVLQSS GLYSLSSVVT VPSSSLGTQT
YICNVNHKPS NTKVDKRVEP KSCDKTHTCP PCPAPELLGG
PSVFLFPPKP KDTLMISRTP EVTCVVVDVS HEDPEVKFNW
YVDGVEVHNA KTKPREEQYN STYRVVSVLT VLHQDWLNGK
EYKCKVSNKA LPAPIEKTIS KAKGQPREPQ VYTLPPSREE
MTKNQVSLTC LVKGFYPSDI AVEWESNGQP ENNYKTTPPV
LDSDGSFFLY SKLTVDKSRW QQGNVFSCSV MHEALHNHYT
QKSLSLSPGK (SEQ ID NO: 215)

HC  IgG1 (N297A) mutant constant region amino
acid sequence (EU Numbering)
ASTKGPSVFP LAPSSKSTSG GTAALGCLVK DYFPEPVTVS
WNSGALTSGV HTFPAVLQSS GLYSLSSVVT VPSSSLGTQT
YICNVNHKPS NTKVDKRVEP KSCDKTHTCP PCPAPELLGG
PSVFLFPPKP KDTLMISRTP EVTCVVVDVS HEDPEVKFNW TABLE 3-continued Constant region amino acid sequences of human
IgG heavy chains and human kappa light chain YVDGVEVHNA KTKPREEQYA STYRVVSVLT VLHQDWLNGK
EYKCKVSNKA LPAPIEKTIS KAKGQPREPQ VYTLPPSREE
MTKNQVSLTC LVKGFYPSDI AVEWESNGQP ENNYKTTPPV
LDSDGSFFLY SKLTVDKSRW QQGNVFSCSV MHEALHNHYT
QKSLSLSPGK (SEQ ID NO: 216)

HC  IgG1 (D265A, P329A) mutant constant region
amino acid sequence (EU Numbering)
ASTKGPSVFP LAPSSKSTSG GTAALGCLVK DYFPEPVTVS
WNSGALTSGV HTFPAVLQSS GLYSLSSVVT VPSSSLGTQT
YICNVNHKPS NTKVDKRVEP KSCDKTHTCP PCPAPELLGG
PSVFLFPPKP KDTLMISRTP EVTCVVVAVS HEDPEVKFNW
YVDGVEVHNA KTKPREEQYN STYRVVSVLT VLHQDWLNGK
EYKCKVSNKA LAAPIEKTIS KAKGQPREPQ VYTLPPSREE
MTKNQVSLTC LVKGFYPSDI AVEWESNGQP ENNYKTTPPV
LDSDGSFFLY SKLTVDKSRW QQGNVFSCSV MHEALHNHYT
QKSLSLSPGK (SEQ ID NO: 217)

HC  IgG1 (L234A, L235A) mutant constant region
amino acid sequence (EU Numbering)
ASTKGPSVFP LAPSSKSTSG GTAALGCLVK DYFPEPVTVS
WNSGALTSGV HTFPAVLQSS GLYSLSSVVT VPSSSLGTQT
YICNVNHKPS NTKVDKRVEP KSCDKTHTCP PCPAPEAAGG
PSVFLFPPKP KDTLMISRTP EVTCVVVDVS HEDPEVKFNW
YVDGVEVHNA KTKPREEQYN STYRVVSVLT VLHQDWLNGK
EYKCKVSNKA LPAPIEKTIS KAKGQPREPQ VYTLPPSREE
MTKNQVSLTC LVKGFYPSDI AVEWESNGQP ENNYKTTPPV
LDSDGSFFLY SKLTVDKSRW QQGNVFSCSV MHEALHNHYT
QKSLSLSPGK (SEQ ID NO: 218)

TABLE 4

Amino acid sequences of the heavy and light
chain leader sequences for humanized mAbs
BAP049-Clone-A to BAP049-Clone-E

| BAP049-Clone-A | HC | MEWSWVFLFFLSVTTGVHS (SEQ ID NO: 219) |
|---|---|---|
| | LC | MSVPTQVLGLLLLWLTDARC (SEQ ID NO: 220) |
| BAP049-Clone-B | HC | MAWVWTLPFLMAAAQSVQA (SEQ ID NO: 221) |
| | LC | MSVLTQVLALLLLWLTGTRC (SEQ ID NO: 222) |

TABLE 4-continued

Amino acid sequences of the heavy and light
chain leader sequences for humanized mAbs
BAP049-Clone-A to BAP049-Clone-E

| BAP049-Clone-C | HC | MEWSWVFLFFLSVTTGVHS (SEQ ID NO: 219) |
| | LC | MSVPTQVLGLLLLWLTDARC (SEQ ID NO: 220) |
| BAP049-Clone-D | HC | MEWSWVFLFFLSVTTGVHS (SEQ ID NO: 219) |

TABLE 4-continued

Amino acid sequences of the heavy and light
chain leader sequences for humanized mAbs
BAP049-Clone-A to BAP049-Clone-E

| | LC | MSVPTQVLGLLLLWLTDARC (SEQ ID NO: 220) |
| BAP049-Clone-E | HC | MAWVWTLPFLMAAAQSVQA (SEQ ID NO: 221) |
| | LC | MSVLTQVLALLLLWLTGTRC (SEQ ID NO: 222) |

TABLE 7

Selected therapeutic agents that can be administered in combination with the anti-PD-1 antibody molecules, e.g.,
as a single agent or in combination with other immunomodulators described herein. Each publication listed in this Table
is herein incorporated by reference in its entirety, including all structural formulae therein.

| Compound Designation | Generic Name Tradename | Compound Structure | Patents/Patent Application Publications |
|---|---|---|---|
| A1 | Sotrastaurin | | EP 1682103 US 2007/142401 WO 2005/039549 |
| A2 | Nilotinib HCl monohydrate TASIGNA ® | HCl•H₂O | WO 2004/005281 U.S. Pat. No. 7,169,791 |
| A3 | | | WO 2010/060937 WO 2004/072051 EP 1611112 U.S. Pat. No. 8,450,310 |

TABLE 7-continued

Selected therapeutic agents that can be administered in combination with the anti-PD-1 antibody molecules, e.g.,
as a single agent or in combination with other immunomodulators described herein. Each publication listed in this Table
is herein incorporated by reference in its entirety, including all structural formulae therein.

| Compound Designation | Generic Name Tradename | Compound Structure | Patents/Patent Application Publications |
|---|---|---|---|
| A4 | Dactolisib | | WO 2006/122806 |
| A5 | | | U.S. Pat. No. 8,552,002 |
| A6 | Buparlisib | | WO 2007/084786 |

TABLE 7-continued

Selected therapeutic agents that can be administered in combination with the anti-PD-1 antibody molecules, e.g.,
as a single agent or in combination with other immunomodulators described herein. Each publication listed in this Table
is herein incorporated by reference in its entirety, including all structural formulae therein.

| Compound Designation | Generic Name Tradename | Compound Structure | Patents/Patent Application Publications |
|---|---|---|---|
| A7 | | | WO 2009/141386 US 2010/0105667 |
| A8 | | | WO 2010/029082 |
| A9 | CYP17 inhibitor | | WO 2010/149755 U.S. Pat. No. 8,263,635 B2 EP 2445903 B1 |
| A10 | | | WO 2011/076786 |

TABLE 7-continued

Selected therapeutic agents that can be administered in combination with the anti-PD-1 antibody molecules, e.g.,
as a single agent or in combination with other immunomodulators described herein. Each publication listed in this Table
is herein incorporated by reference in its entirety, including all structural formulae therein.

| Compound Designation | Generic Name Tradename | Compound Structure | Patents/Patent Application Publications |
|---|---|---|---|
| A11 | Deferasirox EXJADE ® | | WO 1997/049395 |
| A12 | Letrozole FEMARA ® | | U.S. Pat. No. 4,978,672 |
| A13 | | | WO 2013/124826 US 2013/0225574 |
| A14 | | | WO 2013/111105 |

TABLE 7-continued

Selected therapeutic agents that can be administered in combination with the anti-PD-1 antibody molecules, e.g.,
as a single agent or in combination with other immunomodulators described herein. Each publication listed in this Table
is herein incorporated by reference in its entirety, including all structural formulae therein.

| Compound Designation | Generic Name Tradename | Compound Structure | Patents/Patent Application Publications |
|---|---|---|---|
| A15 | | | WO 2005/073224 |
| A16 | Imatinib mesylate GLEEVEC ® | | WO 1999/003854 |

Mesylate

TABLE 7-continued

Selected therapeutic agents that can be administered in combination with the anti-PD-1 antibody molecules, e.g.,
as a single agent or in combination with other immunomodulators described herein. Each publication listed in this Table
is herein incorporated by reference in its entirety, including all structural formulae therein.

| Compound Designation | Generic Name Tradename | Compound Structure | Patents/Patent Application Publications |
|---|---|---|---|
| A17 | |  Dihydrochloric salt | EP 2099447 U.S. Pat. No. 7,767,675 U.S. Pat. No. 8,420,645 |
| A18 | Ruxolitinib Phosphate JAKAFI ® |  $H_3PO_4$ | WO 2007/070514 EP 2474545 U.S. Pat. No. 7,598,257 WO 2014/018632 |
| A19 | Panobinostat | | WO 2014/072493 WO 2002/022577 EP 1870399 |
| A20 | Osilodrostat | | WO 2007/024945 |

Selected therapeutic agents that can be administered in combination with the anti-PD-1 antibody molecules, e.g.,
as a single agent or in combination with other immunomodulators described herein. Each publication listed in this Table
is herein incorporated by reference in its entirety, including all structural formulae therein.

| Compound Designation | Generic Name Tradename | Compound Structure | Patents/Patent Application Publications |
|---|---|---|---|
| A21 | | | WO 2008/016893 EP 2051990 U.S. Pat. No. 8,546,336 |
| A22 | Sonidegib phosphate | | WO 2007/131201 EP 2021328 U.S. Pat. No. 8,178,563 |
| A23 | ceritinib ZYKADIA ™ | | WO 2008/073687 U.S. Pat. No. 8,039,479 |

TABLE 7-continued

Selected therapeutic agents that can be administered in combination with the anti-PD-1 antibody molecules, e.g.,
as a single agent or in combination with other immunomodulators described herein. Each publication listed in this Table
is herein incorporated by reference in its entirety, including all structural formulae therein.

| Compound Designation | Generic Name Tradename | Compound Structure | Patents/Patent Application Publications |
|---|---|---|---|
| A24 | | | U.S. Pat. No. 8,415,355<br>U.S. Pat. No. 8,685,980 |
| A25 | | | WO 2010/007120 |
| A26 | | Human monoclonal antibody to PRLR | U.S. Pat. No. 7,867,493 |
| A27 | | | WO 2010/026124<br>EP 2344474<br>US 2010/0056576<br>WO 2008/106692 |

TABLE 7-continued

Selected therapeutic agents that can be administered in combination with the anti-PD-1 antibody molecules, e.g., as a single agent or in combination with other immunomodulators described herein. Each publication listed in this Table is herein incorporated by reference in its entirety, including all structural formulae therein.

| Compound Designation | Generic Name Tradename | Compound Structure | Patents/Patent Application Publications |
|---|---|---|---|
| A28 | | | WO 2010/101849 |
| A29 | Encorafenib | | WO 2011/025927 |
| A30 | | | WO 2011/101409 |
| A31 | | Human monoclonal antibody to HER3 | WO 2012/022814 EP 2606070 U.S. Pat. No. 8,735,551 |
| A32 | | Antibody Drug Conjugate (ADC) | WO 2014/160160 Ab: 12425 (see Table 1, paragraph [00191]) |

TABLE 7-continued

Selected therapeutic agents that can be administered in combination with the anti-PD-1 antibody molecules, e.g.,
as a single agent or in combination with other immunomodulators described herein. Each publication listed in this Table
is herein incorporated by reference in its entirety, including all structural formulae therein.

| Compound Designation | Generic Name Tradename | Compound Structure | Patents/Patent Application Publications |
|---|---|---|---|
| | | | Linker. SMCC (see paragraph [00117] Payload: DM1 (see paragraph [00111] See also Claim 29 |
| A33 | | Monoclonal antibody or Fab to M-CSF | WO 2004/045532 |
| A34 | Binimetinib | | WO 2003/077914 |
| A35 | Midostaurin | | WO 2003/037347 EP 1441737 US 2012/252785 |
| A36 | Everolimus AFINITOR ® | | WO 2014/085318 |

TABLE 7-continued

Selected therapeutic agents that can be administered in combination with the anti-PD-1 antibody molecules, e.g.,
as a single agent or in combination with other immunomodulators described herein. Each publication listed in this Table
is herein incorporated by reference in its entirety, including all structural formulae therein.

| Compound Designation | Generic Name Tradename | Compound Structure | Patents/Patent Application Publications |
|---|---|---|---|
| A37 | | | WO 2007/030377 U.S. Pat. No. 7,482,367 |
| A38 | Pasireotide diaspartate SIGNIFOR ® | | WO 2002/010192 U.S. Pat. No. 7,473,761 |

TABLE 7-continued

Selected therapeutic agents that can be administered in combination with the anti-PD-1 antibody molecules, e.g.,
as a single agent or in combination with other immunomodulators described herein. Each publication listed in this Table
is herein incorporated by reference in its entirety, including all structural formulae therein.

| Compound Designation | Generic Name Tradename | Compound Structure | Patents/Patent Application Publications |
|---|---|---|---|
| A39 | Dovitinib | | WO 2009/115562 U.S. Pat. No. 8,563,556 |
| A40 | | | WO 2013/184757 |
| A41 | | | WO 2006/122806 |

TABLE 7-continued

Selected therapeutic agents that can be administered in combination with the anti-PD-1 antibody molecules, e.g., as a single agent or in combination with other immunomodulators described herein. Each publication listed in this Table is herein incorporated by reference in its entirety, including all structural formulae therein.

| Compound Designation | Generic Name Tradename | Compound Structure | Patents/Patent Application Publications |
|---|---|---|---|
| A42 | | | WO 2008/073687 U.S. Pat. No. 8,372,858 |
| A43 | | | WO 2010/002655 U.S. Pat. No. 8,519,129 |

TABLE 7-continued

Selected therapeutic agents that can be administered in combination with the anti-PD-1 antibody molecules, e.g.,
as a single agent or in combination with other immunomodulators described herein. Each publication listed in this Table
is herein incorporated by reference in its entirety, including all structural formulae therein.

| Compound Designation | Generic Name Tradename | Compound Structure | Patents/Patent Application Publications |
|---|---|---|---|
| A44 | | | WO 2010/002655 U.S. Pat. No. 8,519,129 |
| A45 | | | WO 2010/002655 |

TABLE 7-continued

Selected therapeutic agents that can be administered in combination with the anti-PD-1 antibody molecules, e.g.,
as a single agent or in combination with other immunomodulators described herein. Each publication listed in this Table
is herein incorporated by reference in its entirety, including all structural formulae therein.

| Compound Designation | Generic Name Tradename | Compound Structure | Patents/Patent Application Publications |
|---|---|---|---|
| A46 | Valspodar AMDRAY ™ | | EP 296122 |
| A47 | Vatalanib succinate | | WO 98/35958 |
| | | succinate | |
| A48 | IDH inhibitor | | WO 2014/141104 |
| A49 | BCR-ABL inhibitor | | WO 2013/171639 WO 2013/171640 WO 2013/171641 WO 2013/171642 |
| A50 | cRAF inhibitor | | WO 2014/151616 |
| A51 | ERK1/2 ATP competitive inhibitor | | WO 2015/066188 |

EXAMPLES

The Examples below are set forth to aid in the understanding of the inventions but are not intended to, and should not be construed to, limit its scope in any way.

Example 1: Pharmacokinetics Analysis of Flat Dosing Schedules

Based on pharmacokinetic (PK) modeling, utilizing flat dose is expected provide the exposure to patients at the appropriate Cmin concentrations. Over 99.5% of patients will be above EC50 and over 93% of patients will be above EC90. Predicted steady state mean Cmin for the exemplary anti-PD-1 antibody molecule utilizing either 300 mg once every three weeks (Q3W) or 400 mg once every four weeks (Q4W) is expected to be above 20 ug/mL (with highest weight, 150 kg) on average.

TABLE 5

Exemplary PK parameters based on flat dosing schedules

| | |
|---|---|
| Number of patients in PK dataset | 46 |
| CL (mL/h) | 10.9 [8.9, 13.2]; IIV: 62% |
| Exponent of Weight on CL | 0.54 [0.021, 1.06] |
| Volume of distribution at SS (L) | 7.2 [6.5, 7.9]; IIV: 22% |
| Half-Life (days) | 20 [17, 23]; IIV: 64% |
| Predicted Cmin (ug/mL) for 80 kg patient | 31 [22, 42] (400 mg q4w) 35 [26, 47] (300 mg q3w) |

The expected mean steady state Cmin concentrations for the exemplary anti-PD-1 antibody molecule observed with either doses/regimens (300 mg q3w or 400 mg q4w) will be at least 77 fold higher than the EC50 (0.42 ug/mL) and about 8.6 fold higher than the EC90. The ex vivo potency is based on IL-2 change in SEB ex-vivo assay.

Less than 10% of patients are expected to achieve Cmin concentrations below 3.6 ug/mL for either 300 mg Q3W or 400 mg Q4W. Less than 0.5% of patients are expected to achieve Cmin concentrations below 0.4 μg/mL for either 300 mg Q3W or 400 mg Q4W.

Figure 12:
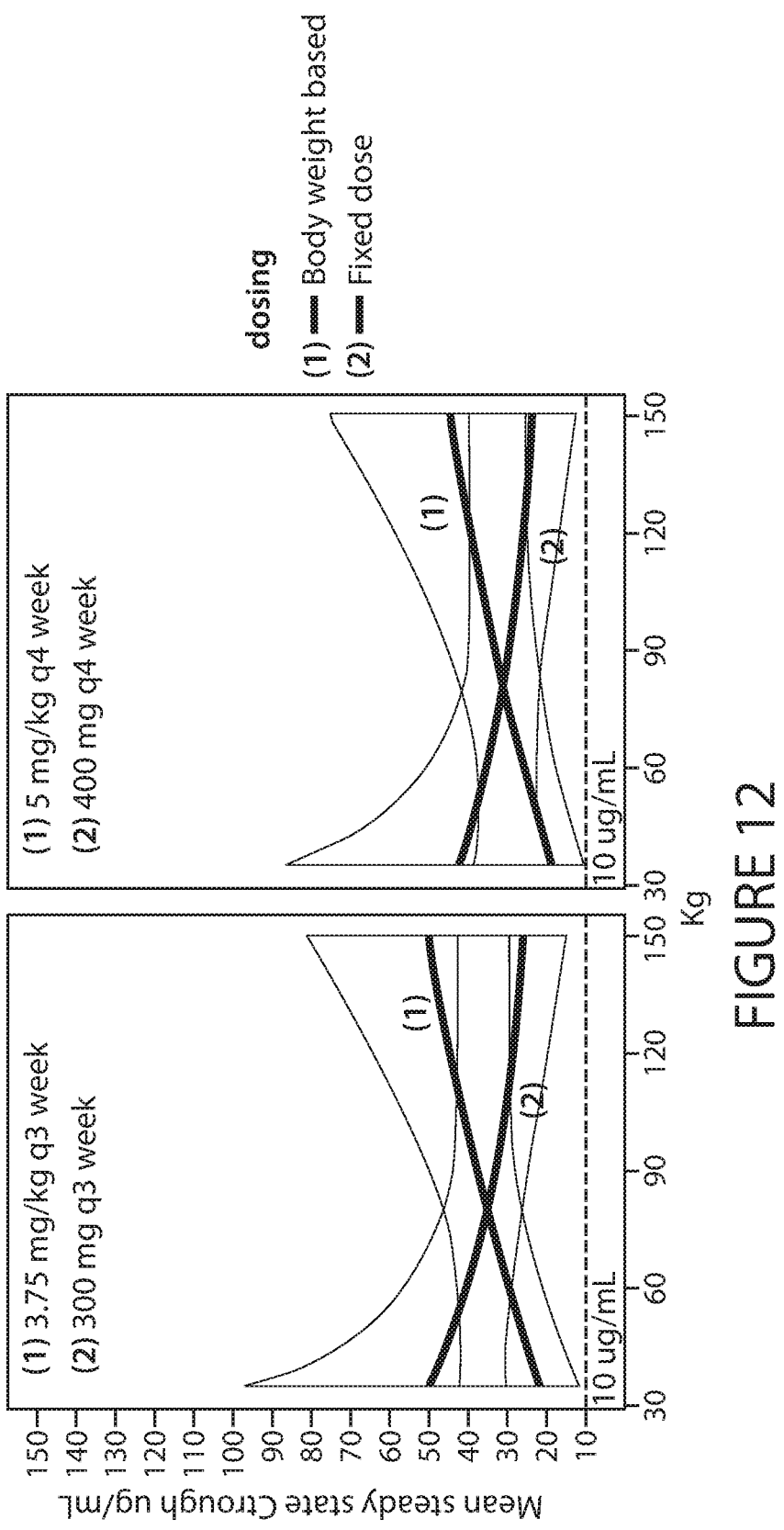
FIG. 12 depicts the predicted $C_{trough}$ ($C_{min}$) concentrations across the different weights for patients while receiving the same dose of an exemplary anti-PD-1 antibody molecule. A comparison of predicted mean steady state $C_{trough}$ after body weight versus flat/fixed dosing of two regimens of the anti-PD-1 antibody molecule is shown.

Predicted Ctrough (Cmin) concentrations across the different weights for patients while receiving the same dose of the exemplary anti-PD-1 antibody molecule are shown in FIG. 12. Body weight based dosing is compared to fixed dose (3.75 mg/kg Q3W vs. 300 mg Q3W and 5 mg/kg Q4W vs. 400 mg Q4W). FIG. 12 supports flat dosing of the exemplary anti-PD-1 antibody molecule.

Figure 13:
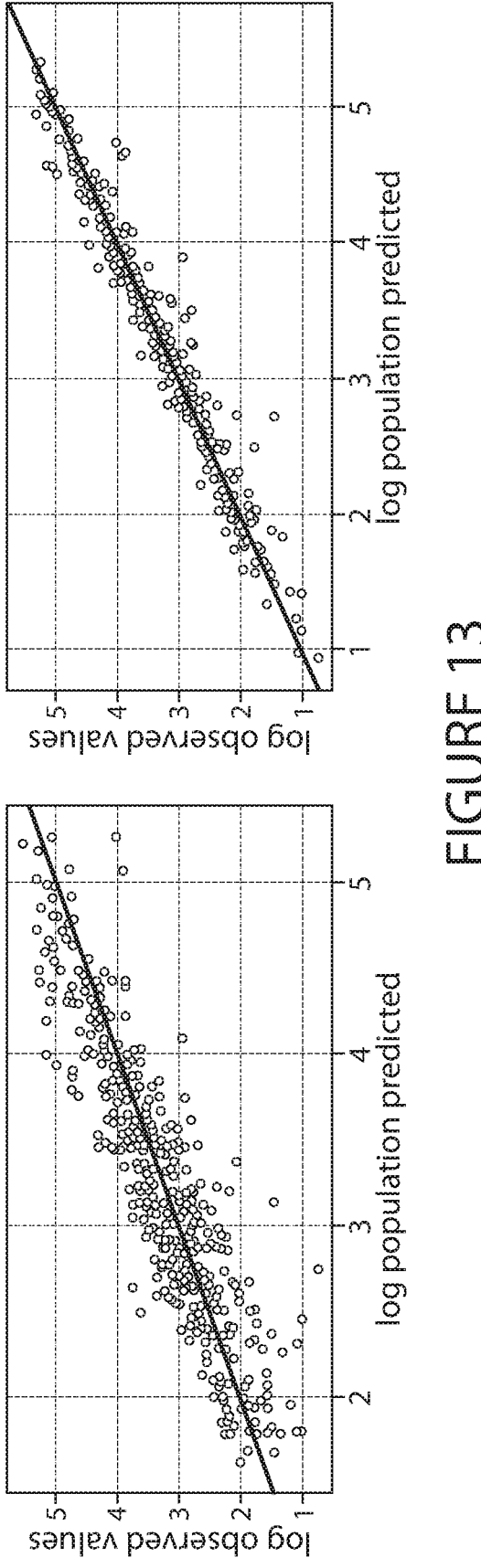
FIG. 13 depicts observed versus model predicted (population or individual based) Cmin concentrations.

The PK model further is validated. As shown in FIG. 13, the observed versus model predicted concentrations lie on the line of unity. FIGS. 14A-14B show that the model captures accumulation, time course, and within subject variability.

Example 2: In Vivo Pharmacology for Combination of Anti-PD-1 Antibody and Compound A21

Compound A21 was combined in vivo with an exemplary anti-PD-1 antibody molecule in a murine syngeneic tumor model, MC38. C57B1/6 mice were implanted with $1 \times 10^6$ MC38 cells/mouse. Vehicle and Compound A21 (50 mg/kg orally twice daily QW) were given for four doses, starting on day 4 post-tumor implant. Isotype and anti-mouse PD-1 were given 10 mg/kg IV QW.

Figure 15:
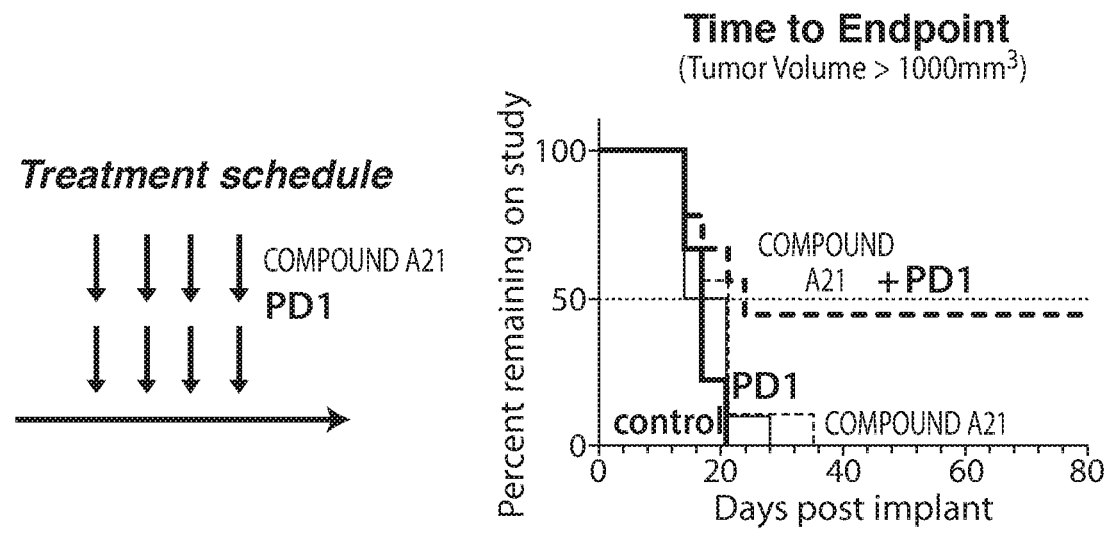
FIG. 15 depicts the percent survival of mice implanted with MC38 cells after treatment with anti-PD-1 antibody, Compound A21, or a combination of anti-PD-1 antibody and Compound A21.

As shown in FIG. 15, synergistic activity was observed with the combination of Compound A21 (100 mg/kg orally once weekly, given at split of 50 mg/kg, b.i.d.) and anti- PD-1 antibody (10 mg/kg IV once weekly), independent of LCL161 single agent efficacy. The combination cohort achieved 4 complete responses (CRs) whereas neither single agent treatment yielded any CRs.

Example 3: In Vivo Pharmacology for Combination of Anti-PD-1 Antibody and Panobinostat (Compound A19)

Figure 16A:
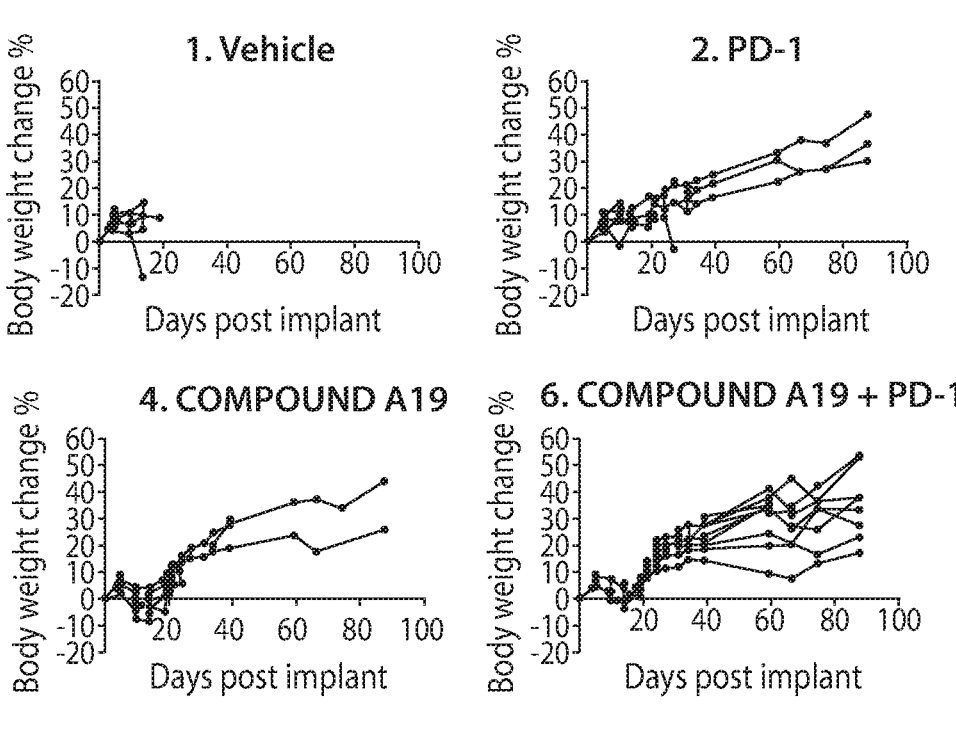
FIG. 16A depicts the body weights for ten animals per group treated with vehicle, anti-mouse PD-1 antibody (10 mg/kg IV QW for four doses), panobinostat (Compound A19, 10 mg/kg QOD for five doses), or the combination of panobinostat and anti-mouse PD-1 antibody.
Figure 16B:
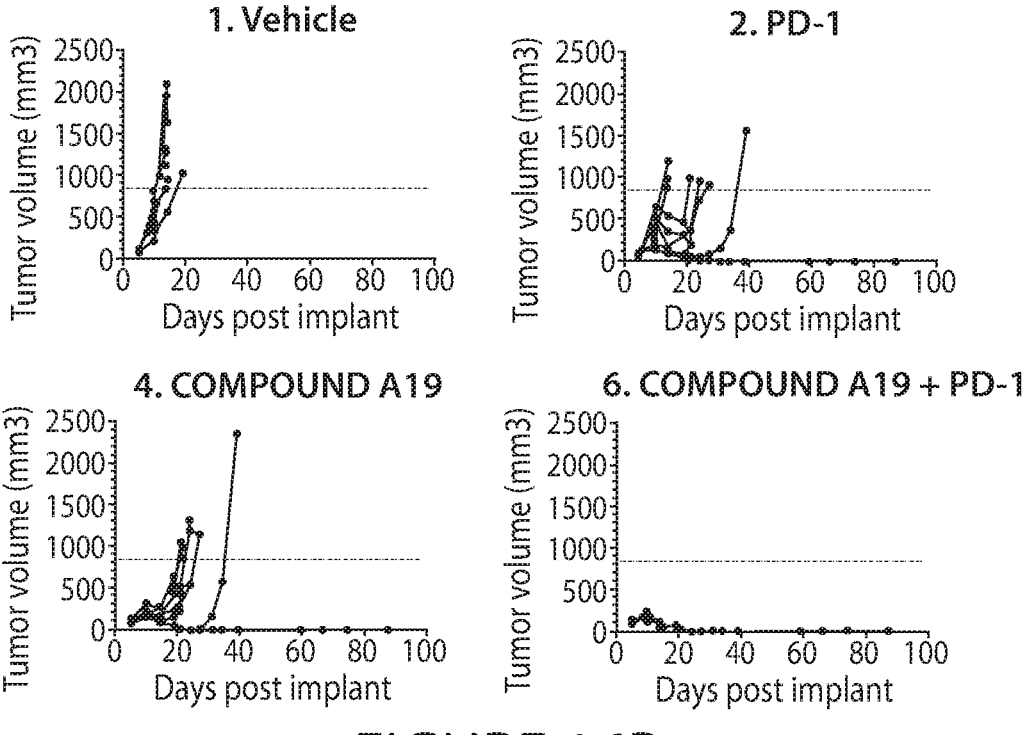
FIG. 16B depicts the responses of individual tumors to treatment with vehicle control, anti-mouse PD-1 antibody, panobinostat (Compound A19), or the combination of panobinostat and anti-mouse PD-1 antibody.

Panobinostat (Compound A19) was combined in vivo with an exemplary anti-PD-1 antibody molecule in a murine syngeneic tumor model, MC38. Panobinostat (Compound A19) was dosed every other day at 12 mg/kg, a dose that results in drug exposure comparable to that observed in patients treated at the approved dose and schedule. Some reduction in body weight was observed with the single agent panobinostat and with the combination, with recovery after dosing of panobinostat was completed. As shown in FIGS. 16A-16B, substantial synergistic activity was observed with the combination of panobinostat (Compound A19) and the anti-PD1 antibody molecule (10 mg/kg IV once weekly): all of the ten animals treated with the combination achieved CRs, compared to three of ten animals treated with single agent PD-1 inhibitor or two of ten treated with single agent panobinostat.

Example 4: In Vivo Pharmacology for Combination of Anti-PD-L1 Antibody and Compound A40

Figure 17:
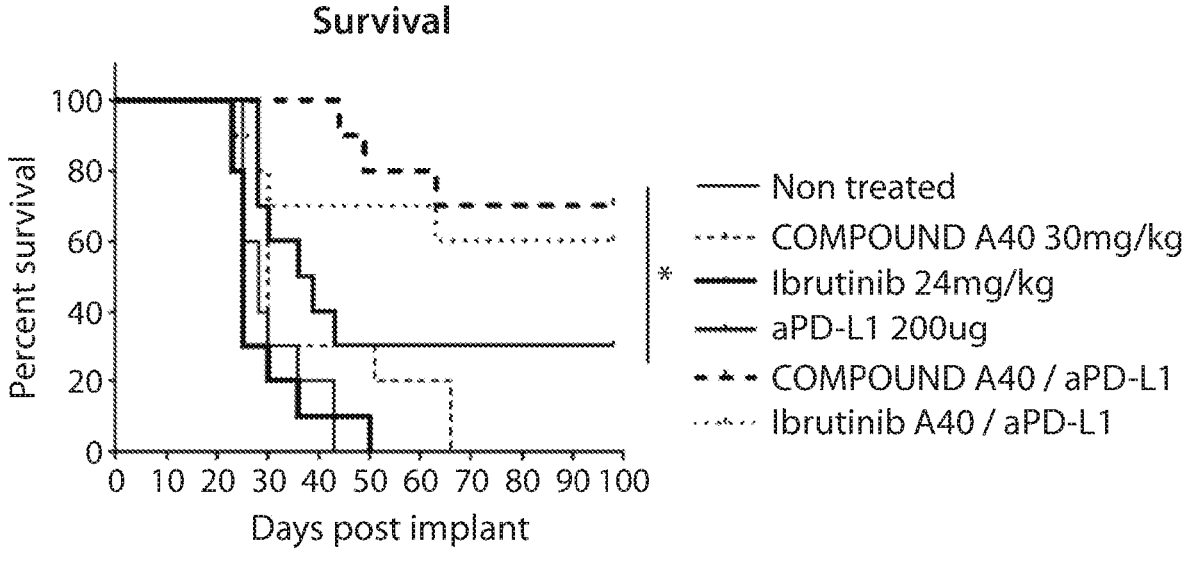
FIG. 17 depicts the percent survival of mice bearing A20 lymphoma allografts after treatment with Compound A40, ibrutinib, anti-PD-L1 antibody, a combination of Compound A40 and anti-PD-L1 antibody, or a combination of ibrutinib and anti-PD-L1 antibody (anti-PD-L1 indicated as aPD-L1).
Figure 18:
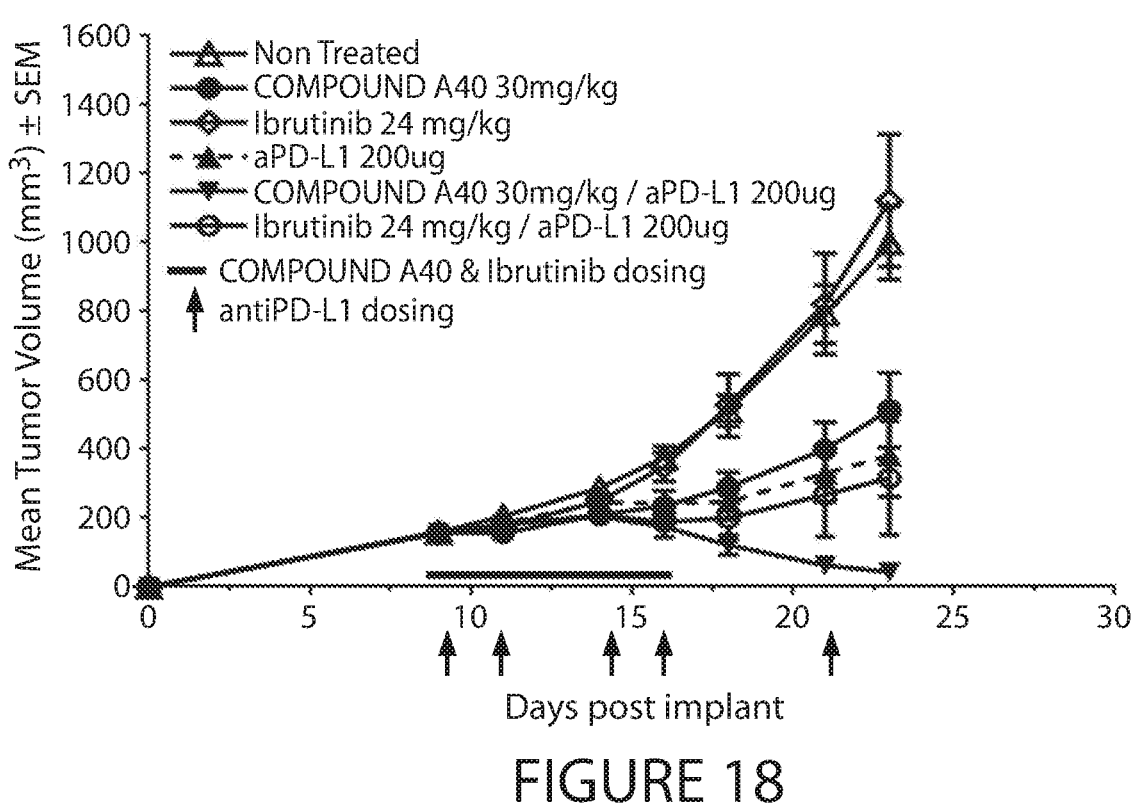
FIG. 18 depicts the mean tumor volume in mice bearing A20 lymphoma allografts after treatment with Compound A40, ibrutinib, anti-PD-L1 antibody, a combination of Compound A40 and anti-PD-L1 antibody, or a combination of ibrutinib and anti-PD-L1 antibody (anti-PD-L1 indicated as aPD-L1).

Compound A40 was combined in vivo with an exemplary anti-PD-L1 antibody molecule in an A20 lymphoma model. As shown in FIG. 17, the combination of anti-PD-L1 antibody and Compound A40, or anti-PD-L1 antibody and ibrutinib, were more effective than any single agent. Compound A40 and ibrutinib were dosed for only ten days, and a total of 5 doses of anti-PD-L1-antibody were given. Even though Compound A40 and ibrutinib were only dosed transiently, the effects of Compound A40 plus anti-PD-L1 antibody and ibrutinib plus anti-PD-L1 antibody on survival extended beyond 60 days. As shown in FIG. 18, the combination of anti-PD-L1 antibody and Compound A40 also resulted in tumor regression in mice bearing A20 lymphoma allografts.

Example 5: A First-in-Human Phase I/II Study of an Exemplary Anti-PD-1 Antibody Molecule in Patients with Advanced Solid Tumors Antibody Molecules The exemplary antibody molecule (BAP049-Clone-E) tested in this study is a humanized anti-programmed death-1 (PD-1) IgG4 monoclonal antibody (mAb) that blocks binding of programmed cell death ligand-1 (PD-L1) and programmed cell death ligand-2 (PD-L2) to PD-1. It binds to PD-1 with high affinity and inhibits its biological activity. The amino acid sequences of this antibody molecule are described in Table 1 herein (VH: SEQ ID NO: 38; VL: SEQ ID NO: 70). Results from pre-clinical toxicology studies have shown that it has a favorable safety profile. Its pharmacodynamic activity has also been demonstrated in vivo. This Example presents data from the first-in-human Phase I/II study of this antibody molecule in adults with advanced solid tumors.

Methods

Study Design and Treatment

Figure 19:
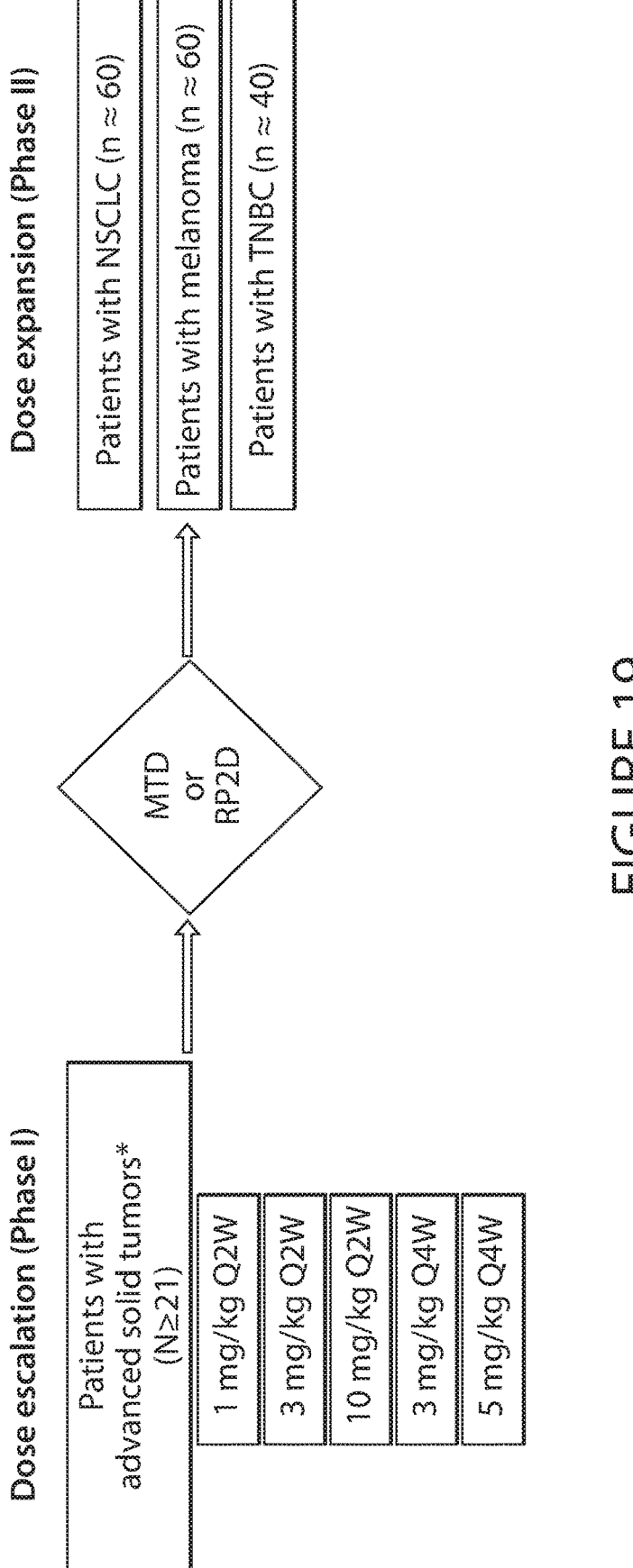
FIG. 19 depicts the study design of a first-in-human phase I/II study of an exemplary anti-PD-1 antibody molecule in patients with advanced solid tumors. *At least 21 patients were required to define the MTD. Tumor assessments were performed at screening, then every 2 cycles (1 cycle=28 days)±1 week from Cycle 3 Day 1 up to Cycle 11 Day 1, and every 3 cycles thereafter until progression of disease per irRC or patient withdrawal. irRC, immune-related Response Evaluation Criteria in Solid Tumors; MTD, maximum-tolerated dose; NSCLC, non-small cell lung cancer; RP2D, recommended phase II dose; TNBC, triple-negative breast cancer.

FIG. 19 shows the study design for a Phase I/II, multi-center, open-label dose-escalation and -expansion study of the safety and efficacy of the exemplary antibody molecule administered to patients with advanced solid tumors.

Patients were treated with the antibody molecule until they experienced unacceptable toxicity, progressive disease per modified immune-related Response Evaluation Criteria in Solid Tumors ([irRC], defined as ≥20% increase in the sum of diameters of all measured target lesions. Progression must be confirmed in a second evaluation ≥4 weeks later, taking as reference the smallest sum of diameters of all target lesions recorded at or after baseline. The sum must also demonstrate an absolute increase of ≥5 mm), and/or treatment discontinuation at the discretion of the investigator or the patient.

In the dose-escalation phase of the study, the antibody molecule was administered intravenously (i.v.) every 2 weeks (Q2W) or every 4 weeks (Q4W). Five dosing regimens of the antibody molecule were evaluated: 1 mg/kg Q2W, 3 mg/kg Q2W, 10 mg/kg Q2W, 3 mg/kg Q4W, and 5 mg/kg Q4W. Patients were to be treated with the antibody molecule until the maximum-tolerated dose (MTD) was reached or until a lower recommended Phase II dose (RP2D) was established. A Bayesian linear model of dose-exposure relationship for the antibody molecule and an adaptive Bayesian logistic regression model following the escalation with overdose control principle were used to guide dose escalation.

Study Objectives and Endpoints

The objectives and endpoints of the study are shown in Table 9.

TABLE 9

| Study objectives and endpoints | |
| --- | --- |
| Objectives | Endpoints |
| Primary | |
| Estimate RP2D and/or MTD for the anti-PD-1 antibody molecule | Exposure ($AUC_{[0-336h]}$) after first dose of treatment; incidence of DLTs |
| Secondary | |
| Characterize PK profile of the anti-PD-1 antibody molecule | Serum PK parameters (e.g., AUC, $C_{max}$, $T_{max}$, half-life); serum concentration versus time profiles |
| Characterize safety and tolerability of the anti-PD-1 antibody molecule | Safety: incidence and severity of AEs and SAEs, including changes in laboratory parameters, vital signs and ECGs<br>Tolerability: dose interruptions, reductions and dose intensity |
| Evaluate preliminary antitumor activity of the anti-PD-1 antibody molecule | ORR, PFS, DOR, and DCR |
| Exploratory | |
| Assess the pharmacodynamic effect of the antibody molecule | CD8+ tumor infiltrating lymphocyte counts |

AEs, adverse events;

AUC, area under curve;

DCR, disease control rate;

DLTs, dose-limiting toxicities;

DOR, duration of response;

ECGs, electrocardiograms;

i.v. intravenous;

ORR, objective response rate;

PK, pharmacokinetics;

PFS, progression-free survival;

SAEs, serious adverse events.

Key Inclusion Criteria

Patients with advanced/metastatic solid tumors, with measurable or non-measurable disease as determined by Response Evaluation Criteria in Solid Tumors (RECIST) version 1.1, who have progressed despite standard therapy or are intolerant of standard therapy, or for whom no standard therapy exists, were included. Eastern Cooperative Oncology Group Performance Status was ≤2. Tumor was amenable to biopsy and patient consented to tumor biopsy at baseline and during therapy with study drug.

Key Exclusion Criteria

Patients with symptomatic central nervous system (CNS) metastases, or CNS metastases that require local CNS-directed therapy (such as radiotherapy or surgery), or increasing doses of corticosteroids within the prior 2 weeks, were excluded. Patients were excluded, if they received systemic anticancer therapy within 2 weeks of the first dose of study treatment, or prior PD-1- or PD-L1-directed therapy. Patients requiring chronic treatment with systemic steroid therapy, other than replacement-dose steroids in the setting of adrenal insufficiency, or having history of severe hypersensitivity reactions to other mAbs, were also excluded.

Assessments

Adverse events (AEs) were graded using the National Cancer Institute's Common Terminology Criteria for Adverse Events (NCI CTCAE) version 4.03. Comprehensive pharmacokinetic (PK) sampling across multiple time points (up to 336 hours post-dose for Q2W and 672 post-dose for Q4W) was obtained from all patients in Phase I. Preliminary population PK analysis was conducted to estimate PK parameters and assess the impact of weight as a covariate on clearance and volume of distribution. Radiologic response was assessed by computed tomography (CT) according to RECIST version 1.1. Scans were performed every 2 cycles from Cycle 3 Day 1 up to Cycle 11 Day 1, then every 3 cycles until progression of disease per irRC or patient withdrawal. For biomarker analyses, an archival tumor sample and a newly obtained pre-treatment tumor biopsy were collected at screening. An additional tumor biopsy was obtained during treatment.

Results

Patient Demographics and Characteristics

As shown in Table 10, 58 patients were enrolled in the Phase I part of the study. Patients presented with a diverse range of advanced solid tumors. 4/58 (7%) patients received 0 prior antineoplastic regimens, 7/58 (12%) received 1 prior antineoplastic regimen, 13/58 (22%) received 2 prior antineoplastic regimens, and 34/58 (59%) received ≥3 prior antineoplastic regimens.

TABLE 10

Patient demographics and characteristics

| Characteristic | All Phase I patients N = 58 |
|---|---|
| Median age, years (range) | 55 (23-82) |
| Sex, n (%) | |
| Female | 26 (45) |
| Male | 32 (55) |
| Race, n (%) | |
| Caucasian | 44 (76) |
| Black | 2 (3) |
| Asian | 9 (16) |

TABLE 10-continued

Patient demographics and characteristics

| Characteristic | All Phase I patients N = 58 |
|---|---|
| Unknown | 1 (2) |
| Other | 2 (3) |
| WHO/ECOG performance status, n (%) | |
| 0 | 24 (41) |
| 1 | 33 (57) |
| 2 | 1 (2) |
| Disease diagnosis, n (%) | |
| Anal cancer | 2 (3) |
| Breast cancer | 2 (3) |
| Cholangiocarcinoma | 2 (3) |
| Cutaneous melanoma | 1 (2) |
| Esophageal cancer | 1 (2) |
| Gastric cancer | 1 (2) |
| Head and neck cancer | 3 (5) |
| Hepatocellular carcinoma | 2 (3) |
| Liposarcoma | 3 (5) |
| Metastatic RCC | 6 (10) |
| NSCLC | 1 (2) |
| Prostate cancer | 1 (2) |
| SCLC | 2 (3) |
| TNBC | 1 (2) |
| Other | 30 (52) |
| Number of prior antineoplastic regimens, n (%) | |
| 0 | 4 (7) |
| 1 | 7 (12) |
| 2 | 13 (22) |
| ≥3 | 34 (59) |

ECOG, Eastern Cooperative Oncology Group;

NSCLC, non-small cell lung cancer;

RCC, renal cell carcinoma;

SCLC, small cell lung cancer;

TNBC, triple-negative breast cancer;

WHO, World Health Organization.

Patient Disposition and Exposure

As shown in Table 11, 11/58 (19%) patients were receiving study drug. For 58 patients as of data cutoff, 46 patients were on study for >8 weeks; 34 patients for >12 weeks; 20 patients for >20 weeks; 6 patients for >36 weeks. Table 11 also indicates that the primary reason for end of treatment was progressive disease, occurring in 39/58 (67%) patients. In Phase I patients, the median duration of exposure was 14 weeks (range 2-46); in Phase II patients, the median duration of exposure was 2.86 weeks (range 0.6-9.9).

TABLE 11

| | 1 mg/kg Q2W N = 16 n (%) | 3 mg/kg Q2W N = 15 n (%) | 10 mg/kg Q2W N = 11 n (%) | All Q2W patients N = 42 n (%) | 3 mg/kg Q4W N = 6 n (%) | 5 mg/kg Q4W N = 10 n (%) | All Q4W patients N = 16 n (%) | All Phase I patients N = 58 n (%) |
|---|---|---|---|---|---|---|---|---|
| Disposition reason | | | | | | | | |
| Patients treated | | | | | | | | |
| Treatment discontinued | 13 (81) | 11 (73) | 9 (82) | 33 (79) | 6 (100) | 8 (80) | 14 (88) | 47 (81) |
| Treatment ongoing* | 3 (19) | 4 (27) | 2 (18) | 9 (21) | 0 | 2 (20) | 2 (13) | 11 (19) |
| Primary reason for end of treatment | | | | | | | | |
| Adverse event | 1 (6) | 0 | 0 | 1 (2) | 0 | 0 | 0 | 1 (2) |
| Progressive disease | 11 (69) | 8 (53) | 7 (64) | 26 (62) | 6 (100) | 7 (70) | 13 (81) | 39 (67) |
| Patient/guardian decision | 0 | 2 (13) | 1 (9) | 3 (7) | 0 | 0 | 0 | 3 (5) |
| Death | 1 (6) | 1 (7) | 1 (9) | 3 (7) | 0 | 1 (10) | 1 (6) | 4 (7) |

*Patients ongoing at the time of the cut-off.

Dose-Limiting Toxicities (DLTs), Clinical PK, and RP2D

No dose-limiting toxicities were reported. The model predicted concentration-time profiles (Cycle 1/Cycle 3, where available; semi-log view) for the antibody molecule by dose and dosing regimen is shown in FIG. 14. The maximum serum concentrations (Cmax) occurred generally at 1 hour after the end of the infusion. Approximately dose-proportional increases in exposure were observed from 1-10 mg/kg. The antibody molecule achieves an $AUC_{0-336h}$ of approximately 1000 µg*day/mL at Cycle 3 with 3 mg/kg Q2W or 5 mg/kg Q4W.

Accumulation of approximately 2.1-3.4-fold was observed with Q2W dosing and 1.6~2.2-fold with Q4W dosing. PK variability was low to moderate; between subject variability (Geometric mean CV %) ranged from 0.5 to 39.2% for Cmax and from 3.6 to 47.7% for AUC0-336 hrs (Cycle 1). The estimated half-life from the preliminary population PK analysis in patients is 20 (95% CI:17-23) days.

Based on a population pharmacokinetic (PK) analysis, a flat dose of 400 mg Q4W is predicted to achieve mean steady-state $C_{trough}$ concentrations of approximately 31 µg/mL (90% CI: 22-42), which exceeds the ex vivo $EC_{50}$ for PD-1 blockade of 0.42 µg/mL (FIG. 12). The recommended phase II dose (RP2D) for the antibody molecule was therefore selected as 400 mg Q4W. An alternative dosing regimen of 300 mg Q3W is expected to achieve similar exposure to 400 mg Q4W, and may be utilized in combination regimens where a Q3W schedule is more convenient.

Safety and Tolerability

In Phase I patients, the most common (occurring in ≥20% of patients) all grade adverse events (AEs) regardless of study drug relationship were nausea, fatigue, anemia, diarrhea, dyspnea, vomiting, abdominal pain, decreased appetite, and constipation (Table 12). The most common (occurring in ≥10% of patients) grade 3/4 AE regardless of study drug relationship was anemia. The most common (occurring in ≥20% of patients) all grade AE suspected of being related to study drug was fatigue. Grade 3/4 AEs suspected of being study drug related were rare, occurring in only 3.4% of patients. No trend was observed in the adverse events profile across dosing cohorts.

TABLE 12

| Adverse events regardless of study drug relationship (any grade occurring in ≥20% of patients - safety set) | |
|---|---|
| Preferred term | All grades n (%) |
| Nausea | 23 (40) |
| Fatigue | 21 (36) |
| Anemia | 19 (33) |
| Diarrhea | 17 (29) |
| Dyspnea | 17 (29) |
| Vomiting | 14 (24) |
| Abdominal pain | 13 (22) |
| Decreased appetite | 13 (22) |
| Constipation | 12 (21) |

Only adverse events occurring during treatment or within 90 days of the last study medication are reported.

In Phase II patients, the most common (occurring in ≥10% of patients) all grade AEs regardless of study drug relationship were abdominal pain, constipation, cough, decreased appetite, dyspnea, fatigue, and increased gamma-glutamyl transferase. The most common (occurring in ≥5% of patients) grade 3/4 AE regardless of study drug relationship were abdominal pain and increased gamma-glutamyl transferase. The most common (occurring in ≥5% of patients) all grade AE suspected of being related to study drug were fatigue, nausea, and pruritus. No Grade 3/4 AEs suspected of being study drug related were reported.

No infusion reactions or dose reductions were reported. One patient discontinued treatment due to an adverse event (Grade 3 dyspnea), not suspected of being study drug-related.

Efficacy

Figure 20:
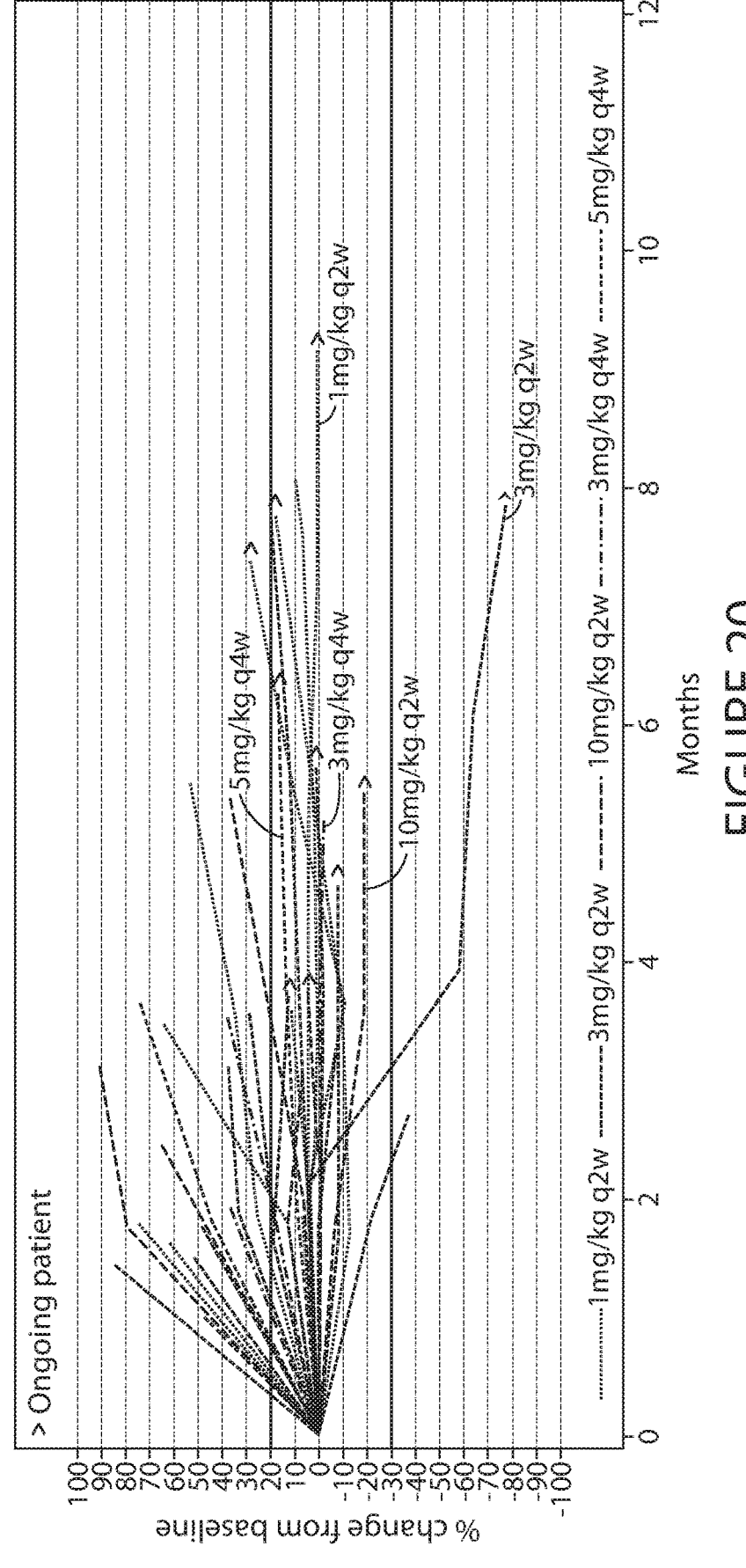
FIG. 20 depicts the percent change in target lesions over time for each of the radiographically evaluable patients treated with the anti-PD-1 antibody molecule in the phase I/II study. Patients were treated at the following dosing schedules: 1 mg/kg q2w, 3 mg/kg q2w, 10 mg/kg q2w, 3 mg/kg q4w, or 5 mg/kg q4w (exemplary lines in the figure are indicated with the dosing schedules).
Figure 21A:
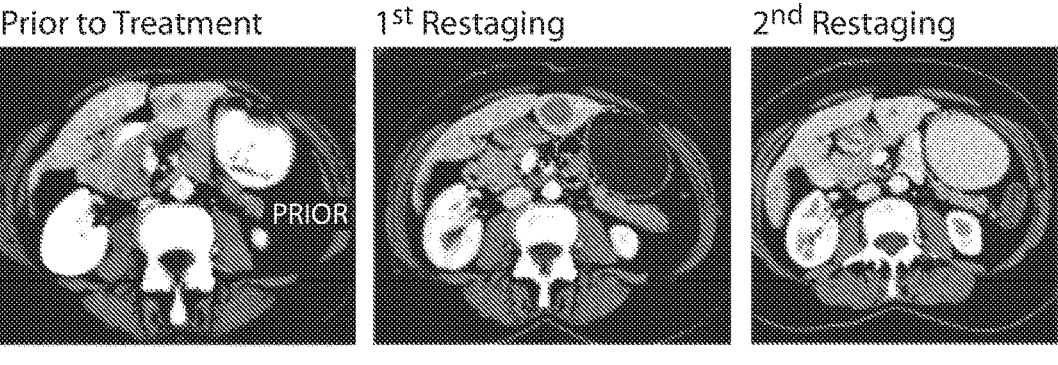
FIGS. 21A-21C depict the tumor assessments and immunohistochemical detection of CD8+T lymphocytes in a patient having metastatic atypical pulmonary carcinoid tumor with clinical response to the anti-PD-1 antibody molecule in the phase I/II study.
Figure 21B:
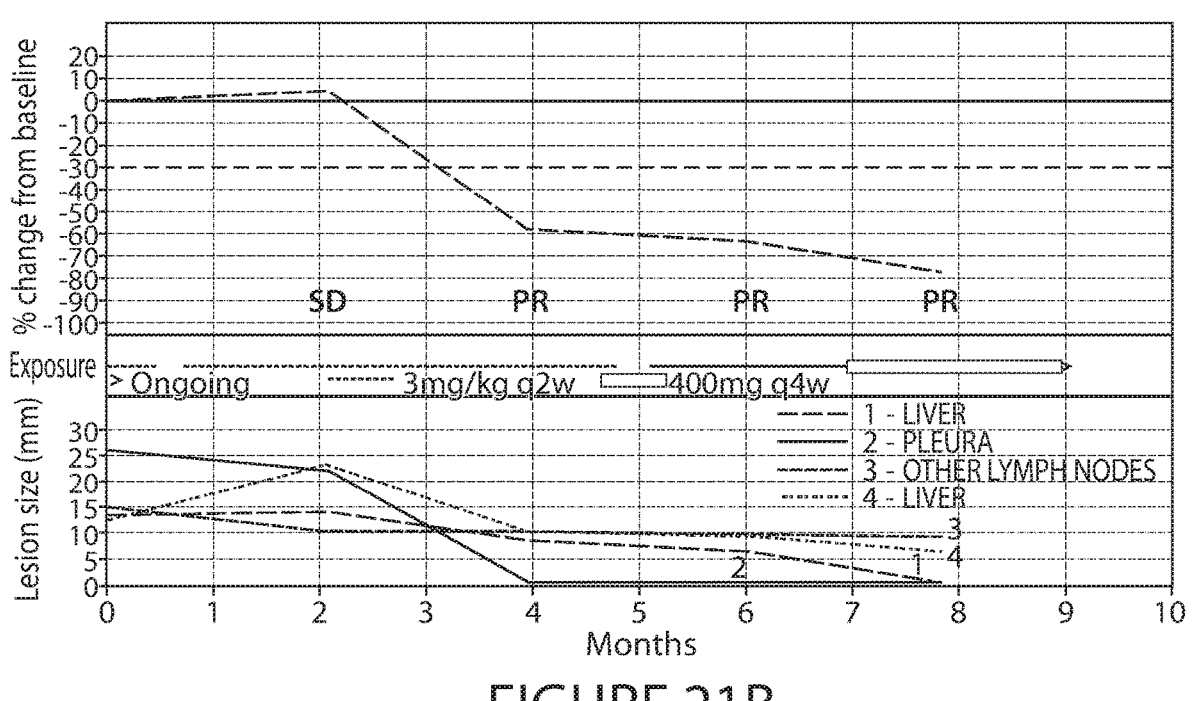
Figure 21C:
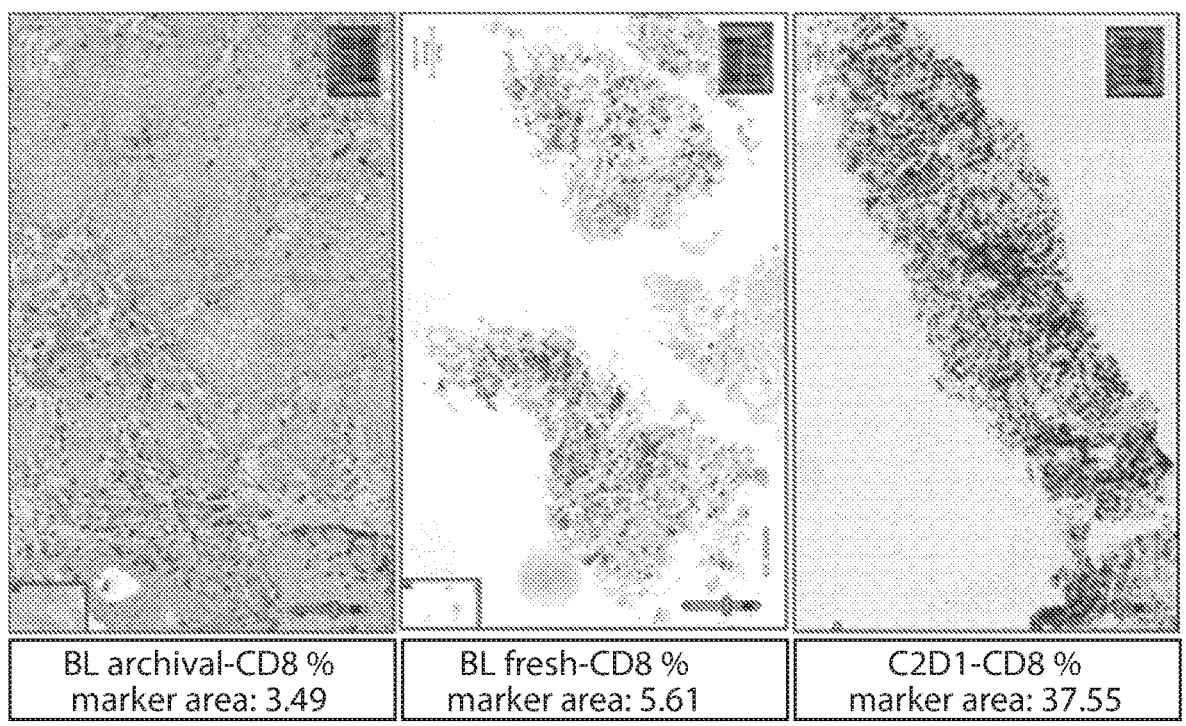

The overall response rate and disease control rate across the wide range of tumor types were 2% and 41%, respectively (Table 13). Changes in tumor burden over time for each of the radiographically evaluable patients can be seen in FIG. 20. Diagnoses of patients remaining on study as of cutoff from phase I include: liposarcoma (two patients), testicular cancer, atypical lung carcinoid, anaplastic thyroid carcinoma, Merkel cell carcinoma, clear cell renal cell carcinoma, melanoma, and triple negative breast cancer (TNBC). As shown in FIGS. 21A-21B, a partial response following pseudo-progression was observed in one patient with a metastatic atypical pulmonary carcinoid tumor. As shown in FIG. 21C, high levels of CD8+ T lymphocytes were detected by immunohistochemistry staining in a tumor sample obtained from this patient during Cycle 2 Day 1.

TABLE 13

| Best overall response (based on investigator's assessment of disease status using RECIST v1.1 criteria) | | | | | | | | |
|---|---|---|---|---|---|---|---|---|
| | 1 mg/kg Q2W (N = 16) n (%) | 3 mg/kg Q2W (N = 15) n (%) | 10 mg/kg Q2W (N = 11) n (%) | All Q2W patients (N = 42) n (%) | 3 mg/kg Q4W (N = 6) n (%) | 5 mg/kg Q4W (N = 10) n (%) | All Q4W patients (N = 16) n (%) | All Phase I patients (N = 58) n (%) |
| Evaluable patients* | 16 | 15 | 11 | 42 | 6 | 10 | 16 | 58 |
| Best overall response | | | | | | | | |
| Complete response (CR) | 0 (0) | 0 (0) | 0 (0) | 0 (0) | 0 (0) | 0 (0) | 0 (0) | 0 (0) |
| Partial response (PR) | 0 (0) | 1 (7) | 0 (0) | 1 (2) | 0 (0) | 0 (0) | 0 (0) | 1 (2) |
| Stable disease (SD) | 9 (56) | 6 (40) | 3 (27) | 18 (43) | 3 (50) | 2 (20) | 5 (31) | 23 (40) |
| Progressive disease (PD) | 5 (31) | 6 (40) | 4 (36) | 15 (36) | 3 (50) | 7 (70) | 10 (63) | 25 (43) |
| Unknown | 2 (13) | 2 (13) | 4 (36) | 8 (19) | 0 (0) | 1 (10) | 1 (6) | 9 (16) |
| Overall response rate (CR or PR) | 0 (0) | 1 (7) | 0 (0) | 1 (2) | 0 (0) | 0 (0) | 0 (0) | 1 (2) |
| 90% Confidence interval* | [0; 17] | [0; 28] | [0; 24] | [0; 11] | [0; 39] | [0; 26] | [0; 17] | [0; 8] |
| Disease control rate (CR or PR or SD) | 9 (56) | 7 (47) | 3 (27) | 19 (45) | 3 (50) | 2 (20) | 5 (31) | 24 (41) |
| 90% Confidence interval | [33; 77] | [24; 70] | [8; 56] | [32; 59.0] | [15; 85] | [4; 51] | [13; 55] | [30; 53] |

SD includes patients with best overall response Non-CR/Non-PD;
90% Confidence interval was calculated using the exact (Clopper-Pearson) interval.
*Evaluable patients are defined as the patients with at least one post treatment evaluation or discontinued prior to the first post baseline evaluation.

SUMMARY

The exemplary antibody molecule was well tolerated and had a manageable safety profile. The RP2D was selected as 400 mg Q4W. An alternative dosing schedule of 300 mg Q3W is expected to achieve similar exposure, and may be a more convenient alternative for evaluating certain combination treatment regimens involving the antibody molecule. Preliminary efficacy data in one patient suggest an antitumor response driven by enhanced activity of CD8+ T lymphocytes, as expected for a clinically active PD-1 inhibitor.

Example 6: In Vivo Pharmacology for Combination of Anti-PD-1 Antibody and Compound A15

Figure 22A:
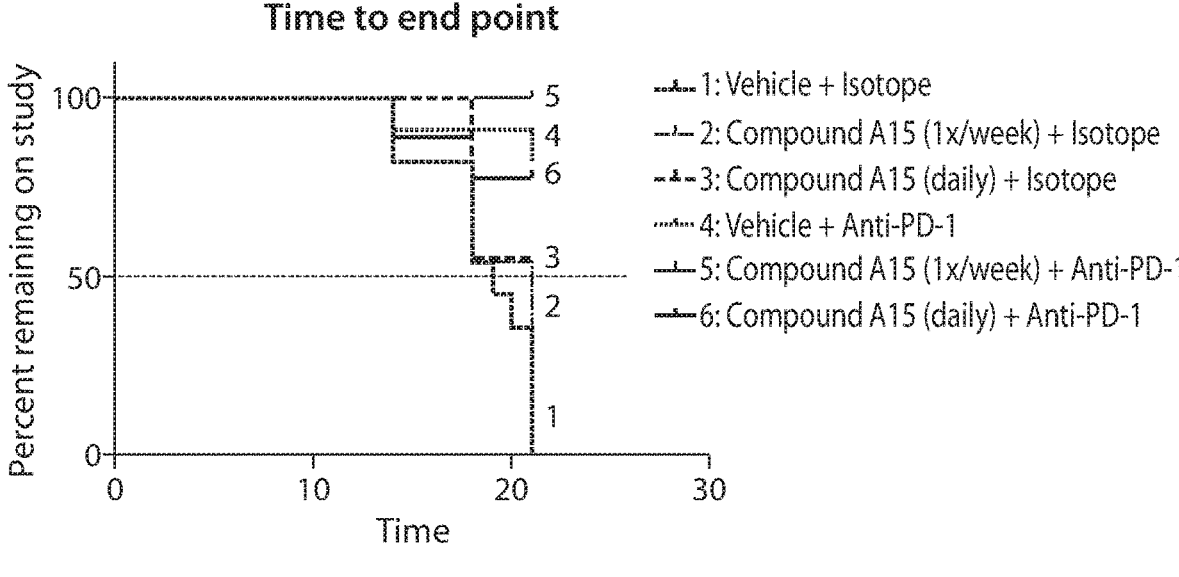
FIG. 22A depicts the percent survival of mice implanted with MC38 cells after treatment with anti-PD-1 antibody, Compound A15 (once a week or daily), or a combination of anti-PD-1 antibody and Compound A15 (once a week or daily).
Figure 22B:
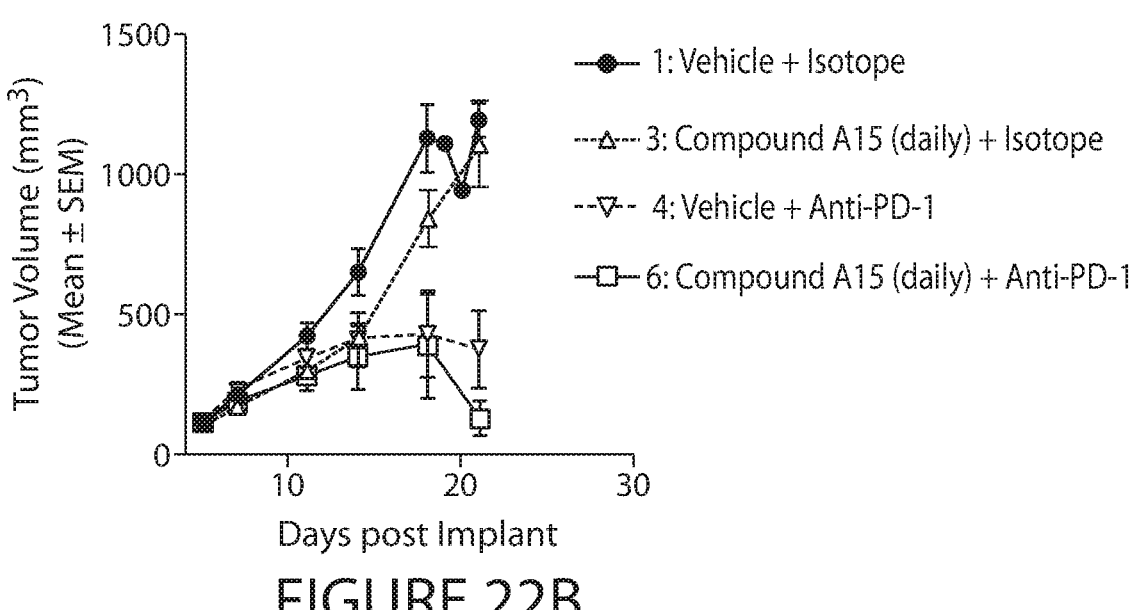
FIG. 22B depicts the mean tumor volume in mice implanted with MC38 cells after treatment with anti-PD-1 antibody, Compound A15 (daily), or a combination of anti-PD-1 antibody and Compound A15 (daily).
Figure 22C:
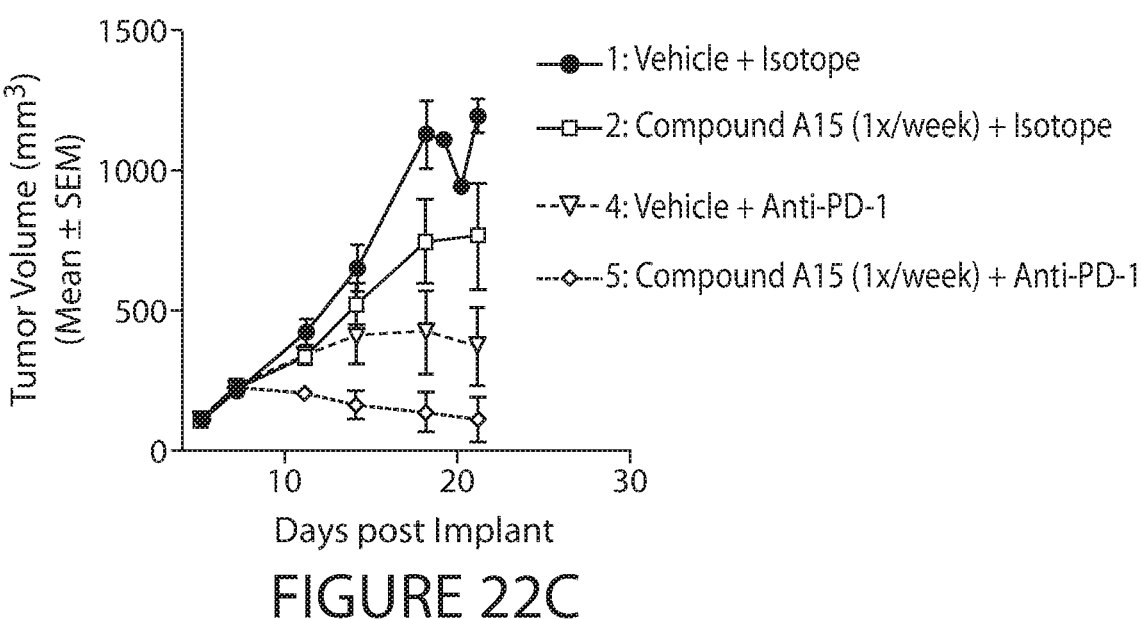
FIG. 22C depicts the mean tumor volume in mice implanted with MC38 cells after treatment with anti-PD-1 antibody, Compound A15 (once a week), or a combination of anti-PD-1 antibody and Compound A15 (once a week).

Compound A15 was tested in combination with an exemplary anti-PD-1 antibody molecule in the MC38 syngeneic colorectal cancer model, chosen based on the presence of TAMs and response to anti-PD-1. As shown in FIGS. 22A-22C, the combination of anti-PD-1 antibody and Compound A15 inhibited tumor growth and enhance survival as compared to anti-PD-1 alone. In this study, weekly administration of Compound A15 (200 mg/kg) in combination with the anti-PD-1 antibody molecule was more efficacious (8 of 11 complete responders) than daily administration of Compound A15 (200 mg/kg) in combination with a weekly dose of the anti-PD-1 antibody molecule (4 of 11 complete responders) and the anti-PD-1 antibody molecule alone (5 of 11 complete responders, weekly dosing). A modest decrease in TAMs was observed 2 days after the second dose of the weekly schedule of Compound A15. The observed TAM kinetic upon weekly schedule of Compound A15 and anti-PD-1 combination was transient as TAMs' numbers return to normal by 7 days post second dose. A decrease in tumor Tregs was observed at all time-points tested (2 and 7 days post dose) upon Compound A15 plus the anti-PD-1 antibody molecule on a weekly schedule.

Figure 23:
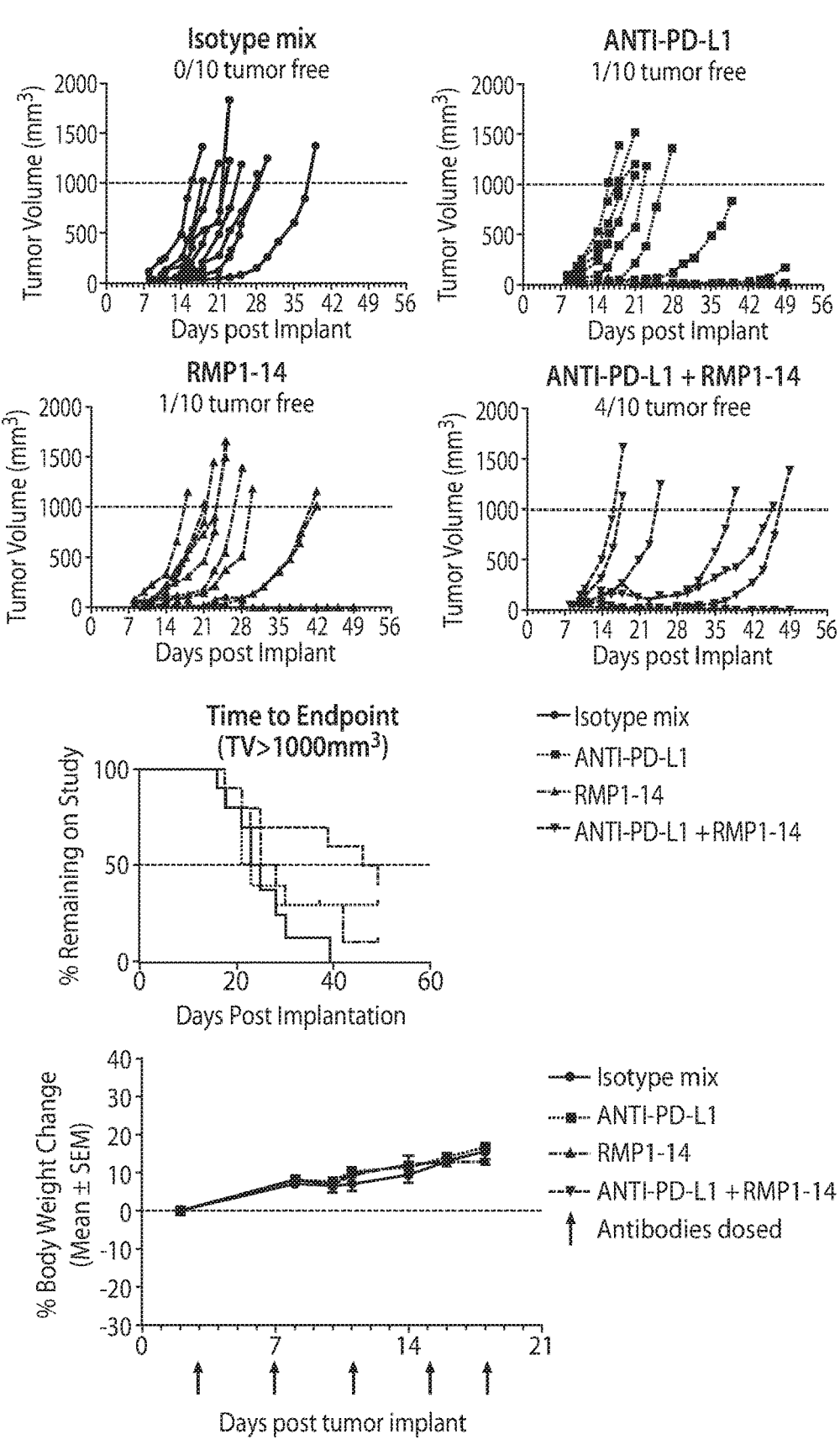
FIG. 23 depicts the enhancement in time to end point observed in animals treated with an anti-PD-L1 antibody molecule in combination with an anti-PD-1 antibody.

Example 7: Activity of Anti-PD-L1 Antibody in MC38 Colon Carcinoma Model in Combination with Anti-PD-1 Antibody The combination of an exemplary anti-PD-1 antibody molecule and an exemplary anti-PD-L1 antibody molecule was tested in the MC38 murine model of colon adenocarcinoma. A surrogate anti-mouse PD-1 antibody, RMP1-14, was used. As shown in FIG. 23, co-administration of RMP1-14 and the anti-PD-L1 antibody molecule resulted in enhanced anti-tumor activity relative to both single agents in this model. Specifically, the anti-PD-L1 antibody molecule and RMP1-14 in combination resulted in 4/10 animals with complete responses as well as 3/10 animals demonstrating partial responses. In addition, combination therapy resulted in non-significant enhancement of the median time to end point to 46 days, which was 21 days longer than animals treated with isotype and over 20 days longer than either antibody alone.

Other embodiments and examples including figures and tables are disclosed in International Patent Application Publication No. WO 2015/112900 and U.S. Patent Application Publication No. US 2015/0210769, entitled "Antibody Molecules to PD-1 and Uses Thereof," which are incorporated by reference in its entirety.

INCORPORATION BY REFERENCE

All publications, patents, and Accession numbers mentioned herein are hereby incorporated by reference in their entirety as if each individual publication or patent was specifically and individually indicated to be incorporated by reference.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

SEQUENCE LISTING

```
<160> NUMBER OF SEQ ID NOS: 327

<210> SEQ ID NO 1
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Thr Tyr Trp Met His
1               5

<210> SEQ ID NO 2
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Asn Ile Tyr Pro Gly Thr Gly Gly Ser Asn Phe Asp Glu Lys Phe Lys
1               5                   10                  15

Asn

<210> SEQ ID NO 3
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Trp Thr Thr Gly Thr Gly Ala Tyr
1               5

<210> SEQ ID NO 4
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Tyr Thr Phe Thr Thr Tyr
1               5

<210> SEQ ID NO 5
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Tyr Pro Gly Thr Gly Gly
1               5
```

```
<210> SEQ ID NO 6
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Thr Tyr
            20                  25                  30

Trp Met His Trp Val Arg Gln Arg Pro Gly Gln Gly Leu Glu Trp Ile
        35                  40                  45

Gly Asn Ile Tyr Pro Gly Thr Gly Gly Ser Asn Phe Asp Glu Lys Phe
    50                  55                  60

Lys Asn Arg Thr Ser Leu Thr Val Asp Thr Ser Ser Thr Thr Ala Tyr
65                  70                  75                  80

Met His Leu Ala Ser Leu Thr Ser Glu Asp Ser Ala Val Tyr Tyr Cys
                85                  90                  95

Thr Arg Trp Thr Thr Gly Thr Gly Ala Tyr Trp Gly Gln Gly Thr Leu
            100                 105                 110

Val Thr Val Ser Ala
        115

<210> SEQ ID NO 7
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 7
caggtccagc tgcagcaacc tgggtctgag ctggtgaggc ctggagcttc agtgaagctg      60
tcctgcaagg cgtctggcta cacattcacc acttactgga tgcactgggt gaggcagagg     120
cctggacaag gccttgagtg gattggaaat atttatcctg gtactggtgg ttctaacttc     180
gatgagaagt tcaaaaacag gacctcactg actgtagaca tcctccacac acagcctac      240 atgcacctcg ccagcctgac atctgaggac tctgcggtct attactgtac aagatggact     300
actgggacgg gagcttattg gggccaaggg actctggtca ctgtctctgc a              351

<210> SEQ ID NO 8
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Gln Val Gln Leu Gln Gln Ser Gly Ser Glu Leu Val Arg Pro Gly Ala
1               5                   10                  15

Ser Val Lys Leu Ser Cys Lys Ala Ser Gly Tyr Thr Phe Thr Thr Tyr
            20                  25                  30

Trp Met His Trp Val Arg Gln Arg Pro Gly Gln Gly Leu Glu Trp Ile
```

-continued

```
            35              40              45
Gly Asn Ile Tyr Pro Gly Thr Gly Gly Ser Asn Phe Asp Glu Lys Phe
    50              55              60

Lys Asn Arg Thr Ser Leu Thr Val Asp Thr Ser Ser Thr Thr Ala Tyr
65              70              75              80

Met His Leu Ala Ser Leu Thr Ser Glu Asp Ser Ala Val Tyr Tyr Cys
                85              90              95

Thr Arg Trp Thr Thr Gly Thr Gly Ala Tyr Trp Gly Gln Gly Thr Leu
            100             105             110

Val Thr Val Ser Ala
        115

<210> SEQ ID NO 9
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9
caggtccagc tgcagcagtc tgggtctgag ctggtgaggc ctggagcttc agtgaagctg        60
tcctgcaagg cgtctggcta cacattcacc acttactgga tgcactgggt gaggcagagg       120
cctggacaag gccttgagtg gattggaaat atttatcctg gtactggtgg ttctaacttc       180
gatgagaagt tcaaaaacag gacctcactg actgtagaca tcctccac cacagcctac        240 atgcacctcg ccagcctgac atctgaggac tctgcggtct attactgtac aagatggact       300
actgggacgg gagcttattg gggccaaggg actctggtca ctgtctctgc a               351

<210> SEQ ID NO 10
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Lys Ser Ser Gln Ser Leu Leu Asp Ser Gly Asn Gln Lys Asn Phe Leu
1               5               10              15

Thr

<210> SEQ ID NO 11
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Trp Ala Ser Thr Arg Glu Ser
1               5

<210> SEQ ID NO 12
<211> LENGTH: 9
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 12

Gln Asn Asp Tyr Ser Tyr Pro Cys Thr
1               5

<210> SEQ ID NO 13
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Ser Gln Ser Leu Leu Asp Ser Gly Asn Gln Lys Asn Phe
1               5                   10

<210> SEQ ID NO 14
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Trp Ala Ser
1

<210> SEQ ID NO 15
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Asp Tyr Ser Tyr Pro Cys
1               5

<210> SEQ ID NO 16
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Thr Gly Ser Gly Ser Val Thr Asp Phe Thr Leu Thr
```

```
65                  70                  75                  80

Ile Ser Ser Val Gln Ala Glu Asp Leu Ala Val Tyr Tyr Cys Gln Asn
                    85                  90                  95

Asp Tyr Ser Tyr Pro Cys Thr Phe Gly Gly Gly Thr Lys Leu Glu Ile
                    100                 105                 110

Lys
```

```
<210> SEQ ID NO 17
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 17
gacattgtga tgacccagtc tccatcctcc ctgactgtga cagcaggaga gaaggtcact      60
atgagctgca agtccagtca gagtctgtta gacagtggaa tcaaaagaa cttcttgacc      120 tggtaccagc agaaaccagg gcagcctcct aaactgttga tcttctgggc atccactagg      180
gaatctgggg tccctgatcg cttcacaggc agtggatctg taacagattt cactctcacc      240
atcagcagtg tgcaggctga agacctggca gtttattact gtcagaatga ttatagttat      300
ccgtgcacgt tcggagggggg gaccaagctg gaaataaaa                             339
```

```
<210> SEQ ID NO 18
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Thr Tyr
                20                  25                  30

Trp Met His Trp Val Arg Gln Arg Pro Gly Gln Gly Leu Glu Trp Ile
            35                  40                  45

Gly Asn Ile Tyr Pro Gly Thr Gly Gly Ser Asn Phe Asp Glu Lys Phe
        50                  55                  60

Lys Asn Arg Thr Ser Leu Thr Val Asp Thr Ser Ser Thr Thr Ala Tyr
65                  70                  75                  80

Met His Leu Ala Ser Leu Thr Ser Glu Asp Ser Ala Val Tyr Tyr Cys
                85                  90                  95

Thr Arg Trp Thr Thr Gly Thr Gly Ala Tyr Trp Gly Gln Gly Thr Thr
                100                 105                 110

Val Thr Val Ser Ser
        115
```

```
<210> SEQ ID NO 19
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

-continued

<400> SEQUENCE: 19

```
caggtccagc tgcagcagcc tgggtctgag ctggtgaggc ctggagcttc agtgaagctg        60
tcctgcaagg cgtctggcta cacattcacc acttactgga tgcactgggt gaggcagagg       120
cctggacaag gccttgagtg gattggaaat atttatcctg gtactggtgg ttctaacttc       180
gatgagaagt tcaaaaacag gacctcactg actgtagaca catcctccac cacagcctac       240
atgcacctcg ccagcctgac atctgaggac tctgcggtct attactgtac aagatggact       300
actgggacgg agcttattg gggccaggg accaccgtga ccgtgtcctc c                   351
```

```
<210> SEQ ID NO 20
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 20

```
Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Thr Tyr
                20                  25                  30

Trp Met His Trp Val Arg Gln Arg Pro Gly Gln Gly Leu Glu Trp Ile
            35                  40                  45

Gly Asn Ile Tyr Pro Gly Thr Gly Gly Ser Asn Phe Asp Glu Lys Phe
        50                  55                  60

Lys Asn Arg Thr Ser Leu Thr Val Asp Thr Ser Ser Thr Thr Ala Tyr
65                  70                  75                  80

Met His Leu Ala Ser Leu Thr Ser Glu Asp Ser Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
```

-continued

```
            275                 280                 285
Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys
                435                 440
```

<210> SEQ ID NO 21
<211> LENGTH: 1332
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21

```
caggtccagc tgcagcagcc tgggtctgag ctggtgaggc ctggagcttc agtgaagctg      60
tcctgcaagg cgtctggcta cacattcacc acttactgga tgcactgggt gaggcagagg     120
cctggacaag gccttgagtg gattggaaat atttatcctg gtactggtgg ttctaacttc     180
gatgagaagt tcaaaaacag gacctcactg actgtagaca tcctccacac cagcctac       240 atgcacctcg ccagcctgac atctgaggac tctgcggtct attactgtac aagatggact     300
actgggacgg gagcttattg gggccagggc accaccgtga ccgtgtcctc cgcttccacc     360
aagggcccat ccgtcttccc cctggcgccc tgctccagga gcacctccga gagcacagcc     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacgaagac ctacacctgc     600
aacgtagatc acaagcccag caacaccaag gtggacaaga gagttgagtc caaatatggt     660
cccccatgcc caccgtgccc agcacctgag ttcctggggg gaccatcagt cttcctgttc     720
cccccaaaac ccaaggacac tctcatgatc tcccggaccc ctgaggtcac gtgcgtggtg     780
gtggacgtga gccaggaaga ccccgaggtc cagttcaact ggtacgtgga tggcgtggag     840
gtgcataatg ccaagacaaa gccgcgggag gagcagttca acagcacgta ccgtgtggtc     900
agcgtcctca ccgtcctgca ccaggactgg ctgaacggca aggagtacaa gtgcaaggtg     960
tccaacaaag gcctcccgtc ctccatcgag aaaaccatct ccaaagccaa agggcagccc    1020
cgagagccac aggtgtacac cctgcccccca tcccaggagg agatgaccaa gaaccaggtc    1080
```

-continued

```
agcctgacct gcctggtcaa aggcttctac cccagcgaca tcgccgtgga gtgggagagc    1140
aatgggcagc cggagaacaa ctacaagacc acgcctcccg tgctggactc cgacggctcc    1200
ttcttcctct acagcaggct aaccgtggac aagagcaggt ggcaggaggg gaatgtcttc    1260
tcatgctccg tgatgcatga ggctctgcac aaccactaca cacagaagag cctctccctg    1320
tctctgggta aa                                                       1332
```

```
<210> SEQ ID NO 22
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Gln Val Gln Leu Gln Gln Ser Gly Ser Glu Leu Val Arg Pro Gly Ala
1               5                   10                  15

Ser Val Lys Leu Ser Cys Lys Ala Ser Gly Tyr Thr Phe Thr Thr Tyr
            20                  25                  30

Trp Met His Trp Val Arg Gln Arg Pro Gly Gln Gly Leu Glu Trp Ile
        35                  40                  45

Gly Asn Ile Tyr Pro Gly Thr Gly Gly Ser Asn Phe Asp Glu Lys Phe
    50                  55                  60

Lys Asn Arg Thr Ser Leu Thr Val Asp Thr Ser Ser Thr Thr Ala Tyr
65                  70                  75                  80

Met His Leu Ala Ser Leu Thr Ser Glu Asp Ser Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser
        115
```

```
<210> SEQ ID NO 23
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 23
caggtccagc tgcagcagtc tgggtctgag ctggtgaggc ctggagcttc agtgaagctg     60
tcctgcaagg cgtctggcta cacattcacc acttactgga tgcactgggt gaggcagagg    120
cctggacaag gccttgagtg gattggaaat atttatcctg gtactggtgg ttctaacttc    180
gatgagaagt tcaaaaacag gacctcactg actgtagaca tcctccacac acagcctac     240 atgcacctcg ccagcctgac atctgaggac tctgcggtct attactgtac aagatggact    300
actgggacgg gagcttattg gggccagggc accaccgtga ccgtgtcctc c            351
```

```
<210> SEQ ID NO 24
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
```

-continued

Synthetic polypeptide"

<400> SEQUENCE: 24

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Thr Gly Ser Gly Ser Val Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Cys Thr Phe Gly Gln Gly Thr Lys Val Glu Ile
            100                 105                 110

Lys

<210> SEQ ID NO 25
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 25
gacattgtga tgacccagtc tccatcctcc ctgactgtga cagcaggaga gaaggtcact      60
atgagctgca agtccagtca gagtctgtta gacagtggaa atcaaaagaa cttcttgacc     120
tggtaccagc agaaaccagg gcagcctcct aaactgttga tcttctgggc atccactagg     180
gaatctgggg tccctgatcg cttcacaggc agtggatctg taacagattt cactctcacc     240
atcagcagtg tgcaggctga agacctggca gtttattact gtcagaatga ttatagttat     300
ccgtgcacgt tcggccaagg gaccaaggtg gaaatcaaa                            339

<210> SEQ ID NO 26
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Thr Gly Ser Gly Ser Val Thr Asp Phe Thr Leu Thr
65                  70                  75                  80

Ile Ser Ser Val Gln Ala Glu Asp Leu Ala Val Tyr Tyr Cys Gln Asn

-continued

```
                    85              90              95
Asp Tyr Ser Tyr Pro Cys Thr Phe Gly Gln Gly Thr Lys Val Glu Ile
            100             105             110

Lys Arg Thr Val Ala Ala Pro Ser Val Phe Ile Phe Pro Pro Ser Asp
        115             120             125

Glu Gln Leu Lys Ser Gly Thr Ala Ser Val Val Cys Leu Leu Asn Asn
    130             135             140

Phe Tyr Pro Arg Glu Ala Lys Val Gln Trp Lys Val Asp Asn Ala Leu
145             150             155             160

Gln Ser Gly Asn Ser Gln Glu Ser Val Thr Glu Gln Asp Ser Lys Asp
            165             170             175

Ser Thr Tyr Ser Leu Ser Ser Thr Leu Thr Leu Ser Lys Ala Asp Tyr
            180             185             190

Glu Lys His Lys Val Tyr Ala Cys Glu Val Thr His Gln Gly Leu Ser
        195             200             205

Ser Pro Val Thr Lys Ser Phe Asn Arg Gly Glu Cys
    210             215             220
```

```
<210> SEQ ID NO 27
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 27
gacattgtga tgacccagtc tccatcctcc ctgactgtga cagcaggaga gaaggtcact      60
atgagctgca agtccagtca gagtctgtta gacagtggaa tcaaaagaa cttcttgacc      120 tggtaccagc agaaaccagg gcagcctcct aaactgttga tcttctgggc atccactagg      180
gaatctgggg tccctgatcg cttcacaggc agtggatctg taacagattt cactctcacc      240
atcagcagtg tgcaggctga agacctggca gtttattact gtcagaatga ttatagttat      300
ccgtgcacgt tcggccaagg gaccaaggtg gaaatcaaac gtacggtggc tgcaccatct      360
gtcttcatct tcccgccatc tgatgagcag ttgaaatctg gaactgcctc tgttgtgtgc      420
ctgctgaata acttctatcc cagagaggcc aaagtacagt ggaaggtgga taacgccctc      480
caatcgggta actcccagga gagtgtcaca gagcaggaca gcaaggacag cacctacagc      540
ctcagcagca ccctgacgct gagcaaagca gactacgaga aacacaaagt ctacgcctgc      600
gaagtcaccc atcagggcct gagctcgccc gtcacaaaga gcttcaacag gggagagtgt      660

<210> SEQ ID NO 28

<400> SEQUENCE: 28

000

<210> SEQ ID NO 29

<400> SEQUENCE: 29

000

<210> SEQ ID NO 30
<211> LENGTH: 444
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 30

Gln Val Gln Leu Gln Gln Ser Gly Ser Glu Leu Val Arg Pro Gly Ala
1               5                   10                  15

Ser Val Lys Leu Ser Cys Lys Ala Ser Gly Tyr Thr Phe Thr Thr Tyr
            20                  25                  30

Trp Met His Trp Val Arg Gln Arg Pro Gly Gln Gly Leu Glu Trp Ile
        35                  40                  45

Gly Asn Ile Tyr Pro Gly Thr Gly Gly Ser Asn Phe Asp Glu Lys Phe
    50                  55                  60

Lys Asn Arg Thr Ser Leu Thr Val Asp Thr Ser Ser Thr Thr Ala Tyr
65                  70                  75                  80

Met His Leu Ala Ser Leu Thr Ser Glu Asp Ser Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
    370                 375                 380
```

-continued

Glu Asn Asn Tyr Lys Thr Thr Pro Pro Val Leu Asp Ser Asp Gly Ser
385                 390             395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys
            435                 440

<210> SEQ ID NO 31
<211> LENGTH: 1332
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 31
caggtccagc tgcagcagtc tgggtctgag ctggtgaggc ctggagcttc agtgaagctg        60
tcctgcaagg cgtctggcta cacattcacc acttactgga tgcactgggt gaggcagagg       120
cctggacaag gccttgagtg gattggaaat atttatcctg gtactggtgg ttctaacttc       180
gatgagaagt tcaaaaacag gacctcactg actgtagaca catcctccac cacagcctac       240
atgcacctcg ccagcctgac atctgaggac tctgcggtct attactgtac aagatggact       300
actgggacgg gagcttattg gggccagggc accaccgtga ccgtgtcctc cgcttccacc       360
aagggcccat ccgtcttccc cctggcgccc tgctccagga gcacctccga gagcacagcc       420
gccctgggct gcctggtcaa ggactacttc cccgaaccgg tgacggtgtc gtggaactca       480
ggcgccctga ccagcggcgt gcacaccttc ccggctgtcc tacagtcctc aggactctac       540
tccctcagca gcgtggtgac cgtgccctcc agcagcttgg gcacgaagac ctacacctgc       600
aacgtagatc acaagcccag caacaccaag gtggacaaga gagttgagtc caaatatggt       660
cccccatgcc caccgtgccc agcacctgag ttcctggggg gaccatcagt cttcctgttc       720
cccccaaaac ccaaggacac tctcatgatc tcccggaccc ctgaggtcac gtgcgtggtg       780
gtggacgtga gccaggaaga ccccgaggtc cagttcaact ggtacgtgga tggcgtggag       840
gtgcataatg ccaagacaaa gccgcgggag gagcagttca acagcacgta ccgtgtggtc       900
agcgtcctca ccgtcctgca ccaggactgg ctgaacggca aggagtacaa gtgcaaggtg       960
tccaacaaag gcctcccgtc ctccatcgag aaaaccatct ccaaagccaa agggcagccc      1020
cgagagccac aggtgtacac cctgcccccä tcccaggagg agatgaccaa gaaccaggtc      1080
agcctgacct gcctggtcaa aggcttctac cccagcgaca tcgccgtgga gtgggagagc      1140
aatgggcagc cggagaacaa ctacaagacc acgcctcccg tgctggactc cgacggctcc      1200
ttcttcctct acagcaggct aaccgtggac aagagcaggt ggcaggaggg gaatgtcttc      1260
tcatgctccg tgatgcatga ggctctgcac aaccactaca cacagaagag cctctccctg      1320
tctctgggta aa                                                          1332

<210> SEQ ID NO 32
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

-continued

<400> SEQUENCE: 32

Gln Asn Asp Tyr Ser Tyr Pro Tyr Thr
1               5

<210> SEQ ID NO 33
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Asp Tyr Ser Tyr Pro Tyr
1               5

<210> SEQ ID NO 34
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asp Ser
                20                  25                  30

Gly Asn Gln Lys Asn Phe Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Thr Gly Ser Gly Ser Val Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys

<210> SEQ ID NO 35
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 35
gacattgtga tgacccagtc tccatcctcc ctgactgtga cagcaggaga gaaggtcact      60
atgagctgca agtccagtca gagtctgtta gacagtggaa atcaaaagaa cttcttgacc     120
tggtaccagc agaaaccagg gcagcctcct aaactgttga tcttctgggc atccactagg     180
gaatctgggg tccctgatcg cttcacaggc agtggatctg taacagattt cactctcacc     240
atcagcagtg tgcaggctga agacctggca gtttattact gtcagaatga ttatagttat     300
ccgtacacgt tcggccaagg gaccaaggtg gaaatcaaa                            339

<210> SEQ ID NO 36
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Thr Gly Ser Gly Ser Val Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 37
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 37
gacattgtga tgacccagtc tccatcctcc ctgactgtga cagcaggaga gaaggtcact      60
atgagctgca agtccagtca gagtctgtta gacagtggaa atcaaaagaa cttcttgacc     120
tggtaccagc agaaaccagg gcagcctcct aaactgttga tcttctgggc atccactagg     180
gaatctgggg tccctgatcg cttcacaggc agtggatctg taacagattt cactctcacc     240
atcagcagtg tgcaggctga agacctggca gtttattact gtcagaatga ttatagttat     300
ccgtacacgt tcggccaagg gaccaaggtg gaaatcaaac gtacggtggc tgcaccatct     360

```
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaagt ctacgcctgc    600 gaagtcaccc atcagggcct gagctcgccc gtcacaaaga gcttcaacag gggagagtgt    660
```

<210> SEQ ID NO 38
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Thr Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser
        115

<210> SEQ ID NO 39
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 39

```
gaagtgcagc tggtgcagtc tggagcagag gtgaaaaagc ccggggagtc tctgaggatc     60
tcctgtaagg gttctggcta cacattcacc acttactgga tgcactgggt gcgacaggcc    120
actggacaag gcttgagtg gatgggtaat atttatcctg gtactggtgg ttctaacttc    180
gatgagaagt tcaagaacag agtcacgatt accgcggaca atccacgag cacagcctac    240 atggagctga gcagcctgag atctgaggac acggccgtgt attactgtac aagatggact    300
actgggacgg gagcttattg gggccagggc accaccgtga ccgtgtcctc c             351
```

<210> SEQ ID NO 40
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

-continued

<400> SEQUENCE: 40

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Thr Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
```

-continued

```
              405                 410                 415
Gly Asn Val Phe Ser Cys Ser Val Met His Glu Ala Leu His Asn His
          420                 425                 430

Tyr Thr Gln Lys Ser Leu Ser Leu Ser Leu Gly Lys
          435                 440
```

```
<210> SEQ ID NO 41
<211> LENGTH: 1332
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 41
gaagtgcagc tggtgcagtc tggagcagag gtgaaaaagc ccggggagtc tctgaggatc      60
tcctgtaagg gttctggcta cacattcacc acttactgga tgcactgggt gcgacaggcc     120
actggacaag ggcttgagtg gatgggtaat atttatcctg gtactggtgg ttctaacttc     180
gatgagaagt tcaagaacag agtcacgatt accgcggaca atccacgag cacagcctac      240 atggagctga gcagcctgag atctgaggac acggccgtgt attactgtac aagatggact     300
actgggacgg agcttattg gggccagggc accaccgtga ccgtgtcctc cgcttccacc      360
aagggcccat ccgtcttccc cctggcgccc tgctccagga gcacctccga gagcacagcc     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacgaagac ctacacctgc     600
aacgtagatc acaagcccag caacaccaag gtggacaaga gagttgagtc caaatatggt     660
cccccatgcc caccgtgccc agcacctgag ttcctggggg gaccatcagt cttcctgttc     720
cccccaaaac ccaaggacac tctcatgatc tcccggaccc ctgaggtcac gtgcgtggtg     780
gtggacgtga gccaggaaga ccccgaggtc cagttcaact ggtacgtgga tggcgtggag     840
gtgcataatg ccaagacaaa gccgcgggag gagcagttca acagcacgta ccgtgtggtc     900
agcgtcctca ccgtcctgca ccaggactgg ctgaacggca aggagtacaa gtgcaaggtg     960
tccaacaaag gcctcccgtc ctccatcgag aaaaccatct ccaaagccaa agggcagccc    1020
cgagagccac aggtgtacac cctgcccccca tcccaggagg agatgaccaa gaaccaggtc    1080
agcctgacct gcctggtcaa aggcttctac cccagcgaca tcgccgtgga gtgggagagc    1140
aatgggcagc cggagaacaa ctacaagacc acgcctcccg tgctggactc cgacggctcc    1200
ttcttcctct acagcaggct aaccgtggac aagagcaggt ggcaggaggg gaatgtcttc    1260
tcatgctccg tgatgcatga ggctctgcac aaccactaca cacagaagag cctctcoctg    1320 tctctgggta aa                                                       1332
```

```
<210> SEQ ID NO 42
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Glu Ile Val Leu Thr Gln Ser Pro Ala Thr Leu Ser Leu Ser Pro Gly
```

-continued

```
1                5                10               15
Glu Arg Ala Thr Leu Ser Cys Lys Ser Ser Gln Ser Leu Leu Asp Ser
            20                   25                   30

Gly Asn Gln Lys Asn Phe Leu Thr Trp Tyr Gln Gln Lys Pro Gly Gln
        35                   40                   45

Ala Pro Arg Leu Leu Ile Tyr Trp Ala Ser Thr Arg Glu Ser Gly Val
    50                   55                   60

Pro Ser Arg Phe Ser Gly Ser Gly Ser Gly Thr Glu Phe Thr Leu Thr
65                   70                   75                   80

Ile Ser Ser Leu Gln Pro Asp Asp Phe Ala Thr Tyr Tyr Cys Gln Asn
                85                   90                   95

Asp Tyr Ser Tyr Pro Tyr Thr Phe Gly Gln Gly Thr Lys Val Glu Ile
            100                  105                  110

Lys
```

```
<210> SEQ ID NO 43
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 43
gaaattgtgt tgacacagtc tccagccacc ctgtctttgt ctccagggga aagagccacc      60
ctctcctgca agtccagtca gagtctgtta gacagtggaa atcaaaagaa cttcttgacc     120
tggtaccagc agaaacctgg ccaggctccc aggctcctca tctattgggc atccactagg     180
gaatctgggg tccatcaag gttcagcggc agtggatctg ggacagaatt cactctcacc     240
atcagcagcc tgcagcctga tgattttgca acttattact gtcagaatga ttatagttat     300
ccgtacacgt tcggccaagg gaccaaggtg gaaatcaaa                             339
```

```
<210> SEQ ID NO 44
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44
```

```
Glu Ile Val Leu Thr Gln Ser Pro Ala Thr Leu Ser Leu Ser Pro Gly
1                5                10               15

Glu Arg Ala Thr Leu Ser Cys Lys Ser Ser Gln Ser Leu Leu Asp Ser
            20                   25                   30

Gly Asn Gln Lys Asn Phe Leu Thr Trp Tyr Gln Gln Lys Pro Gly Gln
        35                   40                   45

Ala Pro Arg Leu Leu Ile Tyr Trp Ala Ser Thr Arg Glu Ser Gly Val
    50                   55                   60

Pro Ser Arg Phe Ser Gly Ser Gly Ser Gly Thr Glu Phe Thr Leu Thr
65                   70                   75                   80

Ile Ser Ser Leu Gln Pro Asp Asp Phe Ala Thr Tyr Tyr Cys Gln Asn
                85                   90                   95

Asp Tyr Ser Tyr Pro Tyr Thr Phe Gly Gln Gly Thr Lys Val Glu Ile
            100                  105                  110
```

-continued

```
Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

```
<210> SEQ ID NO 45
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 45
gaaattgtgt tgacacagtc tccagccacc ctgtctttgt ctccagggga aagagccacc        60
ctctcctgca agtccagtca gagtctgtta gacagtggaa atcaaaagaa cttcttgacc       120
tggtaccagc agaaacctgg ccaggctccc aggctcctca tctattgggc atccactagg       180
gaatctgggg tcccatcaag gttcagcggc agtggatctg ggacagaatt cactctcacc       240
atcagcagcc tgcagcctga tgattttgca acttattact gtcagaatga ttatagttat       300
ccgtacacgt tcggccaagg gaccaaggtg gaaatcaaac gtacggtggc tgcaccatct       360
gtcttcatct tcccgccatc tgatgagcag ttgaaatctg gaactgcctc tgttgtgtgc       420
ctgctgaata acttctatcc cagagaggcc aaagtacagt ggaaggtgga taacgccctc       480
caatcgggta actcccagga gagtgtcaca gagcaggaca gcaaggacag cacctacagc       540
ctcagcagca ccctgacgct gagcaaagca gactacgaga aacacaaagt ctacgcctgc       600
gaagtcaccc atcagggcct gagctcgccc gtcacaaaga gcttcaacag gggagagtgt       660
```

```
<210> SEQ ID NO 46
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asp Ser
                20                  25                  30

Gly Asn Gln Lys Asn Phe Leu Thr Trp Tyr Gln Gln Lys Pro Gly Gln
            35                  40                  45

Ala Pro Arg Leu Leu Ile Tyr Trp Ala Ser Thr Arg Glu Ser Gly Ile
    50                  55                  60
```

-continued

```
Pro Pro Arg Phe Ser Gly Ser Gly Tyr Gly Thr Asp Phe Thr Leu Thr
65              70              75              80

Ile Asn Asn Ile Glu Ser Glu Asp Ala Ala Tyr Tyr Phe Cys Gln Asn
                85              90              95

Asp Tyr Ser Tyr Pro Tyr Thr Phe Gly Gln Gly Thr Lys Val Glu Ile
            100             105             110

Lys
```

<210> SEQ ID NO 47
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 47

```
gacatccaga tgacccagtc tccatcctcc ctgtctgcat ctgtaggaga cagagtcacc      60
atcacttgca agtccagtca gagtctgtta gacagtggaa atcaaaagaa cttcttgacc     120
tggtaccagc agaaacctgg ccaggctccc aggctcctca tctattgggc atccactagg     180
gaatctggga tcccacctcg attcagtggc agcgggtatg gaacagattt taccctcaca     240
attaataaca tagaatctga ggatgctgca tattacttct gtcagaatga ttatagttat     300
ccgtacacgt tcggccaagg gaccaaggtg gaaatcaaa                            339
```

<210> SEQ ID NO 48
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

```
Asp Ile Gln Met Thr Gln Ser Pro Ser Ser Leu Ser Ala Ser Val Gly
1               5               10              15

Asp Arg Val Thr Ile Thr Cys Lys Ser Ser Gln Ser Leu Leu Asp Ser
                20              25              30

Gly Asn Gln Lys Asn Phe Leu Thr Trp Tyr Gln Gln Lys Pro Gly Gln
            35              40              45

Ala Pro Arg Leu Leu Ile Tyr Trp Ala Ser Thr Arg Glu Ser Gly Ile
        50              55              60

Pro Pro Arg Phe Ser Gly Ser Gly Tyr Gly Thr Asp Phe Thr Leu Thr
65              70              75              80

Ile Asn Asn Ile Glu Ser Glu Asp Ala Ala Tyr Tyr Phe Cys Gln Asn
                85              90              95

Asp Tyr Ser Tyr Pro Tyr Thr Phe Gly Gln Gly Thr Lys Val Glu Ile
            100             105             110

Lys Arg Thr Val Ala Ala Pro Ser Val Phe Ile Phe Pro Pro Ser Asp
            115             120             125

Glu Gln Leu Lys Ser Gly Thr Ala Ser Val Val Cys Leu Leu Asn Asn
        130             135             140

Phe Tyr Pro Arg Glu Ala Lys Val Gln Trp Lys Val Asp Asn Ala Leu
145             150             155             160

Gln Ser Gly Asn Ser Gln Glu Ser Val Thr Glu Gln Asp Ser Lys Asp
            165             170             175
```

```
Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220
```

<210> SEQ ID NO 49
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 49

```
gacatccaga tgacccagtc tccatcctcc ctgtctgcat ctgtaggaga cagagtcacc      60
atcacttgca agtccagtca gagtctgtta gacagtggaa atcaaaagaa cttcttgacc     120
tggtaccagc agaaacctgg ccaggctccc aggctcctca tctattgggc atccactagg     180
gaatctggga tcccacctcg attcagtggc agcgggtatg gaacagattt taccctcaca     240
attaataaca tagaatctga ggatgctgca tattacttct gtcagaatga ttatagttat     300
ccgtacacgt tcggccaagg gaccaaggtg gaaatcaaac gtacggtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga aacacaaagt ctacgcctgc     600
gaagtcaccc atcagggcct gagctcgccc gtcacaaaga gcttcaacag gggagagtgt     660
```

<210> SEQ ID NO 50
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 50

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Ile Arg Gln Ser Pro Ser Arg Gly Leu Glu Trp Leu
        35                  40                  45

Gly Asn Ile Tyr Pro Gly Thr Gly Gly Ser Asn Phe Asp Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser
        115
```

```
<210> SEQ ID NO 51
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 51
gaagtgcagc tggtgcagtc tggagcagag gtgaaaaagc ccggggagtc tctgaggatc        60
tcctgtaagg gttctggcta cacattcacc acttactgga tgcactggat caggcagtcc       120
ccatcgagag gccttgagtg gctgggtaat atttatcctg gtactggtgg ttctaacttc       180
gatgagaagt tcaagaacag attcaccatc tccagagaca attccaagaa cacgctgtat       240
cttcaaatga acagcctgag agccgaggac acggccgtgt attactgtac aagatggact       300
actgggacgg gagcttattg gggccagggc accaccgtga ccgtgtcctc c                351

<210> SEQ ID NO 52
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Ile Arg Gln Ser Pro Ser Arg Gly Leu Glu Trp Leu
        35                  40                  45

Gly Asn Ile Tyr Pro Gly Thr Gly Gly Ser Asn Phe Asp Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220
```

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys
        435                 440

<210> SEQ ID NO 53
<211> LENGTH: 1332
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 53
gaagtgcagc tggtgcagtc tggagcagag gtgaaaaagc ccggggagtc tctgaggatc      60
tcctgtaagg gttctggcta cacattcacc acttactgga tgcactggat caggcagtcc     120
ccatcgagag gccttgagtg gctgggtaat atttatcctg gtactggtgg ttctaacttc     180
gatgagaagt tcaagaacag attcaccatc tccagagaca attccaagaa cacgctgtat     240
cttcaaatga acagcctgag agccgaggac acggccgtgt attactgtac aagatggact     300
actgggacgg gagcttattg gggccagggc accaccgtga ccgtgtcctc cgcttccacc     360
aagggcccat ccgtcttccc cctggcgccc tgctccagga gcacctccga gagcacagcc     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacgaagac ctacacctgc     600
aacgtagatc acaagcccag caacaccaag gtggacaaga gagttgagtc caaatatggt     660
cccccatgcc caccgtgccc agcacctgag ttcctggggg gaccatcagt cttcctgttc     720
cccccaaaac ccaaggacac tctcatgatc tcccggaccc ctgaggtcac gtgcgtggtg     780

-continued

```
gtggacgtga gccaggaaga cccccgaggtc cagttcaact ggtacgtgga tggcgtggag      840
gtgcataatg ccaagacaaa gccgcgggag gagcagttca acagcacgta ccgtgtggtc      900
agcgtcctca ccgtcctgca ccaggactgg ctgaacggca aggagtacaa gtgcaaggtg      960
tccaacaaag gcctcccgtc ctccatcgag aaaaccatct ccaaagccaa agggcagccc     1020
cgagagccac aggtgtacac cctgccccca tcccaggagg agatgaccaa gaaccaggtc     1080
agcctgacct gcctggtcaa aggcttctac cccagcgaca tcgccgtgga gtgggagagc     1140
aatgggcagc cggagaacaa ctacaagacc acgcctcccg tgctggactc cgacggctcc     1200
ttcttcctct acagcaggct aaccgtggac aagagcaggt ggcaggaggg gaatgtcttc     1260
tcatgctccg tgatgcatga ggctctgcac aaccactaca cacagaagag cctctccctg     1320
tctctgggta aa                                                        1332
```

```
<210> SEQ ID NO 54
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys
```

```
<210> SEQ ID NO 55
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 55
gaaattgtgt tgacacagtc tccagccacc ctgtctttgt ctccagggga aagagccacc       60
ctctcctgca gtccagtca gagtctgtta gacagtggaa tcaaaagaa cttcttgacc       120 tggtatcagc agaaaccagg gaaagctcct aagctcctga tctattgggc atccactagg      180
gaatctgggg tcccatcaag gttcagtgga agtggatctg ggacagattt tactttcacc      240
atcagcagcc tgcagcctga agatattgca acatattact gtcagaatga ttatagttat      300
ccgtacacgt tcggccaagg gaccaaggtg gaaatcaaa                             339
```

```
<210> SEQ ID NO 56
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 57
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 57
gaaattgtgt tgacacagtc tccagccacc ctgtctttgt ctccagggga aagagccacc        60
ctctcctgca agtccagtca gagtctgtta gacagtggaa atcaaaagaa cttcttgacc       120
tggtatcagc agaaaccagg gaaagctcct aagctcctga tctattgggc atccactagg       180
gaatctgggg tcccatcaag gttcagtgga agtggatctg ggacagattt tactttcacc       240
atcagcagcc tgcagcctga agatattgca acatattact gtcagaatga ttatagttat       300
ccgtacacgt tcggccaagg gaccaaggtg gaaatcaaac gtacggtggc tgcaccatct       360
```

-continued

```
gtcttcatct tcccgccatc tgatgagcag ttgaaatctg gaactgcctc tgttgtgtgc      420
ctgctgaata acttctatcc cagagaggcc aaagtacagt ggaaggtgga taacgccctc      480
caatcgggta actcccagga gagtgtcaca gagcaggaca gcaaggacag cacctacagc      540
ctcagcagca ccctgacgct gagcaaagca gactacgaga acacaaagt ctacgcctgc       600 gaagtcaccc atcagggcct gagctcgccc gtcacaaaga gcttcaacag gggagagtgt      660
```

```
<210> SEQ ID NO 58
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys
```

```
<210> SEQ ID NO 59
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 59
gatattgtga tgacccagac tccactctcc ctgcccgtca cccctggaga gccggcctcc       60
atctcctgca gtccagtca gagtctgtta gacagtggaa atcaaaagaa cttcttgacc       120
tggtaccagc agaaacctgg ccaggctccc aggctcctca tctattgggc atccactagg      180
gaatctgggg tcccctcgag gttcagtggc agtggatctg ggacagattt caccttacc       240 atcagtagcc tggaagctga agatgctgca acatattact gtcagaatga ttatagttat      300
ccgtacacgt tcggccaagg gaccaaggtg gaaatcaaa                             339
```

```
<210> SEQ ID NO 60
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

```
<400> SEQUENCE: 60

Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 61
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 61
gatattgtga tgacccagac tccactctcc ctgcccgtca cccctggaga gccggcctcc      60
atctcctgca gtccagtca gagtctgtta gacagtggaa atcaaaagaa cttcttgacc      120
tggtaccagc agaaacctgg ccaggctccc aggctcctca tctattgggc atccactagg      180
gaatctgggg tccctcgag gttcagtggc agtggatctg ggacagattt cacctttacc      240
atcagtagcc tggaagctga agatgctgca acatattact gtcagaatga ttatagttat      300
ccgtacacgt tcggccaagg gaccaaggtg gaaatcaaac gtacggtggc tgcaccatct      360
gtcttcatct tcccgccatc tgatgagcag ttgaaatctg gaactgcctc tgttgtgtgc      420
ctgctgaata acttctatcc cagagaggcc aaagtacagt ggaaggtgga taacgccctc      480
caatcgggta actcccagga gagtgtcaca gagcaggaca gcaaggacag cacctacagc      540
ctcagcagca ccctgacgct gagcaaagca gactacgaga aacacaaagt ctacgcctgc      600
gaagtcaccc atcagggcct gagctcgccc gtcacaaaga gcttcaacag gggagagtgt      660
```

-continued

```
<210> SEQ ID NO 62
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys

<210> SEQ ID NO 63
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 63
gaaattgtgt tgacacagtc tccagccacc ctgtctttgt ctccagggga aagagccacc       60
ctctcctgca gtccagtca gagtctgtta gacagtggaa atcaaaagaa cttcttgacc       120
tggtatcagc agaaaccagg gaaagctcct aagctcctga tctattgggc atccactagg      180
gaatctgggg tcccctcgag gttcagtggc agtggatctg ggacagattt cacctttacc      240
atcagtagcc tggaagctga agatgctgca acatattact gtcagaatga ttatagttat      300
ccgtacacgt tcggccaagg gaccaaggtg gaaatcaaa                              339

<210> SEQ ID NO 64
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45
```

```
Ala Pro Lys Leu Leu Ile Tyr Trp Ala Ser Thr Arg Glu Ser Gly Val
    50              55              60
```

```
Pro Ser Arg Phe Ser Gly Ser Gly Ser Gly Thr Asp Phe Thr Phe Thr
65              70              75              80
```

```
Ile Ser Ser Leu Glu Ala Glu Asp Ala Ala Thr Tyr Tyr Cys Gln Asn
            85              90              95
```

```
Asp Tyr Ser Tyr Pro Tyr Thr Phe Gly Gln Gly Thr Lys Val Glu Ile
            100             105             110
```

```
Lys Arg Thr Val Ala Ala Pro Ser Val Phe Ile Phe Pro Pro Ser Asp
        115             120             125
```

```
Glu Gln Leu Lys Ser Gly Thr Ala Ser Val Val Cys Leu Leu Asn Asn
    130             135             140
```

```
Phe Tyr Pro Arg Glu Ala Lys Val Gln Trp Lys Val Asp Asn Ala Leu
145             150             155             160
```

```
Gln Ser Gly Asn Ser Gln Glu Ser Val Thr Glu Gln Asp Ser Lys Asp
            165             170             175
```

```
Ser Thr Tyr Ser Leu Ser Ser Thr Leu Thr Leu Ser Lys Ala Asp Tyr
            180             185             190
```

```
Glu Lys His Lys Val Tyr Ala Cys Glu Val Thr His Gln Gly Leu Ser
        195             200             205
```

```
Ser Pro Val Thr Lys Ser Phe Asn Arg Gly Glu Cys
    210             215             220
```

```
<210> SEQ ID NO 65
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 65
gaaattgtgt tgacacagtc tccagccacc ctgtctttgt ctccagggga aagagccacc        60
ctctcctgca agtccagtca gagtctgtta gacagtggaa atcaaaagaa cttcttgacc       120
tggtatcagc agaaaccagg gaaagctcct aagctcctga tctattgggc atccactagg       180
gaatctgggg tcccctcgag gttcagtggc agtggatctg ggacagattt cacctttacc       240
atcagtagcc tggaagctga agatgctgca acatattact gtcagaatga ttatagttat       300
ccgtacacgt tcggccaagg gaccaaggtg gaaatcaaac gtacggtggc tgcaccatct       360
gtcttcatct tcccgccatc tgatgagcag ttgaaatctg gaactgcctc tgttgtgtgc       420
ctgctgaata acttctatcc cagagaggcc aaagtacagt ggaaggtgga taacgccctc       480
caatcgggta actcccagga gagtgtcaca gagcaggaca gcaaggacag cacctacagc       540
ctcagcagca ccctgacgct gagcaaagca gactacgaga aacacaaagt ctacgcctgc       600
gaagtcaccc atcagggcct gagctcgccc gtcacaaaga gcttcaacag gggagagtgt       660

<210> SEQ ID NO 66
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66
```

```
Glu Ile Val Leu Thr Gln Ser Pro Asp Phe Gln Ser Val Thr Pro Lys
1               5                   10                  15

Glu Lys Val Thr Ile Thr Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys
```

```
<210> SEQ ID NO 67
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 67
gaaattgtgc tgactcagtc tccagacttt cagtctgtga ctccaaagga gaaagtcacc      60
atcacctgca agtccagtca gagtctgtta gacagtggaa atcaaaagaa cttcttgacc     120
tggtaccagc agaaacctgg ccaggctccc aggctcctca tctattgggc atccactagg     180
gaatctgggg tcccctcgag gttcagtggc agtggatctg ggacagattt cacctttacc     240
atcagtagcc tggaagctga agatgctgca acatattact gtcagaatga ttatagttat     300
ccgtacacgt tcggccaagg gaccaaggtg gaaatcaaa                            339
```

```
<210> SEQ ID NO 68
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Glu Ile Val Leu Thr Gln Ser Pro Asp Phe Gln Ser Val Thr Pro Lys
1               5                   10                  15

Glu Lys Val Thr Ile Thr Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110
```

```
Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220
```

<210> SEQ ID NO 69
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 69

```
gaaattgtgc tgactcagtc tccagacttt cagtctgtga ctccaaagga gaaagtcacc      60
atcacctgca gtccagtca gagtctgtta gacagtggaa atcaaaagaa cttcttgacc     120
tggtaccagc agaaacctgg ccaggctccc aggctcctca tctattgggc atccactagg     180
gaatctgggg tccctcgag gttcagtggc agtggatctg ggacagattt caccttttacc    240 atcagtagcc tggaagctga agatgctgca acatattact gtcagaatga ttatagttat     300
ccgtacacgt tcggccaagg gaccaaggtg gaaatcaaac gtacggtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga aacacaaagt ctacgcctgc     600
gaagtcaccc atcagggcct gagctcgccc gtcacaaaga gcttcaacag gggagagtgt     660
```

<210> SEQ ID NO 70
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

```
Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60
```

-continued

```
Pro Ser Arg Phe Ser Gly Ser Gly Ser Gly Thr Asp Phe Thr Phe Thr
65              70              75              80

Ile Ser Ser Leu Glu Ala Glu Asp Ala Ala Thr Tyr Tyr Cys Gln Asn
            85              90              95

Asp Tyr Ser Tyr Pro Tyr Thr Phe Gly Gln Gly Thr Lys Val Glu Ile
        100             105             110

Lys
```

<210> SEQ ID NO 71
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 71

```
gaaattgtgt tgacacagtc tccagccacc ctgtctttgt ctccagggga aagagccacc        60
ctctcctgca agtccagtca gagtctgtta gacagtggaa atcaaaagaa cttcttgacc       120
tggtaccagc agaaacctgg ccaggctccc aggctcctca tctattgggc atccactagg       180
gaatctgggg tcccctcgag gttcagtggc agtggatctg ggacagattt cacctttacc       240
atcagtagcc tggaagctga agatgctgca acatattact gtcagaatga ttatagttat       300
ccgtacacgt tcggccaagg gaccaaggtg gaaatcaaa                               339
```

<210> SEQ ID NO 72
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

```
Glu Ile Val Leu Thr Gln Ser Pro Ala Thr Leu Ser Leu Ser Pro Gly
1               5               10              15

Glu Arg Ala Thr Leu Ser Cys Lys Ser Ser Gln Ser Leu Leu Asp Ser
            20              25              30

Gly Asn Gln Lys Asn Phe Leu Thr Trp Tyr Gln Gln Lys Pro Gly Gln
        35              40              45

Ala Pro Arg Leu Leu Ile Tyr Trp Ala Ser Thr Arg Glu Ser Gly Val
    50              55              60

Pro Ser Arg Phe Ser Gly Ser Gly Ser Gly Thr Asp Phe Thr Phe Thr
65              70              75              80

Ile Ser Ser Leu Glu Ala Glu Asp Ala Ala Thr Tyr Tyr Cys Gln Asn
            85              90              95

Asp Tyr Ser Tyr Pro Tyr Thr Phe Gly Gln Gly Thr Lys Val Glu Ile
        100             105             110

Lys Arg Thr Val Ala Ala Pro Ser Val Phe Ile Phe Pro Pro Ser Asp
        115             120             125

Glu Gln Leu Lys Ser Gly Thr Ala Ser Val Val Cys Leu Leu Asn Asn
    130             135             140

Phe Tyr Pro Arg Glu Ala Lys Val Gln Trp Lys Val Asp Asn Ala Leu
145             150             155             160

Gln Ser Gly Asn Ser Gln Glu Ser Val Thr Glu Gln Asp Ser Lys Asp
```

```
              165              170              175
Ser Thr Tyr Ser Leu Ser Ser Thr Leu Thr Leu Ser Lys Ala Asp Tyr
            180              185              190

Glu Lys His Lys Val Tyr Ala Cys Glu Val Thr His Gln Gly Leu Ser
        195              200              205

Ser Pro Val Thr Lys Ser Phe Asn Arg Gly Glu Cys
        210              215              220
```

<210> SEQ ID NO 73
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 73

```
gaaattgtgt tgacacagtc tccagccacc ctgtctttgt ctccagggga aagagccacc      60
ctctcctgca agtccagtca gagtctgtta gacagtggaa atcaaaagaa cttcttgacc     120
tggtaccagc agaaacctgg ccaggctccc aggctcctca tctattgggc atccactagg     180
gaatctgggg tcccctcgag gttcagtggc agtggatctg ggacagattt cacctttacc     240
atcagtagcc tggaagctga agatgctgca acatattact gtcagaatga ttatagttat     300
ccgtacacgt tcggccaagg gaccaaggtg gaaatcaaac gtacggtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga aacacaaagt ctacgcctgc     600
gaagtcaccc atcagggcct gagctcgccc gtcacaaaga gcttcaacag gggagagtgt     660
```

<210> SEQ ID NO 74
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

```
Asp Ile Gln Met Thr Gln Ser Pro Ser Ser Leu Ser Ala Ser Val Gly
1               5               10              15

Asp Arg Val Thr Ile Thr Cys Lys Ser Ser Gln Ser Leu Leu Asp Ser
            20              25              30

Gly Asn Gln Lys Asn Phe Leu Thr Trp Tyr Leu Gln Lys Pro Gly Gln
        35              40              45

Ser Pro Gln Leu Leu Ile Tyr Trp Ala Ser Thr Arg Glu Ser Gly Val
        50              55              60

Pro Ser Arg Phe Ser Gly Ser Gly Ser Gly Thr Asp Phe Thr Phe Thr
65              70              75              80

Ile Ser Ser Leu Glu Ala Glu Asp Ala Ala Thr Tyr Tyr Cys Gln Asn
            85              90              95

Asp Tyr Ser Tyr Pro Tyr Thr Phe Gly Gln Gly Thr Lys Val Glu Ile
        100              105              110

Lys
```

<210> SEQ ID NO 75
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 75
gacatccaga tgacccagtc tccatcctcc ctgtctgcat ctgtaggaga cagagtcacc        60
atcacttgca agtccagtca gagtctgtta gacagtggaa atcaaaagaa cttcttgacc       120
tggtacctgc agaagccagg gcagtctcca cagctcctga tctattgggc atccactagg       180
gaatctgggg tcccctcgag gttcagtggc agtggatctg ggacagattt cacctttacc       240
atcagtagcc tggaagctga agatgctgca acatattact gtcagaatga ttatagttat       300
ccgtacacgt tcggccaagg gaccaaggtg gaaatcaaa                               339

<210> SEQ ID NO 76
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 76

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asp Ser
            20                  25                  30

Gly Asn Gln Lys Asn Phe Leu Thr Trp Tyr Leu Gln Lys Pro Gly Gln
        35                  40                  45

Ser Pro Gln Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 77
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 77
gacatccaga tgacccagtc tccatcctcc ctgtctgcat ctgtaggaga cagagtcacc        60
atcacttgca agtccagtca gagtctgtta gacagtggaa atcaaaagaa cttcttgacc       120
tggtacctgc agaagccagg gcagtctcca cagctcctga tctattgggc atccactagg       180
gaatctgggg tcccctcgag gttcagtggc agtggatctg ggacagattt cacctttacc       240
atcagtagcc tggaagctga agatgctgca acatattact gtcagaatga ttatagttat       300
ccgtacacgt tcggccaagg gaccaaggtg gaaatcaaac gtacggtggc tgcaccatct       360
gtcttcatct tcccgccatc tgatgagcag ttgaaatctg gaactgcctc tgttgtgtgc       420
ctgctgaata acttctatcc cagagaggcc aaagtacagt ggaaggtgga taacgccctc       480
caatcgggta actcccagga gagtgtcaca gagcaggaca gcaaggacag cacctacagc       540
ctcagcagca ccctgacgct gagcaaagca gactacgaga aacacaaagt ctacgcctgc       600
gaagtcaccc atcagggcct gagctcgccc gtcacaaaga gcttcaacag gggagagtgt       660

<210> SEQ ID NO 78
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys

<210> SEQ ID NO 79
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

-continued

<400> SEQUENCE: 79
gatgttgtga tgactcagtc tccactctcc ctgcccgtca cccttggaca gccggcctcc          60
atctcctgca agtccagtca gagtctgtta gacagtggaa atcaaaagaa cttcttaacc         120
tggtatcagc agaaaccagg gaaagctcct aagctcctga tctattgggc atccactagg         180
gaatctgggg tcccctcgag gttcagtggc agtggatctg ggacagattt cacctttacc         240
atcagtagcc tggaagctga agatgctgca acatattact gtcagaatga ttatagttat         300
ccgtacacgt tcggccaagg gaccaaggtg gaaatcaaa                                 339

<210> SEQ ID NO 80
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 81
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 81

```
gatgttgtga tgactcagtc tccactctcc ctgcccgtca cccttggaca gccggcctcc      60
atctcctgca agtccagtca gagtctgtta gacagtggaa atcaaaagaa cttcttaacc     120
tggtatcagc agaaaccagg gaaagctcct aagctcctga tctattgggc atccactagg     180
gaatctgggg tcccctcgag gttcagtggc agtggatctg ggacagattt cacctttacc     240
atcagtagcc tggaagctga agatgctgca acatattact gtcagaatga ttatagttat     300
ccgtacacgt tcggccaagg gaccaaggtg gaaatcaaac gtacggtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga aacacaaagt ctacgcctgc     600
gaagtcaccc atcagggcct gagctcgccc gtcacaaaga gcttcaacag gggagagtgt     660
```

```
<210> SEQ ID NO 82
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
                20                  25                  30

Trp Met His Trp Ile Arg Gln Ser Pro Ser Arg Gly Leu Glu Trp Leu
        35                  40                  45

Gly Asn Ile Tyr Pro Gly Thr Gly Gly Ser Asn Phe Asp Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser
        115
```

```
<210> SEQ ID NO 83
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 83
caggttcagc tggtgcagtc tggagctgag gtgaagaagc ctggggcctc agtgaaggtc      60
tcctgcaagg cttctggcta cacattcacc acttactgga tgcactggat caggcagtcc     120
ccatcgagag gccttgagtg gctgggtaat atttatcctg gtactggtgg ttctaacttc     180
gatgagaagt tcaagaacag attcaccatc tccagagaca attccaagaa cacgctgtat     240
```
cttcaaatga acagcctgag agccgaggac acggccgtgt attactgtac aagatggact          300
actgggacgg gagcttactg gggccagggc accaccgtga ccgtgtcctc c                   351

```
<210> SEQ ID NO 84
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Met His Trp Ile Arg Gln Ser Pro Ser Arg Gly Leu Glu Trp Leu
        35                  40                  45

Gly Asn Ile Tyr Pro Gly Thr Gly Gly Ser Asn Phe Asp Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Thr Thr Gly Thr Gly Ala Tyr Trp Gly Gln Gly Thr Thr
                100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
        210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
                275                 280                 285

Arg Glu Glu Gln Phe Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335
```

-continued

```
Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440
```

```
<210> SEQ ID NO 85
<211> LENGTH: 1332
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 85
caggttcagc tggtgcagtc tggagctgag gtgaagaagc ctggggcctc agtgaaggtc      60
tcctgcaagg cttctggcta cacattcacc acttactgga tgcactggat caggcagtcc     120
ccatcgagag gccttgagtg gctgggtaat atttatcctg gtactggtgg ttctaacttc     180
gatgagaagt tcaagaacag attcaccatc tccagagaca attccaagaa cacgctgtat     240
cttcaaatga acagcctgag agccgaggac acggccgtgt attactgtac aagatggact     300
actgggacgg gagcttactg gggccagggc accaccgtga ccgtgtcctc cgcttccacc     360
aagggcccat ccgtcttccc cctggcgccc tgctccagga gcacctccga gagcacagcc     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacgaagac ctacacctgc     600
aacgtagatc acaagcccag caacaccaag gtggacaaga gagttgagtc caaatatggt     660
cccccatgcc caccgtgccc agcacctgag ttcctggggg gaccatcagt cttcctgttc     720
cccccaaaac ccaaggacac tctcatgatc tcccggaccc ctgaggtcac gtgcgtggtg     780
gtggacgtga gccaggaaga ccccgaggtc cagttcaact ggtacgtgga tggcgtggag     840
gtgcataatg ccaagacaaa gccgcgggag gagcagttca acagcacgta ccgtgtggtc     900
agcgtcctca ccgtcctgca ccaggactgg ctgaacggca aggagtacaa gtgcaaggtg     960
tccaacaaag gcctcccgtc ctccatcgag aaaaccatct ccaaagccaa agggcagccc    1020
cgagagccac aggtgtacac cctgccccca tcccaggagg agatgaccaa gaaccaggtc    1080
agcctgacct gcctggtcaa aggcttctac cccagcgaca tcgccgtgga gtgggagagc    1140
aatgggcagc cggagaacaa ctacaagacc acgcctcccg tgctggactc cgacggctcc    1200
ttcttcctct acagcaggct aaccgtggac aagagcaggt ggcaggaggg gaatgtcttc    1260
tcatgctccg tgatgcatga ggctctgcac aaccactaca cacagaagag cctctccctg    1320
tctctgggta aa                                                       1332
```

-continued

```
<210> SEQ ID NO 86
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser
        115

<210> SEQ ID NO 87
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 87
gaagtgcagc tggtgcagtc tggagcagag gtgaaaaagc ccggggagtc tctgaggatc      60
tcctgtaagg gttctggcta cacattcacc acttactgga tgcactgggt gcgacaggcc     120
cctggacaag ggcttgagtg gatgggtaat atttatcctg gtactggtgg ttctaacttc     180
gatgagaagt tcaagaacag attcaccatc tccagagaca attccaagaa cacgctgtat     240
cttcaaatga acagcctgag agccgaggac acggccgtgt attactgtac aagatggact     300
actgggacgg gagcttattg gggccagggc accaccgtga ccgtgtcctc c              351

<210> SEQ ID NO 88
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Pro Gly Gln Gly Leu Glu Trp Met
```

-continued

```
              35                   40                   45
Gly Asn Ile Tyr Pro Gly Thr Gly Gly Ser Asn Phe Asp Glu Lys Phe
    50                   55                   60
Lys Asn Arg Phe Thr Ile Ser Arg Asp Asn Ser Lys Asn Thr Leu Tyr
65                   70                   75                   80
Leu Gln Met Asn Ser Leu Arg Ala Glu Asp Thr Ala Val Tyr Tyr Cys
                85                   90                   95
Thr Arg Trp Thr Thr Gly Thr Gly Ala Tyr Trp Gly Gln Gly Thr Thr
            100                  105                  110
Val Thr Val Ser Ser Ala Ser Thr Lys Gly Pro Ser Val Phe Pro Leu
            115                  120                  125
Ala Pro Cys Ser Arg Ser Thr Ser Glu Ser Thr Ala Ala Leu Gly Cys
    130                  135                  140
Leu Val Lys Asp Tyr Phe Pro Glu Pro Val Thr Val Ser Trp Asn Ser
145                  150                  155                  160
Gly Ala Leu Thr Ser Gly Val His Thr Phe Pro Ala Val Leu Gln Ser
            165                  170                  175
Ser Gly Leu Tyr Ser Leu Ser Ser Val Val Thr Val Pro Ser Ser Ser
            180                  185                  190
Leu Gly Thr Lys Thr Tyr Thr Cys Asn Val Asp His Lys Pro Ser Asn
            195                  200                  205
Thr Lys Val Asp Lys Arg Val Glu Ser Lys Tyr Gly Pro Pro Cys Pro
    210                  215                  220
Pro Cys Pro Ala Pro Glu Phe Leu Gly Gly Pro Ser Val Phe Leu Phe
225                  230                  235                  240
Pro Pro Lys Pro Lys Asp Thr Leu Met Ile Ser Arg Thr Pro Glu Val
            245                  250                  255
Thr Cys Val Val Val Asp Val Ser Gln Glu Asp Pro Glu Val Gln Phe
            260                  265                  270
Asn Trp Tyr Val Asp Gly Val Glu Val His Asn Ala Lys Thr Lys Pro
            275                  280                  285
Arg Glu Glu Gln Phe Asn Ser Thr Tyr Arg Val Val Ser Val Leu Thr
    290                  295                  300
Val Leu His Gln Asp Trp Leu Asn Gly Lys Glu Tyr Lys Cys Lys Val
305                  310                  315                  320
Ser Asn Lys Gly Leu Pro Ser Ser Ile Glu Lys Thr Ile Ser Lys Ala
            325                  330                  335
Lys Gly Gln Pro Arg Glu Pro Gln Val Tyr Thr Leu Pro Pro Ser Gln
            340                  345                  350
Glu Glu Met Thr Lys Asn Gln Val Ser Leu Thr Cys Leu Val Lys Gly
            355                  360                  365
Phe Tyr Pro Ser Asp Ile Ala Val Glu Trp Glu Ser Asn Gly Gln Pro
    370                  375                  380
Glu Asn Asn Tyr Lys Thr Thr Pro Pro Val Leu Asp Ser Asp Gly Ser
385                  390                  395                  400
Phe Phe Leu Tyr Ser Arg Leu Thr Val Asp Lys Ser Arg Trp Gln Glu
            405                  410                  415
Gly Asn Val Phe Ser Cys Ser Val Met His Glu Ala Leu His Asn His
            420                  425                  430
Tyr Thr Gln Lys Ser Leu Ser Leu Ser Leu Gly Lys
            435                  440
```

<210> SEQ ID NO 89

-continued

```
<211> LENGTH: 1332
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 89
gaagtgcagc tggtgcagtc tggagcagag gtgaaaaagc ccggggagtc tctgaggatc      60
tcctgtaagg gttctggcta cacattcacc acttactgga tgcactgggt gcgacaggcc     120
cctggacaag ggcttgagtg gatgggtaat atttatcctg gtactggtgg ttctaacttc     180
gatgagaagt tcaagaacag attcaccatc tccagagaca attccaagaa cacgctgtat     240
cttcaaatga acagcctgag agccgaggac acggccgtgt attactgtac aagatggact     300
actgggacgg gagcttattg gggccagggc accaccgtga ccgtgtcctc cgcttccacc     360
aagggcccat ccgtcttccc cctggcgccc tgctccagga gcacctccga gagcacagcc     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacgaagac ctacacctgc     600
aacgtagatc acaagcccag caacaccaag gtggacaaga gagttgagtc caaatatggt     660
cccccatgcc caccgtgccc agcacctgag ttcctggggg gaccatcagt cttcctgttc     720 ccccaaaac ccaaggacac tctcatgatc tcccggaccc ctgaggtcac gtgcgtggtg     780
gtggacgtga gccaggaaga ccccgaggtc cagttcaact ggtacgtgga tggcgtggag     840
gtgcataatg ccaagacaaa gccgcgggag gagcagttca acagcacgta ccgtgtggtc     900
agcgtcctca ccgtcctgca ccaggactgg ctgaacggca aggagtacaa gtgcaaggtg     960
tccaacaaag gcctcccgtc ctccatcgag aaaaccatct ccaaagccaa agggcagccc    1020
cgagagccac aggtgtacac cctgcccca tcccaggagg agatgaccaa gaaccaggtc    1080
agcctgacct gcctggtcaa aggcttctac cccagcgaca tcgccgtgga gtgggagagc    1140
aatgggcagc cggagaacaa ctacaagacc acgcctcccg tgctggactc cgacggctcc    1200
ttcttcctct acagcaggct aaccgtggac aagagcaggt ggcaggaggg gaatgtcttc    1260
tcatgctccg tgatgcatga ggctctgcac aaccactaca cacagaagag cctctccctg    1320
tctctgggta aa                                                       1332

<210> SEQ ID NO 90
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 90
gaagtgcagc tggtgcagtc tggcgccgaa gtgaagaagc ctggcgagtc cctgcggatc      60
tcctgcaagg gctctggcta caccttcacc acctactgga tgcactgggt gcgacaggct     120
accggccagg gcctggaatg gatgggcaac atctatcctg gcaccggcgg ctccaacttc     180
gacgagaagt tcaagaacag agtgaccatc accgccgaca gtccacctc caccgcctac     240 atggaactgt cctccctgag atccgaggac accgccgtgt actactgcac ccggtggaca     300
accggcacag gcgcttattg gggccagggc accacagtga ccgtgtcctc t             351
```

```
<210> SEQ ID NO 91
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 91

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Thr Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350
```

```
Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
        435                 440
```

```
<210> SEQ ID NO 92
<211> LENGTH: 1329
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 92
gaagtgcagc tggtgcagtc tggcgccgaa gtgaagaagc ctggcgagtc cctgcggatc      60
tcctgcaagg gctctggcta caccttcacc acctactgga tgcactgggt gcgacaggct     120
accggccagg gcctggaatg gatgggcaac atctatcctg gcaccggcgg ctccaacttc     180
gacgagaagt tcaagaacag agtgaccatc accgccgaca gtccacctc caccgcctac      240 atggaactgt cctccctgag atccgaggac accgccgtgt actactgcac ccggtggaca     300
accggcacag cgcttattg gggccagggc accacagtga ccgtgtcctc tgcttctacc     360
aagggcccca gcgtgttccc cctggccccc tgctccagaa gcaccagcga gagcacagcc     420
gccctgggct gcctggtgaa ggactacttc cccgagcccg tgaccgtgtc ctggaacagc     480
ggagccctga ccagcggcgt gcacaccttc cccgccgtgc tgcagagcag cggcctgtac     540
agcctgagca gcgtggtgac cgtgcccagc agcagcctgg gcaccaagac ctacacctgt     600
aacgtggacc acaagcccag caacaccaag gtggacaaga gggtggagag caagtacggc     660
ccaccctgcc cccctgccc agcccccgag ttcctgggcg acccagcgt gttcctgttc       720 cccccaagc ccaaggacac cctgatgatc agcagaaccc ccgaggtgac ctgtgtggtg      780
gtggacgtgt cccaggagga ccccgaggtc cagttcaact ggtacgtgga cggcgtggag     840
gtgcacaacg ccaagaccaa gcccagagag gagcagtta acagcaccta ccgggtggtg      900
tccgtgctga ccgtgctgca ccaggactgg ctgaacggca agagtacaa gtgtaaggtc      960 tccaacaagg cctgccaag cagcatcgaa aagaccatca gcaaggccaa gggccagcct    1020
agagagcccc aggtctacac cctgccaccc agccaagagg agatgaccaa gaaccaggtg    1080
tccctgacct gtctggtgaa gggcttctac ccaagcgaca tcgccgtgga gtgggagagc    1140
aacggccagc ccgagaacaa ctacaagacc acccccccag tgctggacag cgacggcagc    1200
ttcttcctgt acagcaggct gaccgtggac aagtccagat ggcaggaggg caacgtcttt    1260
agctgctccg tgatgcacga ggccctgcac aaccactaca cccagaagag cctgagcctg    1320
tccctgggc                                                            1329
```

```
<210> SEQ ID NO 93
<211> LENGTH: 339
```

-continued

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 93
gagatcgtgc tgacccagtc ccctgccacc ctgtcactgt ctccaggcga gagagctacc      60
ctgtcctgca agtcctccca gtccctgctg gactccggca accagaagaa cttcctgacc     120
tggtatcagc agaagcccgg ccaggccccc agactgctga tctactgggc ctccacccgg     180
gaatctggcg tgccctctag attctccggc tccggctctg gcaccgagtt taccctgacc     240
atctccagcc tgcagcccga cgacttcgcc acctactact gccagaacga ctactcctac     300
ccctacacct tcggccaggg caccaaggtg gaaatcaag                             339

<210> SEQ ID NO 94
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 94
gagatcgtgc tgacccagtc ccctgccacc ctgtcactgt ctccaggcga gagagctacc      60
ctgtcctgca agtcctccca gtccctgctg gactccggca accagaagaa cttcctgacc     120
tggtatcagc agaagcccgg ccaggccccc agactgctga tctactgggc ctccacccgg     180
gaatctggcg tgccctctag attctccggc tccggctctg gcaccgagtt taccctgacc     240
atctccagcc tgcagcccga cgacttcgcc acctactact gccagaacga ctactcctac     300
ccctacacct tcggccaggg caccaaggtg gaaatcaagc gtacggtggc cgctcccagc     360
gtgttcatct tccccccaag cgacgagcag ctgaagagcg gcaccgccag cgtggtgtgt     420
ctgctgaaca acttctaccc cagggaggcc aaggtgcagt ggaaggtgga caacgccctg     480
cagagcggca cagccagga gagcgtcacc gagcaggaca gcaaggactc cacctacagc     540
ctgagcagca ccctgaccct gagcaaggcc gactacgaga gcacaaggt gtacgcctgt     600 gaggtgaccc accagggcct gtccagcccc gtgaccaaga gcttcaacag gggcgagtgc     660

<210> SEQ ID NO 95
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 95
gaggtgcagc tggtgcagtc aggcgccgaa gtgaagaagc ccggcgagtc actgagaatt      60
agctgtaaag gttcaggcta caccttcact acctactgga tgcactgggt ccgccaggct     120
accggtcaag gcctcgagtg gatgggtaat atctacccg gcaccggcgg ctctaacttc     180
gacgagaagt ttaagaatag agtgactatc accgccgata agtctactag caccgcctat     240
atggaactgt ctagcctgag atcagaggac accgccgtct actactgcac taggtggact     300
accggcacag gcgcctactg gggtcaaggc actaccgtga ccgtgtctag c              351
```

<210> SEQ ID NO 96
<211> LENGTH: 1329
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 96
gaggtgcagc tggtgcagtc aggcgccgaa gtgaagaagc ccggcgagtc actgagaatt      60
agctgtaaag gttcaggcta caccttcact acctactgga tgcactgggt ccgccaggct     120
accggtcaag gcctcgagtg gatgggtaat atctacccg gcaccggcgg ctctaacttc      180
gacgagaagt ttaagaatag agtgactatc accgccgata agtctactag caccgcctat     240
atggaactgt ctagcctgag atcagaggac accgccgtct actactgcac taggtggact     300
accggcacag gcgcctactg gggtcaaggc actaccgtga ccgtgtctag cgctagcact     360
aagggcccgt ccgtgttccc cctggcacct tgtagccgga gcactagcga atccaccgct     420
gccctcggct gcctggtcaa ggattacttc ccggagcccg tgaccgtgtc ctggaacagc      480
ggagccctga cctccggagt gcacaccttc cccgctgtgc tgcagagctc cgggctgtac     540
tcgctgtcgt cggtggtcac ggtgccttca tctagcctgg gtaccaagac ctacacttgc      600
aacgtggacc acaagccttc caacactaag gtggacaagc gcgtcgaatc gaagtacggc     660
ccaccgtgcc cgccttgtcc cgcgccggag ttcctcggcg gtccctcggt ctttctgttc     720
ccaccgaagc ccaaggacac tttgatgatt tcccgcaccc ctgaagtgac atgcgtggtc     780
gtggacgtgt cacaggaaga tccggaggtg cagttcaatt ggtacgtgga tggcgtcgag     840
gtgcacaacg ccaaaaccaa gccgagggag gagcagttca actccactta ccgcgtcgtg     900
tccgtgctga cggtgctgca tcaggactgg ctgaacggga aggagtacaa gtgcaaagtg      960
tccaacaagg gacttcctag ctcaatcgaa aagaccatct cgaaagccaa gggacagccc     1020
cgggaacccc aagtgtatac cctgccaccg agccaggaag aaatgactaa gaaccaagtc     1080
tcattgactt gccttgtgaa gggcttctac ccatcggata tcgccgtgga atgggagtcc     1140
aacggccagc cggaaaacaa ctacaagacc acccctccgg tgctggactc agacggatcc     1200
ttcttcctct actcgcggct gaccgtggat aagagcagat ggcaggaggg aaatgtgttc     1260
agctgttctg tgatgcatga agccctgcac aaccactaca ctcagaagtc cctgtccctc     1320
tccctggga                                                            1329

<210> SEQ ID NO 97
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 97
gagatcgtcc tgactcagtc acccgctacc ctgagcctga gcctggcga gcgggctaca       60 ctgagctgta aatctagtca gtcactgctg gatagcggta atcagaagaa cttcctgacc     120
tggtatcagc agaagcccgg taaagcccct aagctgctga tctactgggc ctctactaga     180
gaatcaggcg tgccctctag gtttagcggt agcggtagtg gcaccgactt caccttcact     240
atctctagcc tgcagcccga ggatatcgct acctactact gtcagaacga ctatagctac     300

-continued

```
ccctacacct tcggtcaagg cactaaggtc gagattaag                        339

<210> SEQ ID NO 98
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 98
gagatcgtcc tgactcagtc acccgctacc ctgagcctga gccctggcga gcgggctaca     60
ctgagctgta aatctagtca gtcactgctg gatagcggta atcagaagaa cttcctgacc    120
tggtatcagc agaagcccgg taaagcccct aagctgctga tctactgggc ctctactaga    180
gaatcaggcg tgccctctag gtttagcggt agcggtagtg gcaccgactt caccttcact    240
atctctagcc tgcagcccga ggatatcgct acctactact gtcagaacga ctatagctac    300
ccctacacct tcggtcaagg cactaaggtc gagattaagc gtacggtggc cgctcccagc    360
gtgttcatct ccccccccag cgacgagcag ctgaagagcg gcaccgccag cgtggtgtgc    420
ctgctgaaca acttctaccc ccgggaggcc aaggtgcagt ggaaggtgga caacgccctg    480
cagagcggca acagccagga gagcgtcacc gagcaggaca gcaaggactc cacctacagc    540
ctgagcagca ccctgaccct gagcaaggcc gactacgaga gcataaggt gtacgcctgc    600 gaggtgaccc accagggcct gtccagcccc gtgaccaaga gcttcaacag gggcgagtgc    660

<210> SEQ ID NO 99
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 99
gagatcgtgc tgacccagtc ccccgacttc cagtccgtga cccccaaaga aaaagtgacc     60
atcacatgca agtcctccca gtccctgctg gactccggca accagaagaa cttcctgacc    120
tggtatcagc agaagcccgg ccaggccccc agactgctga tctactgggc ctccacccgg    180
gaatctggcg tgccctctag attctccggc tccggctctg gcaccgactt taccttcacc    240
atctccagcc tggaagccga ggacgccgcc acctactact gccagaacga ctactcctac    300
ccctacacct tcggccaggg caccaaggtg gaaatcaag                           339

<210> SEQ ID NO 100
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 100
gagatcgtgc tgacccagtc ccccgacttc cagtccgtga cccccaaaga aaaagtgacc     60
atcacatgca agtcctccca gtccctgctg gactccggca accagaagaa cttcctgacc    120
tggtatcagc agaagcccgg ccaggccccc agactgctga tctactgggc ctccacccgg    180
```

-continued

```
gaatctggcg tgccctctag attctccggc tccggctctg gcaccgactt taccttcacc    240
atctccagcc tggaagccga ggacgccgcc acctactact gccagaacga ctactcctac    300
ccctacacct tcggccaggg caccaaggtg gaaatcaagc gtacggtggc cgctcccagc    360
gtgttcatct tcccccccaag cgacgagcag ctgaagagcg gcaccgccag cgtggtgtgt    420
ctgctgaaca acttctaccc cagggaggcc aaggtgcagt ggaaggtgga caacgccctg    480
cagagcggca cagccagga gagcgtcacc gagcaggaca gcaaggactc cacctacagc    540
ctgagcagca ccctgaccct gagcaaggcc gactacgaga agcacaaggt gtacgcctgt    600
gaggtgaccc accagggcct gtccagcccc gtgaccaaga gcttcaacag gggcgagtgc    660
```

```
<210> SEQ ID NO 101
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 101
gaagtgcagc tggtgcagtc tggcgccgaa gtgaagaagc ctggcgagtc cctgcggatc     60
tcctgcaagg gctctggcta caccttcacc acctactgga tgcactggat ccggcagtcc    120
ccctctaggg gcctggaatg gctgggcaac atctaccctg gcaccggcgg ctccaacttc    180
gacgagaagt tcaagaacag gttcaccatc tcccgggaca actccaagaa caccctgtac    240
ctgcagatga actccctgcg ggccgaggac accgccgtgt actactgtac cagatggacc    300
accggaaccg gcgcctattg gggccagggc acaacagtga ccgtgtcctc c             351
```

```
<210> SEQ ID NO 102
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 102

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Ile Arg Gln Ser Pro Ser Arg Gly Leu Glu Trp Leu
        35                  40                  45

Gly Asn Ile Tyr Pro Gly Thr Gly Gly Ser Asn Phe Asp Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140
```

```
Leu Val Lys Asp Tyr Phe Pro Glu Pro Val Thr Val Ser Trp Asn Ser
145             150             155             160

Gly Ala Leu Thr Ser Gly Val His Thr Phe Pro Ala Val Leu Gln Ser
                165             170             175

Ser Gly Leu Tyr Ser Leu Ser Ser Val Val Thr Val Pro Ser Ser Ser
                180             185             190

Leu Gly Thr Lys Thr Tyr Thr Cys Asn Val Asp His Lys Pro Ser Asn
            195             200             205

Thr Lys Val Asp Lys Arg Val Glu Ser Lys Tyr Gly Pro Pro Cys Pro
        210             215             220

Pro Cys Pro Ala Pro Glu Phe Leu Gly Gly Pro Ser Val Phe Leu Phe
225             230             235             240

Pro Pro Lys Pro Lys Asp Thr Leu Met Ile Ser Arg Thr Pro Glu Val
                245             250             255

Thr Cys Val Val Val Asp Val Ser Gln Glu Asp Pro Glu Val Gln Phe
                260             265             270

Asn Trp Tyr Val Asp Gly Val Glu Val His Asn Ala Lys Thr Lys Pro
            275             280             285

Arg Glu Glu Gln Phe Asn Ser Thr Tyr Arg Val Val Ser Val Leu Thr
        290             295             300

Val Leu His Gln Asp Trp Leu Asn Gly Lys Glu Tyr Lys Cys Lys Val
305             310             315             320

Ser Asn Lys Gly Leu Pro Ser Ser Ile Glu Lys Thr Ile Ser Lys Ala
                325             330             335

Lys Gly Gln Pro Arg Glu Pro Gln Val Tyr Thr Leu Pro Pro Ser Gln
            340             345             350

Glu Glu Met Thr Lys Asn Gln Val Ser Leu Thr Cys Leu Val Lys Gly
            355             360             365

Phe Tyr Pro Ser Asp Ile Ala Val Glu Trp Glu Ser Asn Gly Gln Pro
    370             375             380

Glu Asn Asn Tyr Lys Thr Thr Pro Pro Val Leu Asp Ser Asp Gly Ser
385             390             395             400

Phe Phe Leu Tyr Ser Arg Leu Thr Val Asp Lys Ser Arg Trp Gln Glu
            405             410             415

Gly Asn Val Phe Ser Cys Ser Val Met His Glu Ala Leu His Asn His
            420             425             430

Tyr Thr Gln Lys Ser Leu Ser Leu Ser Leu Gly
            435             440
```

<210> SEQ ID NO 103
<211> LENGTH: 1329
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 103
gaagtgcagc tggtgcagtc tggcgccgaa gtgaagaagc ctggcgagtc cctgcggatc      60
tcctgcaagg gctctggcta caccttcacc acctactgga tgcactggat ccggcagtcc     120
ccctctaggg gcctggaatg gctgggcaac atctaccctg gcaccggcgg ctccaacttc     180
gacgagaagt tcaagaacag gttcaccatc tcccgggaca actccaagaa caccctgtac     240
ctgcagatga actccctgcg ggccgaggac accgccgtgt actactgtac cagatggacc     300

```
accggaaccg gcgcctattg gggccagggc acaacagtga ccgtgtcctc cgcttctacc      360
aaggggccca gcgtgttccc cctggccccc tgctccagaa gcaccagcga gagcacagcc      420
gccctgggct gcctggtgaa ggactacttc cccgagcccg tgaccgtgtc ctggaacagc      480
ggagccctga ccagcggcgt gcacaccttc cccgccgtgc tgcagagcag cggcctgtac      540
agcctgagca gcgtggtgac cgtgcccagc agcagcctgg gcaccaagac ctacacctgt      600
aacgtggacc acaagcccag caacaccaag gtggacaaga gggtggagag caagtacggc      660
ccaccctgcc cccctgccc agcccccgag ttcctgggcg gacccagcgt gttcctgttc      720
ccccccaagc ccaaggacac cctgatgatc agcagaaccc ccgaggtgac ctgtgtggtg      780
gtggacgtgt cccaggagga ccccgaggtc cagttcaact ggtacgtgga cggcgtggag      840
gtgcacaacg ccaagaccaa gcccagagag gagcagttta acagcaccta ccgggtggtg      900
tccgtgctga ccgtgctgca ccaggactgg ctgaacggca agagtacaa gtgtaaggtc      960 tccaacaagg gcctgccaag cagcatcgaa aagaccatca gcaaggccaa gggccagcct     1020
agagagcccc aggtctacac cctgccaccc agccaagagg agatgaccaa gaaccaggtg     1080
tccctgacct gtctggtgaa gggcttctac ccaagcgaca tcgccgtgga gtgggagagc     1140
aacggccagc ccgagaacaa ctacaagacc acccccccag tgctggacag cgacggcagc     1200
ttcttcctgt acagcaggct gaccgtggac aagtccagat ggcaggaggg caacgtcttt     1260
agctgctccg tgatgcacga ggccctgcac aaccactaca cccagaagag cctgagcctg     1320
tccctgggc                                                           1329
```

```
<210> SEQ ID NO 104
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 104
gagatcgtgc tgacccagtc ccctgccacc ctgtcactgt ctccaggcga gagagctacc       60
ctgtcctgca gtcctcccca gtccctgctg gactccggca accagaagaa cttcctgacc      120
tggtatcagc agaagcccgg ccaggccccc agactgctga tctactgggc ctccacccgg      180
gaatctggcg tgccctctag attctccggc tccggctctg gcaccgactt taccttcacc      240
atctccagcc tggaagccga ggacgccgcc acctactact gccagaacga ctactcctac      300
ccctacacct tcggccaggg caccaaggtg gaaatcaag                            339
```

```
<210> SEQ ID NO 105
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 105
gagatcgtgc tgacccagtc ccctgccacc ctgtcactgt ctccaggcga gagagctacc       60
ctgtcctgca gtcctcccca gtccctgctg gactccggca accagaagaa cttcctgacc      120
tggtatcagc agaagcccgg ccaggccccc agactgctga tctactgggc ctccacccgg      180
gaatctggcg tgccctctag attctccggc tccggctctg gcaccgactt taccttcacc      240
```

-continued

```
atctccagcc tggaagccga ggacgccgcc acctactact gccagaacga ctactcctac        300
ccctacacct tcggccaggg caccaaggtg gaaatcaagc gtacggtggc cgctcccagc        360
gtgttcatct ccccccaag cgacgagcag ctgaagagcg gcaccgccag cgtggtgtgt        420
ctgctgaaca acttctaccc cagggaggcc aaggtgcagt ggaaggtgga caacgccctg        480
cagagcggca acagccagga gagcgtcacc gagcaggaca gcaaggactc cacctacagc        540
ctgagcagca ccctgaccct gagcaaggcc gactacgaga agcacaaggt gtacgcctgt        600
gaggtgaccc accagggcct gtccagcccc gtgaccaaga gcttcaacag gggcgagtgc        660
```

```
<210> SEQ ID NO 106
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

```
<400> SEQUENCE: 106
```

```
gagatcgtcc tgactcagtc acccgctacc ctgagcctga gccctggcga gcgggctaca         60
ctgagctgta aatctagtca gtcactgctg gatagcggta atcagaagaa cttcctgacc        120
tggtatcagc agaagcccgg tcaagcccct agactgctga tctactgggc ctctactaga        180
gaatcaggcg tgccctctag gtttagcggt agcggtagtg gcaccgactt caccttcact        240
atctctagcc tggaagccga ggacgccgct acctactact gtcagaacga ctatagctac        300
ccctacacct tcggtcaagg cactaaggtc gagattaag                               339
```

```
<210> SEQ ID NO 107
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

```
<400> SEQUENCE: 107
```

```
gagatcgtcc tgactcagtc acccgctacc ctgagcctga gccctggcga gcgggctaca         60
ctgagctgta aatctagtca gtcactgctg gatagcggta atcagaagaa cttcctgacc        120
tggtatcagc agaagcccgg tcaagcccct agactgctga tctactgggc ctctactaga        180
gaatcaggcg tgccctctag gtttagcggt agcggtagtg gcaccgactt caccttcact        240
atctctagcc tggaagccga ggacgccgct acctactact gtcagaacga ctatagctac        300
ccctacacct tcggtcaagg cactaaggtc gagattaagc gtacggtggc cgctcccagc        360
gtgttcatct ccccccaag cgacgagcag ctgaagagcg gcaccgccag cgtggtgtgc        420
ctgctgaaca acttctaccc ccgggaggcc aaggtgcagt ggaaggtgga caacgccctg        480
cagagcggca acagccagga gagcgtcacc gagcaggaca gcaaggactc cacctacagc        540
ctgagcagca ccctgaccct gagcaaggcc gactacgaga agcataaggt gtacgcctgc        600
gaggtgaccc accagggcct gtccagcccc gtgaccaaga gcttcaacag gggcgagtgc        660
```

```
<210> SEQ ID NO 108
<211> LENGTH: 15
<212> TYPE: DNA
<213> ORGANISM: Artificial Sequence
<220> FEATURE:
```

-continued

<221> NAME/KEY: source
<223> OTHER INFORMATION: /note="Description of Artificial Sequence:
      Synthetic oligonucleotide"

<400> SEQUENCE: 108
acttactgga tgcac                                                      15

<210> SEQ ID NO 109
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
aatatttatc ctggtactgg tggttctaac ttcgatgaga agttcaagaa c              51

<210> SEQ ID NO 110
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
tggactactg ggacgggagc ttat                                            24

<210> SEQ ID NO 111
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
ggctacacat tcaccactta c                                               21

<210> SEQ ID NO 112
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
tatcctggta ctggtggt                                                   18

<210> SEQ ID NO 113
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 113
aagtccagtc agagtctgtt agacagtgga aatcaaaaga acttcttgac c              51

-continued

```
<210> SEQ ID NO 114
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114
tgggcatcca ctagggaatc t                                              21

<210> SEQ ID NO 115
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
cagaatgatt atagttatcc gtgcacg                                        27

<210> SEQ ID NO 116
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116
agtcagagtc tgttagacag tggaaatcaa aagaacttc                           39

<210> SEQ ID NO 117
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117 tgggcatcc                                                            9

<210> SEQ ID NO 118
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118
gattatagtt atccgtgc                                                  18

<210> SEQ ID NO 119
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

```
<400> SEQUENCE: 119
cagaatgatt atagttatcc gtacacg                                    27

<210> SEQ ID NO 120
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120
gattatagtt atccgtac                                              18

<210> SEQ ID NO 121
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121
aagtccagtc agagtctgtt agacagtgga aatcaaaaga acttcttaac c         51

<210> SEQ ID NO 122
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122
acctactgga tgcac                                                 15

<210> SEQ ID NO 123
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
aacatctatc ctggcaccgg cggctccaac ttcgacgaga agttcaagaa c         51

<210> SEQ ID NO 124
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124
tggacaaccg gcacaggcgc ttat                                       24

<210> SEQ ID NO 125
<211> LENGTH: 21
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 125
ggctacacct tcaccaccta c                                              21

<210> SEQ ID NO 126
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126
tatcctggca ccggcggc                                                  18

<210> SEQ ID NO 127
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127
aagtcctccc agtccctgct ggactccggc aaccagaaga acttcctgac c            51

<210> SEQ ID NO 128
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128
tgggcctcca cccgggaatc t                                              21

<210> SEQ ID NO 129
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129
cagaacgact actcctaccc ctacacc                                        27

<210> SEQ ID NO 130
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130
tcccagtccc tgctggactc cggcaaccag aagaacttc                           39
```

<210> SEQ ID NO 131
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 131 tgggcctcc                                                              9

<210> SEQ ID NO 132
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
gactactcct acccctac                                                    18

<210> SEQ ID NO 133
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
acctactgga tgcac                                                       15

<210> SEQ ID NO 134
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134
aatatctacc ccggcaccgg cggctctaac ttcgacgaga agtttaagaa t              51

<210> SEQ ID NO 135
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135
tggactaccg gcacaggcgc ctac                                             24

<210> SEQ ID NO 136
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

-continued

<400> SEQUENCE: 136
ggctacacct tcactaccta c                                              21

<210> SEQ ID NO 137
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137
taccccggca ccggcggc                                                  18

<210> SEQ ID NO 138
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
aaatctagtc agtcactgct ggatagcggt aatcagaaga acttcctgac c             51

<210> SEQ ID NO 139
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139
tgggcctcta ctagagaatc a                                              21

<210> SEQ ID NO 140
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
cagaacgact atagctaccc ctacacc                                        27

<210> SEQ ID NO 141
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
agtcagtcac tgctggatag cggtaatcag aagaacttc                           39

<210> SEQ ID NO 142
<211> LENGTH: 9
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142 tgggcctct                                                            9

<210> SEQ ID NO 143
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
gactatagct acccctac                                                  18

<210> SEQ ID NO 144
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
aacatctacc ctggcaccgg cggctccaac ttcgacgaga agttcaagaa c             51

<210> SEQ ID NO 145
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
tggaccaccg gaaccggcgc ctat                                           24

<210> SEQ ID NO 146
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
taccctggca ccggcggc                                                  18

<210> SEQ ID NO 147
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 147

Glu Val Gln Leu Val Gln Ser Gly Ala Glu Val Lys Lys Pro Gly Glu
```

```
1               5               10              15

Ser Leu Arg Ile Ser Cys Lys Gly Ser
            20              25

<210> SEQ ID NO 148
<211> LENGTH: 75
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
gaagtgcagc tggtgcagtc tggagcagag gtgaaaaagc ccggggagtc tctgaggatc      60
tcctgtaagg gttct                                                       75

<210> SEQ ID NO 149
<211> LENGTH: 75
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
gaagtgcagc tggtgcagtc tggcgccgaa gtgaagaagc ctggcgagtc cctgcggatc      60
tcctgcaagg gctct                                                       75

<210> SEQ ID NO 150
<211> LENGTH: 75
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 150
gaggtgcagc tggtgcagtc aggcgccgaa gtgaagaagc ccggcgagtc actgagaatt      60
agctgtaaag gttca                                                       75

<210> SEQ ID NO 151
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 151

Gln Val Gln Leu Val Gln Ser Gly Ala Glu Val Lys Lys Pro Gly Ala
1               5               10              15

Ser Val Lys Val Ser Cys Lys Ala Ser
            20              25

<210> SEQ ID NO 152
<211> LENGTH: 75
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 152
caggttcagc tggtgcagtc tggagctgag gtgaagaagc ctggggcctc agtgaaggtc      60
tcctgcaagg cttct                                                     75

<210> SEQ ID NO 153
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 153

Trp Val Arg Gln Ala Thr Gly Gln Gly Leu Glu Trp Met Gly
1               5                   10

<210> SEQ ID NO 154
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154
tgggtgcgac aggccactgg acaagggctt gagtggatgg gt                        42

<210> SEQ ID NO 155
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155
tgggtgcgac aggctaccgg ccagggcctg gaatggatgg gc                        42

<210> SEQ ID NO 156
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 156
tgggtccgcc aggctaccgg tcaaggcctc gagtggatgg gt                        42

<210> SEQ ID NO 157
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 157

Trp Ile Arg Gln Ser Pro Ser Arg Gly Leu Glu Trp Leu Gly
1               5                   10

<210> SEQ ID NO 158
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158
tggatcaggc agtccccatc gagaggcctt gagtggctgg gt                      42

<210> SEQ ID NO 159
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 159
tggatccggc agtccccctc taggggcctg gaatggctgg gc                      42

<210> SEQ ID NO 160
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 160

Trp Val Arg Gln Ala Pro Gly Gln Gly Leu Glu Trp Met Gly
1               5                   10

<210> SEQ ID NO 161
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 161
tgggtgcgac aggcccctgg acaagggctt gagtggatgg gt                      42

<210> SEQ ID NO 162
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 162

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Thr Arg
                20                  25                  30

<210> SEQ ID NO 163
<211> LENGTH: 96

<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 163
agagtcacga ttaccgcgga caaatccacg agcacagcct acatggagct gagcagcctg       60
agatctgagg acacggccgt gtattactgt acaaga                                  96

<210> SEQ ID NO 164
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 164
agagtgacca tcaccgccga caagtccacc tccaccgcct acatggaact gtcctccctg       60
agatccgagg acaccgccgt gtactactgc acccgg                                  96

<210> SEQ ID NO 165
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 165
agagtgacta tcaccgccga taagtctact agcaccgcct atatggaact gtctagcctg       60
agatcagagg acaccgccgt ctactactgc actagg                                  96

<210> SEQ ID NO 166
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 166

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Thr Arg
            20                  25                  30

<210> SEQ ID NO 167
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 167
agattcacca tctccagaga caattccaag aacacgctgt atcttcaaat gaacagcctg       60
agagccgagg acacggccgt gtattactgt acaaga                                  96

```
<210> SEQ ID NO 168
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168
aggttcacca tctcccggga caactccaag aacaccctgt acctgcagat gaactccctg         60
cgggccgagg acaccgccgt gtactactgt accaga                                   96

<210> SEQ ID NO 169
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 169

Trp Gly Gln Gly Thr Thr Val Thr Val Ser Ser
1               5                   10

<210> SEQ ID NO 170
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170
tggggccagg gcaccaccgt gaccgtgtcc tcc                                      33

<210> SEQ ID NO 171
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
tggggccagg gcaccacagt gaccgtgtcc tct                                      33

<210> SEQ ID NO 172
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
tggggtcaag gcactaccgt gaccgtgtct agc                                      33

<210> SEQ ID NO 173
<211> LENGTH: 33
<212> TYPE: DNA
<213> ORGANISM: Artificial Sequence
<220> FEATURE:
```

<221> NAME/KEY: source
<223> OTHER INFORMATION: /note="Description of Artificial Sequence:
      Synthetic oligonucleotide"

<400> SEQUENCE: 173
tggggccagg gcacaacagt gaccgtgtcc tcc                                        33

<210> SEQ ID NO 174
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 174

Glu Ile Val Leu Thr Gln Ser Pro Asp Phe Gln Ser Val Thr Pro Lys
1               5                   10                  15

Glu Lys Val Thr Ile Thr Cys
            20

<210> SEQ ID NO 175
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175
gaaattgtgc tgactcagtc tccagacttt cagtctgtga ctccaaagga gaaagtcacc      60
atcacctgc                                                              69

<210> SEQ ID NO 176
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176
gagatcgtgc tgacccagtc ccccgacttc cagtccgtga cccccaaaga aaaagtgacc      60
atcacatgc                                                              69

<210> SEQ ID NO 177
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 177

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 178
<211> LENGTH: 69

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178
gaaattgtgt tgacacagtc tccagccacc ctgtctttgt ctccagggga aagagccacc        60
ctctcctgc                                                                69

<210> SEQ ID NO 179
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179
gagatcgtgc tgacccagtc ccctgccacc ctgtcactgt ctccaggcga gagagctacc        60
ctgtcctgc                                                                69

<210> SEQ ID NO 180
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180
gagatcgtcc tgactcagtc acccgctacc ctgagcctga gccctggcga gcgggctaca        60
ctgagctgt                                                                69

<210> SEQ ID NO 181
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 181

Asp Ile Val Met Thr Gln Thr Pro Leu Ser Leu Pro Val Thr Pro Gly
1               5                   10                  15

Glu Pro Ala Ser Ile Ser Cys
            20

<210> SEQ ID NO 182
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182
gatattgtga tgacccagac tccactctcc ctgcccgtca cccctggaga gccggcctcc        60
atctcctgc                                                                69

-continued

<210> SEQ ID NO 183
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 183

Asp Val Val Met Thr Gln Ser Pro Leu Ser Leu Pro Val Thr Leu Gly
1               5                   10                  15

Gln Pro Ala Ser Ile Ser Cys
            20

<210> SEQ ID NO 184
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184
gatgttgtga tgactcagtc tccactctcc ctgcccgtca cccttggaca gccggcctcc      60
atctcctgc                                                              69

<210> SEQ ID NO 185
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 185

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 186
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186
gacatccaga tgacccagtc tccatcctcc ctgtctgcat ctgtaggaga cagagtcacc      60
atcacttgc                                                              69

<210> SEQ ID NO 187
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 187

```
Trp Tyr Gln Gln Lys Pro Gly Gln Ala Pro Arg Leu Leu Ile Tyr
1               5                   10                  15
```

<210> SEQ ID NO 188
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188
tggtaccagc agaaacctgg ccaggctccc aggctcctca tctat                      45

<210> SEQ ID NO 189
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189
tggtatcagc agaagcccgg ccaggccccc agactgctga tctac                      45

<210> SEQ ID NO 190
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190
tggtatcagc agaagcccgg tcaagcccct agactgctga tctac                      45

<210> SEQ ID NO 191
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 191

Trp Tyr Gln Gln Lys Pro Gly Lys Ala Pro Lys Leu Leu Ile Tyr
1               5                   10                  15

<210> SEQ ID NO 192
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192
tggtatcagc agaaaccagg gaaagctcct aagctcctga tctat                      45

<210> SEQ ID NO 193
<211> LENGTH: 45
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 193
tggtatcagc agaagcccgg taaagcccct aagctgctga tctac                           45

<210> SEQ ID NO 194
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 194

Trp Tyr Leu Gln Lys Pro Gly Gln Ser Pro Gln Leu Leu Ile Tyr
1               5                   10                  15

<210> SEQ ID NO 195
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195
tggtacctgc agaagccagg gcagtctcca cagctcctga tctat                           45

<210> SEQ ID NO 196
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 196

Gly Val Pro Ser Arg Phe Ser Gly Ser Gly Ser Gly Thr Asp Phe Thr
1               5                   10                  15

Phe Thr Ile Ser Ser Leu Glu Ala Glu Asp Ala Ala Thr Tyr Tyr Cys
            20                  25                  30

<210> SEQ ID NO 197
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197
ggggtcccct cgaggttcag tggcagtgga tctgggacag atttcacctt taccatcagt           60
agcctggaag ctgaagatgc tgcaacatat tactgt                                     96

<210> SEQ ID NO 198
<211> LENGTH: 96
<212> TYPE: DNA
<213> ORGANISM: Artificial Sequence
<220> FEATURE:

-continued

```
<221> NAME/KEY: source
<223> OTHER INFORMATION: /note="Description of Artificial Sequence:
      Synthetic oligonucleotide"

<400> SEQUENCE: 198
ggcgtgccct ctagattctc cggctccggc tctggcaccg actttacctt caccatctcc      60
agcctggaag ccgaggacgc cgccacctac tactgc                                96

<210> SEQ ID NO 199
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
ggcgtgccct ctaggtttag cggtagcggt agtggcaccg acttcacctt cactatctct      60
agcctggaag ccgaggacgc cgctacctac tactgt                                96

<210> SEQ ID NO 200
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 200

Gly Ile Pro Pro Arg Phe Ser Gly Ser Gly Tyr Gly Thr Asp Phe Thr
1               5                   10                  15

Leu Thr Ile Asn Asn Ile Glu Ser Glu Asp Ala Ala Tyr Tyr Phe Cys
            20                  25                  30

<210> SEQ ID NO 201
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
gggatcccac ctcgattcag tggcagcggg tatggaacag attttaccct cacaattaat      60
aacatagaat ctgaggatgc tgcatattac ttctgt                                96

<210> SEQ ID NO 202
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 202

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30
```

```
<210> SEQ ID NO 203
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
ggggtcccat caaggttcag cggcagtgga tctgggacag aattcactct caccatcagc      60
agcctgcagc ctgatgattt tgcaacttat tactgt                                96

<210> SEQ ID NO 204
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
ggcgtgccct ctagattctc cggctccggc tctggcaccg agtttaccct gaccatctcc      60
agcctgcagc ccgacgactt cgccacctac tactgc                                96

<210> SEQ ID NO 205
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 205

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 206
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
ggggtcccat caaggttcag tggaagtgga tctgggacag attttacttt caccatcagc      60
agcctgcagc ctgaagatat tgcaacatat tactgt                                96

<210> SEQ ID NO 207
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 207
ggcgtgccct ctaggtttag cggtagcggt agtggcaccg acttcacctt cactatctct      60
```

-continued

```
agcctgcagc ccgaggatat cgctacctac tactgt                                 96

<210> SEQ ID NO 208
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 208

Phe Gly Gln Gly Thr Lys Val Glu Ile Lys
1               5                   10

<210> SEQ ID NO 209
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209
ttcggccaag ggaccaaggt ggaaatcaaa                                         30

<210> SEQ ID NO 210
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
ttcggccagg gcaccaaggt ggaaatcaag                                         30

<210> SEQ ID NO 211
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
ttcggtcaag gcactaaggt cgagattaag                                         30

<210> SEQ ID NO 212
<211> LENGTH: 327
<212> TYPE: PRT
<213> ORGANISM: Homo sapiens

<400> SEQUENCE: 212

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Ser Leu Gly Thr Lys Thr
65              70              75              80

Tyr Thr Cys Asn Val Asp His Lys Pro Ser Asn Thr Lys Val Asp Lys
                85              90              95

Arg Val Glu Ser Lys Tyr Gly Pro Pro Cys Pro Pro Cys Pro Ala Pro
            100             105             110

Glu Phe Leu Gly Gly Pro Ser Val Phe Leu Phe Pro Pro Lys Pro Lys
            115             120             125

Asp Thr Leu Met Ile Ser Arg Thr Pro Glu Val Thr Cys Val Val Val
        130             135             140

Asp Val Ser Gln Glu Asp Pro Glu Val Gln Phe Asn Trp Tyr Val Asp
145             150             155             160

Gly Val Glu Val His Asn Ala Lys Thr Lys Pro Arg Glu Glu Gln Phe
                165             170             175

Asn Ser Thr Tyr Arg Val Val Ser Val Leu Thr Val Leu His Gln Asp
            180             185             190

Trp Leu Asn Gly Lys Glu Tyr Lys Cys Lys Val Ser Asn Lys Gly Leu
            195             200             205

Pro Ser Ser Ile Glu Lys Thr Ile Ser Lys Ala Lys Gly Gln Pro Arg
        210             215             220

Glu Pro Gln Val Tyr Thr Leu Pro Pro Ser Gln Glu Glu Met Thr Lys
225             230             235             240

Asn Gln Val Ser Leu Thr Cys Leu Val Lys Gly Phe Tyr Pro Ser Asp
                245             250             255

Ile Ala Val Glu Trp Glu Ser Asn Gly Gln Pro Glu Asn Asn Tyr Lys
            260             265             270

Thr Thr Pro Pro Val Leu Asp Ser Asp Gly Ser Phe Phe Leu Tyr Ser
            275             280             285

Arg Leu Thr Val Asp Lys Ser Arg Trp Gln Glu Gly Asn Val Phe Ser
        290             295             300

Cys Ser Val Met His Glu Ala Leu His Asn His Tyr Thr Gln Lys Ser
305             310             315             320

Leu Ser Leu Ser Leu Gly Lys
                325

<210> SEQ ID NO 213
<211> LENGTH: 107
<212> TYPE: PRT
<213> ORGANISM: Homo sapiens

<400> SEQUENCE: 213

Arg Thr Val Ala Ala Pro Ser Val Phe Ile Phe Pro Pro Ser Asp Glu
1               5               10              15

Gln Leu Lys Ser Gly Thr Ala Ser Val Val Cys Leu Leu Asn Asn Phe
            20              25              30

Tyr Pro Arg Glu Ala Lys Val Gln Trp Lys Val Asp Asn Ala Leu Gln
            35              40              45

Ser Gly Asn Ser Gln Glu Ser Val Thr Glu Gln Asp Ser Lys Asp Ser
        50              55              60

Thr Tyr Ser Leu Ser Ser Thr Leu Thr Leu Ser Lys Ala Asp Tyr Glu
65              70              75              80

Lys His Lys Val Tyr Ala Cys Glu Val Thr His Gln Gly Leu Ser Ser
                85              90              95

Pro Val Thr Lys Ser Phe Asn Arg Gly Glu Cys
            100             105
```

<210> SEQ ID NO 214
<211> LENGTH: 326
<212> TYPE: PRT
<213> ORGANISM: Homo sapiens

<400> SEQUENCE: 214

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 215
<211> LENGTH: 330
<212> TYPE: PRT
<213> ORGANISM: Homo sapiens

<400> SEQUENCE: 215

-continued

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 216
<211> LENGTH: 330
<212> TYPE: PRT
<213> ORGANISM: Homo sapiens

<400> SEQUENCE: 216
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
```

-continued

```
             35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Pro Lys Ser Cys Asp Lys Thr His Thr Cys Pro Pro Cys
                100                 105                 110
Pro Ala Pro Glu Leu Leu Gly Gly Pro Ser Val Phe Leu Phe Pro Pro
                115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Ala Ser Thr Tyr Arg Val Val Ser Val Leu Thr Val Leu
                180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
                275                 280                 285
Leu Tyr Ser Lys Leu Thr Val Asp Lys Ser Arg Trp Gln Gln Gly Asn
        290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

```
<210> SEQ ID NO 217
<211> LENGTH: 330
<212> TYPE: PRT
<213> ORGANISM: Homo sapiens

<400> SEQUENCE: 217
```

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
```

```
Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Ala Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 218
<211> LENGTH: 330
<212> TYPE: PRT
<213> ORGANISM: Homo sapiens

<400> SEQUENCE: 218

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
            115                 120                 125
```

-continued

```
Lys Pro Lys Asp Thr Leu Met Ile Ser Arg Thr Pro Glu Val Thr Cys
    130             135             140

Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
            165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
            195             200             205

Lys Ala Leu Pro Ala Pro Ile Glu Lys Thr Ile Ser Lys Ala Lys Gly
    210             215             220

Gln Pro Arg Glu Pro Gln Val Tyr Thr Leu Pro Pro Ser Arg Glu Glu
225             230             235             240

Met Thr Lys Asn Gln Val Ser Leu Thr Cys Leu Val Lys Gly Phe Tyr
            245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
            275             280             285

Leu Tyr Ser Lys Leu Thr Val Asp Lys Ser Arg Trp Gln Gln Gly Asn
    290             295             300

Val Phe Ser Cys Ser Val Met His Glu Ala Leu His Asn His Tyr Thr
305             310             315             320

Gln Lys Ser Leu Ser Leu Ser Pro Gly Lys
            325             330
```

```
<210> SEQ ID NO 219
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 219

Met Glu Trp Ser Trp Val Phe Leu Phe Phe Leu Ser Val Thr Thr Gly
1               5               10              15

Val His Ser
```

```
<210> SEQ ID NO 220
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 220

Met Ser Val Pro Thr Gln Val Leu Gly Leu Leu Leu Leu Trp Leu Thr
1               5               10              15

Asp Ala Arg Cys
            20
```

```
<210> SEQ ID NO 221
<211> LENGTH: 19
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 221

Met Ala Trp Val Trp Thr Leu Pro Phe Leu Met Ala Ala Ala Gln Ser
1               5                   10                  15

Val Gln Ala

<210> SEQ ID NO 222
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 222

Met Ser Val Leu Thr Gln Val Leu Ala Leu Leu Leu Leu Trp Leu Thr
1               5                   10                  15

Gly Thr Arg Cys
            20

<210> SEQ ID NO 223
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223
tggactactg ggacgggagc ttac                                           24

<210> SEQ ID NO 224
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 224

Gly Tyr Thr Phe Thr Thr Tyr Trp Met His
1               5                   10

<210> SEQ ID NO 225
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 225

Cys Asn Gly Arg Cys
1               5

<210> SEQ ID NO 226

<400> SEQUENCE: 226
```

000

<210> SEQ ID NO 227

<400> SEQUENCE: 227

000

<210> SEQ ID NO 228
<211> LENGTH: 134
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 228

Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Thr Tyr
            20                  25                  30

Trp Met His Trp Val Arg Gln Arg Pro Gly Gln Gly Leu Glu Trp Ile
        35                  40                  45

Gly Asn Ile Tyr Pro Gly Thr Gly Gly Ser Asn Phe Asp Glu Lys Phe
    50                  55                  60

Lys Asn Arg Thr Ser Leu Thr Val Asp Thr Ser Ser Thr Thr Ala Tyr
65                  70                  75                  80

Met His Leu Ala Ser Leu Thr Ser Glu Asp Ser Ala Val Tyr Tyr Cys
                85                  90                  95

Thr Arg Trp Thr Thr Gly Thr Gly Ala Tyr Trp Gly Gln Gly Thr Leu
            100                 105                 110

Val Thr Val Ser Ala Ala Lys Thr Thr Pro Pro Ser Val Tyr Pro Leu
        115                 120                 125

Ala Pro Gly Ser Ala Ala
    130

<210> SEQ ID NO 229
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 229

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Thr Gly Ser Gly Ser Val Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Cys Thr Phe Gly Gly Gly Thr Lys Leu Glu Ile
            100                 105                 110

Lys Arg Ala Asp
        115

<210> SEQ ID NO 230
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 230

Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg His Gly Gln Gly Leu Glu Trp Ile
        35                  40                  45

Gly Asn Ile Tyr Pro Gly Ser Gly Ser Thr Asn Tyr Asp Glu Lys Phe
    50                  55                  60

Lys Ser Lys Gly Thr Leu Thr Val Asp Thr Ser Ser Ser Thr Ala Tyr
65                  70                  75                  80

Met His Leu Ser Ser Leu Thr Ser Glu Asp Ser Ala Val Tyr Tyr Cys
                85                  90                  95

Thr Arg

<210> SEQ ID NO 231
<211> LENGTH: 101
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 231

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro
            100

<210> SEQ ID NO 232
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:

```
      Synthetic oligonucleotide"
<220> FEATURE:
<221> NAME/KEY: CDS
<222> LOCATION: (2)..(37)

<400> SEQUENCE: 232 g tgc acg ttc gga ggg ggg acc aag ctg gaa ata aaa                        37
  Cys Thr Phe Gly Gly Gly Thr Lys Leu Glu Ile Lys
  1               5                   10

<210> SEQ ID NO 233
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 233

Cys Thr Phe Gly Gly Gly Thr Lys Leu Glu Ile Lys
1               5                   10

<210> SEQ ID NO 234
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: CDS
<222> LOCATION: (2)..(37)

<400> SEQUENCE: 234 g tac acg ttc gga ggg ggg acc aag ctg gaa ata aaa c                      38
  Tyr Thr Phe Gly Gly Gly Thr Lys Leu Glu Ile Lys
  1               5                   10

<210> SEQ ID NO 235
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 235

Tyr Thr Phe Gly Gly Gly Thr Lys Leu Glu Ile Lys
1               5                   10

<210> SEQ ID NO 236
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 236

Met Tyr Pro Pro Tyr
1               5

<210> SEQ ID NO 237
<211> LENGTH: 4
<212> TYPE: PRT
```

-continued

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 237

Arg Gly Asp Ser
1

<210> SEQ ID NO 238
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 238

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Asn
            20                  25                  30

Val Ile Ser Trp Val Arg Gln Ala Pro Gly Gln Gly Leu Glu Trp Met
        35                  40                  45

Gly Gly Val Ile Pro Ile Val Asp Ile Ala Asn Tyr Ala Gln Arg Phe
    50                  55                  60

Lys Gly Arg Val Thr Ile Thr Ala Asp Glu Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Ala Ser Thr Leu Gly Leu Val Leu Asp Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Ser Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300
```

-continued

```
Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445

<210> SEQ ID NO 239
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 239

Glu Thr Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Pro Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Asp Ser Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205
```

Ser Phe Asn Arg Gly Glu Cys
    210                 215

<210> SEQ ID NO 240
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 240

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Trp Glu Val Arg Ala Leu Pro Ser Val Tyr Trp Gly
            100                 105                 110

Gln Gly Thr Leu Val Thr Val Ser Ser
        115                 120

<210> SEQ ID NO 241
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 241

Ser Tyr Glu Leu Thr Gln Pro Pro Ser Val Ser Val Ala Pro Gly Gln
1               5                   10                  15

Thr Ala Arg Ile Thr Cys Gly Ala Asn Asp Ile Gly Ser Lys Ser Val
            20                  25                  30

His Trp Tyr Gln Gln Lys Ala Gly Gln Ala Pro Val Leu Val Val Ser
        35                  40                  45

Glu Asp Ile Ile Arg Pro Ser Gly Ile Pro Glu Arg Ile Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Arg Asp Ser Asp Gln
                85                  90                  95

Tyr Val Phe Gly Thr Gly Thr Lys Val Thr Val Leu Gly
            100                 105

<210> SEQ ID NO 242
<211> LENGTH: 440
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 242

```
Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
            165                 170                 175

Ser Leu Ser Ser Val Val Thr Val Pro Ser Ser Ser Leu Gly Thr Lys
        180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
            325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400
```

-continued

```
Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 243
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 243

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 244
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 244

Gln Val Gln Leu Val Gln Ser Gly Val Glu Val Lys Lys Pro Gly Ala
1               5                   10                  15
```

```
Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
            50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                    85                  90                  95

Ala Arg Arg Asp Tyr Arg Phe Asp Met Gly Phe Asp Tyr Trp Gly Gln
                100                 105                 110

Gly Thr Thr Val Thr Val Ser Ser Ala Ser Thr Lys Gly Pro Ser Val
                115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
```

```
            435                440                445

<210> SEQ ID NO 245
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 245

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
                20                  25                  30

Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 246
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 246

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ile Met Met Trp Val Arg Gln Ala Pro Gly Lys Gly Leu Glu Trp Val
            35                  40                  45

Ser Ser Ile Tyr Pro Ser Gly Gly Ile Thr Phe Tyr Ala Asp Lys Gly
    50                  55                  60
```

```
Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Ile Lys Leu Gly Thr Val Thr Thr Val Asp Tyr Trp Gly Gln Gly Thr
            100                 105                 110

Leu Val Thr Val Ser Ser
        115
```

```
<210> SEQ ID NO 247
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 247
```

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
            100                 105                 110
```

```
<210> SEQ ID NO 248
<211> LENGTH: 253
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 248
```

```
Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Asp Tyr
            20                  25                  30

Lys Asp Asp Asp Asp Lys Ile Glu Gly Arg Ile Thr Cys Pro Pro Pro
        35                  40                  45

Met Ser Val Glu His Ala Asp Ile Trp Val Lys Ser Tyr Ser Leu Tyr
    50                  55                  60

Ser Arg Glu Arg Tyr Ile Cys Asn Ser Gly Phe Lys Arg Lys Ala Gly
65                  70                  75                  80

Thr Ser Ser Leu Thr Glu Cys Val Leu Asn Lys Ala Thr Asn Val Ala
                85                  90                  95

His Trp Thr Thr Pro Ser Leu Lys Cys Ile Arg Asp Pro Ala Leu Val
            100                 105                 110
```

-continued

```
His Gln Arg Pro Ala Pro Pro Ser Gly Gly Ser Gly Gly Gly Gly Ser
        115             120             125

Gly Gly Gly Ser Gly Gly Gly Gly Ser Leu Gln Asn Trp Val Asn Val
        130             135             140

Ile Ser Asp Leu Lys Lys Ile Glu Asp Leu Ile Gln Ser Met His Ile
145             150             155             160

Asp Ala Thr Leu Tyr Thr Glu Ser Asp Val His Pro Ser Cys Lys Val
        165             170             175

Thr Ala Met Lys Cys Phe Leu Leu Glu Leu Gln Val Ile Ser Leu Glu
        180             185             190

Ser Gly Asp Ala Ser Ile His Asp Thr Val Glu Asn Leu Ile Ile Leu
        195             200             205

Ala Asn Asn Ser Leu Ser Ser Asn Gly Asn Val Thr Glu Ser Gly Cys
        210             215             220

Lys Glu Cys Glu Glu Leu Glu Glu Lys Asn Ile Lys Glu Phe Leu Gln
225             230             235             240

Ser Phe Val His Ile Val Gln Met Phe Ile Asn Thr Ser
        245             250
```

<210> SEQ ID NO 249
<211> LENGTH: 263
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 249

```
Met Asp Ser Lys Gly Ser Ser Gln Lys Ala Gly Ser Arg Leu Leu Leu
1               5               10              15

Leu Leu Val Val Ser Asn Leu Leu Leu Cys Gln Gly Val Val Ser Thr
        20              25              30

Thr Arg Asp Tyr Lys Asp Asp Asp Lys Ile Glu Gly Arg Asn Trp
        35              40              45

Val Asn Val Ile Ser Asp Leu Lys Lys Ile Glu Asp Leu Ile Gln Ser
        50              55              60

Met His Ile Asp Ala Thr Leu Tyr Thr Glu Ser Asp Val His Pro Ser
65              70              75              80

Cys Lys Val Thr Ala Met Lys Cys Phe Leu Leu Glu Leu Gln Val Ile
        85              90              95

Ser Leu Glu Ser Gly Asp Ala Ser Ile His Asp Thr Val Glu Asn Leu
        100             105             110

Ile Ile Leu Ala Asn Asn Ser Leu Ser Ser Asn Gly Asn Val Thr Glu
        115             120             125

Ser Gly Cys Lys Glu Cys Glu Glu Leu Glu Glu Lys Asn Ile Lys Glu
        130             135             140

Phe Leu Gln Ser Phe Val His Ile Val Gln Met Phe Ile Asn Thr Ser
145             150             155             160

Ser Gly Gly Gly Ser Gly Gly Gly Gly Ser Gly Gly Gly Gly Ser Gly
        165             170             175

Gly Gly Gly Ser Gly Gly Gly Ser Leu Gln Ile Thr Cys Pro Pro Pro
        180             185             190

Met Ser Val Glu His Ala Asp Ile Trp Val Lys Ser Tyr Ser Leu Tyr
        195             200             205

Ser Arg Glu Arg Tyr Ile Cys Asn Ser Gly Phe Lys Arg Lys Ala Gly
```

```
        210                 215                 220
Thr Ser Ser Leu Thr Glu Cys Val Leu Asn Lys Ala Thr Asn Val Ala
225                 230                 235                 240

His Trp Thr Thr Pro Ser Leu Lys Cys Ile Arg Asp Pro Ala Leu Val
                245                 250                 255

His Gln Arg Pro Ala Pro Pro
            260
```

<210> SEQ ID NO 250
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 250

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Gly Ser Tyr Gly Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Val Asn Phe Gly Met Asp Tyr Trp Gly Gln Gly Thr Leu
            100                 105                 110

Val Thr Val Ser Ser
        115
```

<210> SEQ ID NO 251
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 251

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Arg Asn Pro Pro
                85                  90                  95

Thr Phe Gly Gln Gly Thr Lys Leu Glu Ile Lys
            100                 105
```

-continued

```
<210> SEQ ID NO 252
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 252

Gly Phe Thr Phe Ser Ser Tyr Ala
1               5

<210> SEQ ID NO 253
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 253

Ile Gly Ser Tyr Gly Gly Gly Thr
1               5

<210> SEQ ID NO 254
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 254

Ala Arg Tyr Val Asn Phe Gly Met Asp Tyr
1               5                   10

<210> SEQ ID NO 255
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 255

Gln Ser Ile Ser Ser Tyr
1               5

<210> SEQ ID NO 256
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 256

Ala Ala Ser
1

<210> SEQ ID NO 257
<211> LENGTH: 9
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 257

Gln Gln Tyr Gly Arg Asn Pro Pro Thr
1               5

<210> SEQ ID NO 258
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 258

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Val Trp Gly Phe Asp Tyr Trp Gly Gln Gly Thr Leu Val
            100                 105                 110

Thr Val Ser Ser
        115

<210> SEQ ID NO 259
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 259

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Val Tyr Pro Phe
                85                  90                  95

Thr Phe Gly Gln Gly Thr Lys Leu Glu Ile Lys
```

-continued

```
                  100                 105

<210> SEQ ID NO 260
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 260

Ile Ser Gly Ser Gly Gly Ser Thr
1               5

<210> SEQ ID NO 261
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 261

Ala Arg Arg Val Trp Gly Phe Asp Tyr
1               5

<210> SEQ ID NO 262
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 262

Gln Gln Tyr Gly Val Tyr Pro Phe Thr
1               5

<210> SEQ ID NO 263
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (120)..(120)
<223> OTHER INFORMATION: Any amino acid
<220> FEATURE:
<221> NAME/KEY: MOD_RES
<222> LOCATION: (124)..(125)
<223> OTHER INFORMATION: Any amino acid

<400> SEQUENCE: 263

Glu Val Arg Leu Gln Gln Ser Gly Ala Asp Leu Val Lys Pro Gly Ala
1               5                   10                  15

Ser Val Lys Leu Ser Cys Ala Ser Gly Phe Ile Ile Lys Ala Thr Tyr
            20                  25                  30

Met His Trp Val Arg Gln Arg Pro Glu Gln Gly Leu Glu Trp Ile Gly
        35                  40                  45

Arg Ile Asp Pro Ala Asn Gly Glu Lys Tyr Asp Pro Lys Phe Gln Val
    50                  55                  60
```

-continued

```
Lys Ala Ile Thr Ala Asp Thr Ser Ser Ser Thr Ala Tyr Leu Gln Leu
65                  70                  75                  80

Asn Ser Leu Thr Ser Asp Asp Thr Ala Val Tyr Tyr Cys Ala Arg Tyr
                85                  90                  95

Ala Trp Tyr Phe Asp Val Trp Gly Ala Gly Thr Thr Val Thr Val Ser
                100                 105                 110

Ser Ala Lys Thr Thr Pro Pro Xaa Val Tyr Pro Xaa Xaa Pro Gly Ser
        115                 120                 125
```

<210> SEQ ID NO 264
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 264

```
Asp Ile Gln Met Thr Gln Ser Pro Ala Ser Leu Ser Ala Ser Val Gly
1               5                   10                  15

Asp Thr Val Thr Ile Thr Cys Arg Ala Ser Glu Asn Ile Tyr Ser Phe
                20                  25                  30

Leu Ala Trp Tyr His Gln Lys Gln Gly Arg Ser Pro Gln Leu Leu Val
        35                  40                  45

Tyr His Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Ala
65                  70                  75                  80

Glu Asp Phe Gly Ser Tyr Tyr Cys Gln His Tyr Tyr Gly Ser Pro Leu
                85                  90                  95

Thr Phe Gly Ala Gly Thr Lys Leu Glu Val Lys Arg Ala Asp Ala Ala
                100                 105                 110

Pro Thr Val Ser Ile Phe Pro Pro Ser Ser Glu Glu Leu Ser Leu
        115                 120                 125
```

<210> SEQ ID NO 265
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 265

```
Gly Phe Ile Ile Lys Ala Thr Tyr Met His
1               5                   10
```

<210> SEQ ID NO 266
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 266

```
Arg Ile Asp Pro Ala Asn Gly Glu Thr Lys Tyr Asp Pro Lys Phe Gln
1               5                   10                  15

Val
```

```
<210> SEQ ID NO 267
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 267

Tyr Ala Trp Tyr Phe Asp Val
1               5

<210> SEQ ID NO 268
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 268

Arg Ala Ser Glu Asn Ile Tyr Ser Phe Leu Ala
1               5                   10

<210> SEQ ID NO 269
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 269

His Ala Lys Thr Leu Ala Glu
1               5

<210> SEQ ID NO 270
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 270

Gln His Tyr Tyr Gly Ser Pro Leu Thr
1               5

<210> SEQ ID NO 271
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 271

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30
```

```
Trp Met Asn Trp Val Arg Gln Ala Pro Gly Lys Gly Leu Glu Trp Val
        35                  40                  45

Ala Ala Ile Asn Gln Asp Gly Ser Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Val Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125
```

```
<210> SEQ ID NO 272
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 272

Asn Tyr Trp Met Asn
1               5
```

```
<210> SEQ ID NO 273
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 273

Ala Ile Asn Gln Asp Gly Ser Glu Lys Tyr Tyr Val Gly Ser Val Lys
1               5                   10                  15

Gly
```

```
<210> SEQ ID NO 274
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 274

Asp Tyr Tyr Asp Ile Leu Thr Asp Tyr Tyr Ile His Tyr Trp Tyr Phe
1               5                   10                  15

Asp Leu
```

```
<210> SEQ ID NO 275
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 275
```

Arg Ala Ser Gln Ser Val Ser Ser Ser Tyr Leu Ala
1               5                   10

<210> SEQ ID NO 276
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 276

Gly Ala Ser Ser Arg Ala Thr
1               5

<210> SEQ ID NO 277
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 277

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ser Leu Tyr Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val

-continued

```
            260               265                270
Lys Phe Asn Trp Tyr Val Asp Gly Val Glu Val His Asn Ala Lys Thr
        275               280               285

Lys Pro Arg Glu Glu Gln Tyr Asn Ser Thr Tyr Arg Val Val Ser Val
    290               295               300

Leu Thr Val Leu His Gln Asp Trp Leu Asn Gly Lys Glu Tyr Lys Cys
305               310               315               320

Lys Val Ser Asn Lys Ala Leu Pro Ala Pro Ile Glu Lys Thr Ile Ser
            325               330               335

Lys Ala Lys Gly Gln Pro Arg Glu Pro Gln Val Tyr Thr Leu Pro Pro
            340               345               350

Ser Arg Glu Glu Met Thr Lys Asn Gln Val Ser Leu Thr Cys Leu Val
        355               360               365

Lys Gly Phe Tyr Pro Ser Asp Ile Ala Val Glu Trp Glu Ser Asn Gly
    370               375               380

Gln Pro Glu Asn Asn Tyr Lys Thr Thr Pro Pro Val Leu Asp Ser Asp
385               390               395               400

Gly Ser Phe Phe Leu Tyr Ser Lys Leu Thr Val Asp Lys Ser Arg Trp
            405               410               415

Gln Gln Gly Asn Val Phe Ser Cys Ser Val Met His Glu Ala Leu His
            420               425               430

Asn His Tyr Thr Gln Lys Ser Leu Ser Leu Ser Pro Gly Lys
            435               440               445
```

```
<210> SEQ ID NO 278
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 278

Ala Ile Gln Leu Thr Gln Ser Pro Ser Ser Leu Ser Ala Ser Val Gly
1               5                10                15

Asp Arg Val Thr Ile Thr Cys Arg Pro Ser Gln Gly Ile Asn Trp Glu
            20                25                30

Leu Ala Trp Tyr Gln Gln Lys Pro Gly Lys Ala Pro Lys Leu Leu Ile
        35                40                45

Tyr Asp Ala Ser Ser Leu Glu Gln Gly Val Pro Ser Arg Phe Ser Gly
    50                55                60

Ser Gly Ser Gly Thr Asp Phe Thr Leu Thr Ile Ser Ser Leu Gln Pro
65                70                75                80

Glu Asp Phe Ala Thr Tyr Tyr Cys Gln Gln Phe Asn Ser Tyr Pro Leu
            85                90                95

Thr Phe Gly Gly Gly Thr Lys Val Glu Ile Lys Arg Thr Val Ala Ala
            100               105               110

Pro Ser Val Phe Ile Phe Pro Pro Ser Asp Glu Gln Leu Lys Ser Gly
        115               120               125

Thr Ala Ser Val Val Cys Leu Leu Asn Asn Phe Tyr Pro Arg Glu Ala
    130               135               140

Lys Val Gln Trp Lys Val Asp Asn Ala Leu Gln Ser Gly Asn Ser Gln
145               150               155               160

Glu Ser Val Thr Glu Gln Asp Ser Lys Asp Ser Thr Tyr Ser Leu Ser
            165               170               175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 279
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 279

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Ile His Trp Val Arg Gln Ala Pro Gly Gln Gly Leu Glu Trp Met
        35                  40                  45

Gly Val Ile Asn Pro Met Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Phe Thr Gly Thr Gly Val Tyr Trp Gly Gln Gly
            100                 105                 110

Thr Leu Val Thr Val Ser Ser
        115

<210> SEQ ID NO 280
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 280

Asp Ile Val Met Thr Gln Thr Pro Leu Ser Leu Ser Val Thr Pro Gly
1               5                   10                  15

Gln Pro Ala Ser Ile Ser Cys Arg Ser Ser Arg Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ile Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Leu Pro Phe Thr Phe Gly Gln Gly Thr Lys Leu Glu Ile Lys
            100                 105                 110
```

```
<210> SEQ ID NO 281
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 281

Arg Tyr Gly Ile Ser
1               5

<210> SEQ ID NO 282
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 282

Trp Ile Ser Thr Tyr Ser Gly Asn Thr Asn Tyr Ala Gln Lys Leu Gln
1               5                   10                  15

Gly

<210> SEQ ID NO 283
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 283

Arg Gln Leu Tyr Phe Asp Tyr
1               5

<210> SEQ ID NO 284
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 284

Arg Ala Ser Gln Ser Val Ser Ser Asn Leu Ala
1               5                   10

<210> SEQ ID NO 285
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 285

Asp Ala Ser Thr Arg Ala Thr
1               5

<210> SEQ ID NO 286
```

-continued

```
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 286

Gln Gln Tyr Asp Asn Trp Pro Leu Thr
1               5

<210> SEQ ID NO 287
<211> LENGTH: 137
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 287

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Val Tyr Gly Met Asn Trp Val Arg Gln Ala Pro Gly Lys Gly Leu
    50                  55                  60

Glu Trp Val Ala Ile Ile Trp Tyr Asp Gly Asp Asn Gln Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Gly Leu Arg Ala Glu Asp Thr Ala Val
            100                 105                 110

Tyr Tyr Cys Ala Arg Asp Leu Arg Thr Gly Pro Phe Asp Tyr Trp Gly
        115                 120                 125

Gln Gly Thr Leu Val Thr Val Ser Ser
    130                 135

<210> SEQ ID NO 288
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 288

Met Leu Pro Ser Gln Leu Ile Gly Phe Leu Leu Leu Trp Val Pro Ala
1               5                   10                  15

Ser Arg Gly Glu Ile Val Leu Thr Gln Ser Pro Asp Phe Gln Ser Val
            20                  25                  30

Thr Pro Lys Glu Lys Val Thr Ile Thr Cys Arg Ala Ser Gln Ser Ile
        35                  40                  45

Gly Ser Ser Leu His Trp Tyr Gln Gln Lys Pro Asp Gln Ser Pro Lys
    50                  55                  60

Leu Leu Ile Lys Tyr Ala Ser Gln Ser Phe Ser Gly Val Pro Ser Arg
65                  70                  75                  80
```

```
Phe Ser Gly Ser Gly Ser Gly Thr Asp Phe Thr Leu Thr Ile Asn Ser
                85                  90                  95

Leu Glu Ala Glu Asp Ala Ala Ala Tyr Tyr Cys His Gln Ser Ser Ser
            100                 105                 110

Leu Pro Phe Thr Phe Gly Pro Gly Thr Lys Val Asp Ile Lys
        115                 120                 125

<210> SEQ ID NO 289
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 289

Gly Asp Ser Val Ser Ser Asn Ser Ala Ala Trp Gly
1               5                   10

<210> SEQ ID NO 290
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 290

Arg Ile Tyr Tyr Arg Ser Lys Trp Tyr Asn Ser Tyr Ala Val Ser Val
1               5                   10                  15

Lys Ser

<210> SEQ ID NO 291
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 291

Arg Ala Ser Gln Phe Ile Ser Ser Ser Tyr Leu Ser
1               5                   10

<210> SEQ ID NO 292
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 292

Leu Leu Ile Tyr Gly Ser Ser Ser Arg Ala Thr
1               5                   10

<210> SEQ ID NO 293
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 293

Gln Gln Leu Tyr Ser Ser Pro Met
1               5

<210> SEQ ID NO 294
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 294

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
                20                  25                  30

Ser Ala Ala Trp Gly Trp Ile Arg Gln Ser Pro Gly Arg Gly Leu Glu
            35                  40                  45

Trp Leu Gly Arg Ile Tyr Tyr Arg Ser Lys Trp Tyr Asn Ser Tyr Ala
        50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Tyr Asp Trp Val Pro Lys Ile Gly Val Phe Asp
            100                 105                 110

Ser Trp Gly Gln Gly Thr Leu Val Thr Val Ser Ser
        115                 120

<210> SEQ ID NO 295
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 295

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Phe Ile Ser Ser Ser
                20                  25                  30

Tyr Leu Ser Trp Tyr Gln Gln Lys Pro Gly Gln Ala Pro Arg Leu Leu
        35                  40                  45

Ile Tyr Gly Ser Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Leu Tyr Ser Ser Pro
                85                  90                  95

Met Thr Phe Gly Gln Gly Thr Lys Val Glu Ile Lys Arg Thr
            100                 105                 110

<210> SEQ ID NO 296
<211> LENGTH: 454

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 296

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Gly Trp Ile Arg Gln Ser Pro Gly Arg Gly Leu Glu
        35                  40                  45

Trp Leu Gly Arg Ile Tyr Tyr Arg Ser Lys Trp Tyr Asn Ser Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Tyr Asp Trp Val Pro Lys Ile Gly Val Phe Asp
            100                 105                 110

Ser Trp Gly Gln Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Arg Val Glu Pro
        210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
```

```
      370              375              380

Ala Val Glu Trp Glu Ser Asn Gly Gln Pro Glu Asn Asn Tyr Lys Thr
385              390              395              400

Thr Pro Pro Val Leu Asp Ser Asp Gly Ser Phe Phe Leu Tyr Ser Lys
                 405              410              415

Leu Thr Val Asp Lys Ser Arg Trp Gln Gln Gly Asn Val Phe Ser Cys
                 420              425              430

Ser Val Met His Glu Ala Leu His Asn His Tyr Thr Gln Lys Ser Leu
                 435              440              445

Ser Leu Ser Pro Gly Lys
        450

<210> SEQ ID NO 297
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 297

Asp Ile Val Leu Thr Gln Ser Pro Ala Thr Leu Ser Leu Ser Pro Gly
1               5               10              15

Glu Arg Ala Thr Leu Ser Cys Arg Ala Ser Gln Phe Ile Ser Ser Ser
                20              25              30

Tyr Leu Ser Trp Tyr Gln Gln Lys Pro Gly Gln Ala Pro Arg Leu Leu
        35              40              45

Ile Tyr Gly Ser Ser Ser Arg Ala Thr Gly Val Pro Ala Arg Phe Ser
    50              55              60

Gly Ser Gly Ser Gly Thr Asp Phe Thr Leu Thr Ile Ser Ser Leu Glu
65              70              75              80

Pro Glu Asp Phe Ala Val Tyr Tyr Cys Gln Gln Leu Tyr Ser Ser Pro
                85              90              95

Met Thr Phe Gly Gln Gly Thr Lys Val Glu Ile Lys Arg Thr Val Ala
                100             105             110

Ala Pro Ser Val Phe Ile Phe Pro Pro Ser Asp Glu Gln Leu Lys Ser
        115             120             125

Gly Thr Ala Ser Val Val Cys Leu Leu Asn Asn Phe Tyr Pro Arg Glu
        130             135             140

Ala Lys Val Gln Trp Lys Val Asp Asn Ala Leu Gln Ser Gly Asn Ser
145             150             155             160

Gln Glu Ser Val Thr Glu Gln Asp Ser Lys Asp Ser Thr Tyr Ser Leu
                165             170             175

Ser Ser Thr Leu Thr Leu Ser Lys Ala Asp Tyr Glu Lys His Lys Val
        180             185             190

Tyr Ala Cys Glu Val Thr His Gln Gly Leu Ser Ser Pro Val Thr Lys
        195             200             205

Ser Phe Asn Arg Gly Glu Cys
    210             215

<210> SEQ ID NO 298
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
```

-continued

Synthetic polypeptide"

<400> SEQUENCE: 298

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Cys Thr Phe Gly Gln Gly Thr Arg Leu Glu Ile Lys Arg
            100                 105
```

<210> SEQ ID NO 299
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 299

```
Gln Gln Tyr Gly Ser Ser Pro Cys Thr
1               5
```

<210> SEQ ID NO 300
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 300

```
Tyr Asp Trp Val Pro Lys Ile Gly Val Phe Asp Ser
1               5                   10
```

<210> SEQ ID NO 301
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 301

```
Gly Phe Ser Leu Ser Ser Tyr
1               5
```

<210> SEQ ID NO 302
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 302

Trp Gly Gly Gly Gly
1               5

<210> SEQ ID NO 303
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 303

His Ala Tyr Gly His Asp Gly Gly Phe Ala Met Asp Tyr
1               5                   10

<210> SEQ ID NO 304
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 304

Ser Glu Ser Val Ser Ser Asn
1               5

<210> SEQ ID NO 305
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 305

Gly Ala Ser
1

<210> SEQ ID NO 306
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 306

Ser Tyr Ser Tyr Pro Phe
1               5

<210> SEQ ID NO 307
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 307

Ser Tyr Gly Val Asp
```

-continued

```
1               5
```

```
<210> SEQ ID NO 308
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 308

Val Ile Trp Gly Gly Gly Gly Thr Tyr Tyr Ala Ser Ser Leu Met Gly
1               5                   10                  15

<210> SEQ ID NO 309
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 309

Arg Ala Ser Glu Ser Val Ser Ser Asn Val Ala
1               5                   10

<210> SEQ ID NO 310
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 310

Gly Ala Ser Asn Arg Ala Thr
1               5

<210> SEQ ID NO 311
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 311

Gly Gln Ser Tyr Ser Tyr Pro Phe Thr
1               5

<210> SEQ ID NO 312
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 312

Glu Val Gln Leu Val Glu Ser Gly Gly Gly Leu Val Gln Ser Gly Gly
1               5                   10                  15

Ser Leu Arg Leu Ser Cys Ala Ala Ser Gly Phe Ser Leu Ser Ser Tyr
            20                  25                  30
```

```
Gly Val Asp Trp Val Arg Gln Ala Pro Gly Lys Gly Leu Glu Trp Val
        35                  40                  45

Gly Val Ile Trp Gly Gly Gly Thr Tyr Tyr Ala Ser Ser Leu Met
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg His Ala Tyr Gly His Asp Gly Gly Phe Ala Met Asp Tyr Trp Gly
            100                 105                 110

Gln Gly Thr Leu Val Thr Val Ser Ser
        115                 120
```

```
<210> SEQ ID NO 313
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 313

Glu Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ser Ser Asn
                20                  25                  30

Val Ala Trp Tyr Gln Gln Arg Pro Gly Gln Ala Pro Arg Leu Leu Ile
        35                  40                  45

Tyr Gly Ala Ser Asn Arg Ala Thr Gly Ile Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gly Gln Ser Tyr Ser Tyr Pro Phe
                85                  90                  95

Thr Phe Gly Gln Gly Thr Lys Leu Glu Ile Lys
            100                 105
```

```
<210> SEQ ID NO 314
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 314

Glu Val Gln Leu Val Glu Ser Gly Gly Gly Leu Val Gln Ser Gly Gly
1               5                   10                  15

Ser Leu Arg Leu Ser Cys Ala Ala Ser Gly Phe Ser Leu Ser Ser Tyr
                20                  25                  30

Gly Val Asp Trp Val Arg Gln Ala Pro Gly Lys Gly Leu Glu Trp Val
        35                  40                  45

Gly Val Ile Trp Gly Gly Gly Gly Thr Tyr Tyr Ala Ser Ser Leu Met
    50                  55                  60

Gly Arg Phe Thr Ile Ser Arg Asp Asn Ser Lys Asn Thr Leu Tyr Leu
65                  70                  75                  80
```

```
Gln Met Asn Ser Leu Arg Ala Glu Asp Thr Ala Val Tyr Tyr Cys Ala
            85                  90                  95

Arg His Ala Tyr Gly His Asp Gly Gly Phe Ala Met Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450
```

<210> SEQ ID NO 315
<211> LENGTH: 214
<212> TYPE: PRT
<213> ORGANISM: Artificial Sequence
<220> FEATURE:
<221> NAME/KEY: source -continued
<223> OTHER INFORMATION: /note="Description of Artificial Sequence:
      Synthetic polypeptide"

<400> SEQUENCE: 315

Glu Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ser Ser Asn
            20                  25                  30

Val Ala Trp Tyr Gln Gln Arg Pro Gly Gln Ala Pro Arg Leu Leu Ile
        35                  40                  45

Tyr Gly Ala Ser Asn Arg Ala Thr Gly Ile Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gly Gln Ser Tyr Ser Tyr Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 316
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 316

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Tyr Trp Val Arg Gln Ala Arg Gly Gln Arg Leu Glu Trp Ile
        35                  40                  45

Gly Arg Ile Asp Pro Asn Ser Gly Ser Thr Lys Tyr Asn Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120

<210> SEQ ID NO 317
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 317

Ala Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Leu Gln Lys Pro Gly Gln Ser Pro Gln Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Tyr Asn Ser Tyr Pro Leu
                85                  90                  95

Thr Phe Gly Gln Gly Thr Lys Val Glu Ile Lys
            100                 105

<210> SEQ ID NO 318
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 318

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Tyr Trp Val Arg Gln Ala Thr Gly Gln Gly Leu Glu Trp Met
        35                  40                  45

Gly Arg Ile Asp Pro Asn Ser Gly Ser Thr Lys Tyr Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120

<210> SEQ ID NO 319
<211> LENGTH: 107
<212> TYPE: PRT
<213> ORGANISM: Artificial Sequence
<220> FEATURE:

<400> SEQUENCE: 319

Asp Val Val Met Thr Gln Ser Pro Leu Ser Leu Pro Val Thr Leu Gly
1               5                   10                  15

Gln Pro Ala Ser Ile Ser Cys Lys Ala Ser Gln Asp Val Gly Thr Ala
                20                  25                  30

Val Ala Trp Tyr Gln Gln Lys Pro Gly Gln Ala Pro Arg Leu Leu Ile
            35                  40                  45

Tyr Trp Ala Ser Thr Arg His Thr Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Leu
                85                  90                  95

Thr Phe Gly Gln Gly Thr Lys Val Glu Ile Lys
            100                 105

<210> SEQ ID NO 320
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 320

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Leu Thr Asn Tyr
                20                  25                  30

Gly Met Asn Trp Val Arg Gln Ala Arg Gly Gln Arg Leu Glu Trp Ile
            35                  40                  45

Gly Trp Ile Asn Thr Asp Thr Gly Glu Pro Thr Tyr Ala Asp Asp Phe
        50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser
        115                 120                 125

<210> SEQ ID NO 321
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 321

Asp Ile Gln Met Thr Gln Ser Pro Ser Ser Leu Ser Ala Ser Val Gly
1               5                   10                  15

Asp Arg Val Thr Ile Thr Cys Ser Ser Ser Gln Asp Ile Ser Asn Tyr

-continued

```
                20                  25                  30

Leu Asn Trp Tyr Leu Gln Lys Pro Gly Gln Ser Pro Gln Leu Leu Ile
        35                  40                  45

Tyr Tyr Thr Ser Thr Leu His Leu Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Asn Leu Pro Trp
                85                  90                  95

Thr Phe Gly Gln Gly Thr Lys Val Glu Ile Lys
                100                 105

<210> SEQ ID NO 322
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 322

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Leu Thr Asn Tyr
                20                  25                  30

Gly Met Asn Trp Val Arg Gln Ala Pro Gly Gln Gly Leu Glu Trp Met
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asn Pro Pro Tyr Tyr Tyr Gly Thr Asn Asn Ala Glu Ala Met
                100                 105                 110

Asp Tyr Trp Gly Gln Gly Thr Thr Val Thr Val Ser Ser
                115                 120                 125

<210> SEQ ID NO 323
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 323

Asp Ile Gln Met Thr Gln Ser Pro Ser Ser Leu Ser Ala Ser Val Gly
1               5                   10                  15

Asp Arg Val Thr Ile Thr Cys Ser Ser Ser Gln Asp Ile Ser Asn Tyr
                20                  25                  30

Leu Asn Trp Tyr Gln Gln Lys Pro Gly Lys Ala Pro Lys Leu Leu Ile
        35                  40                  45

Tyr Tyr Thr Ser Thr Leu His Leu Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80
```

Glu Asp Ala Ala Tyr Tyr Phe Cys Gln Gln Tyr Tyr Asn Leu Pro Trp
                85                  90                  95

Thr Phe Gly Gln Gly Thr Lys Val Glu Ile Lys
            100                 105

<210> SEQ ID NO 324
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 324

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Ile
        35                  40                  45

Gly Asp Ile Tyr Pro Gly Gln Gly Asp Thr Ser Tyr Asn Gln Lys Phe
    50                  55                  60

Lys Gly Arg Ala Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Leu Val Thr Val Ser Ser
        115

<210> SEQ ID NO 325
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 325

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Arg
                85                  90                  95

Lys Asp Pro Ser Thr Phe Gly Gly Gly Thr Lys Val Glu Ile Lys
            100                 105                 110

<210> SEQ ID NO 326
<211> LENGTH: 118

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 326

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

Asn Met His Trp Val Arg Gln Ala Pro Gly Gln Gly Leu Glu Trp Met
        35                  40                  45

Gly Asp Ile Tyr Pro Gly Asn Gly Asp Thr Ser Tyr Asn Gln Lys Phe
    50                  55                  60

Lys Gly Arg Val Thr Ile Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
                100                 105                 110

Thr Val Thr Val Ser Ser
            115

<210> SEQ ID NO 327
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 327

Ala Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Glu Tyr Tyr
                20                  25                  30

Gly Thr Ser Leu Met Gln Trp Tyr Gln Gln Lys Pro Gly Lys Ala Pro
        35                  40                  45

Lys Leu Leu Ile Tyr Ala Ala Ser Asn Val Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Phe Cys Gln Gln Ser Arg
                85                  90                  95

Lys Asp Pro Ser Thr Phe Gly Gly Gly Thr Lys Val Glu Ile Lys
                100                 105                 110
```

What is claimed is:

1. A method of treating a cancer in a subject, the method comprising administering to the subject an anti-PD-1 antibody molecule at a flat dose of 300 mg once every three weeks or 400 mg once every four weeks, wherein the anti-PD-1 antibody molecule comprises a heavy chain comprising the amino acid sequence of SEQ ID NO: 91 and a light chain comprising the amino acid sequence of SEQ ID NO: 72; and wherein the method does not comprise administering an A2AR antagonist to the subject.

2. The method of claim 1, wherein the anti-PD-1 antibody molecule is administered in combination with one or more therapeutic agents chosen from one, two, or all of the following categories (i)-(iii):

(i) an agent that enhances tumor antigen presentation chosen from one or more of: a STING agonist, a TLR agonist, an oncolytic virus, a TIM-3 modulator, a vascular endothelial growth factor receptor (VEGFR) inhibitor, a c-Met inhibitor, a TGFb inhibitor, an IDO/ TDO inhibitor, a vaccine, or a bi- or tri-specific cell engager;

(ii) an agent that enhances an effector cell response chosen from one or more of: a GITR agonist, a PD-L1 inhibitor, an inhibitor of IAP (Inhibitor of Apoptosis Protein), an inhibitor of EGFR (Epidermal Growth Factor Receptor), an inhibitor of target of rapamycin (mTOR), IL-15 or a variant thereof, a CTLA-4 inhibitor, a bispecific antibody molecule that binds to CD3 and a tumor antigen, a CD40 agonist, an OX40 agonist, or a CD27 agonist; or (iii) an agent that decreases tumor immunosuppression chosen from one or more of: a GITR agonist, an inhibitor of an immune checkpoint molecule chosen from one or more of PD-L1, LAG-3, TIM-3 or CTLA-4, a CSF-1/1R inhibitor, an IL-17 inhibitor, an IL-1β inhibitor, a CXCR2 inhibitor, an inhibitor of PI3Kγ or PI3Kδ, a BAFF-R inhibitor, a MALT-1/BTK inhibitor, a JAK inhibitor, a CRTH2 inhibitor, a VEGFR inhibitor, an IL-15 or a variant thereof, a CTLA-4 inhibitor, an IDO/TDO inhibitor, a TGFb inhibitor, or a PFKFB3 inhibitor.

3. The method of claim 1, wherein the anti-PD-1 antibody molecule is administered at a flat dose of 300 mg once every three weeks.

4. The method of claim 1, wherein the anti-PD-1 antibody molecule is administered at a flat dose of 400 mg once every four weeks.

5. The method of claim 1, wherein the cancer is a solid tumor or a hematological cancer.

6. The method of claim 1, wherein the cancer is chosen from a lung cancer, a kidney cancer, a liver cancer, a myeloma, a prostate cancer, a breast cancer, a colorectal cancer (CRC), a gastric cancer, a pancreatic cancer, a thyroid cancer, a neuroendocrine tumor (NET), an ovarian cancer, a fallopian tube cancer, a lymphoma, a leukemia, a myelodysplastic syndrome (MDS), a skin cancer, a brain cancer, a glioblastoma multiforme (GBM), a uterine cancer, an endometrial carcinoma, or a metastatic lesion of the cancer.

7. The method of claim 6, wherein the skin cancer is a Merkel cell carcinoma or a melanoma.

8. The method of claim 6, wherein the breast cancer is a triple negative breast cancer (TNBC), a HER2-negative breast cancer, or an ER+ breast cancer.

9. The method of claim 6, wherein the kidney cancer is a renal cell carcinoma.

10. The method of claim 9, wherein the renal cell carcinoma is a clear cell renal cell carcinoma (CCRCC) or a non-clear cell renal cell carcinoma (nccRCC).

11. The method of claim 6, wherein the thyroid cancer is an anaplastic thyroid carcinoma (ATC).

12. The method of claim 6, wherein the neuroendocrine tumor (NET) is an atypical pulmonary carcinoid tumor or an NET in pancreas, gastrointestinal (GI) tract, or lung.

13. The method of claim 6, wherein the lung cancer is a non-small cell lung cancer (NSCLC).

14. The method of claim 13, wherein the NSCLC is a squamous NSCLC, a non-squamous NSCLC, or a NSCLC adenocarcinoma.

15. The method of claim 6, wherein the colorectal cancer (CRC) is a microsatellite instability-high colorectal cancer (MSI-high CRC) or a microsatellite stable colorectal cancer (MSS CRC).

16. The method of claim 6, wherein the leukemia is an acute myeloid leukemia (AML).

17. The method of claim 16, wherein the acute myeloid leukemia (AML) is a relapsed or refractory AML or a de novo AML.

18. The method of claim 6, wherein the myelodysplastic syndrome (MDS) is a high risk MDS.

19. The method of claim 6, wherein the liver cancer is a hepatocellular carcinoma.

20. The method of claim 6, wherein the gastric cancer is an EBV+ gastric cancer.

21. The method of claim 6, wherein the lymphoma is a non-Hodgkin's lymphoma.

22. The method of claim 1, wherein the anti-PD-1 antibody molecule is administered in combination with an IAP inhibitor.

23. The method of claim 1, wherein the anti-PD-1 antibody molecule is administered in combination with an mTOR inhibitor.

24. The method of claim 1, wherein the anti-PD-1 antibody molecule is administered in combination with a DAC inhibitor.

25. The method of claim 1, wherein the anti-PD-1 antibody molecule is administered in combination with an IL-1β inhibitor.

26. The method of claim 1, wherein the anti-PD-1 antibody molecule is administered in combination with an IL-17 inhibitor.

27. The method of claim 1, wherein the anti-PD-1 antibody molecule is administered in combination with a MEK inhibitor.

28. The method of claim 1, wherein the anti-PD-1 antibody molecule is administered in combination with an EGFR inhibitor.

29. The method of claim 1, wherein the anti-PD-1 antibody molecule is administered in combination with a CSF-1/1R binding agent.

30. The method of claim 1, wherein the anti-PD-1 antibody molecule is administered in combination with an inhibitor of 6-phosphofructo-2-kinase/fructose-2,6-biphosphatase 3 (PFKFB3).

31. The method of claim 1, wherein the anti-PD-1 antibody molecule is used in combination with a chemotherapeutic agent, wherein the chemotherapeutic agent is a paclitaxel.

32. The method of claim 1, wherein the anti-PD-1 antibody molecule is administered in combination with a BRAF inhibitor and a MEK inhibitor.

33. The method of claim 1, wherein the anti-PD-1 antibody molecule is administered in combination with a TGF-β inhibitor.

34. The method of claim 1, wherein the anti-PD-1 antibody molecule is administered in combination with an inhibitor of PD-L1.

35. The method of claim 1, wherein the anti-PD-1 antibody molecule is administered in combination with a hypomethylating agent.

36. The method of claim 35, wherein the combination further comprises an inhibitor of TIM-3.

37. The method of claim 1, wherein the anti-PD-1 antibody molecule is administered in combination with a second inhibitor of PD-1.

38. The method of claim 1, wherein the cancer comprises a BRAF mutation.

39. The method of claim 38, wherein the BRAF mutation is a V600E mutation.

40. The method of claim 38, wherein the cancer is a melanoma.

41. The method of claim 38, wherein the cancer is a non-small cell lung cancer.

42. The method of claim 38, wherein the cancer is a colorectal cancer.

43. The method of claim 38, wherein the cancer is a pancreatic cancer.

* * * * *